US012364774B2

(12) United States Patent
Liu et al.

(10) Patent No.: US 12,364,774 B2
(45) Date of Patent: Jul. 22, 2025

(54) NUCLEIC ACID MOLECULES AND USES THEREOF FOR NON-VIRAL GENE THERAPY

(71) Applicant: BIOVERATIV THERAPEUTICS INC., Waltham, MA (US)

(72) Inventors: Tongyao Liu, Lexington, MA (US); Alexey Seregin, Westford, MA (US); Robert T. Peters, Needham, MA (US); Jiayun Liu, Wellesley, MA (US); Philip Zakas, Waltham, MA (US); Douglas Drager, Waltham, MA (US); Susannah Patarroyo-White, Waltham, MA (US)

(73) Assignee: BIOVERATIV THERAPEUTICS INC., Waltham, MA (US)

( * ) Notice: Subject to any disclaimer, the term of this patent is extended or adjusted under 35 U.S.C. 154(b) by 714 days.

(21) Appl. No.: 16/537,192

(22) Filed: Aug. 9, 2019

(65) Prior Publication Data

US 2020/0069817 A1    Mar. 5, 2020

Related U.S. Application Data

(60) Provisional application No. 62/716,826, filed on Aug. 9, 2018.

(51) Int. Cl.
| | |
|---|---|
| *C12N 15/861* | (2006.01) |
| *A61K 9/00* | (2006.01) |
| *A61K 35/76* | (2015.01) |
| *A61K 48/00* | (2006.01) |
| *A61P 7/04* | (2006.01) |
| *C07K 14/755* | (2006.01) |
| *C12N 7/00* | (2006.01) |
| *C12N 7/01* | (2006.01) |
| *C12N 15/11* | (2006.01) |
| *C12N 15/86* | (2006.01) |

(52) U.S. Cl.
CPC ........ *A61K 48/0058* (2013.01); *A61K 9/0019* (2013.01); *A61K 48/0016* (2013.01); *A61K 48/0033* (2013.01); *A61K 48/0066* (2013.01); *A61P 7/04* (2018.01); *C07K 14/755* (2013.01); *C12N 7/00* (2013.01); *C12N 15/86* (2013.01); *C12N 2750/14143* (2013.01); *C12N 2750/14171* (2013.01); *C12N 2750/14343* (2013.01); *C12N 2750/14371* (2013.01); *C12N 2830/42* (2013.01); *C12N 2830/50* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Kary | |
| 4,770,999 A | 9/1988 | Kaufman et al. | |
| 4,800,159 A | 1/1989 | Mullis et al. | |
| 4,868,112 A | 9/1989 | Toole, Jr. | |
| 4,965,188 A | 10/1990 | Mullis et al. | |
| 5,112,950 A | 5/1992 | Meulien et al. | |
| 5,171,844 A | 12/1992 | Van Ooyen et al. | |
| 5,304,489 A | 4/1994 | Rosen | |
| 5,543,502 A | 8/1996 | Nordfang et al. | |
| 5,595,886 A | 1/1997 | Chapman et al. | |
| 5,610,278 A | 3/1997 | Nordfang et al. | |
| 5,648,260 A | 7/1997 | Winter et al. | |
| 5,658,570 A | 8/1997 | Newman et al. | |
| 5,712,122 A | 1/1998 | Boime et al. | |
| 5,736,137 A | 4/1998 | Andersopn et al. | |
| 5,739,277 A | 4/1998 | Presta et al. | |
| 5,741,957 A | 4/1998 | Deboer et al. | |
| 5,789,203 A | 8/1998 | Chapman et al. | |
| 5,834,250 A | 11/1998 | Wells et al. | |
| 5,849,992 A | 12/1998 | Meade et al. | |
| 5,869,046 A | 2/1999 | Presta et al. | |
| 5,972,885 A | 10/1999 | Spira et al. | |
| 6,030,613 A | 2/2000 | Blumberg et al. | |

(Continued)

FOREIGN PATENT DOCUMENTS

| | | |
|---|---|---|
| CN | 101124328 A | 2/2008 |
| CN | 103215308 A | 7/2013 |

(Continued)

OTHER PUBLICATIONS

Ward et al, Codon optimization of human factor VIII cDNAs leads to high-level expression, Blood, 2011, pp. 798-807.*

Nguyen et al, Evaluation of Gene Promoters For Liver Expression By Hydrodynamic Gene Transfer, J Surg Res. Jul. 2008 ; 148(1): 60-66.*

Bzymek et al., "Evidence for Two Mechanisms of Palindrome-Stimulated Deletion in *Escherichia coli*: Single-Strand Annealing and Replication Slipped Mispairing", Genetics, vol. 158, Jun. 2001, pp. 527-540.

(Continued)

*Primary Examiner* — Maria Marvich
(74) *Attorney, Agent, or Firm* — LATHROP GPM LLP; James H. Velema, Esq.; James V. DeGiulio, Esq.

(57) ABSTRACT

The present disclosure provides nucleic acid molecules comprising a first inverted terminal repeat (ITR), a second ITR, and a genetic cassette encoding a target sequence. In some embodiments, the target sequence encodes a miRNA and/or a therapeutic protein. In certain embodiments, the therapeutic protein comprises a clotting factor, a growth factor, a hormone, a cytokine, an antibody, a fragment thereof, and a combination thereof. In some embodiments, the first ITR and/or the second ITR is an ITR of a non-adeno-associated virus (AAV). The present disclosure also provides methods of treating a metabolic disorder of the liver in a subject comprising administering to the subject the nucleic acid molecule or a polypeptide encoded thereby.

46 Claims, 14 Drawing Sheets

Specification includes a Sequence Listing.

(56) References Cited

U.S. PATENT DOCUMENTS

| | | |
|---|---|---|
| 6,033,885 A | 3/2000 | Latta et al. |
| 6,048,720 A | 4/2000 | Dalborg et al. |
| 6,060,447 A | 5/2000 | Chapman et al. |
| 6,086,875 A | 7/2000 | Blumberg et al. |
| 6,096,871 A | 8/2000 | Presta et al. |
| 6,121,022 A | 9/2000 | Presta et al. |
| 6,159,730 A | 12/2000 | Reff |
| 6,193,980 B1 | 2/2001 | Efstathiou et al. |
| 6,194,551 B1 | 2/2001 | Idusogie et al. |
| 6,228,620 B1 | 5/2001 | Chapman et al. |
| 6,242,195 B1 | 6/2001 | Idusogie et al. |
| 6,251,632 B1 | 6/2001 | Lillicrap et al. |
| 6,277,375 B1 | 8/2001 | Ward |
| 6,291,214 B1 | 9/2001 | Richards et al. |
| 6,316,226 B1 | 11/2001 | Van Ooyen et al. |
| 6,346,513 B1 | 2/2002 | Van Ooyen et al. |
| 6,413,777 B1 | 7/2002 | Reff et al. |
| 6,458,563 B1 | 10/2002 | Lollar |
| 6,485,726 B1 | 11/2002 | Blumberg et al. |
| 6,491,907 B1 | 12/2002 | Rabinowitz |
| 6,528,624 B1 | 3/2003 | Idusogie et al. |
| 6,538,124 B1 | 3/2003 | Idusogie et al. |
| 6,696,245 B2 | 2/2004 | Winter et al. |
| 6,723,551 B2 | 4/2004 | Kotin et al. |
| 6,737,056 B1 | 5/2004 | Presta |
| 6,808,905 B2 | 10/2004 | McArthur et al. |
| 6,821,505 B2 | 11/2004 | Ward |
| 6,998,253 B1 | 2/2006 | Presta et al. |
| 7,041,635 B2 | 5/2006 | Kim et al. |
| 7,083,784 B2 | 8/2006 | Dall'Acqua et al. |
| 7,179,903 B2 | 2/2007 | McArthur et al. |
| 7,271,002 B2 | 9/2007 | Kotin et al. |
| 7,317,091 B2 | 1/2008 | Lazar et al. |
| 7,404,956 B2 | 7/2008 | Peters et al. |
| 7,598,071 B2 | 10/2009 | Brown et al. |
| 7,700,734 B2 | 4/2010 | Lin et al. |
| 7,745,179 B2 | 6/2010 | McArthur et al. |
| 7,939,632 B2 | 5/2011 | Metzner et al. |
| 8,071,751 B2 | 12/2011 | Delwart et al. |
| 8,110,350 B2 | 2/2012 | Allander et al. |
| 8,945,918 B2 | 2/2015 | Chen et al. |
| 9,062,098 B2 | 6/2015 | Allander et al. |
| 9,115,373 B2 | 8/2015 | Hermens et al. |
| 9,186,381 B2 | 11/2015 | Zender et al. |
| 9,212,374 B2 | 12/2015 | Roy et al. |
| 9,828,587 B2 | 11/2017 | Yan et al. |
| 9,856,468 B2 | 1/2018 | Salas et al. |
| 9,879,279 B2 | 1/2018 | Chen |
| 9,890,365 B2 * | 2/2018 | Wang ............... A61K 48/0058 |
| 9,943,611 B2 | 4/2018 | Balazs et al. |
| 10,793,835 B2 | 10/2020 | Yan et al. |
| 11,066,679 B2 | 7/2021 | Kotin et al. |
| 11,103,597 B2 | 8/2021 | Gray et al. |
| 11,142,775 B2 | 10/2021 | Yan et al. |
| 11,634,742 B2 | 4/2023 | De Beer et al. |
| 12,168,776 B2 | 12/2024 | Liu et al. |
| 2003/0069395 A1 | 4/2003 | Sato et al. |
| 2003/0235536 A1 | 12/2003 | Blumberg et al. |
| 2006/0008469 A1 | 1/2006 | Brown et al. |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0243188 A1 | 10/2007 | Lazar et al. |
| 2007/0248603 A1 | 10/2007 | Lazar et al. |
| 2007/0253936 A1 | 11/2007 | Kay et al. |
| 2007/0286859 A1 | 12/2007 | Lazar et al. |
| 2008/0004206 A1 | 1/2008 | Rosen et al. |
| 2008/0057056 A1 | 3/2008 | Lazar et al. |
| 2008/0153751 A1 | 6/2008 | Rosen et al. |
| 2008/0161243 A1 | 7/2008 | Rosen et al. |
| 2008/0194481 A1 | 8/2008 | Rosen et al. |
| 2008/0213233 A1 * | 9/2008 | Wang ............... A61P 27/02 536/23.7 |
| 2008/0260738 A1 | 10/2008 | Moore et al. |
| 2008/0261877 A1 | 10/2008 | Ballance et al. |
| 2009/0087411 A1 | 4/2009 | Fares et al. |
| 2010/0136514 A1 * | 6/2010 | Brown ............... C12Q 1/701 435/235.1 |
| 2010/0239554 A1 | 9/2010 | Schellenberger et al. |
| 2010/0292130 A1 | 11/2010 | Skerra et al. |
| 2010/0323956 A1 | 12/2010 | Schellenberger et al. |
| 2011/0046060 A1 | 2/2011 | Schellenberger et al. |
| 2011/0046061 A1 | 2/2011 | Schellenberger et al. |
| 2011/0077199 A1 | 3/2011 | Schellenberger et al. |
| 2011/0172146 A1 | 7/2011 | Schellenberger et al. |
| 2011/0190166 A1 | 8/2011 | Wong et al. |
| 2013/0109742 A1 | 5/2013 | Hewitt et al. |
| 2014/0107186 A1 * | 4/2014 | Garcia ............... A61P 25/00 536/23.1 |
| 2014/0271551 A1 | 9/2014 | Hirsch et al. |
| 2014/0308280 A1 | 10/2014 | Maloney et al. |
| 2014/0370035 A1 | 12/2014 | Jiang et al. |
| 2015/0023959 A1 | 1/2015 | Chhabra et al. |
| 2015/0111955 A1 | 4/2015 | High et al. |
| 2015/0158929 A1 | 6/2015 | Schellenberger et al. |
| 2016/0102297 A1 * | 4/2016 | Hewitt ............... C12N 15/8645 435/363 |
| 2016/0229904 A1 | 8/2016 | Xiao et al. |
| 2016/0296607 A1 * | 10/2016 | Jiang ............... A61P 7/04 |
| 2016/0311885 A1 * | 10/2016 | Peters ............... A61K 38/36 |
| 2017/0021037 A1 | 1/2017 | Wang et al. |
| 2017/0081392 A1 | 3/2017 | Wilson et al. |
| 2017/0130245 A1 * | 5/2017 | Kotin ............... C07K 14/005 |
| 2017/0356009 A1 | 12/2017 | Lu et al. |
| 2017/0362608 A1 | 12/2017 | McLaughlin et al. |
| 2019/0048362 A1 | 2/2019 | Kyostio-Moore et al. |
| 2019/0185543 A1 | 6/2019 | Tan et al. |
| 2019/0203229 A1 | 7/2019 | Engelhardt et al. |
| 2020/0069817 A1 | 3/2020 | Liu et al. |
| 2020/0224220 A1 | 7/2020 | Finer et al. |
| 2020/0283794 A1 | 9/2020 | Kotin et al. |
| 2021/0010028 A1 | 1/2021 | Horowitz et al. |
| 2021/0163986 A1 | 6/2021 | Seregin et al. |
| 2022/0042040 A1 | 2/2022 | Grabherr et al. |
| 2022/0090130 A1 | 3/2022 | Maghodia et al. |
| 2022/0175970 A1 | 6/2022 | Kerr et al. |
| 2022/0243201 A1 | 8/2022 | Maghodia et al. |
| 2022/0356490 A1 | 11/2022 | Liu et al. |
| 2023/0063208 A1 | 3/2023 | Ceruti et al. |
| 2023/0084036 A1 | 3/2023 | Maghodia et al. |
| 2023/0091932 A1 | 3/2023 | Maghodia et al. |
| 2024/0294940 A1 | 9/2024 | Maghodia et al. |
| 2024/0350671 A1 | 10/2024 | Maghodia et al. |

FOREIGN PATENT DOCUMENTS

| | | |
|---|---|---|
| CN | 107531774 A | 1/2018 |
| CN | 111247251 A | 6/2020 |
| EP | 0295597 A2 | 12/1988 |
| EP | 1395293 A1 | 3/2004 |
| EP | 1572893 B1 | 1/2009 |
| EP | 2292781 A1 | 3/2011 |
| EP | 2061891 B1 | 4/2012 |
| EP | 2508607 A1 | 10/2012 |
| EP | 2195439 B1 | 6/2013 |
| EP | 2698163 * | 2/2014 |
| EP | 2698163 A1 | 2/2014 |
| EP | 3230441 A4 | 10/2018 |
| EP | 3294309 A4 | 1/2019 |
| EP | 3476860 A1 | 5/2019 |
| EP | 2914731 B1 | 9/2019 |
| EP | 3665289 A1 | 6/2020 |
| EP | 3722434 A1 | 10/2020 |
| EP | 3678710 A4 | 6/2021 |
| EP | 3833766 A1 | 6/2021 |
| EP | 3423110 B1 | 8/2021 |
| EP | 3877528 A1 | 9/2021 |
| EP | 3914717 A1 | 12/2021 |
| EP | 4199971 A1 | 6/2023 |
| EP | 4392444 A1 | 7/2024 |
| EP | 4392445 A1 | 7/2024 |
| EP | 4392566 A2 | 7/2024 |
| JP | 2002-527493 A | 8/2002 |

(56) References Cited

FOREIGN PATENT DOCUMENTS

| | | |
|---|---|---|
| JP | 2011-067212 A | 4/2011 |
| JP | 2014-511180 A | 5/2014 |
| JP | 2014-511690 A | 5/2014 |
| RU | 2569183 C2 | 11/2015 |
| TW | 201629225 A | 8/2016 |
| WO | WO 1987/004187 A1 | 7/1987 |
| WO | WO 1988/000831 A1 | 2/1988 |
| WO | WO 1988/007089 A1 | 9/1988 |
| WO | WO 1991/009122 A1 | 6/1991 |
| WO | WO 1994/028157 A1 | 12/1994 |
| WO | WO 1995/009923 A1 | 4/1995 |
| WO | WO 1995/023867 A1 | 9/1995 |
| WO | WO 1996/014339 A1 | 5/1996 |
| WO | WO 1998/005787 A1 | 2/1998 |
| WO | WO 1998/023289 A1 | 6/1998 |
| WO | WO 1999/051642 A1 | 10/1999 |
| WO | WO 1999/058572 A1 | 11/1999 |
| WO | WO 2000/005355 A1 | 2/2000 |
| WO | WO 2000/009560 A2 | 2/2000 |
| WO | WO 2000/023116 A1 | 4/2000 |
| WO | WO 2000/028004 A1 | 5/2000 |
| WO | WO 2000/032767 A1 | 6/2000 |
| WO | WO 2000/042072 A2 | 7/2000 |
| WO | WO 2001/075092 A2 | 10/2001 |
| WO | WO 2002/044215 A2 | 6/2002 |
| WO | WO 2002/060919 A2 | 8/2002 |
| WO | WO 2002/040544 A3 | 10/2002 |
| WO | WO 2002/092134 A1 | 11/2002 |
| WO | WO 2003/020764 A2 | 3/2003 |
| WO | WO 2003/042361 A2 | 5/2003 |
| WO | WO 2003/074569 A2 | 9/2003 |
| WO | WO 2003/077834 A2 | 9/2003 |
| WO | WO 2004/016750 A2 | 2/2004 |
| WO | WO 2004/029207 A2 | 4/2004 |
| WO | WO 2004/035752 A2 | 4/2004 |
| WO | WO 2004/044859 A1 | 5/2004 |
| WO | WO 2004/063351 A2 | 7/2004 |
| WO | WO 2004/074455 A2 | 9/2004 |
| WO | WO 2004/094642 A2 | 11/2004 |
| WO | WO 2004/099249 A2 | 11/2004 |
| WO | WO 2005/040217 A2 | 5/2005 |
| WO | WO 2005/070963 A1 | 8/2005 |
| WO | WO 2005/077981 A2 | 8/2005 |
| WO | WO 2005/085456 A1 | 9/2005 |
| WO | WO 2005/092925 A2 | 10/2005 |
| WO | WO 2007/057062 A1 | 11/2005 |
| WO | WO 2005/123780 A2 | 12/2005 |
| WO | WO 2006/019447 A1 | 2/2006 |
| WO | WO 2006/033756 A | 3/2006 |
| WO | WO 2006/047350 A2 | 5/2006 |
| WO | WO 2006/085967 A2 | 8/2006 |
| WO | WO 2007/000668 A2 | 1/2007 |
| WO | WO 2007/021494 A2 | 2/2007 |
| WO | WO 2007/149406 A2 | 12/2007 |
| WO | WO 2008/012543 A1 | 1/2008 |
| WO | WO 2008/016391 A2 | 2/2008 |
| WO | WO 2008/024998 A2 | 2/2008 |
| WO | WO 2008/033413 A2 | 3/2008 |
| WO | WO 2008/118507 A2 | 10/2008 |
| WO | WO 2008/141400 A1 | 11/2008 |
| WO | WO 2008/143954 A2 | 11/2008 |
| WO | WO 2008/155134 A1 | 12/2008 |
| WO | WO 2009/038462 A1 | 3/2009 |
| WO | WO 2009/051717 A2 | 4/2009 |
| WO | WO 2009/058322 A1 | 5/2009 |
| WO | WO 2009/130198 A2 | 10/2009 |
| WO | WO 2009/137254 A2 | 11/2009 |
| WO | WO 2009/140015 A2 | 11/2009 |
| WO | WO 2009/146210 A2 | 12/2009 |
| WO | WO 2010/055413 A1 | 5/2010 |
| WO | WO 2010/091122 A1 | 8/2010 |
| WO | WO 2010/125471 A2 | 11/2010 |
| WO | WO 2010/140148 A1 | 12/2010 |
| WO | WO 2010/144502 A2 | 12/2010 |
| WO | WO 2010/144508 A1 | 12/2010 |
| WO | WO 2011/020710 A2 | 2/2011 |
| WO | WO 2011/028228 A1 | 3/2011 |
| WO | WO 2011/028229 A1 | 3/2011 |
| WO | WO 2011/028344 A2 | 3/2011 |
| WO | WO 2011/088081 A1 | 7/2011 |
| WO | WO 2011/100330 A2 | 8/2011 |
| WO | WO 2011/112090 A2 | 9/2011 |
| WO | WO 2012/006624 A2 | 1/2012 |
| WO | WO 2012/006635 A1 | 1/2012 |
| WO | WO 2012/115980 A1 | 8/2012 |
| WO | WO 2012/136859 A1 | 10/2012 |
| WO | WO 2013/123457 A1 | 8/2013 |
| WO | WO 2014/011819 A2 | 1/2014 |
| WO | WO 2014/070949 A1 | 5/2014 |
| WO | WO 2014/127215 A1 | 8/2014 |
| WO | WO 2014/143932 A1 | 9/2014 |
| WO | WO 2014/168953 A1 | 10/2014 |
| WO | WO 2015/023891 A2 | 2/2015 |
| WO | WO 2015/038625 A1 | 3/2015 |
| WO | WO 2015/106052 A1 | 7/2015 |
| WO | WO 2015/191508 A1 | 12/2015 |
| WO | WO 2016/004113 A1 | 1/2016 |
| WO | WO 2016/081927 A2 | 5/2016 |
| WO | WO 2016/094783 A1 | 6/2016 |
| WO | WO 2016/127057 A1 | 8/2016 |
| WO | WO 2016/134338 A1 | 8/2016 |
| WO | WO 2016/183422 A1 | 11/2016 |
| WO | WO 2017/075619 A1 | 5/2017 |
| WO | WO 2017/136358 A1 | 8/2017 |
| WO | WO 2017/152149 A1 | 9/2017 |
| WO | WO 2017/205739 A1 | 11/2017 |
| WO | WO 2018/024998 A1 | 2/2018 |
| WO | WO 2018/132747 A1 | 7/2018 |
| WO | WO 2019/014623 A1 | 1/2019 |
| WO | WO 2008/016391 A1 | 2/2019 |
| WO | WO 2019/032102 A1 | 2/2019 |
| WO | WO 2019/032898 A1 | 2/2019 |
| WO | WO 2019/051255 A1 | 3/2019 |
| WO | WO 2019/051289 A1 | 3/2019 |
| WO | WO 2019/067766 A1 | 4/2019 |
| WO | WO 2019/113310 A1 | 6/2019 |
| WO | WO 2019/143885 A1 | 7/2019 |
| WO | WO 2019/161059 A1 | 8/2019 |
| WO | WO 2019/165050 A1 | 8/2019 |
| WO | WO 2019/169232 A1 | 9/2019 |
| WO | WO 2019/169233 A1 | 9/2019 |
| WO | WO 2019/173434 A1 | 9/2019 |
| WO | WO 2019/246544 A3 | 12/2019 |
| WO | WO 2020/033863 A1 | 2/2020 |
| WO | WO 2020/069429 A1 | 4/2020 |
| WO | WO 2020/077250 A1 | 4/2020 |
| WO | WO 2020/097417 A1 | 5/2020 |
| WO | WO 2020/154645 A1 | 7/2020 |
| WO | WO 2020/161168 A1 | 8/2020 |
| WO | WO 2020/168222 A1 | 8/2020 |
| WO | WO 2020/181182 A1 | 9/2020 |
| WO | WO 2020/186207 A2 | 9/2020 |
| WO | WO 2020/208379 A1 | 10/2020 |
| WO | WO 2020/225405 A1 | 11/2020 |
| WO | WO 2020/257590 A1 | 12/2020 |
| WO | WO 2021/011840 A1 | 1/2021 |
| WO | WO 2021/216975 A1 | 10/2021 |
| WO | WO 2022/046665 A1 | 3/2022 |
| WO | WO 2023/028440 A2 | 3/2023 |
| WO | WO 2023/028441 A1 | 3/2023 |
| WO | WO 2023/028455 A1 | 3/2023 |

OTHER PUBLICATIONS

Cotter et al., "The induction of Inflammation by Adenovirus Vectors used for Gene Therapy", Frontiers in Bioscience vol. 10, May 1, 2005, pp. 10-18-1105.

Doherty et al., "*Escherichia coli* host strains SURE™ and SRB fail to preserve a palindrome cloned in lambda phage: improved alternate host strains", Gene, vol. 124 pp. 29-35, 1993.

Dong et al., "Quantitative Analysis of the Packaging Capacity of Recombinant Adeno-Associated Virus", Human Gene Therapy vol. 7, pp. 2101-2112, Nov. 10, 1996.

(56) References Cited

OTHER PUBLICATIONS

Gottlieb et al., "In vitro Excision of Adeno-Associated Virus DNA from Recombinant Plasmids: Isolation of an Enzyme Fraction from HeLa Cells That Cleaves DNA at Poly(G) Sequences", Molecular and Cellular Biology, vol. 6, No. 8, Jun. 1988, pp. 2513-2522.
Kulkarni et al., "Interaction Between the sbcC Gene of *Escherichia coli* and the gam Gene of Phage λ" Genetics, vol. 123, Oct. 1989, pp. 249-253.
Leach, "Long DNA Palindromes, Cruciform Structures, Genetic Instability and Secondary Structure Repair", BioEssays, vol. 16, No. 12, Dec. 1994, pp. 893-900.
Li et al., "Production and characterization of Novel Recombinant Adeno-Associated Virus Replicative-Form Genomes: A Eukaryotic Source of DNA for Gene Transfer", PLoS ONE vol. 8, Issue 8, e69879, Aug. 2013.
Lilley, David M.J., "In vivo consequences of Plasmid Topology", Nature, vol. 292, Jul. 23, 1981, pp. 380-382.
McLaughlin et al., "Adeno-Associated Virus General Transduction Vectors: Analysis of Proviral Structures", Journal of Virology, vol. 62, No. 6, Jun. 1988, pp. 1963-1973.
Naso et al., "Adeno-Associated Virus (AAV) as a Bector for Gene Therapy", BioDrugs, vol. 31, 2017, pp. 317-334.
Ni et al., "Virus-Inspired Nucleic Acid Delivery System: Linking Virus and Viral Mimicry", Advanced Drug Delivery Reviews vol. 106, 2016, pp. 3-26.
Samulski et al., "Rescue of Adeno-Associated Virus from Recombinant Plasmids: Gene Correction Within the Terminal Repeats of AAV", Cell, vol. 33, Issue 1, May 1983, pp. 135-143.
Samulski et al., "A Recombinant Plasmid from Which an Infectious Adeno-Associated Virus Genome Can Be Excised In Vitro and Its Use to Study Viral Replication", Journal of Virology, vol. 61, No. 10, Oct. 1987, pp. 3096-3101.
Samulski et al., "Helper-Free Stocks of Recombinant Adeno-Associated Viruses: Normal Integration Does Not Require Viral Gene Expression", Journal of Virology, vol. 63, No. 9, Sep. 1989, pp. 3822-3828.
Senapathy et al., "Molecular Cloning of Adeno-Associated Virus Variant Genomes and Generation of Infectious Virus by Recombination in Mammalian Cells", Journal of Biological Chemistry, vol. 259, No. 7, Apr. 10, 1984, pp. 4661-4666.
Zhou et al., "Deletion of the B-B' and C-C' regions of inverted terminal repeats reduces rAAV productivity but increases transgene expression", Scientific Reports 7: 5432.
Luo et al. "Human parvovirus B19: a mechanistic overview of infection and DNA replication", Future Virology, vol. 10, No. 2, Feb. 1, 2015, pp. 155-167, XP055637456, UK.
Manaresi et al. "A Parvovirus B19 synthetic genome: sequence features and functional competence", Virology, vol. 508, May 10, 2017, pp. 54-62, XP085068336, Amsterdam, NL.
Wang et al. "Sequencing and generation of an infectious clone of the pathogenic goose parvovirus strain LH", Archives of Virology, vol. 160, No. 3, Jan. 7, 2015, pp. 711-718, XP035455223, AT.
Connelly et al. "The sbcC and sbcD genes of *Escherichia coli* encode a nuclease involved in palindrome inviability and genetic recombination", Genes to Cells, Mar. 1, 1996, pp. 285-291, XP055638433, Oxford BSL.
Armour et al., "Recombinant Human IgG Molecules Lacking Fc Gamma Receptor I Binding And Monocyte Triggering Activities", European Journal of Immunology, vol. 29, No. 8, pp. 2613-2624, Aug. 1999.
Babkin et al., "A study of the human bocavirus replicative genome structures", Virus Research, Oct. 31, 2014, 195: 196-202.
Baldassarre et al., "Production of Transgenic Goats By Pronuclear Microinjection Of In Vitro Produced Zygotes Derived From Oocytes Recovered By Laparoscopy", Theriogenology, vol. 59, Issues 3-4, pp. 831-839, Feb. 2003.
Beerli et al. (2002) "Engineering polydactyl zinc-finger transcription factors", Nature Biotechnol., 20: 135-141.

Behrman et al., "A CHOP-Regulated MicroRNA Controls Rhodopsin Expression", Journal of Cell Biology, 2011, vol. 192, No. 6, pp. 919-927.
Benhar et al., "Cloning, Expression and Characterization Of The Fv Fragments Of The Anti-Carbohydrate mAbs BI and B5 As Single-Chain Immunotoxins", Protein Engineering, Design and Selection, vol. 7, No. 12, pp. 1509-1515, Dec. 1994.
Bril et al. (2006) "Tolerance to factor VIII in a transgenic mouse expressing human factor VIII cDNA carrying an Arg$^{593}$ to Cys substitution", Thromb. Haemost. 95(2): 341-347.
Brinster et al., "Expression of A Microinjected Immunoglobulin Gene In The Spleen Of Transgenic Mice", Nature, vol. 306, No. 5941, pp. 332-336, 1983.
Brinster et al., "Factors Affecting the Efficiency of Introducing Foreign DNA Into Mice by Microinjecting Eggs", Proceedings of the National Academy of Sciences of the United States of America, vol. 82, No. 13, pp. 4438-4442, Jul. 1, 1985.
Brown et al., "Production of Recombinant H1 Parvovirus Stocks Devoid of Replication-Competent Viruses", Human Gene Therapy, vol. 13, No. 18, pp. 2135-2145, Dec. 10, 2002.
Burmeister et al., "Crystal Structure of the Complex of Rat Neonatal Fc Receptor with Fc", Nature, Nov. 24, 1994, vol. 372, No. 6504, pp. 379-383.
Cameron et al., "The Canine Factor VIII cDNA and 5' Flanking Sequence", Journal of Thrombosis and Haemostasis, Feb. 1998, vol. 79, No. 2, pp. 317-322.
Capon et al. (1989) "Designing CD4 immunoadhesins for AIDS therapy," Nature, 337, 525-531.
Chen et al. (2005) "MicroRNAs as regulators of mammalian hematopoiesis," Seminars in Immunology, 17:155-165.
Chiorini et al. (1997) "Cloning of adeno-associated virus type 4 (AAV4) and generation of recombinant AAV4 particles", J. Vir., 71: 6823-6833.
Chiorini et al. (1999) "Cloning and Characterization of Adeno-Associated Virus Type 5", J. Vir. 73: 1309-1319.
Cho et al., (2015) "DNA repair: ends with alternative endings", Nature 518, 174-176.
Choo et al. (2000) "Advances in zinc finger engineering", Curr. Opin. Struct. Biol. 10(4): 411-416.
Choo et al., "Molecular Cloning of The Gene for Human Anti-Haemophilic Factor IX", Nature, 1982, vol. 299, No. 5879, pp. 178-180.
Connelly et al., "The sbcC and sbcD genes of *Escherichia coli* encode a nuclease involved in palindrome inviability and genetic recombination", Mar. 1996, p. 285-291.
Costa et al. (1986) "Transcriptional Control of the Mouse Prealbumin (Transthyretin) Gene: Both Promoter Sequences and a Distinct Enhancer Are Cell Specific," Molecular and Cellular Biology, 6(12):4697-4708.
Cutler et al., "The Identification and Classification Of 41 Novel Mutations In The Factor VIII Gene (F8c)", Human Mutation, Mar. 2002, vol. 19, No. 3, pp. 274-278.
Dalkara et al. (2013) "In Vivo-Directed Evolution of a New Adeno-Associated Virus for Therapeutic Outer Retinal Gene Delivery from the Vitreous", Sci. Transl. Med. 5(189): 189ra76.
Deng et al., "Site-Directed Mutagenesis of Virtually any Plasmid by Eliminating a Unique Site", Analytical Biochemistry, Jan. 1, 1992, vol. 200, Issue 1, pp. 81-88.
Dennis et al. (2002) "Albumin binding as a general strategy for improving the pharmacokinetics of proteins," The Journal of Biological Chemistry, 277(38):35035-35043.
Dirren et al., "SOD1 Silencing in Motoneurons or Glia Rescues Neuromuscular Function in ALS Mice", Annals of Clinical and Translational Neurology, Feb. 2015, vol. 2, No. 2, pp. 167-184.
Eaton et al., "Construction and Characterization of an Active Factor VIII Variant Lacking the Central One-Third of the Molecule", Biochemistry, Dec. 1986, vol. 25, No. 26, pp. 8343-8347.
Ellman et al. (1991) "Biosynthetic Method for Introducing Unnatural Amino Acids Site-Specifically into Proteins," Methods In Enzymology, 202 (15): 301-336.
Esvelt et al. (Nov. 2013) "Orthogonal Cas9 proteins for RNA-guided gene regulation and editing", Nat Methods., 10(11): 1116-1121.

(56) References Cited

OTHER PUBLICATIONS

Evers et al., "AAV5-miHTT Gene Therapy Demonstrates Broad Distribution and Strong Human Mutant Huntingtin Lowering in a Huntington's Disease Minipig Model", Molecular Therapy, Sep. 5, 2018, vol. 26, Issue 9, pp. 2163-2177.
Fair et al., "Human Hepatoma Cells Secrete Single Chain Factor X, Prothrombin, And Antithrombin III", Blood, 1984, vol. 64, No. 1, pp. 194-204.
Fallaux et al. (1996) "The Human Clotting Factor VIII cDNA Contains an Autonomously Replicating Sequence Consensus- and Matrix Attachment Region-Like Sequence That Binds a Nuclear Factor, Represses Heterologous Gene Expression, and Mediates the Transcriptional Effects of Sodium Butyrate," Molecular and Cellular Biology, 16 (8): 4264-4272.
Figueiredo et al., "Cis-Acting Elements and Transcription Factors Involved in the Promoter Activity of The Human Factor VIII Gene", Journal of Biological Chemistry, May 19, 1995, vol. 270, No. 20, pp. 11828-11838.
Friend et al. (1999) "Phase I Study of an Engineered Aglycosylated Humanized CD3 Antibody in Renal Transplant Rejection," Transplantation, 68 (11): 1632-1637.
Gao et al., "Clades of Adeno-Associated Viruses are Widely Disseminated in Human Tissues", Journal of Virology, Jun. 15, 2004, vol. 78, No. 12, pp. 6381-6388.
Genbank, "", GenBank Accession No. U25749.1, Dec. 12, 1995, Retrieved From: https://www.ncbi.nlm.nih.gov/nuccore/U25749.1.
Genbank, "Adeno-associated virus-2, complete genome", GenBank Accession No. NC_001401.2, Aug. 13, 2019, Retrieved From: https://www.ncbi.nlm.nih.gov/nuccore/NC_001401.2.
Genbank, "Adeno-associated virus 2, complete genome", GenBank Accession No. AF043303.1, May 20, 2010, Retrieved From: <<http://www.ncbi.nlm.nih.gov/nuccore/AF043303>>.
Genbank, "Adeno-associated virus 5 DNA binding trs helicase (Rep22) and capsid protein (VP1) genes, complete cds", GenBank Accession No. AF085716.1, Feb. 9, 1999, Retrieved From: <<http://www.ncbi.nlm.nih.gov/nuccore/AF085716>>.
Genbank, "Goose parvovirus, complete genome", GenBank Accession No. NC001701.1, Aug. 13, 2018, Retrieved From: <<http://www.ncbi.nlm.nih.gov/nuccore/NC001701>>.
Genbank, "*Homo sapiens* Transferrin (TF), mRNA", GenBank Accession No. XM002793, May 13, 2002, 2 pages, Retrieved from: <<https://www.ncbi.nlm.nih.gov/nuccore/XM_002793.7?report=genbank>>.
Genbank, "*Homo sapiens* Transferrin (TF), mRNA", GenBank Accession No. XM039847, Jul. 16, 2001, 2 pages, Retrieved From <<https://www.ncbi.nlm.nih.gov/nuccore/XM_039847.1?report=genbank>>.
Genbank, "*Homo sapiens* transferrin (TF), mRNA", GenBank Accession No. XM_039845.1, Jul. 16, 2001, Retrieved From: https://www.ncbi.nlm.nih.gov/nuccore/XM_039845.1?report=genbank.
Genbank, "*Homo sapiens* Transferrin (TF), Transcript Variant 1, mRNA", GenBank Accession No. NM001063, Sep. 3, 2009, 5 pages, Retrieved from: <<http://www.ncbi.nlm.nih.gov/nuccore/NM_001063>>.
Genbank, "*Homo sapiens* Von Willebrand Factor (VWF), mRNA", NCBI Reference Sequence: NM_000552.3, Mar. 29, 2016, 10 pages, Retrieved from: <<https://www.ncbi.nlm.nih.gov/nuccore/NM_000552.3>>.
Genbank, "Human parvovirus B19, complete genome", GenBank Accession No. NC000883.2, Aug. 13, 2018, Retrieved From: <<http://www.ncbi.nlm.nih.gov/nuccore/NC000883>>.
Genbank, "Human Transferrin mRNA, Complete cds", GenBank Accession No. M12530, Jan. 14, 1995, 2 pages, Retrieved From: <<http://www.ncbi.nlm.nih.gov/nuccore/M12530>>.
Genbank, "Minute virus of mice, complete genome", GenBank Accession No. NC001510.1, Aug. 13, 2018, Retrieved From: <<http://www.ncbi.nlm.nih.gov/nuccore/NC001510>>.
Genbank, "Snake parvovirus 1, complete genome", GenBank Accession No. NC 0096148.1, Aug. 13, 2018, Retrieved From: <<http://www.ncbi.nlm.nih.gov/nuccore/NC006148>>.
Genbank, "Synthetic construct hepatocyte-restricted expression cassette", GenBank Accession No. AY661265, Sep. 29, 2009, Retrieved From: https://www.ncbi.nlm.nih.gov/nuccore/AY661265.
Genbank, "Synthetic parvovirus B19, complete genome", GenBank Accession No. KY940273.1, May 29, 2017, Retrieved From: https://www.ncbi.nlm.nih.gov/nuccore/KY940273.1.
Genbank, "Transferrin [Human, Liver, mRNA, 2347 nt]", GenBank Accession No. S95936, May 7, 1993, 2 pages, Retrieved From: <<http://www.ncbi.nlm.nih.gov/nuccore/S95936>>.
Genbank, "Transferrin Precursor [*Homo sapiens*]", GenBank Accession No. AAA61140.1, Jan. 14, 1995, 1 page, Retrieved from: <<http://www.ncbi.nlm.nih.gov/protein/AAA61140.1>>.
Genbank, "Von Willebrand Factor Preproprotein [*Homo sapiens*]". NCBI Reference Sequence: NP_000543.2, Mar. 29, 2016, 8 pages, Retrieved from: <<http://www.ncbi.nlm.nih.gov/protein/NP_000543.2>>.
Gonçalves, M.A. (2005) "Adeno-associated virus: from defective virus to effective vector", Virol Journal, 2(43).
Grimm et al. (1999) "Progress in Adeno-Associated Virus Type 2 Vector Production: Promises and Prospects for Clinical Use", Hum. Gene Ther., 10(15): 2445-2450.
Groth et al. (2000) "A phage integrase directs efficient site-specific integration in human cells", Proc. Natl. Acad. Sci. USA, 97(11): 5995-6000.
Ho et al. (1989) "Site-directed mutagenesis by overlap extension using the polymerase chain reaction," Elsevier Science Pub. B.V. (Biomed. Div.), Gene, 77: 51-59.
Hoeben et al. (1995) "Expression of the blood-clotting factor-VIII cDNA is repressed by a transcriptional silencer located in its coding region", Blood, 85(9): 2447-2454.
Hoeben et al., "Expression Of Functional Factor VIII In Primary Human Skin Fibroblasts After Retrovirus-Mediated Gene Transfer", Journal of Biological Chemistry, May 1990, vol. 265, No. 13, pp. 7318-7323.
Holt et al. (2008) "Anti-serum albumin domain antibodies for extending the half-lives of short lived drugs," Protein Engineering, Design and Selection, 21(5):283-288.
Horton et al. (1993) "Gene Splicing by Overlap Extension," Methods in Enzymology, 217 (17): 270-279.
Ill et al., (1997) "Optimization Of The Human Factor VIII Complementary DNA Expression Plasmid For Gene Therapy Of Hemophilia A", Blood Coagulation & Fibrinolysis: An International Journal In Haemostasis And Thrombosis, vol. 8, pp. S23-S30.
Isalan et al. (2001) "A rapid, generally applicable method to engineer zinc fingers illustrated by targeting the HIV-1 promoter", Nature Biotechnol., 19(7): 656-660,.
Israel et al. (1997) "Expression of the neonatal Fc receptor, FcRn, on human intestinal epithelial cells," Immunology 92: 69-74.
Kasuda et al., "Establishment Of Embryonic Stem Cells Secreting Human Factor VIII For Cell-Based Treatment Of Hemophilia A", Journal of Thrombosis and Haemostasis, Aug. 2008, vol. 6, No. 8, pp. 1352-1359.
Klinman et al. (1996) "CpG motifs present in bacteria DNA rapidly induce lymphocytes to secrete interleukin 6, interleukin 12, and interferon gamma", PNAS, 93(7): 2879-2883.
Kobayashi et al. (2002) "FcRn-mediated transcytosis of immunoglobulin G in human renal proximal tubular epithelial cells," Am J Physiol Renal Physiol 282: F358-F365.
Koeberl et al., (1995) "Sequences Within the Coding Regions of Clotting Factor VIII and CFTR Block Transcriptional Elongation", Hum. Gene. Ther., 6(4): 469-479.
Konig et al. (1998) "Use of an albumin-binding domain for the selective immobilisation of recombinant capture antibody fragments on ELISA plates," Journal of Immunological Methods, 218:73-83.
Kotterman et al. (2014) "Engineering adeno-associated viruses for clinical gene therapy", Nat. Rev. Genet., 15(7): 455-451.
Kraulis et al. (1996) "The serum albumin-binding domain of streptococcal protein G is a three-helical bundle: a heteronuclear NMR study," FEBS Letters, 378:190-194.
Kudla et al. (2006) "High Guanine and Cytosine Content Increases mRNA Levels in Mammalian Cells," PloS Biol, e180.

(56) References Cited

OTHER PUBLICATIONS

Kurachi et al., "Isolation And Characterization Of A cDNA Coding For Human Factor IX", Proceedings of the National Academy of Sciences, 1982, pp. 6461-6464.
Langner et al., "Synthesis Of Biologically Active Deletion Mutants Of Human Factor VIII:C", Behring Institute Mitteilungen, Apr. 1988, No. 82, pp. 16-25.
Larrick et al. (1989) "Rapid Cloning of Rearranged Immunoglobulin Genes From Human Hybridoma Cells Using Mixed Primers and the Polymerase Chain Reaction," Biochem. and Biophys. Res. Comm. 160 (3): 1250-1256.
Lenting et al., "Clearance Mechanisms of von Willebrand Factor and Factor VIII", Journal of Thrombosis and Haemostasis, Jul. 2007, vol. 5, No. 7, pp. 1353-1360.
Lenting et al., "The Life Cycle of Coagulation Factor VIII in View of its Structure and Function", Blood, Dec. 1, 1998, vol. 92, No. 11, pp. 3983-3996.
Linhult et al. (2002) "Mutational analysis of the interaction between albumin-binding domain from streptococcal protein G and human serum albumin," Protein Science, 11:206-213.
Loeb et al. (1999) "Enhanced expression of transgenes from adeno-associated virus vectors with the woodchuck hepatitis virus post-transcriptional regulatory element: implications for gene therapy", Hum Gene Ther., 10(14): 2295-2305.
Luo et al., "Human parvovirus B19: a mechanistic overview of infection and DNA replication", Future Virology, vol. 10, No. 2, Feb. 2015, p. 155-167.
Lynch et al. (1993) "Sequences in the Coding Region of Clotting Factor VIII Act as Dominant Inhibitors of RNA Accumulation and Protein Production," Human Gene Therapy 4: 259-272.
Malassagne et al. (Apr. 14, 2003) "Hypodermin A, A New Inhibitor of Human Complement for the Prevention of Xenogeneic Hyperacute Rejection", Xenotransplantation, vol. 10, Issue 3, pp. 267-277.
Manaresi et al., "A Parvovirus B19 synthetic genome: sequence features and functional competence", Virology, vol. 508, May 2017, p. 54-62.
Manco-Johnson et al. (2007) "Prophylaxis versus Episodic Treatment to Prevent Joint Disease in Boys with Severe Hemophilia," N. Engl. J. Med. 357 (6): 535-44.
Maxwell et al.m "Autonomous Parvovirus Vectors", Methods, 2002, vol. 28, Issue 2, pp. 168-181.
McKnight et al. (Sep. 1983) "Expression of The Chicken Transferrin Gene in Transgenic Mice", Cell, vol. 34, Issue 2, pp. 335-341.
Meulien et al., "A New Recombinant Procoagulant Protein Derived From The Cdna Encoding Human Factor VIII", Protein Engineering, Design and Selection, Oct. 1, 1988, vol. 2, No. 4, pp. 301-306.
Miao et al., "Bioengineering of Coagulation Factor VIII for Improved Secretion", Blood, May 1, 2004, vol. 103, No. 9, pp. 3412-3419.
Morfini et al. (2003) "Pharmacokinetics of factor VIII and factor IX," Haemophilia, 9 (Suppl. 1): 94-100.
Mori et al., "Two novel adeno-associated viruses from cynomolgus monkey: pseudotyping characterization of capsid protein", Virology, Dec. 2004, 330(2): 375-383.
Muller et al. (Aug. 2007) "Recombinant Bispecific Antibodies for Cellular Cancer Immunotherapy", Current opinion in molecular therapeutics, vol. 9, No. 4, pp. 319-326.
Nakamura et al. (2000) "Codon usage tabulated from international DNA sequence databases: status for the year 2000," Nucleic Acids Research, 28 (1): 292.
Narita et al. (1998) "The low-density lipoprotein receptor-related protein (LRP) mediates clearance of coagulation factor Xa in Vivo," Blood, 91(2):555-560.
NCBI, "Codon Usage Database", Retrieved from <<http://www.kazusa.or.jp/codon/>>, 2013, pp. 1-2.
Neumann et al., (1982) "Gene transfer into mouse lyoma cells by electroporation in high electric fields", EMBO J., 1(7): 841-845.
Ni et al. (2016) "Virus-inspired nucleic acid delivery system: Linking virus and viral mimicry", Adv Drug Deliv Rev., 106(Pt A): 3-26.
Noren et al. (1989) "A General Method for Site-specific Incorporation of Unnatural Amino Acids into Proteins", Science, 244(4901): 182-188.
O'Gorman et al. (1991) "Recombinase-Mediated Gene Activation and Site-Specific Integration in Mammalian Cells", Science, 251(4999): 1351-1355.
Pabo et al. (2001) "Design and selection of novel Cys2His2 zinc finger proteins", Ann. Rev. Biochem., 70: 313-340.
Pipe et al., "Functional Factor VIII Made With Von Willebrand Factor At High Levels In Transgenic Milk", Journal of Thrombosis and Haemostasis, Nov. 2011, vol. 9, No. 11, pp. 2235-2242.
Rennie et al., "STarMirDB: A Database of MicroRNA Binding Sites", RNA Biology, May 4, 2016, vol. 13, No. 6, pp. 554-560.
Ridgway, (1988) "Introduction of Vector into Host Cells", Mammalian Expression Vectors, Chapter 24.2, pp. 470-472.
Ritchie et al. (Dec. 6, 1984) "Allelic Exclusion and Control of Endogenous Immunoglobulin Gene Rearrangement in κ Transgenic Mice", Nature, vol. 312, No. 5994, pp. 517-520.
Robl et al. (Jan. 1, 2003) "Artificial Chromosome Vectors and Expression of Complex Proteins in Transgenic Animals", Theriogenology, vol. 59, Issue 1, pp. 107-113.
Rodriguez-Merchan (2003) "Management of musculoskeletal complications of hemophilia", Thromb. Hemost., 29(1): 87-96.
Roovers et al. (2007) "Efficient inhibition of EGFR signalling and of tumour growth by antagonistic anti-EGFR Nanobodies," Cacer Immunol Immunother, 56:303-317.
Rouet et al. (1992) "A potent enhancer made of clustered liver-specific elements in the transcription control sequences of human α1-Microglobulin/bikunin," The Journal of Biological Chemistry, 267(29):20765-20773.
Rouet et al. (1995) "Hierarchy and positive/negative interplays of the hepatocyte nuclear factors HNF-1,-3 and -4 in the liver-specific enhancer for the human α-1-microglobulin/bikunin precursor," Nucleic Acids Research, 23(3):395-404.
Rouet et al. (1998) "An array of binding sites for hepatocyte nuclear factor of 4 of high and low affinities modulates the liver-specific enhancer for the human α1-microglobulin/bikunin precursor," Biochem. J., 334:577-584.
Routledge et al. (1995) "The Effect of Aglycosylation on the Immunogenicity of a Humanized Therapeutic CD3 Monoclonal Antibody," Transplantation, 60 (8): 847-853.
Ruberti et al. (1994) "The use of the RACE method to clone hybridoma cDNA when V region primers fail," Journal of Immunological Methods, 173: 33-39.
Ruther et al. (1983) "Easy identification of cDNA clones", EMBO J., 2(10): 1791-1794.
Rutledge et al. (1998) "Infectious clones and vectors derived from adeno-associated virus (AAV) serotypes other than AAV type 2", J. Vir., 72(1): 309-319.
Sarver et al., "Stable Expression Of Recombinant Factor VIII Molecules Using A Bovine Papillomavirus Vector", DNA, Dec. 1987, vol. 6, No. 6, pp. 553-564.
Sauer et al. (1988) "Site-specific DNA recombination in mammalian cells by the Cre recombinase of bacteriophage P1", Proc. Natl. Acad. Sci., 85(14): 5166-5170.
Schmidt et al., "Structure-Function Relationships In Factor IX and Factor IXa", Trends in Cardiovascular Medicine, 2003, vol. 13, No. 1, pp. 39-45.
Segal et al. (2001) "Custom DNA-binding proteins come of age: polydactyl zinc-finger proteins", Curr. Opin. Biotechnol. 12: 632-637.
Senapathy et al., "Replication of adeno-associated virus DNA. Complementation of naturally occurring rep-mutants by a wild-type genome or an ori-mutant and correction of terminal palindrome deletions", Journ Mol Biol., Oct. 15, 1984, 179(1): 1-20.
Shields et al. (2001) "High Resolution Mapping of the Binding Site on Human IgG1 for FcγRI, FcγRII, FcγRIII, and FcRn and Design of IgG1 Variants with Improved Binding to the FcγR," J. Biol. Chem., 276 (9) 6591-6604.
Srivastava et al. (1983) "Nucleotide sequence and organization of the adeno-associated virus 2 genome", J. Vir., 45(2): 555-564.
Story et al. (1994) "A Major Histocompatibility Complex Class I-like Fc Receptor Cloned from Human Placenta: Possible Role in

(56) References Cited

OTHER PUBLICATIONS

Transfer of Immunoglobulin G from Mother to Fetus," J. Exp. Med., Brief Definitive Report, 180: 2377-2381.
Toole et al., "A Large Region (Approximately Equal To 95 kDa) Of Human Factor VIII Is Dispensable For In Vitro Procoagulant Activity", Proceedings of the National Academy of Sciences, Aug. 1986, vol. 83, No. 16, pp. 5939-5942.
Tratschin et al. (1985) "Adeno-associated virus vector for high-frequency integration, expression, and rescue of genes in mammalian cells", Mol. Cell Biol., 5(11): 3251-3260.
Trüssel et al. (2009) "New Strategy for the Extension of the Serum Half-Life of Antibody Fragments," Bioconjugate Chem., 20:2286-2292.
Vigna et al. (2004) "Efficient Tet-Dependent Expression of Human Factor IX in Vivo by a New Self-Regulating Lentiviral Vector," Molecular Therapy, 11(5):763-775.
Wagner et al., "Microinjection Of A Rabbit Beta-Globin Gene Into Zygotes And Its Subsequent Expression In Adult Mice And Their Offspring", Proceedings of the National Academy of Sciences of the United States of America, Oct. 1, 1981, vol. 78, No. 10, pp. 6376-6380.
Wang et al., "Sequencing and generation of an infectious clone of the pathogenic goose parvovirus strain LH", Jan. 2015, vol. 160, No. 3, p. 711-718.
Wang et al., "Analysis of the genome sequence of the pathogenic Muscovy duck parvovirus strain YY reveals a 14-nucleotide-pair deletion in the inverted terminal repeats", Arch Virol., 2016, 161: 2589-2594.
Ward et al., "The Effector Functions Of Immunoglobulins: Implications For Therapy", Therapeutic immunology, vol. 2, No. 2, pp. 77-94. (Apr. 1995).
White et al. (1997) "A multicenter study of recombinant factor VIII (Recombinate) in previously treated patients with haemophilia," Thrombosis and Heamostasis, 4:660-667.
Wigler et al. (1978) "Biochemical transfer of single-copy eucaryotic genes using total cellular DNA as donor", Cell, 14(3): 725-731.
Wold et al. (2013) "Adenovirus vectors for gene therapy, vaccination and cancer gene therapy", Curr Gene Ther., 13(6): 421-433.
Woychik et al. (1984) "Requirement for the 3'flanking region of the bovine growth hormone gene for accurate polyadenylylation", PNAS, 81: 3944-3948.
Wu et al. (2000) "Mutational analysis of the adeno-associated virus type 2 (AAV2) capsid gene and construction of AAV2 vectors with altered tropism", J. Vir., 74(18): 8635-8647.
Yew et al. (2002). "CpG-Depleted Plasmid DNA Vectors with Enhanced Safety and Long-Term Gene Expression in Vivo", Mol Ther., 5(6): 731-738.
Zhang et al. (2014) "Comparison of non-canonical PAMs for CRISPR/Cas9-mediated DNA cleavage in human cells", Sci Rep., 2014, 4(5405).
Zufferey, et al., "Multiply Attenuated Lentiviral Vector Achieves Efficient Gene Delivery In Vivo", Nature Biotechnology, vol. 15, No. 9, pp. 871-875, Sep. 1, 1997.
Chen et al., "Vector-based siRNA Delivery Strategies for High-throughput Screening of Novel Target Genes", Journal of RNAi and Gene Silencing: An International Journal of RNA and Gene Targeting Research, Jul. 27, 2005, 1(1): 5-11.
Generation Bio, "Generation Bio Announces Two Non-Viral Gene Therapy Milestone Achievements: Target Levels of Factor VIII Expression in Hemophilia A Mice and Translation of Expression from Mice to Non-Human Primates", Jan. 4, 2021, obtained from url: <https://www.globenewswire.com/en/news-release/2021/01/04/2152472/0/en/Generation-Bio-Announces-Two-Non-Viral-Gene-Therapy-Milestone-Achievements-Target-Levels-of-Factor-VIII-Expression-in-Hemophilia-A-Mice-and-Translation-of-Expression-from-Mice-to-N.html>.
Meyer, "Development of an Integrated Expression Platform for Protein Production in Eukaryotic Hosts", Thesis, 2012.
Rohrmann et al., "Chapter 10: Baculovirus expression technology: Theory and application", Baculovirus Molecular Biology [internet], 4th Edition.
Chambers et al., "Overview of the Baculovirus Expression System", Unit 5.4.1, Production of Recombinant Proteins, Current Protocols in Protein Science, Feb. 2018, Suppl. 91: 5.4.1-5.4.6.
Li et al., "A Novel Recombinant AAV Production System with Low Side-Toxicity Pollution", Science Engine, Jan. 15, 2003, 48(1), abstract only.
Rohrmann et al., "Chapter 2: Structural proteins of baculovirus occlusion bodies and virions", Baculovirus Molecular Biology [internet], 4th Edition, 2019.
Zakas, "Evolutionary approaches to coagulation factor VIII biopharmaceutical engineering", Dissertation, Emory University, 2016.
Chambers et al., "Overview of the Baculovirus Expression System", Unit 5.4.1, Production of Recombinant Proteins, Current Protocols in Protein Science, Feb. 2018, Suppl. 91: 5.4.1-5.4.6., pp. 1-6.
Dongmei et al., "Isolation, Identification and Complete Genomic Sequence Analysis of Goose Parvovirus HN Strain", Progress in Veterinary Medicine, Dec. 31, 2016, 37(12): 13-18.
Hu et al., "Enhancement and Prolongation of Baculovirus-Mediated Expression in Mammalian Cells: Focuses on Strategic Infection and Feeding", Biotechnology Progress, 2003, 19: 373-379.
Li et al., "A Novel Recombinant AAV Production System with Low Side-Toxicity Pollution", Science Engine, Jan. 15, 2003, 48(1), pp. 52-54, abstract only in English.
Rohrmann et al., "Chapter 2: Structural proteins of baculovirus occlusion bodies and virions", Baculovirus Molecular Biology [internet], 4th Edition, 2019, pp. 1-36.
Sarafanov et al., "Identification of Coagulation Factor VIII A2 Domain Residues Forming the Binding Epitope for Low-Density Lipoprotein Receptor-Related Protein", Biochemistry, 2006, 45: 1829-1840.
Wickham et al., "Comparison of Different Cell Lines for the Production of Recombinant Baculovirus Proteins", Methods in Molecular Biology, 1995, Chapter 22, vol. 39: 385-395.
Zakas, "Evolutionary approaches to coagulation factor VIII biopharmaceutical engineering", Dissertation, Emory University, 2016, pp. 1-202.
Gray et al., "Design and construction of functional AAV vectors", Methods Mol Biol., Jan. 1, 2011, Chapter 2, 807: 25-46.

* cited by examiner

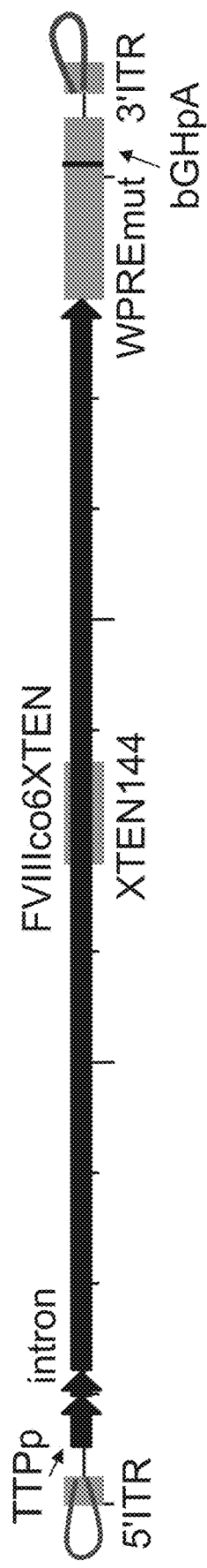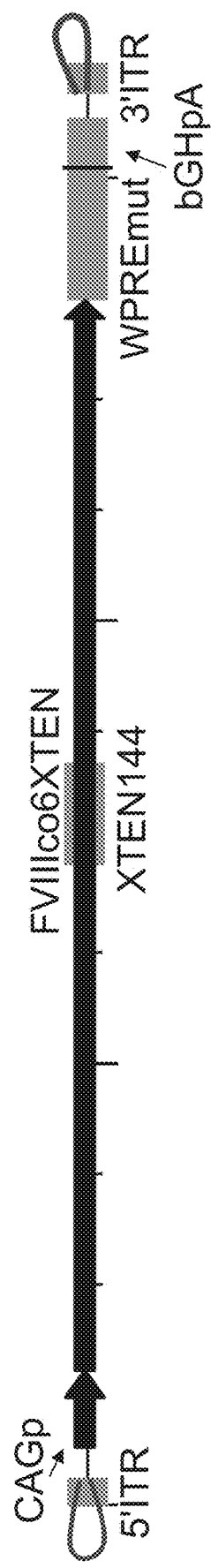

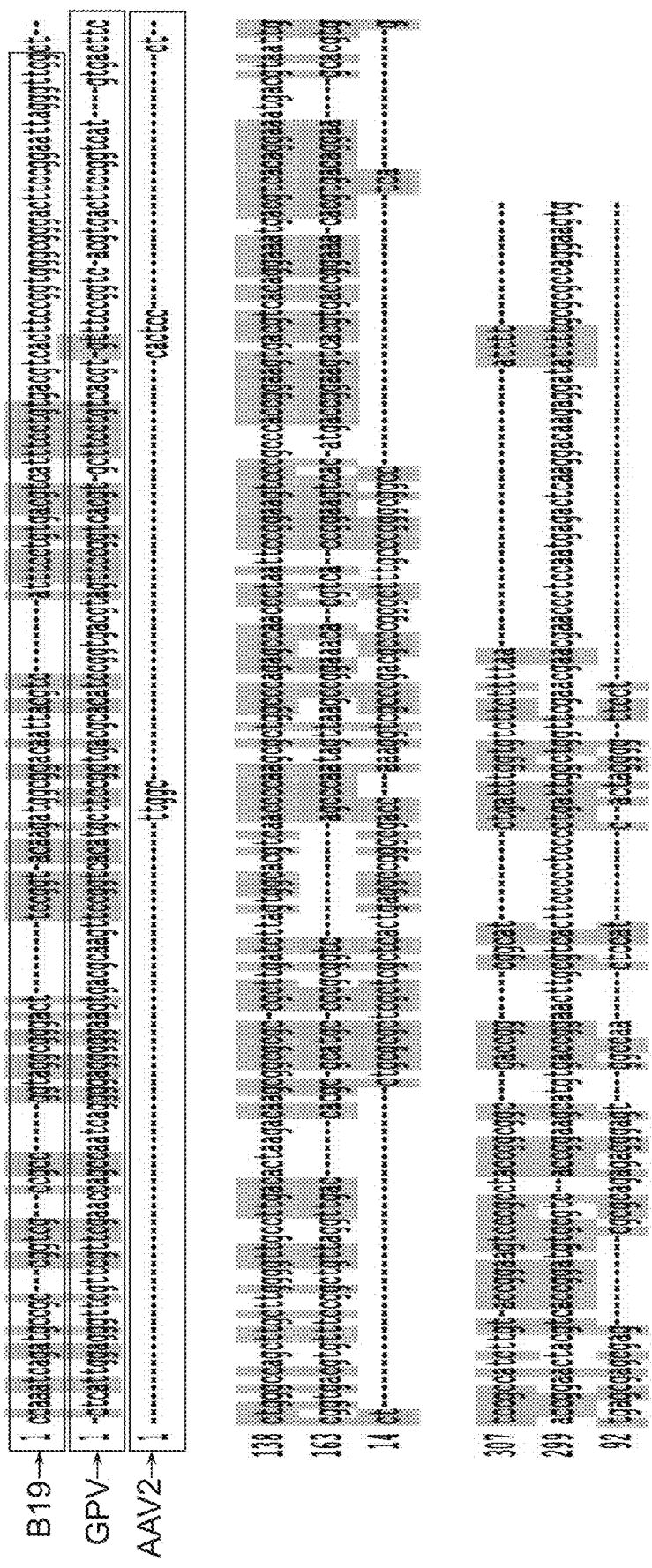

Fig. 3B

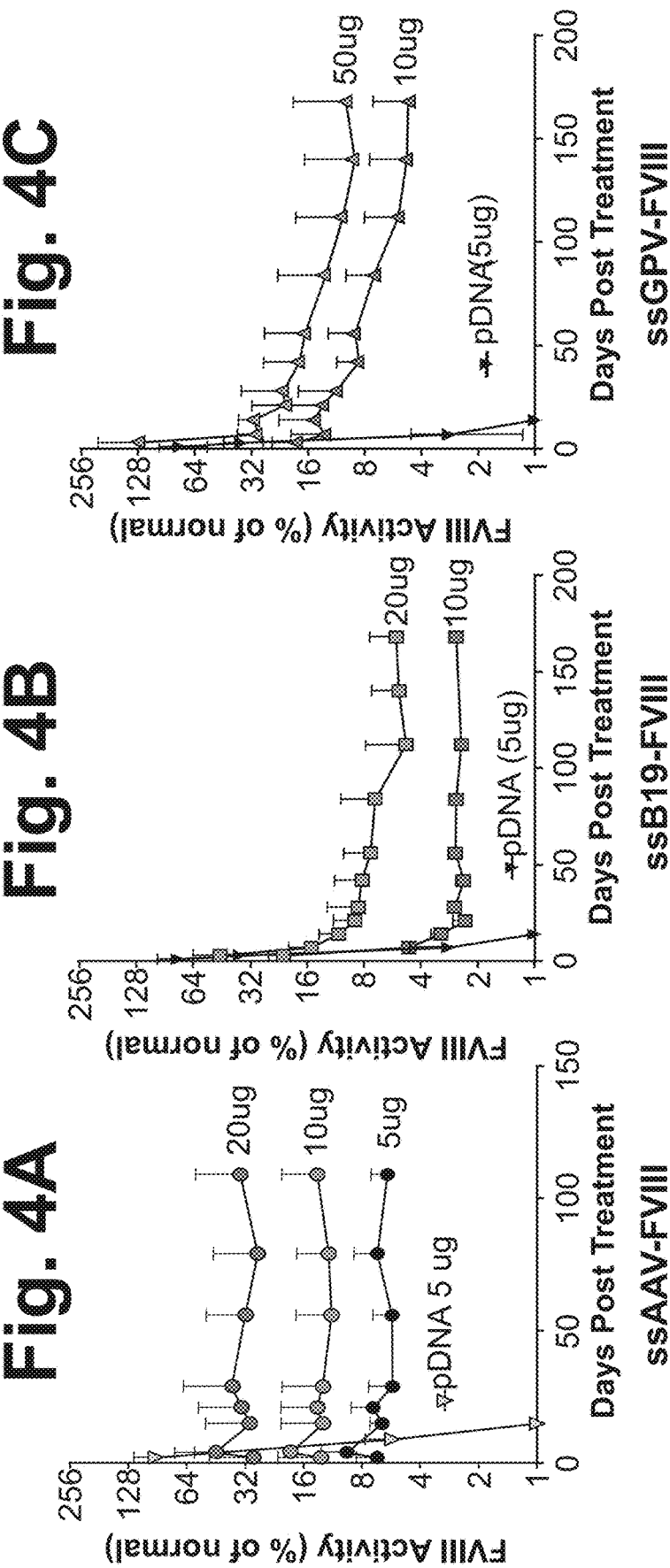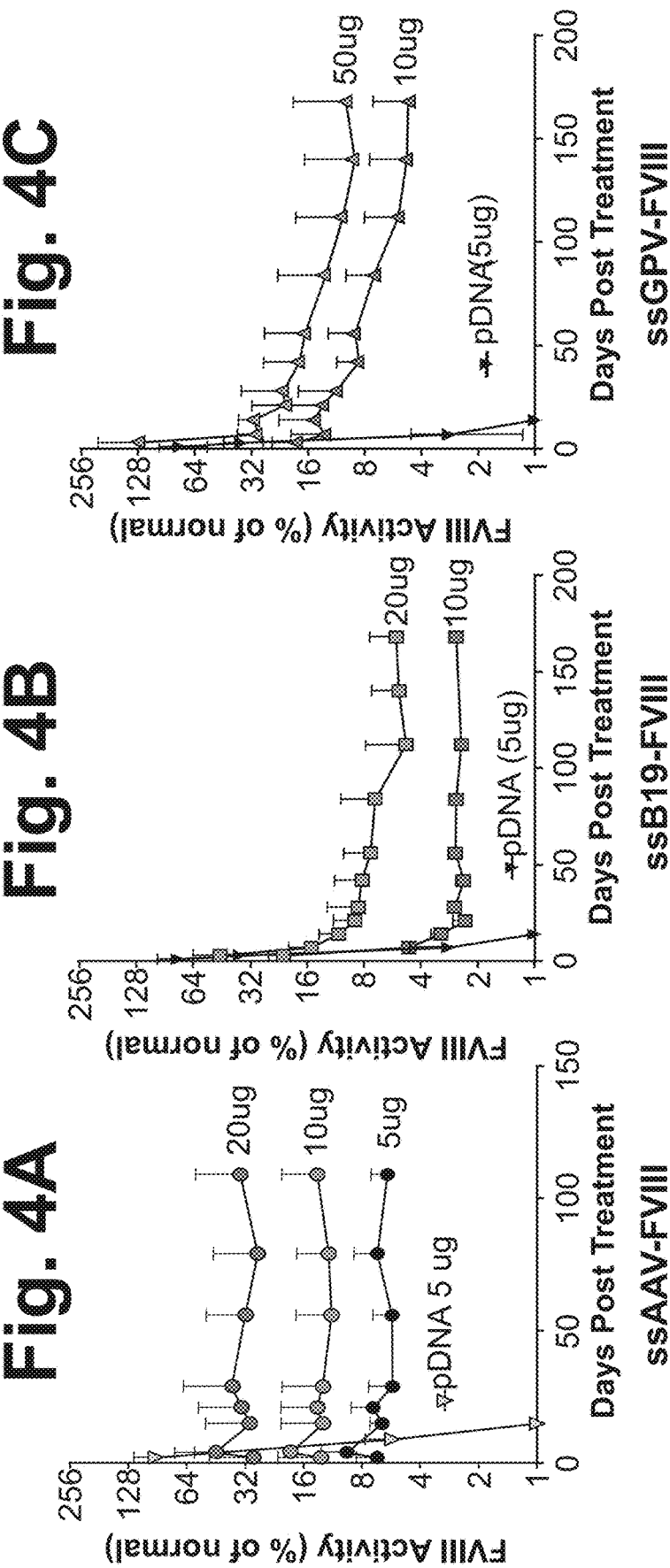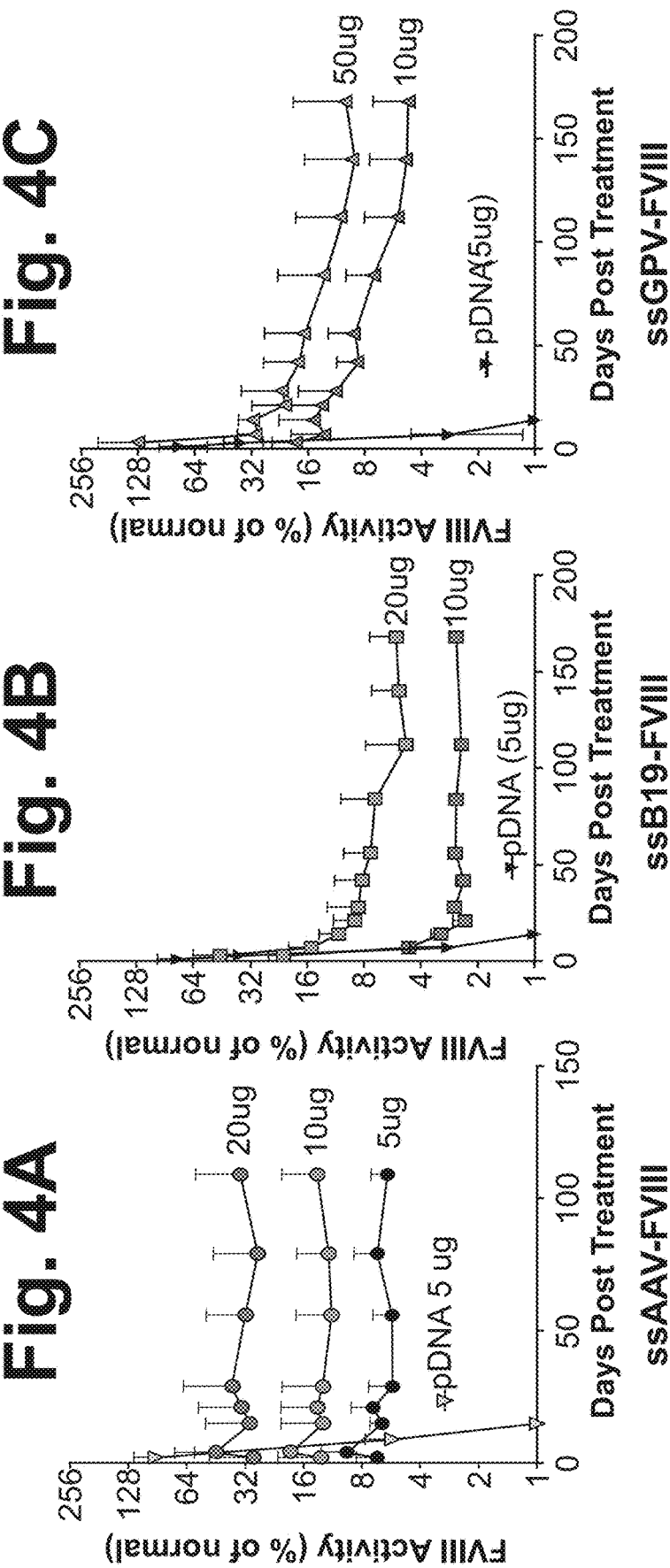

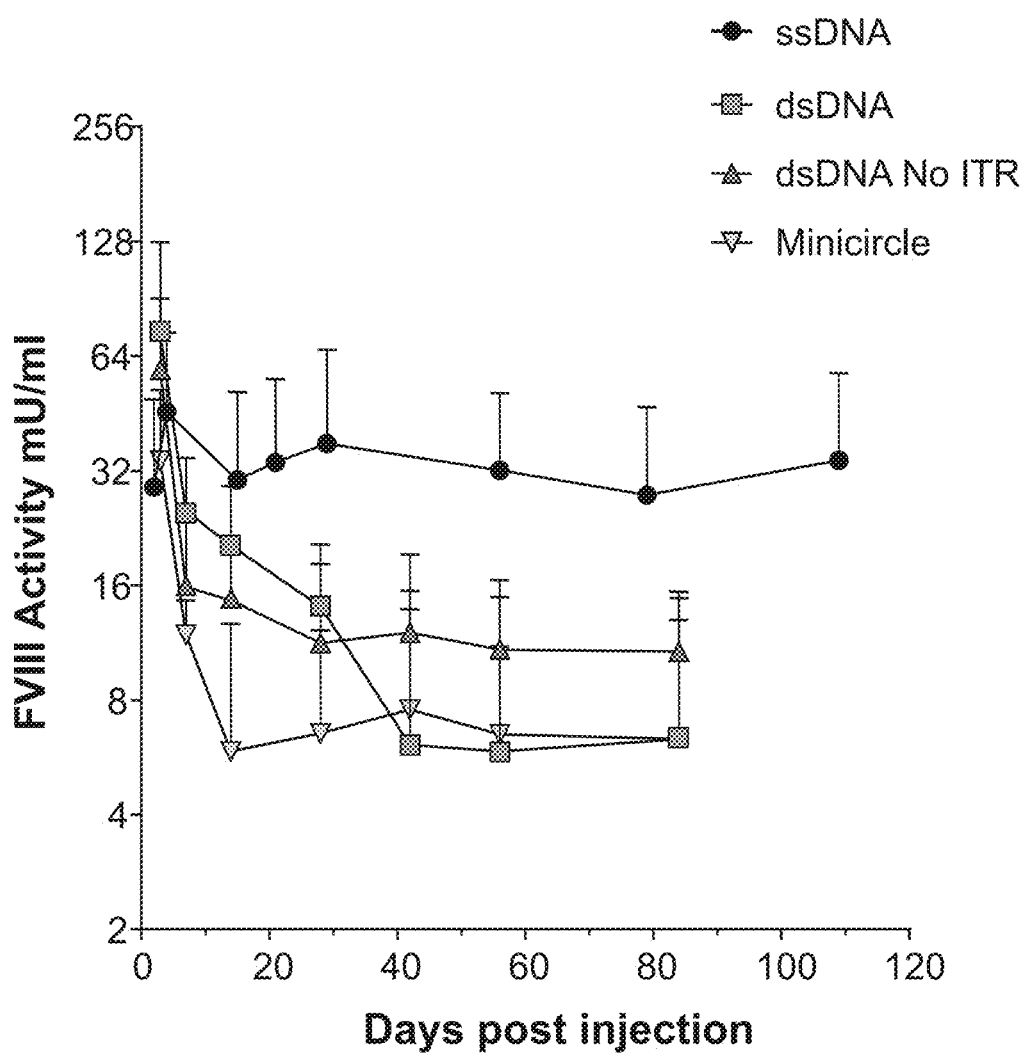

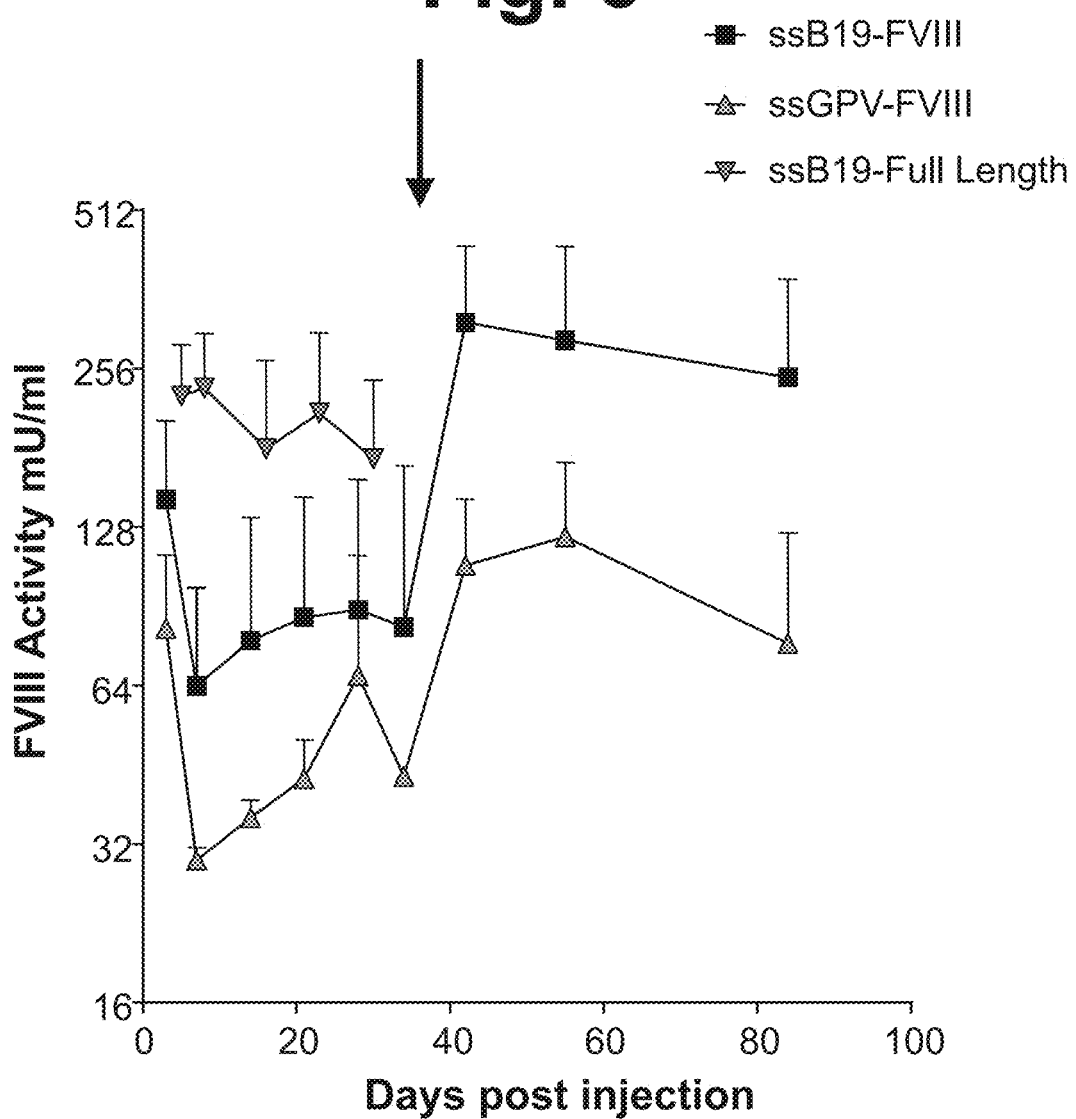

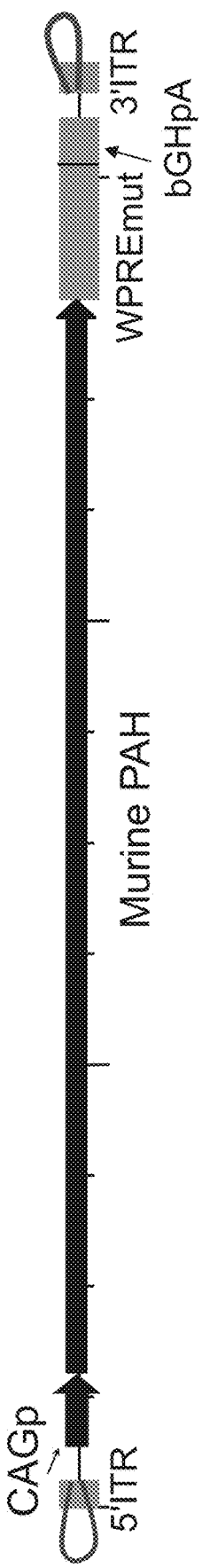
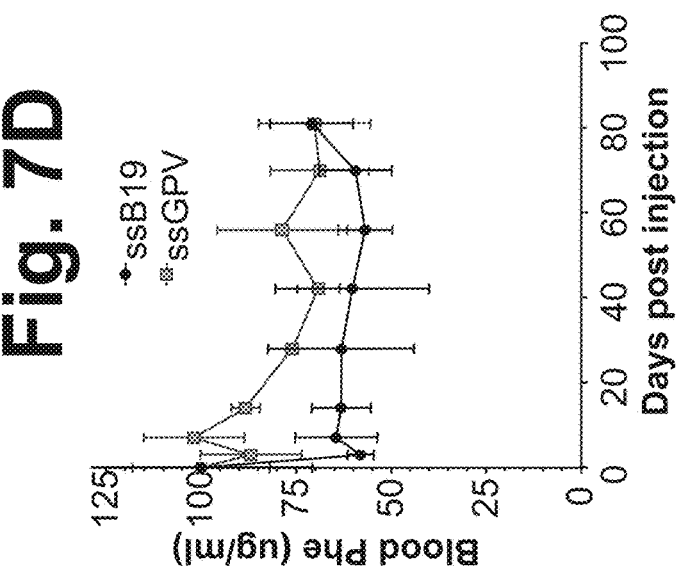
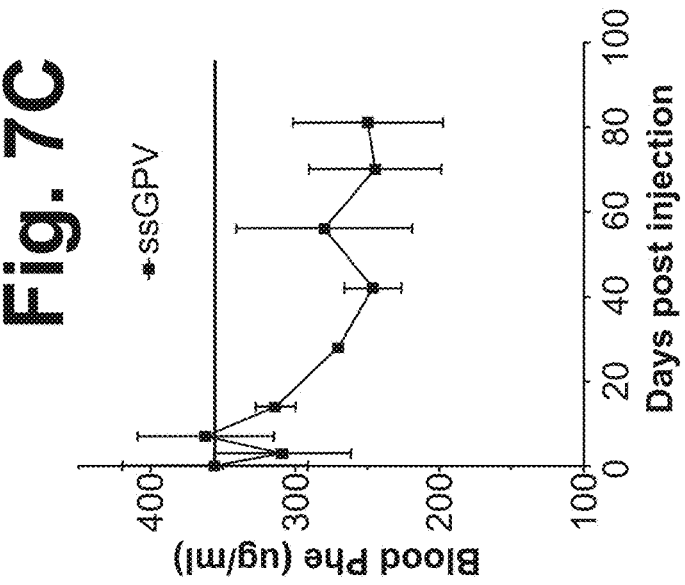
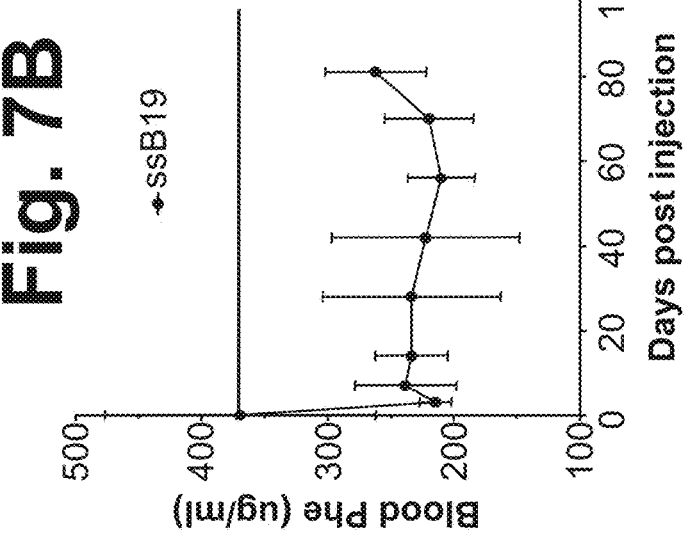

NUCLEIC ACID MOLECULES AND USES THEREOF FOR NON-VIRAL GENE THERAPY

RELATED APPLICATIONS

This application claims priority to U.S. Provisional Patent Application Ser. No. 62/716,826, filed Aug. 9, 2018, the entire disclosure of which is hereby incorporated herein by reference.

REFERENCE TO SEQUENCE LISTING SUBMITTED ELECTRONICALLY

The content of the electronically submitted sequence listing in ASCII text file (Name: 615114_SA9-465 ST25.txt; Size: 480,487 bytes; and Date of Creation: Apr. 20, 2023) is incorporated herein by reference in its entirety.

BACKGROUND OF THE DISCLOSURE

Gene therapy offers the potential for a lasting means of treating a variety of diseases. In the past, many gene therapy treatments typically relied on the use of viruses. There are numerous viral agents that could be selected for this purpose, each with distinct properties that would make them more or less suitable for gene therapy. Zhou et al., Adv Drug Deliv Rev. 106(Pt A):3-26, 2016. However, the undesired properties of some viral vectors, including their immunogenic profiles or their propensity to cause cancer, have resulted in clinical safety concerns and, until recently, limited their clinical use to certain applications, for example, vaccines and oncolytic strategies. Cotter et al., Front Biosci. 10:1098-105 (2005).

Adeno-associated virus (AAV) is one of the most commonly investigated gene therapy vectors. AAV is a protein shell surrounding and protecting a small, single-stranded DNA genome of approximately 4.8 kilobases (kb). Naso et al., BioDrugs, 31(4): 317-334, 2017. AAV belongs to the parvovirus family and is dependent on co-infection with other viruses, mainly adenoviruses, in order to replicate. Id. Its single-stranded genome contains three genes, Rep (Replication), Cap (Capsid), and aap (Assembly). Id. These coding sequences are flanked by inverted terminal repeats (ITRs) that are required for genome replication and packaging. Id. The two cis-acting AAV ITRs are approximately 145 nucleotides in length with interrupted palindromic sequences that can fold into T shaped hairpin structures that function as primers during initiation of DNA replication.

The use of conventional AAV as a gene delivery vector has certain drawbacks, however. One of the major drawbacks is associated with the AAV's limited viral packaging capacity of about 4.5 kb of heterologous DNA. (Dong et al., Hum Gene Ther. 7(17): 2101-12, 1996). In addition, administration of AAV vectors can induce an immune response in humans. Although AAV has been shown to be less immunogenic than some other viruses (i.e. adenovirus), the capsid proteins can trigger various components of the human immune system. See Naso et al., 2017. AAV is a common virus in the human population, and most people have been exposed to AAV, accordingly most people have already developed an immune response against the particular variants to which they had previously been exposed. This pre-existing adaptive response can include neutralizing antibodies (NAbs) and T cells that could diminish the clinical efficacy of subsequent re-infections with AAV and/or the elimination of cells that have been transduced, which may disqualify patients with pre-existing anti-AAV immunity to AVV based gene therapy treatment. Furthermore, evidence suggests that the T-shaped hairpin loops of AAV ITRs are susceptible to inhibition by host cell proteins/protein complexes that bind the T-shaped hairpin structures of AAV ITRs. See, e.g., Zhou et al., Scientific Reports 7:5432 (Jul. 14, 2017).

Thus, there exists a need in the art to efficiently and persistently express target sequences, e.g., therapeutic proteins and/or miRNAs, in in vitro and in vivo settings, while avoiding some of the unintended consequences and limitations of existing AAV vector technology.

SUMMARY OF THE DISCLOSURE

In certain aspects, a nucleic acid molecule comprising a first inverted terminal repeat (ITR) and a second ITR flanking a genetic cassette comprising a heterologous polynucleotide sequence, wherein the first ITR and/or second ITR comprises a nucleotide sequence at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NO: 180, 181, 183, 184, 185, 186, 187 or 188, or a functional derivative thereof, is provided In certain exemplary embodiments, the first ITR comprises the nucleotide sequence set forth in SEQ ID NO: 180 and the second ITR comprises the nucleotide sequence set forth in SEQ ID NO: 181. In certain exemplary embodiments, the first ITR comprises the nucleotide sequence set forth in SEQ ID NO: 183 and the second ITR comprises the nucleotide sequence set forth in SEQ ID NO: 184. In certain exemplary embodiments, the first ITR comprises the nucleotide sequence set forth in SEQ ID NO: 185 and the second ITR comprises the nucleotide sequence set forth in SEQ ID NO: 186. In certain exemplary embodiments, the first ITR comprises the nucleotide sequence set forth in SEQ ID NO: 187 and the second ITR comprises the nucleotide sequence set forth in SEQ ID NO: 188.

In certain exemplary embodiments, the first ITR and/or the second ITR consists of a nucleotide sequence set forth in SEQ ID NO: 180, 181, 183, 184, 185, 186, 187 or 188. In certain exemplary embodiments, the first ITR and the second ITR are reverse complements of each other.

In certain exemplary embodiments, the nucleic acid molecule further comprises a promoter. In certain exemplary embodiments, the promoter is a tissue-specific promoter. In certain exemplary embodiments, the promoter drives expression of the heterologous polynucleotide sequence in an organ selected from the muscle, central nervous system (CNS), ocular, liver, heart, kidney, pancreas, lungs, skin, bladder, urinary tract, or any combination thereof. In certain exemplary embodiments, the promoter drives expression of the heterologous polynucleotide sequence in hepatocytes, endothelial cells, cardiac muscle cells, skeletal muscle cells, sinusoidal cells, afferent neurons, efferent neurons, interneurons, glial cells, astrocytes, oligodendrocytes, microglia, ependymal cells, lung epithelial cells, Schwann cells, satellite cells, photoreceptor cells, retinal ganglion cells, or any combination thereof. In certain exemplary embodiments, the promoter is positioned 5' to the heterologous polynucleotide sequence. In certain exemplary embodiments, the promoter is selected from the group consisting of a mouse thyretin promoter (mTTR), an endogenous human factor VIII promoter (F8), a human alpha-1-antitrypsin promoter (hAAT), a human albumin minimal promoter, a mouse albumin promoter, a tristetraprolin (TTP) promoter, a CASI promoter, a CAG promoter, a cytomegalovirus (CMV) promoter, α1-antitrypsin (AAT), muscle creatine kinase (MCK), myosin heavy chain alpha (αMHC), myoglobin (MB), desmin (DES), SPc5-12, 2R5Sc5-12, dMCK, tMCK, and a phosphoglycerate kinase (PGK) promoter.

In certain exemplary embodiments, the heterologous polynucleotide sequence further comprises an intronic sequence. In certain exemplary embodiments, the intronic sequence is positioned 5' to the heterologous polynucleotide sequence. In certain exemplary embodiments, the intronic sequence is positioned 3' to the promoter. In certain exemplary embodiments, the intronic sequence comprises a synthetic intronic sequence. In certain exemplary embodiments, the intronic sequence comprises SEQ ID NO: 115 or 192.

In certain exemplary embodiments, the genetic cassette further comprises a post-transcriptional regulatory element. In certain exemplary embodiments, the post-transcriptional regulatory element is positioned 3' to the heterologous polynucleotide sequence. In certain exemplary embodiments, the post-transcriptional regulatory element comprises a mutated woodchuck hepatitis virus post-transcriptional regulatory element (WPRE), a microRNA binding site, a DNA nuclear targeting sequence, or any combination thereof. In certain exemplary embodiments, the microRNA binding site comprises a binding site to miR142-3p.

In certain exemplary embodiments, the genetic cassette further comprises a 3'UTR poly(A) tail sequence. In certain exemplary embodiments, the 3'UTR poly(A) tail sequence is selected from the group consisting of bGH poly(A), actin poly(A), hemoglobin poly(A), and any combination thereof. In certain exemplary embodiments, the 3'UTR poly(A) tail sequence comprises bGH poly(A).

In certain exemplary embodiments, the genetic cassette further comprises an enhancer sequence. In certain exemplary embodiments, the enhancer sequence is positioned between the first ITR and the second ITR.

In certain exemplary embodiments, the nucleic acid molecule comprises from 5' to 3': the first ITR, the genetic cassette, and the second ITR; wherein the genetic cassette comprises a tissue-specific promoter sequence, an intronic sequence, the heterologous polynucleotide sequence, a post-transcriptional regulatory element, and a 3'UTR poly(A) tail sequence. In certain exemplary embodiments, the genetic cassette comprises from 5' to 3': a tissue-specific promoter sequence, an intronic sequence, the heterologous polynucleotide sequence, a post-transcriptional regulatory element, and a 3'UTR poly(A) tail sequence. In certain exemplary embodiments, the tissue specific promoter sequence comprises a TTT promoter; the intron is a synthetic intron; the post-transcriptional regulatory element comprises WPRE; and the 3'UTR poly(A) tail sequence comprises bGHpA.

In certain exemplary embodiments, the genetic cassette comprises a single stranded nucleic acid. In certain exemplary embodiments, the genetic cassette comprises a double stranded nucleic acid.

In certain exemplary embodiments, the heterologous polynucleotide sequence encodes a clotting factor, a growth factor, a hormone, a cytokine, an antibody, a fragment thereof, or any combination thereof.

In certain exemplary embodiments, the heterologous polynucleotide sequence encodes a growth factor selected from the group consisting of adrenomedullin (AM), angiopoietin (Ang), autocrine motility factor, a bone morphogenetic protein (BMP) (e.g. BMP2, BMP4, BMP5, BMP7), a ciliary neurotrophic factor family member (e.g., ciliary neurotrophic factor (CNTF), leukemia inhibitory factor (LIF), interleukin-6 (IL-6)), a colony-stimulating factor (e.g., macrophage colony-stimulating factor (m-CSF), granulocyte colony-stimulating factor (G-CSF), granulocyte macrophage colony-stimulating factor (GM-CSF)), an epidermal growth factor (EGF), an ephrin (e.g., ephrin A1, ephrin A2, ephrin A3, ephrin A4, ephrin A5, ephrin B1, ephrin B2, ephrin B3), erythropoietin (EPO), a fibroblast growth factor (FGF) (e.g., FGF1, FGF2, FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22, FGF23), foetal bovine somatotrophin (FBS), a GDNF family member (e.g., glial cell line-derived neurotrophic factor (GDNF), neurturin, persephin, artemin), growth differentiation factor-9 (GDF9), hepatocyte growth factor (HGF), hepatoma-derived growth factor (HDGF), insulin, an insulin-like growth factors (e.g., insulin-like growth factor-1 (IGF-1) or IGF-2, an interleukin (IL) (e.g., IL-1, IL-2, IL-3, IL-4, IL-5, IL-6, IL-7), keratinocyte growth factor (KGF), migration-stimulating factor (MSF), macrophage-stimulating protein (MSP or hepatocyte growth factor-like protein (HGFLP)), myostatin (GDF-8), a neuregulin (e.g., neuregulin 1 (NRG1), NRG2, NRG3, NRG4), a neurotrophin (e.g., brain-derived neurotrophic factor (BDNF), nerve growth factor (NGF), a neurotrophin-3 (NT-3), NT-4, placental growth factor (PGF), platelet-derived growth factor (PDGF), renalase (RNLS), T-cell growth factor (TCGF), thrombopoietin (TPO), a transforming growth factor (e.g., transforming growth factor alpha (TGF-α), TGF-β, tumor necrosis factor-alpha (TNF-α), and vascular endothelial growth factor (VEGF), and any combination thereof.

In certain exemplary embodiments, the heterologous polynucleotide sequence encodes a hormone.

In certain exemplary embodiments, the heterologous polynucleotide sequence encodes a cytokine.

In certain exemplary embodiments, the heterologous polynucleotide sequence encodes an antibody or a fragment thereof.

In certain exemplary embodiments, the heterologous polynucleotide sequence encodes a gene selected from dystrophin X-linked, MTM1 (myotubularin), tyrosine hydroxylase, AADC, cyclohydrolase, SMN1, FXN (frataxin), GUCY2D, RS1, CFH, HTRA, ARMS, CFB/CC2, CNGA/CNGB, Prf65, ARSA, PSAP, IDUA (MPS I), IDS (MPS II), PAH, GAA (acid alpha-glucosidase), and any combination thereof.

In certain exemplary embodiments, the heterologous polynucleotide sequence encodes a microRNA (miRNA). In certain exemplary embodiments, the miRNA down regulates the expression of a target gene selected from SOD1, HTT, RHO, and any combination thereof.

In certain exemplary embodiments, the heterologous polynucleotide sequence encodes a clotting factor selected from the group consisting of factor I (FI), factor II (FII), factor III (FIII), factor IV (FVI), factor V (FV), factor VI (FVI), factor VII (FVII), factor VIII (FVIII), factor IX (FIX), factor X (FX), factor XI (FXI), factor XII (FXII), factor XIII (FVIII), Von Willebrand factor (VWF), prekallikrein, high-molecular weight kininogen, fibronectin, antithrombin III, heparin cofactor II, protein C, protein S, protein Z, Protein Z-related protease inhibitor (ZPI), plasminogen, alpha 2-antiplasmin, tissue plasminogen activator (tPA), urokinase, plasminogen activator inhibitor-1 (PAI-1), plasminogen activator inhibitor-2 (PAI2), and any combination thereof.

In certain exemplary embodiments, the clotting factor is FVIII. In certain exemplary embodiments, the FVIII comprises full-length mature FVIII. In certain exemplary embodiments, the FVIII comprises an amino acid sequence at least about 70%, at least about 75%, at least about 80%, at least about 85%, at least about 90%, at least about 95%, at least about 96%, at least about 97%, at least about 98%, at least about 99%, or 100% identical to an amino acid sequence having SEQ ID NO: 106.

In certain exemplary embodiments, the FVIII comprises A1 domain, A2 domain, A3 domain, C1 domain, C2 domain, and a partial or no B domain. In certain exemplary embodiments, the FVIII comprises an amino acid sequence at least about 70%, at least about 75%, at least about 80%, at least about 85%, at least about 90%, at least about 95%, at least about 96%, at least about 97%, at least about 98%, at least about 99%, or 100% identical to the amino acid sequence of SEQ ID NO:109.

In certain exemplary embodiments, the clotting factor comprises a heterologous moiety. In certain exemplary embodiments, the heterologous moiety is selected from the group consisting of albumin or a fragment thereof, an immunoglobulin Fc region, the C-terminal peptide (CTP) of the β subunit of human chorionic gonadotropin, a PAS sequence, a HAP sequence, a transferrin or a fragment thereof, an albumin-binding moiety, a derivative thereof, or any combination thereof. In certain exemplary embodiments, the heterologous moiety is linked to the N-terminus or the C-terminus of the FVIII or inserted between two amino acids in the FVIII. In certain exemplary embodiments, the heterologous moiety is inserted between two amino acids at one or more insertion site selected from the insertion sites listed in Table 4.

In certain exemplary embodiments, the FVIII further comprises A1 domain, A2 domain, C1 domain, C2 domain, an optional B domain, and a heterologous moiety, wherein the heterologous moiety is inserted immediately downstream of amino acid 745 corresponding to mature FVIII (SEQ ID NO:106).

In certain exemplary embodiments, the FVIII further comprises an FcRn binding partner. In certain exemplary embodiments, the FcRn binding partner comprises an Fc region of an immunoglobulin constant domain.

In certain exemplary embodiments, the nucleic acid sequence encoding the FVIII is codon optimized. In certain exemplary embodiments, the nucleic acid sequence encoding the FVIII is codon optimized for expression in a human.

In certain exemplary embodiments, the nucleic acid sequence encoding the FVIII comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to a nucleotide sequence of SEQ ID NO: 107.

In certain exemplary embodiments, the nucleic acid sequence encoding the FVIII comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of SEQ ID NO: 71.

In certain exemplary embodiments, the heterologous polynucleotide sequence is codon optimized. In certain exemplary embodiments, the heterologous polynucleotide sequence is codon optimized for expression in a human.

In certain exemplary embodiments, the nucleic acid molecule is formulated with a delivery agent. In certain exemplary embodiments, the delivery agent comprises a lipid nanoparticle. In certain exemplary embodiments, the delivery agent is selected from the group consisting of liposomes, non-lipid polymeric molecules, and endosomes, and any combination thereof.

In certain exemplary embodiments, the nucleic acid molecule is formulated for intravenous, transdermal, intradermal, subcutaneous, pulmonary, or oral delivery, or any combination thereof. In certain exemplary embodiments, the nucleic acid molecule is formulated for intravenous delivery.

In certain aspects, a vector comprising a nucleic acid molecule as described herein, is provided.

In certain aspects, a host cell comprising a nucleic acid molecule as described herein, is provided.

In certain aspects, a pharmaceutical composition comprising a nucleic acid molecule or a vector as described herein, and a pharmaceutically acceptable excipient, is provided.

In certain aspects, a pharmaceutical composition comprising a host cell as described herein, and a pharmaceutically acceptable excipient, is provided.

In certain aspects, a kit, comprising a nucleic acid molecule as described herein, and instructions for administering the nucleic acid molecule to a subject in need thereof, is provided.

In certain aspects, a baculovirus system for production of a nucleic acid molecule as described herein, is provided.

In certain exemplary embodiments, a nucleic acid molecule as described herein, is produced in insect cells.

In certain aspects, a nanoparticle delivery system comprising a nucleic acid molecule as described herein, is provided.

In certain aspects, a method of producing a polypeptide, comprising culturing a host cell as described herein under suitable conditions and recovering the polypeptide, is provided.

In certain aspects, a method of producing a polypeptide with clotting activity, comprising: culturing a host cell as described herein under suitable conditions and recovering the polypeptide with clotting activity, is provided.

In certain aspects, a method of expressing a heterologous polynucleotide sequence in a subject in need thereof, comprising administering to the subject a nucleic acid molecule as described herein, a vector as described herein, or a pharmaceutical composition as described herein, is provided.

In certain aspects, a method of expressing a clotting factor in a subject in need thereof, comprising administering to the subject a nucleic acid molecule as described herein, a vector as described herein, a polypeptide as described herein, or a pharmaceutical composition as described herein, is provided.

In certain aspects, a method of treating a disease or disorder in a subject in need thereof, comprising administering to the subject a nucleic acid molecule as described herein, a vector as described herein, or a pharmaceutical composition as described herein, is provided.

In certain aspects, a method of treating a subject having a clotting factor deficiency, comprising administering to the subject a nucleic acid molecule as described herein, a vector as described herein, a polypeptide as described herein, or a pharmaceutical composition as described herein, is provided.

In certain aspects, a method of treating a clotting factor deficiency in a subject in need thereof, comprising administering to the subject a nucleic acid molecule as described herein, a vector as described herein, a polypeptide as described herein, or a pharmaceutical composition as described herein, is provided.

In certain exemplary embodiments, the nucleic acid molecule is administered intravenously, transdermally, intradermally, subcutaneously, orally, pulmonarily, or any combination thereof. In certain exemplary embodiments, the nucleic acid molecule is administered intravenously.

In certain exemplary embodiments, the method further comprising administering to the subject a second agent.

In certain exemplary embodiments, the subject is a mammal. In certain exemplary embodiments, the subject is a human.

In certain exemplary embodiments, the administration of the nucleic acid molecule to the subject results in an increased FVIII activity, relative to a FVIII activity in the subject prior to the administration, wherein the FVIII activity is increased by at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 20-fold, at least about 25-fold, at least about 30-fold, at least about 35-fold, at least about 40-fold, at least about 50-fold, at least about 60-fold, at least about 70-fold, at least about 80-fold, at least about 90-fold, or at least about 100-fold.

In certain exemplary embodiments, the subject has a bleeding disorder. In certain exemplary embodiments, the bleeding disorder is a hemophilia. In certain exemplary embodiments, the bleeding disorder is hemophilia A.

In certain aspects, a method of treating a bleeding disorder in a subject in need thereof, comprising administering to the subject a nucleic acid molecule comprising a first inverted terminal repeat (ITR) and a second ITR flanking a genetic cassette comprising a heterologous polynucleotide sequence encoding a clotting factor, wherein the first ITR and/or second ITR comprises a nucleotide sequence at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NO: 180, 181, 183, 184, 185, 186, 187 or 188, or a functional derivative thereof, is provided.

In certain aspects, a method of treating hemophilia A in a subject in need thereof, comprising administering to the subject a nucleic acid molecule comprising a first inverted terminal repeat (ITR) and a second ITR flanking a genetic cassette comprising a heterologous polynucleotide sequence encoding factor VIII (FVIII), wherein the first ITR and/or second ITR comprises a nucleotide sequence at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NO: 180, 181, 183, 184, 185, 186, 187 or 188, or a functional derivative thereof, is provided In certain aspects, a method of treating a metabolic disorder of the liver in a subject in need thereof, comprising administering to the subject a nucleic acid molecule comprising a first inverted terminal repeat (ITR) and a second ITR flanking a genetic cassette comprising a heterologous polynucleotide sequence encoding a liver-associated metabolic enzyme that is deficient in the subject, wherein the first ITR and/or second ITR are an ITR of a non-adeno-associated virus (non-AAV), is provided.

In certain exemplary embodiments, the the first ITR and/or second ITR comprises a nucleotide sequence at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NO: 180, 181, 183, 184, 185, 186, 187 or 188, or a functional derivative thereof.

In certain aspects, a method of treating a metabolic disorder of the liver in a subject in need thereof, comprising administering to the subject a nucleic acid molecule comprising a first inverted terminal repeat (ITR) and a second ITR flanking a genetic cassette comprising a heterologous polynucleotide sequence encoding a liver-associated metabolic enzyme that is deficient in the subject, wherein the first ITR and/or second ITR comprises a nucleotide sequence at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NO: 180, 181, 183, 184, 185, 186, 187 or 188, or a functional derivative thereof, is provided.

In certain exemplary embodiments, the genetic cassette comprises a single stranded nucleic acid. In certain exemplary embodiments, the genetic cassette comprises a double stranded nucleic acid.

In certain exemplary embodiments, the metabolic disorder of the liver is selected from the group consisting of phenylketonuria (PKU), a urea cycle disease, a lysosomal storage disorder, and a glycogen storage disease. In certain exemplary embodiments, the metabolic disorder of the liver is phenylketonuria (PKU).

In certain exemplary embodiments, the nucleic acid molecule is administered intravenously, transdermally, intradermally, subcutaneously, orally, pulmonarily, or any combination thereof. In certain exemplary embodiments, the nucleic acid molecule is administered intravenously.

In certain exemplary embodiments, the method further comprising administering to the subject a second agent.

In certain exemplary embodiments, the subject is a mammal. In certain exemplary embodiments, the subject is a human.

In certain aspects, a method of treating phenylketonuria (PKU) in a subject in need thereof, comprising administering to the subject a nucleic acid molecule comprising a first inverted terminal repeat (ITR) and a second ITR flanking a genetic cassette comprising a heterologous polynucleotide sequence encoding phenylalanine hydroxylase, wherein the first ITR and/or second ITR comprises a nucleotide sequence at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NO: 180, 181, 183, 184, 185, 186, 187 or 188, or a functional derivative thereof, is provided.

In certain exemplary embodiments, the genetic cassette comprises a single stranded nucleic acid. In certain exemplary embodiments, the genetic cassette comprises a double stranded nucleic acid.

In certain exemplary embodiments, the nucleic acid molecule is formulated with a delivery agent. In certain exemplary embodiments, the delivery agent comprises a lipid nanoparticle.

In certain aspects, a method of cloning a nucleic acid molecule, comprising inserting a nucleic acid molecule capable of complex secondary structures into a suitable vector, and introducing the resulting vector into a bacterial host strain comprising a disruption in the SbcCD complex, is provided In certain exemplary embodiments, the the disruption in the SbcCD complex comprises a genetic disruption in the SbcC gene and/or SbcD gene. In certain exemplary embodiments, the disruption in the SbcCD complex comprises a genetic disruption in the SbcC gene. In certain exemplary embodiments, the disruption in the SbcCD complex comprises a genetic disruption in the SbcD gene.

In certain exemplary embodiments, the nucleic acid molecule comprises a first inverted terminal repeat (ITR) and a second ITR, wherein the first and/or second ITR is a non-adeno-associated virus (non-AAV) ITR.

In certain exemplary embodiments, the first ITR and/or second ITR comprises a nucleotide sequence at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NO: 180, 181, 183, 184, 185, 186, 187 or 188, or a functional derivative thereof.

In certain exemplary embodiments, the nucleic acid molecule further comprises a genetic cassette, wherein the genetic cassette is flanked by the first ITR and second ITR.

In certain exemplary embodiments, the genetic cassette comprises a heterologous polynucleotide sequence.

In certain exemplary embodiments, the uitable vector is a low copy vector. In certain exemplary embodiments, the suitable vector is pBR322.

In certain exemplary embodiments, the bacterial host strain is incapable of resolving cruciform DNA structures.

In certain exemplary embodiments, the bacterial host strain is PMC103, comprising the genotype sbcC, recD, mcrA, ΔmcrBCF. In certain exemplary embodiments, the bacterial host strain is PMC107, comprising the genotype recBC, recJ, sbcBC, mcrA, ΔmcrBCF. In certain exemplary embodiments, the bacterial host strain is SURE, comprising the genotype recB, recJ, sbcC, mcrA, ΔmcrBCF, umuC, uvrC.

In certain aspects, a method of cloning a nucleic acid molecule, comprising inserting a nucleic acid molecule capable of complex secondary structures into a suitable vector, and introducing the resulting vector into a bacterial host strain comprising a disruption in the SbcCD complex, wherein the nucleic acid molecule comprises a first inverted terminal repeat (ITR) and a second ITR, wherein the first ITR and/or second ITR comprises a nucleotide sequence at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NO: 180, 181, 183, 184, 185, 186, 187 or 188, or a functional derivative thereof, is provided

BRIEF DESCRIPTION OF THE DRAWINGS

FIG. 1A-1B are schematic representations of a single strand clotting factor (e.g., FVIII) expression cassette. The locations of 5' ITR from a non-AAV (with hairpin loop at the end of the ssDNA structure), 3' ITR from a non-AAV (with hairpin loop), a promotor sequence (e.g., TTPp or CAGp), and a transgene sequence, e.g., FVIIIco6XTEN sequence with an XTEN144 inserted within the B domain are shown. The exemplary expression cassettes also show additional possible elements, e.g., an intron sequence, WPREmut sequence, and bGHpA sequence.

Figure 3B:
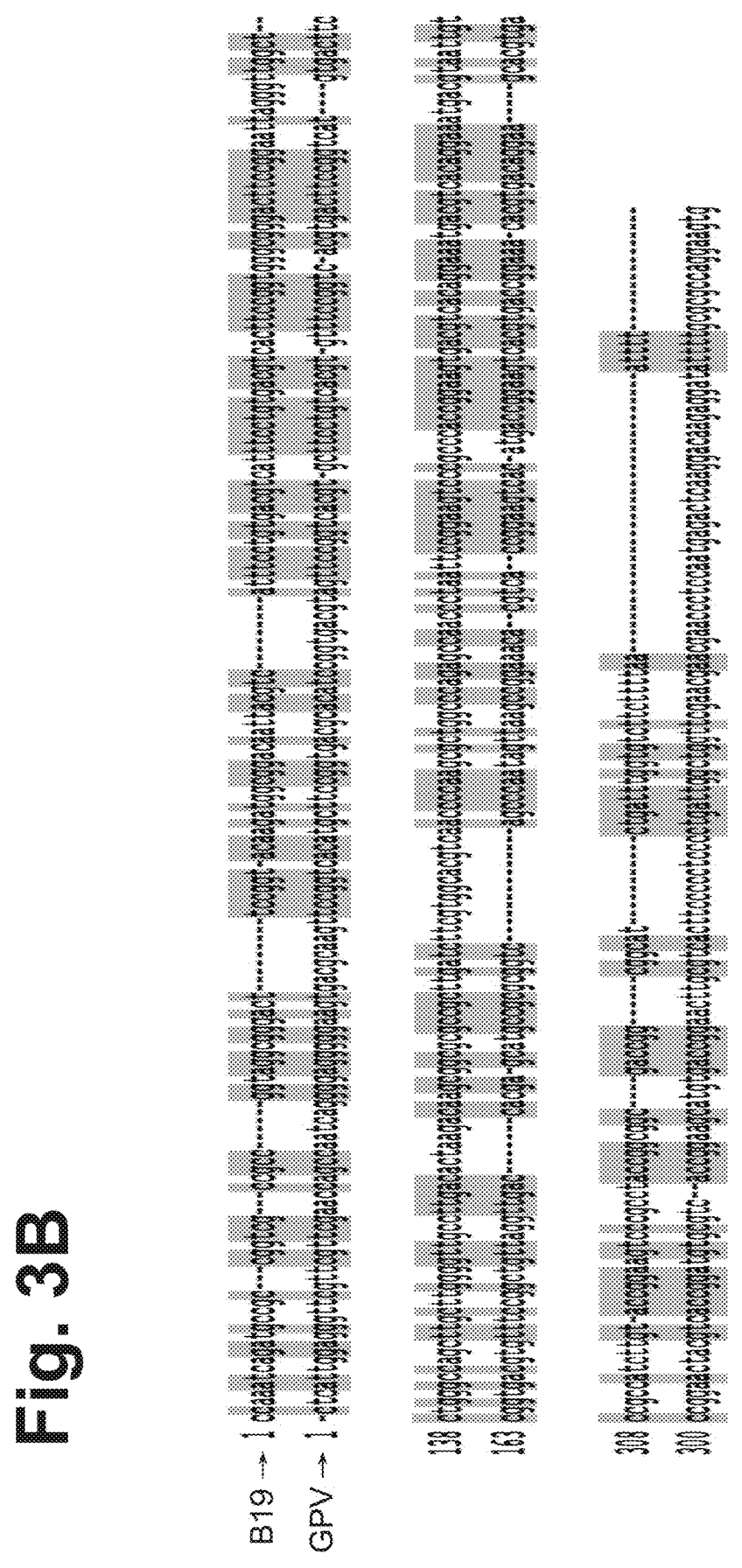

FIGS. 3A and 3B are alignments of the ITRs of B19 (SEQ ID NO: 167), GPV (SEQ ID NO: 172), and AAV2 (SEQ ID NO: 145) (FIG. 3A) and B19 and GPV (FIG. 3B). Gray shading shows homology.

FIGS. 4A-4C show FVIII plasma activity following single-stranded FVIII-AAV naked DNA (ssAAV-FVIII; FIG. 1C), ssDNA-B19 FVIII (FIG. 1D), or ssDNA-GPV FVIII (FIG. 1E) administration via hydrodynamic injection (HDI) in Hem A mice. FVIII Activity was measured (as a percentage of normal physiological levels in humans) in plasma samples at 24 hours, 3 days, 2 weeks, 3 weeks, 1 month, 2 months, 3 months, 4 months, 5 months, and 6 months in mice treated with a single HDI of ssDNA at 50 μg/mouse (FIG. 4C), 20 μg/mouse (FIGS. 4A and 4B), 10 μg/mouse (FIGS. 4A, 4B, and 4C), or 5 μg/mouse (FIG. 4A). An HDI of 5 μg/mouse of plasmid DNA was given as a control (FIGS. 4A, 4B, and 4C).

FIG. 5 shows FVIII activity in hemophilia A mouse plasma following a single hydrodynamic injection of equal molar amounts of single-stranded naked DNA (ssAAV-FVIII, FIG. 1A), double-stranded AAV-FVIII DNA containing the ITR sequence (dsDNA), double-stranded FVIII DNA without the ITR sequence (dsDNA No ITR), or circularized double-stranded FVIII DNA without ITR or bacterial sequences (minicircle). dsDNA was generated by enzyme cleavage of the AAV-FVIII plasmid (FIG. 2C) with PvuII but not heat denatured. dsDNA No ITR was generated by enzyme cleavage of the AAV-FVIII plasmid (FIG. 2C) with AflII and subsequently purified. Minicircle DNA was generated by ligation of the dsDNA No ITR DNA at AflI sites. Mouse plasma was collected over 3 months or 4 months and FVIII was determined by chromogenic activity assay.

FIG. 6 shows FVIII activity in hemophilia A mouse plasma following a hydrodynamic injection of 30 μg of single-stranded naked FVIII-DNA (FIG. 1A, FIGS. 1D-1F). Plasma was collected weekly for 7 weeks and FVIII activity was determined by chromogenic assay. After 35 days (depicted as black arrow), mice receiving FVIII-B19d135 and FVIII-GPVd162 ssDNA were re-administered 30 μg via hydrodynamic injection.

FIG. 7A is a schematic representations of a single strand murine phenylalanine hydroxylase (e.g., PAH) expression cassette. The locations of 5' ITR from a non-AAV (with hairpin loop at the end of the ssDNA structure), 3' ITR from a non-AAV (with hairpin loop), a promotor sequence (e.g., CAGp), and a transgene sequence, e.g., 3xFLAG_mPAH sequence are shown. The exemplary expression cassettes also show additional possible elements, e.g., WPREmut sequence, and bGHpA sequence.

FIGS. 7B-7D show plasma concentrations of phenylalanine (Phe) in phenylketonuria (PKU) mice before (day 0) and after single administration of single-stranded DNA containing the murine PAH cDNA and non-AAV ITRs B19d135 or GPVd162 via hydrodynamic injection. Plasma was collected at days 3, 7, 14, 28, 42, and 56 following ssDNA administration. Residual phenylalanine levels are shown as concentration in μg/ml (FIGS. 7B-7C) or as percent prior to administration (FIG. 7D). The horizontal line depicts baseline Phe levels prior to administration.

DETAILED DESCRIPTION OF THE DISCLOSURE

Figure 1C:
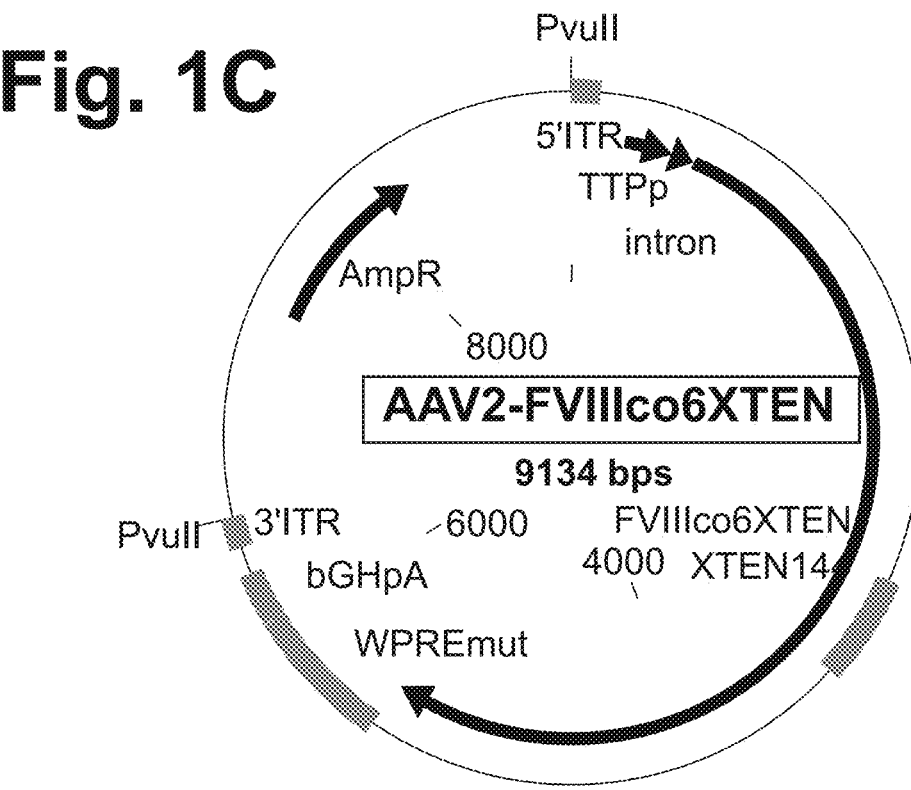
FIGS. 1C-1F are schematic representations of plasmids used to prepare single strand clotting factor expression cassettes, such as the cassette shown in FIG. 1A-1B, wherein the ITRs of the cassette are derived from AAV2 (FIG. 1C), B19 (FIG. 1D), GPV (FIG. 1E), or are the wildtype B19 ITR sequence (FIG. 1F). A plasmid construct comprising an ssFVIII expression cassette as shown here was digested with PvuII (at PvuII sites) (FIG. 1C) or LguI (at LguI sites) (FIGS. 1D-1F) to precisely release the sequence comprising the ITRs and expression cassette. The double stranded DNA was heat denatured at 95° C. to produce ssDNA and then incubated at 4° C. to allow for ITR structure formation.

The present disclosure describes plasmid-like nucleic acid molecules comprising a first inverted terminal repeat (ITR), a second ITR, and a genetic cassette, e.g., encoding a target sequence (also referred to herein as a heterologous polynucleotide sequence), e.g., a therapeutic protein or a miRNA, wherein the first ITR and/or the second ITR are an ITR of a non-adeno-associated virus (e.g., the first ITR and/or the second ITR are from a non-AAV). In some embodiments, the genetic cassette encodes a therapeutic protein, e.g., the target sequence encodes a therapeutic protein. In some embodiments, the therapeutic protein comprises a protein selected from a clotting factor, a growth factor, a hormone, a cytokine, an antibody, a fragment thereof, or a combination thereof. In some embodiments, the genetic cassette encodes dystrophin X-linked, MTM1 (myotubularin), tyrosine hydroxylase, AADC, cyclohydrolase, SMN1, FXN (frataxin), GUCY2D, RS1, CFH, HTRA, ARMS, CFB/CC2, CNGA/CNGB, Prf65, ARSA, PSAP, IDUA (MPS I), IDS (MPS II), PAH, GAA (acid alpha-glucosidase), or any combination thereof.

In some embodiments, the therapeutic protein comprises a clotting factor. In one particular embodiment, the therapeutic protein comprises a FVIII or a FIX protein.

In some embodiments, the genetic cassette encodes a miRNA. In certain embodiments, the miRNA down regulates the expression of a target gene selected from SOD1, HTT, RHO, or any combination thereof.

In certain embodiments, the non-AAV is selected from the group consisting of a member of the viral family Parvoviridae and any combination thereof. The present disclosure is further directed to methods of expressing a therapeutic protein, e.g., a clotting factor, e.g., a FVIII, in a subject in need thereof, comprising administering to the subject a nucleic acid molecule comprising a first inverted terminal repeat (ITR), a second ITR, and a genetic cassette, e.g., encoding a therapeutic protein or an miRNA, wherein the first ITR and/or the second ITR are an ITR of a non-adeno-associated virus (non-AAV). In certain embodiments, the disclosure describes an isolated nucleic acid molecule comprising a nucleotide sequence, which has sequence homology to a nucleotide sequence selected from SEQ ID NOs: 113 and 120.

In certain embodiments, the present disclosure provides nucleic acid molecules comprising a first inverted terminal repeat (ITR) and a second ITR flanking a genetic cassette comprising a heterologous polynucleotide sequence, wherein the first and/or second ITR is derived from parvovirus B19 or goose parvovirus (GPV).

Exemplary constructs of the disclosure are illustrated in the accompanying figures and sequence listing. In order to provide a clear understanding of the specification and claims, the following definitions are provided below.

I. Definitions

It is to be noted that the term "a" or "an" entity refers to one or more of that entity: for example, "a nucleotide sequence" is understood to represent one or more nucleotide sequences. Similarly, "a therapeutic protein" and "a miRNA" is understood to represent one or more therapeutic protein and one or more miRNA, respectively. As such, the terms "a" (or "an"), "one or more," and "at least one" can be used interchangeably herein.

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

Also as used herein, "and/or" refers to and encompasses any and all possible combinations of one or more of the associated listed items, as well as the lack of combinations when interpreted in the alternative ("or").

"Nucleic acids," "nucleic acid molecules," "nucleotides," "nucleotide(s) sequence," and "polynucleotide" are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Single stranded nucleic acid sequences refer to single-stranded DNA (ssDNA) or single-stranded RNA (ssRNA). Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes, but is not limited to, cDNA, genomic DNA, plasmid DNA, synthetic DNA, and semi-synthetic DNA. A "nucleic acid composition" of the disclosure comprises one or more nucleic acids as described herein.

As used herein, an "inverted terminal repeat" (or "ITR") refers to a nucleic acid subsequence located at either the 5' or 3' end of a single stranded nucleic acid sequence, which comprises a set of nucleotides (initial sequence) followed downstream by its reverse complement, i.e., palindromic sequence. The intervening sequence of nucleotides between the initial sequence and the reverse complement can be any length including zero. In one embodiment, the ITR useful for the present disclosure comprises one or more "palindromic sequences." An ITR can have any number of functions. In some embodiments, an ITR described herein forms a hairpin structure. In some embodiments, the ITR forms a T-shaped hairpin structure. In some embodiments, the ITR forms a non-T-shaped hairpin structure, e.g., a U-shaped hairpin structure. In some embodiments, the ITR promotes the long-term survival of the nucleic acid molecule in the nucleus of a cell. In some embodiments, the ITR promotes the permanent survival of the nucleic acid molecule in the nucleus of a cell (e.g., for the entire life-span of the cell). In some embodiments, the ITR promotes the stability of the nucleic acid molecule in the nucleus of a cell. In some embodiments, the ITR promotes the retention of the nucleic acid molecule in the nucleus of a cell. In some embodiments, the ITR promotes the persistence of the nucleic acid molecule in the nucleus of a cell. In some embodiments, the ITR inhibits or prevents the degradation of the nucleic acid molecule in the nucleus of a cell.

In one embodiment, the initial sequence and/or the reverse complement comprise about 2-600 nucleotides, about 2-550 nucleotides, about 2-500 nucleotides, about 2-450 nucleotides, about 2-400 nucleotides, about 2-350 nucleotides, about 2-300 nucleotides, or about 2-250 nucleotides. In some embodiments, the initial sequence and/or the reverse complement comprise about 5-600 nucleotides, about 10-600 nucleotides, about 15-600 nucleotides, about 20-600 nucleotides, about 25-600 nucleotides, about 30-600 nucleotides, about 35-600 nucleotides, about 40-600 nucleotides, about 45-600 nucleotides, about 50-600 nucleotides, about 60-600 nucleotides, about 70-600 nucleotides, about 80-600 nucleotides, about 90-600 nucleotides, about 100-600 nucleotides, about 150-600 nucleotides, about 200-600 nucleotides, about 300-600 nucleotides, about 350-600 nucleotides, about 400-600 nucleotides, about 450-600 nucleotides, about 500-600 nucleotides, or about 550-600 nucleotides. In some embodiments, the initial sequence and/or the reverse complement comprise about 5-550 nucleotides, about 5 to 500 nucleotides, about 5-450 nucleotides, about 5 to 400 nucleotides, about 5-350 nucleotides, about 5 to 300 nucleotides, or about 5-250 nucleotides. In some embodiments, the initial sequence and/or the reverse complement comprise about 10-550 nucleotides, about 15-500 nucleotides, about 20-450 nucleotides, about 25-400 nucleotides, about 30-350 nucleotides, about 35-300 nucleotides, or about 40-250 nucleotides. In certain embodiments, the initial sequence and/or the reverse complement comprise about 225 nucleotides, about 250 nucleotides, about 275 nucleotides, about 300 nucleotides, about 325 nucleotides, about 350 nucleotides, about 375 nucleotides, about 400 nucleotides, about 425 nucleotides, about 450 nucleotides, about 475 nucleotides, about 500 nucleotides, about 525 nucleotides, about 550 nucleotides, about 575 nucleotides, or about 600 nucleotides. In particular embodiments, the initial sequence and/or the reverse complement comprise about 400 nucleotides.

In other embodiments, the initial sequence and/or the reverse complement comprise about 2-200 nucleotides, about 5-200 nucleotides, about 10-200 nucleotides, about 20-200 nucleotides, about 30-200 nucleotides, about 40-200 nucleotides, about 50-200 nucleotides, about 60-200 nucleotides, about 70-200 nucleotides, about 80-200 nucleotides, about 90-200 nucleotides, about 100-200 nucleotides, about 125-200 nucleotides, about 150-200 nucleotides, or about 175-200 nucleotides. In other embodiments, the initial sequence and/or the reverse complement comprise about 2-150 nucleotides, about 5-150 nucleotides, about 10-150 nucleotides, about 20-150 nucleotides, about 30-150 nucleotides, about 40-150 nucleotides, about 50-150 nucleotides, about 75-150 nucleotides, about 100-150 nucleotides, or about 125-150 nucleotides. In other embodiments, the initial sequence and/or the reverse complement comprise about 2-100 nucleotides, about 5-100 nucleotides, about 10-100 nucleotides, about 20-100 nucleotides, about 30-100 nucleotides, about 40-100 nucleotides, about 50-100 nucleotides, or about 75-100 nucleotides. In other embodiments, the initial sequence and/or the reverse complement comprise about 2-50 nucleotides, about 10-50 nucleotides, about 20-50 nucleotides, about 30-50 nucleotides, about 40-50 nucleotides, about 3-30 nucleotides, about 4-20 nucleotides, or about 5-10 nucleotides. In another embodiment, the initial sequence and/or the reverse complement consist of two nucleotides, three nucleotides, four nucleotides, five nucleotides, six nucleotides, seven nucleotides, eight nucleotides, nine nucleotides, ten nucleotides, 11 nucleotides, 12 nucleotides, 13 nucleotides, 14 nucleotides, 15 nucleotides, 16 nucleotides, 17 nucleotides, 18 nucleotides, 19 nucleotides, or 20 nucleotides. In other embodiments, an intervening nucleotide between the initial sequence and the reverse complement is (e.g., consists of) 0 nucleotide, 1 nucleotide, two nucleotides, three nucleotides, four nucleotides, five nucleotides, six nucleotides, seven nucleotides, eight nucleotides, nine nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, or 20 nucleotides.

Therefore, an "ITR" as used herein can fold back on itself and form a double stranded segment. For example, the sequence GATCXXXXGATC comprises an initial sequence of GATC and its complement (3'CTAGS') when folded to form a double helix. In some embodiments, the ITR comprises a continuous palindromic sequence (e.g., GATC-GATC) between the initial sequence and the reverse complement. In some embodiments, the ITR comprises an interrupted palindromic sequence (e.g., GATCXXXX-GATC) between the initial sequence and the reverse complement. In some embodiments, the complementary sections of the continuous or interrupted palindromic sequence interact with each other to form a "hairpin loop" structure. As used herein, a "hairpin loop" structure results when at least two complimentary sequences on a single-stranded nucleotide molecule base-pair to form a double stranded section. In some embodiments, only a portion of the ITR forms a hairpin loop. In other embodiments, the entire ITR forms a hairpin loop.

In the present disclosure, at least one ITR is an ITR of a non-adenovirus associated virus (non-AAV). In certain embodiments, the ITR is an ITR of a non-AAV member of the viral family Parvoviridae. In some embodiments, the ITR is an ITR of a non-AAV member of the genus *Dependovirus* or the genus *Erythrovirus*. In particular embodiments, the ITR is an ITR of a goose parvovirus (GPV), a Muscovy duck parvovirus (MDPV), or an *erythrovirus* parvovirus B19 (also known as parvovirus B19, primate erythroparvovirus 1, B19 virus, and *erythrovirus*). In certain embodiments, one ITR of two ITRs is an ITR of an AAV. In other embodiments, one ITR of two ITRs in the construct is an ITR of an AAV serotype selected from serotype 1, 2, 3, 4, 5, 6, 7, 8, 9, 10, 11 and any combination thereof. In one particular embodiment, the ITR is derived from AAV serotype 2, e.g., an ITR of AAV serotype 2.

In certain aspects of the present disclosure, the nucleic acid molecule comprises two ITRs, a 5' ITR and a 3' ITR, wherein the 5' ITR is located at the 5' terminus of the nucleic acid molecule, and the 3' ITR is located at the 3' terminus of the nucleic acid molecule. The 5' ITR and the 3' ITR can be derived from the same virus or different viruses. In certain embodiments, the 5' ITR is derived from an AAV and the 3' ITR is not derived from an AAV virus (e.g., a non-AAV). In some embodiments, the 3' ITR is derived from an AAV and the 5' ITR is not derived from an AAV virus (e.g., a non-AAV). In other embodiments, the 5' ITR is not derived from an AAV virus (e.g., a non-AAV), and the 3' ITR is derived from the same or a different non-AAV virus.

The term "parvovirus" as used herein encompasses the family Parvoviridae, including but not limited to autonomously-replicating parvoviruses and Dependoviruses. The autonomous parvoviruses include, for example, members of the genera *Bocavirus, Dependovirus, Erythrovirus, Amdovirus, Parvovirus, Densovirus, Iteravirus, Contravirus, Aveparvovirus, Copiparvovirus, Protoparvovirus, Tetraparvovirus, Ambidensovirus, Brevidensovirus, Hepandensovirus*, and *Penstyldensovirus*.

Exemplary autonomous parvoviruses include, but are not limited to, porcine parvovirus, mice minute virus, canine parvovirus, mink entertitus virus, bovine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al. VIROLOGY, volume 2, chapter 69 (4th ed., Lippincott-Raven Publishers).

The term "non-AAV" as used herein encompasses nucleic acids, proteins, and viruses from the family Parvoviridae excluding any adeno-associated viruses (AAV) of the Parvoviridae family. "Non-AAV" includes but is not limited to autonomously-replicating members of the genera *Bocavirus, Dependovirus, Erythrovirus, Amdovirus, Parvovirus, Densovirus, Iteravirus, Contravirus, Aveparvovirus, Copiparvovirus, Protoparvovirus, Tetraparvovirus, Ambidensovirus, Brevidensovirus, Hepandensovirus*, and *Penstyldensovirus*.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, those AAV serotypes and clades disclosed by Gao et al. (J. Virol. 78:6381 (2004)) and Moris et al. (Virol. 33:375 (2004)), and any other AAV now known or later discovered. See, e.g., FIELDS et al. VIROLOGY, volume 2, chapter 69 (4th ed., Lippincott-Raven Publishers).

The term "derived from," as used herein, refers to a component that is isolated from or made using a specified molecule or organism, or information (e.g., amino acid or nucleic acid sequence) from the specified molecule or organism. For example, a nucleic acid sequence (e.g., ITR) that is derived from a second nucleic acid sequence (e.g., ITR) can include a nucleotide sequence that is identical or substantially similar to the nucleotide sequence of the second nucleic acid sequence. In the case of nucleotides or polypeptides, the derived species can be obtained by, for example, naturally occurring mutagenesis, artificial directed mutagenesis or artificial random mutagenesis. The mutagenesis used to derive nucleotides or polypeptides can be intentionally directed or intentionally random, or a mixture of each. The mutagenesis of a nucleotide or polypeptide to create a different nucleotide or polypeptide derived from the first can be a random event (e.g., caused by polymerase infidelity) and the identification of the derived nucleotide or polypeptide can be made by appropriate screening methods, e.g., as discussed herein. Mutagenesis of a polypeptide typically entails manipulation of the polynucleotide that encodes the polypeptide. In some embodiments, a nucleotide or amino acid sequence that is derived from a second nucleotide or amino acid sequence has a sequence identity of at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to the second nucleotide or amino acid sequence, respectively, wherein the first nucleotide or amino acid sequence retains the biological activity of the second nucleotide or amino acid sequence. In other embodiments, an ITR derived from an ITR of a non-AAV (or AAV) is at least 90% identical to the non-AAV ITR (or AAV ITR, respectively), wherein the non-AAV (or AAV) ITR retains a functional property of the non-AAV ITR (or AAV ITR, respectively). In some embodiments, an ITR derived from an ITR of a non-AAV (or AAV) is at least 80% identical to the non-AAV ITR (or AAV ITR, respectively), wherein the non-AAV (or AAV) ITR retains a functional property of the non-AAV ITR (or AAV ITR, respectively). In some embodiments, an ITR derived from an ITR of a non-AAV (or AAV) is at least 70% identical to the non-AAV ITR (or AAV ITR, respectively), wherein the non-AAV (or AAV) ITR retains a functional property of the non-AAV ITR (or AAV ITR, respectively). In some embodiments, an ITR derived from an ITR of a non-AAV (or AAV) is at least 60% identical to the non-AAV ITR (or AAV ITR, respectively), wherein the non-AAV (or AAV) ITR retains a functional property of the non-AAV ITR (or AAV ITR, respectively). In some embodiments, an ITR derived from an ITR of a non-AAV (or AAV) is at least 50% identical to the non-AAV ITR (or AAV ITR, respectively), wherein the non-AAV (or AAV) ITR retains a functional property of the non-AAV ITR (or AAV ITR, respectively).

In certain embodiments, an ITR derived from an ITR of a non-AAV (or AAV) comprises or consists of a fragment of the ITR of the non-AAV (or AAV). In some embodiments, the ITR derived from an ITR of a non-AAV (or AAV) comprises or consists of a fragment of the ITR of the non-AAV (or AAV), wherein the fragment comprises at least about 5 nucleotides, at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, at least about 100 nucleotides, at least about 125 nucleotides, at least about 150 nucleotides, at least about 175 nucleotides, at least about 200 nucleotides, at least about 225 nucleotides, at least about 250 nucleotides, at least about 275 nucleotides, at least about 300 nucleotides, at least about 325 nucleotides, at least about 350 nucleotides, at least about 375 nucleotides, at least about 400 nucleotides, at least about 425 nucleotides, at least about 450 nucleotides, at least about 475 nucleotides, at least about 500 nucleotides, at least about 525 nucleotides, at least about 550 nucleotides, at least about 575 nucleotides, or at least about 600 nucleotides; wherein the ITR derived from an ITR of a non-AAV (or AAV) retains a functional property of the non-AAV ITR (or AAV ITR, respectively). In certain embodiments, the ITR derived from an ITR of a non-AAV (or AAV) comprises or consists of a fragment of the ITR of the non-AAV (or AAV), wherein the fragment comprises at least about 129 nucleotides, and wherein the ITR derived from an ITR of a non-AAV (or AAV) retains a functional property of the non-AAV ITR (or AAV ITR, respectively). In certain embodiments, the ITR derived from an ITR of a non-AAV (or AAV) comprises or consists of a fragment of the ITR of the non-AAV (or AAV), wherein the fragment comprises at least about 102 nucleotides, and wherein the ITR derived from an ITR of a non-AAV (or AAV) retains a functional property of the non-AAV ITR (or AAV ITR, respectively).

In some embodiments, the ITR derived from an ITR of a non-AAV (or AAV) comprises or consists of a fragment of the ITR of the non-AAV (or AAV), wherein the fragment comprises at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the length of the ITR of the non-AAV (or AAV).

In certain embodiments, a nucleotide or amino acid sequence that is derived from a second nucleotide or amino acid sequence has a sequence identity of at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to a homologous portion of the second nucleotide or amino acid sequence, respectively, when properly aligned, wherein the first nucleotide or amino acid sequence retains the biological activity of the second nucleotide or amino acid sequence. In other embodiments, an ITR derived from an ITR of a non-AAV (or AAV) is at least 90% identical to a homologous portion of the non-AAV ITR (or AAV ITR, respectively), when properly aligned, wherein the first nucleotide or amino acid sequence retains the biological activity of the second nucleotide or amino acid sequence. In some embodiments, an ITR derived from an ITR of a non-AAV (or AAV) is at least 80% identical to a homologous portion of the non-AAV ITR (or AAV ITR, respectively), when properly aligned, wherein the first nucleotide or amino acid sequence retains the biological activity of the second nucleotide or amino acid sequence. In some embodiments, an ITR derived from an ITR of a non-AAV (or AAV) is at least 70% identical to a homologous portion of the non-AAV ITR (or AAV ITR, respectively), when properly aligned, wherein the first nucleotide or amino acid sequence retains the biological activity of the second nucleotide or amino acid sequence. In some embodiments, an ITR derived from an ITR of a non-AAV (or AAV) is at least 60% identical to a homologous portion of the non-AAV ITR (or AAV ITR, respectively), when properly aligned, wherein the first nucleotide or amino acid sequence retains the biological activity of the second nucleotide or amino acid sequence. In some embodiments, an ITR derived from an ITR of a non-AAV (or AAV) is at least 50% identical to a homologous portion of the non-AAV ITR (or AAV ITR, respectively), when properly aligned, wherein the first nucleotide or amino acid sequence retains the biological activity of the second nucleotide or amino acid sequence.

A "capsid-free" or "capsid-less" vector or nucleic acid molecule refers to a vector construct free from a capsid. In some embodiments, the capsid-less vector or nucleic acid molecule does not contain sequences encoding, e.g., an AAV Rep protein.

As used herein, a "coding region" or "coding sequence" is a portion of polynucleotide which consists of codons translatable into amino acids. Although a "stop codon" (TAG, TGA, or TAA) is typically not translated into an amino acid, it can be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. Two or more coding regions can be present in a single polynucleotide construct, e.g., on a single vector, or in separate polynucleotide constructs, e.g., on separate (different) vectors. It follows, then, that a single vector can contain just a single coding region, or comprise two or more coding regions.

Certain proteins secreted by mammalian cells are associated with a secretory signal peptide which is cleaved from the mature protein once export of the growing protein chain across the rough endoplasmic reticulum has been initiated. Those of ordinary skill in the art are aware that signal peptides are generally fused to the N-terminus of the polypeptide, and are cleaved from the complete or "full-length" polypeptide to produce a secreted or "mature" form of the polypeptide. In certain embodiments, a native signal peptide or a functional derivative of that sequence that retains the ability to direct the secretion of the polypeptide that is operably associated with it. Alternatively, a heterologous mammalian signal peptide, e.g., a human tissue plasminogen activator (TPA) or mouse ß-glucuronidase signal peptide, or a functional derivative thereof, can be used.

The term "downstream" refers to a nucleotide sequence that is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

As used herein, the term "gene regulatory region" or "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions can include promoters, translation leader sequences, introns, polyadenylation recognition sequences, RNA processing sites, effector binding sites, or stem-loop structures. If a coding region is intended for expression in a eukaryotic cell, a polyadenylation signal and transcription termination sequence will usually be located 3' to the coding sequence.

A polynucleotide which encodes a product, e.g., a miRNA or a gene product (e.g., a polypeptide such as a therapeutic protein), can include a promoter and/or other expression (e.g., transcription or translation) control elements operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other expression control elements, besides a promoter, for example enhancers, operators, repressors, and transcription termination signals, can also be operably associated with a coding region to direct gene product expression.

"Transcriptional control sequences" refer to DNA regulatory sequences, such as promoters, enhancers, terminators, and the like, that provide for the expression of a coding sequence in a host cell. A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit ß-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), small hairpin RNA (shRNA), small interfering RNA (siRNA) or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage. The term "yield," as used herein, refers to the amount of a polypeptide produced by the expression of a gene.

A "vector" refers to any vehicle for the cloning of and/or transfer of a nucleic acid into a host cell. A vector can be a replicon to which another nucleic acid segment can be attached so as to bring about the replication of the attached segment. A "replicon" refers to any genetic element (e.g., plasmid, phage, cosmid, chromosome, virus) that functions as an autonomous unit of replication in vivo, i.e., capable of replication under its own control. The term "vector" includes vehicles for introducing the nucleic acid into a cell in vitro, ex vivo or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini.

Vectors can be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), β-galactosidase (LacZ), β-glucuronidase (Gus), and the like. Selectable markers can also be considered to be reporters.

The term "host cell" as used herein refers to, for example microorganisms, yeast cells, insect cells, and mammalian cells, that can be, or have been, used as recipients of ssDNA or vectors. The term includes the progeny of the original cell which has been transduced. Thus, a "host cell" as used herein generally refers to a cell which has been transduced with an exogenous DNA sequence. It is understood that the progeny of a single parental cell may not necessarily be completely identical in morphology or in genomic or total DNA complement to the original parent, due to natural, accidental, or deliberate mutation. In some embodiments, the host cell can be an in vitro host cell.

The term "selectable marker" refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes can also be considered reporter genes.

"Promoter" and "promoter sequence" are used interchangeably and refer to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths can have identical promoter activity.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease 51), as well as protein binding domains (consensus sequences) responsible for the binding of RNA polymerase.

In some embodiments, the nucleic acid molecule comprises a tissue specific promoter. In certain embodiments, the tissue specific promoter drives expression of the therapeutic protein, e.g., the clotting factor, in the liver, e.g., in hepatocytes and/or endothelial cells. In particular, embodiments, the promoter is selected from the group consisting of a mouse thyretin promoter (mTTR), an endogenous human factor VIII promoter (F8), a human alpha-1-antitrypsin promoter (hAAT), a human albumin minimal promoter, a mouse albumin promoter, a tristetraprolin (TTP) promoter, a CASI promoter, a CAG promoter, a cytomegalovirus (CMV) promoter, a phosphoglycerate kinase (PGK) promoter and any combination thereof. In some embodiments, the promoter is selected from a liver specific promoter (e.g., α1-antitrypsin (AAT)), a muscle specific promoter (e.g., muscle creatine kinase (MCK), myosin heavy chain alpha (αMHC), myoglobin (MB), and desmin (DES)), a synthetic promoter (e.g., SPc5-12, 2R5Sc5-12, dMCK, and tMCK) and any combination thereof. In one particular embodiment, the promoter comprises a TTP promoter.

The terms "restriction endonuclease" and "restriction enzyme" are used interchangeably and refer to an enzyme that binds and cuts within a specific nucleotide sequence within double stranded DNA.

The term "plasmid" refers to an extra-chromosomal element often carrying a gene that is not part of the central metabolism of the cell, and usually in the form of circular double-stranded DNA molecules. Such elements can be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construct, which is capable of introducing a promoter fragment and DNA sequence for a selected gene product along with appropriate 3' untranslated sequence into a cell.

Eukaryotic viral vectors that can be used include, but are not limited to, adenovirus vectors, retrovirus vectors, adeno-associated virus vectors, poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

A "cloning vector" refers to a "replicon," which is a unit length of a nucleic acid that replicates sequentially and which comprises an origin of replication, such as a plasmid, phage or cosmid, to which another nucleic acid segment can be attached so as to bring about the replication of the attached segment. Certain cloning vectors are capable of replication in one cell type, e.g., bacteria and expression in another, e.g., eukaryotic cells. Cloning vectors typically comprise one or more sequences that can be used for selection of cells comprising the vector and/or one or more multiple cloning sites for insertion of nucleic acid sequences of interest.

The term "expression vector" refers to a vehicle designed to enable the expression of an inserted nucleic acid sequence following insertion into a host cell. The inserted nucleic acid sequence is placed in operable association with regulatory regions as described above.

Vectors are introduced into host cells by methods well known in the art, e.g., transfection, electroporation, microinjection, transduction, cell fusion, DEAE dextran, calcium phosphate precipitation, lipofection (lysosome fusion), use of a gene gun, or a DNA vector transporter. "Culture," "to culture" and "culturing," as used herein, means to incubate cells under in vitro conditions that allow for cell growth or division or to maintain cells in a living state. "Cultured cells," as used herein, means cells that are propagated in vitro.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced recombinant technology, but is not necessarily translated from a designated nucleic acid sequence. It can be generated in any manner, including by chemical synthesis.

The term "amino acid" includes alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V). Non-traditional amino acids are also within the scope of the disclosure and include norleucine, ornithine, norvaline, homoserine, and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA. Introduction of the non-traditional amino acid can also be achieved using peptide chemistries known in the art. As used herein, the term "polar amino acid" includes amino acids that have net zero charge, but have non-zero partial charges in different portions of their side chains (e.g., M, F, W, S, Y, N, Q, C). These amino acids can participate in hydrophobic interactions and electrostatic interactions. As used herein, the term "charged amino acid" includes amino acids that can have non-zero net charge on their side chains (e.g., R, K, H, E, D). These amino acids can participate in hydrophobic interactions and electrostatic interactions.

Also included in the present disclosure are fragments or variants of polypeptides, and any combination thereof. The term "fragment" or "variant" when referring to polypeptide binding domains or binding molecules of the present disclosure include any polypeptides which retain at least some of the properties (e.g., FcRn binding affinity for an FcRn binding domain or Fc variant, coagulation activity for an FVIII variant, or FVIII binding activity for the VWF fragment) of the reference polypeptide. Fragments of polypeptides include proteolytic fragments, as well as deletion fragments, in addition to specific antibody fragments discussed elsewhere herein, but do not include the naturally occurring full-length polypeptide (or mature polypeptide). Variants of polypeptide binding domains or binding molecules of the present disclosure include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

The term "percent identity" as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case can be, as determined by the match between strings of such sequences. "Identity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity are codified in publicly available computer programs. Sequence alignments and percent identity calculations can be performed using sequence analysis software such as the Megalign program of the LASERGENE bioinformatics computing suite (DNASTAR Inc., Madison, WI), the GCG suite of programs (Wisconsin Package Version 9.0, Genetics Computer Group (GCG), Madison, WI), BLASTP, BLASTN, BLASTX (Altschul et al., *J. Mol. Biol.* 215:403 (1990)), and DNASTAR (DNASTAR, Inc. 1228 S. Park St. Madison, WI 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized. For the purposes of determining percent identity between a therapeutic protein, e.g., a clotting factor, sequence of the disclosure and a reference sequence, only nucleotides in the reference sequence corresponding to nucleotides in the therapeutic protein, e.g., the clotting factor, sequence of the disclosure are used to calculate percent identity. For example, when comparing a full length FVIII nucleotide sequence containing the B domain to an optimized B domain deleted (BDD) FVIII nucleotide sequence of the disclosure, the portion of the alignment including the A1, A2, A3, C1, and C2 domain will be used to calculate percent identity. The nucleotides in the portion of the full length FVIII sequence encoding the B domain (which will result in a large "gap" in the alignment) will not be counted as a mismatch. In addition, in determining percent identity between an optimized BDD FVIII sequence of the disclosure, or a designated portion thereof (e.g., nucleotides 58-2277 and 2320-4374 of SEQ ID NO:3), and a reference sequence, percent identity will be calculated by aligning dividing the number of matched nucleotides by the total number of nucleotides in the complete sequence of the optimized BDD-FVIII sequence, or a designated portion thereof, as recited herein.

As used herein, nucleotides corresponding to nucleotides in a particular sequence of the disclosure are identified by alignment of the sequence of the disclosure to maximize the identity to a reference sequence. The number used to identify an equivalent amino acid in a reference sequence is based on the number used to identify the corresponding amino acid in the sequence of the disclosure.

A "fusion" or "chimeric" protein comprises a first amino acid sequence linked to a second amino acid sequence with which it is not naturally linked in nature. The amino acid sequences which normally exist in separate proteins can be brought together in the fusion polypeptide, or the amino acid sequences which normally exist in the same protein can be placed in a new arrangement in the fusion polypeptide, e.g., fusion of a Factor VIII domain of the disclosure with an Ig Fc domain. A fusion protein is created, for example, by chemical synthesis, or by creating and translating a polynucleotide in which the peptide regions are encoded in the desired relationship. A chimeric protein can further comprises a second amino acid sequence associated with the first amino acid sequence by a covalent, non-peptide bond or a non-covalent bond.

As used herein, the term "insertion site" refers to a position in a polypeptide, or fragment, variant, or derivative thereof, which is immediately upstream of the position at which a heterologous moiety can be inserted. An "insertion site" is specified as a number, the number being the number of the amino acid in a reference sequence. For example, an "insertion site" in FVIII refers to the number of the amino acid sequence in mature native FVIII (SEQ ID NO: 15) to which the insertion site corresponds, which is immediately N-terminal to the position of the insertion. For example, the phrase "a3 comprises a heterologous moiety at an insertion site which corresponds to amino acid 1656 of SEQ ID NO: 15" indicates that the heterologous moiety is located between two amino acids corresponding to amino acid 1656 and amino acid 1657 of SEQ ID NO: 15.

The phrase "immediately downstream of an amino acid" as used herein refers to position right next to the terminal carboxyl group of the amino acid. Similarly, the phrase "immediately upstream of an amino acid" refers to the position right next to the terminal amine group of the amino acid.

The terms "inserted," "is inserted," "inserted into" or grammatically related terms, as used herein refer to the position of a heterologous moiety in a polypeptide, e.g., a clotting factor, relative to the analogous position in the parental polypeptide. For example, in certain embodiment, "inserted" and the like refer to the position of a heterologous moiety in a recombinant FVIII polypeptide, relative to the analogous position in native mature human FVIII. As used herein the terms refer to the characteristics of the polypeptide, and do not indicate, imply or infer any methods or process by which the polypeptide was made.

As used herein, the term "half-life" refers to a biological half-life of a particular polypeptide in vivo. Half-life can be represented by the time required for half the quantity administered to a subject to be cleared from the circulation and/or other tissues in the animal. When a clearance curve of a given polypeptide is constructed as a function of time, the curve is usually biphasic with a rapid α-phase and longer β-phase. The α-phase typically represents an equilibration of the administered Fc polypeptide between the intra- and extra-vascular space and is, in part, determined by the size of the polypeptide. The β-phase typically represents the catabolism of the polypeptide in the intravascular space. In some embodiments, the therapeutic protein, e.g., the clotting factor, e.g., FVIII, and chimeric proteins comprising the same are monophasic, and thus do not have an alpha phase, but just the single beta phase. Therefore, in certain embodiments, the term half-life as used herein refers to the half-life of the polypeptide in the β-phase.

The term "linked" as used herein refers to a first amino acid sequence or nucleotide sequence covalently or non-covalently joined to a second amino acid sequence or nucleotide sequence, respectively. The first amino acid or nucleotide sequence can be directly joined or juxtaposed to the second amino acid or nucleotide sequence or alternatively an intervening sequence can covalently join the first sequence to the second sequence. The term "linked" means not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively). In one embodiment, the first amino acid sequence can be linked to a second amino acid sequence by a peptide bond or a linker. The first nucleotide sequence can be linked to a second nucleotide sequence by a phosphodiester bond or a linker. The linker can be a peptide or a polypeptide (for polypeptide chains) or a nucleotide or a nucleotide chain (for nucleotide chains) or any chemical moiety (for both polypeptide and polynucleotide chains). The term "linked" is also indicated by a hyphen (-).

Hemostasis, as used herein, means the stopping or slowing of bleeding or hemorrhage; or the stopping or slowing of blood flow through a blood vessel or body part.

Hemostatic disorder, as used herein, means a genetically inherited or acquired condition characterized by a tendency to hemorrhage, either spontaneously or as a result of trauma, due to an impaired ability or inability to form a fibrin clot. Examples of such disorders include the hemophilias. The three main forms are hemophilia A (factor VIII deficiency), hemophilia B (factor IX deficiency or "Christmas disease") and hemophilia C (factor XI deficiency, mild bleeding tendency). Other hemostatic disorders include, e.g., von Willebrand disease, Factor XI deficiency (PTA deficiency), Factor XII deficiency, deficiencies or structural abnormalities in fibrinogen, prothrombin, Factor V, Factor VII, Factor X or factor XIII, Bernard-Soulier syndrome, which is a defect or deficiency in GPIb. GPIb, the receptor for vWF, can be defective and lead to lack of primary clot formation (primary hemostasis) and increased bleeding tendency), and thrombasthenia of Glanzman and Naegeli (Glanzmann thrombasthenia). In liver failure (acute and chronic forms), there is insufficient production of coagulation factors by the liver; this can increase bleeding risk.

The isolated nucleic acid molecules, isolated polypeptides, or vectors comprising the isolated nucleic acid molecule of the disclosure can be used prophylactically. As used herein the term "prophylactic treatment" refers to the administration of a molecule prior to a bleeding episode. In one embodiment, the subject in need of a general hemostatic agent is undergoing, or is about to undergo, surgery. A polynucleotide, polypeptide, or vector of the disclosure can be administered prior to or after surgery as a prophylactic. The polynucleotide, polypeptide, or vector of the disclosure can be administered during or after surgery to control an acute bleeding episode. The surgery can include, but is not limited to, liver transplantation, liver resection, dental procedures, or stem cell transplantation.

The isolated nucleic acid molecules, isolated polypeptides, or vectors of the disclosure are also used for on-demand treatment. The term "on-demand treatment" refers to the administration of an isolated nucleic acid molecule, isolated polypeptide, or vector in response to symptoms of a bleeding episode or before an activity that can cause bleeding. In one aspect, the on-demand treatment can be given to a subject when bleeding starts, such as after an injury, or when bleeding is expected, such as before surgery. In another aspect, the on-demand treatment can be given prior to activities that increase the risk of bleeding, such as contact sports.

As used herein the term "acute bleeding" refers to a bleeding episode regardless of the underlying cause. For example, a subject can have trauma, uremia, a hereditary bleeding disorder (e.g., factor VII deficiency) a platelet disorder, or resistance owing to the development of antibodies to clotting factors.

Treat, treatment, treating, as used herein refers to, e.g., the reduction in severity of a disease or condition; the reduction in the duration of a disease course; the amelioration of one or more symptoms associated with a disease or condition; the provision of beneficial effects to a subject with a disease or condition, without necessarily curing the disease or condition, or the prophylaxis of one or more symptoms associated with a disease or condition. In one embodiment, the term "treating" or "treatment" means maintaining, e.g., a FVIII trough level at least about 1 IU/dL, 2 IU/dL, 3 IU/dL, 4 IU/dL, 5 IU/dL, 6 IU/dL, 7 IU/dL, 8 IU/dL, 9 IU/dL, 10 IU/dL, 11 IU/dL, 12 IU/dL, 13 IU/dL, 14 IU/dL, 15 IU/dL, 16 IU/dL, 17 IU/dL, 18 IU/dL, 19 IU/dL, 20 IU/dL, 25 IU/dL, 30 IU/dL, 35 IU/dL, 40 IU/dL, 45 IU/dL, 50 IU/dL, 55 IU/dL, 60 IU/dL, 65 IU/dL, 70 IU/dL, 75 IU/dL, 80 IU/dL, 85 IU/dL, 90 IU/dL, 95 IU/dL, 100 IU/dL, 105 IU/dL, 110 IU/dL, 115 IU/dL, 120 IU/dL, 125 IU/dL, 130 IU/dL, 135 IU/dL, 140 IU/dL, 145 IU/dL, or 150 IU/dL in a subject by administering an isolated nucleic acid molecule, isolated polypeptide or vector of the disclosure. In another embodiment, treating or treatment means maintaining a FVIII trough level between about 1 and about 150 IU/dL, about 1 and about 125 IU/dL, about 1 and about 100 IU/dL, about 1 and about 90 IU/dL, about 1 and about 85 IU/dL, about 1 and about 80 IU/dL, about 1 and about 75 IU/dL, about 1 and about 70 IU/dL, about 1 and about 65 IU/dL, about 1 and about 60 IU/dL, about 1 and about 55 IU/dL, about 1 and about 50 IU/dL, about 1 and about 45 IU/dL, about 1 and about 40 IU/dL, about 1 and about 35 IU/dL, about 1 and about 30 IU/dL, about 1 and about 25 IU/dL, about 25 and about 125 IU/dL, about 50 and about 100 IU/dL, about 50 and about 75 IU/dL, about 75 and about 100 IU/dL, about 1 and about 20 IU/dL, about 2 and about 20 IU/dL, about 3 and about 20 IU/dL, about 4 and about 20 IU/dL, about 5 and about 20 IU/dL, about 6 and about 20 IU/dL, about 7 and about 20 IU/dL, about 8 and about 20 IU/dL, about 9 and about 20 IU/dL, or about 10 and about 20 IU/dL. Treatment or treating of a disease or condition can also include maintaining FVIII activity in a subject at a level comparable to at least about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, or 150% of the FVIII activity in a non-hemophiliac subject. The minimum trough level required for treatment can be measured by one or more known methods and can be adjusted (increased or decreased) for each person.

"Administering," as used herein, means to give a pharmaceutically acceptable nucleic acid molecule, polypeptide expressed therefrom, or vector comprising the nucleic acid molecule of the disclosure to a subject via a pharmaceutically acceptable route. Routes of administration can be intravenous, e.g., intravenous injection and intravenous infusion. Additional routes of administration include, e.g., subcutaneous, intramuscular, oral, nasal, and pulmonary administration. The nucleic acid molecules, polypeptides, and vectors can be administered as part of a pharmaceutical composition comprising at least one excipient.

The term "pharmaceutically acceptable" as used herein refers to molecular entities and compositions that are physiologically tolerable and do not typically produce toxicity or an allergic or similar untoward reaction, such as gastric upset, dizziness and the like, when administered to a human. Optionally, as used herein, the term "pharmaceutically acceptable" means approved by a regulatory agency of the federal or a state government or listed in the U.S. Pharmacopeia or other generally recognized pharmacopeia for use in animals, and more particularly in humans.

As used herein, the phrase "subject in need thereof" includes subjects, such as mammalian subjects, that would benefit from administration of a nucleic acid molecule, polypeptide, or vector of the disclosure, e.g., to improve hemostasis. In one embodiment, the subjects include, but are not limited to, individuals with hemophilia. In another embodiment, the subjects include, but are not limited to, individuals who have developed an inhibitor to the therapeutic protein, e.g., the clotting factor, e.g., FVIII, and thus are in need of a bypass therapy. The subject can be an adult or a minor (e.g., under 12 years old).

As used herein, the term "therapeutic protein" refers to any polypeptide known in the art that can be administered to a subject. In some embodiments, the therapeutic protein comprises a protein selected from a clotting factor, a growth factor, an antibody, a functional fragment thereof, or a combination thereof. As used herein, the term "clotting factor," refers to molecules, or analogs thereof, naturally occurring or recombinantly produced which prevent or decrease the duration of a bleeding episode in a subject. In other words, it means molecules having pro-clotting activity, i.e., are responsible for the conversion of fibrinogen into a mesh of insoluble fibrin causing the blood to coagulate or clot. "Clotting factor" as used herein includes an activated clotting factor, its zymogen, or an activatable clotting factor. An "activatable clotting factor" is a clotting factor in an inactive form (e.g., in its zymogen form) that is capable of being converted to an active form. The term "clotting factor" includes but is not limited to factor I (FI), factor II (FII), factor V (FV), FVII, FVIII, FIX, factor X (FX), factor XI (FXI), factor XII (FXII), factor XIII (FXIII), Von Willebrand factor (VWF), prekallikrein, high-molecular weight kininogen, fibronectin, antithrombin III, heparin cofactor II, protein C, protein S, protein Z, Protein Z-related protease inhibitor (ZPI), plasminogen, alpha 2-antiplasmin, tissue plasminogen activator (tPA), urokinase, plasminogen activator inhibitor-1 (PAI-1), plasminogen activator inhibitor-2 (PAI2), zymogens thereof, activated forms thereof, or any combination thereof.

Clotting activity, as used herein, means the ability to participate in a cascade of biochemical reactions that culminates in the formation of a fibrin clot and/or reduces the severity, duration or frequency of hemorrhage or bleeding episode.

A "growth factor," as used herein, includes any growth factor known in the art including cytokines and hormones. In some embodiments, the growth factor is selected from adrenomedullin (AM), angiopoietin (Ang), autocrine motility factor, a bone morphogenetic protein (BMP) (e.g. BMP2, BMP4, BMP5, BMP7), a ciliary neurotrophic factor family member (e.g., ciliary neurotrophic factor (CNTF), leukemia inhibitory factor (LIF), interleukin-6 (IL-6)), a colony-stimulating factor (e.g., macrophage colony-stimulating factor (m-CSF), granulocyte colony-stimulating factor (G-CSF), granulocyte macrophage colony-stimulating factor (GM-CSF)), an epidermal growth factor (EGF), an ephrin (e.g., ephrin A1, ephrin A2, ephrin A3, ephrin A4, ephrin A5, ephrin B1, ephrin B2, ephrin B3), erythropoietin (EPO), a fibroblast growth factor (FGF) (e.g., FGF1, FGF2, FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22, FGF23), foetal bovine somatotrophin (FBS), a GDNF family member (e.g., glial cell line-derived neurotrophic factor (GDNF), neurturin, persephin, artemin), growth differentiation factor-9 (GDF9), hepatocyte growth factor (HGF), hepatoma-derived growth factor (HDGF), insulin, an insulin-like growth factors (e.g., insulin-like growth factor-1 (IGF-1) or IGF-2, an interleukin (IL) (e.g., IL-1, IL-2, IL-3, IL-4, IL-5, IL-6, IL-7), keratinocyte growth factor (KGF), migration-stimulating factor (MSF), macrophage-stimulating protein (MSP or hepatocyte growth factor-like protein (HGFLP)), myostatin (GDF-8), a neuregulin (e.g., neuregulin 1 (NRG1), NRG2, NRG3, NRG4), a neurotrophin (e.g., brain-derived neurotrophic factor (BDNF), nerve growth factor (NGF), a neurotrophin-3 (NT-3), NT-4, placental growth factor (PGF), platelet-derived growth factor (PDGF), renalase (RNLS), T-cell growth factor (TCGF), thrombopoietin (TPO), a transforming growth factor (e.g., transforming growth factor alpha (TGF-α), TGF-β, tumor necrosis factor-alpha (TNF-α), and vascular endothelial growth factor (VEGF).

In some embodiments, the therapeutic protein is encoded by a gene selected from dystrophin X-linked, MTM1 (myotubularin), tyrosine hydroxylase, AADC, cyclohydrolase, SMN1, FXN (frataxin), GUCY2D, RS1, CFH, HTRA, ARMS, CFB/CC2, CNGA/CNGB, Prf65, ARSA, PSAP, IDUA (MPS I), IDS (MPS II), PAH, GAA (acid alpha-glucosidase), or any combination thereof.

As used herein the terms "heterologous" or "exogenous" refer to such molecules that are not normally found in a given context, e.g., in a cell or in a polypeptide. For example, an exogenous or heterologous molecule can be introduced into a cell and are only present after manipulation of the cell, e.g., by transfection or other forms of genetic engineering or a heterologous amino acid sequence can be present in a protein in which it is not naturally found.

As used herein, the term "heterologous nucleotide sequence" refers to a nucleotide sequence that does not naturally occur with a given polynucleotide sequence. In one embodiment, the heterologous nucleotide sequence encodes a polypeptide capable of extending the half-life of the therapeutic protein, e.g., the clotting factor, e.g., FVIII. In another embodiment, the heterologous nucleotide sequence encodes a polypeptide that increases the hydrodynamic radius of the therapeutic protein, e.g., the clotting factor, e.g., FVIII. In other embodiments, the heterologous nucleotide sequence encodes a polypeptide that improves one or more pharmacokinetic properties of the therapeutic protein without significantly affecting its biological activity or function (e.g., a procoagulant activity). In some embodiments, the therapeutic protein is linked or connected to the polypeptide encoded by the heterologous nucleotide sequence by a linker. Non-limiting examples of polypeptide moieties encoded by heterologous nucleotide sequences include an immunoglobulin constant region or a portion thereof, albumin or a fragment thereof, an albumin-binding moiety, a transferrin, the PAS polypeptides of U.S. Pat Application No. 20100292130, a HAP sequence, transferrin or a fragment thereof, the C-terminal peptide (CTP) of the β subunit of human chorionic gonadotropin, albumin-binding small molecule, an XTEN sequence, FcRn binding moieties (e.g., complete Fc regions or portions thereof which bind to FcRn), single chain Fc regions (ScFc regions, e.g., as described in US 2008/0260738, WO 2008/012543, or WO 2008/1439545), polyglycine linkers, polyserine linkers, peptides and short polypeptides of 6-40 amino acids of two types of amino acids selected from glycine (G), alanine (A), serine (S), threonine (T), glutamate (E) and proline (P) with varying degrees of secondary structure from less than 50% to greater than 50%, amongst others, or two or more combinations thereof. In some embodiments, the polypeptide encoded by the heterologous nucleotide sequence is linked to a non-polypeptide moiety. Non-limiting examples of the non-polypeptide moieties include polyethylene glycol (PEG), albumin-binding small molecules, polysialic acid, hydroxyethyl starch (HES), a derivative thereof, or any combinations thereof.

As used herein, the term "Fc region" is defined as the portion of a polypeptide which corresponds to the Fc region of native Ig, i.e., as formed by the dimeric association of the respective Fc domains of its two heavy chains. A native Fc region forms a homodimer with another Fc region. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence).

In one embodiment, the "Fc region" refers to the portion of a single Ig heavy chain beginning in the hinge region just upstream of the papain cleavage site (i.e., residue 216 in IgG, taking the first residue of heavy chain constant region to be 114) and ending at the C-terminus of the antibody. Accordingly, a complete Fc domain comprises at least a hinge domain, a CH2 domain, and a CH3 domain.

The Fc region of an Ig constant region, depending on the Ig isotype can include the CH2, CH3, and CH4 domains, as well as the hinge region. Chimeric proteins comprising an Fc region of an Ig bestow several desirable properties on a chimeric protein including increased stability, increased serum half-life (see Capon et al., 1989, Nature 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entireties.

A "reference nucleotide sequence," when used herein as a comparison to a nucleotide sequence of the disclosure, is a polynucleotide sequence essentially identical to the nucleotide sequence of the disclosure except that sequence is not optimized. For example, the reference nucleotide sequence for a nucleic acid molecule consisting of the codon optimized BDD FVIII of SEQ ID NO: 1 and a heterologous nucleotide sequence that encodes a single chain Fc region linked to SEQ ID NO: 1 at its 3' end is a nucleic acid molecule consisting of the original (or "parent") BDD FVIII of SEQ ID NO: 16 and the identical heterologous nucleotide sequence that encodes a single chain Fc region linked to SEQ ID NO: 16 at its 3' end.

As used herein, the term "optimized," with regard to nucleotide sequences, refers to a polynucleotide sequence that encodes a polypeptide, wherein the polynucleotide sequence has been mutated to enhance a property of that polynucleotide sequence. In some embodiments, the optimization is done to increase transcription levels, increase translation levels, increase steady-state mRNA levels, increase or decrease the binding of regulatory proteins such as general transcription factors, increase or decrease splicing, or increase the yield of the polypeptide produced by the polynucleotide sequence. Examples of changes that can be made to a polynucleotide sequence to optimize it include codon optimization, G/C content optimization, removal of repeat sequences, removal of AT rich elements, removal of cryptic splice sites, removal of cis-acting elements that repress transcription or translation, adding or removing poly-T or poly-A sequences, adding sequences around the transcription start site that enhance transcription, such as Kozak consensus sequences, removal of sequences that could form stem loop structures, removal of destabilizing sequences, and two or more combinations thereof.

II. Nucleic Acid Molecules

The present disclosure is directed to a plasmid-like, capsid free, nucleic acid molecule that encodes a target sequence, wherein the target sequence encodes a therapeutic protein or a gene that can modulate expression of a target protein, e.g., a miRNA. A capsid, the protein shell of a virus, encloses the genetic material of the virus. Capsids are known to aid the functions of the virion by protecting the viral genome, delivering the genome to a host, and interacting with the host. Nonetheless, the viral capsids may be a factor in limiting the packaging capacity of the vectors and/or inducing immune responses, especially when used in gene therapy.

AAV vectors have emerged as one of the more common types of gene therapy vectors. However, the presence of the capsid limits the utility of an AAV vector in gene therapy. In particular, the capsid itself can limit the size of the transgene that is included in the vector to as low as less than 4.5 kb. Various therapeutic proteins that may be useful in a gene therapy can easily exceed this size even before regulatory elements are added.

Furthermore, proteins that make up the capsid can serve as antigens that can be targeted by a subject's immune system. AAV is very common in the general population, with most people having been exposed to an AAV throughout their lives. As a result, most potential gene therapy recipients have likely already developed an immune response to an AAV, and thus are more likely to reject the therapy.

Certain aspects of the present disclosure aim to overcome these deficiencies of AAV vectors. In particular, certain aspects of the present disclosure are directed to a nucleic acid molecule, comprising a first ITR, a second ITR, and a genetic cassette, e.g., encoding a therapeutic protein and/or a miRNA. In some embodiments, the first ITR and second ITR flank a genetic cassette comprising a heterologous polynucleotide sequence. In some embodiments, the nucleic acid molecule does not comprise a gene encoding a capsid protein, a replication protein, and/or an assembly protein. In some embodiments, the genetic cassette encodes a therapeutic protein. In some embodiments, the therapeutic protein comprises a clotting factor. In some embodiments, the genetic cassette encodes a miRNA. In certain embodiments, the genetic cassette is positioned between the first ITR and the second ITR. In some embodiments, the nucleic acid molecule further comprises one or more noncoding region. In certain embodiments, the one or more non-coding region comprises a promoter sequence, an intron, a post-transcriptional regulatory element, a 3'UTR poly(A) sequence, or any combination thereof.

In one embodiment, the genetic cassette is a single stranded nucleic acid. In another embodiment, the genetic cassette is a double stranded nucleic acid.

In one embodiment, the nucleic acid molecule comprises:
 (a) a first ITR that is an ITR of a non-AAV family member of Parvoviridae (e.g., a B19 or GPV ITR);
 (b) a tissue specific promoter sequence, e.g., TTP promoter;
 (c) an intron, e.g., a synthetic intron;
 (d) a nucleotide encoding a miRNA or a therapeutic protein, e.g., a clotting factor;
 (e) a post-transcriptional regulatory element, e.g., WPRE;
 (f) a 3'UTR poly(A) tail sequence, e.g., bGHpA;
 (g) a second ITR that is an ITR of a non-AAV family member of Parvoviridae (e.g., a B19 or GPV ITR).

In one embodiment, the nucleic acid molecule comprises:
 (a) a first ITR that is an ITR of a non-AAV family member of Parvoviridae;
 (b) a tissue specific promoter sequence, e.g., TTP promoter;
 (c) an intron, e.g., a synthetic intron;
 (d) a nucleotide encoding a miRNA, wherein the miRNA down regulates the expression of a target gene selected from SOD1, HTT, RHO, and any combination thereof;
 (e) a post-transcriptional regulatory element, e.g., WPRE;
 (f) a 3'UTR poly(A) tail sequence, e.g., bGHpA;
 (g) a second ITR that is an ITR of a non-AAV family member of Parvoviridae In one embodiment, the nucleic acid molecule comprises:
 (a) a first ITR that is an ITR of a non-AAV family member of Parvoviridae;
 (b) a tissue specific promoter sequence, e.g., TTP promoter;
 (c) an intron, e.g., a synthetic intron;
 (d) a nucleotide encoding dystrophin X-linked, MTM1 (myotubularin), tyrosine hydroxylase, AADC, cyclohydrolase, SMN1, FXN (frataxin), GUCY2D, RS1, CFH, HTRA, ARMS, CFB/CC2, CNGA/CNGB, Prf65, ARSA, PSAP, IDUA (MPS I), IDS (MPS II), PAH, GAA (acid alpha-glucosidase), or any combination thereof;
 (e) a post-transcriptional regulatory element, e.g., WPRE;
 (f) a 3'UTR poly(A) tail sequence, e.g., bGHpA;
 (g) a second ITR that is an ITR of a non-AAV family member of Parvoviridae In one embodiment, the nucleic acid molecule comprises:
 (a) a first ITR that is an ITR of an AAV, e.g., an AAV serotype 2 genome;
 (b) a tissue specific promoter sequence, e.g., TTP promoter;
 (c) an intron, e.g., a synthetic intron;
 (d) a nucleotide encoding FVIII; wherein the nucleotide has at least 85%, at least 90%, at least 95%, at least 96%, at least 97%, at least 98%, or at least 99% sequence identity to a nucleotide sequence selected from SEQ ID NOs: 1-14 or SEQ ID NO: 71, wherein the FVIII encoded by the nucleotide retains a FVIII activity;
 (e) a post-transcriptional regulatory element, e.g., WPRE;

(f) a 3'UTR poly(A) tail sequence, e.g., bGHpA; and
(g) a second ITR that is an ITR of an AAV, e.g., an AAV serotype 2 genome.

In one embodiment, the nucleic acid molecule comprises:
(a) a first ITR that is an ITR of an AAV, e.g., an AAV serotype 2 genome;
(b) a tissue specific promoter sequence, e.g., TTP promoter;
(c) an intron, e.g., a synthetic intron;
(d) a nucleotide encoding a miRNA, wherein the miRNA down regulates the expression of a target gene, e.g., SOD1, HTT, RHO, and any combination thereof;
(f) a 3'UTR poly(A) tail sequence, e.g., bGHpA; and
(g) a second ITR that is an ITR of an AAV, e.g., an AAV serotype 2 genome.

In one embodiment, the nucleic acid molecule comprises:
(a) a first ITR that is an ITR of an AAV, e.g., an AAV serotype 2 genome;
(b) a tissue specific promoter sequence, e.g., TTP promoter;
(c) an intron, e.g., a synthetic intron;
(d) a nucleotide encoding dystrophin X-linked, MTM1 (myotubularin), tyrosine hydroxylase, AADC, cyclohydrolase, SMN1, FXN (frataxin), GUCY2D, RS1, CFH, HTRA, ARMS, CFB/CC2, CNGA/CNGB, Prf65, ARSA, PSAP, IDUA (MPS I), IDS (MPS II), PAH, GAA (acid alpha-glucosidase), or any combination thereof;
(f) a 3'UTR poly(A) tail sequence, e.g., bGHpA; and
(g) a second ITR that is an ITR of an AAV, e.g., an AAV serotype 2 genome.

In another embodiment, the nucleic acid molecule comprises:
(a) a first ITR;
(b) a tissue specific promoter sequence, e.g., TTP promoter;
(c) an intron, e.g., a synthetic intron;
(d) a nucleotide encoding a miRNA or a therapeutic protein, e.g., clotting factor;
(e) a post-transcriptional regulatory element, e.g., WPRE;
(f) a 3'UTR poly(A) tail sequence, e.g., bGHpA; and
(g) a second ITR,
wherein one of the first ITR or the second ITR is an ITR of a non-AAV family member of Parvoviridae and the other ITR is an ITR of an AAV, e.g., an AAV serotype 2 genome.

In another embodiment, the nucleic acid molecule comprises:
(a) a 5' ITR bearing the AAV2 5' ITR sequence set forth in SEQ ID NO: 111;
(b) a tissue specific promoter sequence, e.g., TTP promoter;
(c) an intron, e.g., a synthetic intron;
(d) a heterologous polynucleotide sequence encoding FVIII, e.g., FVIIIco6XTEN;
(e) a post-transcriptional regulatory element, e.g., WPRE;
(f) a 3'UTR poly(A) tail sequence, e.g., bGHpA; and/or
(g) a 3' ITR bearing the AAV2 3' ITR sequence set forth in SEQ ID NO: 124.

In another embodiment, the nucleic acid molecule comprises:
(a) a 5' ITR bearing the AAV2 5' ITR sequence set forth in SEQ ID NO: 111;
(b) a tissue specific promoter sequence, e.g., CAG promoter;
(c) an intron, e.g., a synthetic intron;
(d) a heterologous polynucleotide sequence encoding FVIII, e.g., FVIIIco6XTEN;
(e) a post-transcriptional regulatory element, e.g., WPRE;
(f) a 3'UTR poly(A) tail sequence, e.g., bGHpA; and/or
(g) a 3' ITR bearing the AAV2 3' ITR sequence set forth in SEQ ID NO: 193.

In another embodiment, the nucleic acid molecule comprises:
(a) a first ITR;
(b) a tissue specific promoter sequence, TTP promoter;
(c) an intron, e.g., a synthetic intron;
(d) a nucleotide encoding a miRNA or a therapeutic protein, e.g., clotting factor;
(e) a post-transcriptional regulatory element, e.g., WPRE;
(f) a 3'UTR poly(A) tail sequence, e.g., bGHpA; and
(g) a second ITR,
wherein the first ITR is a synthetic ITR, the second ITR is a synthetic ITR, or both the first ITR and the second ITR are synthetic ITRs.

In another embodiment, the nucleic acid molecule comprises:
(a) a first B19 ITR;
(b) a tissue specific promoter sequence, e.g., TTP promoter;
(c) an intron, e.g., a synthetic intron;
(d) a heterologous polynucleotide sequence encoding therapeutic protein selected from the group consisting of a clotting factor, a growth factor, a hormone, a cytokine, an antibody, a fragment thereof, and a combination thereof;
(e) a post-transcriptional regulatory element, e.g., WPRE;
(f) a 3'UTR poly(A) tail sequence, e.g., bGHpA; and/or
(g) a second B19 ITR.

In another embodiment, the nucleic acid molecule comprises:
(a) a first GPV ITR;
(b) a tissue specific promoter sequence, e.g., TTP promoter;
(c) an intron, e.g., a synthetic intron;
(d) a heterologous polynucleotide sequence encoding therapeutic protein selected from the group consisting of a clotting factor, a growth factor, a hormone, a cytokine, an antibody, a fragment thereof, and a combination thereof;
(e) a post-transcriptional regulatory element, e.g., WPRE;
(f) a 3'UTR poly(A) tail sequence, e.g., bGHpA; and/or
(g) a second GPV ITR.

In another embodiment, the nucleic acid molecule comprises:
(a) a first B19 ITR;
(b) a ubiquitous promoter sequence, e.g., CAG promoter;
(c) an intron, e.g., a synthetic intron;
(d) a heterologous polynucleotide sequence encoding therapeutic protein selected from the group consisting of a clotting factor, a growth factor, a hormone, a cytokine, an antibody, a fragment thereof, and a combination thereof;
(e) a post-transcriptional regulatory element, e.g., WPRE;
(f) a 3'UTR poly(A) tail sequence, e.g., bGHpA; and/or
(g) a second B19 ITR.

In another embodiment, the nucleic acid molecule comprises:
(a) a first GPV ITR;
(b) a ubiquitous promoter sequence, e.g., CAG promoter;
(c) an intron, e.g., a synthetic intron;
(d) a heterologous polynucleotide sequence encoding therapeutic protein selected from the group consisting of a clotting factor, a growth factor, a hormone, a cytokine, an antibody, a fragment thereof, and a combination thereof;
(e) a post-transcriptional regulatory element, e.g., WPRE;
(f) a 3'UTR poly(A) tail sequence, e.g., bGHpA; and/or
(g) a second GPV ITR.

In another embodiment, the nucleic acid molecule comprises:
(a) a first B19 ITR;
(b) a tissue specific promoter sequence, e.g., TTP promoter;
(c) an intron, e.g., a synthetic intron;
(d) a heterologous polynucleotide sequence encoding phenylalanine hydroxylase (PAH);
(e) a post-transcriptional regulatory element, e.g., WPRE;
(f) a 3'UTR poly(A) tail sequence, e.g., bGHpA; and/or
(g) a second B19 ITR.

In another embodiment, the nucleic acid molecule comprises:
(a) a first GPV ITR;
(b) a tissue specific promoter sequence, e.g., TTP promoter;
(c) an intron, e.g., a synthetic intron;
(d) a heterologous polynucleotide sequence encoding phenylalanine hydroxylase (PAH);
(e) a post-transcriptional regulatory element, e.g., WPRE;
(f) a 3'UTR poly(A) tail sequence, e.g., bGHpA; and/or
(g) a second GPV ITR.

In another embodiment, the nucleic acid molecule comprises:
(a) a 5' ITR bearing the B19d135 5' ITR sequence set forth in SEQ ID NO: 180;
(b) a tissue specific promoter sequence, e.g., TTP promoter;
(c) an intron, e.g., a synthetic intron;
(d) a heterologous polynucleotide sequence encoding FVIII, e.g., FVIIIco6XTEN;
(e) a post-transcriptional regulatory element, e.g., WPRE;
(f) a 3'UTR poly(A) tail sequence, e.g., bGHpA; and/or
(g) a 3' ITR bearing the B19d135 3' ITR sequence set forth in SEQ ID NO: 181.

In another embodiment, the nucleic acid molecule comprises:
(a) a 5' ITR bearing the GPVd162 5' ITR sequence set forth in SEQ ID NO: 183;
(b) a tissue specific promoter sequence, e.g., TTP promoter;
(c) an intron, e.g., a synthetic intron;
(d) a heterologous polynucleotide sequence encoding FVIII, e.g., FVIIIco6XTEN;
(e) a post-transcriptional regulatory element, e.g., WPRE;
(f) a 3'UTR poly(A) tail sequence, e.g., bGHpA; and/or
(g) a 3' ITR bearing the GPVd162 3' ITR sequence set forth in SEQ ID NO: 184.

In another embodiment, the nucleic acid molecule comprises:
(a) a 5' ITR bearing the full length B19 5' ITR sequence set forth in SEQ ID NO: 185;
(b) a tissue specific promoter sequence, e.g., TTP promoter;
(c) an intron, e.g., a synthetic intron;
(d) a heterologous polynucleotide sequence encoding FVIII, e.g., FVIIIco6XTEN;
(e) a post-transcriptional regulatory element, e.g., WPRE;
(f) a 3'UTR poly(A) tail sequence, e.g., bGHpA; and/or
(g) a 3' ITR bearing the full length B19 3' ITR sequence set forth in SEQ ID NO: 186.

In another embodiment, the nucleic acid molecule comprises:
(a) a 5' ITR bearing the full length GPV 5' ITR sequence set forth in SEQ ID NO: 187;
(b) a tissue specific promoter sequence, e.g., TTP promoter;
(c) an intron, e.g., a synthetic intron;
(d) a heterologous polynucleotide sequence encoding FVIII, e.g., FVIIIco6XTEN;
(e) a post-transcriptional regulatory element, e.g., WPRE;
(f) a 3'UTR poly(A) tail sequence, e.g., bGHpA; and/or
(g) a 3' ITR bearing the full length GPV 3' ITR sequence set forth in SEQ ID NO: 188.

In another embodiment, the nucleic acid molecule comprises:
(a) a 5' ITR bearing the B19d135 5' ITR sequence set forth in SEQ ID NO: 180;
(b) a tissue specific promoter sequence, e.g., CAG promoter;
(c) an intron, e.g., a synthetic intron;
(d) a heterologous polynucleotide sequence encoding PAH;
(e) a post-transcriptional regulatory element, e.g., WPRE;
(f) a 3'UTR poly(A) tail sequence, e.g., bGHpA; and/or
(g) a 3' ITR bearing the B19d135 3' ITR sequence set forth in SEQ ID NO: 181.

In another embodiment, the nucleic acid molecule comprises:
(a) a 5' ITR bearing the GPVd162 5' ITR sequence set forth in SEQ ID NO: 183;
(b) a tissue specific promoter sequence, e.g., CAG promoter;
(c) an intron, e.g., a synthetic intron;
(d) a heterologous polynucleotide sequence encoding PAH;
(e) a post-transcriptional regulatory element, e.g., WPRE;
(f) a 3'UTR poly(A) tail sequence, e.g., bGHpA; and/or
(g) a 3' ITR bearing the GPVd162 3' ITR sequence set forth in SEQ ID NO: 184.

In another embodiment, the nucleic acid molecule comprises:
(a) a 5' ITR bearing the full length B19 5' ITR sequence set forth in SEQ ID NO: 185;
(b) a tissue specific promoter sequence, e.g., CAG promoter;
(c) an intron, e.g., a synthetic intron;
(d) a heterologous polynucleotide sequence encoding PAH;
(e) a post-transcriptional regulatory element, e.g., WPRE;
(f) a 3'UTR poly(A) tail sequence, e.g., bGHpA; and/or
(g) a 3' ITR bearing the full length B19 3' ITR sequence set forth in SEQ ID NO: 186.

In another embodiment, the nucleic acid molecule comprises:
(a) a 5' ITR bearing the full length GPV 5' ITR sequence set forth in SEQ ID NO: 187;
(b) a tissue specific promoter sequence, e.g., CAG promoter;
(c) an intron, e.g., a synthetic intron;
(d) a heterologous polynucleotide sequence encoding PAH;
(e) a post-transcriptional regulatory element, e.g., WPRE;
(f) a 3'UTR poly(A) tail sequence, e.g., bGHpA; and/or
(g) a 3' ITR bearing the full length GPV 3' ITR sequence set forth in SEQ ID NO: 188.

A. Inverted Terminal Repeats

Certain aspects of the present disclosure are directed to a nucleic acid molecule comprising a first ITR, e.g., a 5' ITR, and second ITR, e.g., a 3' ITR. Typically, ITRs are involved in parvovirus (e.g., AAV) DNA replication and rescue, or excision, from prokaryotic plasmids (Samulski et al., 1983, 1987; Senapathy et al., 1984; Gottlieb and Muzyczka, 1988). In addition, ITRs appear to be the minimum sequences required for AAV proviral integration and for packaging of AAV DNA into virions (McLaughlin et al., 1988; Samulski et al., 1989). These elements are essential for efficient multiplication of a parvovirus genome. It is hypothesized that the minimal defining elements indispensable for ITR function are a Rep-binding site (e.g., RBS; GCGCGCTCGCTCGCTC (SEQ ID NO: 104) for AAV2) and a terminal resolution site (e.g., TRS; AGTTGG (SEQ ID NO: 105) for AAV2) plus a variable palindromic sequence allowing for hairpin formation. Palindromic nucleotide regions normally function together in cis as origins of DNA replication and as packaging signals for the virus. Complimentary sequences in the ITRs fold into a hairpin structure during DNA replication. In some embodiments, the ITRs fold into a hairpin T-shaped structure. In other embodiments, the ITRs fold into non-T-shaped hairpin structures, e.g., into a U-shaped hairpin structure. Data suggests that the T-shaped hairpin structures of AAV ITRs may inhibit the expression of a transgene flanked by the ITRs. See, e.g., Zhou et al., *Scientific Reports* 7:5432 (Jul. 14, 2017). By utilizing an ITR that does not form T-shaped hairpin structures, this form of inhibition may be avoided. Therefore, in certain aspects, a polynucleotide comprising a non-AAV ITR has an improved transgene expression compared to a polynucleotide comprising an AAV ITR that forms a T-shaped hairpin.

In some embodiments, the ITR comprises a naturally occurring ITR, e.g. the ITR comprises all or a portion of a parvovirus ITR. In some embodiments, the ITR comprises a synthetic sequence. In one embodiment, the first ITR or the second ITR comprises a synthetic sequence. In another embodiment, each of the first ITR and the second ITR comprises a synthetic sequence. In some embodiments, the first ITR or the second ITR comprises a naturally occurring sequence. In another embodiment, each of the first ITR and the second ITR comprises a naturally occurring sequence.

In some embodiments, the ITR comprises or consists of a portion of a naturally occurring ITR, e.g., a truncated ITR. In some embodiments, the ITR comprises or consists of a fragment of a naturally occurring ITR, wherein the fragment comprises at least about 5 nucleotides, at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, at least about 100 nucleotides, at least about 125 nucleotides, at least about 150 nucleotides, at least about 175 nucleotides, at least about 200 nucleotides, at least about 225 nucleotides, at least about 250 nucleotides, at least about 275 nucleotides, at least about 300 nucleotides, at least about 325 nucleotides, at least about 350 nucleotides, at least about 375 nucleotides, at least about 400 nucleotides, at least about 425 nucleotides, at least about 450 nucleotides, at least about 475 nucleotides, at least about 500 nucleotides, at least about 525 nucleotides, at least about 550 nucleotides, at least about 575 nucleotides, or at least about 600 nucleotides; wherein the ITR retains a functional property of the naturally occurring ITR. In certain embodiments, the ITR comprises or consists of a fragment of a naturally occurring ITR, wherein the fragment comprises at least about 129 nucleotides; wherein the ITR retains a functional property of the naturally occurring ITR. In certain embodiments, the ITR comprises or consists of a fragment of a naturally occurring ITR, wherein the fragment comprises at least about 102 nucleotides; wherein the ITR retains a functional property of the naturally occurring ITR.

In some embodiments, the ITR comprises or consists of a portion of a naturally occurring ITR, wherein the fragment comprises at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% of the length of the naturally occurring ITR; wherein the fragment retains a functional property of the naturally occurring ITR.

In certain embodiments, the ITR comprises or consists of a sequence that has a sequence identity of at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to a homologous portion of a naturally occurring ITR, when properly aligned; wherein the ITR retains a functional property of the naturally occurring ITR. In other embodiments, the ITR comprises or consists of a sequence that has a sequence identity of at least 90% to a homologous portion of a naturally occurring ITR, when properly aligned; wherein the ITR retains a functional property of the naturally occurring ITR. In some embodiments, the ITR comprises or consists of a sequence that has a sequence identity of at least 80% to a homologous portion of a naturally occurring ITR, when properly aligned; wherein the ITR retains a functional property of the naturally occurring ITR. In some embodiments, the ITR comprises or consists of a sequence that has a sequence identity of at least 70% to a homologous portion of a naturally occurring ITR, when properly aligned; wherein the ITR retains a functional property of the naturally occurring ITR. In some embodiments, the ITR comprises or consists of a sequence that has a sequence identity of at least 60% to a homologous portion of a naturally occurring ITR, when properly aligned; wherein the ITR retains a functional property of the naturally occurring ITR. In some embodiments, the ITR comprises or consists of a sequence that has a sequence identity of at least 50% to a homologous portion of a naturally occurring ITR, when properly aligned; wherein the ITR retains a functional property of the naturally occurring ITR.

In some embodiments, the ITR comprises an ITR from an AAV genome. In some embodiments, the ITR is an ITR of an AAV genome selected from AAV1, AAV2, AAV3, AAV4, AAV5, AAV6, AAV7, AAV8, AAV9, AAV10 AAV11, and any combination thereof. In a particular embodiment, the ITR is an ITR of the AAV2 genome. In another embodiment, the ITR is a synthetic sequence genetically engineered to include at its 5' and 3' ends ITRs derived from one or more of AAV genomes.

In some embodiments, the ITR is not derived from an AAV genome. In some embodiments, the ITR is an ITR of a non-AAV. In some embodiments, the ITR is an ITR of a non-AAV genome from the viral family Parvoviridae selected from, but not limited to, the group consisting of *Bocavirus, Dependovirus, Erythrovirus, Amdovirus, Parvovirus, Densovirus, Iteravirus, Contravirus, Aveparvovirus, Copiparvovirus, Protoparvovirus, Tetraparvovirus, Ambidensovirus, Brevidensovirus, Hepandensovirus, Penstyldensovirus* and any combination thereof. In certain embodiments, the ITR is derived from *erythrovirus* parvovirus B19 (human virus). In another embodiment, the ITR is derived from a Muscovy duck parvovirus (MDPV) strain. In certain embodiments, the MDPV strain is attenuated, e.g., MDPV strain FZ91-30. In other embodiments, the MDPV strain is pathogenic, e.g., MDPV strain YY. In some embodiments, the ITR is derived from a porcine parvovirus, e.g., porcine parvovirus U44978. In some embodiments, the ITR is derived from a mice minute virus, e.g., mice minute virus U34256. In some embodiments, the ITR is derived from a canine parvovirus, e.g., canine parvovirus M19296. In some embodiments, the ITR is derived from a mink enteritis virus, e.g., mink enteritis virus D00765. In some embodiments, the ITR is derived from a Dependoparvovirus. In one embodiment, the Dependoparvovirus is a *Dependovirus* Goose parvovirus (GPV) strain. In a specific embodiment, the GPV strain is attenuated, e.g., GPV strain 82-0321V. In another specific embodiment, the GPV strain is pathogenic, e.g., GPV strain B.

The first ITR and the second ITR of the nucleic acid molecule can be derived from the same genome, e.g., from the genome of the same virus, or from different genomes, e.g., from the genomes of two or more different virus genomes. In certain embodiments, the first ITR and the second ITR are derived from the same AAV genome. In a specific embodiment, the two ITRs present in the nucleic acid molecule of the invention are the same, and can in particular be AAV2 ITRs. In other embodiments, the first ITR is derived from an AAV genome and the second ITR is not derived from an AAV genome (e.g., a non-AAV genome). In other embodiments, the first ITR is not derived from an AAV genome (e.g., a non-AAV genome) and the second ITR is derived from an AAV genome. In still other embodiments, both the first ITR and the second ITR are not derived from an AAV genome (e.g., a non-AAV genome). In one particular embodiment, the first ITR and the second ITR are identical.

In some embodiments, the first ITR is derived from an AAV genome, and the second ITR is derived from a genome selected from the group consisting of *Bocavirus, Dependovirus, Erythrovirus, Amdovirus, Parvovirus, Densovirus, Iteravirus, Contravirus, Aveparvovirus, Copiparvovirus, Protoparvovirus, Tetraparvovirus, Ambidensovirus, Brevidensovirus, Hepandensovirus, Penstyldensovirus* and any combination thereof. In other embodiments, the second ITR is derived from an AAV genome, and the first ITR is derived from a genome selected from the group consisting of *Bocavirus, Dependovirus, Erythrovirus, Amdovirus, Parvovirus, Densovirus, Iteravirus, Contravirus, Aveparvovirus, Copiparvovirus, Protoparvovirus, Tetraparvovirus, Ambidensovirus, Brevidensovirus, Hepandensovirus, Penstyldensovirus*, and any combination thereof. In other embodiments, the first ITR and the second ITR are derived from a genome selected from the group consisting of *Bocavirus, Dependovirus, Erythrovirus, Amdovirus, Parvovirus, Densovirus, Iteravirus, Contravirus, Aveparvovirus, Copiparvovirus, Protoparvovirus, Tetraparvovirus, Ambidensovirus, Brevidensovirus, Hepandensovirus, Penstyldensovirus*, and any combination thereof, wherein the first ITR and the second ITR are derived from the same genome. In other embodiments, the first ITR and the second ITR are derived from a genome selected from the group consisting of *Bocavirus, Dependovirus, Erythrovirus, Amdovirus, Parvovirus, Densovirus, Iteravirus, Contravirus, Aveparvovirus, Copiparvovirus, Protoparvovirus, Tetraparvovirus, Ambidensovirus, Brevidensovirus, Hepandensovirus, Penstyldensovirus*, and any combination thereof, wherein the first ITR and the second ITR are derived from the different genomes.

In some embodiments, the first ITR is derived from an AAV genome, and the second ITR is derived from *erythrovirus* parvovirus B19 (human virus). In other embodiments, the second ITR is derived from an AAV genome, and the first ITR is derived from *erythrovirus* parvovirus B19 (human virus).

In certain embodiments, the first ITR and/or the second ITR comprises or consists of all or a portion of an ITR derived from B19. In some embodiments, the first ITR and/or the second ITR comprises or consists of a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to a nucleotide sequence selected from SEQ ID NOs: 167, 168, 169, 170, and 171, wherein the first ITR and/or the second ITR retains a functional property of the B19 ITR from which it is derived. In some embodiments, the first ITR and/or the second ITR comprises or consists of a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to a nucleotide sequence selected from SEQ ID NOs: 167, 168, 169, 170, and 171, wherein the first ITR and/or the second ITR is capable of forming a hairpin structure. In certain embodiments, the hairpin structure does not comprise a T-shaped hairpin.

In some embodiments, the first ITR and/or the second ITR comprises or consists of a nucleotide sequence selected from SEQ ID NOs: 167, 168, 169, 170, and 171. In some embodiments, the first ITR and/or the second ITR comprises or consists of the nucleotide sequence set forth in SEQ ID NO: 167. In some embodiments, the first ITR and/or the second ITR comprises or consists of the nucleotide sequence set forth in SEQ ID NO: 168. In some embodiments, the first ITR and/or the second ITR comprises or consists of the nucleotide sequence set forth in SEQ ID NO: 169. In some embodiments, the first ITR and/or the second ITR comprises or consists of the nucleotide sequence set forth in SEQ ID NO: 170. In some embodiments, the first ITR and/or the second ITR comprises or consists of the nucleotide sequence set forth in SEQ ID NO: 171.

TABLE 1

Sample Parvovirus ITR Sequences.

| Parvovirus | ITR ID | Description | Length (nt) | Sequence |
|---|---|---|---|---|
| B19 | wt | Gene Bank: KY940273.1 | 383 | CCAAATCAGATGCCGCCGGTCGCCGCCGGTAGGC GGGACTTCCGGTACAAGATGGCGGACAATTACGT CATTTCCTGTGACGTCATTTCCTGTGACGTCACT TCCGGTGGGCGGGACTTCCGGAATTAGGGTTGGC TCTGGGCCAGCTTGCTTGGGGTTGCCTTGACACT AAGACAAGCGGCGCGCCGCTTGATCTTAGTGGCA CGTCAACCCCAAGCGCTGGCCCAGAGCCAACCCT AATTCCGGAAGTCCCGCCCACCGGAAGTGACGTC ACAGGAAATGACGTCACAGGAAATGACGTAATTG TCCGCCATCTTGTACCGGAAGTCCCGCCTACCGG CGGCGACCGGCGGCATCTGATTTGGTGTCTTCTT TTAAATTTT (SEQ ID NO: 167) |
| | d135 | excludes first 135 nucleotides | 248 | CTCTGGGCCAGCTTGCTTGGGGTTGCCTTGACAC TAAGACAAGCGGCGCGCCGCTTGATCTTAGTGGC ACGTCAACCCCAAGCGCTGGCCCAGAGCCAACCC TAATTCCGGAAGTCCCGCCCACCGGAAGTGACGT CACAGGAAATGACGTCACAGGAAATGACGTAATT GTCCGCCATCTTGTACCGGAAGTCCCGCCTACCG GCGGCGACCGGCGGCATCTGATTTGGTGTCTTCT TTTAAATTTT (SEQ ID NO: 168) |
| | v1 | minimal sequence based on comparison with AAV2 | 129 | CGGCGCGCCGCTTGATCTTAGTGGCACGTCAACC AGCGCTGGCCCAGAGCCAACCCTAATTCCGGAAG TCCTCAGTCCGCCATCTTGCCCGCCTACCGGCGG CGACCGGCGGCATCATTTGGTGTTCTT (SEQ ID NO: 169) |
| | v2 | excludes first 135 nucleotides and corresponding complementary 135 nucleotides in palindrome | 113 | CTCTGGGCCAGCTTGCTTGGGGTTGCCTTGACAC TAAGACAAGCGGCGCGCCGCTTGATCTTAGTGGC ACGTCAACCCCAAGCGCTGGCCCAGAGTGTCTTC TTTTAAATTTT (SEQ ID NO: 170) |
| | v3 | minimal sequence based on comparison with GPV | 340 | CAAATCAGATGCCGCCGGTCGCCGCCGGTAGGCG GGACTTCCGGTACAAGATGGCGGACAATTACGTC ATTTCCTGTGACGTATTTCCTGTGACGTACTTCC GGTGGCGGGACTTCCGGAATTTTGGCTCTGGGCC AGCTTGCTTGGGGTTGCCTTGACCAAGCGCGCGC CGCTTGATCACCCCAAGCGCTGGCCCAGAGCCAC CTAACCGGAAGTCCCCCCACCGGAAGTGACGTCA CAGGAAAGACGTCACAGGAAGTAATTGTCCGCCA TCTTGTACCGGAAGTCCCGCACCGGCGGCGACCG GCGGCATCTGATTTGGTGTCTTCTTTTAAATTTT (SEQ ID NO: 171) |
| GPV | wt | Gene Bank: U25749.1 | 444 | CTCATTGGAGGGTTCGTTCGTTCGAACCAGCCAA TCAGGGGAGGGGGAAGTGACGCAAGTTCCGGTCA CATGCTTCCGGTGACGCACATCCGGTGACGTAGT TCCGGTCACGTGCTTCCTGTCACGTGTTTCCGGT CACGTGACTTCCGGTCATGTGACTTCCGGTGACG TGTTTCCGGCTGTTAGGTTGACCACGCGCATGCC GCGCGGTCAGCCCAATAGTTAAGCCGGAAACACG TCACCGGAAGTCACATGACCGGAAGTCACGTGAC CGGAAACACGTGACAGGAAGCACGTGACCGGAAC TACGTCACCGGATGTGCGTCACCGGAAGCATGTG ACCGGAACTTGCGTCACTTCCCCCTCCCCTGATT GGCTGGTTCGAACGAACGAACCCTCCAATGAGAC TCAAGGACAAGAGGATATTTTGCGCGCCAGGAAG TG (SEQ ID NO: 172) |
| | d162 | excludes first 162 nucleotides | 282 | CGGTGACGTGTTTCCGGCTGTTAGGTTGACCACG CGCATGCCGCGCGGTCAGCCCAATAGTTAAGCCG GAAACACGTCACCGGAAGTCACATGACCGGAAGT CACGTGACCGGAAACACGTGACAGGAAGCACGTG ACCGGAACTACGTCACCGGATGTGCGTCACCGGA AGCATGTGACCGGAACTTGCGTCACTTCCCCCTC CCCTGATTGGCTGGTTCGAACGAACGAACCCTCC AATGAGACTCAAGGACAAGAGGATATTTTGCGCG CCAGGAAGTG (SEQ ID NO: 173) |
| | v1 | minimal sequence based on comparison with AAV2 | 145 | TTGACCACGCGCATGCCGCGCGGTCAGCCCAATA GTTAAGCCGGGTGACCACACGTGACAGGAAGCAC GGGATGTGCGTCACCGGAAGCAGTGACCGGGCTG GTTCGAACGAACGAACCCTCCAACTCAAGGACAA GAGGATATT (SEQ ID NO: 174) |

TABLE 1-continued

Sample Parvovirus ITR Sequences.

| Parvovirus | ITR ID | Description | Length (nt) | Sequence |
|---|---|---|---|---|
| | v2 | excludes first 162 nucleotides and corresponding complementary 162 nucleotides in palindrome | 120 | CGGTGACGTGTTTCCGGCTGTTAGGTTGACCACG CGCATGCCGCGCGGTCAGCCCAATAGTTAAGCCG GAAACACGTCACCGACTCAAGGACAAGAGGATAT TTTGCGCGCCAGGAAGTG (SEQ ID NO: 175) |
| | v3 | minimal sequence based on comparison with B19 | 102 | GGGAACAATCAGGGGAAGTGACCGGTGACGTCAT GTAACTTGCGTCACTTCCCGTTCGAACGAACGAA CGAGACTCAAGGACAAGAGGCGCGCCAGGAAGTG (SEQ ID NO: 176) |
| AAV2 | wt | Gene Bank: NC_001401.2 | 145 | TTGGCCACTCCCTCTCTGCGCGCTCGCTCGCTCA CTGAGGCCGGGCGACCAAAGGTCGCCCGACGCCC GGGCTTTGCCCGGGCGGCCTCAGTGAGCGAGCGA GCGCGCAGAGAGGGAGTGGCCAACTCCATCACTA GGGGTTCCT (SEQ ID NO: 177) |
| | GTx | used in GTx vectors | 130 | CTGCGCGCTCGCTCGCTCACTGAGGCCGCCCGGG CAAAGCCCGGGCGTCGGGCGACCTTTGGTCGCCC GGCCTCAGTGAGCGAGCGAGCGCGCAGAGAGGGA GTGGCCAACTCCATCACTAGGGGTTCCT (SEQ ID NO: 178) |

In certain embodiments, the first ITR and/or the second ITR comprises a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 167. In certain embodiments, the first ITR and/or the second ITR consists of SEQ ID NO: 167. In certain embodiments, the first ITR and/or the second ITR comprises a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 168. In certain embodiments, the first ITR and/or the second ITR consists of SEQ ID NO: 168. In certain embodiments, the first ITR and/or the second ITR comprises a nucleotide sequence, wherein the nucleotide sequence comprises the minimal nucleotide sequence set forth in SEQ ID NO: 169, and wherein the nucleotide sequence is a at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 167, retains a functional property of the B19 ITR from which it is derived. In some embodiments, the first ITR and/or the second ITR comprises a nucleotide sequence, wherein the nucleotide sequence comprises the minimal nucleotide sequence set forth in SEQ ID NO: 169, and wherein the nucleotide sequence is a at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 167, wherein the first ITR and/or the second ITR is capable of forming a hairpin structure. In certain embodiments, the hairpin structure does not comprise a T-shaped hairpin.

In certain embodiments, the first ITR and/or the second ITR comprises or consists of all or a portion of an ITR derived from B19. In some embodiments, the second ITR is a reverse complement of the first ITR. In some embodiments, the first ITR is a reverse complement of the second ITR. In some embodiments, the first ITR and/or the second ITR comprises or consists of a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to a nucleotide sequence selected from SEQ ID NOs: 180, 181, 185, and 186, or a functional derivative thereof. In some embodiments, the functional derivative retains a functional property of the B19 ITR from which it is derived. In some embodiments, the first ITR and/or the second ITR comprises or consists of a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to a nucleotide sequence selected from SEQ ID NOs: 180, 181, 185, and 186, or a functional derivative thereof. In some embodiments, the functional derivative is capable of forming a hairpin structure. In certain embodiments, the hairpin structure does not comprise a T-shaped hairpin.

In certain embodiments, the first ITR and/or the second ITR comprises a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 180. In certain embodiments, the first ITR and/or the second ITR consists of SEQ ID NO: 180. In certain embodiments, the first ITR and/or the second ITR comprises a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 181. In certain embodiments, the first ITR and/or the second ITR consists of SEQ ID NO: 181. In certain embodiments, the first ITR and/or the second ITR comprises a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 185. In certain embodiments, the first ITR and/or the second ITR consists of SEQ ID NO: 185. In certain embodiments, the first ITR and/or the second ITR comprises a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 186. In certain embodiments, the first ITR and/or the second ITR consists of SEQ ID NO: 186.

In some embodiments, the first ITR and/or the second ITR comprises or consists of a nucleotide sequence selected from SEQ ID NOs: 180, 181, 185, and 186. In some embodiments, the first ITR comprises or consists of the nucleotide sequence set forth in SEQ ID NO: 180. In some embodiments, the first ITR comprises or consists of the nucleotide sequence set forth in SEQ ID NO: 181. In some embodiments, the first ITR comprises or consists of the nucleotide sequence set forth in SEQ ID NO: 185. In some embodiments, the first ITR comprises or consists of the nucleotide sequence set forth in SEQ ID NO: 186. In some embodiments, the second ITR comprises or consists of the nucleotide sequence set forth in SEQ ID NO: 180. In some embodiments, the second ITR comprises or consists of the nucleotide sequence set forth in SEQ ID NO: 181. In some embodiments, the second ITR comprises or consists of the nucleotide sequence set forth in SEQ ID NO: 185. In some embodiments, the second ITR comprises or consists of the nucleotide sequence set forth in SEQ ID NO: 186.

In some embodiments, the first ITR comprises or consists of the nucleotide sequence set forth in SEQ ID NO:180, and the second ITR comprises or consists of the nucleotide sequence set forth in SEQ ID NO: 181. In some embodiments, the first ITR comprises or consists of the nucleotide sequence set forth in SEQ ID NO:181, and the second ITR comprises or consists of the nucleotide sequence set forth in SEQ ID NO: 180. In some embodiments, the first ITR comprises or consists of the nucleotide sequence set forth in SEQ ID NO:185, and the second ITR comprises or consists of the nucleotide sequence set forth in SEQ ID NO: 186. In some embodiments, the first ITR comprises or consists of the nucleotide sequence set forth in SEQ ID NO:186, and the second ITR comprises or consists of the nucleotide sequence set forth in SEQ ID NO: 185.

In some embodiments, the first ITR is derived from an AAV genome, and the second ITR is derived from GPV. In other embodiments, the second ITR is derived from an AAV genome, and the first ITR is derived from GPV.

In certain embodiments, the first ITR and/or the second ITR comprises a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 172. In certain embodiments, the first ITR and/or the second ITR consists of SEQ ID NO: 172. In certain embodiments, the first ITR and/or the second ITR comprises a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 173. In certain embodiments, the first ITR and/or the second ITR consists of SEQ ID NO: 173. In certain embodiments, the first ITR and/or the second ITR comprises or consists of all or a portion of an ITR derived from GPV. In some embodiments, the first ITR and/or the second ITR comprises or consists of a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to a nucleotide sequence selected from SEQ ID NOs: 172, 173, 174, 175, and 176, wherein the first ITR and/or the second ITR retains a functional property of the GPV ITR from which it is derived. In some embodiments, the first ITR and/or the second ITR comprises or consists of all or a portion of an ITR derived from GPV. In some embodiments, the first ITR and/or the second ITR comprises or consists of a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to a nucleotide sequence selected from SEQ ID NOs: 172, 173, 174, 175, and 176, wherein the first ITR and/or the second ITR is capable of forming a hairpin structure. In certain embodiments, the hairpin structure does not comprise a T-shaped hairpin. In some embodiments, the first ITR and/or the second ITR comprises or consists of a nucleotide sequence selected from SEQ ID NOs: 172, 173, 174, 175, and 176. In some embodiments, the first ITR and/or the second ITR comprises or consists of the nucleotide sequence set forth in SEQ ID NO: 172. In some embodiments, the first ITR and/or the second ITR comprises or consists of the nucleotide sequence set forth in SEQ ID NO: 173. In some embodiments, the first ITR and/or the second ITR comprises or consists of the nucleotide sequence set forth in SEQ ID NO: 174. In some embodiments, the first ITR and/or the second ITR comprises or consists of the nucleotide sequence set forth in SEQ ID NO: 175. In some embodiments, the first ITR and/or the second ITR comprises or consists of the nucleotide sequence set forth in SEQ ID NO: 176.

In certain embodiments, the first ITR and/or the second ITR comprises a nucleotide sequence, wherein the nucleotide sequence comprises the minimal nucleotide sequence set forth in SEQ ID NO: 174, and wherein the nucleotide sequence is a at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 172, wherein the first ITR and/or the second ITR retains a functional property of the GPV ITR from which it is derived. In some embodiments, the first ITR and/or the second ITR comprises a nucleotide sequence, wherein the nucleotide sequence comprises the minimal nucleotide sequence set forth in SEQ ID NO: 174, and wherein the nucleotide sequence is a at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 172, wherein the first ITR and/or the second ITR is capable of forming a hairpin structure. In certain embodiments, the hairpin structure does not comprise a T-shaped hairpin.

In certain embodiments, the first ITR and/or the second ITR comprises a nucleotide sequence, wherein the nucleotide sequence comprises the minimal nucleotide sequence set forth in SEQ ID NO: 176, and wherein the nucleotide sequence is a at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 172, wherein the first ITR and/or the second ITR retains a functional property of the GPV ITR from which it is derived. In some embodiments, the first ITR and/or the second ITR comprises a nucleotide sequence, wherein the nucleotide sequence comprises the minimal nucleotide sequence set forth in SEQ ID NO: 176, and wherein the nucleotide sequence is a at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 172, wherein the first ITR and/or the second ITR is capable of forming a hairpin structure. In certain embodiments, the hairpin structure does not comprise a T-shaped hairpin.

In certain embodiments, the first ITR and/or the second ITR comprises or consists of all or a portion of an ITR derived from GPV. In some embodiments, the second ITR is a reverse complement of the first ITR. In some embodiments, the first ITR is a reverse complement of the second ITR. In some embodiments, the first ITR and/or the second ITR comprises or consists of a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to a nucleotide sequence selected from SEQ ID NOs: 183, 184, 187 and 188, or a functional derivative thereof. In some embodiments, the functional derivative retains a functional property of the GPV ITR from which it is derived. In some embodiments, the first ITR and/or the second ITR comprises or consists of a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to a nucleotide sequence selected from SEQ ID NOs: 183, 184, 187 and 188, or a functional derivative thereof. In some embodiments, the functional derivative is capable of forming a hairpin structure. In certain embodiments, the hairpin structure does not comprise a T-shaped hairpin.

In certain embodiments, the first ITR and/or the second ITR comprises a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 183. In certain embodiments, the first ITR and/or the second ITR consists of SEQ ID NO: 183. In certain embodiments, the first ITR and/or the second ITR comprises a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 184. In certain embodiments, the first ITR and/or the second ITR consists of SEQ ID NO: 184. In certain embodiments, the first ITR and/or the second ITR comprises a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 187. In certain embodiments, the first ITR and/or the second ITR consists of SEQ ID NO: 187. In certain embodiments, the first ITR and/or the second ITR comprises a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to the nucleotide sequence set forth in SEQ ID NO: 188. In certain embodiments, the first ITR and/or the second ITR consists of SEQ ID NO: 188.

In some embodiments, the first ITR and/or the second ITR comprises or consists of a nucleotide sequence selected from SEQ ID NOs: 183, 184, 187 and 188. In some embodiments, the first ITR comprises or consists of the nucleotide sequence set forth in SEQ ID NO: 183. In some embodiments, the first ITR comprises or consists of the nucleotide sequence set forth in SEQ ID NO: 184. In some embodiments, the first ITR comprises or consists of the nucleotide sequence set forth in SEQ ID NO: 187. In some embodiments, the first ITR comprises or consists of the nucleotide sequence set forth in SEQ ID NO: 188. In some embodiments, the second ITR comprises or consists of the nucleotide sequence set forth in SEQ ID NO: 183. In some embodiments, the second ITR comprises or consists of the nucleotide sequence set forth in SEQ ID NO: 184. In some embodiments, the second ITR comprises or consists of the nucleotide sequence set forth in SEQ ID NO: 187. In some embodiments, the second ITR comprises or consists of the nucleotide sequence set forth in SEQ ID NO: 188.

In some embodiments, the first ITR comprises or consists of the nucleotide sequence set forth in SEQ ID NO:183, and the second ITR comprises or consists of the nucleotide sequence set forth in SEQ ID NO: 184. In some embodiments, the first ITR comprises or consists of the nucleotide sequence set forth in SEQ ID NO:184, and the second ITR comprises or consists of the nucleotide sequence set forth in SEQ ID NO: 183. In some embodiments, the first ITR comprises or consists of the nucleotide sequence set forth in SEQ ID NO:187, and the second ITR comprises or consists of the nucleotide sequence set forth in SEQ ID NO: 188. In some embodiments, the first ITR comprises or consists of the nucleotide sequence set forth in SEQ ID NO:188, and the second ITR comprises or consists of the nucleotide sequence set forth in SEQ ID NO: 187.

In certain embodiments, one of the first ITR or the second ITR comprises or consists of all or a portion of an ITR derived from AAV2. In some embodiments, the first ITR or the second ITR comprises or consists of a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NOs: 177 or 178, wherein the first ITR and/or the second ITR retains a functional property of the AAV2 ITR from which it is derived. In some embodiments, the first ITR or the second ITR comprises or consists of a nucleotide sequence at least about 50%, at least about 55%, at least about 60%, at least about 65%, at least about 65%, at least about 70%, at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NOs: 177 or 178, wherein the first ITR and/or the second ITR is capable of forming a hairpin structure. In certain embodiments, the hairpin structure does not comprise a T-shaped hairpin. In some embodiments, the first ITR and/or the second ITR comprises or consists of a nucleotide sequence set forth in SEQ ID NOs: 177 or 178. In some embodiments, the first ITR and/or the second ITR comprises or consists of the nucleotide sequence set forth in SEQ ID NO: 177. In some embodiments, the first ITR and/or the second ITR comprises or consists of the nucleotide sequence set forth in SEQ ID NO: 178.

In some embodiments, the first ITR is derived from an AAV genome, and the second ITR is derived from a Muscovy duck parvovirus (MDPV) strain. In other embodiments, the second ITR is derived from an AAV genome, and the first ITR is derived from a Muscovy duck parvovirus (MDPV) strain. In certain embodiments, the MDPV strain is attenuated, e.g., MDPV strain FZ91-30. In other embodiments, the MDPV strain is pathogenic, e.g., MDPV strain YY.

In some embodiments, the first ITR is derived from an AAV genome, and the second ITR is derived from a Dependoparvovirus. In some embodiments, the second ITR is derived from an AAV genome, and the first ITR is derived from a Dependoparvovirus. In other embodiments, the first ITR is derived from an AAV genome, and the second ITR is derived from a *Dependovirus* goose parvovirus (GPV) strain. In other embodiments, the second ITR is derived from an AAV genome, and the first ITR is derived from a *Dependovirus* GPV strain. In certain embodiments, the GPV strain is attenuated, e.g., GPV strain 82-0321V. In other embodiments, the GPV strain is pathogenic, e.g., GPV strain B.

In certain embodiments, the first ITR is derived from an AAV genome, and the second ITR is derived from a genome selected from the group consisting of porcine parvovirus, e.g., porcine parvovirus strain U44978; mice minute virus, e.g., mice minute virus strain U34256; canine parvovirus, e.g., canine parvovirus strain M19296; mink enteritis virus, e.g., mink enteritis virus strain D00765; and any combination thereof. In other embodiments, the second ITR is derived from an AAV genome, and the first ITR is derived from a genome selected from the group consisting of porcine parvovirus, e.g., porcine parvovirus strain U44978; mice minute virus, e.g., mice minute virus strain U34256; canine parvovirus, e.g., canine parvovirus strain M19296; mink enteritis virus, e.g., mink enteritis virus strain D00765; and any combination thereof.

In another particular embodiment, the ITR is a synthetic sequence genetically engineered to include at its 5' and 3' ends ITRs not derived from an AAV genome. In another particular embodiment, the ITR is a synthetic sequence genetically engineered to include at its 5' and 3' ends ITRs derived from one or more of non-AAV genomes. The two ITRs present in the nucleic acid molecule of the invention can be the same or different non-AAV genomes. In particular, the ITRs can be derived from the same non-AAV genome. In a specific embodiment, the two ITRs present in the nucleic acid molecule of the invention are the same, and can in particular be AAV2 ITRs.

In some embodiments, the ITR sequence comprises one or more palindromic sequence. A palindromic sequence of an ITR disclosed herein includes, but is not limited to, native palindromic sequences (i.e., sequences found in nature), synthetic sequences (i.e., sequences not found in nature), such as pseudo palindromic sequences, and combinations or modified forms thereof. A "pseudo palindromic sequence" is a palindromic DNA sequence, including an imperfect palindromic sequence, which shares less than 80% including less than 70%, 60%, 50%, 40%, 30%, 20%, 10%, or 5%, or no, nucleic acid sequence identity to sequences in native AAV or non-AAV palindromic sequence which form a secondary structure. The native palindromic sequences can be obtained or derived from any genome disclosed herein. The synthetic palindromic sequence can be based on any genome disclosed herein.

The palindromic sequence can be continuous or interrupted. In some embodiments, the palindromic sequence is interrupted, wherein the palindromic sequence comprises an insertion of a second sequence. In some embodiments, the second sequence comprises a promoter, an enhancer, an integration site for an integrase (e.g., sites for Cre or Flp recombinase), an open reading frame for a gene product, or a combination thereof.

In some embodiments, the ITRs form hairpin loop structures. In one embodiment, the first ITR forms a hairpin structure. In another embodiment, the second ITR forms a hairpin structure. Still in another embodiment, both the first ITR and the second ITR form hairpin structures. In some embodiments, the first ITR and/or the second ITR does not form a T-shaped hairpin structure. In certain embodiments, the first ITR and/or the second ITR forms a non-T-shaped hairpin structure. In some embodiments, the non-T-shaped hairpin structure comprises a U-shaped hairpin structure.

In some embodiments, an ITR in a nucleic acid molecule described herein may be a transcriptionally activated ITR. A transcriptionally-activated ITR can comprise all or a portion of a wild-type ITR that has been transcriptionally activated by inclusion of at least one transcriptionally active element. Various types of transcriptionally active elements are suitable for use in this context. In some embodiments, the transcriptionally active element is a constitutive transcriptionally active element. Constitutive transcriptionally active elements provide an ongoing level of gene transcription, and are preferred when it is desired that the transgene be expressed on an ongoing basis. In other embodiments, the transcriptionally active element is an inducible transcriptionally active element. Inducible transcriptionally active elements generally exhibit low activity in the absence of an inducer (or inducing condition), and are up-regulated in the presence of the inducer (or switch to an inducing condition). Inducible transcriptionally active elements may be preferred when expression is desired only at certain times or at certain locations, or when it is desirable to titrate the level of expression using an inducing agent. Transcriptionally active elements can also be tissue-specific; that is, they exhibit activity only in certain tissues or cell types.

Transcriptionally active elements, can be incorporated into an ITR in a variety of ways. In some embodiments, a transcriptionally active element is incorporated 5' to any portion of an ITR or 3' to any portion of an ITR. In other embodiments, a transcriptionally active element of a transcriptionally-activated ITR lies between two ITR sequences. If the transcriptionally active element comprises two or more elements which must be spaced apart, those elements may alternate with portions of the ITR. In some embodiments, a hairpin structure of an ITR is deleted and replaced with inverted repeats of a transcriptional element. This latter arrangement would create a hairpin mimicking the deleted portion in structure. Multiple tandem transcriptionally active elements can also be present in a transcriptionally-activated ITR, and these may be adjacent or spaced apart. In addition, protein binding sites (e.g., Rep binding sites) can be introduced into transcriptionally active elements of the transcriptionally-activated ITRs. A transcriptionally active element can comprise any sequence enabling the controlled transcription of DNA by RNA polymerase to form RNA, and can comprise, for example, a transcriptionally active element, as defined below.

Transcriptionally-activated ITRs provide both transcriptional activation and ITR functions to the nucleic acid molecule in a relatively limited nucleotide sequence length which effectively maximizes the length of a transgene which can be carried and expressed from the nucleic acid molecule. Incorporation of a transcriptionally active element into an ITR can be accomplished in a variety of ways. A comparison of the ITR sequence and the sequence requirements of the transcriptionally active element can provide insight into ways to encode the element within an ITR. For example, transcriptional activity can be added to an ITR through the introduction of specific changes in the ITR sequence that replicates the functional elements of the transcriptionally active element. A number of techniques exist in the art to efficiently add, delete, and/or change particular nucleotide sequences at specific sites (see, for example, Deng and Nickoloff (1992) Anal. Biochem. 200:81-88). Another way to create transcriptionally-activated ITRs involves the introduction of a restriction site at a desired location in the ITR. In addition, multiple transcriptionally activate elements can be incorporated into a transcriptionally-activated ITR, using methods known in the art.

By way of illustration, transcriptionally-activated ITRs can be generated by inclusion of one or more transcriptionally active elements such as: TATA box, GC box, CCAAT box, Sp1 site, Inr region, CRE (cAMP regulatory element) site, ATF-1/CRE site, APBβ. box, APBα box, CArG box, CCAC box, or any other element involved in transcription as known in the art.

Aspects of the present disclosure provide a method of cloning a nucleic acid molecule described herein, comprising inserting a nucleic acid molecule capable of complex secondary structures into a suitable vector, and introducing the resulting vector into a suitable bacterial host strain. As known in the art, complex secondary structures (e.g., long palindromic regions) of nucleic acids may be unstable and difficult to clone in bacterial host strains. For example, nucleic acid molecules comprising a first ITR and a second ITR (e.g., non-AAV parvoviral ITRs, e.g., B19 or GPV ITRs) of the present disclosure may be difficult to clone using conventional methodologies. Long DNA plindromes inhibit DNA replication and are unstable in the genomes of *E. coli*, *Bacillus*, *Steptococcus*, *Streptomyces*, *S. cerevisiae*, mice, and humans. These effects result from the formation of hairpin or cruciform structures by intrastrand base pairing. In *E. coli* the inhibition of DNA replication can be significantly overcome in SbcC or SbcD mutants. SbcD is the nuclease subunit, and SbcC is the ATPase subunit of the SbcCD complex. The *E. coli* SbcCD complex is an exonuclease complex responsible for preventing the replication of long palindromes. The SbcCD complex is a nuclear with ATP-dependent double-stranded DNA exonuclease activity and ATP-independent single-stranded DNA endonuclease activity. SbcCD may recognize DNA plaindromes and collapse replication forks by attacking hairpin structures that arise.

In certain embodiments, a suitable bacterial host strain is incapable of resolving cruciform DNA structures. In certain embodiments, a suitable bacterial host strain comprises a disruption in the SbcCD complex. In some embodiments, the disruption in the SbcCD complex comprises a genetic disruption in the SbcC gene and/or SbcD gene. In certain embodiments, the disruption in the SbcCD complex comprises a genetic disruption in the SbcC gene. Various bacterial host strains that comprise a genetic disruption in the SbcC gene are known in the art. For example, without limitation, the bacterial host strain PMC103 comprises the genotype sbcC, recD, mcrA, ΔmcrBCF; the bacterial host strain PMC107 comprises the genotype recBC, recJ, sbcBC, mcrA, ΔmcrBCF; and the bacterial host strain SURE comprises the genotype recB, recJ, sbcC, mcrA, ΔmcrBCF, umuC, uvrC. Accordingly, in some embodiments a method of cloning a nucleic acid molecule described herein comprises inserting a nucleic acid molecule capable of complex secondary structures into a suitable vector, and introducing the resulting vector into host strain PMC103, PMC107, or SURE. In certain embodiments, the method of cloning a nucleic acid molecule described herein comprises inserting a nucleic acid molecule capable of complex secondary structures into a suitable vector, and introducing the resulting vector into host strain PMC103.

Suitable vectors are known in the art and described elsewhere herein. In certain embodiments, a suitable vector for use in a cloning methodology of the present disclosure is a low copy vector. In certain embodiments, a suitable vector for use in a cloning methodology of the present disclosure is pBR322.

Accordingly, the present disclosure provides a method of cloning a nucleic acid molecule, comprising inserting a nucleic acid molecule capable of complex secondary structures into a suitable vector, and introducing the resulting vector into a bacterial host strain comprising a disruption in the SbcCD complex, wherein the nucleic acid molecule comprises a first inverted terminal repeat (ITR) and a second ITR, wherein the first ITR and/or second ITR comprises a nucleotide sequence at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NO: 180, 181, 183, 184, 185, 186, 187 or 188, or a functional derivative thereof.

B. Therapeutic Proteins

Certain aspects of the present disclosure are directed to a nucleic acid molecule comprising a first ITR, a second ITR, and a genetic cassette encoding a target sequence, wherein the target sequence encodes a therapeutic protein. In some embodiments, the genetic cassette encodes one therapeutic protein. In some embodiments, the genetic cassette encodes more than one therapeutic protein. In some embodiments, the genetic cassette encodes two or more copies of the same therapeutic protein. In some embodiments, the genetic cassette encodes two or more variants of the same therapeutic protein. In some embodiments, the genetic cassette encodes two or more different therapeutic proteins.

Certain embodiments of the present disclosure are directed to a nucleic acid molecule comprising a first ITR, a second ITR, and a genetic cassette encoding a therapeutic protein, wherein the therapeutic protein comprises a clotting factor. In some embodiments, the clotting factor is selected from the group consisting of FI, FII, FIII, FIV, FV, FVI, FVII, FVIII, FIX, FX, FXI, FXII, FXIII), VWF, prekallikrein, high-molecular weight kininogen, fibronectin, antithrombin III, heparin cofactor II, protein C, protein S, protein Z, Protein Z-related protease inhibitor (ZPI), plasminogen, alpha 2-antiplasmin, tissue plasminogen activator (tPA), urokinase, plasminogen activator inhibitor-1 (PAI-1), plasminogen activator inhibitor-2 (PAI2), any zymogen thereof, any active form thereof, and any combination thereof. In one embodiment, the clotting factor comprises FVIII or a variant or fragment thereof. In another embodiment, the clotting factor comprises FIX or a variant or fragment thereof. In another embodiment, the clotting factor comprises FVII or a variant or fragment thereof. In another embodiment, the clotting factor comprises VWF or a variant or fragment thereof.

1. Clotting Factors

In some embodiments, the nucleic acid molecule comprises a first ITR, a second ITR, and a genetic cassette encoding a target sequence, wherein the target sequence encodes a therapeutic protein, wherein the therapeutic protein comprises a factor VIII polypeptide. "Factor VIII," abbreviated throughout the instant application as "FVIII," as used herein, means functional FVIII polypeptide in its normal role in coagulation, unless otherwise specified. Thus, the term FVIII includes variant polypeptides that are functional. "A FVIII protein" is used interchangeably with FVIII polypeptide (or protein) or FVIII. Examples of the FVIII functions include, but are not limited to, an ability to activate coagulation, an ability to act as a cofactor for factor IX, or an ability to form a tenase complex with factor IX in the presence of $Ca^{2+}$ and phospholipids, which then converts Factor X to the activated form Xa. The FVIII protein can be the human, porcine, canine, rat, or murine FVIII protein. In addition, comparisons between FVIII from humans and other species have identified conserved residues that are likely to be required for function (Cameron et al., *Thromb. Haemost.* 79:317-22 (1998); U.S. Pat. No. 6,251,632). The full length polypeptide and polynucleotide sequences are known, as are many functional fragments, mutants and modified versions. Various FVIII amino acid and nucleotide sequences are disclosed in, e.g., US Publication Nos. 2015/0158929 A1, 2014/0308280 A1, and 2014/0370035 A1 and International Publication No. WO 2015/106052 A1. FVIII polypeptides include, e.g., full-length FVIII, full-length FVIII minus Met at the N-terminus, mature FVIII (minus the signal sequence), mature FVIII with an additional Met at the N-terminus, and/or FVIII with a full or partial deletion of the B domain. FVIII variants include B domain deletions, whether partial or full deletions.

a. FVIII and Polynucleotide Sequences Encoding the FVIII Protein

In some embodiments, the nucleic acid molecule comprises a first ITR, a second ITR, and a genetic cassette encoding a target sequence, wherein the target sequence encodes a therapeutic protein, wherein the therapeutic protein comprises a factor VIII polypeptide. "Factor VIII," abbreviated throughout the instant application as "FVIII," as used herein, means functional FVIII polypeptide in its normal role in coagulation, unless otherwise specified. Thus, the term FVIII includes variant polypeptides that are functional. "A FVIII protein" is used interchangeably with FVIII polypeptide (or protein) or FVIII. Examples of the FVIII functions include, but are not limited to, an ability to activate coagulation, an ability to act as a cofactor for factor IX, or an ability to form a tenase complex with factor IX in the presence of $Ca^{2+}$ and phospholipids, which then converts Factor X to the activated form Xa. The FVIII protein can be the human, porcine, canine, rat, or murine FVIII protein. In addition, comparisons between FVIII from humans and other species have identified conserved residues that are likely to be required for function (Cameron et al., *Thromb. Haemost.* 79:317-22 (1998); U.S. Pat. No. 6,251,632). The full-length polypeptide and polynucleotide sequences are known, as are many functional fragments, mutants and modified versions. Various FVIII amino acid and nucleotide sequences are disclosed in, e.g., US Publication Nos. 2015/0158929 A1, 2014/0308280 A1, and 2014/0370035 A1 and International Publication No. WO 2015/106052 A1. FVIII polypeptides include, e.g., full-length FVIII, full-length FVIII minus Met at the N-terminus, mature FVIII (minus the signal sequence), mature FVIII with an additional Met at the N-terminus, and/or FVIII with a full or partial deletion of the B domain. FVIII variants include B domain deletions, whether partial or full deletions.

The FVIII portion in the chimeric protein used herein has FVIII activity. FVIII activity can be measured by any known methods in the art. A number of tests are available to assess the function of the coagulation system: activated partial thromboplastin time (aPTT) test, chromogenic assay, ROTEM assay, prothrombin time (PT) test (also used to determine INR), fibrinogen testing (often by the Clauss method), platelet count, platelet function testing (often by PFA-100), TCT, bleeding time, mixing test (whether an abnormality corrects if the patient's plasma is mixed with normal plasma), coagulation factor assays, antiphospholipid antibodies, D-dimer, genetic tests (e.g., factor V Leiden, prothrombin mutation G20210A), dilute Russell's viper venom time (dRVVT), miscellaneous platelet function tests, thromboelastography (TEG or Sonoclot), thromboelastometry (TEM®, e.g., ROTEM®), or euglobulin lysis time (ELT).

The aPTT test is a performance indicator measuring the efficacy of both the "intrinsic" (also referred to the contact activation pathway) and the common coagulation pathways. This test is commonly used to measure clotting activity of commercially available recombinant clotting factors, e.g., FVIII. It is used in conjunction with prothrombin time (PT), which measures the extrinsic pathway.

ROTEM analysis provides information on the whole kinetics of haemostasis: clotting time, clot formation, clot stability and lysis. The different parameters in thromboelastometry are dependent on the activity of the plasmatic coagulation system, platelet function, fibrinolysis, or many factors which influence these interactions. This assay can provide a complete view of secondary haemostasis.

The chromogenic assay mechanism is based on the principles of the blood coagulation cascade, where activated FVIII accelerates the conversion of Factor X into Factor Xa in the presence of activated Factor IX, phospholipids and calcium ions. The Factor Xa activity is assessed by hydrolysis of a p-nitroanilide (pNA) substrate specific to Factor Xa. The initial rate of release of p-nitroaniline measured at 405 nM is directly proportional to the Factor Xa activity and thus to the FVIII activity in the sample.

The chromogenic assay is recommended by the FVIII and Factor IX Subcommittee of the Scientific and Standardization Committee (SSC) of the International Society on Thrombosis and Hemostatsis (ISTH). Since 1994, the chromogenic assay has also been the reference method of the European Pharmacopoeia for the assignment of FVIII concentrate potency. Thus, in one embodiment, the chimeric polypeptide comprising FVIII has FVIII activity comparable to a chimeric polypeptide comprising mature FVIII or a BDD FVIII (e.g., ADVATE®, REFACTO®, or ELOCTATE®).

In another embodiment, the chimeric protein comprising FVIII of this disclosure has a Factor Xa generation rate comparable to a chimeric protein comprising mature FVIII or a BDD FVIII (e.g., ADVATE®, REFACTO®, or ELOCTATE®).

In order to activate Factor X to Factor Xa, activated Factor IX (Factor IXa) hydrolyzes one arginine-isoleucine bond in Factor X to form Factor Xa in the presence of $Ca^{2+}$, membrane phospholipids, and a FVIII cofactor. Therefore, the interaction of FVIII with Factor IX is critical in coagulation pathway. In certain embodiments, the chimeric polypeptide comprising FVIII can interact with Factor IXa at a rate comparable to a chimeric polypeptide comprising mature FVIII sequence or a BDD FVIII (e.g., ADVATE®, REFACTO®, or ELOCTATE®).

In addition, FVIII is bound to von Willebrand Factor while inactive in circulation. FVIII degrades rapidly when not bound to VWF and is released from VWF by the action of thrombin. In some embodiments, the chimeric polypeptide comprising FVIII binds to von Willebrand Factor at a level comparable to a chimeric polypeptide comprising mature FVIII sequence or a BDD FVIII (e.g., ADVATE®, REFACTO®, or ELOCTATE®).

FVIII can be inactivated by activated protein C in the presence of calcium and phospholipids. Activated protein C cleaves FVIII heavy chain after Arginine 336 in the A1 domain, which disrupts a Factor X substrate interaction site, and cleaves after Arginine 562 in the A2 domain, which enhances the dissociation of the A2 domain as well as disrupts an interaction site with the Factor IXa. This cleavage also bisects the A2 domain (43 kDa) and generates A2-N (18 kDa) and A2-C (25 kDa) domains. Thus, activated protein C can catalyze multiple cleavage sites in the heavy chain. In one embodiment, the chimeric polypeptide comprising FVIII is inactivated by activated Protein C at a level comparable to a chimeric polypeptide comprising mature FVIII sequence or a BDD FVIII (e.g., ADVATE®, REFACTO®, or ELOCTATE®).

In other embodiments, the chimeric protein comprising FVIII has FVIII activity in vivo comparable to a chimeric polypeptide comprising mature FVIII sequence or a BDD FVIII (e.g., ADVATE®, REFACTO®, or ELOCTATE®). In a particular embodiment, the chimeric polypeptide comprising FVIII is capable of protecting a HemA mouse at a level comparable to a chimeric polypeptide comprising mature FVIII sequence or a BDD FVIII (e.g., ADVATE®, REFACTO®, or ELOCTATE®) in a HemA mouse tail vein transection model.

A "B domain" of FVIII, as used herein, is the same as the B domain known in the art that is defined by internal amino acid sequence identity and sites of proteolytic cleavage by thrombin, e.g., residues Ser741-Arg1648 of mature human FVIII. The other human FVIII domains are defined by the following amino acid residues, relative to mature human FVIII: A1, residues Ala1-Arg372; A2, residues Ser373-Arg740; A3, residues Ser1690-Ile2032; C1, residues Arg2033-Asn2172; C2, residues Ser2173-Tyr2332 of mature FVIII. The sequence residue numbers used herein without referring to any SEQ ID Numbers correspond to the FVIII sequence without the signal peptide sequence (19 amino acids) unless otherwise indicated. The A3-C1-C2 sequence, also known as the FVIII heavy chain, includes residues Ser1690-Tyr2332. The remaining sequence, residues Glu1649-Arg1689, is usually referred to as the FVIII light chain activation peptide. The locations of the boundaries for all of the domains, including the B domains, for porcine, mouse and canine FVIII are also known in the art. In one embodiment, the B domain of FVIII is deleted ("B-domain-deleted FVIII" or "BDD FVIII"). An example of a BDD FVIII is REFACTO® (recombinant BDD FVIII). In one particular embodiment the B domain deleted FVIII variant comprises a deletion of amino acid residues 746 to 1648 of mature FVIII.

A "B-domain-deleted FVIII" may have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563 and Intl Publ. No. WO 2015106052 A1 (PCT/US2015/010738). In some embodiments, a B-domain-deleted FVIII sequence used in the methods of the present disclosure comprises any one of the deletions disclosed at col. 4, line 4 to col. 5, line 28 and Examples 1-5 of U.S. Pat. No. 6,316,226 (also in U.S. Pat. No. 6,346,513). In another embodiment, a B-domain deleted Factor VIII is the 5743/Q1638 B-domain deleted Factor VIII (SQ BDD FVIII) (e.g., Factor VIII having a deletion from amino acid 744 to amino acid 1637, e.g., Factor VIII having amino acids 1-743 and amino acids 1638-2332 of mature FVIII). In some embodiments, a B-domain-deleted FVIII used in the methods of the present disclosure has a deletion disclosed at col. 2, lines 26-51 and examples 5-8 of U.S. Pat. No. 5,789,203 (also U.S. Pat. Nos. 6,060,447, 5,595,886, and 6,228,620). In some embodiments, a B-domain-deleted Factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B-domain-deleted FVIII has a deletion of most of the B domain, but still contains amino-terminal sequences of the B domain that are essential for in vivo proteolytic processing of the primary translation product into two polypeptide chain, as disclosed in WO 91/09122. In some embodiments, a B-domain-deleted FVIII is constructed with a deletion of amino acids 747-1638, i.e., virtually a complete deletion of the B domain. Hoeben R. C., et al. *J. Biol. Chem.* 265 (13): 7318-7323 (1990). A B-domain-deleted Factor VIII may also contain a deletion of amino acids 771-1666 or amino acids 868-1562 of FVIII. Meulien P., et al. *Protein Eng.* 2(4): 301-6 (1988). Additional B domain deletions that are part of the invention include: deletion of amino acids 982 through 1562 or 760 through 1639 (Toole et al., *Proc. Natl. Acad. Sci. U.S.A.* (1986) 83, 5939-5942)), 797 through 1562 (Eaton, et al. *Biochemistry* (1986) 25:8343-8347)), 741 through 1646 (Kaufman (PCT published application No. WO 87/04187)), 747-1560 (Sarver, et al., DNA (1987) 6:553-564)), 741 through 1648 (Pasek (PCT application No. 88/00831)), or 816 through 1598 or 741 through 1648 (Lagner (Behring Inst. Mitt. (1988) No 82:16-25, EP 295597)). In one particular embodiment, the B-domain-deleted FVIII comprises a deletion of amino acid residues 746 to 1648 of mature FVIII. In another embodiment, the B-domain-deleted FVIII comprises a deletion of amino acid residues 745 to 1648 of mature FVIII. In some embodiments, the BDD FVIII comprises single chain FVIII that contains a deletion in amino acids 765 to 1652 corresponding to the mature full length FVIII (also known as rVIII-SingleChain and AFSTYLA®). See U.S. Pat. No. 7,041,635.

In other embodiments, BDD FVIII includes a FVIII polypeptide containing fragments of the B-domain that retain one or more N-linked glycosylation sites, e.g., residues 757, 784, 828, 900, 963, or optionally 943, which correspond to the amino acid sequence of the full-length FVIII sequence. Examples of the B-domain fragments include 226 amino acids or 163 amino acids of the B-domain as disclosed in Miao, H. Z., et al., *Blood* 103(a): 3412-3419 (2004), Kasuda, A, et al., *J. Thromb. Haemost.* 6: 1352-1359 (2008), and Pipe, S. W., et al., *J. Thromb. Haemost.* 9: 2235-2242 (2011) (i.e., the first 226 amino acids or 163 amino acids of the B domain are retained). In still other embodiments, BDD FVIII further comprises a point mutation at residue 309 (from Phe to Ser) to improve expression of the BDD FVIII protein. See Miao, H. Z., et al., Blood 103(a): 3412-3419 (2004). In still other embodiments, the BDD FVIII includes a FVIII polypeptide containing a portion of the B-domain, but not containing one or more furin cleavage sites (e.g., Arg1313 and Arg 1648). See Pipe, S. W., et al., *J. Thromb. Haemost.* 9: 2235-2242 (2011). In some embodiments, the BDD FVIII comprises single chain FVIII that contains a deletion in amino acids 765 to 1652 corresponding to the mature full length FVIII (also known as rVIII-SingleChain and AFSTYLA®). See U.S. Pat. No. 7,041,635. Each of the foregoing deletions may be made in any FVIII sequence.

A great many functional FVIII variants are known, as is discussed above and below. In addition, hundreds of non-functional mutations in FVIII have been identified in hemophilia patients, and it has been determined that the effect of these mutations on FVIII function is due more to where they lie within the 3-dimensional structure of FVIII than on the nature of the substitution (Cutler et al., *Hum. Mutat.* 19:274-8 (2002)), incorporated herein by reference in its entirety. In addition, comparisons between FVIII from humans and other species have identified conserved residues that are likely to be required for function (Cameron et al., Thromb. Haemost. 79:317-22 (1998); U.S. Pat. No. 6,251,632), incorporated herein by reference in its entirety.

In some embodiments, the FVIII polypeptide comprises a FVIII variant or fragment thereof, wherein the FVIII variant or the fragment thereof has a FVIII activity. In some embodiments, the genetic cassette encodes a full-length FVIII polypeptide. In other embodiments, the genetic cassette encodes a B domain-deleted (BDD) FVIII polypeptide, wherein all or a portion of the B domain of FVIII is deleted. In one particular embodiment, the genetic cassette encodes a polypeptide comprising an amino acid sequence having at least about 80%, at least about 85%, at least about 86%, at least about 87%, at least about 88%, at least about 89%, at least about 90%, at least about 95%, at least about 96%, at least about 97%, at least about 98%, or at least about 99% sequence identity to SEQ ID NOs: 106, 107, 109, 110, 111, or 112. In some embodiments, the genetic cassette encodes a polypeptide having the amino acid sequence of SEQ ID NO: 17 or a fragment thereof. In some embodiments, the genetic cassette encodes a polypeptide having the amino acid sequence of SEQ ID NO: 106 or a fragment thereof. In some embodiments, the genetic cassette comprises a nucleotide sequence which has at least 85%, at least 90%, at least 95%, at least 96%, at least 97%, at least 98%, or at least 99% sequence identity to SEQ ID NO: 107. In some embodiments, the genetic cassette encodes a polypeptide having the amino acid sequence of SEQ ID NO: 109 or a fragment thereof. In some embodiments, the genetic cassette comprises a nucleotide sequence which has at least 85%, at least 90%, at least 95%, at least 96%, at least 97%, at least 98%, or at least 99% sequence identity to SEQ ID NO: 16. In some embodiments, the genetic cassette comprises a nucleotide sequence which has at least 85%, at least 90%, at least 95%, at least 96%, at least 97%, at least 98%, or at least 99% sequence identity to SEQ ID NO: 109.

In some embodiments, the genetic cassette of the disclosure encodes a FVIII polypeptide comprising a signal peptide or a fragment thereof. In other embodiments, the genetic cassette encodes a FVIII polypeptide which lacks a signal peptide. In some embodiments, the signal peptide comprises amino acids 1-19 of SEQ ID NO: 17.

In some embodiments, the genetic cassette comprises a nucleotide sequence encoding a FVIII polypeptide, wherein the nucleotide sequence is codon optimized. In certain embodiments, the genetic cassette comprises a nucleotide sequence which is disclosed in International Application No. PCT/US2017/015879, which is incorporated by reference in its entirety. In some embodiments, the genetic cassette comprises a nucleotide sequence encoding a FVIII polypeptide, wherein the nucleotide sequence is codon optimized. In certain embodiments, the genetic cassette comprises a nucleotide sequence which has at least 85%, at least 90%, at least 95%, at least 96%, at least 97%, at least 98%, or at least 99% sequence identity to a nucleotide sequence selected from SEQ ID NOs: 1-14. In some embodiments, the genetic cassette comprises a nucleotide sequence which has at least 85%, at least 90%, at least 95%, at least 96%, at least 97%, at least 98%, or at least 99% sequence identity to SEQ ID NO: 71. In some embodiments, the genetic cassette comprises a nucleotide sequence which has at least 85%, at least 90%, at least 95%, at least 96%, at least 97%, at least 98%, or at least 99% sequence identity to SEQ ID NO: 19.

i. Codon Optimized Nucleotide Sequences Encoding FVIII Polypeptides

In some embodiments, a nucleic acid molecule of the present disclosure comprises a first ITR, a second ITR, and a genetic cassette encoding a target sequence, wherein the target sequence encodes a therapeutic protein, wherein the first ITR and the second ITR are derived from an AAV genome, and wherein the genetic cassette comprises a codon optimized nucleotide sequence encoding a FVIII polypeptide. In some embodiments, the codon optimized nucleotide sequence encodes a full-length FVIII polypeptide. In other embodiments, the codon optimized nucleotide sequence encodes a B domain-deleted (BDD) FVIII polypeptide, wherein all or a portion of the B domain of FVIII is deleted. In one particular embodiment, the codon optimized nucleotide sequence encodes a polypeptide comprising an amino acid sequence having at least about 80%, at least about 85%, at least about 86%, at least about 87%, at least about 88%, at least about 89%, at least about 90%, at least about 95%, at least about 96%, at least about 97%, at least about 98%, or at least about 99% sequence identity to SEQ ID NO: 17 or a fragment thereof. In one embodiment, the codon optimized nucleotide sequence encodes a polypeptide having the amino acid sequence of SEQ ID NO: 17 or a fragment thereof.

In some embodiments, the codon optimized nucleotide sequence encodes a FVIII polypeptide comprising a signal peptide or a fragment thereof. In other embodiments, the codon optimized sequence encodes a FVIII polypeptide which lacks a signal peptide. In some embodiments, the signal peptide comprises amino acids 1-19 of SEQ ID NO: 17.

In some embodiments, the codon optimized nucleotide sequence encoding a FVIII polypeptide comprises a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least 85%, at least 90%, at least 95%, at least 96%, at least 97%, at least 98%, or at least 99% sequence identity to (i) nucleotides 58-1791 of SEQ ID NO: 3 or (ii) nucleotides 58-1791 of SEQ ID NO: 4; and wherein the N-terminal portion and the C-terminal portion together have a FVIII polypeptide activity. In one particular embodiment, the first nucleic acid sequence has at least 85%, at least 90%, at least 95%, at least 96%, at least 97%, at least 98%, or at least 99% sequence identity to nucleotides 58-1791 of SEQ ID NO: 3. In another embodiment, the first nucleic acid sequence has at least 85%, at least 90%, at least 95%, at least 96%, at least 97%, at least 98%, or at least 99% sequence identity to nucleotides 58-1791 of SEQ ID NO: 4. In other embodiments, the first nucleotide sequence comprises nucleotides 58-1791 of SEQ ID NO: 3 or nucleotides 58-1791 of SEQ ID NO: 4.

In other embodiments, the codon optimized nucleotide sequence encoding a FVIII polypeptide comprises a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least 85%, at least 90%, at least 95%, at least 96%, at least 97%, at least 98%, or at least 99% sequence identity to (i) nucleotides 1-1791 of SEQ ID NO: 3 or (ii) nucleotides 1-1791 of SEQ ID NO: 4; and wherein the N-terminal portion and the C-terminal portion together have a FVIII polypeptide activity. In one embodiment, the first nucleotide sequence comprises nucleotides 1-1791 of SEQ ID NO: 3 or nucleotides 1-1791 of SEQ ID NO: 4. In another embodiment, the second nucleotide sequence has at least 60%, at least 70%, at least 80%, at least 90%, at least 95%, at least 96%, at least 97%, at least 98%, or at least 99% sequence identity to nucleotides 1792-4374 of SEQ ID NO: 3 or 1792-4374 of SEQ ID NO: 4. In one particular embodiment, the second nucleotide sequence comprises nucleotides 1792-4374 of SEQ ID NO: 3 or 1792-4374 of SEQ ID NO: 4. In still another embodiment, the second nucleotide sequence has at least 60%, at least 70%, at least 80%, at least 90%, at least 95%, at least 96%, at least 97%, at least 98%, or at least 99% sequence identity to nucleotides 1792-2277 and 2320-4374 of SEQ ID NO: 3 or 1792-2277 and 2320-4374 of SEQ ID NO: 4 (i.e., nucleotides 1792-4374 of SEQ ID NO: 3 or 1792-4374 of SEQ ID NO: 4 without the nucleotides encoding the B domain or B domain fragment). In one particular embodiment, the second nucleotide sequence comprises nucleotides 1792-2277 and 2320-4374 of SEQ ID NO: 3 or 1792-2277 and 2320-4374 of SEQ ID NO: 4 (i.e., nucleotides 1792-4374 of SEQ ID NO: 3 or 1792-4374 of SEQ ID NO: 4 without the nucleotides encoding the B domain or B domain fragment).

In some embodiments, the codon optimized nucleotide sequence encoding a FVIII polypeptide comprises a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least 85%, at least 90%, at least 95%, at least 96%, at least 97%, at least 98%, or at least 99% sequence identity to (i) nucleotides 1792-4374 of SEQ ID NO: 5 or (ii) 1792-4374 of SEQ ID NO: 6; and wherein the N-terminal portion and the C-terminal portion together have a FVIII polypeptide activity. In certain embodiments, the second nucleic acid sequence has at least 85%, at least 90%, at least 95%, at least 96%, at least 97%, at least 98%, or at least 99% sequence identity to nucleotides 1792-4374 of SEQ ID NO: 5. In other embodiments, the second nucleic acid sequence has at least 85%, at least 90%, at least 95%, at least 96%, at least 97%, at least 98%, or at least 99% sequence identity to nucleotides 1792-4374 of SEQ ID NO: 6. In one particular embodiment, the second nucleic acid sequence comprises nucleotides 1792-4374 of SEQ ID NO: 5 or 1792-4374 of SEQ ID NO: 6. In some embodiments, the first nucleic acid sequence linked to the second nucleic acid sequence listed above has at least 60%, at least 70%, at least 80%, at least 90%, at least 95%, at least 96%, at least 97%, at least 98%, or at least 99% sequence identity to nucleotides 58-1791 of SEQ ID NO: 5 or nucleotides 58-1791 of SEQ ID NO: 6. In other embodiments, the first nucleic acid sequence linked to the second nucleic acid sequence listed above has at least 60%, at least 70%, at least 80%, at least 90%, at least 95%, at least 96%, at least 97%, at least 98%, or at least 99% sequence identity to nucleotides 1-1791 of SEQ ID NO: 5 or nucleotides 1-1791 of SEQ ID NO: 6.

In other embodiments, the codon optimized nucleotide sequence encoding a FVIII polypeptide comprises a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least 85%, at least 90%, at least 95%, at least 96%, at least 97%, at least 98%, or at least 99% sequence identity to (i) nucleotides 1792-2277 and 2320-4374 of SEQ ID NO: 5 (i.e., nucleotides 1792-4374 of SEQ ID NO: 5 without the nucleotides encoding the B domain or B domain fragment) or (ii) 1792-2277 and 2320-4374 of SEQ ID NO: 6 (i.e., nucleotides 1792-4374 of SEQ ID NO: 6 without the nucleotides encoding the B domain or B domain fragment); and wherein the N-terminal portion and the C-terminal portion together have a FVIII polypeptide activity. In certain embodiments, the second nucleic acid sequence has at least 85%, at least 90%, at least 95%, at least 96%, at least 97%, at least 98%, or at least 99% sequence identity to nucleotides 1792-2277 and 2320-4374 of SEQ ID NO: 5 (i.e., nucleotides 1792-4374 of SEQ ID NO: 5 without the nucleotides encoding the B domain or B domain fragment). In other embodiments, the second nucleic acid sequence has at least 85%, at least 90%, at least 95%, at least 96%, at least 97%, at least 98%, or at least 99% sequence identity to nucleotides 1792-2277 and 2320-4374 of SEQ ID NO: 6 (i.e., nucleotides 1792-4374 of SEQ ID NO: 6 without the nucleotides encoding the B domain or B domain fragment). In one particular embodiment, the second nucleic acid sequence comprises nucleotides 1792-2277 and 2320-4374 of SEQ ID NO: 5 or 1792-2277 and 2320-4374 of SEQ ID NO: 6 (i.e., nucleotides 1792-4374 of SEQ ID NO: 5 or 1792-4374 of SEQ ID NO: 6 without the nucleotides encoding the B domain or B domain fragment). In some embodiments, the first nucleic acid sequence linked to the second nucleic acid sequence listed above has at least 60%, at least 70%, at least 80%, at least 90%, at least 95%, at least 96%, at least 97%, at least 98%, or at least 99% sequence identity to nucleotides 58-1791 of SEQ ID NO: 5 or nucleotides 58-1791 of SEQ ID NO: 6. In other embodiments, the first nucleic acid sequence linked to the second nucleic acid sequence listed above has at least 60%, at least 70%, at least 80%, at least 90%, at least 95%, at least 96%, at least 97%, at least 98%, or at least 99% sequence identity to nucleotides 1-1791 of SEQ ID NO: 5 or nucleotides 1-1791 of SEQ ID NO: 6.

In some embodiments, the codon optimized nucleotide sequence encoding a FVIII polypeptide comprises a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least 90%, at least 95%, at least 96%, at least 97%, at least 98%, or at least 99% sequence identity to (i) nucleotides 58-1791 of SEQ ID NO: 1, (ii) nucleotides 58-1791 of SEQ ID NO: 2, (iii) nucleotides 58-1791 of SEQ ID NO: 70, or (iv) nucleotides 58-1791 of SEQ ID NO: 71; and wherein the N-terminal portion and the C-terminal portion together have a FVIII polypeptide activity. In other embodiments, the first nucleotide sequence comprises nucleotides 58-1791 of SEQ ID NO: 1, nucleotides 58-1791 of SEQ ID NO: 2, (iii) nucleotides 58-1791 of SEQ ID NO: 70, or (iv) nucleotides 58-1791 of SEQ ID NO: 71.

In other embodiments, the codon optimized nucleotide sequence encoding a FVIII polypeptide comprises a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least 90%, at least 95%, at least 96%, at least 97%, at least 98%, or at least 99% sequence identity to (i) nucleotides 1-1791 of SEQ ID NO: 1, (ii) nucleotides 1-1791 of SEQ ID NO: 2, (iii) nucleotides 1-1791 of SEQ ID NO: 70, or (iv) nucleotides 1-1791 of SEQ ID NO: 71; and wherein the N-terminal portion and the C-terminal portion together have a FVIII polypeptide activity. In one embodiment, the first nucleotide sequence comprises nucleotides 1-1791 of SEQ ID NO: 1, nucleotides 1-1791 of SEQ ID NO: 2, (iii) nucleotides 1-1791 of SEQ ID NO: 70, or (iv) nucleotides 1-1791 of SEQ ID NO: 71. In another embodiment, the second nucleotide sequence linked to the first nucleotide sequence has at least 60%, at least 70%, at least 80%, at least 90%, at least 95%, at least 96%, at least 97%, at least 98%, or at least 99% sequence identity to nucleotides 1792-4374 of SEQ ID NO: 1, 1792-4374 of SEQ ID NO: 2, (iii) nucleotides 1792-4374 of SEQ ID NO: 70, or (iv) nucleotides 1792-4374 of SEQ ID NO: 71. In one particular embodiment, the second nucleotide sequence linked to the first nucleotide sequence comprises (i) nucleotides 1792-4374 of SEQ ID NO: 1, (ii) nucleotides 1792-4374 of SEQ ID NO: 2, (iii) nucleotides 1792-4374 of SEQ ID NO: 70, or (iv) nucleotides 1792-4374 of SEQ ID NO: 71. In other embodiments, the second nucleotide sequence linked to the first nucleotide sequence has at least 60%, at least 70%, at least 80%, at least 90%, at least 95%, at least 96%, at least 97%, at least 98%, or at least 99% sequence identity to (i) nucleotides 1792-2277 and 2320-4374 of SEQ ID NO: 1, (ii) nucleotides 1792-2277 and 2320-4374 of SEQ ID NO: 2, (iii) nucleotides 1792-2277 and 2320-4374 of SEQ ID NO: 70, or (iv) nucleotides 1792-2277 and 2320-4374 of SEQ ID NO: 71. In one embodiment, the second nucleotide sequence comprises (i) nucleotides 1792-2277 and 2320-4374 of SEQ ID NO: 1, (ii) nucleotides 1792-2277 and 2320-4374 of SEQ ID NO: 2, (iii) nucleotides 1792-2277 and 2320-4374 of SEQ ID NO: 70, or (iv) nucleotides 1792-2277 and 2320-4374 of SEQ ID NO: 71.

In another embodiment, the codon optimized nucleotide sequence encoding a FVIII polypeptide comprises a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least 90%, at least 95%, at least 96%, at least 97%, at least 98%, or at least 99% sequence identity to (i) nucleotides 1792-4374 of SEQ ID NO: 1, (ii) nucleotides 1792-4374 of SEQ ID NO: 2, (iii) nucleotides 1792-4374 of SEQ ID NO: 70, or (iv) nucleotides 1792-4374 of SEQ ID NO: 71; and wherein the N-terminal portion and the C-terminal portion together have a FVIII polypeptide activity. In one particular embodiment, the second nucleic acid sequence comprises (i) nucleotides 1792-4374 of SEQ ID NO: 1, (ii) nucleotides 1792-4374 of SEQ ID NO: 2, (iii) nucleotides 1792-4374 of SEQ ID NO: 70, or (iv) nucleotides 1792-4374 of SEQ ID NO: 71. In some embodiments, the codon optimized sequence encoding a FVIII polypeptide comprises a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least 90%, at least 95%, at least 96%, at least 97%, at least 98%, or at least 99% sequence identity to (i) nucleotides 1792-2277 and 2320-4374 of SEQ ID NO: 1, (ii) nucleotides 1792-2277 and 2320-4374 of SEQ ID NO: 2, (iii) nucleotides 1792-2277 and 2320-4374 of SEQ ID NO: 70, or (iv) nucleotides 1792-2277 and 2320-4374 of SEQ ID NO: 71 (i.e., nucleotides 1792-4374 of SEQ ID NO: 1, nucleotides 1792-4374 of SEQ ID NO: 2, nucleotides 1792-4374 of SEQ ID NO: 70, or nucleotides 1792-4374 of SEQ ID NO: 71 without the nucleotides encoding the B domain or B domain fragment); and wherein the N-terminal portion and the C-terminal portion together have a FVIII polypeptide activity. In one embodiment, the second nucleic acid sequence comprises (i) nucleotides 1792-2277 and 2320-4374 of SEQ ID NO: 1, (ii) nucleotides 1792-2277 and 2320-4374 of SEQ ID NO: 2, (iii) nucleotides 1792-2277 and 2320-4374 of SEQ ID NO: 70, or (iv) nucleotides 1792-2277 and 2320-4374 of SEQ ID NO: 71 (i.e., nucleotides 1792-4374 of SEQ ID NO: 1, nucleotides 1792-4374 of SEQ ID NO: 2, nucleotides 1792-

4374 of SEQ ID NO: 70, or nucleotides 1792-4374 of SEQ ID NO: 71 without the nucleotides encoding the B domain or B domain fragment).

In some embodiments, the codon optimized nucleotide sequence encoding a FVIII polypeptide comprises a nucleotide sequence encoding a polypeptide with FVIII activity, wherein the nucleotide sequence comprises a nucleic acid sequence having at least 90%, at least 91%, at least 92%, at least 93%, at least 94%, at least 95%, at least 96%, at least 97%, at least 98%, or at least 99% sequence identity to nucleotides 58 to 4374 of SEQ ID NO: 1. In other embodiments, the nucleotide sequence comprises a nucleic acid sequence having at least 90%, at least 91%, at least 92%, at least 93%, at least 94%, at least 95%, at least 96%, at least 97%, at least 98%, or at least 99% sequence identity to nucleotides 58-2277 and 2320-4374 of SEQ ID NO: 1 (i.e., nucleotides 58-4374 of SEQ ID NO: 1 without the nucleotides encoding the B domain or B domain fragment). In other embodiments, the nucleic acid sequence has at least 90%, at least 91%, at least 92%, at least 93%, at least 94%, at least 95%, at least 96%, at least 97%, at least 98%, or at least 99% sequence identity to SEQ ID NO: 1. In other embodiments, the nucleotide sequence comprises nucleotides 58-2277 and 2320-4374 of SEQ ID NO: 1 (i.e., nucleotides 58-4374 of SEQ ID NO: 1 without the nucleotides encoding the B domain or B domain fragment) or nucleotides 58 to 4374 of SEQ ID NO: 1. In still other embodiments, the nucleotide sequence comprises nucleotides 1-2277 and 2320-4374 of SEQ ID NO: 1 (i.e., nucleotides 1-4374 of SEQ ID NO: 1 without the nucleotides encoding the B domain or B domain fragment) or nucleotides 1 to 4374 of SEQ ID NO: 1.

In some embodiments, the codon optimized nucleotide sequence encoding a FVIII polypeptide comprises a nucleotide sequence encoding a polypeptide with FVIII activity, wherein the nucleotide sequence comprises a nucleic acid sequence having at least 94%, at least 95%, at least 96%, at least 97%, at least 98%, or at least 99% sequence identity to nucleotides 58 to 4374 of SEQ ID NO: 2. In other embodiments, the nucleotide sequence comprises a nucleic acid sequence having at least 94%, at least 95%, at least 96%, at least 97%, at least 98%, or at least 99% sequence identity to nucleotides 58-2277 and 2320-4374 of SEQ ID NO: 2. In other embodiments, the nucleic acid sequence has at least 94%, at least 95%, at least 96%, at least 97%, at least 98%, or at least 99% sequence identity to SEQ ID NO: 2. In other embodiments, the nucleotide sequence comprises nucleotides 58-2277 and 2320-4374 of SEQ ID NO: 2 (i.e., nucleotides 58-4374 of SEQ ID NO: 2 without the nucleotides encoding the B domain or B domain fragment) or nucleotides 58 to 4374 of SEQ ID NO: 2. In still other embodiments, the nucleotide sequence comprises nucleotides 1-2277 and 2320-4374 of SEQ ID NO: 2 (i.e., nucleotides 1-4374 of SEQ ID NO: 2 without the nucleotides encoding the B domain or B domain fragment) or nucleotides 1 to 4374 of SEQ ID NO: 2.

In some embodiments, the codon optimized nucleotide sequence encoding a FVIII polypeptide comprises a nucleotide sequence encoding a polypeptide with FVIII activity, wherein the nucleotide sequence comprises a nucleic acid sequence having at least 85%, at least 86%, at least 87%, at least 88%, at least 89%, at least 90%, at least 91%, at least 95%, at least 96%, at least 97%, at least 98%, or at least 99% sequence identity to nucleotides 58 to 4374 of SEQ ID NO: 70. In other embodiments, the nucleotide sequence comprises a nucleic acid sequence having at least 85%, at least 86%, at least 87%, at least 88%, at least 89%, at least 90%, at least 91%, at least 95%, at least 96%, at least 97%, at least 98%, or at least 99% sequence identity to nucleotides 58-2277 and 2320-4374 of SEQ ID NO: 70 (i.e., nucleotides 58-4374 of SEQ ID NO: 70 without the nucleotides encoding the B domain or B domain fragment). In other embodiments, the nucleic acid sequence has at least 85%, at least 86%, at least 87%, at least 88%, at least 89%, at least 90%, at least 91%, at least 95%, at least 96%, at least 97%, at least 98%, or at least 99% sequence identity to SEQ ID NO: 70. In other embodiments, the nucleotide sequence comprises nucleotides 58-2277 and 2320-4374 of SEQ ID NO: 70 (i.e., nucleotides 58-4374 of SEQ ID NO: 70 without the nucleotides encoding the B domain or B domain fragment) or nucleotides 58 to 4374 of SEQ ID NO: 70. In still other embodiments, the nucleotide sequence comprises nucleotides 1-2277 and 2320-4374 of SEQ ID NO: 70 (i.e., nucleotides 1-4374 of SEQ ID NO: 70 without the nucleotides encoding the B domain or B domain fragment) or nucleotides 1 to 4374 of SEQ ID NO: 70.

In some embodiments, the codon optimized nucleotide sequence encoding a FVIII polypeptide comprises a nucleotide sequence encoding a polypeptide with FVIII activity, wherein the nucleotide sequence comprises a nucleic acid sequence having at least 85%, at least 86%, at least 87%, at least 88%, at least 89%, at least 90%, at least 91%, at least 95%, at least 96%, at least 97%, at least 98%, or at least 99% sequence identity to nucleotides 58 to 4374 of SEQ ID NO: 71. In other embodiments, the nucleotide sequence comprises a nucleic acid sequence having at least 85%, at least 86%, at least 87%, at least 88%, at least 89%, at least 90%, at least 91%, at least 95%, at least 96%, at least 97%, at least 98%, or at least 99% sequence identity to nucleotides 58-2277 and 2320-4374 of SEQ ID NO: 71 (i.e., nucleotides 58-4374 of SEQ ID NO: 71 without the nucleotides encoding the B domain or B domain fragment). In other embodiments, the nucleic acid sequence has at least 85%, at least 86%, at least 87%, at least 88%, at least 89%, at least 90%, at least 91%, at least 95%, at least 96%, at least 97%, at least 98%, or at least 99% sequence identity to SEQ ID NO: 71. In other embodiments, the nucleotide sequence comprises nucleotides 58-2277 and 2320-4374 of SEQ ID NO: 71 (i.e., nucleotides 58-4374 of SEQ ID NO: 71 without the nucleotides encoding the B domain or B domain fragment) or nucleotides 58 to 4374 of SEQ ID NO: 71. In still other embodiments, the nucleotide sequence comprises nucleotides 1-2277 and 2320-4374 of SEQ ID NO: 71 (i.e., nucleotides 1-4374 of SEQ ID NO: 71 without the nucleotides encoding the B domain or B domain fragment) or nucleotides 1 to 4374 of SEQ ID NO: 71.

In some embodiments, the codon optimized nucleotide sequence encoding a FVIII polypeptide comprises a nucleotide sequence encoding a polypeptide with FVIII activity, wherein the nucleotide sequence comprises a nucleic acid sequence having at least 92%, at least 93%, at least 94%, at least 95%, at least 96%, at least 97%, at least 98%, or at least 99% sequence identity to nucleotides 58 to 4374 of SEQ ID NO: 3. In other embodiments, the nucleotide sequence comprises a nucleic acid sequence having at least 92%, at least 93%, at least 94%, at least 95%, at least 96%, at least 97%, at least 98%, or at least 99% sequence identity to nucleotides 58-2277 and 2320-4374 of SEQ ID NO: 3 (i.e., nucleotides 58-4374 of SEQ ID NO: 3 without the nucleotides encoding the B domain or B domain fragment). In certain embodiments, the nucleic acid sequence has at least 92%, at least 93%, at least 94%, at least 95%, at least 96%, at least 97%, at least 98%, or at least 99% sequence identity to SEQ ID NO: 3. In some embodiments, the nucleotide sequence comprises nucleotides 58-2277 and 2320-4374 of SEQ ID NO: 3 (i.e., nucleotides 58-4374 of SEQ ID NO: 3 without the nucleotides encoding the B domain or B domain fragment) or nucleotides 58 to 4374 of SEQ ID NO: 3. In still other embodiments, the nucleotide sequence comprises nucleotides 58-2277 and 2320-4374 of SEQ ID NO: 3 (i.e., nucleotides 1-4374 of SEQ ID NO: 3 without the nucleotides encoding the B domain or B domain fragment) or nucleotides 1 to 4374 of SEQ ID NO: 3.

In some embodiments, the codon optimized nucleotide sequence encoding a FVIII polypeptide comprises a nucleotide sequence encoding a polypeptide with FVIII activity, wherein the nucleotide sequence comprises a nucleic acid sequence having at least 91%, at least 92%, at least 93%, at least 94%, at least 95%, at least 96%, at least 97%, at least 98%, or at least 99% sequence identity to nucleotides 58 to 4374 of SEQ ID NO: 4. In other embodiments, the nucleotide sequence comprises a nucleic acid sequence having at least 91%, at least 92%, at least 93%, at least 94%, at least 95%, at least 96%, at least 97%, at least 98%, or at least 99% sequence identity to nucleotides 58-2277 and 2320-4374 of SEQ ID NO: 4 (i.e., nucleotides 58-4374 of SEQ ID NO: 4 without the nucleotides encoding the B domain or B domain fragment). In other embodiments, the nucleic acid sequence has at least 91%, at least 92%, at least 93%, at least 94%, at least 95%, at least 96%, at least 97%, at least 98%, or at least 99% sequence identity to SEQ ID NO: 4. In other embodiments, the nucleotide sequence comprises nucleotides 58-2277 and 2320-4374 of SEQ ID NO: 4 (i.e., nucleotides 58-4374 of SEQ ID NO: 4 without the nucleotides encoding the B domain or B domain fragment) or nucleotides 58 to 4374 of SEQ ID NO: 4. In still other embodiments, the nucleotide sequence comprises nucleotides 1-2277 and 2320-4374 of SEQ ID NO: 4 (i.e., nucleotides 1-4374 of SEQ ID NO: 4 without the nucleotides encoding the B domain or B domain fragment) or nucleotides 1 to 4374 of SEQ ID NO: 4.

In some embodiments, the codon optimized nucleotide sequence encoding a FVIII polypeptide comprises a nucleotide sequence encoding a polypeptide with FVIII activity, wherein the nucleotide sequence comprises a nucleic acid sequence having at least 89%, at least 90%, at least 91%, at least 92%, at least 93%, at least 94%, at least 95%, at least 96%, at least 97%, at least 98%, or at least 99% sequence identity to nucleotides 58 to 4374 of SEQ ID NO: 5. In other embodiments, the nucleotide sequence comprises a nucleic acid sequence having at least 89%, at least 90%, at least 91%, at least 92%, at least 93%, at least 94%, at least 95%, at least 96%, at least 97%, at least 98%, or at least 99% sequence identity to nucleotides 58-2277 and 2320-4374 of SEQ ID NO: 5 (i.e., nucleotides 58-4374 of SEQ ID NO: 5 without the nucleotides encoding the B domain or B domain fragment). In certain embodiments, the nucleic acid sequence has at least 89%, at least 90%, at least 91%, at least 92%, at least 93%, at least 94%, at least 95%, at least 96%, at least 97%, at least 98%, or at least 99% sequence identity to SEQ ID NO: 5. In some embodiments, the nucleotide sequence comprises nucleotides 58-2277 and 2320-4374 of SEQ ID NO: 5 (i.e., nucleotides 58-4374 of SEQ ID NO: 5 without the nucleotides encoding the B domain or B domain fragment) or nucleotides 58 to 4374 of SEQ ID NO: 5. In still other embodiments, the nucleotide sequence comprises nucleotides 1-2277 and 2320-4374 of SEQ ID NO: 5 (i.e., nucleotides 1-4374 of SEQ ID NO: 5 without the nucleotides encoding the B domain or B domain fragment) or nucleotides 1 to 4374 of SEQ ID NO: 5.

In some embodiments, the codon optimized nucleotide sequence encoding a FVIII polypeptide comprises a nucleotide sequence encoding a polypeptide with FVIII activity, wherein the nucleotide sequence comprises a nucleic acid sequence having at least 89%, at least 90%, at least 91%, at least 92%, at least 93%, at least 94%, at least 95%, at least 96%, at least 97%, at least 98%, or at least 99% sequence identity to nucleotides 58 to 4374 of SEQ ID NO: 6. In other embodiments, the nucleotide sequence comprises a nucleic acid sequence having at least 89%, at least 90%, at least 91%, at least 92%, at least 93%, at least 94%, at least 95%, at least 96%, at least 97%, at least 98%, or at least 99% sequence identity to nucleotides 58-2277 and 2320-4374 of SEQ ID NO: 6 (i.e., nucleotides 58-4374 of SEQ ID NO: 6 without the nucleotides encoding the B domain or B domain fragment). In certain embodiments, the nucleic acid sequence has at least 89%, at least 90%, at least 91%, at least 92%, at least 93%, at least 94%, at least 95%, at least 96%, at least 97%, at least 98%, or at least 99% sequence identity to SEQ ID NO: 6. In some embodiments, the nucleotide sequence comprises nucleotides 58-2277 and 2320-4374 of SEQ ID NO: 6 (i.e., nucleotides 58-4374 of SEQ ID NO: 6 without the nucleotides encoding the B domain or B domain fragment) or nucleotides 58 to 4374 of SEQ ID NO: 6. In still other embodiments, the nucleotide sequence comprises nucleotides 1-2277 and 2320-4374 of SEQ ID NO: 6 (i.e., nucleotides 1-4374 of SEQ ID NO: 6 without the nucleotides encoding the B domain or B domain fragment) or nucleotides 1 to 4374 of SEQ ID NO: 6.

In some embodiments, the codon optimized nucleotide sequence encoding a FVIII polypeptide comprises a nucleic acid sequence encoding a signal peptide. In certain embodiments, the signal peptide is a FVIII signal peptide. In some embodiments, the nucleic acid sequence encoding a signal peptide is codon optimized. In one particular embodiment, the nucleic acid sequence encoding a signal peptide has at least 60%, at least 70%, at least 80%, at least 90%, at least 95%, at least 96%, at least 97%, at least 98%, at least 99%, or 100% sequence identity to (i) nucleotides 1 to 57 of SEQ ID NO: 1; (ii) nucleotides 1 to 57 of SEQ ID NO: 2; (iii) nucleotides 1 to 57 of SEQ ID NO: 3; (iv) nucleotides 1 to 57 of SEQ ID NO: 4; (v) nucleotides 1 to 57 of SEQ ID NO: 5; (vi) nucleotides 1 to 57 of SEQ ID NO: 6; (vii) nucleotides 1 to 57 of SEQ ID NO: 70; (viii) nucleotides 1 to 57 of SEQ ID NO: 71; or (ix) nucleotides 1 to 57 of SEQ ID NO: 68.

SEQ ID NOs: 1-6, 70, and 71 are optimized versions of SEQ ID NO: 16, the starting or "parental" or "wild-type" FVIII nucleotide sequence. SEQ ID NO: 16 encodes a B domain-deleted human FVIII. While SEQ ID NOs: 1-6, 70, and 71 are derived from a specific B domain-deleted form of FVIII (SEQ ID NO: 16), it is to be understood that the present disclosure also includes optimized versions of nucleic acids encoding other versions of FVIII. For example, other versions of FVIII can include full length FVIII, other B-domain deletions of FVIII (described herein), or other fragments of FVIII that retain FVIII activity.

In one embodiment, the genetic cassette comprises a FVIII construct, which includes a polynucleotide sequence as listed in Tables 2A-2F. In one embodiment, the genetic cassette comprises a FVIII construct, which includes a polynucleotide sequence set forth in Table 2A. In one embodiment, the genetic cassette comprises a FVIII construct, which includes a polynucleotide sequence set forth in Table 2B. In one embodiment, the genetic cassette comprises a FVIII construct, which includes a polynucleotide sequence set forth in Table 2C. In one embodiment, the genetic cassette comprises a FVIII construct, which includes a polynucleotide sequence set forth in Table 2D. In one embodiment, the genetic cassette comprises a FVIII construct, which includes a polynucleotide sequence set forth in Table 2E. In one embodiment, the genetic cassette comprises a FVIII construct, which includes a polynucleotide sequence set forth in Table 2F In certain embodiments, the isolated nucleic acid molecule comprises a nucleotide sequence having at least about 60%, at least about 65%, at least about 70%, at least about 75%, at least about 80%, at least about 85%, at least about 90%, at least about 95%, at least about 96%, at least about 97%, at least about 98%, at least about 99%, or about 100% sequence identity to the nucleotide sequence of SEQ ID NO: 179, 182, 189, or 194. In some embodiments, the isolated nucleic acid molecule comprises a nucleotide sequence having at least about 60%, at least about 65%, at least about 70%, at least about 75%, at least about 80%, at least about 85%, at least about 90%, at least about 95%, at least about 96%, at least about 97%, at least about 98%, at least about 99%, or about 100% sequence identity to the nucleotide sequence of SEQ ID NO: 179. In some embodiments, the isolated nucleic acid molecule comprises a nucleotide sequence having at least about 60%, at least about 65%, at least about 70%, at least about 75%, at least about 80%, at least about 85%, at least about 90%, at least about 95%, at least about 96%, at least about 97%, at least about 98%, at least about 99%, or about 100% sequence identity to the nucleotide sequence of SEQ ID NO: 182. In some embodiments, the isolated nucleic acid molecule comprises a nucleotide sequence having at least about 60%, at least about 65%, at least about 70%, at least about 75%, at least about 80%, at least about 85%, at least about 90%, at least about 95%, at least about 96%, at least about 97%, at least about 98%, at least about 99%, or about 100% sequence identity to the nucleotide sequence of SEQ ID NO: 189. In some embodiments, the isolated nucleic acid molecule comprises a nucleotide sequence having at least about 60%, at least about 65%, at least about 70%, at least about 75%, at least about 80%, at least about 85%, at least about 90%, at least about 95%, at least about 96%, at least about 97%, at least about 98%, at least about 99%, or about 100% sequence identity to the nucleotide sequence of SEQ ID NO: 194. In some embodiments, the isolated nucleic acid molecule retains the ability to express a functional FVIII protein.

TABLE 2A

Example AAV-FVIII construct (nucleotides 1-6526; SEQ ID NO: 110)

| Description | Sequence |
| --- | --- |
| 5'ITR (5'-end AAV2 inverted terminal repeat) (SEQ ID NO: 111) | 1 -- CTGCGCGCTCGCTCGCTCACTGAGGCCGCCCGGGCAAAGCCCGGGCGTCGGGCGACC TTTGGTCGCCCGGCCTCAGTGAGCGAGCGAGCGCGCAGAGAGGGAGTGGCCAACTCC ATCACTAGGGGTTCCT -- 130 |
| Plasmid Backbone Sequence (PBS)-1 (SEQ ID NO: 112) | 131 -- GCGGCAATTCAGTCGATAACTATAACGGTCCTAAGGTAGCGATTTAAATACGCGCTC TCTTAAGGTAGCCCCGGGACGCGTCAATTGAGATCTGGATCCGGTACCGAATTCGCG GCCGCCTCGACGACTAGCGTTTAATTAA -- 272 |
| TTPp (liver-specific promoter) (SEQ ID NO: 113) | 273 -- ACGCGTGTCTGTCTGCACATTTCGTAGAGCGAGTGTTCCGATACTCTAATCTCCCTA GGCAAGGTTCATATTTGTGTAGGTTACTTATTCTCCTTTTGTTGACTAAGTCAATAA TCAGAATCAGCAGGTTTGGAGTCAGCTTGGCAGGGATCAGCAGCCTGGGTTGGAAGG AGGGGGTATAAAAGCCCCTTCACCAGGAGAAGCCGTCACACAGATCCACAAGCTCCT G -- 501 |
| PBS-2 (SEQ ID NO: 114) | 502 -- AG -- 503 |
| Synthetic Intron (SEQ ID NO: 115) | 504 -- GTAAGTGCCGTGTGTGGTTCCCGCGGGCCTGGCCTCTTTACGGGTTATGGCCCTTGC GTGCCTTGAATTACTGACACTGACATCCACTTTTTCTTTTTCTCCACAG --609 |
| PBS-3 (SEQ ID NO: 116) | 610 -- CTAGCGCCACC -- 620 |
| FVIIIco6XTEN (SEQ ID NO: 117) (open reading frame for codon-optimized FVIII version 6 containing XTEN144; the XTEN sequence is marked by double underlining (SEQ ID NO: 118)) | 621 -- ATGCAGATTGAGCTGTCCACTTGTTTCTTCCTGTGCCTCCTGCGCTTCTGTTTCTCC GCCACTCGCCGGTACTACCTTGGAGCCGTGGAGCTTTCATGGGACTACATGCAGAGC GACCTGGGCGAACTCCCCGTGGATGCCAGATTCCCCCCCCGCGTGCCAAAGTCCTTC CCCTTTAACACCTCCGTGGTGTACAAGAAAACCCTCTTTGTCGAGTTCACTGACCAC CTGTTCAACATCGCCAAGCCGCGCCCACCTTGGATGGGCCTCCTGGGACCGACCATT CAAGCTGAAGTGTACGACACCGTGGTGATCACCCTGAAGAACATGGCGTCCCACCCC GTGTCCCTGCATGCGGTCGGAGTGTCCTACTGGAAGGCCTCCGAAGGAGCTGAGTAC GACGACCAGACTAGCCAGCGGGAAAAGGAGGACGATAAAGTGTTCCCGGGCGGCTCG CATACTTACGTGTGGCAAGTCCTGAAGGAAAACGGACCTATGGCATCCGATCCTCTG TGCCTGACTTACTCCTACCTTTCCCATGTGGACCTCGTGAAGGACCTGAACAGCGGG CTGATTGGTGCACTTCTCGTGTGCCGCGAAGGTTCGCTCGCTAAGGAAAAGACCCAG ACCCTCCATAAGTTCATCCTTTTGTTCGCTGTGTTCGATGAAGGAAAGTCATGGCAT TCCGAAACTAAGAACTCGCTGATGCAGGACCGGGATGCCGCCTCAGCCCGCGCCTGG CCTAAAATGCATACAGTCAACGGATACGTGAATCGTGGTCTGCCCGGGCTCATCGGT TGTCACAGAAAGTCCGTGTACTGGCACGTCATCGGCATGGGCACTGCGCCTGAAGTG CACTCCATCTTCCTGGAAGGGCACACCTTCCTCGTGCGCAACCACCGCCAGGCCTCT CTGGAAATCTCCCCGATTACCTTCTGACCGCCCAGACTCTGCTCATGGACCTGGGG CAGTTCCTTCTCTTCTGCCACATCTCCAGCCATCAGCACGACGGAATGGAGGCCTAC GTGAAGGTGGACTCATGCCCGGAAGAACCTCAGTTGCGGATGAAGAACAACGAGGAG |

TABLE 2A-continued

Example AAV-FVIII construct (nucleotides 1-6526; SEQ ID NO: 110)

| Description | Sequence |
|---|---|
| | GCCGAGGACTATGACGACGATTTGACTGACTCCGAGATGGACGTCGTGCGGTTCGAT<br>GACGACAACAGCCCCAGCTTCATCCAGATTCGCAGCGTGGCCAAGAAGCACCCCAAA<br>ACCTGGGTGCACTACATCGCGGCCGAGGAAGAAGATTGGGACTACGCCCCGTTGGTG<br>CTGGCACCCGATGACCGGTCGTACAAGTCCCAGTATCTGAACAATGGTCCGCAGCGG<br>ATTGGCAGAAAGTACAAGAAAGTGCGGTTCATGGCGTACACTGACGAAACGTTTAAG<br>ACCCGGGAGGCCATTCAACATGAGAGCGGCATTCTGGGACCACTGCTGTACGGAGAG<br>GTCGGCGATACCCTGCTCATCATCTTCAAAAACCAGGCCTCCCGGCCTTACAACATC<br>TACCCTCACGGAATCACCGACGTGCGGCCACTCTACTCGCGGCGCCTGCCGAAGGGC<br>GTCAAGCACCTGAAAGACTTCCCTATCCTGCCGGGCGAAATCTTCAAGTATAAGTGG<br>ACCGTCACCGTGGAGGACGGGCCCACCAAGAGCGATCCTAGGTGTCTGACTCGGTAC<br>TACTCCAGCTTCGTGAACATGGAACGGGACCTGGCATCGGGACTCATTGGACCGCTG<br>CTGGATCTGCTACAAAGAGTCGGTGGATCAACGCGGCAACCAGATCATGTCCGACAAG<br>CGCAACGTGATCCTGTTCTCCGTGTTTGATGAAAACAGATCCTGGTACCTCACTGAA<br>AACATCCAGAGGTTCCTCCCAAACCCCGCAGGAGTGCAACTGGAGGACCCTGAGTTT<br>CAGGCCTCGAATATCATGCACTCGATTAACGGTTACGTGTTCGACTCGCTGCAACTG<br>AGCGTGTGCCTCCATGAAGTCGCTTACTGGTACATTCTGTCCATCGGCGCCCAGACT<br>GACTTCCTGAGCGTGTTCTTTTCCGGTTACACCTTTAAGCACAAGATGGTGTACGAA<br>GATACCCTGACCCTGTTCCCTTTCTCCGGCGAAACGGTGTTCATGTCGATGGAGAAC<br>CCGGGTCTGTGGATTCTGGGATGCCACAACAGCGACTTTCGGAACCGCGGAATGACT<br>GCCCTGCTGAAGGTGTCCTCATGCGACAAGAACACCGGAGACTACTACGAGGACTCC<br>TACGAGGATATCTCAGCCTACCTCCTGTCCAAGAACAACGCGATCGAGCCGCGCAGC<br>TTCAGCCAGAAC<u>GGCGCGCCAACATCAGAGAGCGCCACCCCTGAAAGTGGTCCCGGG<br>AGCGAGCCAGCCACATCTGGGTCGGAAACGCCAGGCACAAGTGAGTCTGCAACTCCC<br>GAGTCCGGACCTGGCTCCGAGCCTGCCACTAGCGGCTCCGAGACTCCGGGAACTTCC<br>GAGAGCGCTACACCAGAAAGCGGACCCGGAACCAGTACCGAACCTAGCGAGGGCTCT<br>GCTCCGGGCAGCCCAGCCGGCTCTCCTACATCCACGGAGGAGGGCACTTCCGAATCC<br>GCCACCCCGGAGTCAGGGCCAGGATCTGAACCCGCTACCTCAGGCAGTGAGACGCCA<br>GGAACGAGCGAGTCCGCTACACCGGAGAGTGGGCCAGGGAGCCCTGCTGGATCTCCT<br>ACGTCCACTGAGGAAGGGTCACCAAGCGGGCTCGCCCACCAGCACTGAAGAAGGTGCC<br>TCGAGC</u>CCGCCTGTGCTGAAGAGGCACCAGCGAGAAATTACCCGGACCACCCTCCAA<br>TCGGATCAGGAGGAAATCGACTACGACGACACCATCTCGGTGGAAATGAAGAAGGAA<br>GATTTCGATATCTACGACGAGGACGAAAATCAGTCCCCTGCTCATTCCAAAAGAAA<br>ACTAGACACTACTTTATCGCCGCGGTGGAAAGACTGTGGGACTATGGAATGTCATCC<br>AGCCCTCACGTCCTTCGGAACCGGGCCCAGAGCGGATCGGTGCCTCAGTTCAAGAAA<br>GTGGTGTTCCAGGAGTTCACCGACGGCAGCTTCACCCAGCCGCTGTACCGGGGAGAA<br>CTGAACGAACACCTGGGCCTGCTCGGTCCCTACATCCGCGCGGAAGTGGAGGATAAC<br>ATCATGGTGACCTTCCGTAACCAAGCATCCAGACCTTACTCCTTCTATTCCTCCCTG<br>ATCTCATACGAGGAGGACCAGCGCCAAGGCGCCGAGCCCCGCAAGAACTTCGTCAAG<br>CCCAACGAGACTAAGACCTACTTCTGGAAGGTCCAACACCATATGGCCCCGACCAAG<br>GATGAGTTTGACTGCAAGGCCTGGGCCTACTTCTCCGACGTGGACCTTGAGAAGGAT<br>GTCCATTCCGGCCTGATCGGCCGCTGCTCGTGTGTCACACCAACACCCTGAACCCA<br>GCGCATGGACGCCAGGTCACCGTCCAGGAGTTTGCTCTGTTCTTCACCATTTTTGAC<br>GAAACTAAGTCCTGGTACTTCACCGAGAATATGGAGCGAAACTGTAGAGCGCCCTGC<br>AATATCCAGATGGAAGATCCGACTTTCAAGGAGAACTATAGATTCCACGCCATCAAC<br>GGGTACATCATGGATACTCTGCCGGGGCTGGTCATGGCCCAGGATCAGAGGATTCGG<br>TGGTACTTGCTGTCAATGGGATCGAACGAAAACATTCACTCCATTCACTTCTCCGGT<br>CACGTGTTCACTGTGCGCAAGAAGGAGGAGTACAAGATGGCGCTGTACAATCTGTAC<br>CCCGGGGTGTTCGAAACTGTGGAGATGCTGCCGTCCAAGGCCGGCATCTGGAGAGTG<br>GAGTGCCTGATCGGAGAGCACCTCCACGCGGGGATGTCCACCCTCTTCCTGGTGTAC<br>TCGAATAAGTGCCAGACCCCGCTGGGCATGGCCTCGGGCCACATCAGAGACTTCCAG<br>ATCACAGCAAGCGGACAATACGGCCAATGGGCGCCGAAGCTGGCCCGCTTGCACTAC<br>TCCGGATCGATCAACGCATGGTCCACCAAGGAACCGTTCTCGTGGATTAAGGTGGAC<br>CTCCTGGCCCCTATGATTATCCACGGAATTAAGACCCAGGGCGCCAGGCAGAAGTTC<br>TCCTCCCTGTACATCTCGCAATTCATCATCATGTACAGCCTGGACGGGAAGAAGTGG<br>CAGACTTACAGGGGAAACTCCACCGGCACCCTGATGGTCTTTTTCGGCAACGTGGAT<br>TCCTCCGGCATTAAGCACAACATCTTCAACCCACCGATCATAGCCAGATATATTAGG<br>CTCCACCCCACTCACTACTCAATCCGCTCAACTCTTCGGATGGAACTCATGGGGTGC<br>GACCTGAACTCCTGCTCCATGCCGTTGGGGATGGAATCAAAGGCTATTAGCGACGCC<br>CAGATCACCGCGAGCTCCTACTTCACTAACATGTTCGCCACCTGGAGCCCCTCCAAG<br>GCCAGGCTGCACTTGCAGGGACGGTCAAATGCCTGGCGGCCGCAAGTGAACAATCCG<br>AAGGAATGGCTTCAAGTGGATTTTCCAAAAGACCATGAAAGTGACCGGAGTCACCACC<br>CAGGGAGTGAAGTCCCTTCTGACCTCGATGTATGTGAAGGAGTTCCTGATTAGCAGC<br>AGCCAGGACGGGCACCAGTGGACCCTGTTCTTCCAAAACGGAAAGGTCAAGGTGTTC<br>CAGGGGAACCAGGACTCGTTCACACCCGTGGTGAACTCCCTGGACCCCCCACTGCTG<br>ACGCGGTACTTGAGGATTCATCCTCAGTCCTGGGTCCATCAGATTGCATTGCGAATG<br>GAAGTCCTGGGCTGCGAGGCCCAGGACCTGTACTGA -- 5444 |
| PBS-4 (SEQ ID NO: 119) | 5445 -- ATCAGCCTGAGCTCGCTGA -- 5463 |
| WPRE (mutated woodchuck hepatitis virus post-transcriptional regulatory | 5464 --<br>TCATAATCAACCTCTGGATTACAAAATTTGTGAAAGATTGACTGGTATTCTTAACTA<br>TGTTGCTCCTTTTACGCTATGTGGATACGCTGCTTTAATGCCTTTGTATCATGCTAT<br>TGCTTCCCGTATGGCTTTCATTTTCTCCTCCTTGTATAAATCCTGGTTGCTGTCTCT<br>TTATGAGGAGTTGTGGCCCGTTGTCAGGCAACGTGGCGTGGTGTGCACTGTGTTTGC<br>TGACGCAACCCCCACTGGTTGGGGCATTGCCACCACCTGTCAGCTCCTTTCCGGGAC |

TABLE 2A-continued

Example AAV-FVIII construct (nucleotides 1-6526; SEQ ID NO: 110)

| Description | Sequence |
|---|---|
| element) (SEQ ID NO: 120) | TTTCGCTTTCCCCCTCCCTATTGCCACGGCGGAACTCATCGCCGCCTGCCTTGCCCG CTGCTGGACAGGGGCTCGGCTGTTGGGCACTGACAATTCCGTGGTGTTGTCGGGGAA ATCATCGTCCTTTCCTTGGCTGCTCGCCTGTGTTGCCACCTGGATTCTGCGCGGGAC GTCCTTCTGCTACGTCCCTTCGGCCCTCAATCAGCGGACCTTCCTTCCCGCGGCCT GCTGCCGGCTCTGCGGCCTCTTCCGCGTCTTCGCCTTCGCCCTCAGACGAGTCGGAT CTCCCTTTGGGCCGCCTCCCCGCTG -- 6058 |
| PBS-5 (SEQ ID NO: 121) | 6059 -- ATCAGCCT -- 6066 |
| bGHpA (bovine growth hormone polyadenylation signal) (SEQ ID NO: 122) | 6067 -- CGACTGTGCCTTCTAGTTGCCAGCCATCTGTTGTTTGCCCCTCCCCCGTGCCTTCCT TGACCCTGGAAGGTGCCACTCCCACTGTCCTTTCCTAATAAAATGAGGAAATTGCAT CGCATTGTCTGAGTAGGTGTCATTCTATTCTGGGGGGTGGGGTGGGGCAGGACAGCA AGGGGGAGGATTGGGAAGACAATAGCAGGCATGCTGGGGA -- 6277 |
| PBS-6 (SEQ ID NO: 123) | 6278 -- TGCGGTGGGCTCTATGGCTTCTGAGGCGGAAAGAACGGGCTCGAGAAGCTTCTAGAT ATCCTCTCTTAAGGTAGCATCGAGATTTAAATTAGGGATAACAGGGTAATGGCGCGG GCCGC -- 6396 |
| 3'ITR (3'-end AAV2 inverted terminal repeat) (SEQ ID NO: 124) | 6397 -- AGGAACCCCTAGTGATGGAGTTGGCCACTCCCTCTCTGCGCGCTCGCTCGCTCACTG AGGCCGGGCGACCAAAGGTCGCCCGACGCCCGGGCTTTGCCCGGGCGGCCTCAGTGA GCGAGCGAGCGCGCAG -- 6526 |

TABLE 2B

Example B19-FVIII construct bearing B19d135 ITRs (nucleotides 1-6762; SEQ ID NO: 179)

| Description | Sequence |
|---|---|
| 5'ITR (SEQ ID NO: 180) | 1 - CTCTGGGCCAGCTTGCTTGGGGTTGCCTTGACACTAAGACAAGCGGCGCGCCGCTTG ATCTTAGTGGCACGTCAACCCCAAGCGCTGGCCCAGAGCCAACCCTAATTCCGGAAG TCCCGCCCACCGGAAGTGACGTCACAGGAAATGACGTCACAGGAAATGACGTAATTG TCCGCCATCTTGTACCGGAAGTCCCGCCTACCGGCGGCGACCGGCGGCATCTGATTT GGTGTCTTCTTTTAAATTTT -- 248 |
| TTPp (liver - specific promoter) (SEQ ID NO: 113) | 391 - ACGCGTGTCTGTCTGCACATTTCGTAGAGCGAGTGTTCCGATACTCTAATCTCCCTA GGCAAGGTTCATATTTGTGTAGGTTACTTATTCTCCTTTTGTTGACTAAGTCAATAA TCAGAATCAGCAGGTTTGGAGTCAGCTTGGCAGGGATCAGCAGCCTGGGTTGGAAGG AGGGGGTATAAAAGCCCCTTCACCAGGAGAAGCCGTCACACAGATCCACAAGCTCCT G -- 619 |
| Synthetic Intron (SEQ ID NO: 115) | 622 - GTAAGTGCCGTGTGTGGTTCCCGCGGGCCTGGCCTCTTTACGGGTTATGGCCCTTGC GTGCCTTGAATTACTGACACTGACATCCACTTTTTCTTTTTCTCCACAG --727 |
| FVIIIco6XTEN (SEQ ID NO: 117) (open reading frame for codon - optimized FVIII version 6 containing XTEN144; the XTEN sequence is marked by double underlining (SEQ ID NO: 118)) | 739 - ATGCAGATTGAGCTGTCCACTTGTTTCTTCCTGTGCCTCCTGCGCTTCTGTTTCTCC GCCACTCGCCGGTACTACCTTGGAGCCGTGGAGCTTTCATGGGACTACATGCAGAGC GACCTGGGCGAACTCCCCGTGGATGCCAGATTCCCCCCCCGCGTGCCAAAGTCCTTC CCCTTTAACACCTCCGTGGTGTACAAGAAAACCCTCTTTGTCGAGTTCACTGACCAC CTGTTCAACATCGCCAAGCCGCGCCCACCTTGGATGGGCCTCCTGGGACCGACCATT CAAGCTGAAGTGTACGACACCGTGGTGATCACCCTGAAGAACATGGCGTCCCACCCC GTGTCCCTGCATGCGGTCGGAGTGTCCTACTGGAAGGCCTCCGAAGGAGCTGAGTAC GACGACCAGACTAGCCAGCGGGAAAAGGAGGACGATAAAGTGTTCCCGGGCGGCTCG CATACTTACGTGTGGCAAGTCCTGAAGGAAAACGGACCTATGGCATCCGATCCTCTG TGCCTGACTTACTCCTACCTTTCCCATGTGGACCTCGTGAAGGACCTGAACAGCGGG CTGATTGGTGCACTTCTCGTGTGCCGCGAAGGTTCGCTCGCTAAGGAAAAGACCCAG ACCCTCCATAAGTTCATCCTTTTGTTCGCTGTGTTCGATGAAGGAAAGTCATGGCAT TCCGAAACTAAGAACTCGCTGATGCAGGACCGGGATGCCGCCTCAGCCCGCGCCTGG CCTAAAATGCATACAGTCAACGGATACGTGAATCGGTCACTGCCCGGGCTCATCGGT TGTCACAGAAAGTCCGTGTACTGGCACGTCATCGGCATGGGCACTACGCCTGAAGTG CACTCCATCTTCCTGGAAGGGCACACCTTCCTCGTGCGCAACCACCGCCAGGCCTCT CTGGAAATCTCCCCGATTACCTTTCTGACCGCCCAGACTCTGCTCATGGACCTGGGG CAGTTCCTTCTCTTCTGCCACATCTCCAGCCATCAGCACGACGGAATGGAGGCCTAC GTGAAGGTGGACTCATGCCCGGAAGAACCTCAGTTGCGGATGAAGAACAACGAGGAG GCCGAGGACTATGACGACGATTTGACTGACTCCGAGATGGACGTCGTCGGGTTCGAT GACGACAACAGCCCCAGCTTCATCCAGATTCGCAGCGTGGCCAAGAAGCACCCCAAA |

TABLE 2B-continued

| Example B19-FVIII construct bearing B19d135 ITRs (nucleotides 1-6762; SEQ ID NO: 179) | |
|---|---|
| | ACCTGGGTGCACTACATCGCGGCCGAGGAAGAAGATTGGGACTACGCCCCGTTGGTG<br>CTGGCACCCGATGACCGGTCGTACAAGTCCCAGTATCTGAACAATGGTCCGCAGCGG<br>ATTGGCAGAAAGTACAAGAAAGTGCGGTTCATGGCGTACACTGACGAAACGTTTAAG<br>ACCCGGGAGGCCATTCAACATGAGAGCGGCATTCTGGGACCACTGCTGTACGGAGAG<br>GTCGGCGATACCCTGCTCATCATCTTCAAAAACCAGGCCTCCCGGCCTTACAACATC<br>TACCCTCACGGAATCACCGACGTGCGGCCACTCTACTCGCGGCGCCTGCCGAAGGGC<br>GTCAAGCACCTGAAAGACTTCCCTATCCTGCCGGGCGAAATCTTCAAGTATAAGTGG<br>ACCGTCACCGTGGAGGACGGGCCCACCAAGAGCGATCCTAGGTGTCTGACTCGGTAC<br>TACTCCAGCTTCGTGAACATGGAACGGGACCTGGCATCGGGACTCATTGGACCGCTG<br>CTGATCTGCTACAAAGAGTCGGTGGATCAACGCGGCAACCAGATCATGTCCGACAAG<br>CGCAACGTGATCCTGTTCTCCGTGTTTGATGAAAACAGATCCTGGTACCTCACTGAA<br>AACATCCAGAGGTTCCTCCCAAACCCCGCAGGAGTGCAACTGGAGGACCCTGAGTTT<br>CAGGCCTCGAATATCATGCACTCGATTAACGGTTACGTGTTCGACTCGCTGCAACTG<br>AGCGTGTGCCTCCATGAAGTCGCTTACTGGTACATTCTGTCCATCGGCGCCCAGACT<br>GACTTCCTGAGCGTGTTCTTTTCCGGTTACACCTTTAAGCACAAGATGGTGTACGAA<br>GATACCCTGACCCTGTTCCCTTTCTCCGGCGAAACGGTGTTCATGTCGATGGAGAAC<br>CCGGGTCTGTGGATTCTGGGATGCCACAACAGCGACTTTCGGAACCGCGGAATGACT<br>GCCCTGCTGAAGGTGTCCTCATGCGACAAGAACACCGGAGACTACTACGAGGACTCC<br>TACGAGGATATCTCAGCCTACCTCCTGTCCAAGAACAACGCGATCGAGCCGCGCAGC<br>TTCAGCCAGAACGGCGCGCCAACATCAGAGAGCGCCACCCCTGAAAGTGGTCCCGGG<br>AGCGAGCCAGCCACATCTGGGTCGGAAACGCCAGGCACAAGTGAGTCTGCAACTCCC<br>GAGTCCGGACCTGGCTCCGAGCCTGCCACTAGCGGCTCCGAGACTCCGGGAACTTCC<br>GAGAGCGCTACACCAGAAAGCGGACCCGGAACCAGTACCGAACCTAGCGAGGGCTCT<br>GCTCCGGGCAGCCCAGCCGGCTCTCCTACATCCACGGAGGAGGGCACTTCCGAATCC<br>GCCACCCCGGAGTCAGGGCCAGGATCTGAACCCGCTACCTCAGGCAGTGAGACGCCA<br>GGAACGAGCGAGTCCGCTACACCGGAGAGTGGGCCAGGGAGCCCTGCTGGATCTCCT<br>ACGTCCACTGAGGAAGGGTCACCAGCGGGCTCGCCCACCAGCACTGAAGAAGGTGCC<br>TCGAGCCCGCCTGTGCTGAAGAGGCACCAGCGAGAAATTACCCGGACCACCCTCCAA<br>TCGGATCAGGAGGAAATCGACTACGACGACACCATCTCGGTGGAAATGAAGAAGGAA<br>GATTTCGATATCTACGACGAGGACGAAAATCAGTCCCCTCGCTCATTCCAAAAGAAA<br>ACTAGACACTACTTTATCGCCGCGGTGGAAAGACTGTGGGACTATGGAATGTCATCC<br>AGCCCTCACGTCCTTCGGAACCGGGCCCAGAGCGGATCGGTGCCTCAGTTCAAGAAA<br>GTGGTGTTCCAGGAGTTCACCGACGGCAGCTTCACCCAGCCGCTGTACCGGGGAGAA<br>CTGAACGAACACCTGGGCCTGCTCGGTCCCTACATCCGCGCGGAAGTGGAGGATAAC<br>ATCATGGTGACCTTCCGTAACCAAGCATCCAGACCTTACTCCTTCTATTCCTCCCTG<br>ATCTCATACGAGGAGGACCAGCGCCAAGGCGCCGAGCCCCGCAAGAACTTCGTCAAG<br>CCCAACGAGACTAAGACCTACTTCTGGAAGGTCCAACACCATATGGCCCCGACCAAG<br>GATGAGTTTGACTGCAAGGCCTGGGCCTACTTCTCCGACGTGGACCTTGAGAAGGAT<br>GTCCATTCCGGCCTGATCGGGCCGCTGCTCGTGTGTCACACCAACACCCTGAACCCA<br>GCGCATGGACGCCAGGTCACCGTCCAGGAGTTTGCTCTGTTCTTCACCATTTTTGAC<br>GAAACTAAGTCCTGGTACTTCACCGAGAATATGGAGCGAAACTGTAGAGCGCCCTGC<br>AATATCCAGATGGAAGATCCGACTTTCAAGGAGAACTATAGATTCCACGCCATCAAC<br>GGGTACATCATGGATACTCTGCCGGGGCTGGTCATGGCCCAGGATCAGAGGATTCGG<br>TGGTACTTGCTGTCAATGGGATCGAACGAAAACATTCACTCCATTCACTTCTCCGGT<br>CACGTGTTCACTGTGCGCAAGAAGGAGGAGTACAAGATGGCGCTGTACAATCTGTAC<br>CCCGGGGTGTTCGAAACTGTGGAGATGCTGCCGTCCAAGGCCGGCATCTGGAGAGTG<br>GAGTGCCTGATCGGAGAGCACCTCCACGCGGGGATGTCCACCCTCTTCCTGGTGTAC<br>TCGAATAAGTGCCAGACCCCGCTGGGCATGGCCTCGGGCCACATCAGAGACTTCCAG<br>ATCACAGCAAGCGGACAATACGGCCAATGGGCGCCGAAGCTGGCCCGCTTGCACTAC<br>TCCGGATCGATCAACGCATGGTCCACCAAGGAACCGTTCTCGTGGATTAAGGTGGAC<br>CTCCTGGCCCCTATGATTATCCACGGAATTAAGACCCAGGGCGCCAGGCAGAAGTTC<br>TCCTCCCTGTACATCTCGCAATTCATCATCATGTACAGCCTGGACGGGAAGAAGTGG<br>CAGACTTACAGGGGAAACTCCACCGGCACCCTGATGGTCTTTTTCGGCAACGTGGAT<br>TCCTCCGGCATTAAGCACAACATCTTCAACCCACCGATCATAGCCAGATATATTAGG<br>CTCCACCCCACTCACTACTCAATCCGCTCAACTCTTCGGATGGAACTCATGGGGTGC<br>GACCTGAACTCCTGCTCCATGCCGTTGGGGATGGAATCAAAGGCTATTAGCGACGCC<br>CAGATCACCGCGAGCTCCTACTTCACTAACATGTTCGCCACCTGGAGCCCCTCCAAG<br>GCCAGGCTGCACTTGCAGGGACGGTCAAATGCCTGGCGGCCGCAAGTGAACAATCCG<br>AAGGAATGGCTTCAAGTGGATTTCCAAAAGACCATGAAAGTGACCGGAGTCACCACC<br>CAGGGAGTGAAGTCCCTTCTGACCTCGATGTATGTGAAGGAGTTCCTGATTAGCAGC<br>AGCCAGGACGGGCACCAGTGGACCCTGTTCTTCCAAAACGGAAAGGTCAAGGTGTTC<br>CAGGGGAACCAGGACTCGTTCACACCCGTGGTGAACTCCCTGGACCCCCCACTGCTG<br>ACGCGGTACTTGAGGATTCATCCTCAGTCCTGGGTCCATCAGATTGCATTGCGAATG<br>GAAGTCCTGGGCTGCGAGGCCCAGGACCTGTACTGA -- 5562 |
| WPRE (mutated woodchuck hepatitis virus post - transcriptional regulatory element) (SEQ ID NO: 120) | 5582 -<br>TCATAATCAACCTCTGGATTACAAAATTTGTGAAAGATTGACTGGTATTCTTAACTA<br>TGTTGCTCCTTTTACGCTATGTGGATACGCTGCTTTAATGCCTTTGTATCATGCTAT<br>TGCTTCCCGTATGGCTTTCATTTTCTCCTCCTTGTATAAATCCTGGTTGCTGTCTCT<br>TTATGAGGAGTTGTGGCCCGTTGTCAGGCAACGTGGCGTGGTGTGCACTGTGTTTGC<br>TGACGCAACCCCCACTGGTTGGGGCATTGCCACCACCTGTCAGCTCCTTTCCGGGAC<br>TTTCGCTTTCCCCCTCCCTATTGCCACGGCGGAACTCATCGCCGCCTGCCTTGCCCG<br>CTGCTGGACAGGGGCTCGGCTGTTGGGCACTGACAATTCCGTGGTGTTGTCGGGGAA<br>ATCATCGTCCTTTCCTTGGCTGCTCGCCTGTGTTGCCACCTGGATTCTGCGCGGGAC<br>GTCCTTCTGCTACGTCCCTTCGGCCCTCAATCCAGCGGACCTTCCTTCCCGCGGCCT<br>GCTGCCGGCTCTGCGGCCTCTTCCGCGTCTTCGCCTTCGCCCTCAGACGAGTCGGAT<br>CTCCCTTTGGGCCGCCTCCCCGCTG -- 6176 |

TABLE 2B-continued

Example B19-FVIII construct bearing B19d135 ITRs (nucleotides 1-6762; SEQ ID NO: 179)

| | |
|---|---|
| bGHpA (bovine growth hormone polyadenylation signal) (SEQ ID NO: 122) | 6185 - CGACTGTGCCTTCTAGTTGCCAGCCATCTGTTGTTTGCCCCTCCCCCGTGCCTTCCT TGACCCTGGAAGGTGCCACTCCCACTGTCCTTTCCTAATAAAATGAGGAAATTGCAT CGCATTGTCTGAGTAGGTGTCATTCTATTCTGGGGGGTGGGGTGGGGCAGGACAGCA AGGGGGAGGATTGGGAAGACAATAGCAGGCATGCTGGGGA -- 6395 |
| 3' ITR inverted terminal repeat (SEQ ID NO: 181) | 6515 - AAAATTTAAAAGAAGACACCCAAATCAGATGCCGCCGGTCGCCGCCGGTAGGCGGGAC TTCCGGTACAAGATGGCGGACAATTACGTCATTTCCTGTGACGTCATTTCCTGTGAC GTCACTTCCGGTGGGCGGGACTTCCGGAATTAGGGTTGGCTCTGGGCCAGCGCTTGG GGTTGACGTGCCACTAAGATCAAGCGGCGCGCCGCTTGTCTTAGTGTCAAGGCAACC CCAAGCAAGCTGGCCCAGAG -- 6762 |

Full-length Sequence (SEQ ID NO: 179)

CTCTGGGCCAGCTTGCTTGGGGTTGCCTTGACACTAAGACAAGCGGCGCGCCGCTTGATCTTAGTGGCACGTC
AACCCCAAGCGCTGGCCCAGAGCCAACCCTAATTCCGGAAGTCCCGCCCACCGGAAGTGACGTCACAGGAAAT
GACGTCACAGGAAATGACGTAATTGTCCGCCATCTTGTACCGGAAGTCCCGCCTACCGGCGGCGACCGGCGGC
ATCTGATTTGGTGTCTTCTTTTAAATTTTGCGGCAATTCAGTCGATAACTATAACGGTCCTAAGGTAGCGATT
TAAATACGCGCTCTCTTAAGGTAGCCCCGGGACGCGTCAATTGAGATCTGGATCCGGTACCGAATTCGCGGCC
GCCTCGACGACTAGCGTTTAATTAAACGCGTGTCTGTCTGCACATTTCGTAGAGCGAGTGTTCCGATACTCTA
ATCTCCCTAGGCAAGGTTCATATTTGTGTAGGTTACTTATTCTCCTTTTGTTGACTAAGTCAATAATCAGAAT
CAGCAGGTTTGGAGTCAGCTTGGCAGGGATCAGCAGCCTGGGTTGGAAGGAGGGGGTATAAAAGCCCCTTCAC
CAGGGAGAAGCCGTCACACAGATCCACAAGCTCCTGAGGTAAGTGCCGTGTGTGGTTCCCGCGGGCCTGGCCTC
TTTACGGGTTATGGCCCTTGCGTGCCTTGAATTACTGACACTGACATCCACTTTTTCTTTTTCTCCACAGCTA
GCGCCACCATGCAGATTGAGCTGTCCACTTGTTTCTTCCTGTGCCTCCTGCGCTTCTGTTTCTCCGCCACTCG
CCGGTACTACCTTGGAGCCGTGGAGCTTTCATGGGACTACATGCAGAGCGACCTGGGCGAACTCCCCGTGGAT
GCCAGATTCCCCCCCGCGTGCCAAAGTCCTTCCCCTTTAACACCTCCGTGGTGTACAAGAAAACCCTCTTTG
TCGAGTTCACTGACCACCTGTTCAACATCGCCAAGCCGCGCCCACCTTGGATGGGCCTCCTGGGACCGACCAT
TCAAGCTGAAGTGTACGACACCGTGGTGATCACCCTGAAGAACATGGCGTCCCACCCCGTGTCCCTGCATGCG
GTCGGAGTGTCCTACTGGAAGGCCTCCGAAGGAGCTGAGTACGACGACCAGACTAGCCAGCGGGAAAGGAGG
ACGATAAAGTGTTCCCGGGCGGCTCGCATACTTACGTGTGGCAAGTCCTGAAGGAAAACGGACCTATGGCATC
CGATCCTCTGTGCCTGACTTACTCCTACCTTTCCCATGTGGACCTCGTGAAGGACCTGAACAGCGGGCTGATT
GGTGCACTTCTCGTGTGCCGCGAAGGTTCGCTCGCTAAGGAAAAGACCCAGACCCTCCATAAGTTCATCCTTT
TGTTCGCTGTGTTCGATGAAGGAAAGTCATGGCATTCCGAAACTAAGAACTCGCTGATGCAGGACCGGGATGC
CGCCTCAGCCCGCGCCTGGCCTAAAATGCATACAGTCAACGGATACGTGAATCGGTCACTGCCCGGGCTCATC
GGTTGTCACAGAAAGTCCGTGTACTGGCACGTCATCGGCATGGGCACTACGCCTGAAGTGCACTCCATCTTCC
TGGAAGGGCACACCTTCCTCGTGCGCAACCACCGCCAGGCCTCTCTGGAAATCTCCCCGATTACCTTTCTGAC
CGCCCAGACTCTGCTCATGGACCTGGGGCAGTTCCTTCTCTTGCCACATCTCCAGCCATCAGCACGACGGA
ATGGAGGCCTACGTGAAGGTGGACTCATGCCCGGAAGAACCTCAGTTGCGGATGAAGAACAACGAGGAGGCCG
AGGACTATGACGACGATTTGACTGACTCCGAGATGGACGTCGTGCGGTTCGATGACGACAACAGCCCCAGCTT
CATCCAGATTCGCAGCGTGGCCAAGAAGCACCCCAAAACCTGGGTGCACTACATCGCGGCCGAGGAAGAAGAT
TGGGACTACGCCCCGTTGGTGCTGGCACCCGATGACCGGTCGTACAAGTCCCAGTATCTGAACAATGGTCCGC
AGCGGATTGGCAGAAAGTACAAGAAAGTGCGGTTCATGGCGTACACTGACGAAACGTTTAAGACCCGGGAGGC
CATTCAACATGAGAGCGGCATTCTGGGACCACTGCTGTACGGAGAGGTCGGCGATACCCTGCTCATCATCTTC
AAAAACCAGGCCTCCCGGCCTTACAACATCTACCCTCACGGAATCACCGACGTGCGGCCACTCTACTCGCGGC
GCCTGCCGAAGGGCGTCAAGCACCTGAAAGACTTCCCTATCCTGCCGGGCGAAATCTTCAAGTATAAGTGGAC
CGTCACCGTGGAGGACGGGCCCACCAAGAGCGATCCTAGGTGTCTGACTCGGTACTACTCCAGCTTCGTGAAC
ATGGAACGGGACCTGGCATCGGGACTCATTGGACCGCTGCTGATCTGCTACAAAGAGTCGGTGGATCAACGCG
GCAACCAGATCATGTCCGACAAGCGCAACGTGATCCTGTTCTCCGTGTTTGATGAAAACAGATCCTGGTACCT
CACTGAAAACATCCAGAGGTTCCTCCCAAACCCCGCAGGAGTGCAACTGGAGGACCCTGAGTTTCAGGCCTCG
AATATCATGCACTCGATTAACGGTTACGTGTTCGACTCGCTGCAACTGAGCGTGTGCCTCCATGAAGTCGCTT
ACTGGTACATTCTGTCCATCGGCGCCCAGACTGACTTCCTGAGCGTGTTCTTTTCCGGTTACACCTTTAAGCA
CAAGATGGTGTACGAAGATACCCTGACCCTGTTCCCCTTTCTCCGGCGAAACGGTGTTCATGTCGATGGAGAAC
CCGGGTCTGTGGATTCTGGGATGCCACAACAGCGACTTTCGGAACCGCGGAATGACTGCCCTGCTGAAGGTGT
CCTCATGCGACAAGAACACCGGAGACTACTACGAGGACTCCTACGAGGATATCTCAGCCTACCTCCTGTCCAA
GAACAACGCGATCGAGCCGCGCAGCTTCAGCCAGAACGGCGCGCCAACATCAGAGAGCGCCACCCCTGAAAGT
GGTCCCGGGAGCGAGCCAGCCACATCTGGGTCGGAAACGCCAGGCACAAGTGAGTCTGCAACTCCCGAGTCCG
GACCTGGCTCCGAGCCTGCCACTAGCGGCTCCGAGACTCCGGGAACTTCCGAGAGCGCTACACCAGAAAGCGG
ACCCGGAACCAGTACCGAACCTAGCGAGGGCTCTGCTCCGGGACAGCCCAGCCGGCTCTCCTACATCCACGGAG
GAGGGCACTTCCGAATCCGCCACCCCGGAGTCAGGGCCAGGATCTGAACCCGCTACCTCAGGCAGTGAGACGC
CAGGAACGAGCGAGTCCGCTACACCGGAGAGTGGGCCAGGGAGCCCTGCTGGATCTCCTACGTCCACTGAGGA
AGGGTCACCAGCGGGCTCGCCCACCAGCACTGAAGAAGGTGCCTCAAGGCCTGGGCCTCAGCCGCCCATCCAG
CGAGAAATTACCCGGACCACCCTCCAATCGGATCAGGAGGAAATCGACTACGACGACACCATCGGTGGAAA
TGAAGAAGGAAGATTTCGATATCTACGACGAGGACGAAAATCAGTCCCCTCGCTCATTCAAAAGAAAACTAG
ACACTACTTTATCGCCGCGGTGGAAAGACTGTGGGACTATGGAATGTCATCCAGCCCTCACGTCCTTCGGAAC
CGGGCCCAGAGCGGATCGGTGCCTCAGTTCAAGAAAGTGGTGTTCCAGGAGTTCACCGACGGCAGCTTCACCC
AGCCGCTGTACCGGGGAGAACTGAACGAACACCTGGGCCTGCTCGGTCCCTACATCCGCGCGGAAGTGGAGGA
TAACATCATGGTGACCTTCCGTAACCAAGCATCCAGACCTTACTCCTTCTATTCCTCCCTGATCTCATACGAG
GAGGACCAGCGCCAAGGCGCCGAGCCCCGCAAGAACTTCGTCAAGCCCAACGAGACTAAGACCTACTTCTGGA
AGGTCCAACACCATATGGCCCCGACCAAGGATGAGTTTGACTGCAAGGCCTGGGCCTACTTCTCCGACGTGGA
CCTTGAGAAGGATGTCCATTCCGGCCTGATCGGGCCGCTGCTCGTGTGTCACACCAACACCCTGAACCCAGCG
CATGGACGCCAGGTCACCGTCCAGGAGTTTGCTCTGTTCTTCACCATTTTTGACGAAACTAAGTCCTGGTACT
TCACCGAGAATATGGAGCGAAACTGTAGAGCGCCCTGCAATATCCAGATGGAAGATCCGACTTTCAAGGAGAA
CTATAGATTCCACGCCATCAACGGGTACATCATGGATACTCTGCCGGGGCTGGTCATGGCCCAGGATCAGAGG
ATTCGGTGGTACTTGCTGTCAATGGGATCGAACGAAAACATTCACTCCATTCACTTCTCCGGTCACGTGTTCA

TABLE 2B-continued

Example B19-FVIII construct bearing B19d135 ITRs (nucleotides 1-6762;
SEQ ID NO: 179)

```
CTGTGCGCAAGAAGGAGGAGTACAAGATGGCGCTGTACAATCTGTACCCCGGGG

TABLE 2C-continued

Example GPV-FVIII construct bearing GPVd162 ITRs
(nucleotides 1-6830; SEQ ID NO: 182)

```
GAAGGGCACACCTTCCTCGTGCGCAACCACCGCCAGGCCTCTCTGGAAATCTCCCCGA
TTACCTTTCTGACCGCCCAGACTCTGCTCATGGACCTGGGGCAGTTCCTTCTCTTCTG
CCACATCTCCAGCCATCAGCACGACGGAATGGAGGCCTACGTGAAGGTGGACTCATGC
CCGGAAGAACCTCAGTTGCGGATGAAGAACAACGAGGAGGCCGAGGACTATGACGACG
ATTTGACTGACTCCGAGATGGACGTCGTGCGGTTCGATGACGACAACAGCCCCAGCTT
CATCCAGATTCGCAGCGTGGCCAAGAAGCACCCCAAAACCTGGGTGCACTACATCGCG
GCCGAGGAAGAAGATTGGGACTACGCCCCGTTGGTGCTGGCACCCGATGACCGGTCGT
ACAAGTCCCAGTATCTGAACAATGGTCCGCAGCGGATTGGCAGAAAGTACAAGAAAGT
GCGGTTCATGGCGTACACTGACGAAACGTTTAAGACCCGGGAGGCCATTCAACATGAG
AGCGGCATTCTGGGACCACTGCTGTACGGAGAGGTCGGCGATACCCTGCTCATCATCT
TCAAAAACCAGGCCTCCCGGCCTTACAACATCTACCCTCACGGAATCACCGACGTGCG
GCCACTCTACTCGCGGCGCCTGCCGAAGGGCGTCAAGCACCTGAAAGACTTCCCTATC
CTGCCGGGCGAAATCTTCAAGTATAAGTGGACCGTCACCGTGGAGGACGGGCCCACCA
AGAGCGATCCTAGGTGTCTGACTCGGTACTACTCCAGCTTCGTGAACATGGAACGGGA
CCTGGCATCGGGACTCATTGGACCGCTGCTGATCTGCTACAAAGAGTCGGTGGATCAA
CGCGGCAACCAGATCATGTCCGACAAGCGCAACGTGATCCTGTTCTCCGTGTTTGATG
AAAACAGATCCTGGTACCTCACTGAAAACATCCAGAGGTTCCTCCCAAACCCCGCAGG
AGTGCAACTGGAGGACCCTGAGTTTCAGGCCTCGAATATCATGCACTCGATTAACGGT
TACGTGTTCGACTCGCTGCAACTGAGCGTGTGCCTCCATGAAGTCGCTTACTGGTACA
TTCTGTCCATCGGCGCCCAGACTGACTTCCTGAGCGTGTTCTTTTCCGGTTACACCTT
TAAGCACAAGATGGTGTACGAAGATACCCTGACCCTGTTCCCTTTCTCCGGCGAAACG
GTGTTCATGTCGATGGAGAACCCGGGTCTGTGGATTCTGGGATGCCACAACAGCGACT
TTCGGAACCGCGGAATGACTGCCCTGCTGAAGGTGTCCTCATGCGACAAGAACACCGG
AGACTACTACGAGGACTCCTACGAGGATATCTCAGCCTACCTCCTGTCCAAGAACAAC
GCGATCGAGCCGCGCAGCTTCAGCCAGAACGGCGCGCCAACATCAGAGAGCGCCACCC
CTGAAAGTGGTCCCGGGAGCGAGCCAGCCACATCTGGGTCGGAAACGCCAGGCACAAG
TGAGTCTGCAACTCCCGAGTCCGGACCTGGCTCCGAGCCTGCCACTAGCGGCTCCGAG
ACTCCGGGAACTTCCGAGAGCGCTACACCAGAAAGCGGACCCGGAACCAGTACCGAAC
CTAGCGAGGGCTCTGCTCCGGGCAGCCCAGCCGGCTCTCCTACATCCACGGAGGAGGG
CACTTCCGAATCCGCCACCCCGGAGTCAGGGCCAGGATCTGAACCCGCTACCTCAGGC
AGTGAGACGCCAGGAACGAGCGAGTCCGCTACACCGGAGAGTGGGCCAGGGAGCCCTG
CTGGATCTCCTACGTCCACTGAGGAAGGGTCACCAGCGGGCTCGCCCACCAGCACTGA
AGAAGGTGCCTCGAGCCCGCCTGTGCTGAAGAGGCACCAGCGAGAAATTACCCGGACC
ACCCTCCAATCGGATCAGGAGGAAATCGACTACGACGACACCATCTCGGTGGAAATGA
AGAAGGAAGATTTCGATATCTACGACGAGGACGAAAATCAGTCCCCTCGCTCATTCCA
AAAGAAAACTAGACACTACTTTATCGCCGCGGTGGAAAGACTGTGGGACTATGGAATG
TCATCCAGCCCTCACGTCCTTCGGAACCGGGCCCAGAGCGGATCGGTGCCTCAGTTCA
AGAAAGTGGTGTTCCAGGAGTTCACCGACGGCAGCTTCACCCAGCCGCTGTACCGGGG
AGAACTGAACGAACACCTGGGCCTGCTCGGTCCCTACATCCGCGCGGAAGTGGAGGAT
AACATCATGGTGACCTTCCGTAACCAAGCATCCAGACCTTACTCCTTCTATTCCTCCC
TGATCTCATACGAGGAGGACCAGCGCCAAGGCGCCGAGCCCCGCAAGAACTTCGTCAA
GCCCAACGAGACTAAGACCTACTTCTGGAAGGTCCAACACCATATGGCCCCGACCAAG
GATGAGTTTGACTGCAAGGCCTGGGCCTACTTCTCCGACGTGGACCTTGAGAAGGATG
TCCATTCCGGCCTGATCGGGCCGCTGCTCGTGTGTCACACCAACACCCTGAACCCAGC
GCATGGACGCCAGGTCACCGTCCAGGAGTTTGCTCTGTTCTTCACCATTTTTGACGAA
ACTAAGTCCTGGTACTTCACCGAGAATATGGAGCGAAACTGTAGAGCGCCCTGCAATA
TCCAGATGGAAGATCCGACTTTCAAGGAGAACTATAGATTCCACGCCATCAACGGGTA
CATCATGGATACTCTGCCGGGGCTGGTCATGGCCCAGGATCAGAGGATTCGGTGGTAC
TTGCTGTCAATGGGATCGAACGAAAACATTCACTCCATTCACTTCTCCGGTCACGTGT
TCACTGTGCGCAAGAAGGAGGAGTACAAGATGGCGCTGTACAATCTGTACCCCGGGGT
GTTCGAAACTGTGGAGATGCTGCCGTCCAAGGCCGGCATCTGGAGAGTGGAGTGCCTG
ATCGGAGAGCACCTCCACGCGGGGATGTCCACCCTCTTCCTGGTGTACTCGAATAAGT
GCCAGACCCCGCTGGGCATGGCCTCGGGCCACATCAGAGACTTCCAGATCACAGCAAG
CGGACAATACGGCCAATGGGCGCCGAAGCTGGCCCGCTTGCACTACTCCGGATCGATC
AACGCATGGTCCACCAAGGAACCGTTCTCGTGGATTAAGGTGGACCTCCTGGCCCCTA
TGATTATCCACGGAATTAAGACCCAGGGCGCCAGGCAGAAGTTCTCCTCCCTGTACAT
CTCGCAATTCATCATCATGTACAGCCTGGACGGGAAGAAGTGGCAGACTTACAGGGGA
AACTCCACCGGCACCCTGATGGTCTTTTTCGGCAACGTGGATTCCTCCGGCATTAAGC
ACAACATCTTCAACCCACCGATCATAGCCAGATATATTAGGCTCCACCCCACTCACTA
CTCAATCCGCTCAACTCTTCGGATGGAACTCATGGGGTGCGACCTGAACTCCTGCTCC
ATGCCGTTGGGGATGGAATCAAAGGCTATTAGCGACGCCCAGATCACCGCGAGCTCCT
ACTTCACTAACATGTTCGCCACCTGGAGCCCCTCCAAGGCCAGGCTGCACTTGCAGGG
ACGGTCAAATGCCTGGCGGCCGCAAGTGAACAATCCGAAGGAATGGCTTCAAGTGGAT
TTCCAAAAGACCATGAAAGTGACCGGAGTCACCACCCAGGGAGTGAAGTCCTTCTGA
CCTCGATGTATGTGAAGGAGTTCCTGATTAGCAGCAGCCAGGACGGGCACCAGTGGAC
CCTGTTCTTCCAAAACGGAAAGGTCAAGGTGTTCCAGGGGAACCAGGACTCGTTCACA
CCCGTGGTGAACTCCCTGGACCCCCCACTGCTGACGCGGTACTTGAGGATTCATCCTC
AGTCCTGGGTCCATCAGATTGCATTGCGAATGGAAGTCCTGGGCTGCGAGGCCCAGGA
CCTGTACTGA -- 5596
```

| WPRE (mutated woodchuck hepatitis virus post-transcriptional regulatory | 5616 -<br>TCATAATCAACCTCTGGATTACAAAATTTGTGAAAGATTGACTGGTATTCTTAACTAT<br>GTTGCTCCTTTTACGCTATGTGGATACGCTGCTTTAATGCCTTTGTATCATGCTATTG<br>CTTCCCGTATGGCTTTCATTTTCTCCTCCTTGTATAAATCCTGGTTGCTGTCTCTTTA<br>TGAGGAGTTGTGGCCCGTTGTCAGGCAACGTGGCGTGGTGTGCACTGTGTTTGCTGAC<br>GCAACCCCCACTGGTTGGGGCATTGCCACCACCTGTCAGCTCCTTTCCGGGACTTTCG |
|---|---|

TABLE 2C-continued

Example GPV-FVIII construct bearing GPVd162 ITRs (nucleotides 1-6830; SEQ ID NO: 182)

| | |
|---|---|
| element) (SEQ ID NO: 120) | CTTTCCCCCTCCCTATTGCCACGGCGGAACTCATCGCCGCCTGCCTTGCCCGCTGCTG<br>GACAGGGGCTCGGCTGTTGGGCACTGACAATTCCGTGGTGTTGTCGGGGAAATCATCG<br>TCCTTTCCTTGGCTGCTCGCCTGTGTTGCCACCTGGATTCTGCGCGGGACGTCCTTCT<br>GCTACGTCCCTTCGGCCCTCAATCCAGCGGACCTTCCTTCCCGCGGCCTGCTGCCGGC<br>TCTGCGGCCTCTTCCGCGTCTTCGCCTTCGCCCTCAGACGAGTCGGATCTCCCTTTGG<br>GCCGCCTCCCCGCTG -- 6210 |
| bGHpA (bovine growth hormone polyadenylation signal) (SEQ ID NO: 122) | 6219 -<br>CGACTGTGCCTTCTAGTTGCCAGCCATCTGTTGTTTGCCCCTCCCCCGTGCCTTCCTT<br>GACCCTGGAAGGTGCCACTCCCACTGTCCTTTCCTAATAAAATGAGGAAATTGCATCG<br>CATTGTCTGAGTAGGTGTCATTCTATTCTGGGGGGTGGGGTGGGGCAGGACAGCAAGG<br>GGGAGGATTGGGAAGACAATAGCAGGCATGCTGGGGA -- 6429 |
| 3' ITR inverted terminal repeat (SEQ ID NO: 184) | 6549 --<br>CACTTCCTGGCGCGCAAAATATCCTCTTGTCCTTGAGTCTCATTGGAGGGTTCGTTCG<br>TTCGAACCAGCCAATCAGGGGAGGGGGAAGTGACGCAAGTTCCGGTCACATGCTTCCG<br>GTGACGCACATCCGGTGACGTAGTTCCGGTCACGTGCTTCCTGTCACGTGTTTCCGGT<br>CACGTGACTTCCGGTCATGTGACTTCCGGTGACGTGTTTCCGGCTTAACTATTGGGCT<br>GACCGCGCGGCATGCGCGTGGTCAACCTAACAGCCGGAAACACGTCACCG -- 6830 |

Full-length Sequence (SEQ ID NO: 182)

CGGTGACGTGTTTCCGGCTGTTAGGTTGACCACGCGCATGCCGCGCGGTCAGCCCAATAGTTAAGCCGGAAAC
ACGTCACCGGAAGTCACATGACCGGAAGTCACGTGACCGGAAACACGTGACAGGAAGCACGTGACCGGAACTA
CGTCACCGGATGTGCGTCACCGGAAGCATGTGACCGGAACTTGCGTCACTTCCCCCTCCCCTGATTGGCTGGT
TCGAACGAACGAACCCTCCAATGAGACTCAAGGACAAGAGGATATTTTGCGCGCCAGGAAGTGGCGGCAATTC
AGTCGATAACTATAACGGTCCTAAGGTAGCGATTTAAATACGCGCTCTCTTAAGGTAGCCCCGGGACGCGTCA
ATTGAGATCTGGATCCGGTACCGAATTCGCGGCCGCCTCGACGACTAGCGTTTAATTAAACGCGTGTCTGTCT
GCACATTTCGTAGAGCGAGTGTTCCGATACTCTAATCTCCCTAGGCAAGGTTCATATTTGTGTAGGTTACTTA
TTCTCCTTTTGTTGACTAAGTCAATAATCAGAATCAGCAGGTTTGGAGTCAGCTTGGCAGGGATCAGCAGCCT
GGGTTGGAAGGAGGGGGTATAAAAGCCCCTTCACCAGGAGAAGCCGTCACACAGATCCACAAGCTCCTGAGGT
AAGTGCCGTGTGTGGTTCCCGCGGGCCTGGCCTCTTTACGGGTTATGGCCCTTGCGTGCCTTGAATTACTGAC
ACTGACATCCACTTTTTCTTTTTCTCCACAGCTAGCGCCACCATGCAGATTGAGCTGTCCACTTGTTTCTTCC
TGTGCCTCCTGCGCTTCTGTTTCTCCGCCACTCGCCGGTACTACCTTGGAGCCGTGGAGCTTTCATGGGACTA
CATGCAGAGCGACCTGGGCGAACTCCCCGTGGATGCCAGATTCCCCCCCCGCGTGCCAAAGTCCTTCCCCTTT
AACACCTCCGTGGTGTACAAGAAAACCCTCTTTGTCGAGTTCACTGACCACCTGTTCAACATCGCCAAGCCGC
GCCCACCTTGGATGGGCCTCCTGGGACCGACCATTCAAGCTGAAGTGTACGACACCGTGGTGATCACCCTGAA
GAACATGGCGTCCCACCCCGTGTCCCTGCATGCGGTCGGAGTGTCCTACTGGAAGGCCTCCGAAGGAGCTGAG
TACGACGACCAGACTAGCCAGCGGGAAAAGGAGGACGATAAAGTGTTCCCGGGCGGCTCGCATACTTACGTGT
GGCAAGTCCTGAAGGAAAACGGACCTATGGCATCCGATCCTCTGTGCCTGACTTACTCCTACCTTTCCCATGT
GGACCTCGTGAAGGACCTGAACAGCGGGCTGATTGGTGCACTTCTCGTGTGCCGCGAAGGTTCGCTCGCTAAG
GAAAAGACCCAGACCCTCCATAAGTTCATCCTTTTTGTTCGCTGTGTTCGATGAAGGAAAGTCATGGCATTCCG
AAACTAAGAACTCGCTGATGCAGGACCGGGATGCCGCCTCAGCCCGCGCCTGGCCTAAAATGCATACAGTCAA
CGGATACGTGAATCGGTCACTGCCCGGGCTCATCGGTTGTCACAGAAAGTCCGTGTACTGGCACGTCATCGGC
ATGGGCACTACGCCTGAAGTGCACTCCATCTTCCTGGAAGGGCACACCTTCCTCGTGCGCAACCACCGCCAGG
CCTCTCTGGAAATCTCCCCGATTACCTTTCTGACCGCCCAGACTCTGCTCATGGACCTGGGGCAGTTCCTTCT
CTTCTGCCACATCTCCAGCCATCAGCACGACGGAATGGAGGCCTACGTGAAGGTGGACTCATGCCCCGGAAGAA
CCTCAGTTGCGGATGAAGAACAACGAGGAGGCCGAGGACTATGACGACGATTTGACTGACTCCGAGATGGACG
TCGTGCGGTTCGATGACGACAACAGCCCCAGCTTCATCCAGATTCGCAGCGTGGCCAAGAAGCACCCCAAAAC
CTGGGTGCACTACATCGCGGCCGAGGAAGAAGATTGGGACTACGCCCCGTTGGTGCTGGCACCCGATGACCGG
TCGTACAAGTCCCAGTATCTGAACAATGGTCCGCAGCGGATTGGCAGAAAGTACAAGAAAGTGCGGTTCATGG
CGTACACTGACGAAACGTTTAAGACCCGGGAGGCCATTCAACATGAGAGCGGCATTCTGGGACCACTGCTGTA
CGGAGAGGTCGGCGATACCCTGCTCATCATCTTCAAAAACCAGGCCTCCCGGCCTTACAACATCTACCCTCAC
GGAATCACCGACGTGCGGCCACTCTACTCGCGGCGCCTGCCGAAGGGCGTCAAGCACCTGAAAGACTTCCCTA
TCCTGCCGGGCGAAATCTTCAAGTATAAGTGGACCGTCACCGTGGAGGACGGGCCCACCAAGAGCGATCCTAG
GTGTCTGACTCGGTACTACTCCAGCTTCGTGAACATGGAACGGGACCTGGCATCGGGACTTCATTGGACCGCTG
CTGATCTGCTACAAAGAGTCGGTGGATCAACGCGGCAACCAGATCATGTCCGACAAGCGCAACGTGATCCTGT
TCTCCGTGTTTGATGAAAACAGATCCTGGTACCTCACTGAAAACATCCAGAGGTTCCTCCCAAACCCCGCAGG
AGTGCAACTGGAGGACCCTGAGTTTCAGGCCTCGAATATCATGCACTCGATTAACGGTTACGTGTTCGACTCG
CTGCAACTGAGCGTGTGCCTCCATGAAGTCGCTTACTGGTACATTCTGTCCATCGGCGCCCAGACTGACTTCC
TGAGCGTGTTCTTTTCCGGTTACACCTTTAAGCACAAGATGGTGTACGAAGATACCCTGACCCTGTTCCCTTT
CTCCGGCGAAACGGTGTTCATGTCGATGGAGAACCCGGGTCTGTGGATTCTGGGATGCCACAACAGCGACTTT
CGGAACCGCGGAATGACTGCCCTGCTGAAGGTGTCCTCATGCGACAAGAACACCGGAGACTACTACGAGGACT
CCTACGAGGATATCTCAGCCTACCTCCTGTCCAAGAACAACGCCATCGAGCCCCGCAGCTTCAGCCAGAACAG
CGCGCCAACATCAGAGAGCGCCACCCCTGAAAGTGGTCCCGGGAGCGAGCCAGCCACATCTGGGTCGGAAACG
CCAGGCACAAGTGAGTCTGCAACTCCCGAGTCCGGACCTGCTCCGAGCCTGCCACTAGCGGCTCCGAGACTC
CGGGAACTTCCGAGAGCGCTACACCAGAAAGCGGACCCGAACCAGTACCGAACCTAGCGAGGGCTCTGCTCC
GGGCAGCCCAGCCGGCTCTCCTACATCCACGGAGGAGGGCACTTCCGAATCCGCCCACCCCGGAGTCAGGGCA
GGATCTGAACCCGCTACCTCAGGCAGTGAGACGCCAGGAAGCAGCCGAGTCCGCTACACCGGAGAGTGGGCCAG
GGAGCCCTGCTGGATCCTCTACGTCCACTGAGGAAGGGTCACCAGCGGGCTCGCCCACCAGCACTGAAGAAGG
TGCCTCGAGCCCGCCTGTGCTGAAGAGGCACCAGCGAGAATTACCCGGACCACCCTCCAATCGGATCAGGAG
GAAATGACTACGACGACACCATCTCGGTGGAAATGAAGAAGGAAGATTTCGATATCTACGACGAGGACGAAAA
ATCAGTCCCCTCGCTCATTCCAAAAGAAAACTAGACACTACTTTATCGCCGCGGTGGAAAGACTGTGGGACTA
TGGAATGTCATCCAGCCCTCACGTCCTTCGGAACCGGGCCCAGAGCGGATCGGTGCCTCAGTTCAAGAAAGTG
GTGTTCCAGGAGTTCACCGACGGCAGCTTCACCCAGCCGCTGTACCGGGGAGAACTGAACGAACACCTGGGCC
TGCTCGGTCCCTACATCCGCGCGGAAGTGGAGGATAACATCATGGTGACCTTCCGTAACCAAGCATCCAGACC
TTACTCCTTCTATTCCTCCCTGATCTCATACGAGGAGGACCAGCGCCAAGGCGCCGAGCCCCGCAAGAACTTC

TABLE 2C-continued

Example GPV-FVIII construct bearing GPVd162 ITRs
(nucleotides 1-6830; SEQ ID NO: 182)

```
GTCAAGCCCAACGAGACTAAGACCTACTTCTGGAAGGTCCAACACCCATATGGCCCCGACCAAGGATGAGTTTG
ACTGCAAGGCCTGGGCCTACTTCTCCGACGTGGACCTTGAGAAGGATGTCCATTCCGGCCTGATCGGGCCGCT
GCTCGTGTGTCACACCAACACCCTGAACCCAGCGCATGGACGCCAGGTCACCGTCCAGGAGTTTGCTCTGTTC
TTCACCATTTTTGACGAAACTAAGTCCTGGTACTTCACCGAGAATATGGAGCGAAACTGTAGAGCGCCCTGCA
ATATCCAGATGGAAGATCCGACTTTCAAGGAGAACTATAGATTCCACGCCATCAACGGGTACATCATGGATAC
TCTGCCGGGGCTGGTCATGGCCCAGGATCAGAGGATTCGGTGGTACTTGCTGTCAATGGGATCGAACGAAAAC
ATTCACTCCATTCACTTCTCCGGTCACGTGTTCACTGTGCGCAAGAAGGAGGAGTACAAGATGGCGCTGTACA
ATCTGTACCCCGGGGTGTTCGAAACTGTGGAGATGCTGCCGTCCAAGGCCGGCATCTGGAGAGTGGAGTGCCT
GATCGGAGAGCACCTCCACGCGGGGATGTCCACCCTCTTCCTGGTGTACTCGAATAAGTGCCAGACCCCGCTG
GGCATGGCCTCGGGCCCACATCAGAGACTTCCAGATCACAGCAAGCGGACAATACGGCCAATGGGCGCCGAAGC
TGGCCCGCTTGCACTACTCCGGATCGATCAACGCATGGTCCACCAAGGAACCGTTCTCGTGATTAAGGTGGA
CCTCCTGGCCCCTATGATTATCCACGGAATTAAGACCCAGGGCGCCAGGCAGAAGTTCTCCTCCCTGTACATC
TCGCAATTCATCATCATGTACAGCCTGGACGGGAAGAAGTGGCAGACTTACAGGGGAAACTCCACCGGCACCC
TGATGGTCTTTTTCGGCAACGTGGATTCCTCCGGCATTAAGCACAACATCTTCAACCCACCGATCATAGCCAG
ATATATTAGGCTCCACCCCACTCACTACTCAATCCGCTCAACTCTTCGGATGGAACTCATGGGGTGCGACCTG
AACTCCTGCTCCATGCCGTTGGGGATGGAATCAAAGGCTATTAGCGACGCCCAGATCACCGCGAGCTCCTACT
TCACTAACATGTTCGCCACCTGGAGCCCCTCCAAGGCCAGGCTGCACTTGCAGGGACGGTCAAATGCCTGGCG
GCCGCAAGTGAACAATCCGAAGGAATGGCTTCAAGTGGATTTCCAAAAGACCATGAAAGTGACCGGAGTCACC
ACCCAGGGAGTGAAGTCCCTTCTGACCTCGATGTATGTGAAGGAGTTCCTGATTAGCAGCAGCCAGGACGGGC
ACCAGTGGACCCTGTTCTTCCAAAACGGAAAGGTCAAGGTGTTCCAGGGGAACCAGGACTCGTTCACACCCGT
GGTGAACTCCCTGGACCCCCCACTGCTGACGCGGTACTTGAGGATTCATCCTCAGTCCTGGGTCCATCAGATT
GCATTGCGAATGGAAGTCCTGGGCTGCGAGGCCCAGGACCTGTACTGAATCAGCCTGAGCTCGCTGATCATAA
TCAACCTCTGGATTACAAAATTTGTGAAAGATTGACTGGTATTCTTAACTATGTTGCTCCTTTTACGCTATGT
GGATACGCTGCTTTAATGCCTTTGTATCATGCTATTGCTTCCCGTATGGCTTTCATTTTCTCCTCCTTGTATA
AATCCTGGTTGCTGTCTCTTTATGAGGAGTTGTGGCCCGTTGTCAGGCAACGTGGCGTGGTGTGCACTGTGTT
TGCTGACGCAACCCCACTGGTTGGGGCATTGCCACCACCTGTGCAGCTCCTTTCCGGGACTTTCGCTTTCCCC
CTCCCTATTGCCACGGCGGAACTCATCGCCGCCTGCCTTGCCCGCTGCTGGACAGGGGCTCGGCTGTTGGGCA
CTGACAATTCCGTGGTGTTGTCGGGGAAATCATCGTCCTTTCCTTGGCTGCTCGCCTGTGTTGCCACCTGGAT
TCTGCGCGGGACGTCCTTCTGCTACGTCCCTTCGGCCCTCAATCCAGCGGACCTTCCTTCCCGCGGCCTGCTG
CCGGCTCTGCGGCCTCTTCCGCGTCTTCGCCTTCGCCCTCAGACGAGTCGGATCTCCCTTTGGGCCGCCTCCC
CGCTGATCAGCCTCGACTGTGCCTTCTAGTTGCCAGCCATCTGTTGTTTGCCCCTCCCCCGTGCCTTCCTTGA
CCCTGGAAGGTGCCACTCCCACTGTCCTTTCCTAATAAAATGAGGAAATTGCATCGCATTGTCTGAGTAGGTG
TCATTCTATTCTGGGGGGTGGGGTGGGGCAGGACAGCAAGGGGGAGGATTGGGAAGACAATAGCAGGCATGCT
GGGGATGCGGTGGGCTCTATGCTTCTGAGGCGGAAAGAACGGGCTCAGAAGCTTCTAGATATCCTCTCTTA
AGGTAGCATCGAGATTTAAATTAGGGATAACAGGGTAATGGCGCGGGCCGCCACTTCCTGGCGCGCAAAATAT
CCTCTTGTCCTTGAGTCTCATTGGAGGGTTCGTTCGTTCGAACCAGCCAATCAGGGGAGGGGAAGTGACGCA
AGTTCCGGTCACATGCTTCCGGTGACGCACATCCGGTGACGTAGTTCCGGTCACGTGCTTCCTGTCACGTGTT
TCCGGTCACGTGACTTCCGGTCATGTGACTTCCGGTGACGTGTTTCCGGCTTAACTATTGGGCTGACCGCGCG
GCATGCGCGTGGTCAACCTAACAGCCGGAAACACGTCACCG
```

TABLE 2D

Example B19-FVIII construct bearing full length B19 ITRs
(nucleotides 1-7032; SEQ ID NO: 189)

| Description | Sequence |
|---|---|
| 5' ITR (SEQ ID NO: 185) | CCAAATCAGATGCCGCCGGTC TABLE 2D-continued Example B19-FVIII construct bearing full length B19 ITRs (nucleotides 1-7032; SEQ ID NO: 189)

| | |
|---|---|
| underlining (SEQ | GTTCATCCTTTTGTTCGCTGTGTTCGATGAAGGAAAGTCATGGCATTCCGAAACTAAG |
| ID NO: 118)) | AACTCGCTGATGCAGGACCGGGATGCCGCCTCAGCCCGCGCCTGGCCTAAAATGCATA |
| | CAGTCAACGGATACGTGAATCGGTCACTGCCCGGGCTCATCGGTTGTCACAGAAAGTC |
| | CGTGTACTGGCACGTCATCGGCATGGGCACTACGCCTGAAGTGCACTCCATCTTCCTG |
| | GAAGGGCACACCTTCCTCGTGCGCAACCACCGCCAGGCCTCTCTGGAAATCTCCCCGA |
| | TTACCTTTCTGACCGCCCAGACTCTGCTCATGGACCTGGGGCAGTTCCTTCTCTTCTG |
| | CCACATCTCCAGCCATCAGCACGACGGAATGGAGGCCTACGTGAAGGTGGACTCATGC |
| | CCGGAAGAACCTCAGTTGCGGATGAAGAACAACGAGGAGGCCGAGGACTATGACGACG |
| | ATTTGACTGACTCCGAGATGGACGTCGTGCGGTTCGATGACGACAACAGCCCCAGCTT |
| | CATCCAGATTCGCAGCGTGGCCAAGAAGCACCCCAAAACCTGGGTGCACTACATCGCG |
| | GCCGAGGAAGAAGATTGGGACTACGCCCCGTTGGTGCTGGCACCCGATGACCGGTCGT |
| | ACAAGTCCCAGTATCTGAACAATGGTCCGCAGCGGATTGGCAGAAAGTACAAGAAAGT |
| | GCGGTTCATGGCGTACACTGACGAAACGTTTAAGACCCGGGAGGCCATTCAACATGAG |
| | AGCGGCATTCTGGGACCACTGCTGTACGGAGAGGTCGGCGATACCCTGCTCATCATCT |
| | TCAAAAACCAGGCCTCCCGGCCTTACAACATCTACCCTCACGGAATCACCGACGTGCG |
| | GCCACTCTACTCGCGGCGCCTGCCGAAGGGCGTCAAGCACCTGAAAGACTTCCCTATC |
| | CTGCCGGGCGAAATCTTCAAGTATAAGTGGACCGTCACCGTGGAGGACGGGCCCACCA |
| | AGAGCGATCCTAGGTGTCTGACTCGGTACTACTCCAGCTTCGTGAACATGGAACGGGA |
| | CCTGGCATCGGGACTCATTGGACCGCTGCTGATCTGCTACAAAGAGTCGGTGGATCAA |
| | CGCGGCAACCAGATCATGTCCGACAAGCGCAACGTGATCCTGTTCTCCGTGTTTGATG |
| | AAAACAGATCCTGGTACCTCACTGAAAACATCCAGAGGTTCCTCCCAAACCCCGCAGG |
| | AGTGCAACTGGAGGACCCTGAGTTTCAGGCCTCGAATATCATGCACTCGATTAACGGT |
| | TACGTGTTCGACTCGCTGCAACTGAGCGTGTGCCTCCATGAAGTCGCTTACTGGTACA |
| | TTCTGTCCATCGGCGCCCAGACTGACTTCCTGAGCGTGTTCTTTTCCGGTTACACCTT |
| | TAAGCACAAGATGGTGTACGAAGATACCCTGACCCTGTTCCCTTTCTCCGGCGAAACG |
| | GTGTTCATGTCGATGGAGAACCCGGGTCTGTGGATTCTGGGATGCCACAACAGCGACT |
| | TTCGGAACCGCGGAATGACTGCCCTGCTGAAGGTGTCCTCATGCGACAAGAACACCGG |
| | AGACTACTACGAGGACTCCTACGAGGATATCTCAGCCTACCTCCTGTCCAAGAACAAC |
| | GCGATCGAGCCGCGCAGCTTCAGCCAGAACGGCGCGCCAACATCAGAGAGCGCCACCC |
| | CTGAAAGTGGTCCCGGGAGCGAGCCAGCCACATCTGGGTCGGAAACGCCAGGCACAAG |
| | TGAGTCTGCAACTCCCGAGTCCGGACCTGGCTCCGAGCCTGCCACTAGCGGCTCCGAG |
| | ACTCCGGGAACTTCCGAGAGCGCTACACCAGAAAGCGGACCCGGAACCAGTACCGAAC |
| | CTAGCGAGGGCTCTGCTCCGGGCAGCCCAGCCGGCTCTCCTACATCCACGGAGGAGGG |
| | CACTTCCGAATCCGCCACCCCGGAGTCAGGGCCAGGATCTGAACCCGCTACCTCAGGC |
| | AGTGAGACGCCAGGAACGAGCGAGTCCGCTACACCGGAGAGTGGGCCAGGGAGCCCTG |
| | CTGGATCTCCTACGTCCACTGAGGAAGGGTCACCAGCGGGCTCGCCCACCAGCACTGA |
| | AGAAGGTGCCTCGAGCCCGCCTGTGCTGAAGAGGCACCAGCGAGAAATTACCCGGACC |
| | ACCCTCCAATCGGATCAGGAGGAAATCGACTACGACGACACCATCTCGGTGGAAATGA |
| | AGAAGGAAGATTTCGATATCTACGACGAGGACGAAAATCAGTCCCCTCGCTCATTCCA |
| | AAAGAAAACTAGACACTACTTTATCGCCGCGGTGGAAAGACTGTGGGACTATGGAATG |
| | TCATCCAGCCCTCACGTCCTTCGGAACCGGGCCCAGAGCGGATCGGTGCCTCAGTTCA |
| | AGAAAGTGGTGTTCCAGGAGTTCACCGACGGCAGCTTCACCCAGCCGCTGTACCGGGG |
| | AGAACTGAACGAACACCTGGGCCTGCTCGGTCCCTACATCCGCGCGGAAGTGGAGGAT |
| | AACATCATGGTGACCTTCCGTAACCAAGCATCCAGACCTTACTCCTTCTATTCCTCCC |
| | TGATCTCATACGAGGAGGACCAGCGCCAAGGCGCCGAGCCCCGCAAGAACTTCGTCAA |
| | GCCCAACGAGACTAAGACCTACTTCTGGAAGGTCCAACACCATATGGCCCCGACCAAG |
| | GATGAGTTTGACTGCAAGGCCTGGGCCTACTTCTCCGACGTGGACCTTGAGAAGGATG |
| | TCCATTCCGGCCTGATCGGGCCGCTGCTCGTGTGTCACACCAACACCCTGAACCCAGC |
| | GCATGGACGCCAGGTCACCGTCCAGGAGTTTGCTCTGTTCTTCACCATTTTTGACGAA |
| | ACTAAGTCCTGGTACTTCACCGAGAATATGGAGCGAAACTGTAGAGCGCCCTGCAATA |
| | TCCAGATGGAAGATCCGACTTTCAAGGAGAACTATAGATTCCACGCCATCAACGGGTA |
| | CATCATGGATACTCTGCCGGGGCTGGTCATGGCCCAGGATCAGAGGATTCGGTGGTAC |
| | TTGCTGTCAATGGGATCGAACGAAAACATTCACTCCATTCACTTCTCCGGTCACGTGT |
| | TCACTGTGCGCAAGAAGGAGGAGTACAAGATGGCGCTGTACAATCTGTACCCCGGGGT |
| | GTTCGAAACTGTGGAGATGCTGCCGTCCAAGGCCGGCATCTGGAGAGTGGAGTGCCTG |
| | ATCGGAGAGCACCTCCACGCGGGGATGTCCACCCTCTTCCTGGTGTACTCGAATAAGT |
| | GCCAGACCCCGCTGGGCATGGCCTCGGGCCACATCAGAGACTTCCAGATCACAGCAAG |
| | CGGACAATACGGCCAATGGGCGCCGAAGCTGGCCCGCTTGCACTACTCCGGATCGATC |
| | AACGCATGGTCCACCAAGGAACCGTTCTCGTGGATTAAGGTGGACCTCCTGGCCCCTA |
| | TGATTATCCACGGAATTAAGACCCAGGGCGCCAGGCAGAAGTTCTCCTCCCTGTACAT |
| | CTCGCAATTCATCATCATGTACAGCCTGGACGGGAAGAAGTGGCAGACTTACAGGGGA |
| | AACTCCACCGGCACCCTGATGGTCTTTTTCGGCAACGTGGATTCCTCCGGCATTAAGC |
| | ACAACATCTTCAACCCACCGATCATAGCCAGATATATTAGGCTCCACCCCACTCACTA |
| | CTCAATCCGCTCAACTCTTCGGATGGAACTCATGGGGTGCGACCTGAACTCCTGCTCC |
| | ATGCCGTTGGGGATGGAATCAAAGGCTATTAGCGACGCCCAGATCACCGCGAGCTCCT |
| | ACTTCACTAACATGTTCGCCACCTGGAGCCCCTCCAAGGCCAGGCTGCACTTGCAGGG |
| | ACGGTCAAATGCCTGGCGGCCGCAAGTGAACAATCCGAAGGAATGGCTTCAAGTGGAT |
| | TTCCAAAAGACCATGAAAGTGACCGGAGTCACCACCCAGGGAGTGAAGTCCCTTCTGA |
| | CCTCGATGTATGTGAAGGAGTTCCTGATTAGCAGCAGCCAGGACGGGCACCAGTGGAC |
| | CCTGTTCTTCCAAAACGGAAAGGTCAAGGTGTTCCAGGGGAACCAGGACTCGTTCACA |
| | CCCGTGGTGAACTCCCTGGACCCCCCACTGCTGACGCGGTACTTGAGGATTCATCCTC |
| | AGTCCTGGGTCCATCAGATTGCATTGCGAATGGAAGTCCTGGGCTGCGAGGCCCAGGA |
| | CCTGTACTGA |
| WPRE (mutated | TCATAATCAACCTCTGGATTACAAAATTTGTGAAAGATTGACTGGTATTCTTAACTAT |
| woodchuck | GTTGCTCCTTTTACGCTATGTGGATACGCTGCTTTAATGCCTTTGTATCATGCTATTG |
| hepatitis virus | CTTCCCGTATGGCTTTCATTTTCTCCTCCTTGTATAAATCCTGGTTGCTGTCTCTTTA |

TABLE 2D-continued

Example B19-FVIII construct bearing full length B19 ITRs
(nucleotides 1-7032; SEQ ID NO: 189)

| | |
|---|---|
| post-transcriptional regulatory element) (SEQ ID NO: 120) | TGAGGAGTTGTGGCCCGTTGT TABLE 2D-continued Example B19-FVIII construct bearing full length B19 ITRs
(nucleotides 1-7032; SEQ ID NO: 189)

```
TCGCCGCGGTGGAAAGACTGTGGGACTATGGAATGTCATCCAGCCCTCACGTCCTTCGGAACCGGGCCCAGAG
CGGATCGGTGCCTCAGTTCAAGAAAGTGGTGTTCCAGGAGTTCACCGACGGCAGCTTCACCCAGCCGCTGTAC
CGGGGAGAACTGAACGAACACCTGGGCCTGCTCGGTCCCTACATCCGCCGCGAAGTGGAGGATAACATCATGG
TGACCTTCCGTAACCAAGCATCCAGACCTTACTCCTTCTATTCCTCCCTGATCTCATACGAGGAGGACCAGCG
CCAAGGCGCCGAGCCCCGCAAGAACTTCGTCAAGCCCAACGAGACTAAGACCTACTTCTGGAAGGTCCAACAC
CATATGGCCCCGACCAAGGATGAGTTTGACTGCAAGGCCTGGGCCTACTTCTCCGACGTGGACCTTGAGAAGG
ATGTCCATTCCGGCCTGATCGGGCCGCTGCTCGTGTGTCACACCAACACCCTGAACCCAGCGCATGGACGCCA
GGTCACCGTCCAGGAGTTTGCTCTGTTCTTCACCATTTTTGACGAAACTAAGTCCTGGTACTTCACCGAGAAT
ATGGAGCGAAACTGTAGAGCGCCCTGCAATATCCAGATGGAAGATCCGACTTTCAAGGAGAACTATAGATTCC
ACGCCATCAACGGGTACATCATGGATACTCTGCCGGGGCTGGTCATGGCCCAGGATCAGAGGATTCGGTGGTA
CTTGCTGTCAATGGGATCGAACGAAAACATTCACTCCATTCACTTCTCCGGTCACGTGTTCACTGTGCGCAAG
AAGGAGGAGTACAAGATGGCGCTGTACAATCTGTACCCCGGGGTGTTCGAAACTGTGGAGATGCTGCCGTCCA
AGGCCGGCATCTGGAGAGTGGAGTGCCTGATCGGAGAGCACCTCCACGCGGGGATGTCCACCCTCTTCCTGGT
GTACTCGAATAAGTGCCAGACCCCGCTGGGCATGGCCTCGGGCCACATCCGAGATCTTCCAGATCACAGCAAGC
GGACAATACGGCCAATGGGCGCCGAAGCTGGCCCGCTTGCACTACTCCGGATCGATCAACGCATGGTCCACCA
AGGAACCGTTCTCGTGGATTAAGGTGGACCTCCTGGCCCCTATGATTATCCACGGAATTAAGACCCAGGGCGC
CAGGCAGAAGTTCTCCTCCCTGTACATCTCGCAATTCATCATCATGTACAGCCTGGACGGGAAGAAGTGGCAG
ACTTACAGGGGAAACTCCACCGGCACCCTGATGGTCTTTTTCGGCAACGTGGATTCCTCCGGCATTAAGCACA
ACATCTTCAACCCACCGATCATAGCCAGATATATTAGGCTCCACCCCACTCACTACTCAATCCGCTCAACTCT
TCGGATGGAACTCATGGGGTGCGACCTGAACTCCTGCTCCATGCCGTTGGGGATGGAATCAAAGGCTATTAGC
GACGCCCAGATCACCGCGAGCTCCTACTTCACTAACATGTTCGCCACCTGGAGCCCCTCCAAGGCCAGGCTGC
ACTTGCAGGGACGGTCAAATGCCTGGCGGCCGCAAGTGAACAATCCGAAGGAATTGGCTTCAAGTGGATTTCCA
AAAAGACCATGAAAGTGACCGGAGTCACCACCCAGGGAGTGAAGTCCCTTCTGACCTCGATGTATGTGAAGGAG
TTCCTGATTAGCAGCAGCCAGGACGGGCACCAGTGGACCCTGTTCTTCCAAAACGGAAAGGTCAAGGTGTTCC
AGGGGAACCAGGACTCGTTCACACCCGTGGTGAACTCCCTGGACCCCCCACTGCTGACGCGGTACTTGAGGAT
TCATCCTCAGTCCTGGGTCCATCAGATTGCATTGCGAATGGAAGTCCTGGGCTGCGAGGCCCAGGACCTGTAC
TGAATCAGCCTGAGCTCGCTGATCATAATCAACCTCTGGATTACAAAATTTGTGAAAGATTGACTGGTATTCT
TAACTATGTTGCTCCTTTTACGCTATGTGGATACGCTGCTTTAATGCCTTTGTATCATGCTATTGCTTCCCGT
ATGGCTTTCATTTTCTCCTCCTTGTATAAATCCTGGTTGCTGTCTCTTTATGAGGAGTTGTGGCCCGTTGTCA
GGCAACGTGGCGTGGTGTGCACTGTGTTTGCTGACGCAACCCCCACTGGTTGGGGCATTGCCACCACCTGTCA
GCTCCTTTCCGGGACTTTCGCTTTCCCCCTCCCTATTGCCACGGCGGAACTCATCGCCGCCTGCCTTGCCCGC
TGCTGGACAGGGGCTCGGCTGTTGGGCACTGACAATTCCGTGGTGTTGTCGGGGAAATCATCGTCCTTTCCTT
GGCTGCTCGCCTGTGTTGCCACCTGGATTCTGCGCGGGACGTCCTTCTGCTACGTCCCTTCGGCCCTCAATCC
AGCGGACCTTCCTTCCCGCGGCCTGCTGCCGGCTCTGCGGCCTCTTCCGCGTCTTCGCCTTCGCCCTCAGACG
AGTCGGATCTCCCTTTGGGCCGCCTCCCCGCTGATCAGCCTCGACTGTGCCTTCTAGTTGCCAGCCATCTGTT
GTTTGCCCCTCCCCCGTGCCTTCCTTGACCCTGGAAGGTGCCACTCCCACTGTCCTTTCCTAATAAAATGAGG
AAATTGCATCGCATTGTCTGAGTAGGTGTCATTCTATTCTGGGGGGTGGGGTGGGCAGGACAGCAAGGGGGA
GGATTGGGAAGACAATAGCAGGCATGCTGGGGATGCGGTGGGCTCTATGGCTTCTGAGGCGGAAAGAACGGGC
TCGAGAAGCTTCTAGATATCCTCTCTTAAGGTAGCATCGAGATTTAAATTAGGGATAACAGGGTAATGGCGCG
GGCCGCAAATTTAAAGAAGACACCAAATCAGATGCCGCCGGTCGCGCCGGTAGGCGGACTTCCGGTACA
AGATGGCGGACAATTACGTCATTTCCTGTGACGTCATTTCCTGTGACGTCACTTCCGGTGGGCGGGACTTCCG
GAATTAGGGTTGGCTCTGGGCCAGCGCTTGGGGTTGACGTGCCACTAAGATCAAGCGGCGCGCCGCTTGTCTT
AGTGTCAAGGCAACCCCAAGCAAGCTGGCCCAGAGCCAACCCTAATTCCGGAAGTCCCGCCCACCGGAAGTGA
CGTCACAGGAAATGACGTCACAGGAAATGACGTAATTGTCCGCCATCTTGTACCGGAAGTCCCGCCTACCGGC
GGCGACCGGCGGCATCTGATTTGG
```

TABLE 2E

Example AAV-FVIII construct (nucleotides 1-6824; SEQ ID NO: 190)

| Description | Sequence |
|---|---|
| 5' ITR (SEQ ID NO: 111) | CTGCGCGCTCGCTCGCTCACTGAGGCCGCCCGGGCAAAGCCCGGGCGTCGGGCGACCT TTGGTCGCCCGGCCTCAGTGAGCGAGCGAGCGCGCAGAGAGGGAGTGGCCAACTCCAT CACTAGGGGTTCCT |
| CAGp (ubiquitous promoter) (SEQ ID NO: 191) | TCGAGGTGAGCCCCACGTTCTGCTTCACTCTCCCCATCTCCCCCCCCTCCCCACCCCC AATTTTGTATTTATTTATTTTTTAATTATTTTGTGCAGCGATGGGGGCGGGGGGGGGG GGGGGCGCGCGCCAGGCGGGGCGGGCGGGCGAGGGGCGGGCGGGCGAGGCGGA GAGGTGCGGCGGCAGCCAATCAGAGCGGCGCGCTCCGAAAGTTTCCTTTTATGGCGAG GCGGCGGCGGCGGCGGCCCTATAAAAAGCGAAGCGCGCGGCGGGCG |
| Synthetic Intron (SEQ ID NO: 192) | GTGAGCGGGCGGGACGGCCCTTCTCCTTCGGGCTGTAATTAGCGCTTGGTTTAATGAC GGCTTGTTTCTTTTCTGTGGCTGCGTGAAAGCCTTGAGGGGCTCCGGGAGGGCCCTTT GTGCGGGGGGAGCGGCTCGGGGCTGTCCGCGGGGGACGGCTGCCTTCGGGGGGACG GGGCAGGGCGGGGTTCGGCTTCTGGCGTGTGACCGGCGGCTCTAGAGCCTCTGCTAAC CATGTTCATGCCTTCTTCTTTTTCCTACAG |
| FVIIIco6XTEN (SEQ ID NO: 117) (open reading frame for codon-optimized FVIII version 6 | ATGCAGATTGAGCTGTCCACTTGTTTCTTCCTGTGCCTCCTGCGCTTCTGTTTCTCCG CCACTCGCCGGTACTACCTTGGAGCCGTGGAGCTTTCATGGGACTACATGCAGAGCGA CCTGGGCGAACTCCCCGTGGATGCCAGATTCCCCCCCGCGTGCCAAAGTCCTTCCCC TTTAACACCTCCGTGGTGTACAAGAAAACCCTCTTTGTCGAGTTCACTGACCACCTGT TCAACATCGCCAAGCCGCGCCCACCTTGGATGGGCCTCCTGGGACCGACCATTCAAGC TGAAGTGTACGACACCGTGGTGATCACCCTGAAGAACATGGCGTCCCACCCCGTGTCC |

TABLE 2E-continued

| | |
|---|---|
| containing XTEN144; the XTEN sequence is marked by double underlining (SEQ ID NO: 118)) | CTGCATGCGGTCGGAGTGTCCTACTGGAAGGCCTCCGAAGGAGCTGAGTACGACGACC AGACTAGCCAGCGGGAAAAGGAGGACGATAAAGTGTTCCCGGGCGGCTCGCATACTTA CGTGTGGCAAGTCCTGAAGGAAAACGGACCTATGGCATCCGATCCTCTGTGCCTGACT TACTCCTACCTTTCCCATGTGGACCTCGTGAAGGACCTGAACAGCGGGCTGATTGGTG CACTTCTCGTGTGCCGCGAAGGTTCGCTCGCTAAGGAAAAGACCCAGACCCTCCATAA GTTCATCCTTTTGTTCGCTGTGTTCGATGAAGGAAAGTCATGGCATTCCGAAACTAAG AACTCGCTGATGCAGGACCGGGATGCCGCCTCAGCCCGCGCCTGGCCTAAAATGCATA CAGTCAACGGATACGTGAATCGGTCACTGCCCGGGCTCATCGGTTGTCACAGAAAGTC CGTGTACTGGCACGTCATCGGCATGGGCACTACGCCTGAAGTGCACTCCATCTTCCTG GAAGGGCACACCTTCCTCGTGCGCAACCACCGCCAGGCCTCTCTGGAAATCTCCCCGA TTACCTTTCTGACCGCCCAGACTCTGCTCATGGACCTGGGGCAGTTCCTTCTCTTCTG CCACATCTCCAGCCATCAGCACGACGGAATGGAGGCCTACGTGAAGGTGGACTCATGC CCGGAAGAACCTCAGTTGCGGATGAAGAACAACGAGGAGGCCGAGGACTATGACGACG ATTTGACTGACTCCGAGATGGACGTCGTGCGGTTCGATGACGACAACAGCCCCAGCTT CATCCAGATTCGCAGCGTGGCCAAGAAGCACCCCAAAACCTGGGTGCACTACATCGCG GCCGAGGAAGAAGATTGGGACTACGCCCCGTTGGTGCTGGCACCCGATGACCGGTCGT ACAAGTCCCAGTATCTGAACAATGGTCCGCAGCGGATTGGCAGAAAGTACAAGAAAGT GCGGTTCATGGCGTACACTGACGAAACGTTTAAGACCCGGGAGGCCATTCAACATGAG AGCGGCATTCTGGGACCACTGCTGTACGGAGAGGTCGGCGATACCCTGCTCATCATCT TCAAAAACCAGGCCTCCCGGCCTTACAACATCTACCCTCACGGAATCACCGACGTGCG GCCCACTCTACTCGCGGCGCCTGCCGAAGGGCGTCAAGCACCTGAAAGACTTCCCTATC CTGCCGGGCGAAATCTTCAAGTATAAGTGGACCGTCACCGTGGAGGACGGGCCCACCA AGAGCGATCCTAGGTGTCTGACTCGGTACTACTCCAGCTTCGTGAACATGGAACGGGA CCTGGCATCGGGACTCATTGGACCGCTGCTGATCTGCTACAAAGAGTCGGTGGATCAA CGCGGCAACCAGATCATGTCCGACAAGCGCAACGTGATCCTGTTCTCCGTGTTTGATG AAAACAGATCCTGGTACCTCACTGAAAACATCCAGAGGTTCCTCCCAAACCCCGCAGG AGTGCAACTGGAGGACCCTGAGTTTCAGGCCTCGAATATCATGCACTCGATTAACGGT TACGTGTTCGACTCGCTGCAACTGAGCGTGTGCCTCCATGAAGTCGCTTACTGGTACA TTCTGTCCATCGGCGCCCAGACTGACTTCCTGAGCGTGTTCTTTTCCGGTTACACCTT TAAGCACAAGATGGTGTACGAAGATACCCTGACCCTGTTCCCTTTCTCCGGCGAAACG GTGTTCATGTCGATGGAGAACCCGGGTCTGTGGATTCTGGGATGCCACAACAGCGACT TTCGGAACCGCGGAATGACTGCCCTGCTGAAGGTGTCCTCATGCGACAAGAACACCGG AGACTACTACGAGGACTCCTACGAGGATATCTCAGCCTACCTCCTGTCCAAGAACAAC GCGATCGAGCCGCGCAGCTTCAGCCAGAACGGCGCGCCAACATCAGAGAGCGCCACCC <u>CTGAAAGTGGTCCCGGGAGCGAGCCAGCCACATCTGGGTCGGAAACGCCAGGCACAAG TGAGTCTGCAACTCCCGAGTCCGGACCTGGCTCCGAGCCTGCCACTAGCGGCTCCGAG ACTCCGGGAACTTCCGAGAGCGCTACACCAGAAAGCGGACCCGGAACCAGTACCGAAC CTAGCGAGGGCTCTGCTCCGGGCAGCCCAGCCGGCTCTCCTACATCCACGGAGGAGGG</u> CACTTCCGAATCCGCCACCCCGGAGTCAGGGCCAGGATCTGAACCCGCTACCTCAGGC AGTGAGACGCCAGGAACGAGCGAGTCCGCTACACCGGAGAGTGGGCCAGGGAGCCCTG CTGGATCTCCTACGTCCACTGAGGAAGGGTCACCAGCGGGCTCGCCCACCAGCACTGA AGAAGGTGCCTCGAGCCCGCCTGTGCTGAAGAGGCACCAGCGAGAAATTACCGGACC ACCCTCCAATCGGATCAGGAGGAAATCGACTACGACGACACCATCTCGGTGGAAATGA AGAAGGAAGATTTCGATATCTACGACGAGGACGAAAATCAGTCCCCTGCTCATTCCA AAAGAAAACTAGACACTACTTTATCGCCGCGGTGGAAAGACTGTGGGACTATGGAATG TCATCCAGCCCTCACGTCCTTCGGAACCGGGCCCAGAGCGGATCGGTGCCTCAGTTCA AGAAAGTGGTGTTCCAGGAGTTCACCGACGGCAGCTTCACCCAGCCGCTGTACCGGGG AGAACTGAACGAACACCTGGGCCTGCTCGGTCCCTACATCCGCGCGGAAGTGGAGGAT AACATCATGGTGACCTTCCGTAACCAAGCATCCAGACCTTACTCCTTCTATTCCTCCC TGATCTCATACGAGGAGGACCAGCGCCAAGGCGCCGAGCCCCGCAAGAACTTCGTCAA GCCCAACGAGACTAAGACCTACTTCTGGAAGGTCCAACACATATGGCCCCGACCAAG GATGAGTTTGACTGCAAGGCCTGGGCCTACTTCTCCGACGTGGACCTTGAGAAGGATG TCCATTCCGGCCTGATCGGGCCGCTGCTCGTGTGTCACACCAACACCCTGAACCCAGC GCATGGACGCCAGGTCACCGTCCAGGAGTTTGCTCTGTTCTTCACCATTTTTGACGAA ACTAAGTCCTGGTACTTCACCGAGAATATGGAGCGAAACTGTAGAGCGCCCTGCAATA TCCAGATGGAAGATCCGACTTTCAAGGAGAACTATAGATTCCACGCCATCAACGGGTA CATCATGGATACTCTGCCGGGGCTGGTCATGGCCCAGGATCAGAGGATTCGGTGGTAC TTGCTGTCAATGGGATCGAACGAAAACATTCACTCCATTCACTTCTCCGGTCACGTGT TCACTGTGCGCAAGAAGGAGGAGTACAAGATGGCGCTGTACAATCTGTACCCCGGGGT GTTCGAAACTGTGGAGATGCTGCCGTCCAAGGCCGGCATCTGGAGAGTGGAGTGCCTG ATCGGAGAGCACCTCCACGCGGGGATGTCCACCCTCTTCCTGGTGTACTCGAATAAGT GCCAGACCCCGCTGGGCATGGCCTCGGGCCACATCAGAGACTTCCAGATCACAGCAAG CGGACAATACGGCCAATGGGCGCCGAAGCTGGCCCGCTTGCACTACTCCGGATCGATC AACGCATGGTCCACCAAGGAACCGTTCTCGTGGATTAAGGTGGACCTCCTGGCCCCTA TGATTATCCACGGAATTAAGACCCAGGGCGCCAGGCAGAAGTTCTCCTCCCTGTACAT CTCGCAATTCATCATCATGTACAGCCTGGACGGGAAGAAGTGGCAGACTTACAGGGGA AACTCCACCGGCACCCTGATGGTCTTTTTCGGCAACGTGGATTCCTCCGGCATTAAGC ACAACATCTTCAACCCACCGATCATAGCCAGATATATTAGGCTCCACCCCACTCACTA CTCAATCCGCTCAACTCTTCGGATGGAACTCATGGGGTGCGACCTGAACTCCTGCTCC ATGCCGTTGGGGATGGAATCAAAGGCTATTAGCGACGCCCAGATCACCGCGAGCTCCT ACTTCACTAACATGTTCGCCACCTGGAGCCCCTCCAAGGCCAGGCTGCACTTGCAGGG ACGGTCAAATGCCTGGCGGCCGCAAGTGAACAATCCGAAGGAATGGCTTCAAGTGGAT TTCCAAAAGACCATGAAAGTGACCGGAGTCACCACCCAGGGAGTGAAGTCCCTTCTGA CCTCGATGTATGTGAAGGAGTTCCTGATTAGCAGCAGCCAGGACGGGCACCAGTGGAC CCTGTTCTTCCAAAACGGAAAGGTCAAGGTGTTCCAGGGGAACCAGGACTCGTTCACA CCCGTGGTGAACTCCCTGGACCCCCCACTGCTGACGCGGTACTTGAGGATTCATCCTC AGTCCTGGGTCCATCAGATTGCATTGCGAATGGAAGTCCTGGGCTGCGAGGCCCAGGA CCTGTACTGA |

TABLE 2E-continued

| | |
|---|---|
| WPRE (mutated woodchuck hepatitis virus post-transcriptional regulatory element) (SEQ ID NO: 120) | TCATAATCAACCTCTGGATTACAAAATTTGTGAAAGATTGACTGGTATTCTTAACTAT GTTGCTCCTTTTACGCTATGTGGATACGCTGCTTTAATGCCTTTGTATCATGCTATTG CTTCCCGTATGGCTTTCATTTTCTCCTCCTTGTATAAATCCTGGTTGCTGTCTCTTTA TGAGGAGTTGTGGCCCGTTGTCAGGCAACGTGGCGTGGTGTGCACTGTGTTTGCTGAC GCAACCCCCACTGGTTGGGGCATTGCCACCACCTGTCAGCTCCTTTCCGGGACTTTCG CTTTCCCCCTCCCTATTGCCACGGCGGAACTCATCGCCGCCTGCCTTGCCCGCTGCTG GACAGGGGCTCGGCTGTTGGGCACTGACAATTCCGTGGTGTTGTCGGGGAAATCATCG TCCTTTCCTTGGCTGCTCGCCTGTGTTGCCACCTGGATTCTGCGCGGGACGTCCTTCT GCTACGTCCCTTCGGCCCTCAATCCAGCGGACCTTCCTTCCCGCGGCCTGCTGCCGGC TCTGCGGCCTCTTCCGCGTCTTCGCCTTCGCCCTCAGACGAGTCGGATCTCCCTTTGG GCCGCCTCCCCGCTG |
| bGHpA (bovine growth hormone polyadenylation signal) (SEQ ID NO: 122) | CGACTGTGCCTTCTAGTTGCCAGCCATCTGTTGTTTGCCCCTCCCCCGTGCCTTCCTT GACCCTGGAAGGTGCCACTCCCACTGTCCTTTCCTAATAAAATGAGGAAATTGCATCG CATTGTCTGAGTAGGTGTCATTCTATTCTGGGGGGTGGGGTGGGGCAGGACAGCAAGG GGGAGGATTGGGAAGACAATAGCAGGCATGCTGGGGA |
| 3' ITR inverted terminal repeat (SEQ ID NO: 193) | AGGAACCCCTAGTGATGGAGTTGGCCACTCCCTCTCTGCGCGCTCGCTCGCTCACTGA GGCCGGGCGACCAAAGGTCGCCCGACGCCCGGGCTTTGCCCGGGCGGCCTCAGTGAGC GAGCGAGCGCGCAG |

| Full-length Sequence (SEQ ID NO: 190) |
|---|
| CTGCGCGCTCGCTCGCTCACTGAGGCCGCCCGGGCAAAGCCCGGGCGTCGGGCGACCTTTGGTCGCCCGGCCT CAGTGAGCGAGCGAGCGCGCAGAGAGGGAGTGGCCAACTCCATCACTAGGGGTTCCTGCGGCAATTCAGTCGA TAACTATAACGGTCCTAAGGTAGCGATTTAAATACGCGCTCTCTTAAGGTAGCCCCGGGACGCGTCAATTGAG ATCTGGATCCGGTACCGAATTCGCGGCCGCCTCGACGACTAGCGTTTAATTAAATCGAGGTGAGCCCCACGTT CTGCTTCACTCTCCCCATCTCCCCCCCCTCCCCACCCCCAATTTTGTATTTATTTATTTTTTAATTATTTTGT GCAGCGATGGGGGCGGGGGGGGGGGGGGCGCGCGCCAGGCGGGGCGGGGCGGGGCGAGGGGCGGGGCGGGG CGAGGCGGAGAGGTGCGGCGGCAGCCAATCAGAGCGGCCGCTCCGAAAGTTTCCTTTTATGGCGAGGCGGCG GCGGCGGCGGCCCTATAAAAAGCGAAGCGCGCGGCGGGCGGGAGTCGCTGCGCGCTGCCTTCGCCCCGTGCCC CGCTCCGCCGCCGCCTCGCGCCGCCCGCCCCGGCTCTGACTGACCGCGTTACTCCCACAGGTGAGCGGGCGGG ACGGCCCTTCTCCTTCGGGCTGTAATTAGCGCTTGGTTTAATGACGCGCTTGTTTCTTTTCTGTGGCTGCGTGA AAGCCTTGAGGGGCTCCGGGAGGGCCCTTTGTGCGGGGGGAGCGGCTCGGGGCTGTCGCGGGGGGACGGCTG CCTTCGGGGGGACGGGGCAGGGCGGGGTTCGGCTTCTGGCGTGACCGGCGGCTCTAGAGCCTCTGCTAAC CATGTTCATGCCTTCTTCTTTTTCCTACAGGCTAGCGCCACCATGCAGATTGAGCTGTCCACTTGTTTCTTCC TGTGCCTCCTGCGCTTCTGTTTCTCCGCCACTCGCCGGTACTACCTTGGAGCCTGGAGCTTTCATGGGACTA CATGCAGAGCGACCTGGGCGAACTCCCCGTGGATGCCAGATTCCCCCCCCGCGTGCCAAAGTCCTTCCCCTTT AACACCTCCGTGGTGTACAAGAAAACCCTCTTTGTCGAGTTCACTGACCACGTGTTCAACATCGCCAAGCCGC GCCCACCTTGGATGGGCCTCCTGGGACCGACCATTCAAGCTGAAGTGTACGACACCGGTGATCACCCTGAA GAACATGGCGTCCCACCCCGTGTCCCTGCATGCGGTCGGAGTGTCCTACTGGAAGGCCTCCGAAGGAGCTGAG TACGACGACCAGACTAGCCAGCGGGAAAAGGAGGACGATAAAGTGTTCCCGGGCGGCTCGCATACTTACGTGT GGCAAGTCCTGAAGGAAAACGACCTATGGCATCCGATCCTCTGTGCCTGACTTACTCCTACCTTTCCCATGT GGACCTCGTGAAGGACCTGAACAGCGGGCTGATTGGTGCACTTCTCGTGTGCCGCGAAGGTTCGCTCGCTAAG GAAAAGACCCAGACCCTCCATAAGTTCATCCTTTTGTTCGCTGTGTTCGATGAAGGAAAGTCATGGCATTCCG AAACTAAGAACTCGCTGATGCAGGACCGGGATGCCGCCTCAGCCCGCGCCTGGCCTAAAATGCATACAGTCAA CGGATACGTGAATCGGTCACTGCCCGGGCTCATCGGTTGTCACAGAAAGTCCGTGTACTGGCACGTCATCGGC ATGGGCACTACGCCTGAAGTGCACTCCATCTTCCTGGAAGGGCACACCTTCCTCGTGCGCAACCACCGCCAGG CCTCTCTGGAAATCTCCCCGATTACCTTTCTGACCGCCCAGACTCTGCTCATGGACCTGGGGCAGTTCCTTCT CTTCTGCCACATCTCCAGCCATCAGCACGACGGAATGGAGGCCTACGTGAAGGTGGACTCATGCCCGGAAGAA CCTCAGTTGCGGATGAAGAACAACGAGGAGGCCGAGGACTATGACGACGATTTGACTGACTCCGAGATGGACG TCGTGCGGTTCGATGACGACAACAGCCCCAGCTTCATCCAGATTCGCAGCGTGGCCAAGAAGCACCCCAAAAC CTGGGTGCACTACATCGCGGCCGAGGAAGAAGATTGGGACTACGCCCCGTTGGTGCTGGCACCCGATGACCGG TCGTACAAGTCCCAGTATCTGAACAATGGTCCGCAGCGGATTGGCAGAAAGTACAAGAAAGTGCGGTTCATGG CGTACACTGACGAAACGTTTAAGACCCGGGAGGCCATTCAACATGAGAGCGGCATTCTGGGACTGCTGTA CGGAGAGGTCGGCGATACCCTGCTCATCATCTTCAAAAACCAGGCCTCCCGGCCTTACAACATCTACCCTCAC GGAATCACCGACGTGCGCCCACTCTACTCGCGGCGCCTGCCGAAGGGCGTCAAGCACCTGAAAGACTTCCCTA TCCTGCCGGGCGAAATCTTCAAGTATAAGTGGACCGTCACCGTGGAGGACGGGCCCACCAAGAGCGATCCTAG GTGTCTGACTCGGTACTACTCCAGCTTCGTGAACATGGAACGGGACCTGGCATCGGGACTCATTGGACGCTG CTGATCTGCTACAAAGAGTCGGTGGATCAACGCGGCAACCGGATCATGTCCGACAAGCGCAACGTGATCCTGT TCTCCGTGTTTGATGAAAACAGATCCTGGTACCTCACTGAAAACATCCAGAGGTTCCTCCCCAACCCCGCAGG AGTGCAACTGGAGGACCCTGAGTTTCAGGCCTCGAATATCATGCACTCGATTAACGTTACGTGTTCGACTCG CTGCAACTGAGCGTGTGCCTCCATGAAGTCGCTTACTGGTACATTCTGTCCATCGGCGCCCAGACTGACTTCC TGAGCGTGTTCTTTTCCGGTTACACCTTTAAGCACAAGATGGTGTACGAGGATACCCTGACCCTGTTCCCTTT CTCCGGCGAAACGGTGTTCATGTCGATGGAGAACCCGGGTCTGTGGATTCTGGGATGCCACAACAGCGACTTT CGGAACCGCGGAATGACTGCCCTGCTGAAGGTGTCCTCATGCGACAAGAACACCGGAGACTACTACGAGGACT CCTACGAGGATATCTCAGCCTACCTCCTGTCCAAGAACAACGCGATCGAGCCGCGCAGCTTCAGCCAGAACGG CGCGCCAATCAGAGAGCGCCACCCCTGAAAGTGGTCCCGGAGCGAGCGAGTCCGCTACCCACATCTGGGTCGGAAACG CCAGGCACAAGTGAGTCTGCAACTCCCGAGTCCGGACCTGGCTCCGAGCCTGCCACTAGCGGCTCCGAGACTC CGGGAACTTCCGAGAGCGCTACACCAGAAAGCGGACCCGAACCAGTACCGAACCTAGCGAGGGCTCTGCTCC GGGCAGCCCAGCCGGCTCTCCTACATCCACGAGGAGGGCACTTCCGAATCCGCCACCCCGGAGTCAGGGCCA GGATCTGAACCCGCTACCTCAGGCAGTGAGACGCCAGGAACGAGCCTCCGTCACTGGAGTGGGCCA GGGAGCCCTGCTGGATCTCCTACGTCCACTGAGGAAGGGTCACCAGCGGGCTCGCCCACCAGCACTGAAGAAGG TGCCTCGAGCCCGCCTGTGCTGAAGAGGCACCAGCGAGAAATTACCCGGACCACCCTCCAATCGGATCAGGAG GAAATCGACTACGACGACACCATCCGGTGGAAATGAAGAAGGAAGATTTCGATATCTACGACGAGGACGAAA ATCAGTCCCCTGCTCATTCCAAAAGAAAACTAGACACTACTTTATCGCCGCGGTGGAAAGACTGTGGGACTA TGGAATGTCATCCAGCCCTCACGTCCTTCGGAACCGGGCCCAGAGCGGATCGGTGCCTCAGTTCAAGAAAGTG |

TABLE 2E-continued

```
GTGTTCCAGGAGTTCACCGACGGCAGCTTCACCCAGCCGCTGTACCGGGGAGAACTGAACGAACACCTGGGCC
TGCTCGGTCCCTACATCCGCGCGGAAGTGGAGGATAACATCATGGTGACCTTCCGTAACCAAGCATCCAGACC
TTACTCCTTCTATTCCTCCCTGATCTCATACGAGGAGGACCAGCGCCAAGGCGCCGAGCCCCGCAAGAACTTC
GTCAAGCCCAACGAGACTAAGACCTACTTCTGGAAGGTCCAACACCATATGGCCCCGACCAAGGATGAGTTTG
ACTGCAAGGCCTGGGCCTACTTCTCCGACGTGGACCTTGAGAAGGATGTCCATTCCGGCCTGATCGGGCCGCT
GCTCGTGTGTCACACCAACACCCTGAACCCAGCGCATGGACGCCAGGTCACCGTCCAGGAGTTTGCTCTGTTC
TTCACCATTTTTGACGAAACTAAGTCCTGGTACTTCACCGAGAATATGGAGCGAAACTGTAGAGCGCCCTGCA
ATATCCAGATGGAAGATCCGACTTTCAAGGAGAACTATAGATTCCACGCCATCAACGGGTACATCATGGATAC
TCTGCCGGGGCTGGTCATGGCCCAGGATCAGAGGATTCGGTGGTACTTGCTGTCAATGGGATCGAACGAAAAC
ATTCACTCCATTCACTTCTCCGGTCACGTGTTCACTGTGCGCAAGAAGGAGGAGTACAAGATGGCGCTGTACA
ATCTGTACCCCGGGGTGTTCGAAACTGTGGAGATGCTGCCGTCCAAGGCCGGCATCTGGAGAGTGGAGTGCCT
GATCGGAGAGCACCTCCACGCGGGGATGTCCACCCTCTTCCTGGTGTACTCGAATAAGTGCCAGACCCCGCTG
GGCATGGCCTCGGGCCACATCAGAGACTTCCAGATCACAGCCAGCGGACAATACGGCCAATGGGCGCCGAAGC
TGGCCCGCTTGCACTACTCCGGATCGATCAACGCATGGTCCACCAAGGAACCGTTCTCGTGGATTAAGGTGGA
CCTCCTGGCCCCTATGATTATCCACGGAATTAAGACCCAGGGCGCCAGGCAGAAGTTCTCCTCCCTGTACATC
TCGCAATTCATCATCATGTACAGCCTGGACGGGAAGAAGTGGCAGACTTACAGGGGAAACTCCACCGGCACCC
TGATGGTCTTTTTCGGCAACGTGGATTCCTCCGGCATTAAGCACAACATCTTCAACCCACCGATCATAGCCAG
ATATATTAGGCTCCACCCCACTCACTACTCAATCCGCTCAACTCTTCGGATGGAACTCATGGGGTGCGACCTG
AACTCCTGCTCCATGCCGTTGGGGATGGAATCAAAGGCTATTAGCGACGCCCAGATCACCGCGAGCTCCTACT
TCACTAACATGTTCGCCACCTGGAGCCCCTCCAAGGCCAGGCTGCACTTGCAGGGACGGTCAAATGCCTGGCG
GCCGCAAGTGAACAATCCGAAGGAATGGCTTCAAGTGGATTTCCAAAAGACCATGAAAGTGACCGGAGTCACC
ACCCAGGGAGTGAAGTCCCTTCTGACCTCGATGTATGTGAAGGAGTTCCTGATTAGCAGCAGCCAGGACGGGC
ACCAGTGGACCCTGTTCTTCCAAAACGGAAAGGTCAAGGTGTTCCAGGGGAACCAGGACTCGTTCACACCCGT
GGTGAACTCCCTGGACCCCCCACTGCTGACGCGGTACTTGAGGATTCATCCTCAGTCCTGGGTCCATCAGATT
GCATTGCGAATGGAAGTCCTGGGCTGCGAGGCCCAGGACCTGTACTGAATCAGCCTGAGCTCGCTGATCATAA
TCAACCTCTGGATTACAAAATTTGTGAAAGATTGACTGGTATTCTTAACTATGTTGCTCCTTTTACGCTATGT
GGATACGCTGCTTTAATGCCTTTGTATCATGCTATTGCTTCCCGTATGGCTTTCATTTTCTCCTCCTTGTATA
AATCCTGGTTGCTGTCTCTTTATGAGGAGTTGTGGCCCGTTGTCAGGCAACGTGGCGTGGTGTGCACTGTGTT
TGCTGACGCAACCCCCACTGGTTGGGGCATTGCCACCACCTGTCAGCTCCTTTCCGGGACTTTCGCTTTCCCC
CTCCCTATTGCCACGGCGGAACTCATCGCCGCCTGCCTTGCCCGCTGCTGGACAGGGGCTCGGCTGTTGGGCA
CTGACAATTCCGTGGTGTTGTCGGGGAAATCATCGTCCTTTCCTTGGCTGCTCGCCTGTGTTGCCACCTGGAT
TCTGCGCGGGACGTCCTTCTGCTACGTCCCTTCGGCCCTCAATCCAGCGGACCTTCCTTCCCGCGGCCTGCTG
CCGGCTCTGCGGCCTCTTCCGCGTCTTCGCCTTCGCCCTCAGACGAGTCGGATCTCCCTTTGGGCCGCCTCCC
CGCTGATCAGCCTCGACTGTGCCTTCTAGTTGCCAGCCATCTGTTGTTTGCCCCTCCCCCGTGCCTTCCTTGA
CCCTGGAAGGTGCCACTCCCACTGTCCTTTCCTAATAAAATGAGGAAATTGCATCGCATTGTCTGAGTAGGTG
TCATTCTATTCTGGGGGGTGGGGTGGGCAGGACAGCAAGGGGGAGGATTGGGAAGACAATAGCAGGCATGCT
GGGGATGCGGTGGGCTCTATGCTTCTGAGGCGGAAAGAACGGGCTCGAAGCTTCTAGATATCCTCTCTTA
AGGTAGCATCGAGATTTAAATTAGGGATAACAGGGTAATGGCGCGGGCCGCAGGAACCCCTAGTGATGGAGTT
GGCCACTCCCTCTCTGCGCGCTCGCTCGCTCACTGAGGCCGGGCGACCAAAGGTCGCCCGACGCCCGGGCTTT
GCCCGGGCGGCCTCAGTGAGCGAGCGAGCGCGCAG
```

TABLE 2F

Example GPV-FVIII construct bearing full length GPV ITRs (nucleotides 1-7154; SEQ ID NO: 194)

| Description | Sequence |
|---|---|
| 5' ITR (SEQ ID NO: 187) | CTCAT

TABLE 2F-continued

| | |
|---|---|
| underlining (SEQ ID NO: 118)) | GTTCATCCTTTTGTTCGCTGTGTTCGATGAAGGAAAGTCATGGCATTCCGAAACTAAG<br>AACTCGCTGATGCAGGACCGGGATGCCGCCTCAGCCCGCGCCTGGCCTAAAATGCATA<br>CAGTCAACGGATACGTGAATCGGTCACTGCCCGGGCTCATCGGTTGTCACAGAAAGTC<br>CGTGTACTGGCACGTCATCGGCATGGGCACTACGCCTGAAGTGCACTCCATCTTCCTG<br>GAAGGGCACACCTTCCTCGTGCGCAACCACCGCCAGGCCTCTCTGGAAATCTCCCCGA<br>TTACCTTTCTGACCGCCCAGACTCTGCTCATGGACCTGGGCAGTTCCTTCTCTTCTG<br>CCACATCTCCAGCCATCAGCACGACGGAATGGAGGCCTACGTGAAGGTGGACTCATGC<br>CCGGAAGAACCTCAGTTGCGGATGAAGAACAACGAGGAGGCCGGAGGACTATGACGACG<br>ATTTGACTGACTCCGAGATGGACGTCGTGCGGTTCGATGACGACAACAGCCCCAGCTT<br>CATCCAGATTCGCAGCGTGGCCAAGAAGCACCCCAAAACCTGGGTGCACTACATCGCG<br>GCCGAGGAAGAAGATTGGGACTACGCCCCGTTGGTGCTGGCACCCGATGACCGGTCGT<br>ACAAGTCCCAGTATCTGAACAATGGTCCGCAGCGGATTGGCAGAAAGTACAAGAAAGT<br>GCGGTTCATGGCGTACACTGACGAAACGTTTAAGACCCGGGAGGCCATTCAACATGAG<br>AGCGGCATTCTGGGACCACTGCTGTACGGAGAGGTCGGCGATACCCTGCTCATCATCT<br>TCAAAAACCAGGCCTCCCGGCCTTACAACATCTACCCTCACGGAATCACCGACGTGCG<br>GCCACTCTACTCGCGGCGCCTGCCGAAGGGCGTCAAGCACCTGAAAGACTTCCCTATC<br>CTGCCGGGCGAAATCTTCAAGTATAAGTGGACCGTCACCGTGGAGGACGGGCCCACCA<br>AGAGCGATCCTAGGTGTCTGACTCGGTACTACTCCAGCTTCGTGAACATGGAACGGGA<br>CCTGGCATCGGGACTCATTGGACCGCTGCTGATCTGCTACAAAGAGTCGGTGGATCAA<br>CGCGGCAACCAGATCATGTCCGACAAGCGCAACGTGATCCTGTTCTCCGTGTTTGATG<br>AAAACAGATCCTGGTACCTCACTGAAAACATCCAGAGGTTCCTCCCAAACCCCGCAGG<br>AGTGCAACTGGAGGACCCTGAGTTTCAGGCCTCGAATATCATGCACTCGATTAACGGT<br>TACGTGTTCGACTCGCTGCAACTGAGCGTGTGCCTCCATGAAGTCGCTTACTGGTACA<br>TTCTGTCCATCGGCGCCCAGACTGACTTCCTGAGCGTGTTCTTTTCCGGTTACACCTT<br>TAAGCACAAGATGGTGTACGAAGATACCCTGACCCTGTTCCCTTTCTCCGGCGAAACG<br>GTGTTCATGTCGATGGAGAACCCGGGTCTGTGGATTCTGGGATGCCACAACAGCGACT<br>TTCGGAACCGCGGAATGACTGCCCTGCTGAAGGTGTCCTCATGCGACAAGAACACCGG<br>AGACTACTACGAGGACTCCTACGAGGATATCTCAGCCTACCTCCTGTCCAAGAACAAC<br>GCGATCGAGCCGCGCAGCTTCAGCCAGAACGGCGCGCCAACATCAGAGAGCGCCACCC<br>CTGAAAGTGGTCCCGGGAGCGAGCCAGCCACATCTGGGTCGGAAACGCCAGGCACAAG<br>TGAGTCTGCAACTCCCGAGTCCGGACCTGGCTCCGAGCCTGCCACTAGCGGCTCCGAG<br>ACTCCGGGAACTTCCGAGAGCGCTACACCAGAAAGCGGACCCGGAACCAGTACCGAAC<br>CTAGCGAGGGCTCTGCTCCGGGCAGCCCAGCCGGCTCTCCTACATCCACGGAGGAGGG<br>CACTTCCGAATCCGCCACCCCGGAGTCAGGGCCAGGATCTGAACCCGCTACCTCAGGC<br>AGTGAGACGCCAGGAACGAGCGAGTCCGCTACACCGGAGAGTGGGCCAGGGAGCCCTG<br>CTGGATCTCCTACGTCCACTGAGGAAGGGTCACCAGCGGGCTCGCCCACCAGCACTGA<br>AGAAGGTGCCTCGAGCCCGCCTGTGCTGAAGAGGCACCAGCGAGAAATTACCCGGACC<br>ACCCTCCAATCGGATCAGGAGGAAATCGACTACGACGACCATCTCGGTGGAAATGA<br>AGAAGGAAGATTTCGATATCTACGACGAGGACGAAAATCAGTCCCCTCGCTCATTCCA<br>AAAGAAAACTAGACACTACTTTATCGCCGCGGTGGAAAGACTGTGGGACTATGGAATG<br>TCATCCAGCCCTCACGTCCTTCGGAACCGGGCCCAGAGCGGATCGGTGCCTCAGTTCA<br>AGAAAGTGGTGTTCCAGGAGTTCACCGACGGCAGCTTCACCCAGCCGCTGTACCGGGG<br>AGAACTGAACGAACACCTGGGCCTGCTCGGTCCCTACATCCGCGCGGAAGTGGAGGAT<br>AACATCATGGTGACCTTCCGTAACCAAGCATCCAGACCTTACTCCTTCTATTCCTCCC<br>TGATCTCATACGAGGAGGACCAGCGCCAAGGCGCCGAGCCCCGCAAGAACTTCGTCAA<br>GCCCAACGAGACTAAGACCTACTTCTGGAAGGTCCAACACCATATGGCCCCGACCAAG<br>GATGAGTTTGACTGCAAGGCCTGGGCCTACTTCTCCGACGTGGACCTTGAGAAGGATG<br>TCCATTCCGGCCTGATCGGGCCGCTGCTCGTGTGTCACACCAACACCCTGAACCCAGC<br>GCATGGACGCCAGGTCACCGTCCAGGAGTTTGCTCTGTTCTTCACCATTTTTGACGAA<br>ACTAAGTCCTGGTACTTCACCGAGAATATGGAGCGAAACTGTAGAGCGCCCTGCAATA<br>TCCAGATGGAAGATCCGACTTTCAAGGAGAACTATAGATTCCACGCCATCAACGGGTA<br>CATCATGGATACTCTGCCGGGGCTGGTCATGGCCCAGGATCAGAGGATTCGGTGGTAC<br>TTGCTGTCAATGGGATCGAACGAAAACATTCACTCCATTCACTTCTCCGGTCACGTGT<br>TCACTGTGCGCAAGAAGGAGGAGTACAAGATGGCGCTGTACAATCTGTACCCCGGGGT<br>GTTCGAAACTGTGGAGATGCTGCCGTCCAAGGCCGGCATCTGGAGAGTGGAGTGCCTG<br>ATCGGAGAGCACCTCCACGCGGGGATGTCCACCCTCTTCCTGGTGTACTCGAATAAGT<br>GCCAGACCCCGCTGGGCATGGCCTCGGGCCACATCAGAGACTTCCAGATCACAGCAAG<br>CGGACAATACGCCAATGGGCGCCGAAGCTGGCCCGCTTGCACTACTCCGGATCGATC<br>AACGCATGGTCCACCAAGGAACCGTTCTCGTGGATTAAGGTGGACCTCCTGGCCCCTA<br>TGATTATCCACGGAATTAAGACCCAGGGCGCCAGGCAGAAGTTCTCCTCCCTGTACAT<br>CTCGCAATTCATCATCATGTACAGCCTGGACGGGAAGAAGTGGCAGACTTACAGGGGA<br>AACTCCACCGGCACCCTGATGGTCTTTTTCGGCAACGTGGATTCCTCCGGCATTAAGC<br>ACAACATCTTCAACCCACCGATCATAGCCAGATATATTAGGCTCCACCCCACTCACTA<br>CTCAATCCGCTCAACTCTTCGGATGGAACTCATGGGGTGCGACCTGAACTCCTGCTCC<br>ATGCCGTTGGGGATGGAATCAAAGGCTATTAGCGACGCCCAGATCACCGCGAGCTCCT<br>ACTTCACTAACATGTTCGCCACCTGGAGCCCCTCCAAGGCCAGGCTGCACTTGCAGGG<br>ACGGTCAAATGCCTGGCGGCCGCAAGTGAACAATCCGAAGGAATGGCTTCAAGTGGAT<br>TTCCAAAAGACCATGAAAGTGACCGGAGTCACCACCCAGGGAGTGAAGTCCCTTCTGA<br>CCTCGATGTATGTGAAGGAGTTCCTGATTAGCAGCAGCCAGGACGGGCACCAGTGGAC<br>CCTGTTCTTCCAAAACGGAAAGGTCAAGGTGTTCCAGGGGAACCAGGACTCGTTCACA<br>CCCGTGGTGAACTCCCTGGACCCCCCACTGCTGACGCGGTACTTGAGGATTCATCCTC<br>AGTCTGGGTCCATCAGATTGCATTGCGAATGGAAGTCCTGGGCTGCGAGGCCCAGGA<br>CCTGTACTGA |
| WPRE (mutated woodchuck hepatitis virus post-transcriptional regulatory | TCATAATCAACCTCTGGATTACAAAATTTGTGAAAGATTGACTGGTATTCTTAACTAT<br>GTTGCTCCTTTTACGCTATGTGGATACGCTGCTTTAATGCCTTTGTATCATGCTATTG<br>CTTCCCGTATGGCTTTCATTTTCTCCTCCTTGTATAAATCCTGGTTGCTGTCTCTTTA<br>TGAGGAGTTGTGGCCCGTTGTCAGGCAACGTGGCGTGGTGTGCACTGTGTTTGCTGAC<br>GCAACCCCCACTGGTTGGGGCATTGCCACCACCTGTCAGCTCCTTTCCGGGACTTTCG<br>CTTTCCCCCTCCCTATTGCCACGGCGGAACTCATCGCCGCCTGCCTTGCCCGCTGCTG |

TABLE 2F-continued

| | |
|---|---|
| element) (SEQ ID NO: 120) | GACAGGGGCTCGGCTGTTGGGCACTGACAATTCCGTGGTGTTGTCGGGGAAATCATCG<br>TCCTTTCCTTGGCTGCTCGCCTGTGTTGCCACCTGGATTCTGCGCGGGACGTCCTTCT<br>GCTACGTCCCTTCGGCCCTCAATCCAGCGGACCTTCCTTCCCGCGGCCTGCTGCCGGC<br>TCTGCGGCCTCTTCCGCGTCTTCGCCTTCGCCCTCAGACGAGTCGGATCTCCCTTTGG<br>GCCGCCTCCCCGCTG |
| bGHpA (bovine growth hormone polyadenylation signal) (SEQ ID NO: 122) | CGACTGTGCCTTCTAGTTGCCAGCCATCTGTTGTTTGCCCCTCCCCCGTGCCTTCCTT<br>GACCCTGGAAGGTGCCACTCCCACTGTCCTTTCCTAATAAAATGAGGAAATTGCATCG<br>CATTGTCTGAGTAGGTGTCATTCTATTCTGGGGGGTGGGGTGGGGCAGGACAGCAAGG<br>GGGAGGATTGGGAAGACAATAGCAGGCATGCTGGGGA |
| 3' ITR inverted terminal repeat (SEQ ID NO: 188) | CACTTCCTGGCGCGCAAAATATCCTCTTGTCCTTGAGTCTCATTGGAGGGTTCGTTCG<br>TTCGAACCAGCCAATCAGGGGAGGGGGAAGTGACGCAAGTTCCGGTCACATGCTTCCG<br>GTGACGCACATCCGGTGACGTAGTTCCGGTCACGTGCTTCCTGTCACGTGTTTCCGGT<br>CACGTGACTTCCGGTCATGTGACTTCCGGTGACGTGTTTCCGGCTTAACTATTGGGCT<br>GACCGCGCGGCATGCGCGTGGTCAACCTAACAGCCGGAAACACGTCACCGGAAGTCAC<br>ATGACCGGAAGTCACGTGACCGGAAACACGTGACAGGAAGCACGTGACCGGAACTACG<br>TCACCGGATGTGCGTCACCGGAAGCATGTGACCGGAACTTGCGTCACTTCCCCCTCCC<br>CTGATTGGCTGGTTCGAACGAACGAACCCTCCAATGAG |

| Full-length Sequence (SEQ ID NO: 194) |
|---|
| CTCATTGGAGGGTTCGTTCGTTCGAACCAGCCAATCAGGGGAGGGGGAAGTGACGCAAGTTCCGGTCACATGC<br>TTCCGGTGACGCACATCCGGTGACGTAGTTCCGGTCACGTGCTTCCTGTCACGTGTTTCCGGTCACGTGACTT<br>CCGGTCATGTGACTTCCGGTGACGTGTTTCCGGCTGTTAGGTTGACCACGCGCATGCCGCGCGGTCAGCCCAA<br>TAGTTAAGCCGGAAACACGTCACCGGAAGTCACATGACCGGAAGTCACGTGACCGGAAACACGTGACAGGAAG<br>CACGTGACCGGAACTACGTCACCGGATGTGCGTCACCGGAAGCATGTGACCGGAACTTGCGTCACTTCCCCCT<br>CCCCTGATTGGCTGGTTCGAACGAACGAACCCTCCAATGAGACTCAAGGACAAGAGGATATTTTGCGCGCCAG<br>GAAGTGGCGGCAATTCAGTCGATAACTATAACGGTCCTAAGGTAGCGATTTAAATACGCGCTCTCTTAAGGTA<br>GCCCCGGGACGCGTCAATTGAGATCTGGATCCGGTACCGAATTCGCGGCCGCCTCGACGACTAGCGTTTAATT<br>AAACGCGTGTCTGTCTGCACATTTCGTAGAGCGAGTGTTCCGATACTCTAATCTCCCTAGGCAAGGTTCATAT<br>TTGTGTAGGTTACTTATTATTCTCCTTTTGTTGACTAAGTCAATAATCAGAATCAGCAGGTTTGGAGTCAGCTTGG<br>CAGGGATCAGCAGCCTGGGTTGGAAGGAGGGGGTATAAAAGCCCCTTCACCAGGAGGAAGCCGTCACACAGATC<br>CACAAGCTCCTGAGGTAAGTGCCGTGTGTGGTTCCCGCGGGCCTGGCCTCTTTACGGGTTATGGCCCTTGCGT<br>GCCTTGAATTACTGACACTGACATCCACTTTTTCTTTTTCTCCACAGCTAGCGCCACCATGCAGATTGAGCTG<br>TCCACTTGTTTCTTCCTGTGCCTCCTGCGCTTCTGTTTCTCCGCCACTCGCCGGTACTACCTTGGAGCCGTGG<br>AGCTTTCATGGGACTACATGCAGAGCGACCTGGGCGAACTCCCCGTGGATGCCAGATTCCCCCCCGCGTGCC<br>AAAGTCCTTCCCCTTTAACACCTCCGTGGTGTACAAGAAAACCCTCTTTGTCGAGTTCACTGACCACCTGTTC<br>AACATCGCCAAGCCGCGCCCACCTTGGATGGGCCTCCTGGGACCGACCATTCAAGCTGAAGTGTACGACACCG<br>TGGTGATCACCCTGAAGAACATGGCGTCCCACCCCGTGTCCCTGCATGCGGTCGGAGTGTCCTACTGGAAGGC<br>CTCCGAAGGAGCTGAGTACGAACGACCAGACTAGCCAGCGGGAAGGACGATAAAGTGTTCCCGGGCGGC<br>TCGCATACTTACGTGTGGCAAGTCCTGAAGGAAAACGGACCTATGGCATCCGATCCTCTGTGCCTGACTTACT<br>CCTACCTTTCCCATGTGGACCTCGTGAAGGACCTGAACAGCGGGCTGATTGGTGCACTTCTCGTGTGCCGCGA<br>AGGTTCGCTCGCTAAGGAAAAGACCCAGACCCTCCATAAGTTCATCCTTTTGTTCGCTGTGTTCGATGAAGGA<br>AAGTCATGGCATTCCGAAACTAAGAACTCGCTGATGCAGGACCGGGATGCCGCCTCAGCCGCGCCTGGCCTA<br>AAATGCATACAGTCAACGGATACGTGAATCGGTCACTGCCCGGGCTCATCGGTTGTCACAGAAAGTCCGTGTA<br>CTGGCACGTCATCGGCATGGGCACTACGCCTGAAGTGCACTCCATCTTCCTGGAAGGGCACACCTTCCTCGTG<br>CGCAACCACCGCCAGGCCTCTCTGAAATCTCCCCGATTACCTTTCTGACCGCCCAGACTCTGCTCATGGACC<br>TGGGGCAGTTCCTTCTCTTCTGCCACATCTCCAGCCATCAGCACGACGGAATGGAGGCCTACGTGAAGGTGGA<br>CTCATGCCCGGAAGAACCTCAGTTGCGGATGAAGAACAACGAGGAGGCCGAGGACTATGACGACGATTTGACT<br>GACTCCGAGATGGACGTCGTGCGGTTCGATGACGACAACAGCCCCAGCTTCATCCAGATTCGCAGCGTGGCCA<br>AGAAGCACCCCAAAACCTGGGTGCACTACATCGCGGCCGAGGAAGAAGATTGGGACTACGCCCCGTTGGTGCT<br>GGCACCCGATGACCGGTCGTACAAGTCCCAGTATCTGAACAATGGTCGGGATTGGCAGAAAGTACAAG<br>AAAGTGCGGTTCATGGCGTACACTGACGAAACGTTTAAGACCCGGGAGGCCATTCAACATGAGAGCGGCATTC<br>TGGGACCACTGCTGTACGGAGAGGTCGGCGATACCCTGCTCATCATCTTCAAAAACCAGGCCTCCCGGCCTTA<br>CAACATCTACCCTCACGGAATCACCGACGTGCGGCCACTCTACTCGCGGCGCCTGCCGAAGGGCGTCAAGCAC<br>CTGAAAGACTTCCCTATCCTGCCGGGCGAAATCTTCAAGTATAAGTGGACCGTCACCGTGGAGGACGGGCCCA<br>CCAAGAGCGATCCTAGGTGTCTGACTCGGTACTACTCCAGCTTCGTGAACATGGAACGGGACCTGGCATCGGG<br>ACTCATTGGACCGCTGCTGATCTGCTACAAAGAGTCGGTGGATCAACGCGGCAACCAGATCATGTCCGACAAG<br>CGCAACGTGATCCTGTTCTCCGTGTTTGATGAAAACAGATCCTGGTACCTCACTGAAAACATCCAGAGGTTCC<br>TCCCAAACCCCGCAGGAGTGCAACTGGAGGACCCTGAGTTTCAGGCCTCGAATATCATGCACTCGATTAACGG<br>TTACGTGTTCGACTCGCTGCAACTGAGCGTGTGCCTCCATGAAGTCGCTTACTGGTACATTCTGTCCATCGGC<br>GCCCAGACTGACTTCCTGAGCGTGTTCTTTTCCGGTTACACCTTTAAGCACAAGATGGTGTACGAAGATACCC<br>TGACCCTGTTCCCTTTCTCCGGCGAAACGGTGTTCATGTCGATGGAGAACCCGGGTCTGTGGATTCTGGGATG<br>CCACAACAGCGACTTTCGGAACCGCGGAATGACTGCCCTGCTGAAGGTGTCCTCATGCGACAAGAACACCGGA<br>GACTACTACGAGGACTCCTACGAGGATATCTCAGCCTACCTCCTGTCCAAGAACAACGCGATCGAGCCGCGCA<br>GCTTCAGCCAGAACGGCGCGCCAACATCAGAGAGCGCCACCCCTGAAAGTGGTCCCGGGAGCGAGCCAGCCAC<br>ATCTGGGTCGGAAACGCCAGGCACAAGTGAGTCTGCAACTCCCGAGTCCGGACCTGGCTCCGAGCCTGCCACT<br>AGCGGCTCCGAGACTCCGGGAACTTCCGAGAGCGCTACACCAGAAAGCGGACCCGGAACCAGTACCGAACCTA<br>GCGAGGGCTCTGCTCCGGGCAGCCCAGCCGGCTCTTCCTACATCCAGGAAGGAGGGGCACTTCCAATCCGCCA<br>CCCGGAGTCAGGGCCAGGATCTGAACCCGCTACCTCAGGCAGTGAGACGGCCAGGAACGAGCGAGTCCGCTACA<br>CCGGAGAGTGGGCCAGGGAGCCCTGCTGGATCTCCTACGTCCACTGAGGAAGGGTCACCAGCGGGCTCGCCCA<br>CCAGCACTGAAGAAGGTGCCTCGAGCCCGCCTGTGCTGAAGAGGCACCAGCGAGAAATTACCGGACCACCCT<br>CCAATCGGATCAGGAGGAAATCGACTACGACGACACCATCTCGGTGGAAATGAAGAAGGAAGATTTCGATATC<br>TACGACGAGGACGAAAATCAGTCCCCTCGCTCATTCAAAAGAAAATAGACACTACTTTATCGCCGCGGTGG<br>AAAGACTGTGGGACTATGGAATGTCATCCAGCCCTCACGTCCTTCGGAACCGGGCCCAGAGCGGATCGGTGCC<br>TCAGTTCAAGAAAGTGGTGTTCCAGGAGTTCACCGACGGCAGCTTCACCCAGCCGCTGTACCGGGGAGAACTG<br>AACGAACACCTGGGCCTGCTCGGTCCCTACATCCGCGCGAAGTGGAGGATAACATCATGGTGACCTTCCGTA<br>ACCAAGCATCCAGACCTTACTCCTTCTATTCCTCCCTGATCTCATACGAGGAGGACCAGCGCCAAGGCGCCGA TABLE 2F-continued

```
GCCCCGCAAGAACTTCGTCAAGCCCAACGAGACTAAGACCTACTTCTGGAAGGTCCAACACCATATGGCCCCG
ACCAAGGATGAGTTTGACTGCAAGGCCTGGGCCTACTTCTCCGACGTGGACCTTGAGAAGGATGTCCATTCCG
GCCTGATCGGGCCGCTGCTCGTGTGTCACACCAACACCCTGAACCCAGCGCATGGACGCCAGGTCACCGTCCA
GGAGTTTGCTCTGTTCTTCACCATTTTTGACGAAACTAAGTCCTGGTACTTCACCGAGAATATGGAGCGAAAC
TGTAGAGCGCCCTGCAATATCCAGATGGAAGATCCGACTTTCAAGGAGAACTATAGATTCCACGCCATCAACG
GGTACATCATGGATACTCTGCCGGGGCTGGTCATGGCCCAGGATCAGAGGATTCGGTGGTACTTGCTGTCAAT
GGGATCGAACGAAAACATTCACTCCATTCACTTCTCCGGTCACGTGTTCACTGTGCGCAAGAAGGAGGAGTAC
AAGATGGCGCTGTACAATCTGTACCCCGGGGTGTTCGAAACTGTGGAGATGCTGCCGTCCAAGGCCGGCATCT
GGAGAGTGGAGTGCCTGATCGGAGAGCACCTCCACGCGGGGATGTCCACCCTCTTCCTGGTGTACTCGAATAA
GTGCCAGACCCCGCTGGGCATGGCCTCGGGCCACATCAGAGACTTCCAGATCACAGCAAGCGGACAATACGGC
CAATGGGCGCCGAAGCTGGCCCGCTTGCACTACTCCGGATCGATCAACGCATGGTCCACCAAGGAACCGTTCT
CGTGGATTAAGGTGGACCTCCTGGCCCCTATGATTATCCACGGAATTAAGACCCAGGGCGCCAGGCAGAAGTT
CTCCTCCCTGTACATCTCGCAATTCATCATCATGTACAGCCTGGACGGGAAGAAGTGGCAGACTTACAGGGGA
AACTCCACCGGCACCCTGATGGTCTTTTTCGGCAACGTGGATTCCTCCGGCATTAAGCACAACATCTTCAACC
CACCGATCATAGCCAGATATATTAGGCTCCACCCCACTCACTACTCAATCCGCTCAACTCTTCGGATGGAACT
CATGGGGTGCGACCTGAACTCCTGCTCCATGCCGTTGGGGATGGAATCAAAGGCTATTAGCGACGCCCAGATC
ACCGCGAGCTCCTACTTCACTAACATGTTCGCCACCTGGAGCCCCTCCAAGGCCAGGCTGCACTTGCAGGGAC
GGTCAAATGCCTGGCGGCCGCAAGTGAACAATCCGAAGGAATGGCTTCAAGTGGATTTCCAAAAGACCATGAA
AGTGACCGGAGTCACCACCCAGGGAGTGAAGTCCCTTCTGACCTCGATGTATGTGAAGGAGTTCCTGATTAGC
AGCAGCCAGGACGGGCACCAGTGGACCCTGTTCTTCCAAAACGGAAAGGTCAAGGTGTTCCAGGGGAACCAGG
ACTCGTTCACACCCGTGGTGAACTCCCTGGACCCCCCACTGCTGACGCGGTACTTGAGGATTCATCCTCAGTC
CTGGGTCCATCAGATTGCATTGCGAATGGAAGTCCTGGGCTGCGAGGCCCAGGACCTGTACTGAATCAGCCTG
AGCTCGCTGATCATAATCAACCTCTGGATTACAAAATTTGTGAAAGATTGACTGGTATTCTTAACTATGTTGC
TCCTTTTACGCTATGTGGATACGCTGCTTTAATGCCTTTGTATCATGCTATTGCTTCCCGTATGGCTTTCATT
TTCTCCTCCTTGTATAAATCCTGGTTGCTGTCTCTTTATGAGGAGTTGTGGCCCGTTGTCAGGCAACGTGGCG
TGGTGTGCACTGTGTTTGCTGACGCAACCCCCACTGGTTGGGGCATTGCCACCACCTGTCAGCTCCTTTCCGG
GACTTTCGCTTTCCCCCTCCCTATTGCCACGGCGGAACTCATCGCCGCCTGCCTGCCCGCTGCTGGACAGGG
GCTCGGCTGTTGGGCACTGACAATTCCGTGGTGTTGTCGGGGAAATCATCGTCCTTTCCTTGGCTGCTCGCCT
GTGTTGCCACCTGGATTCTGCGCGGGACGTCCTTCTGCTACGTCCCTTCGGCCCTCAATCCAGCGGACCTTCC
TTCCCGCGGCCTGCTGCCGGCTCTGCGGCCTCTTCCGCGTCTTCGCCTTCGCCCTCAGACGAGTCGGATCTCC
CTTTGGGCCGCCTCCCCGCTGATCAGCCTCGACTGTGCCTTCTAGTTGCCAGCCATCTGTTGTTTGCCCCTCC
CCCGTGCCTTCCTTGACCCTGGAAGGTGCCACTCCCACTGTCCTTTCCTAATAAAATGAGGAAATTGCATCGC
ATTGTCTGAGTAGGTGTCATTCTATTCTGGGGGGTGGGGTGGGGCAGGACAGCAAGGGGGAGGATTGGGAAGA
CAATAGCAGGCATGCTGGGGATGCGGTGGGCTCTATGGCTTCTGAGGCGGAAAGAACGGGCTCGAGAAGCTTC
TAGATATCCTCTCTTAAGGTAGCATCGAGATTTAAATTAGGGATAACAGGGTAATGGCGCGGGCCGCCACTTC
CTGGCGCGCAAAATATCCTCTTGTCCTTGAGTCTCATTGGAGGGTTCGTTCGTTCGAACCAGCCAATCAGGGG
AGGGGGAAGTGACGCAAGTTCCGGTCACATGCTTCCGGTGACGCACATCCGGTGACGTAGTTCCGGTCACGTG
CTTCCTGTCACGTGTTTCCGGTCACGTGACTTCCGGTCATGTGACTTCCGGTGACGTGTTTCCGGCTTAACTA
TTGGGCTGACCGCGCGGCATGCGCGTGGTCAACCTAACAGCCGGAAACACGTCACCGGAAGTCACATGACCGG
AAGTCACGTGACCGGAAACACGTGACAGGAAGCACGTGACCGGAACTACGTCACCGGATGTGCGTCACCGGAA
GCATGTGACCGGAACTTGCGTCACTTCCCCCTCCCCTGATTGGCTGGTTCGAACGAACGAACCCTCCAATGAG
```

In one embodiment, the genetic cassette comprises a phenylalanine hydroxylase (PAH) construct, which includes a polynucleotide sequence as listed in Tables 10A and 10B. In one embodiment, the genetic cassette comprises a PAH construct, which includes a polynucleotide sequence set forth in Table 10A. In one embodiment, the genetic cassette comprises a PAH construct, which includes a polynucleotide sequence set forth in Table 10B.

In certain embodiments, the isolated nucleic acid molecule comprises a nucleotide sequence having at least about 60%, at least about 65%, at least about 70%, at least about 75%, at least about 80%, at least about 85%, at least about 90%, at least about 95%, at least about 96%, at least about 97%, at least about 98%, at least about 99%, or about 100% sequence identity to the nucleotide sequence of SEQ ID NO: 197 or 198. In some embodiments, the isolated nucleic acid molecule comprises a nucleotide sequence having at least about 60%, at least about 65%, at least about 70%, at least about 75%, at least about 80%, at least about 85%, at least about 90%, at least about 95%, at least about 96%, at least about 97%, at least about 98%, at least about 99%, or about 100% sequence identity to the nucleotide sequence of SEQ ID NO: 197. In some embodiments, the isolated nucleic acid molecule comprises a nucleotide sequence having at least about 60%, at least about 65%, at least about 70%, at least about 75%, at least about 80%, at least about 85%, at least about 90%, at least about 95%, at least about 96%, at least about 97%, at least about 98%, at least about 99%, or about 100% sequence identity to the nucleotide sequence of SEQ ID NO: 198. In some embodiments, the isolated nucleic acid molecule retains the ability to express a functional phenylalanine hydroxylase.

A. Codon Adaptation Index

In one embodiment, the genetic cassette comprises a codon optimized nucleotide sequence encoding a FVIII polypeptide, wherein the human codon adaptation index of the codon optimized nucleotide sequence is increased relative to SEQ ID NO: 16. For example, the codon optimized nucleotide sequence can have a human codon adaptation index that is at least about 0.75 (75%), at least about 0.76 (76%), at least about 0.77 (77%), at least about 0.78 (78%), at least about 0.79 (79%), at least about 0.80 (80%), at least about 0.81 (81%), at least about 0.82 (82%), at least about 0.83 (83%), at least about 0.84 (84%), at least about 0.85 (85%), at least about 0.86 (86%), at least about 0.87 (87%), at least about 0.88 (88%), at least about 0.89 (89%), at least about 0.90 (90%), at least about 0.91 (91%), at least about 0.92 (92%), at least about 0.93 (93%), at least about 0.94 (94%), at least about 0.95 (95%), at least about 0.96 (96%), at least about 0.97 (97%), at least about 0.98 (98%), or at least about 0.99 (99%). In some embodiments, the codon optimized nucleotide sequence has a human codon adaptation index that is at least about 0.88 (88%). In other embodiments, the codon optimized nucleotide sequence has a human codon adaptation index that is at least about 0.91 (91%). In other embodiments, the codon optimized nucleotide sequence has a human codon adaptation index that is at least about 0.91 (97%).

In one particular embodiment, the codon optimized nucleotide sequence encoding a FVIII polypeptide comprises a nucleotide sequence which comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the human codon adaptation index of the nucleotide sequence is increased relative to SEQ ID NO: 16. In some embodiments, the nucleotide sequence has a human codon adaptation index that is at least about 0.75 (75%), at least about 0.76 (76%), at least about 0.77 (77%), at least about 0.78 (78%), at least about 0.79 (79%), at least about 0.80 (80%), at least about 0.81 (81%), at least about 0.82 (82%), at least about 0.83 (83%), at least about 0.84 (84%), at least about 0.85 (85%), at least about 0.86 (86%), at least about 0.87 (87%), at least about 0.88 (88%), at least about 0.89 (89%), at least about 0.90 (90%), or at least about 0.91 (91%). In one particular embodiment, the nucleotide sequence has a human codon adaptation index that is at least about 0.88 (88%). In another embodiment, the nucleotide sequence has a human codon adaptation index that is at least about 0.91 (91%).

In another embodiment, the codon optimized nucleotide sequence encoding a FVIII polypeptide comprises a nucleotide sequence which comprises a first nucleic acid sequence encoding an N-terminal portion of a FVIII polypeptide and a second nucleic acid sequence encoding a C-terminal portion of a FVIII polypeptide; wherein the second nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 1792-2277 and 2320-4374 of SEQ ID NO: 5 or (ii) 1792-2277 and 2320-4374 of SEQ ID NO: 6; wherein the N-terminal portion and the C-terminal portion together have a FVIII polypeptide activity; and wherein the human codon adaptation index of the nucleotide sequence is increased relative to SEQ ID NO: 16. In some embodiments, the nucleotide sequence has a human codon adaptation index that is at least about 0.75 (75%), at least about 0.76 (76%), at least about 0.77 (77%), at least about 0.78 (78%), at least about 0.79 (79%), at least about 0.80 (80%), at least about 0.81 (81%), at least about 0.82 (82%), at least about 0.83 (83%), at least about 0.84 (84%), at least about 0.85 (85%), at least about 0.86 (86%), at least about 0.87 (87%), or at least about 0.88 (88%). In one particular embodiment, the nucleotide sequence has a human codon adaptation index that is at least about 0.83 (83%). In another embodiment, the nucleotide sequence has a human codon adaptation index that is at least about 0.88 (88%).

In other embodiments, the codon optimized nucleotide sequence encoding a FVIII polypeptide comprises a nucleotide sequence encoding a polypeptide with FVIII activity, wherein the nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the human codon adaptation index of the nucleotide sequence is increased relative to SEQ ID NO: 16. In some embodiments, the nucleotide sequence has a human codon adaptation index that is at least about 0.75 (75%), at least about 0.76 (76%), at least about 0.77 (77%), at least about 0.78 (78%), at least about 0.79 (79%), at least about 0.80 (80%), at least about 0.81 (81%), at least about 0.82 (82%), at least about 0.83 (83%), at least about 0.84 (84%), at least about 0.85 (85%), at least about 0.86 (86%), at least about 0.87 (87%), or at least about 0.88 (88%). In one particular embodiment, the nucleotide sequence has a human codon adaptation index that is at least about 0.75 (75%). In another embodiment, the nucleotide sequence has a human codon adaptation index that is at least about 0.83 (83%). In another embodiment, the nucleotide sequence has a human codon adaptation index that is at least about 0.88 (88%). In another embodiment, the nucleotide sequence has a human codon adaptation index that is at least about 0.91 (91%). In another embodiment, the nucleotide sequence has a human codon adaptation index that is at least about 0.97 (97%).

In some embodiments, the codon optimized nucleotide sequence encoding a FVIII polypeptide of the present disclosure has an increased frequency of optimal codons (FOP) relative to SEQ ID NO: 16. In certain embodiments, the FOP of the codon optimized nucleotide sequence encoding a FVIII polypeptide is at least about 40, at least about 45, at least about 50, at least about 55, at least about 60, at least about 64, at least about 65, at least about 70, at least about 75, at least about 79, at least about 80, at least about 85, or at least about 90.

In other embodiments, the codon optimized nucleotide sequence encoding a FVIII polypeptide of the present disclosure has an increased relative synonymous codon usage (RCSU) relative to SEQ ID NO: 16. In some embodiments, the RCSU of the isolated nucleic acid molecule is greater than 1.5. In other embodiments, the RCSU of the isolated nucleic acid molecule is greater than 2.0. In certain embodiments, the RCSU of the isolated nucleic acid molecule is at least about 1.5, at least about 1.6, at least about 1.7, at least about 1.8, at least about 1.9, at least about 2.0, at least about 2.1, at least about 2.2, at least about 2.3, at least about 2.4, at least about 2.5, at least about 2.6, or at least about 2.7.

In still other embodiments, the codon optimized nucleotide sequence encoding a FVIII polypeptide of the present disclosure has a decreased effective number of codons relative to SEQ ID NO: 16. In some embodiments, the codon optimized nucleotide sequence encoding a FVIII polypeptide has an effective number of codons of less than about 50, less than about 45, less than about 40, less than about 35, less than about 30, or less than about 25. In one particular embodiment, the isolated nucleic acid molecule has an effective number of codons of about 40, about 35, about 30, about 25, or about 20.

B. G/C Content Optimization

In some embodiments, the genetic cassette comprises a codon optimized nucleotide sequence encoding a FVIII polypeptide, wherein the codon optimized nucleotide sequence contains a higher percentage of G/C nucleotides compared to the percentage of G/C nucleotides in SEQ ID NO: 16. In other embodiments, the codon optimized nucleotide sequence encoding a FVIII polypeptide has a G/C content that is at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, or at least about 60%.

In one particular embodiment, the codon optimized nucleotide sequence encoding a FVIII polypeptide comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the nucleotide sequence contains a higher percentage of G/C nucleotides compared to the percentage of G/C nucleotides in SEQ ID NO: 16. In some embodiments, the codon optimized nucleotide sequence encoding a FVIII polypeptide comprises has a G/C content that is at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, or at least about 58%. In one particular embodiment, the nucleotide sequence that encodes a polypeptide with FVIII activity has a G/C content that is at least about 58%.

In another embodiment, the codon optimized nucleotide sequence encoding a FVIII polypeptide comprises a first nucleic acid sequence encoding an N-terminal portion of a FVIII polypeptide and a second nucleic acid sequence encoding a C-terminal portion of a FVIII polypeptide; wherein the second nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 1792-4374 of SEQ ID NO: 5; (ii) nucleotides 1792-4374 of SEQ ID NO: 6; (iii) nucleotides 1792-2277 and 2320-4374 of SEQ ID NO: 5 (i.e., nucleotides 1792-4374 of SEQ ID NO: 5 without the nucleotides encoding the B domain or B domain fragment), or (iv) 1792-2277 and 2320-4374 of SEQ ID NO: 6 (i.e., nucleotides 1792-4374 of SEQ ID NO: 6 without the nucleotides encoding the B domain or B domain fragment); wherein the N-terminal portion and the C-terminal portion together have a FVIII polypeptide activity; and wherein the codon optimized nucleotide sequence contains a higher percentage of G/C nucleotides compared to the percentage of G/C nucleotides in SEQ ID NO: 16. In other embodiments, the codon optimized nucleotide sequence encoding a FVIII polypeptide has a G/C content that is at least about 45%, at least about 46%, at least about 47%, at least about 48%, at least about 49%, at least about 50%, at least about 51%, at least about 52%, at least about 53%, at least about 54%, at least about 55%, at least about 56%, or at least about 57%. In one particular embodiment, the codon optimized nucleotide sequence encoding a FVIII polypeptide has a G/C content that is at least about 52%. In another embodiment, the codon optimized nucleotide sequence encoding a FVIII polypeptide has a G/C content that is at least about 55%. In another embodiment, the codon optimized nucleotide sequence encoding a FVIII polypeptide has a G/C content that is at least about 57%.

In other embodiments, the genetic cassette comprises a codon optimized nucleotide sequence encoding a FVIII polypeptide, wherein the codon optimized nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 or (ii) nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the nucleotide sequence contains a higher percentage of G/C nucleotides compared to the percentage of G/C nucleotides in SEQ ID NO: 16. In other embodiments, the codon optimized nucleotide sequence encoding a FVIII polypeptide has a G/C content that is at least about 45%. In one particular embodiment, the codon optimized nucleotide sequence encoding a FVIII polypeptide has a G/C content that is at least about 52%. In another embodiment, the codon optimized nucleotide sequence encoding a FVIII polypeptide has a G/C content that is at least about 55%. In another embodiment, the codon optimized nucleotide sequence encoding a FVIII polypeptide has a G/C content that is at least about 57%. In another embodiment, the codon optimized nucleotide sequence encoding a FVIII polypeptide has a G/C content that is at least about 58%. In still another embodiment, the n codon optimized nucleotide sequence encoding a FVIII polypeptide has a G/C content that is at least about 60%.

"G/C content" (or guanine-cytosine content), or "percentage of G/C nucleotides," refers to the percentage of nitrogenous bases in a DNA molecule that are either guanine or cytosine. G/C content can be calculated using the following formula:

$$\frac{G+C}{A+T+G+C} \times 100 \qquad (III)$$

Human genes are highly heterogeneous in their G/C content, with some genes having a G/C content as low as 20%, and other genes having a G/C content as high as 95%. In general, G/C rich genes are more highly expressed. In fact, it has been demonstrated that increasing the G/C content of a gene can lead to increased expression of the gene, due mostly to an increase in transcription and higher steady state mRNA levels. See Kudla et al., PLoS Biol., 4(6): e180 (2006).

C. Matrix Attachment Region-Like Sequences

In some embodiments, the genetic cassette comprises a codon optimized nucleotide sequence encoding a FVIII polypeptide, wherein the codon optimized nucleotide sequence contains fewer MARS/ARS sequences relative to SEQ ID NO: 16. In other embodiments, the codon optimized nucleotide sequence encoding a FVIII polypeptide contains at most 6, at most 5, at most 4, at most 3, or at most 2 MARS/ARS sequences. In other embodiments, the codon optimized nucleotide sequence encoding a FVIII polypeptide contains at most 1 MARS/ARS sequence. In yet other embodiments, the codon optimized nucleotide sequence encoding a FVIII polypeptide does not contain a MARS/ARS sequence.

In one particular embodiment, the codon optimized nucleotide sequence encoding a FVIII polypeptide comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the codon optimized nucleotide sequence contains fewer MARS/ARS sequences relative to SEQ ID NO: 16. In other embodiments, the nucleotide sequence that encodes a polypeptide with FVIII activity contains at most 6, at most 5, at most 4, at most 3, or at most 2 MARS/ARS sequences. In other embodiments, the codon optimized nucleotide sequence encoding a FVIII polypeptide contains at most 1 MARS/ARS sequence. In yet other embodiments, the codon optimized nucleotide sequence encoding a FVIII polypeptide does not contain a MARS/ARS sequence.

In another embodiment, the codon optimized nucleotide sequence encoding a FVIII polypeptide comprises a first nucleic acid sequence encoding an N-terminal portion of a FVIII polypeptide and a second nucleic acid sequence encoding a C-terminal portion of a FVIII polypeptide; wherein the second nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 1792-4374 of SEQ ID NO: 5; (ii) nucleotides 1792-4374 of SEQ ID NO: 6; (iii) nucleotides 1792-2277 and 2320-4374 of SEQ ID NO: 5 (i.e., nucleotides 1792-4374 of SEQ ID NO: 5 without the nucleotides encoding the B domain or B domain fragment); or (iv) nucleotides 1792-2277 and 2320-4374 of SEQ ID NO: 6 (i.e., nucleotides 1792-4374 of SEQ ID NO: 6 without the nucleotides encoding the B domain or B domain fragment); wherein the N-terminal portion and the C-terminal portion together have a FVIII polypeptide activity; and wherein the nucleotide sequence contains fewer MARS/ARS sequences relative to SEQ ID NO: 16. In other embodiments, the codon optimized nucleotide sequence encoding a FVIII polypeptide contains at most 6, at most 5, at most 4, at most 3, or at most 2 MARS/ARS sequences. In other embodiments, the codon optimized nucleotide sequence encoding a FVIII polypeptide contains at most 1 MARS/ARS sequence. In yet other embodiments, the codon optimized nucleotide sequence encoding a FVIII polypeptide does not contain a MARS/ARS sequence.

In other embodiments, the genetic cassette comprises a codon optimized nucleotide sequence encoding a FVIII polypeptide, wherein the codon optimized nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of SEQ ID NOs: 1, 2, 3, 4, 5, 6, 70, or 71 or (ii) nucleotides 58-2277 and 2320-4374 of SEQ ID NOs: 1, 2, 3, 4, 5, 6, 70, or 71 (i.e., nucleotides 58-4374 of SEQ ID NO: 1, 2, 3, 4, 5, 6, 70, or 71 without the nucleotides encoding the B domain or B domain fragment); and wherein the codon optimized nucleotide sequence contains fewer MARS/ARS sequences relative to SEQ ID NO: 16. In other embodiments, the codon optimized nucleotide sequence encoding a FVIII polypeptide contains at most 6, at most 5, at most 4, at most 3, or at most 2 MARS/ARS sequences. In other embodiments, the codon optimized nucleotide sequence encoding a FVIII polypeptide contains at most 1 MARS/ARS sequence. In yet other embodiments, the codon optimized nucleotide sequence encoding a FVIII polypeptide does not contain a MARS/ARS sequence.

AT-rich elements in the human FVIII nucleotide sequence that share sequence similarity with *Saccharomyces cerevisiae* autonomously replicating sequences (ARSs) and nuclear-matrix attachment regions (MARs) have been identified. (Fallux et al., *Mol. Cell. Biol.* 16:4264-4272 (1996). One of these elements has been demonstrated to bind nuclear factors in vitro and to repress the expression of a chloramphenicol acetyltransferase (CAT) reporter gene. Id. It has been hypothesized that these sequences can contribute to the transcriptional repression of the human FVIII gene. Thus, in one embodiment, all MAR/ARS sequences are abolished in the codon optimized nucleotide sequence encoding a FVIII polypeptide of the present disclosure. There are four MAR/ARS ATATTT sequences (SEQ ID NO: 21) and three MAR/ARS AAATAT sequences (SEQ ID NO: 22) in the parental FVIII sequence (SEQ ID NO: 16). All of these sites were mutated to destroy the MAR/ARS sequences in the optimized FVIII sequences (SEQ ID NOs: 1-6). The location of each of these elements, and the sequence of the corresponding nucleotides in the optimized sequences are shown in Table 3, below.

TABLE 3

Summary of Changes to Repressive Elements

| Location of Element | Starting BDD FVIII Sequence (SEQ ID NO: 16) | Optimized BDD FVIII Sequence | | | | | | | |
|---|---|---|---|---|---|---|---|---|---|
| | | SEQ ID NO: 1 | SEQ ID NO: 2 | SEQ ID NO: 3 | SEQ ID NO: 4 | SEQ ID NO: 5 | SEQ ID NO: 6 | SEQ ID NO: 70 | SEQ ID NO: 71 |
| Destabilizing Sequences | | | | | | | | | |
| 639 | ATTTA | GTTTA | GTTCA | GTTCA | GTTCA | GTTCA | GTTCA | GTTCA | GTTCA |
| 1338 | ATTTA | GTTTA | GTTCA | CTTCA | GTTCA | GTTCA | GTTCA | CTTCA | GTTCA |
| 1449 | ATTTA | CTTTA | CTTCA | CTTCA | CTTCA | CTTCA | CTTCA | CTTCA | CTTCA |

TABLE 3-continued

Summary of Changes to Repressive Elements

| Location of Element | Starting BDD FVIII Sequence (SEQ ID NO: 16) | Optimized BDD FVIII Sequence SEQ ID NO: 1 | SEQ ID NO: 2 | SEQ ID NO: 3 | SEQ ID NO: 4 | SEQ ID NO: 5 | SEQ ID NO: 6 | SEQ ID NO: 70 | SEQ ID NO: 71 |
|---|---|---|---|---|---|---|---|---|---|
| 1590 | TAAAT | TAAAT | CAAGT | CAAGT | TAAGT | CAAGT | CAAGT | CAAGT | TAAGT |
| 1623 | TAAAT | CAAAA | GAAGA | CTAAG | CAAGA | CAAGA | CAAGA | TAAGT | CAAGA |
| 2410 | ATTTA | ATCTA | ATCTA | ATCTA | ATCTA | ATCTA | ATCTA | ATCTA | ATCTA |
| 2586 | ATTTA | GTTTA | GTTCA | GTTCA | GTTCA | GTTCA | GTTCA | GTTCA | GTTCA |
| 2630 | TAAAT | TGAAT | TGAAC | TGAAC | TGAAC | TCAAT | TGAAC | TCAAT | TGAAC |
| 3884 | ATTTA | ATCTG | ACCTG | ACCTG | ACCTG | ATCTG | ACCTG | ATCTG | ACCTG |
| 3887 | TAAAT | TGAAC | TGAAC | TGAAC | TGAAC | TGAAC | TGAAC | TGAAC | TGAAC |
| Potential Promoter Binding Sites | | | | | | | | | |
| 641 | TTATA | TTATC | TCATC | TCATT | TCATC | TCATC | TCATC | TCATT | TCATC |
| 1275 | TATAA | CTATA | TTACA | CTACA | GTACA | CTACA | CTACA | CTACA | GTACA |
| 1276 | TTATA | TATAA | TACAA | TACAA | TACAA | TACAA | TACAA | TACAA | TACAA |
| 1445 | TTATA | TCATC | TCATC | TTATC | TCATC | TCATC | TCATC | TTATC | TCATC |
| 1474 | TATAA | TATAA | TACAA | TACAA | TACAA | TACAA | TACAA | TACAA | TACAA |
| 1588 | TATAA | TATAA | TACAA | TACAA | TATAA | TACAA | TACAA | TACAA | TATAA |
| 2614 | TTATA | CTGTA | CTGTA | CTGTA | CTGTA | TTGTA | CTGTA | TTGTA | CTGTA |
| 2661 | TATAA | CATCA | CATCA | CATCA | CATCA | CATCA | CATCC | CATCA | CATCC |
| 3286 | TATAA | TATAA | TACAA | TACAA | TACAA | TACAA | TACAA | TACAA | TACAA |
| 3840 | TTATA | TTATA | TTACT | CTACA | CTACA | CTACA | CTACT | CTACA | CTACT |
| Matrix Attachment-Like Sequences (MARS/ARS) | | | | | | | | | |
| 1287 | ATATTT | GTATCT | GTACCT | GTACCT | GTATCT | GTACCT | GTACCT | GTACCT | GTATCT |
| 1447 | ATATTT | ATCTTT | ATCTTC | ATCTTC | ATCTTC | ATCTTC | ATCTTC | ATCTTC | ATCTTC |
| 1577 | AAATAT | AAATCT | AGATCT | AAATCT | AAATCT | AGATCT | AGATCT | AAATCT | AAATCT |
| 1585 | AAATAT | AAGTAT | AAGTAC | AAGTAC | AAGTAT | AAGTAC | AAGTAC | AAGTAC | AAGTAT |
| 2231 | ATATTT | ACATCA | ATATCA | ACATCA | ACATCA | ACATCT | ATATCT | ACATCT | ATATCT |
| 3054 | AAATAT | AAACAT | GAATAT | GAACAT | GAACAT | GAACAT | GAATAT | GAACAT | GAATAT |
| 3788 | ATATTT | ATATCT | ATATCT | ACATCT | ACATCT | ACATCT | ACATCT | ACATCT | ACATCT |
| AU Rich Sequence Elements (AREs) | | | | | | | | | |
| 2468 | ATTTTATT | ACTTCATC | ACTTCATC | ACTTCATT | ACTTCATT | ACTTTATT | ACTTTATC | ACTTTATT | ACTTTATC |
| 3790 | ATTTTTAA | ATCTTTAA | ATCTTCAA | ATCTTCAA | ATCTTCAA | ATCTTCAA | ATCTTCAA | ATCTTCAA | ATCTTCAA |
| Poly A/Poly T Sequences | | | | | | | | | |
| 3273 | AAAAAAA | GAAAAAA | GAAGAAG | GAAGAAG | GAAGAAG | GAAGAAG | CAAGAAG | GAAGAAG | CAAGAAG |
| 4195 | TTTTTT | TTCTTT | TTCTTC | TTCTTC | TTCTTC | TTCTTC | TTCTTC | TTCTTCC | TTCTTCC |

TABLE 3-continued

Summary of Changes to Repressive Elements

| Location of Element | Starting BDD FVIII Sequence (SEQ ID NO: 16) | Optimized BDD FVIII Sequence | | | | | | | |
|---|---|---|---|---|---|---|---|---|---|
| | | SEQ ID NO: 1 | SEQ ID NO: 2 | SEQ ID NO: 3 | SEQ ID NO: 4 | SEQ ID NO: 5 | SEQ ID NO: 6 | SEQ ID NO: 70 | SEQ ID NO: 71 |
| Splice Sites | | | | | | | | | |
| 2203 | GGTGAT | GGGGAC | GGCGAC | GGGGAC | GGGGAC | GGAGAC | GGAGAC | GGAGAC | GGAGAC |

D. Destabilizing Sequences

In some embodiments, the genetic cassette comprises a codon optimized nucleotide sequence encoding a FVIII polypeptide, wherein the codon optimized nucleotide sequence contains fewer destabilizing elements relative to SEQ ID NO: 16. In other embodiments, the codon optimized nucleotide sequence encoding a FVIII polypeptide contains at most 9, at most 8, at most 7, at most 6, or at most 5 destabilizing elements. In other embodiments, the codon optimized nucleotide sequence encoding a FVIII polypeptide contains at most 4, at most 3, at most 2, or at most 1 destabilizing elements. In yet other embodiments, the codon optimized nucleotide sequence encoding a FVIII polypeptide does not contain a destabilizing element.

In one particular embodiment, the codon optimized nucleotide sequence encoding a FVIII polypeptide comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the codon optimized nucleotide sequence contains fewer destabilizing elements relative to SEQ ID NO: 16. In other embodiments, the nucleotide sequence that encodes a polypeptide with FVIII activity contains at most 9, at most 8, at most 7, at most 6, or at most 5 destabilizing elements. In other embodiments, the codon optimized nucleotide sequence encoding a FVIII polypeptide contains at most 4, at most 3, at most 2, or at most 1 destabilizing elements. In yet other embodiments, the codon optimized nucleotide sequence encoding a FVIII polypeptide does not contain a destabilizing element.

In another embodiment, the codon optimized nucleotide sequence encoding a FVIII polypeptide comprises a first nucleic acid sequence encoding an N-terminal portion of a FVIII polypeptide and a second nucleic acid sequence encoding a C-terminal portion of a FVIII polypeptide; wherein the second nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 1792-4374 of SEQ ID NO: 5; (ii) nucleotides 1792-4374 of SEQ ID NO: 6; (iii) nucleotides 1792-2277 and 2320-4374 of SEQ ID NO: 5 (i.e., nucleotides 1792-4374 of SEQ ID NO: 5 without the nucleotides encoding the B domain or B domain fragment); or (iv) nucleotides 1792-2277 and 2320-4374 of SEQ ID NO: 6 (i.e., nucleotides 1792-4374 of SEQ ID NO: 6 without the nucleotides encoding the B domain or B domain fragment); wherein the N-terminal portion and the C-terminal portion together have a FVIII polypeptide activity; and wherein the codon optimized nucleotide sequence contains fewer destabilizing elements relative to SEQ ID NO: 16. In other embodiments, the nucleotide sequence that encodes a polypeptide with FVIII activity contains at most 9, at most 8, at most 7, at most 6, or at most 5 destabilizing elements. In other embodiments, the codon optimized nucleotide sequence encoding a FVIII polypeptide contains at most 4, at most 3, at most 2, or at most 1 destabilizing elements. In yet other embodiments, the codon optimized nucleotide sequence encoding a FVIII polypeptide does not contain a destabilizing element.

In other embodiments, the genetic cassette comprises a codon optimized nucleotide sequence encoding a FVIII polypeptide, wherein the codon optimized nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of an amino acid sequence selected from SEQ ID NOs: 1, 2, 3, 4, 5, 6, 70, and 71 or (ii) nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the codon optimized nucleotide sequence contains fewer destabilizing elements relative to SEQ ID NO: 16. In other embodiments, the codon optimized nucleotide sequence encoding a FVIII polypeptide contains at most 9, at most 8, at most 7, at most 6, or at most 5 destabilizing elements. In other embodiments, the codon optimized nucleotide sequence encoding a FVIII polypeptide contains at most 4, at most 3, at most 2, or at most 1 destabilizing elements. In yet other embodiments, the codon optimized nucleotide sequence encoding a FVIII polypeptide does not contain a destabilizing element.

There are ten destabilizing elements in the parental FVIII sequence (SEQ ID NO: 16): six ATTTA sequences (SEQ ID NO: 23) and four TAAAT sequences (SEQ ID NO: 24). In one embodiment, sequences of these sites were mutated to destroy the destabilizing elements in optimized FVIII SEQ ID NOs: 1-6, 70, and 71. The location of each of these elements, and the sequence of the corresponding nucleotides in the optimized sequences are shown in Table 3.

E. Potential Promoter Binding Sites

In some embodiments, the genetic cassette comprises a codon optimized nucleotide sequence encoding a FVIII polypeptide, wherein the nucleotide sequence contains fewer potential promoter binding sites relative to SEQ ID NO: 16. In other embodiments, the codon optimized nucleotide sequence encoding a FVIII polypeptide contains at most 9, at most 8, at most 7, at most 6, or at most 5 potential promoter binding sites. In other embodiments, the codon optimized nucleotide sequence encoding a FVIII polypeptide contains at most 4, at most 3, at most 2, or at most 1 potential promoter binding sites. In yet other embodiments, the codon optimized nucleotide sequence encoding a FVIII polypeptide does not contain a potential promoter binding site.

In one particular embodiment, the codon optimized nucleotide sequence encoding a FVIII polypeptide comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the codon optimized nucleotide sequence contains fewer potential promoter binding sites relative to SEQ ID NO: 16. In other embodiments, the codon optimized nucleotide sequence encoding a FVIII polypeptide contains at most 9, at most 8, at most 7, at most 6, or at most 5 potential promoter binding sites. In other embodiments, the codon optimized nucleotide sequence encoding a FVIII polypeptide contains at most 4, at most 3, at most 2, or at most 1 potential promoter binding sites. In yet other embodiments, the codon optimized nucleotide sequence encoding a FVIII polypeptide does not contain a potential promoter binding site.

In another embodiment, the codon optimized nucleotide sequence encoding a FVIII polypeptide comprises a first nucleic acid sequence encoding an N-terminal portion of a FVIII polypeptide and a second nucleic acid sequence encoding a C-terminal portion of a FVIII polypeptide; wherein the second nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 1792-4374 of SEQ ID NO: 5; (ii) nucleotides 1792-4374 of SEQ ID NO: 6; (iii) nucleotides 1792-2277 and 2320-4374 of SEQ ID NO: 5 (i.e., nucleotides 1792-4374 of SEQ ID NO: 5 without the nucleotides encoding the B domain or B domain fragment); or (iv) nucleotides 1792-2277 and 2320-4374 of SEQ ID NO: 6 (i.e., nucleotides 1792-4374 of SEQ ID NO: 6 without the nucleotides encoding the B domain or B domain fragment); wherein the N-terminal portion and the C-terminal portion together have a FVIII polypeptide activity; and wherein the codon optimized nucleotide sequence contains fewer potential promoter binding sites relative to SEQ ID NO: 16. In other embodiments, the codon optimized nucleotide sequence encoding a FVIII polypeptide contains at most 9, at most 8, at most 7, at most 6, or at most 5 potential promoter binding sites. In other embodiments, the codon optimized nucleotide sequence encoding a FVIII polypeptide contains at most 4, at most 3, at most 2, or at most 1 potential promoter binding sites. In yet other embodiments, the codon optimized nucleotide sequence encoding a FVIII polypeptide does not contain a potential promoter binding site.

In other embodiments, the genetic cassette comprises a codon optimized nucleotide sequence encoding a FVIII polypeptide, wherein the nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of an amino acid sequence selected from SEQ ID NOs: 1, 2, 3, 4, 5, 6, 70, and 71 or (ii) nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the codon optimized nucleotide sequence contains fewer potential promoter binding sites relative to SEQ ID NO: 16. In other embodiments, the codon optimized nucleotide sequence encoding a FVIII polypeptide contains at most 9, at most 8, at most 7, at most 6, or at most 5 potential promoter binding sites. In other embodiments, the codon optimized nucleotide sequence encoding a FVIII polypeptide contains at most 4, at most 3, at most 2, or at most 1 potential promoter binding sites. In yet other embodiments, the codon optimized nucleotide sequence encoding a FVIII polypeptide does not contain a potential promoter binding site.

TATA boxes are regulatory sequences often found in the promoter regions of eukaryotes. They serve as the binding site of TATA binding protein (TBP), a general transcription factor. TATA boxes usually comprise the sequence TATAA (SEQ ID NO: 28) or a close variant. TATA boxes within a coding sequence, however, can inhibit the translation of full-length protein. There are ten potential promoter binding sequences in the wild type BDD FVIII sequence (SEQ ID NO: 16): five TATAA sequences (SEQ ID NO: 28) and five TTATA sequences (SEQ ID NO: 29). In some embodiments, at least 1, at least 2, at least 3, or at least 4 of the promoter binding sites are abolished in the FVIII genes of the present disclosure. In some embodiments, at least 5 of the promoter binding sites are abolished in the FVIII genes of the present disclosure. In other embodiments, at least 6, at least 7, or at least 8 of the promoter binding sites are abolished in the FVIII genes of the present disclosure. In one embodiment, at least 9 of the promoter binging sites are abolished in the FVIII genes of the present disclosure. In one particular embodiment, all promoter binding sites are abolished in the FVIII genes of the present disclosure. The location of each potential promoter binding site and the sequence of the corresponding nucleotides in the optimized sequences are shown in Table 3.

F. Other Cis Acting Negative Regulatory Elements

In addition to the MAR/ARS sequences, destabilizing elements, and potential promoter sites described above, several additional potentially inhibitory sequences can be identified in the wild type BDD FVIII sequence (SEQ ID NO: 16). Two AU rich sequence elements (AREs) can be identified (ATTTTATT (SEQ ID NOs: 30); and ATTTTTAA (SEQ ID NO: 31), along with a poly-A site (AAAAAAA; SEQ ID NO: 26), a poly-T site (TTTTTT; SEQ ID NO: 25), and a splice site (GGTGAT; SEQ ID NO: 27) in the non-optimized BDD FVIII sequence. One or more of these elements can be removed from the optimized FVIII sequences. The location of each of these sites and the sequence of the corresponding nucleotides in the optimized sequences are shown in Table 3.

In certain embodiments, the codon optimized nucleotide sequence encoding a FVIII polypeptide comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the codon optimized nucleotide sequence does not contain one or more cis-acting negative regulatory elements, for example, a splice site, a poly-T sequence, a poly-A sequence, an ARE sequence, or any combinations thereof.

In another embodiment, the codon optimized nucleotide sequence encoding a FVIII polypeptide comprises a first nucleic acid sequence encoding an N-terminal portion of a FVIII polypeptide and a second nucleic acid sequence encoding a C-terminal portion of a FVIII polypeptide; wherein the second nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 1792-4374 of SEQ ID NO: 5; (ii) nucleotides 1792-4374 of SEQ ID NO: 6; (iii) nucleotides 1792-2277 and 2320-4374 of SEQ ID NO: 5 (i.e., nucleotides 1792-4374 of SEQ ID NO: 5 without the nucleotides encoding the B domain or B domain fragment); or (iv) nucleotides 1792-2277 and 2320-4374 of SEQ ID NO: 6 (i.e., nucleotides 1792-4374 of SEQ ID NO: 6 without the nucleotides encoding the B domain or B domain fragment); wherein the N-terminal portion and the C-terminal portion together have a FVIII polypeptide activity; and wherein the codon optimized nucleotide sequence does not contain one or more cis-acting negative regulatory elements, for example, a splice site, a poly-T sequence, a poly-A sequence, an ARE sequence, or any combinations thereof.

In other embodiments, the genetic cassette comprises a codon optimized nucleotide sequence encoding a FVIII polypeptide, wherein the nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of an amino acid sequence selected from SEQ ID NOs: 1, 2, 3, 4, 5, 6, 70, and 71 or (ii) nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the codon optimized nucleotide sequence does not contain one or more cis-acting negative regulatory elements, for example, a splice site, a poly-T sequence, a poly-A sequence, an ARE sequence, or any combinations thereof.

In some embodiments, the codon optimized nucleotide sequence encoding a FVIII polypeptide comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the codon optimized nucleotide sequence does not contain the splice site GGTGAT (SEQ ID NO: 27). In some embodiments, the codon optimized nucleotide sequence encoding a FVIII polypeptide comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the codon optimized nucleotide sequence does not contain a poly-T sequence (SEQ ID NO: 25). In some embodiments, the codon optimized nucleotide sequence encoding a FVIII polypeptide comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the codon optimized nucleotide sequence does not contain a poly-A sequence (SEQ ID NO: 26). In some embodiments, the codon optimized nucleotide sequence encoding a FVIII polypeptide comprises a first nucleic acid sequence encoding an N-terminal portion of a FVIII polypeptide and a second nucleic acid sequence encoding a C-terminal portion of a FVIII polypeptide; wherein the first nucleic acid sequence has at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-1791 of SEQ ID NO: 3; (ii) nucleotides 1-1791 of SEQ ID NO: 3; (iii) nucleotides 58-1791 of SEQ ID NO: 4; or (iv) nucleotides 1-1791 of SEQ ID NO: 4; wherein the N-terminal portion and the C-terminal portion together have a FVIII polypeptide activity; and wherein the codon optimized nucleotide sequence does not contain an ARE element (SEQ ID NO: 30 or SEQ ID NO: 31).

In some embodiments, the genetic cassette comprises a codon optimized nucleotide sequence encoding a FVIII polypeptide, wherein the codon optimized nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of an amino acid sequence selected from SEQ ID NOs: 1, 2, 3, 4, 5, 6, 70, and 71 or (ii) nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the codon optimized nucleotide sequence does not contain the splice site GGTGAT (SEQ ID NO: 27). In some embodiments, the genetic cassette comprises a codon optimized nucleotide sequence encoding a FVIII polypeptide, wherein the codon optimized nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of an amino acid sequence selected from SEQ ID NOs: 1, 2, 3, 4, 5, 6, 70, and 71 or (ii) nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the codon optimized nucleotide sequence does not contain a poly-T sequence (SEQ ID NO: 25). In some embodiments, the genetic cassette comprises a codon optimized nucleotide sequence encoding a FVIII polypeptide, wherein the codon optimized nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of an amino acid sequence selected from SEQ ID NOs: 1, 2, 3, 4, 5, 6, 70, and 71 or (ii) nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the codon optimized nucleotide sequence does not contain a poly-A sequence (SEQ ID NO: 26). In some embodiments, the genetic cassette comprises a codon optimized nucleotide sequence encoding a FVIII polypeptide, wherein the codon optimized nucleotide sequence comprises a nucleic acid sequence having at least about 80%, at least about 85%, at least about 89%, at least about 90%, at least about 91%, at least about 92%, at least about 93%, at least about 94%, at least about 95%, at least about 96%, at least about 97%, at least about 98%, or at least about 99% sequence identity to (i) nucleotides 58-4374 of an amino acid sequence selected from SEQ ID NOs: 1, 2, 3, 4, 5, 6, 70, and 71 or (ii) nucleotides 58-2277 and 2320-4374 of an amino acid sequence selected from SEQ ID NOs: 1, 2, 3, 4, 5, 6, 70, and 71 (i.e., nucleotides 58-4374 of SEQ ID NO: 1, 2, 3, 4, 5, 6, 70, or 71 without the nucleotides encoding the B domain or B domain fragment); and wherein the codon optimized nucleotide sequence does not contain an ARE element (SEQ ID NO: 30 or SEQ ID NO: 31).

In other embodiments, an optimized FVIII sequence of the disclosure does not comprise one or more of antiviral motifs, stem-loop structures, and repeat sequences.

In still other embodiments, the nucleotides surrounding the transcription start site are changed to a kozak consensus sequence (GCCGCCACC<u>ATG</u>C (SEQ ID NO: 32), wherein the underlined nucleotides are the start codon). In other embodiments, restriction sites can be added or removed to facilitate the cloning process.

b. FIX and Polynucleotide Sequences Encoding the FIX Protein

In some embodiments, the nucleic acid molecule comprises a first ITR, a second ITR, and a genetic cassette encoding a target sequence, wherein the target sequence encodes a therapeutic protein, wherein the therapeutic protein comprises a FIX polypeptide. In some embodiments, the FIX polypeptide comprises FIX or a variant or fragment thereof, wherein the FIX or the variant or fragment thereof has a FIX activity.

Human FIX is a serine protease that is an important component of the intrinsic pathway of the blood coagulation cascade. "Factor IX" or "FIX," as used herein, refers to a coagulation factor protein and species and sequence variants thereof, and includes, but is not limited to, the 461 single-chain amino acid sequence of human FIX precursor polypeptide ("prepro"), the 415 single-chain amino acid sequence of mature human FIX (SEQ ID NO: 125), and the R338L FIX (Padua) variant (SEQ ID NO: 126). FIX includes any form of FIX molecule with the typical characteristics of blood coagulation FIX. As used herein "Factor IX" and "FIX" are intended to encompass polypeptides that comprise the domains Gla (region containing γ-carboxyglutamic acid residues), EGF1 and EGF2 (regions containing sequences homologous to human epidermal growth factor), activation peptide ("AP," formed by residues R136-R180 of the mature FIX), and the C-terminal protease domain ("Pro"), or synonyms of these domains known in the art, or can be a truncated fragment or a sequence variant that retains at least a portion of the biological activity of the native protein. FIX or sequence variants have been cloned, as described in U.S. Pat. Nos. 4,770,999 and 7,700,734, and cDNA coding for human FIX has been isolated, characterized, and cloned into expression vectors (see, for example, Choo et al., Nature 299:178-180 (1982); Fair et al., Blood 64:194-204 (1984); and Kurachi et al., Proc. Natl. Acad. Sci., U.S.A. 79:6461-6464 (1982)). One particular variant of FIX, the R338L FIX (Padua) variant (SEQ ID NO: 2), characterized by Simioni et al, 2009, comprises a gain-of-function mutation, which correlates with a nearly 8-fold increase in the activity of the Padua variant relative to native FIX (Table 4). FIX variants can also include any FIX polypeptide having one or more conservative amino acid substitutions, which do not affect the FIX activity of the FIX polypeptide. In some embodiments, the FIX variant comprises rFIX-albumin fused by a cleavable linker, e.g., IDELVION®. See U.S. Pat. No. 7,939,632, incorporated herein by reference in its entirety.

TABLE 4

Example FIX Sequences

SEQ ID NO: 125 (mature FIX polypeptide)
```
  1: YNSGKLEEFV QGNLERECME EKCSFEEARE VFENTERTTE FWKQYVDGDQ CESNPCLNGG
 61: SCKDDINSYE CWCPFGFEGK NCELDVTCNI KNGRCEQFCK NSADNKVVCS CTEGYRLAEN
121: QKSCEPAVPF PCGRVSVSQT SKLTRAETVF PDVDYVNSTE AETILDNITQ STQSFNDFTR
181: VVGGEDAKPG QFPWQVVLNG KVDAFCGGSI VNEKWIVTAA HCVETGVKIT VVAGEHNIEE
241: TEHTEQKRNV IRIIPHHNYN AAINKYNHDI ALLELDEPLV LNSYVTPICI ADKEYTNIFL
301: KFGSGYVSGW GRVFHKGRSA LVLQYLRVPL VDRATCLRST KFTIYNNMFC AGFHEGGRDS
361: CQGDSGGPHV TEVEGTSFLT GIISWGEECA MKGKYGIYTK VSRYVNWIKE KTKLT
```

SEQ ID NO: 126 (mature Padua(R338L)FIX Polypeptide)
```
  1: YNSGKLEEFV QGNLERECME EKCSFEEARE VFENTERTTE FWKQYVDGDQ CESNPCLNGG
 61: SCKDDINSYE CWCPFGFEGK NCELDVTCNI KNGRCEQFCK NSADNKVVCS CTEGYRLAEN
121: QKSCEPAVPF PCGRVSVSQT SKLTRAETVF PDVDYVNSTE AETILDNITQ STQSFNDFTR
181: VVGGEDAKPG QFPWQVVLNG KVDAFCGGSI VNEKWIVTAA HCVETGVKIT VVAGEHNIEE
241: TEHTEQKRNV IRIIPHHNYN AAINKYNHDI ALLELDEPLV LNSYVTPICI ADKEYTNIFL
301: KFGSGYVSGW GRVFHKGRSA LVLQYLRVPL VDRATCLLST KFTIYNNMFC AGFHEGGRDS
361: CQGDSGGPHV TEVEGTSFLT GIISWGEECA MKGKYGIYTK VSRYVNWIKE KTKLT
```

SEQ ID NO: 127 (FIX Signal Polypeptide and Propeptide)
```
  1: MQRVNMIMAE SPGLITICLL GYLLSAECTV FLDHENANKI LNRPKR
```

SEQ ID NO: 160 (FIX-Linker-Albumin)
```
YNSGKLEEFV QGNLERECME EKCSFEEARE VFENTERTTE FWKQYVDGDQ   50
CESNPCLNGG SCKDDINSYE CWCPFGFEGK NCELDVTCNI KNGRCEQFCK  100
NSADNKVVCS CTEGYRLAEN QKSCEPAVPF PCGRVSVSQT SKLTRAETVF  150
PDVDYVNSTE AETILDNITQ STQSFNDFTR VVGGEDAKPG QFPWQVVLNG  200
KVDAFCGGSI VNEKWIVTAA HCVETGVKIT VVAGEHNIEE TEHTEQKRNV  250
IRIIPHHNYN AAINKYNHDI ALLELDEPLV LNSYVTPICI ADKEYTNIFL  300
KFGSGYVSGW GRVFHKGRSA LVLQYLRVPL VDRATCLRST KFTIYNNMFC  350
AGFHEGGRDS CQGDSGGPHV TEVEGTSFLT GIISWGEECA MKGKYGIYTK  400
VSRYVNWIKE KTKLTPVSQT SKLTRAETVF PDVDAHKSEV AHRFKDLGEE  450
NFKALVLIAF AQYLQQCPFE DHVKLVNEVT EFAKTCVADE SAENCDKSLH  500
TLFGDKLCTV ATLRETYGEM ADCCAKQEPE RNECFLQHKD DNPNLPRLVR  550
PEVDVMCTAF HDNEETFLKK YLYEIARRHP YFYAPELLFF AKRYKAAFTE  600
CCQAADKAAC LLPKLDELRD EGKASSAKQR LKCASLQKFG ERAFKAWAVA  650
RLSQRFPKAE FAEVSKLVTD LTKVHTECCH GDLLECADDR ADLAKYICEN  700
QDSISSKLKE CCEKPLLEKS HCIAEVENDE MPADLPSLAA DFVESKDVCK  750
NYAEAKDVFL GMFLYEYARR HPDYSVVLLL RLAKTYETTL EKCCAAADPH  800
ECYAKVFDEF KPLVEEPQNL IKQNCELFEQ LGEYKFQNAL LVRYTKKVPQ  850
VSTPTLVEVS RNLGKVGSKC CKHPEAKRMP CAEDYLSVVL NQLCVLHEKT  900
PVSDRVTKCC TESLVNRRPC FSALEVDETY VPKEFNAETF TFHADICTLS  950
EKERQIKKQT ALVELVKHKP KATKEQLKAV MDDFAAFVEK CCKADDKETC 1000
FAEEGKKLVA ASQAALGL                                   1018
```

SEQ ID NO: 161 (FIX)
```
YNSGKLEEFVQGNLERECMEEKCSFEEAREVFENTERTTEFWKQYVDGDQCESNPCLNGGSCKDDINSYE
CWCPFGFEGKNCELDVTCNIKNGRCEQFCKNSADNKVVCSCTEGYRLAENQKSCEPAVPFPCGRVSVSQT
SKLTRAETVFPDVDYVNSTEAETILDNITQSTQSFNDFTRVVGGEDAKPGQFPWQVVLNGKVDAFCGGSI
VNEKWIVTAAHCVETGVKITVVAGEHNIEETEHTEQKRNVIRIIPHHNYNAAINKYNHDIALLELDEPLV
LNSYVTPICIADKEYTNIFLKFGSGYVSGWGRVFHKGRSALVLQYLRVPLVDRATCLRSTKFTIYNNMFC
AGFHEGGRDSCQGDSGGPHVTEVEGTSFLTGIISWGEECAMKGKYGIYTKVSRYVNWIKEKTKLTPVSQT
SKLT
```

SEQ ID NO: 162 (Linker)
```
RAETVFPDV
```

SEQ ID NO: 163 (Albumin)
```
DAHKSEVAHRFKDLGEENFKALVLIAFAQYLQQCPFEDHVKLVNEVTEFAKTCVADESAENCDKSLHTLF
GDKLCTVATLRETYGEMADCCAKQEPERNECFLQHKDDNPNLPRLVRPEVDVMCTAFHDNEETFLKKYLY
EIARRHPYFYAPELLFFAKRYKAAFTECCQAADKAACLLPKLDELRDEGKASSAKQRLKCASLQKFGERA
FKAWAVARLSQRFPKAEFAEVSKLVTDLTKVHTECCHGDLLECADDRADLAKYICENQDSISSKLKECCE
KPLLEKSHCIAEVENDEMPADLPSLAADFVESKDVCKNYAEAKDVFLGMFLYEYARRHPDYSVVLLLRLA
KTYETTLEKCCAAADPHECYAKVFDEFKPLVEEPQNLIKQNCELFEQLGEYKFQNALLVRYTKKVPQVST
PTLVEVSRNLGKVGSKCCKHPEAKRMPCAEDYLSVVLNQLCVLHEKTPVSDRVTKCCTESLVNRRPCFSA
LEVDETYVPKEFNAETFTFHADICTLSEKERQIKKQTALVELVKHKPKATKEQLKAVMDDFAAFVEKCCK
ADDKETCFAEEGKKLVAASQAALGL
```

TABLE 4-continued

Example FIX Sequences

SEQ ID NO: 164 (FIX(XTEN)-Fc)*
MQRVNMIMAESPGLITICLLGYLLSAECTVFLDHENANKILNRPKRYNSGLKEEFVQGNLERECMEEKCS
FEEAREVFENTERTTEFWKQYVDGDQCESNPCLNGGSCKDDINSYECWCPFGFEGKNCELDVTCNIKNGR
CEQFCKNSADNKVVCSCTEGYRLAENQKSCEPAVPFPCGRVSVSQTSKLTRAETVFPDVDYVNSTEAETI
LDGPSPGSPTSEEGTSESATPESGPGSEPATSGSETPGTSESATPESGPGTSTEPSEGSAPGTSTEPSE
GSAPGASSNITQSTQSFNDFTRVVGGEDAKPGQFPWQVVLNGKVDAFCGGSIVNEKWIVTAAHCVETGVK
ITVVAGEHNIEETEHTEQKRNVIRIIPHHNYNAAINKYNHDIALLELDEPLVLNSYVTPICIADKEYTNI
FLKFGSGYVSGWGRVFHKGRSALVLQYLRVPLVDRATCLLSTKFTIYNNMFCAGFHEGGRDSCQGDSGGP
HVTEVEGTSFLTGIISWGEECAMKGKYGIYTKVSRYVNWIKEKTKLTDKTHTCPPCPAPELLGGPSVFLF
PPKPKDTLMISRTPEVTCVVVDVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHYTQKSLSLSPG

SEQ ID NO: 165 (FIX-FXIa-AE288)*
YNSGKLEEFVQGNLERECMEEKCSFEEAREVFENTERTTEFWKQYVDGDQCESNPCLNGGSCKDDINSYE
CWCPFGFEGKNCELDVTCNIKNGRCEQFCKNSADNKVVCSCTEGYRLAENQKSCEPAVPFPCGRVSVSQT
SKLTRAETVFPDVDYVNSTEAETILDNITQSTQSFNDFTRVVGGEDAKPGQFPWQVVLNGKVDAFCGGSI
VNEKWIVTAAHCVETGVKITVVAGEHNIEETEHTEQKRNVIRIIPHHNYNAAINKYNHDIALLELDEPLV
LNSYVTPICIADKEYTNIFLKFGSGYVSGWGRVFHKGRSALVLQYLRVPLVDRATCLRSTKFTIYNNMFC
AGFHEGGRDSCQGDSGGPHVTEVEGTSFLTGIISWGEECAMKGKYGIYTKVSRYVNWIKEKTKLTGKLTR
AETGGTSESATPESGPGSEPATSGSETPGTSESATPESGPGSEPATSGSETPGTSESATPESGPGTSTEP
SEGSAPGSPAGSPTSTEEGTSESATPESGPGSEPATSGSETPGTSESATPESGPGSPAGSPTSTEEGSPA
GSPTSTEEGTSTEPSEGSAPGTSESATPESGPGTSESATPESGPGTSESATPESGPGSEPATSGSETPGS
EPATSGSETPGSPAGSPTSTEEGTSTEPSEGSAPGTSTEPSEGSAPGSEPATSGSETPGTSESATPESGP
GTSTEPSEGSAP

SEQ ID NO: 166 (FIX-Fc-Fc)**
MQRVNMIMAESPGLITICLLGYLLSAECTVELDHENANKILNRPKRYNSGKLEEFVQGNLERECMEEKCS
FEEAREVFENTERTTEFWKQYVDGDQCESNPCLNGGSCKDDINSYECWCPEGFEGKNCELDVTCNIKNGR
CEQFCKNSADNKVVCSCTEGYRLAENQKSCEPAVPFPCGRVSVSQTSKLTRAETVFPDVDYVNSTEAETI
LDNITQSTQSENDFTRVVGGEDAKPGQFPWQVVLNGKVDAFCGGSIVNEKWIVTAAHCVETGVKITVVAG
EHNIEETEHTEQKRNVIRIIPHHNYNAAINKYNHDIALLELDEPLVLNSYVTPICIADKEYTNIFLKEGS
GYVSGWGRVEHKGRSALVLQYLRVPLVDRATCLRSTKFTIYNNMECAGEHEGGRDSCQGDSGGPHVTEVE
GTSFLTGIISWGEECAMKGKYGIYTKVSRYVNWIKEKTKLTDKTHTCPPCPAPELLGGPSVFLEPPKPKD
TLMISRTPEVTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPSDIAVEWESNGQPEN
NYKTTPPVLDSDGSFELYSKLTVDKSRWQQGNVESCSVMHEALHNHYTQKSLSLSPGKRRRRSGGGGSGG
GGSGGGGSGGGGSRRRRDKTHTCPPCPAPELLGGPSVFLEPPKPKDTLMISRTPEVTCVVVDVSHEDPEV
KFNWYVDGVEVHNAKTKPREEQYNSTYRVVSVLTVLHQDWLNGKEYKCKVSNKALPAPIEKTISKAKGQP
REPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPGK

*Grey shading = signal peptide; underline = XTEN sequence; bold = Fc.
**SEQ ID NO: 67 of U.S. Pat. No. 9,856,468, which is incorporated by reference herein
in its entirety.

The FIX polypeptide is 55 kDa, synthesized as a prepropolypetide chain (SEQ ID NO: 125) composed of three regions: a signal peptide of 28 amino acids (amino acids 1 to 28 of SEQ ID NO: 127), a propeptide of 18 amino acids (amino acids 29 to 46), which is required for gamma-carboxylation of glutamic acid residues, and a mature Factor IX of 415 amino acids (SEQ ID NO: 125 or 126). The propeptide is an 18-amino acid residue sequence N-terminal to the gamma-carboxyglutamate domain. The propeptide binds vitamin K-dependent gamma carboxylase and then is cleaved from the precursor polypeptide of FIX by an endogenous protease, most likely PACE (paired basic amino acid cleaving enzyme), also known as furin or PCSK3. Without the gamma carboxylation, the Gla domain is unable to bind calcium to assume the correct conformation necessary to anchor the protein to negatively charged phospholipid surfaces, thereby rendering Factor IX nonfunctional. Even if it is carboxylated, the Gla domain also depends on cleavage of the propeptide for proper function, since retained propeptide interferes with conformational changes of the Gla domain necessary for optimal binding to calcium and phospholipid. In humans, the resulting mature Factor IX is secreted by liver cells into the blood stream as an inactive zymogen, a single chain protein of 415 amino acid residues that contains approximately 17% carbohydrate by weight (Schmidt, A. E., et al. (2003) Trends Cardiovasc Med, 13: 39).

The mature FIX is composed of several domains that in an N- to C-terminus configuration are: a GLA domain, an EGF1 domain, an EGF2 domain, an activation peptide (AP) domain, and a protease (or catalytic) domain. A short linker connects the EGF2 domain with the AP domain. FIX contains two activation peptides formed by R145-A146 and R180-V181, respectively. Following activation, the single-chain FIX becomes a 2-chain molecule, in which the two chains are linked by a disulfide bond. Clotting factors can be engineered by replacing their activation peptides resulting in altered activation specificity. In mammals, mature FIX must be activated by activated Factor XI to yield Factor IXa. The protease domain provides, upon activation of FIX to FIXa, the catalytic activity of FIX. Activated Factor VIII (FVIIIa) is the specific cofactor for the full expression of FIXa activity.

In certain embodiments, a FIX polypeptide comprises an Thr148 allelic form of plasma derived FIX and has structural and functional characteristics similar to endogenous FIX.

Many functional FIX variants are known in the art. International publication number WO 02/040544 A3 discloses mutants that exhibit increased resistance to inhibition by heparin at page 4, lines 9-30 and page 15, lines 6-31. International publication number WO 03/020764 A2 discloses FIX mutants with reduced T cell immunogenicity in Tables 2 and 3 (on pages 14-24), and at page 12, lines 1-27. International publication number WO 2007/149406 A2 discloses functional mutant FIX molecules that exhibit increased protein stability, increased in vivo and in vitro half-life, and increased resistance to proteases at page 4, line 1 to page 19, line 11. WO 2007/149406 A2 also discloses chimeric and other variant FIX molecules at page 19, line 12 to page 20, line 9. International publication number WO 08/118507 A2 discloses FIX mutants that exhibit increased clotting activity at page 5, line 14 to page 6, line 5. International publication number WO 09/051717 A2 discloses FIX mutants having an increased number of N-linked and/or O-linked glycosylation sites, which results in an increased half-life and/or recovery at page 9, line 11 to page 20, line 2. International publication number WO 09/137254 A2 also discloses Factor IX mutants with increased numbers of glycosylation sites at page 2, paragraph [006] to page 5, paragraph [011] and page 16, paragraph [044] to page 24, paragraph [057]. International publication number WO 09/130198 A2 discloses functional mutant FIX molecules that have an increased number of glycosylation sites, which result in an increased half-life, at page 4, line 26 to page 12, line 6. International publication number WO 09/140015 A2 discloses functional FIX mutants that an increased number of Cys residues, which can be used for polymer (e.g., PEG) conjugation, at page 11, paragraph [0043] to page 13, paragraph [0053]. The FIX polypeptides described in International Application No. PCT/US2011/043569 filed Jul. 11, 2011 and published as WO 2012/006624 on Jan. 12, 2012 are also incorporated herein by reference in its entirety. In some embodiments, the FIX polypeptide comprises a FIX polypeptide fused to an albumin, e.g., FIX-albumin. In certain embodiments, the FIX polypeptide is IDELVION® or rIX-FP.

In addition, hundreds of non-functional mutations in FIX have been identified in hemophilia subjects, many of which are disclosed in Table 6, at pages 11-14 of International publication number WO 09/137254 A2. Such non-functional mutations are not included in the invention, but provide additional guidance for which mutations are more or less likely to result in a functional FIX polypeptide.

In one embodiment, the FIX polypeptide (or Factor IX portion of a fusion polypeptide) comprises an amino acid sequence at least 70%, at least 80%, at least 85%, at least 90%, at least 95%, at least 96%, at least 97%, at least 98%, at least 99%, or 100% identical to the sequence set forth in SEQ ID NO: 1 or 2 (amino acids 1 to 415 of SEQ ID NO: 125 or 126), or alternatively, with a propeptide sequence, or with a propeptide and signal sequence (full length FIX). In another embodiment, the FIX polypeptide comprises an amino acid sequence at least 70%, at least 80%, at least 85%, at least 90%, at least 95%, at least 96%, at least 97%, at least 98%, at least 99%, or 100% identical to the sequence set forth in SEQ ID NO: 2.

FIX coagulant activity is expressed as International Unit(s) (IU). One IU of FIX activity corresponds approximately to the quantity of FIX in one milliliter of normal human plasma. Several assays are available for measuring FIX activity, including the one stage clotting assay (activated partial thromboplastin time; aPTT), thrombin generation time (TGA) and rotational thromboelastometry (ROTEM®). The invention contemplates sequences that have homology to FIX sequences, sequence fragments that are natural, such as from humans, non-human primates, mammals (including domestic animals), and non-natural sequence variants which retain at least a portion of the biologic activity or biological function of FIX and/or that are useful for preventing, treating, mediating, or ameliorating a coagulation factor-related disease, deficiency, disorder or condition (e.g., bleeding episodes related to trauma, surgery, of deficiency of a coagulation factor). Sequences with homology to human FIX can be found by standard homology searching techniques, such as NCBI BLAST.

In certain embodiments, the FIX sequence is codon-optimized. Examples of codon-optimized FIX sequences include, but are not limited to, SEQ ID NOs: 1 and 54-58 of International Publication No. WO 2016/004113 A1, which is incorporated by reference herein in its entirety.

c. FVII and Polynucleotide Sequences Encoding the FVII Protein

In some embodiments, the nucleic acid molecule comprises a first ITR, a second ITR, and a genetic cassette encoding a target sequence, wherein the target sequence encodes a therapeutic protein, wherein the therapeutic protein comprises a Factor VII polypeptide. In some embodiments, the FVII polypeptide comprises FVII or a variant or fragment thereof, wherein the variant or fragment thereof has a FVII activity.

"Factor VII" ("FVII," or "F7;" also referred to as Factor 7, coagulation factor VII, serum factor VII, serum prothrombin conversion accelerator, SPCA, proconvertin and eptacog alpha) is a serine protease that is part of the coagulation cascade. In one embodiment, the clotting factor in the nucleic acid described herein is FVII. Recombinant activated Factor VII ("FVII") has become widely used for the treatment of major bleeding, such as that which occurs in patients having hemophilia A or B, deficiency of coagulation Factor XI, FVII, defective platelet function, thrombocytopenia, or von Willebrand's disease.

Recombinant activated FVII (rFVIIa; NOVOSEVEN®) is used to treat bleeding episodes in (i) hemophilia patients with neutralizing antibodies against FVIII or FIX (inhibitors), (ii) patients with FVII deficiency, or (iii) patients with hemophilia A or B with inhibitors undergoing surgical procedures. However, NOVOSEVEN® displays poor efficacy. Repeated doses of FVIIa at high concentration are often required to control a bleed, due to its low affinity for activated platelets, short half-life, and poor enzymatic activity in the absence of tissue factor. Accordingly, there is an unmet medical need for better treatment and prevention options for hemophilia patients with FVIII and FIX inhibitors and/or with FVII deficiency.

In one embodiment, the genetic cassette encodes a mature form of FVII or a variant thereof. FVII includes a Gla domain, two EGF domains (EGF-1 and EGF-2), and a serine protease domain (or peptidase S1 domain) that is highly conserved among all members of the peptidase S1 family of serine proteases, such as for example with chymotrypsin. FVII occurs as a single chain zymogen (i.e., activatable FVII) and a fully activated two-chain form.

C. Growth Factors

In some embodiments, the nucleic acid molecule comprises a first ITR, a second ITR, and a genetic cassette encoding a target sequence, wherein the target sequence encodes a therapeutic protein, and wherein the therapeutic protein comprises a growth factor. The growth factor can be selected from any growth factor known in the art. In some embodiments, the growth factor is a hormone. In other embodiments, the growth factor is a cytokine. In some embodiments, the growth factor is a chemokine.

In some embodiments, the growth factor is adrenomedullin (AM). In some embodiments, the growth factor is angiopoietin (Ang). In some embodiments, the growth factor is autocrine motility factor. In some embodiments, the growth factor is a Bone morphogenetic protein (BMP). In some embodiments, the BMP is selects from BMP2, BMP4, BMP5, and BMP7. In some embodiments, the growth factor is a ciliary neurotrophic factor family member. In some embodiments, the ciliary neurotrophic factor family member is selected from ciliary neurotrophic factor (CNTF), leukemia inhibitory factor (LIF), interleukin-6 (IL-6). In some embodiments, the growth factor is a colony-stimulating factor. In some embodiments, the colony-stimulating factor is selected from macrophage colony-stimulating factor (m-CSF), granulocyte colony-stimulating factor (G-CSF), and granulocyte macrophage colony-stimulating factor (GM-CSF). In some embodiments, the growth factor is an epidermal growth factor (EGF). In some embodiments, the growth factor is an ephrin. In some embodiments, the ephrin is selected from ephrin A1, ephrin A2, ephrin A3, ephrin A4, ephrin A5, ephrin B1, ephrin B2, and ephrin B3. In some embodiments, the growth factor is erythropoietin (EPO). In some embodiments, the growth factor is a fibroblast growth factor (FGF). In some embodiments, the FGF is selected from FGF1, FGF2, FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22, and FGF23. In some embodiments, the growth factor is foetal bovine somatotrophin (FBS). In some embodiments, the growth factor is a GDNF family member. In some embodiments, the GDNF family member is selected from glial cell line-derived neurotrophic factor (GDNF), neurturin, persephin, and artemin. In some embodiments, the growth factor is growth differentiation factor-9 (GDF9). In some embodiments, the growth factor is hepatocyte growth factor (HGF). In some embodiments, the growth factor is hepatoma-derived growth factor (HDGF). In some embodiments, the growth factor is insulin. In some embodiments, the growth factor is an insulin-like growth factor. In some embodiments, the insulin-like growth factor is insulin-like growth factor-1 (IGF-1) or IGF-2. In some embodiments, the growth factor is an interleukin (IL). In some embodiments, the IL is selected from IL-1, IL-2, IL-3, IL-4, IL-5, IL-6, and IL-7. In some embodiments, the growth factor is keratinocyte growth factor (KGF). In some embodiments, the growth factor is migration-stimulating factor (MSF). In some embodiments, the growth factor is macrophage-stimulating protein (MSP or hepatocyte growth factor-like protein (HGFLP)). In some embodiments, the growth factor is myostatin (GDF-8). In some embodiments, the growth factor is a neuregulin. In some embodiments, the neuregulin is selected from neuregulin 1 (NRG1), NRG2, NRG3, and NRG4. In some embodiments, the growth factor is a neurotrophin. In some embodiments, the growth factor is brain-derived neurotrophic factor (BDNF). In some embodiments, the growth factor is nerve growth factor (NGF). In some embodiments, the NGF is neurotrophin-3 (NT-3) or NT-4. In some embodiments, the growth factor is placental growth factor (PGF). In some embodiments, the growth factor is platelet-derived growth factor (PDGF). In some embodiments, the growth factor is renalase (RNLS). In some embodiments, the growth factor is T-cell growth factor (TCGF). In some embodiments, the growth factor is thrombopoietin (TPO). In some embodiments, the growth factor is a transforming growth factor. In some embodiments, the transforming growth factor is transforming growth factor alpha (TGF-α) or TGF-β. In some embodiments, the growth factor is tumor necrosis factor-alpha (TNF-α). In some embodiments, the growth factor is vascular endothelial growth factor (VEGF).

D. Micro RNAs (miRNAs)

MicroRNAs (miRNAs) are small non-coding RNA molecules (about 18-22 nucleotides) that negatively regulate gene expression by inhibiting translation or inducing messenger RNA (mRNA) degradation. Since their discovery, miRNAs have been implicated in various cellular processes including apoptosis, differentiation and cell proliferation and they have shown to play a key role in carcinogenesis. The ability of miRNAs to regulate gene expression makes expression of miRNAs in vivo a valuable tool in gene therapy.

Certain aspects of the present disclosure are directed to plasmid-like nucleic acid molecules comprising a first ITR, a second ITR, and a genetic cassette encoding a target sequence, wherein the target sequence encodes a miRNA, and wherein the first ITR and/or the second ITR are an ITR of a non-adeno-associated virus (e.g., the first ITR and/or the second ITR are from a non-AAV). The miRNA can be any miRNA known in the art. In some embodiments, the miRNA down regulates the expression of a target gene. In certain embodiments, the target gene is selected from SOD1, HTT, RHO, or any combination thereof.

In some embodiments, the genetic cassette encodes one miRNA. In some embodiments, the genetic cassette encodes more than one miRNA. In some embodiments, the genetic cassette encodes two or more different miRNAs. In some embodiments, the genetic cassette encodes two or more copies of the same miRNA. In some embodiments, the genetic cassette encodes two or more variants of the same therapeutic protein. In certain embodiments, the genetic cassette encodes one or more miRNA and one or more therapeutic protein.

In some embodiments, the miRNA is a naturally occurring miRNA. In some embodiments, the miRNA is an engineered miRNA. In some embodiments, the miRNA is an artificial miRNA. In certain embodiments, the miRNA comprises the miHTT engineered miRNA disclosed by Evers et al., *Molecular Therapy* 26(9):1-15 (epub ahead of print June 2018). In certain embodiments, the miRNA comprises the miR SOD1 artificial miRNA disclosed by Dirren et al., *Annals of Clinical and Translational Neurology* 2(2):167-84 (February 2015). In certain embodiments, the miRNA comprises miR-708, which targets RHO (see Behrman et al., *JCB* 192(6):919-27 (2011).

In some embodiments, the miRNA upregulates expression of a gene by down regulating the expression of an inhibitor of the gene. In some embodiments, the inhibitor is a natural, e.g., wild-type, inhibitor. In some embodiments, the inhibitor results from a mutated, heterologous, and/or misexpressed gene.

E. Heterologous Moieties

In some embodiments, the nucleic acid molecule comprises a first ITR, a second ITR, and a genetic cassette encoding a target sequence, wherein the target sequence encodes a therapeutic protein, and wherein the therapeutic protein comprises at least one heterologous moiety. In some embodiments, the heterologous moiety is fused to the N-terminus or C-terminus of the therapeutic protein. In other embodiments, the heterologous moiety is inserted between two amino acids within the therapeutic protein.

In some embodiments, the therapeutic protein comprises a FVIII polypeptide and a heterologous moiety, which is inserted between two amino acids within the FVIII polypeptide. In some embodiments, the heterologous moiety is inserted within the FVIII polypeptide at one or more insertion site selected from Table 5. In some embodiments, the heterologous amino acid sequence can be inserted within the clotting factor polypeptide encoded by the nucleic acid molecule of the disclosure at any site disclosed in International Publication No. WO 2013/123457 A1, WO 2015/106052 A1 or U.S. Publication No. 2015/0158929 A1, which are herein incorporated by reference in their entirety. In one particular embodiment, the therapeutic protein comprises a FVIII and a heterologous moiety, wherein the heterologous moiety is inserted within the FVIII immediately downstream of amino acid 745 relative to mature FVIII. In one particular embodiment, the therapeutic protein comprises a FVIII and an XTEN wherein the XTEN is inserted within the FVIII immediately downstream of amino acid 745 relative to mature FVIII. In one particular embodiment, the FVIII comprises a deletion of amino acids 746-1646, corresponding to mature human FVIII (SEQ ID NO:15), and the heterologous moiety is inserted immediately downstream of amino acid 745, corresponding to mature human FVIII (SEQ ID NO:15).

TABLE 5

FVIII Heterologous Moiety Insertion Sites

| Insertion Site | Domain |
|---|---|
| 3 | A1 |
| 18 | A1 |
| 22 | A1 |
| 26 | A1 |
| 40 | A1 |
| 60 | A1 |
| 65 | A1 |
| 81 | A1 |
| 116 | A1 |
| 119 | A1 |
| 130 | A1 |
| 188 | A1 |
| 211 | A1 |
| 216 | A1 |
| 220 | A1 |
| 224 | A1 |
| 230 | A1 |
| 333 | A1 |
| 336 | A1 |
| 339 | A1 |
| 375 | A2 |
| 378 | A2 |
| 399 | A2 |
| 403 | A2 |
| 409 | A2 |
| 416 | A2 |
| 442 | A2 |
| 487 | A2 |
| 490 | A2 |
| 494 | A2 |
| 500 | A2 |
| 518 | A2 |
| 599 | A2 |
| 603 | A2 |
| 713 | A2 |
| 745 | B |
| 1656 | a3 region |
| 1711 | A3 |
| 1720 | A3 |
| 1725 | A3 |
| 1749 | A3 |
| 1796 | A3 |
| 1802 | A3 |
| 1827 | A3 |
| 1861 | A3 |
| 1896 | A3 |
| 1900 | A3 |
| 1904 | A3 |
| 1905 | A3 |
| 1910 | A3 |
| 1937 | A3 |
| 2019 | A3 |

TABLE 5-continued

FVIII Heterologous Moiety Insertion Sites

| Insertion Site | Domain |
|---|---|
| 2068 | C1 |
| 2111 | C1 |
| 2120 | C1 |
| 2171 | C2 |
| 2188 | C2 |
| 2227 | C2 |
| 2332 | CT |

In some embodiments, the therapeutic protein comprises a FIX polypeptide and a heterologous moiety, which is inserted between two amino acids within the FIX polypeptide. In some embodiments, the heterologous moiety is inserted within the FIX polypeptide at one or more insertion site selected from Table 5. In some embodiments, the heterologous amino acid sequence can be inserted within the clotting factor polypeptide encoded by the nucleic acid molecule of the disclosure at any site disclosed in International Application No. PCT/US2017/015879, which is herein incorporated by reference in their entirety. In one particular embodiment, the therapeutic protein comprises a FIX polypeptide and a heterologous moiety, wherein the heterologous moiety is inserted within the FIX polypeptide immediately downstream of amino acid 166 relative to mature FIX. In one particular embodiment, the therapeutic protein comprises a FIX polypeptide and an XTEN, wherein the XTEN is inserted within the FIX immediately downstream of amino acid 166 relative to mature FVIII.

TABLE 6

FIX Heterologous Moiety Insertion Sites

| Insertion Site | Domain |
|---|---|
| 52 | EGF1 |
| 59 | EGF1 |
| 66 | EGF1 |
| 80 | EGF1 |
| 85 | EGF2 |
| 89 | EGF2 |
| 103 | EGF2 |
| 105 | EGF2 |
| 113 | EGF2 |
| 129 | Linker |
| 142 | Linker |
| 149 | AP |
| 162 | AP |
| 166 | AP |
| 174 | AP |
| 188 | Catalytic |
| 202 | Catalytic |
| 224 | Catalytic |
| 226 | Catalytic |
| 228 | Catalytic |
| 230 | Catalytic |
| 240 | Catalytic |
| 257 | Catalytic |
| 265 | Catalytic |
| 277 | Catalytic |
| 283 | Catalytic |
| 292 | Catalytic |
| 316 | Catalytic |
| 341 | Catalytic |
| 354 | Catalytic |
| 392 | Catalytic |
| 403 | Catalytic |
| 413 | Catalytic |

In other embodiments, the therapeutic proteins of the disclosure further comprise two, three, four, five, six, seven, or eight heterologous nucleotide sequences. In some embodiments, all the heterologous moieties are identical. In some embodiments, at least one heterologous moiety is different from the other heterologous moieties. In some embodiments, the disclosure can comprise two, three, four, five, six, or more than seven heterologous moieties in tandem.

In some embodiments, the heterologous moiety increases the half-life (is a "half-life extender") of the therapeutic protein.

In some embodiments, the heterologous moiety is a peptide or a polypeptide with either unstructured or structured characteristics that are associated with the prolongation of in vivo half-life when incorporated in a protein of the disclosure. Non-limiting examples include albumin, albumin fragments, Fc fragments of immunoglobulins, the C-terminal peptide (CTP) of the β subunit of human chorionic gonadotropin, a HAP sequence, an XTEN sequence, a transferrin or a fragment thereof, a PAS polypeptide, polyglycine linkers, polyserine linkers, albumin-binding moieties, or any fragments, derivatives, variants, or combinations of these polypeptides. In one particular embodiment, the heterologous amino acid sequence is an immunoglobulin constant region or a portion thereof, transferrin, albumin, or a PAS sequence. In some aspects, a heterologous moiety includes von Willebrand factor or a fragment thereof. In other related aspects a heterologous moiety can include an attachment site (e.g., a cysteine amino acid) for a non-polypeptide moiety such as polyethylene glycol (PEG), hydroxyethyl starch (HES), polysialic acid, or any derivatives, variants, or combinations of these elements. In some aspects, a heterologous moiety comprises a cysteine amino acid that functions as an attachment site for a non-polypeptide moiety such as polyethylene glycol (PEG), hydroxyethyl starch (HES), polysialic acid, or any derivatives, variants, or combinations of these elements.

In one specific embodiment, a first heterologous moiety is a half-life extending molecule which is known in the art, and a second heterologous moiety is a half-life extending molecule which is known in the art. In certain embodiments, the first heterologous moiety (e.g., a first Fc moiety) and the second heterologous moiety (e.g., a second Fc moiety) are associated with each other to form a dimer. In one embodiment, the second heterologous moiety is a second Fc moiety, wherein the second Fc moiety is linked to or associated with the first heterologous moiety, e.g., the first Fc moiety. For example, the second heterologous moiety (e.g., the second Fc moiety) can be linked to the first heterologous moiety (e.g., the first Fc moiety) by a linker or associated with the first heterologous moiety by a covalent or non-covalent bond.

In some embodiments, the heterologous moiety is a polypeptide comprising, consisting essentially of, or consisting of at least about 10, at least about 100, at least about 200, at least about 300, at least about 400, at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, at least about 2500, at least about 3000, or at least about 4000 amino acids. In other embodiments, the heterologous moiety is a polypeptide comprising, consisting essentially of, or consisting of about 100 to about 200 amino acids, about 200 to about 300 amino acids, about 300 to about 400 amino acids, about 400 to about 500 amino acids, about 500 to about 600 amino acids, about 600 to about 700 amino acids, about 700 to about 800 amino acids, about 800 to about 900 amino acids, or about 900 to about 1000 amino acids.

In certain embodiments, a heterologous moiety improves one or more pharmacokinetic properties of the therapeutic protein without significantly affecting its biological activity or function.

In certain embodiments, a heterologous moiety increases the in vivo and/or in vitro half-life of the therapeutic protein of the disclosure. In other embodiments, a heterologous moiety facilitates visualization or localization of the therapeutic protein of the disclosure or a fragment thereof (e.g., a fragment comprising a heterologous moiety after proteolytic cleavage of the FVIII protein). Visualization and/or location of the therapeutic protein of the disclosure or a fragment thereof can be in vivo, in vitro, ex vivo, or combinations thereof.

In other embodiments, a heterologous moiety increases stability of the therapeutic protein of the disclosure or a fragment thereof (e.g., a fragment comprising a heterologous moiety after proteolytic cleavage of the therapeutic protein, e.g., a clotting factor). As used herein, the term "stability" refers to an art-recognized measure of the maintenance of one or more physical properties of the therapeutic protein in response to an environmental condition (e.g., an elevated or lowered temperature). In certain aspects, the physical property can be the maintenance of the covalent structure of the therapeutic protein (e.g., the absence of proteolytic cleavage, unwanted oxidation or deamidation). In other aspects, the physical property can also be the presence of the therapeutic protein in a properly folded state (e.g., the absence of soluble or insoluble aggregates or precipitates). In one aspect, the stability of the therapeutic protein is measured by assaying a biophysical property of the therapeutic protein, for example thermal stability, pH unfolding profile, stable removal of glycosylation, solubility, biochemical function (e.g., ability to bind to a protein, receptor or ligand), etc., and/or combinations thereof. In another aspect, biochemical function is demonstrated by the binding affinity of the interaction. In one aspect, a measure of protein stability is thermal stability, i.e., resistance to thermal challenge. Stability can be measured using methods known in the art, such as, HPLC (high performance liquid chromatography), SEC (size exclusion chromatography), DLS (dynamic light scattering), etc. Methods to measure thermal stability include, but are not limited to differential scanning calorimetry (DSC), differential scanning fluorimetry (DSF), circular dichroism (CD), and thermal challenge assay.

In certain aspects, a therapeutic protein encoded by the nucleic acid molecule of the disclosure comprises at least one half-life extender, i.e., a heterologous moiety which increases the in vivo half-life of the therapeutic protein with respect to the in vivo half-life of the corresponding therapeutic protein lacking such heterologous moiety. In vivo half-life of a therapeutic protein can be determined by any methods known to those of skill in the art, e.g., activity assays (e.g., chromogenic assay or one stage clotting aPTT assay wherein the therapeutic protein comprises a FVIII polypeptide), ELISA, ROTEM®, etc.

In some embodiments, the presence of one or more half-life extenders results in the half-life of the therapeutic protein to be increased compared to the half-life of the corresponding protein lacking such one or more half-life extenders. The half-life of the therapeutic protein comprising a half-life extender is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the in vivo half-life of the corresponding therapeutic protein lacking such half-life extender.

In one embodiment, the half-life of the therapeutic protein comprising a half-life extender is about 1.5-fold to about 20-fold, about 1.5-fold to about 15-fold, or about 1.5-fold to about 10-fold longer than the in vivo half-life of the corresponding protein lacking such half-life extender. In another embodiment, the half-life of therapeutic protein comprising a half-life extender is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to the in vivo half-life of the corresponding protein lacking such half-life extender.

In other embodiments, the half-life of the therapeutic protein comprising a half-life extender is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours.

In still other embodiments, the half-life of the therapeutic protein comprising a half-life extender is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life per subject of the therapeutic protein comprising a half-life extender is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days.

One or more half-life extenders can be fused to C-terminus or N-terminus of therapeutic protein or inserted within therapeutic protein.

1. An Immunoglobulin Constant Region or a Portion Thereof

In another aspect, a heterologous moiety comprises one or more immunoglobulin constant regions or portions thereof (e.g., an Fc region). In one embodiment, an isolated nucleic acid molecule of the disclosure further comprises a heterologous nucleic acid sequence that encodes an immunoglobulin constant region or a portion thereof. In some embodiments, the immunoglobulin constant region or portion thereof is an Fc region.

An immunoglobulin constant region is comprised of domains denoted CH (constant heavy) domains (CH1, CH2, etc.). Depending on the isotype, IgG, IgM, IgA IgD, or IgE), the constant region can be comprised of three or four CH domains. Some isotypes (e.g. IgG) constant regions also contain a hinge region. See Janeway et al. 2001, *Immunobiology*, Garland Publishing, N.Y., N.Y.

An immunoglobulin constant region or a portion thereof of the present disclosure can be obtained from a number of different sources. In one embodiment, an immunoglobulin constant region or a portion thereof is derived from a human immunoglobulin. It is understood, however, that the immunoglobulin constant region or a portion thereof can be derived from an immunoglobulin of another mammalian species, including for example, a rodent (e.g., a mouse, rat, rabbit, guinea pig) or non-human primate (e.g., chimpanzee, macaque) species. Moreover, the immunoglobulin constant region or a portion thereof can be derived from any immunoglobulin class, including IgM, IgG, IgD, IgA and IgE, and any immunoglobulin isotype, including IgG1, IgG2, IgG3 and IgG4. In one embodiment, the human isotype IgG1 is used.

A variety of the immunoglobulin constant region gene sequences (e.g., human constant region gene sequences) are available in the form of publicly accessible deposits. Constant region domains sequence can be selected having a particular effector function (or lacking a particular effector function) or with a particular modification to reduce immunogenicity. Many sequences of antibodies and antibody-encoding genes have been published and suitable Ig constant region sequences (e.g., hinge, CH2, and/or CH3 sequences, or portions thereof) can be derived from these sequences using art recognized techniques. The genetic material obtained using any of the foregoing methods can then be altered or synthesized to obtain polypeptides of the present disclosure. It will further be appreciated that the scope of this disclosure encompasses alleles, variants and mutations of constant region DNA sequences.

The sequences of the immunoglobulin constant region or a portion thereof can be cloned, e.g., using the polymerase chain reaction and primers which are selected to amplify the domain of interest. To clone a sequence of the immunoglobulin constant region or a portion thereof from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, C A (1990); Ho et al. 1989. Gene 77:51; Horton et al. 1993. Methods Enzymol. 217:270). PCR can be initiated by consensus constant region primers or by more specific primers based on the published heavy and light chain DNA and amino acid sequences. PCR also can be used to isolate DNA clones encoding the antibody light and heavy chains. In this case the libraries can be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. *J. Immunol. Methods* 173:33); antibody leader sequences (Larrick et al. 1989 *Biochem. Biophys. Res. Commun.* 160:1250). The cloning of antibody sequences is further described in Newman et al., U.S. Pat. No. 5,658,570, filed Jan. 25, 1995, which is incorporated by reference herein.

An immunoglobulin constant region used herein can include all domains and the hinge region or portions thereof. In one embodiment, the immunoglobulin constant region or a portion thereof comprises CH2 domain, CH3 domain, and a hinge region, i.e., an Fc region or an FcRn binding partner.

As used herein, the term "Fc region" is defined as the portion of a polypeptide which corresponds to the Fc region of native Ig, i.e., as formed by the dimeric association of the respective Fc domains of its two heavy chains. A native Fc region forms a homodimer with another Fc region. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence). See International Publication No. WO 2012/006635, incorporated herein by reference in its entirety.

In one embodiment, the "Fc region" refers to the portion of a single Ig heavy chain beginning in the hinge region just upstream of the papain cleavage site (i.e., residue 216 in IgG, taking the first residue of heavy chain constant region to be 114) and ending at the C-terminus of the antibody. Accordingly, a complete Fc region comprises at least a hinge domain, a CH2 domain, and a CH3 domain.

An immunoglobulin constant region or a portion thereof can be an FcRn binding partner. FcRn is active in adult epithelial tissues and expressed in the lumen of the intestines, pulmonary airways, nasal surfaces, vaginal surfaces, colon and rectal surfaces (U.S. Pat. No. 6,485,726). An FcRn binding partner is a portion of an immunoglobulin that binds to FcRn.

The FcRn receptor has been isolated from several mammalian species including humans. The sequences of the human FcRn, monkey FcRn, rat FcRn, and mouse FcRn are known (Story et al. 1994, J. Exp. Med. 180:2377). The FcRn receptor binds IgG (but not other immunoglobulin classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, Immunology 92:69) renal proximal tubular epithelium (Kobayashi et al. 2002, Am. J. Physiol. Renal Physiol. 282:F358) as well as nasal epithelium, vaginal surfaces, and biliary tree surfaces.

FcRn binding partners useful in the present disclosure encompass molecules that can be specifically bound by the FcRn receptor including whole IgG, the Fc fragment of IgG, and other fragments that include the complete binding region of the FcRn receptor. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U.S. Department of Public Health, Bethesda, Md.

Fc regions or FcRn binding partners bound to FcRn can be effectively shuttled across epithelial barriers by FcRn, thus providing a non-invasive means to systemically administer a desired therapeutic molecule. Additionally, fusion proteins comprising an Fc region or an FcRn binding partner are endocytosed by cells expressing the FcRn. But instead of being marked for degradation, these fusion proteins are recycled out into circulation again, thus increasing the in vivo half-life of these proteins. In certain embodiments, the portions of immunoglobulin constant regions are an Fc region or an FcRn binding partner that typically associates, via disulfide bonds and other non-specific interactions, with another Fc region or another FcRn binding partner to form dimers and higher order multimers.

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a biologically active molecule provides a means of delivering the biologically active molecule orally, buccally, sublingually, rectally, vaginally, as an aerosol administered nasally or via a pulmonary route, or via an ocular route. In another embodiment, the clotting factor protein can be administered invasively, e.g., subcutaneously, intravenously.

An FcRn binding partner region is a molecule or portion thereof that can be specifically bound by the FcRn receptor with consequent active transport by the FcRn receptor of the Fc region. Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than $10^6$ $M^{-1}$, or higher than $10^8$ $M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g., serum albumin, milk casein), etc., can be optimized by a skilled artisan using routine techniques.

In certain embodiments, a therapeutic protein encoded by the nucleic acid molecule of the disclosure comprises one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain). Thus, an Fc region of the disclosure can comprise or consist of an FcRn binding portion. FcRn binding portions can be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

The Fc region can be obtained from a number of different sources. In one embodiment, an Fc region of the polypeptide is derived from a human immunoglobulin. It is understood, however, that an Fc moiety can be derived from an immunoglobulin of another mammalian species, including for example, a rodent (e.g., a mouse, rat, rabbit, guinea pig) or non-human primate (e.g., chimpanzee, macaque) species. Moreover, the polypeptide of the Fc domains or portions thereof can be derived from any immunoglobulin class, including IgM, IgG, IgD, IgA and IgE, and any immunoglobulin isotype, including IgG1, IgG2, IgG3 and IgG4. In another embodiment, the human isotype IgG1 is used.

In certain embodiments, the Fc variant confers a change in at least one effector function imparted by an Fc moiety comprising said wild-type Fc domain (e.g., an improvement or reduction in the ability of the Fc region to bind to Fc receptors (e.g. FcγRI, FcγRII, or FcγRIII) or complement proteins (e.g., C1q), or to trigger antibody-dependent cytotoxicity (ADCC), phagocytosis, or complement-dependent cytotoxicity (CDCC)). In other embodiments, the Fc variant provides an engineered cysteine residue.

The Fc region of the disclosure can employ art-recognized Fc variants which are known to impart a change (e.g., an enhancement or reduction) in effector function and/or FcR or FcRn binding. Specifically, an Fc region of the disclosure can include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein. In one embodiment, the specific change (e.g., the specific substitution of one or more amino acids disclosed in the art) can be made at one or more of the disclosed amino acid positions. In another embodiment, a different change at one or more of the disclosed amino acid positions (e.g., the different substitution of one or more amino acid position disclosed in the art) can be made.

The Fc region or FcRn binding partner of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fc γ1) can be substituted without significant loss of Fc binding affinity for FcRn: P238A, S239A, K246A, K248A, D249A, M252A, T256A, E258A, T260A, D265A, 5267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. As an example, a specific embodiment incorporates the N297A mutation, removing a highly conserved N-glycosylation site. In addition to alanine other amino acids can be substituted for the wild type amino acids at the positions specified above. Mutations can be introduced singly into Fc giving rise to more than one hundred Fc regions distinct from the native Fc. Additionally, combinations of two, three, or more of these individual mutations can be introduced together, giving rise to hundreds more Fc regions.

Certain of the above mutations can confer new functionality upon the Fc region or FcRn binding partner. For example, one embodiment incorporates N297A, removing a highly conserved N-glycosylation site. The effect of this mutation is to reduce immunogenicity, thereby enhancing circulating half-life of the Fc region, and to render the Fc region incapable of binding to FcγRI, FcγRIIA, FcγRIIB, and FcγRIIIA, without compromising affinity for FcRn (Routledge et al. 1995, Transplantation 60:847; Friend et al. 1999, Transplantation 68:1632; Shields et al. 1995, J. Biol. Chem. 276:6591). As a further example of new functionality arising from mutations described above affinity for FcRn can be increased beyond that of wild type in some instances. This increased affinity can reflect an increased "on" rate, a decreased "off" rate or both an increased "on" rate and a decreased "off" rate. Examples of mutations believed to impart an increased affinity for FcRn include, but not limited to, T256A, T307A, E380A, and N434A (Shields et al. 2001, J. Biol. Chem. 276:6591).

Additionally, at least three human Fc gamma receptors appear to recognize a binding site on IgG within the lower hinge region, generally amino acids 234-237. Therefore, another example of new functionality and potential decreased immunogenicity can arise from mutations of this region, as for example by replacing amino acids 233-236 of human IgG1 "ELLG" (SEQ ID NO: 45) to the corresponding sequence from IgG2 "PVA" (with one amino acid deletion). It has been shown that FcγRI, FcγRII, and FcγRIII, which mediate various effector functions will not bind to IgG1 when such mutations have been introduced. Ward and Ghetie 1995, Therapeutic Immunology 2:77 and Armour et al. 1999, Eur. J. Immunol. 29:2613.

In another embodiment, the immunoglobulin constant region or a portion thereof comprises an amino acid sequence in the hinge region or a portion thereof that forms one or more disulfide bonds with a second immunoglobulin constant region or a portion thereof. The second immunoglobulin constant region or a portion thereof can be linked to a second polypeptide, bringing the therapeutic protein and the second polypeptide together. In some embodiments, the second polypeptide is an enhancer moiety. As used herein, the term "enhancer moiety" refers to a molecule, fragment thereof or a component of a polypeptide which is capable of enhancing the activity of the therapeutic protein. The enhancer moiety can be a cofactor, such as, wherein the therapeutic protein is a clotting factor, a soluble tissue factor (sTF), or a procoagulant peptide. Thus, upon activation of the clotting factor, the enhancer moiety is available to enhance clotting factor activity.

In certain embodiments, a therapeutic protein encoded by a nucleic acid molecule of the disclosure comprises an amino acid substitution to an immunoglobulin constant region or a portion thereof (e.g., Fc variants), which alters the antigen-independent effector functions of the Ig constant region, in particular the circulating half-life of the protein.

2. scFc Regions

In another aspect, a heterologous moiety comprises a scFc (single chain Fc) region. In one embodiment, an isolated nucleic acid molecule of the disclosure further comprises a heterologous nucleic acid sequence that encodes a scFc region. The scFc region comprises at least two immunoglobulin constant regions or portions thereof (e.g., Fc moieties or domains (e.g., 2, 3, 4, 5, 6, or more Fc moieties or domains)) within the same linear polypeptide chain that are capable of folding (e.g., intramolecularly or intermolecularly folding) to form one functional scFc region which is linked by an Fc peptide linker. For example, in one embodiment, a polypeptide of the disclosure is capable of binding, via its scFc region, to at least one Fc receptor (e.g., an FcRn, an FcγR receptor (e.g., FcγRIII), or a complement protein (e.g., C1q)) in order to improve half-life or trigger an immune effector function (e.g., antibody-dependent cytotoxicity (ADCC), phagocytosis, or complement-dependent cytotoxicity (CDCC) and/or to improve manufacturability).

3. CTP

In another aspect, a heterologous moiety comprises one C-terminal peptide (CTP) of the β subunit of human chorionic gonadotropin or fragment, variant, or derivative thereof. One or more CTP peptides inserted into a recombinant protein is known to increase the in vivo half-life of that protein. See, e.g., U.S. Pat. No. 5,712,122, incorporated by reference herein in its entirety.

Exemplary CTP peptides include DPRFQDSSSSKAPPPSLPSPSRLPGPSDTPIL (SEQ ID NO: 33) or SSSSKAPPPSLPSPSRLPGPSDTPILPQ (SEQ ID NO: 34). See, e.g., U.S. Patent Application Publication No. US 2009/0087411 A1, incorporated by reference.

4. XTEN Sequence

In some embodiments, a heterologous moiety comprises one or more XTEN sequences, fragments, variants, or derivatives thereof. As used here "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a heterologous moiety, XTENs can serve as a half-life extension moiety. In addition, XTEN can provide desirable properties including but are not limited to enhanced pharmacokinetic parameters and solubility characteristics.

The incorporation of a heterologous moiety comprising an XTEN sequence into a protein of the disclosure can confer to the protein one or more of the following advantageous properties: conformational flexibility, enhanced aqueous solubility, high degree of protease resistance, low immunogenicity, low binding to mammalian receptors, or increased hydrodynamic (or Stokes) radii.

In certain aspects, an XTEN sequence can increase pharmacokinetic properties such as longer in vivo half-life or increased area under the curve (AUC), so that a protein of the disclosure stays in vivo and has procoagulant activity for an increased period of time compared to a protein with the same but without the XTEN heterologous moiety.

In some embodiments, the XTEN sequence useful for the disclosure is a peptide or a polypeptide having greater than about 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, or 2000 amino acid residues. In certain embodiments, XTEN is a peptide or a polypeptide having greater than about 20 to about 3000 amino acid residues, greater than 30 to about 2500 residues, greater than 40 to about 2000 residues, greater than 50 to about 1500 residues, greater than 60 to about 1000 residues, greater than 70 to about 900 residues, greater than 80 to about 800 residues, greater than 90 to about 700 residues, greater than 100 to about 600 residues, greater than 110 to about 500 residues, or greater than 120 to about 400 residues. In one particular embodiment, the XTEN comprises an amino acid sequence of longer than 42 amino acids and shorter than 144 amino acids in length.

The XTEN sequence of the disclosure can comprise one or more sequence motif of 5 to 14 (e.g., 9 to 14) amino acid residues or an amino acid sequence at least 80%, 90%, 91%, 92%, 93%, 94%, 95%, 96%, 97%, 98%, or 99% identical to the sequence motif, wherein the motif comprises, consists essentially of, or consists of 4 to 6 types of amino acids (e.g., 5 amino acids) selected from the group consisting of glycine (G), alanine (A), serine (S), threonine (T), glutamate (E) and proline (P). See US 2010-0239554 A1.

In some embodiments, the XTEN comprises non-overlapping sequence motifs in which about 80%, or at least about 85%, or at least about 90%, or about 91%, or about 92%, or about 93%, or about 94%, or about 95%, or about 96%, or about 97%, or about 98%, or about 99% or about 100% of the sequence consists of multiple units of non-overlapping sequences selected from a single motif family selected from Table 7, resulting in a family sequence. As used herein, "family" means that the XTEN has motifs selected only from a single motif category from Table 7; i.e., AD, AE, AF, AG, AM, AQ, BC, or BD XTEN, and that any other amino acids in the XTEN not from a family motif are selected to achieve a needed property, such as to permit incorporation of a restriction site by the encoding nucleotides, incorporation of a cleavage sequence, or to achieve a better linkage to the therapeutic protein. In some embodiments of XTEN families, an XTEN sequence comprises multiple units of non-overlapping sequence motifs of the AD motif family, or of the AE motif family, or of the AF motif family, or of the AG motif family, or of the AM motif family, or of the AQ motif family, or of the BC family, or of the BD family, with the resulting XTEN exhibiting the range of homology described above. In other embodiments, the XTEN comprises multiple units of motif sequences from two or more of the motif families of Table 7. These sequences can be selected to achieve desired physical/chemical characteristics, including such properties as net charge, hydrophilicity, lack of secondary structure, or lack of repetitiveness that are conferred by the amino acid composition of the motifs, described more fully below. In the embodiments hereinabove described in this paragraph, the motifs incorporated into the XTEN can be selected and assembled using the methods described herein to achieve an XTEN of about 36 to about 3000 amino acid residues.

TABLE 7

XTEN Sequence Motifs of 12 Amino Acids and Motif Families

| Motif Family* | MOTIF SEQUENCE | SEQ ID NO: |
|---|---|---|
| AD | GESPGGSSGSES | 73 |
| AD | GSEGSSGPGESS | 74 |
| AD | GSSESGSSEGGP | 75 |
| AD | GSGGEPSESGSS | 76 |
| AE, AM | GSPAGSPTSTEE | 77 |
| AE, AM, AQ | GSEPATSGSETP | 78 |
| AE, AM, AQ | GTSESATPESGP | 79 |
| AE, AM, AQ | GTSTEPSEGSAP | 80 |
| AF, AM | GSTSESPSGTAP | 81 |
| AF, AM | GTSTPESGSASP | 82 |
| AF, AM | GTSPSGESSTAP | 83 |
| AF, AM | GSTSSTAESPGP | 84 |
| AG, AM | GTPGSGTASSSP | 85 |
| AG, AM | GSSTPSGATGSP | 86 |
| AG, AM | GSSPSASTGTGP | 87 |
| AG, AM | GASPGTSSTGSP | 88 |
| AQ | GEPAGSPTSTSE | 89 |
| AQ | GTGEPSSTPASE | 90 |
| AQ | GSGPSTESAPTE | 91 |
| AQ | GSETPSGPSETA | 92 |
| AQ | GPSETSTSEPGA | 93 |
| AQ | GSPSEPTEGTSA | 94 |
| BC | GSGASEPTSTEP | 95 |
| BC | GSEPATSGTEPS | 96 |
| BC | GTSEPSTSEPGA | 97 |
| BC | GTSTEPSEPGSA | 98 |
| BD | GSTAGSETSTEA | 99 |
| BD | GSETATSGSETA | 100 |
| BD | GTSESATSESGA | 101 |
| BD | GTSTEASEGSAS | 102 |

*Denotes individual motif sequences that, when used together in various permutations, results in a "family sequence"

Examples of XTEN sequences that can be used as heterologous moieties in the therapeutic proteins of the disclosure are disclosed, e.g., in U.S. Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, or WO 2011028344 A2, each of which is incorporated by reference herein in its entirety.

XTEN can have varying lengths for insertion into or linkage to a therapeutic protein. In one embodiment, the length of the XTEN sequence(s) is chosen based on the property or function to be achieved in the fusion protein. Depending on the intended property or function, XTEN can be short or intermediate length sequence or longer sequence that can serve as carriers. In certain embodiments, the XTEN includes short segments of about 6 to about 99 amino acid residues, intermediate lengths of about 100 to about 399 amino acid residues, and longer lengths of about 400 to about 1000 and up to about 3000 amino acid residues. Thus, the XTEN inserted into or linked to a therapeutic protein can have lengths of about 6, about 12, about 36, about 40, about 42, about 72, about 96, about 144, about 288, about 400, about 500, about 576, about 600, about 700, about 800, about 864, about 900, about 1000, about 1500, about 2000, about 2500, or up to about 3000 amino acid residues in length. In other embodiments, the XTEN sequences is about 6 to about 50, about 50 to about 100, about 100 to about 150, about 150 to about 250, about 250 to about 400, about 400 to about 500, about 500 to about 900, about 900 to 1500, about 1500 to 2000, or about 2000 to about 3000 amino acid residues in length. The precise length of an XTEN inserted into or linked to a therapeutic protein can vary without adversely affecting the activity of the therapeutic protein. In one embodiment, one or more of the XTENs used herein have 42 amino acids, 72 amino acids, 144 amino acids, 288 amino acids, 576 amino acids, or 864 amino acids in length and can be selected from one or more of the XTEN family sequences; i.e., AD, AE, AF, AG, AM, AQ, BC or BD.

In some embodiments, the therapeutic protein comprises a FVIII polypeptide and an XTEN, wherein the XTEN comprises 288 amino acids. In one embodiment, the therapeutic protein comprises a FVIII polypeptide and an XTEN, wherein the XTEN comprises 288 amino acids, and the XTEN is inserted within the B domain of the FVIII polypeptide. In one particular embodiment, the therapeutic protein comprises a FVIII polypeptide and an XTEN comprising SEQ ID NO:109, and the XTEN is inserted within the B domain of the FVIII polypeptide. In one particular embodiment, the therapeutic protein comprises a FVIII polypeptide and an XTEN comprising SEQ ID NO:109, and the XTEN is inserted within the FVIII polypeptide immediately downstream of amino acid 745 of mature FVIII.

In some embodiments, the therapeutic protein comprises a FIX polypeptide and an XTEN, wherein the XTEN comprises 72 amino acids. In one embodiment, the therapeutic protein comprises a FIX polypeptide and an XTEN, wherein the XTEN comprises 72 amino acids, and the XTEN is inserted XTEN is inserted within the FIX polypeptide immediately downstream of amino acid 166 of mature FIX.

In some embodiments, the XTEN sequence used in the disclosure is at least 60%, 70%, 80%, 85%, 90%, 91%, 92%, 93%, 94%, 95%, 96%, 97%, 98%, 99%, or 100% identical to a sequence selected from the group consisting of AE42, AG42, AE48, AM48, AE72, AG72, AE108, AG108, AE144, AF144, AG144, AE180, AG180, AE216, AG216, AE252, AG252, AE288, AG288, AE324, AG324, AE360, AG360, AE396, AG396, AE432, AG432, AE468, AG468, AE504, AG504, AF504, AE540, AG540, AF540, AD576, AE576, AF576, AG576, AE612, AG612, AE624, AE648, AG648, AG684, AE720, AG720, AE756, AG756, AE792, AG792, AE828, AG828, AD836, AE864, AF864, AG864, AM875, AE912, AM923, AM1318, BC864, BD864, AE948, AE1044, AE1140, AE1236, AE1332, AE1428, AE1524, AE1620, AE1716, AE1812, AE1908, AE2004A, AG948, AG1044, AG1140, AG1236, AG1332, AG1428, AG1524, AG1620, AG1716, AG1812, AG1908, AG2004, and any combination thereof. See US 2010-0239554 A1. In one particular embodiment, the XTEN comprises AE42, AE72, AE144, AE288, AE576, AE864, AG 42, AG72, AG144, AG288, AG576, AG864, or any combination thereof.

Exemplary XTEN sequences that can be used as heterologous moieties in the therapeutic protein of the disclosure include XTEN AE42-4 (SEQ ID NO: 46, encoded by SEQ ID NO: 47), XTEN AE144-2A (SEQ ID NO: 48, encoded by SEQ ID NO: 49), XTEN AE144-3B (SEQ ID NO: 50, encoded by SEQ ID NO: 51), XTEN AE144-4A (SEQ ID NO: 52, encoded by SEQ ID NO: 53), XTEN AE144-5A (SEQ ID NO: 54, encoded by SEQ ID NO: 55), XTEN AE144-6B (SEQ ID NO: 56, encoded by SEQ ID NO: 57), XTEN AG144-1 (SEQ ID NO: 58, encoded by SEQ ID NO: 59), XTEN AG144-A (SEQ ID NO: 60, encoded by SEQ ID NO: 61), XTEN AG144-B (SEQ ID NO: 62, encoded by SEQ ID NO: 63), XTEN AG144-C(SEQ ID NO: 64, encoded by SEQ ID NO: 65), and XTEN AG144-F (SEQ ID NO: 66, encoded by SEQ ID NO: 67). In one particular embodiment, the XTEN is encoded by SEQ ID NO:18.

In another embodiment, the XTEN sequence is selected from the group consisting of AE36 (SEQ ID NO: 130), AE42 (SEQ ID NO: 131), AE72 (SEQ ID NO: 132), AE78 (SEQ ID NO: 133), AE144 (SEQ ID NO: 134), AE144_2A (SEQ ID NO: 48), AE144_3B (SEQ ID NO: 50), AE144_4A (SEQ ID NO: 52), AE144_5A (SEQ ID NO: 54), AE144_6B (SEQ ID NO: 135), AG144 (SEQ ID NO: 136), AG144_A (SEQ ID NO: 137), AG144_B (SEQ ID NO: 62), AG144_C (SEQ ID NO: 64), AG144_F (SEQ ID NO: 66), AE288 (SEQ ID NO: 138), AE288_2 (SEQ ID NO: 139), AG288 (SEQ ID NO: 140), AE576 (SEQ ID NO: 141), AG576 (SEQ ID NO: 142), AE864 (SEQ ID NO: 143), AG864 (SEQ ID NO: 144), XTEN_AE72_2A_1 (SEQ ID NO:145), XTEN_AE72_2A_2 (SEQ ID NO: 146), XTEN_AE72_3B_1 (SEQ ID NO: 147), XTEN_AE72_3B_2 (SEQ ID NO: 148), XTEN_AE72_4A_2 (SEQ ID NO: 149), XTEN_AE72_5A_2 (SEQ ID NO: 150), XTEN_AE72_6B_1 (SEQ ID NO: 151), XTEN_AE72_6B_2 (SEQ ID NO: 152), XTEN_AE72_1A_1 (SEQ ID NO: 153), XTEN_AE72_1A_2 (SEQ ID NO: 154), XTEN_AE144_1A (SEQ ID NO: 155), AE150 (SEQ ID NO: 156), AG150 (SEQ ID NO: 157), AE294 (SEQ ID NO: 158), AG294 (SEQ ID NO: 159), and any combinations thereof. In a specific embodiment, the XTEN sequence is selected from the group consisting of AE72, AE144, and AE288. The amino acid sequences for certain XTEN sequences of the invention are shown in Table 8.

TABLE 8

| XTEN Sequences | |
|---|---|
| XTEN | Amino Acid Sequence |
| AE42-4 (SEQ ID NO: 46) | GAPGSPAGSPTSTEEGTSESATPESGPGSEPATSGSETPASS |
| AE144-2A (SEQ ID NO: 48) | TSTEPSEGSAPGSPAGSPTSTEEGTSTEPSEGSAPGTSTEPSEGSAPGTSESATPESG PGTSTEPSEGSAPGTSESATPESGPGSEPATSGSETPGTSTEPSEGSAPGTSTEPSEG SAPGTSESATPESGPGTSESATPESGPG |
| A144-3B (SEQ ID NO: 50) | SPAGSPTSTEEGTSESATPESGPGSEPATSGSETPGTSESATPESGPGTSTEPSEGSA PGTSTEPSEGSAPGTSTEPSEGSAPGTSTEPSEGSAPGTSTEPSEG SAPGSPAGSPTSTEEGTSTEPSEGSAPG |
| AE144-4A (SEQ ID NO: 52) | TSESATPESGPGSEPATSGSETPGTSESATPESGPGSEPATSGSETPGTSESATPESG PGTSTEPSEGSAPGTSESATPESGPGSPAGSPTSTEEGSPAGSPTSTEEGSPAGSPTS TEEGTSESATPESGPGTSTEPSEGSAPG |
| AE144-5A (SEQ ID NO: 54) | TSESATPESGPGSEPATSGSETPGTSESATPESGPGSEPATSGSETPGTSESATPESG PGTSTEPSEGSAPGSPAGSPTSTEEGTSESATPESGPGSEPATSGSETPGTSESATPE SGPGSPAGSPTSTEEGSPAGSPTSTEEG |
| AE144-6B (SEQ ID NO: 56) | TSTEPSEGSAPGTSESATPESGPGTSESATPESGPGTSESATPESGPGSEPATSGSET PGSEPATSGSETPGSPAGSPTSTEEGTSTEPSEGSAPGTSTEPSEGSAPGSEPATSGS ETPGTSESATPESGPGTSTEPSEGSAPG |
| AG144-1 (SEQ ID NO: 58) | PGSSPSASTGTGPGSSPSASTGTGPGTPGSGTASSSPGSSTPSGATGSPGSSPSASTG TGPGASPGTSSTGSPGTPGSGTASSSPGSSTPSGATGSPGTPGSGTASSSPGASPGTS STGSPGASPGTSSTGSPGTPGSGTASSS |
| AG144-A (SEQ ID NO: 60) | GASPGTSSTGSPGSSPSASTGTGPGSSPSASTGTGPGTPGSGTASSSPGSSTPSGATG SPGSSPSASTGTGPGASPGTSSTGSPGTPGSGTASSSPGSSTPSGATGSPGTPGSGTA SSSPGASPGTSSTGSPGASPGTSSTGSP |
| AG144-B (SEQ ID NO: 62) | GTPGSGTASSSPGSSTPSGATGSPGASPGTSSTGSPGTPGSGTASSSPGSSTPSGATG SPGSSPSASTGTGPGSSPSASTGTGPGSSTPSGATGSPGSSTPSGATGSPGASPGTSS TGSPGASPGTSSTGSPGASPGTSSTGSP |
| AG144-C (SEQ ID NO: 64) | GTPGSGTASSSPGASPGTSSTGSPGASPGTSSTGSPGASPGTSSTGSPGSSPSASTGT GPGTPGSGTASSSPGASPGTSSTGSPGASPGTSSTGSPGASPGTSSTGSPGSSTPSGA TGSPGSSTPSGATGSPGASPGTSSTGSP |

TABLE 8-continued

XTEN Sequences

| XTEN | Amino Acid Sequence |
|---|---|
| XTEN AG144-F (SEQ ID NO: 66) | GSSPSASTGTGPGSSPSASTGTGPGASPGTSSTGSPGASPGTSSTGSPGSSTPSGATG SPGSSPSASTGTGPGASPGTSSTGSPGSSPSASTGTGPGTPGSGTASSSPGSSTPSGA TGSPGSSTPSGATGSPGASPGTSSTGSP |
| AE36 (SEQ ID NO: 130) | GSPAGSPTSTEEGTSESATPESGPGSEPATSGSETP |
| AE42 (SEQ ID NO: 131) | GAPGSPAGSPTSTEEGTSESATPESGPGSEPATSGSETPASS |
| AE72 (SEQ ID NO: 132) | GAPTSESATPESGPGSEPATSGSETPGTSESATPESGPGSEPATSGSETPGTSESATP ESGPGTSTEPSEGSAPGASS |
| AE78 (SEQ ID NO: 133) | GAPTSESATPESGPGSEPATSGSETPGTSESATPESGPGSEPATSGSETPGTSESATP ESGPGTSTEPSEGSAPGASS |
| AE144 (SEQ ID NO: 134) | GSEPATSGSETPGTSESATPESGPGSEPATSGSETPGSPAGSPTSTEEGTSTEPSEGS APGSEPATSGSETPGSEPATSGSETPGSEPATSGSETPGTSTEPSEGSAPGTSESAPE SGPGSEPATSGSETPGTSTEPSEGSAP |
| AE144_6B (SEQ ID NO: 135) | TSTEPSEGSAPGTSESATPESGPGTSESATPESGPGTSESATPESGPGSEPATSGSET PGSEPATSGSETPGSPAGSPTSTEEGTSTEPSEGSAPGTSTEPSEGSAPGSEPATSGS ETPGTSESATPESGPGTSTEPSEGSAPG |
| AG144 (SEQ ID NO: 136) | GTPGSGTASSSPGSSTPSGATGSPGSSPSASTGTGPGSSPSASTGTGPGASPGTSSTG SPGASPGTSSTGSPGSSTPSGATGSPGSSPSASTGTGPGASPGTSSTGSPGSSPSAST GTGPGTPGSGTASSSPGSSTPSGATGSP |
| AG144_A (SEQ ID NO: 137) | GASPGTSSTGSPGSSPSASTGTGPGSSPSASTGTGPGTPGSGTASSSPGSSTPSGATG SPGSSPSASTGTGPGASPGTSSTGSPGTPGSGTASSSPGSSTPSGATGSPGTPGSGTA SSSPGASPGTSSTGSPGASPGTSSTGSP |
| AE288 (SEQ ID NO: 138) | GTSESATPESGPGSEPATSGSETPGTSESATPESGPGSEPATSGSETPGTSESATPES GPGTSTEPSEGSAPGSPAGSPTSTEEGTSESATPESGPGSEPATSGSETPGTSESATP ESGPGSPAGSPTSTEEGSPAGSPTSTEEGTSTEPSEGSAPGTSESATPESGPGTSESA TPESGPGTSESATPESGPGSEPATSGSETPGSEPATSGSETPGSPAGSPTSTEEGTST EPSEGSAPGTSTEPSEGSAPGSEPATSGSETPGTSESATPESGPGTSTEPSEGSAP |
| AE288_2 (SEQ ID NO: 139) | GSPAGSPTSTEEGTSESATPESGPGSEPATSGSETPGTSESATPESGPGTSTEPSEGS APGTSTEPSEGSAPGTSTEPSEGSAPGTSTEPSEGSAPGTSTEPSEGSAPGTSTEPSE GSAPGSPAGSPTSTEEGTSTEPSEGSAPGTSESATPESGPGSEPATSGSETPGTSESA TPESGPGSEPATSGSETPGTSESATPESGPGTSTEPSEGSAPGTSESATPESGPGSPA GSPTSTEEGSPAGSPTSTEEGSPAGSPTSTEEGTSESATPESGPGTSTEPSEGSAP |
| AG288 (SEQ ID NO: 140) | PGASPGTSSTGSPGASPGTSSTGSPGTPGSGTASSSPGSSTPSGATGSPGTPGSGTAS SSPGSSTPSGATGSPGTPGSGTASSSPGSSTPSGATGSPGSSTPSGATGSPGSSPSAS TGTGPGSSPSASTGTGPGASPGTSSTGSPGTPGSGTASSSPGSSTPSGATGSPGSSPS ASTGTGPGSSPSASTGTGPGASPGTSSTGSPGASPGTSSTGSPGSSTPSGATGSPGSS PSASTGTGPGASPGTSSTGSPGSSPSASTGTGPGTPGSGTASSSPGSSTPSGATGS |
| AE576 (SEQ ID NO: 141) | GSPAGSPTSTEEGTSESATPESGPGTSTEPSEGSAPGSPAGSPTSTEEGTSTEPSEGS APGTSTEPSEGSAPGTSESATPESGPGSEPATSGSETPGSEPATSGSETPGSPAGSPT STEEGTSESATPESGPGTSTEPSEGSAPGTSTEPSEGSAPGSPAGSPTSTEEGTSTEP SEGSAPGTSTEPSEGSAPGTSESATPESGPGTSTEPSEGSAPGTSESATPESGPGSEP ATSGSETPGTSTEPSEGSAPGTSTEPSEGSAPGTSESATPESGPGTSESATPESGPGS PAGSPTSTEEGTSESATPESGPGSEPATSGSETPGTSESATPESGPGTSTEPSEGSAP GTSTEPSEGSAPGTSTEPSEGSAPGTSTEPSEGSAPGTSTEPSEGSAPGTSTEPSEGS APGSPAGSPTSTEEGTSTEPSEGSAPGTSESATPESGPGSEPATSGSETPGTSESATP ESGPGSEPATSGSETPGTSESATPESGPGTSTEPSEGSAPGTSESATPESGPGSPAGS PTSTEEGSPAGSPTSTEEGSPAGSPTSTEEGTSESATPESGPGTSTEPSEGSAP |
| AG576 (SEQ ID NO: 142) | PGTPGSGTASSSPGSSTPSGATGSPGSSPSASTGTGPGSSPSASTGTGPGSSTPSGAT GSPGSSTPSGATGSPGASPGTSSTGSPGASPGTSSTGSPGASPGTSSTGSPGTPGSGT ASSSPGASPGTSSTGSPGASPGTSSTGSPGASPGTSSTGSPGSSPSASTGTGPGTPGS GTASSSPGASPGTSSTGSPGASPGTSSTGSPGASPGTSSTGSPGSSTPSGATGSPGSS TPSGATGSPGASPGTSSTGSPGTPGSGTASSSPGSSTPSGSPGSSTPSGATGSPG SSTPSGATGSPGSSPSASTGTGPGASPGTSSTGSPGASPGTSSTGSPGTPGSGTASSS PGASPGTSSTGSPGASPGTSSTGSPGASPGTSSTGSPGASPGTSSTGSPGTPGSGTAS SSPGSSTPSGATGSPGTPGSGTASSSPGSSTPSGATGSPGTPGSGTASSSPGSSTPSG ATGSPGSSTPSGATGSPGSSPSASTGTGPGSSPSASTGTGPGASPGTSSTGSPGTPGS GTASSSPGSSTPSGATGSPGSSPSASTGTGPGSSPSASTGTGPGASPGTSSTGS |
| AE864 (SEQ ID NO: 143) | GSPAGSPTSTEEGTSESATPESGPGTSTEPSEGSAPGSPAGSPTSTEEGTSTEPSEGS APGTSTEPSEGSAPGTSESATPESGPGSEPATSGSETPGSEPATSGSETPGSPAGSPT STEEGTSESATPESGPGTSTEPSEGSAPGTSTEPSEGSAPGSPAGSPTSTEEGTSTEP |

TABLE 8-continued

| XTEN Sequences | |
|---|---|
| XTEN | Amino Acid Sequence |
| | SEGSAPGTSTEPSEGSAPGTSESATPESGPGTSTEPSEGSAPGTSESATPESGPGSEP<br>ATSGSETPGTSTEPSEGSAPGTSTEPSEGSAPGTSESATPESGPGTSESATPESGPGS<br>PAGSPTSTEEGTSESATPESGPGSEPATSGSETPGTSESATPESGPGTSTEPSEGSAP<br>GTSTEPSEGSAPGTSTEPSEGSAPGTSTEPSEGSAPGTSTEPSEGSAPGTSTEPSEGS<br>APGSPAGSPTSTEEGTSTEPSEGSAPGTSESATPESGPGSEPATSGSETPGTSESATP<br>ESGPGSEPATSGSETPGTSESATPESGPGTSTEPSEGSAPGTSESATPESGPGSPAGS<br>PTSTEEGSPAGSPTSTEEGSPAGSPTSTEEGTSESATPESGPGTSTEPSEGSAPGTSE<br>SATPESGPGSEPATSGSETPGTSESATPESGPGSEPATSGSETPGTSESATPESGPGT<br>STEPSEGSAPGSPTSTEEGTSESATPESGPGSEPATSGSETPGTSESATPESGP<br>GSPAGSPTSTEEGSPAGSPTSTEEGTSTEPSEGSAPGTSESATPESGPGTSESATPES<br>GPGTSESATPESGPGSEPATSGSETPGSEPATSGSETPGSPAGSPTSTEEGTSTEPSE<br>GSAPGTSTEPSEGSAPGSEPATSGSETPGTSESATPESGPGTSTEPSEGSAP |
| AG864<br>(SEQ ID NO: 144) | GASPGTSSTGSPGSSPSASTGTGPGSSPSASTGTGPGTPGSGTASSSPGSSTPSGATG<br>SPGSSPSASTGTGPGASPGTSSTGSPGTPGSGTASSSPGSSTPSGATGSPGTPGSGTA<br>SSSPGASPGTSSTGSPGASPGTSSTGSPGTPGSGTASSSPGSSTPSGATGSPGASPGT<br>SSTGSPGTPGSGTASSSPGSSTPSGATGSPGSSPSASTGTGPGSSPSASTGTGPGSST<br>PSGATGSPGSSTPSGATGSPGASPGTSSTGSPGASPGTSSTGSPGASPGTSSTGSPGT<br>PGSGTASSSPGASPGTSSTGSPGASPGTSSTGSPGASPGTSSTGSPGSSTPSGATGTGP<br>GTPGSGTASSSPGASPGTSSTGSPGASPGTSSTGSPGASPGTSSTGSPGSSTPSGATG<br>SPGSSTPSGATGSPGASPGTSSTGSPGTPGSGTASSSPGSSTPSGATGSPGSSTPSGA<br>TGSPGSSTPSGATGSPGSSPSASTGTGPGASPGTSSTGSPGASPGTSSTGSPGTPGSG<br>TASSSPGASPGTSSTGSPGASPGTSSTGSPGASPGTSSTGSPGASPGTSSTGSPGTPG<br>SGTASSSPGSSTPSGATGSPGTPGSGTASSSPGSSTPSGATGSPGTPGSGTASSSPGS<br>STPSGATGSPGSSTPSGATGSPGSSPSASTGTGPGSSPSASTGTGPGASPGTSSTGSP<br>GTPGSGTASSSPGSSTPSGATGSPGSSPSASTGTGPGSSPSASTGTGPGASPGTSSTG<br>SPGASPGTSSTGSPGSSTPSGATGSPGSSPSASTGTGPGASPGTSSTGSPGSSPSAST<br>GTGPGTPGSGTASSSPGSSTPSGATGSPGSSTPSGATGSPGASPGTSSTGSP |
| XTEN_AE72_2A_1<br>(SEQ ID NO: 145) | TSTEPSEGSAPGSPAGSPTSTEEGTSTEPSEGSAPGTSTEPSEGSAPGTSESATPESG<br>PGTSTEPSEGSAPG |
| XTEN_AE72_2A_2<br>(SEQ ID NO: 146) | TSESATPESGPGSEPATSGSETPGTSTEPSEGSAPGTSTEPSEGSAPGTSESATPESG<br>PGTSESATPESGPG |
| XTEN_AE72_3B_1<br>(SEQ ID NO: 147) | SPAGSPTSTEEGTSESATPESGPGSEPATSGSETPGTSESATPESGPGTSTEPSEGSA<br>PGTSTEPSEGSAPG |
| XTEN_AE72_3B_2<br>(SEQ ID NO: 148) | TSTEPSEGSAPGTSTEPSEGSAPGTSTEPSEGSAPGTSTEPSEGSAPGSPAGSPTSTE<br>EGTSTEPSEGSAPG |
| XTEN_AE72_4A_2<br>(SEQ ID NO: 149) | TSESATPESGPGSPAGSPTSTEEGSPAGSPTSTEEGSPAGSPTSTEEGTSESATPESG<br>PGTSTEPSEGSAPG |
| XTEN_AE72_5A_2<br>(SEQ ID NO: 150) | SPAGSPTSTEEGTSESATPESGPGSEPATSGSETPGTSESATPESGPGSPAGSPTSTE<br>EGSPAGSPTSTEEG |
| XTEN_AE72_6B_1<br>(SEQ ID NO: 151) | TSTEPSEGSAPGTSESATPESGPGTSESATPESGPGTSESATPESGPGSEPATSGSET<br>PGSEPATSGSETPG |
| XTEN_AE72_6B_2<br>(SEQ ID NO: 152) | SPAGSPTSTEEGTSTEPSEGSAPGTSTEPSEGSAPGSEPATSGSETPGTSESATPESG<br>PGTSTEPSEGSAPG |
| XTEN_AE72_1A_1<br>(SEQ ID NO: 153) | SPAGSPTSTEEGTSESATPESGPGTSTEPSEGSAPGSPAGSPTSTEEGTSTEPSEGSA<br>PGTSTEPSEGSAPG |
| XTEN_AE72_1A_2<br>(SEQ ID NO: 154) | TSESATPESGPGSEPATSGSETPGSEPATSGSETPGSPAGSPTSTEEGTSESATPESG<br>PGTSTEPSEGSAPG |
| XTEN_AE144_1A<br>(SEQ ID NO: 155) | SPAGSPTSTEEGTSESATPESGPGTSTEPSEGSAPGSPAGSPTSTEEGTSTEPSEGSA<br>PGTSTEPSEGSAPGTSESATPESGPGSEPATSGSETPGSEPATSGSETPGSPAGSPTS<br>TEEGTSESATPESGPGTSTEPSEGSAPG |
| AE150<br>(SEQ ID NO: 156) | GAPGSEPATSGSETPGTSESATPESGPGSEPATSGSETPGSPAGSPTSTEEGTSTEPS<br>EGSAPGSEPATSGSETPGSEPATSGSETPGSEPATSGSETPGTSTEPSEGSAPGTSES<br>ATPESGPGSEPATSGSETPGTSTEPSEGSAPASS |
| G150<br>(SEQ ID NO: 157) | GAPGTPGSGTASSSPGSSTPSGATGSPGSSPSASTGTGPGSSPSASTGTGPGASPGTS<br>STGSPGASPGTSSTGSPGSSTPSGATGSPGSSPSASTGTGPGASPGTSSTGSPGSSPS<br>ASTGTGPGTPGSGTASSSPGSSTPSGATGSPASS |
| AE294<br>(SEQ ID NO: 158) | GAPGTSESATPESGPGSEPATSGSETPGTSESATPESGPGSEPATSGSETPGTSESAT<br>PESGPGTSTEPSEGSAPGSPAGSPTSTEEGTSESATPESGPGSEPATSGSETPGTSES<br>ATPESGPGSPAGSPTSTEEGSPAGSPTSTEEGTSTEPSEGSAPGTSESATPESGPGTS<br>ESATPESGPGTSESATPESGPGSEPATSGSETPGSEPATSGSETPGSPAGSPTSTEEG |

TABLE 8-continued

XTEN Sequences

| XTEN | Amino Acid Sequence |
|---|---|
| | TSTEPSEGSAPGTSTEPSEGSAPGSEPATSGSETPGTSESATPESGPGTSTEPSEGSA<br>PASS |
| AG294<br>(SEQ ID NO: 159) | GAPPGASPGTSSTGSPGASPGTSSTGSPGTPGSGTASSSPGSSTPSGATGSPGTPGSG<br>TASSSPGSSTPSGATGSPGTPGSGTASSSPGSSTPSGATGSPGSSTPSGATGSPGSSP<br>SASTGTGPGSSPSASTGTGPGASPGTSSTGSPGTPGSGTASSSPGSSTPSGATGSPGS<br>SPSASTGTGPGSSPSASTGTGPGASPGTSSTGSPGASPGTSSTGSPGSSTPSGATGSP<br>GSSPSASTGTGPGASPGTSSTGSPGSSPSASTGTGPGTPGSGTASSSPGSSTPSGATG<br>SASS |

In some embodiments, less than 100% of amino acids of an XTEN are selected from glycine (G), alanine (A), serine (S), threonine (T), glutamate (E) and proline (P), or less than 100% of the sequence consists of the sequence motifs from Table 7 or an XTEN sequence provided herein. In such embodiments, the remaining amino acid residues of the XTEN are selected from any of the other 14 natural L-amino acids, but can be preferentially selected from hydrophilic amino acids such that the XTEN sequence contains at least about 90%, 91%, 92%, 93%, 94%, 95%, 96%, 97%, 98%, or at least about 99% hydrophilic amino acids. The content of hydrophobic amino acids in the XTEN utilized in the conjugation constructs can be less than 5%, or less than 2%, or less than 1% hydrophobic amino acid content. Hydrophobic residues that are less favored in construction of XTEN include tryptophan, phenylalanine, tyrosine, leucine, isoleucine, valine, and methionine. Additionally, XTEN sequences can contain less than 5% or less than 4% or less than 3% or less than 2% or less than 1% or none of the following amino acids: methionine (for example, to avoid oxidation), or asparagine and glutamine (to avoid desamidation).

The one or more XTEN sequences can be inserted at the C-terminus or at the N-terminus of the therapeutic protein or inserted between two amino acids in the amino acid sequence of the therapeutic protein. For example, where the therapeutic protein comprises a FVIII polypeptide, the XTEN can be inserted between two amino acids at one or more insertion site selected from Table 5. Where the therapeutic protein comprises a FIX polypeptide, the XTEN can be inserted between two amino acids at one or more insertion site selected from Table 5.

Additional examples of XTEN sequences that can be used according to the present invention and are disclosed in US Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, WO 2011028344 A2, WO 2014/011819 A2, or WO 2015/023891.

5. Albumin or Fragment, Derivative, or Variant Thereof

In some embodiments, a heterologous moiety comprises albumin or a functional fragment thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Examples of albumin or the fragments or variants thereof are disclosed in US Pat. Publ. Nos. 2008/0194481A1, 2008/0004206 A1, 2008/0161243 A1, 2008/0261877 A1, or 2008/0153751 A1 or PCT Appl. Publ. Nos. 2008/033413 A2, 2009/058322 A1, or 2007/021494 A2, which are incorporated herein by reference in their entireties.

In one embodiment, the therapeutic protein of the disclosure comprises albumin, a fragment, or a variant thereof which is further linked to a second heterologous moiety selected from the group consisting of an immunoglobulin constant region or portion thereof (e.g., an Fc region), a PAS sequence, HES, PEG and any combination thereof.

6. Albumin-Binding Moiety

In certain embodiments, the heterologous moiety is an albumin-binding moiety, which comprises an albumin-binding peptide, a bacterial albumin-binding domain, an albumin-binding antibody fragment, or any combinations thereof.

For example, the albumin-binding protein can be a bacterial albumin-binding protein, an antibody or an antibody fragment including domain antibodies (see U.S. Pat. No. 6,696,245). An albumin-binding protein, for example, can be a bacterial albumin-binding domain, such as the one of streptococcal protein G (Konig, T. and Skerra, A. (1998) J. Immunol. Methods 218, 73-83). Other examples of albumin-binding peptides that can be used as conjugation partner are, for instance, those having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, H is, Ile, Leu, or Lys; $Xaa_3$ is Ala, Asp, Phe, Trp, or Tyr; and $Xaa_4$ is Asp, Gly, Leu, Phe, Ser, or Thr as described in US patent application 2003/0069395 or Dennis et al. (Dennis et al. (2002) J. Biol. Chem. 277, 35035-35043).

Domain 3 from streptococcal protein G, as disclosed by Kraulis et al., FEBS Lett. 378:190-194 (1996) and Linhult et al., Protein Sci. 11:206-213 (2002) is an example of a bacterial albumin-binding domain. Examples of albumin-binding peptides include a series of peptides having the core sequence DICLPRWGCLW (SEQ ID NO: 35). See, e.g., Dennis et al., J. Biol. Chem. 2002, 277: 35035-35043 (2002). Examples of albumin-binding antibody fragments are disclosed in Muller and Kontermann, Curr. Opin. Moi. Ther. 9:319-326 (2007); Roovers et al., Cancer Immunol. Immunother. 56:303-317 (2007), and Holt et al., Prot. Eng. Design Sci., 21:283-288 (2008), which are incorporated herein by reference in their entireties. An example of such albumin-binding moiety is 2-(3-maleimidopropanamido)-6-(4-(4-iodophenyl)butanamido) hexanoate ("Albu" tag) as disclosed by Trussel et al., Bioconjugate Chem. 20:2286-2292 (2009).

Fatty acids, in particular long chain fatty acids (LCFA) and long chain fatty acid-like albumin-binding compounds can be used to extend the in vivo half-life of clotting factor proteins of the disclosure. An example of a LCFA-like albumin-binding compound is 16-(I-(3-(9-(((2,5-dioxopyrrolidin-1-yloxy) carbonyloxy)-methyl)-7-sulfo-9H-fluoren-2-ylamino)-3-oxopropyl)-2,5-dioxopyrrolidin-3-ylthio) hexadecanoic acid (see, e.g., WO 2010/140148).

7. PAS Sequence

In other embodiments, the heterologous moiety is a PAS sequence. A PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. Yet, the skilled person is aware that an amino acid polymer also can form random coil conformation when residues other than alanine, serine, and proline are added as a minor constituent in the PAS sequence. The term "minor constituent" as used herein means that amino acids other than alanine, serine, and proline can be added in the PAS sequence to a certain degree, e.g., up to about 12%, i.e., about 12 of 100 amino acids of the PAS sequence, up to about 10%, i.e. about 10 of 100 amino acids of the PAS sequence, up to about 9%, i.e., about 9 of 100 amino acids, up to about 8%, i.e., about 8 of 100 amino acids, about 6%, i.e., about 6 of 100 amino acids, about 5%, i.e., about 5 of 100 amino acids, about 4%, i.e., about 4 of 100 amino acids, about 3%, i.e., about 3 of 100 amino acids, about 2%, i.e., about 2 of 100 amino acids, about 1%, i.e., about 1 of 100 of the amino acids. The amino acids different from alanine, serine and proline can be selected from the group consisting of Arg, Asn, Asp, Cys, Gln, Glu, Gly, His, Ile, Leu, Lys, Met, Phe, Thr, Trp, Tyr, and Val.

Under physiological conditions, the PAS sequence stretch forms a random coil conformation and thereby can mediate an increased in vivo and/or in vitro stability to the clotting factor protein. Since the random coil domain does not adopt a stable structure or function by itself, the biological activity mediated by the clotting factor protein is essentially preserved. In other embodiments, the PAS sequences that form random coil domain are biologically inert, especially with respect to proteolysis in blood plasma, immunogenicity, isoelectric point/electrostatic behaviour, binding to cell surface receptors or internalisation, but are still biodegradable, which provides clear advantages over synthetic polymers such as PEG.

Non-limiting examples of the PAS sequences forming random coil conformation comprise an amino acid sequence selected from the group consisting of ASPAAPAPASPAAPAPSAPA (SEQ ID NO: 36), AAPASPAPAAPSAPAPAAPS (SEQ ID NO: 37), APSSPSPSAPSSPSPASPSS (SEQ ID NO: 38), APSPSPSAPSSPSPASPS (SEQ ID NO: 39), SSPSAPSPSSPASPSPSSPA (SEQ ID NO: 40), AASPAAPSAPPAAASPAAPSAPPA (SEQ ID NO: 41), ASAAAPAAASAAASAPSAAA (SEQ ID NO: 42) and any combinations thereof. Additional examples of PAS sequences are known from, e.g., US Pat. Publ. No. 2010/0292130 A1 and PCT Appl. Publ. No. WO 2008/155134 A1.

8. HAP Sequence

In certain embodiments, the heterologous moiety is a glycine-rich homo-amino-acid polymer (HAP). The HAP sequence can comprise a repetitive sequence of glycine, which has at least 50 amino acids, at least 100 amino acids, 120 amino acids, 140 amino acids, 160 amino acids, 180 amino acids, 200 amino acids, 250 amino acids, 300 amino acids, 350 amino acids, 400 amino acids, 450 amino acids, or 500 amino acids in length. In one embodiment, the HAP sequence is capable of extending half-life of a moiety fused to or linked to the HAP sequence. Non-limiting examples of the HAP sequence includes, but are not limited to $(Gly)_n$, $(Gly_4Ser)_n$ or $S(Gly_4Ser)_n$, wherein n is 1, 2, 3, 4, 5, 6, 7, 8, 9, 10, 11, 12, 13, 14, 15, 16, 17, 18, 19, or 20. In one embodiment, n is 20, 21, 22, 23, 24, 25, 26, 26, 28, 29, 30, 31, 32, 33, 34, 35, 36, 37, 38, 39, or 40. In another embodiment, n is 50, 60, 70, 80, 90, 100, 110, 120, 130, 140, 150, 160, 170, 180, 190, or 200.

9. Transferrin or Fragment Thereof

In certain embodiments, the heterologous moiety is transferrin or a fragment thereof. Any transferrin can be used to make the clotting factor proteins of the disclosure. As an example, wild-type human TF (TF) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov/), all of which are herein incorporated by reference in their entirety. Transferrin comprises two domains, N domain and C domain. N domain comprises two subdomains, N1 domain and N2 domain, and C domain comprises two subdomains, C1 domain and C2 domain.

In one embodiment, the transferrin heterologous moiety includes a transferrin splice variant. In one example, a transferrin splice variant can be a splice variant of human transferrin, e.g., Genbank Accession AAA61140. In another embodiment, the transferrin portion of the chimeric protein includes one or more domains of the transferrin sequence, e.g., N domain, C domain, N1 domain, N2 domain, C1 domain, C2 domain or any combinations thereof.

10. Clearance Receptors

In certain embodiments, the heterologous moiety is a clearance receptor, fragment, variant, or derivative thereof. LRP1 is a 600 kDa integral membrane protein that is implicated in the receptor-mediate clearance of a variety of proteins, such as Factor X. See, e.g., Narita et al., Blood 91:555-560 (1998).

11. Von Willebrand Factor or Fragments Thereof

In certain embodiments, the heterologous moiety is von Willebrand Factor (VWF) or one or more fragments thereof.

VWF (also known as F8VWF) is a large multimeric glycoprotein present in blood plasma and produced constitutively in endothelium (in the Weibel-Palade bodies), megakaryocytes (α-granules of platelets), and subendothelian connective tissue. The basic VWF monomer is a 2813 amino acid protein. Every monomer contains a number of specific domains with a specific function, the D' and D3 domains (which together bind to Factor VIII), the A1 domain (which binds to platelet GPIb-receptor, heparin, and/or possibly collagen), the A3 domain (which binds to collagen), the C1 domain (in which the RGD domain binds to platelet integrin αIIbβ3 when this is activated), and the "cysteine knot" domain at the C-terminal end of the protein (which VWF shares with platelet-derived growth factor (PDGF), transforming growth factor-β (TGFβ) and β-human chorionic gonadotropin (βHCG)).

The 2813 monomer amino acid sequence for human VWF is reported as Accession Number NP000543.2 in Genbank. The nucleotide sequence encoding the human VWF is reported as Accession Number NM000552.3 in Genbank. SEQ ID NO: 129 is the amino acid sequence encoded by SEQ ID NO: 128. The D' domain includes amino acids 764 to 866 of SEQ ID NO: 129. The D3 domain includes amino acids 867 to 1240 of SEQ ID NO: 44.

In plasma, 95-98% of FVIII circulates in a tight non-covalent complex with full-length VWF. The formation of this complex is important for the maintenance of appropriate plasma levels of FVIIII in vivo. Lenting et al., *Blood.* 92(11): 3983-96 (1998); Lenting et al., *J. Thromb. Haemost.* 5(7): 1353-60 (2007). When FVIII is activated due to proteolysis at positions 372 and 740 in the heavy chain and at position 1689 in the light chain, the VWF bound to FVIII is removed from the activated FVIII.

In certain embodiments, the heterologous moiety is full length von Willebrand Factor. In other embodiments, the heterologous moiety is a von Willebrand Factor fragment. As used herein, the term "VWF fragment" or "VWF fragments" used herein means any VWF fragments that interact with FVIII and retain at least one or more properties that are normally provided to FVIII by full-length VWF, e.g., preventing premature activation to FVIIIa, preventing premature proteolysis, preventing association with phospholipid membranes that could lead to premature clearance, preventing binding to FVIII clearance receptors that can bind naked FVIII but not VWF-bound FVIII, and/or stabilizing the FVIII heavy chain and light chain interactions. In a specific embodiment, the heterologous moiety is a (VWF) fragment comprising a D' domain and a D3 domain of VWF. The VWF fragment comprising the D' domain and the D3 domain can further comprise a VWF domain selected from the group consisting of an A1 domain, an A2 domain, an A3 domain, a D1 domain, a D2 domain, a D4 domain, a B1 domain, a B2 domain, a B3 domain, a C1 domain, a C2 domain, a CK domain, one or more fragments thereof, and any combinations thereof. Additional examples of the polypeptide having FVIII activity fused to the VWF fragment are disclosed in U.S. provisional patent application No. 61/667, 901, filed Jul. 3, 2012, and U.S. Publication No. 2015/0023959 A1, which are both incorporated herein by reference in its entirety.

12. Linker Moieties

In certain embodiments, the heterologous moiety is a peptide linker.

As used herein, the terms "peptide linkers" or "linker moieties" refer to a peptide or polypeptide sequence (e.g., a synthetic peptide or polypeptide sequence) which connects two domains in a linear amino acid sequence of a polypeptide chain.

In some embodiments, peptide linkers can be inserted between the therapeutic protein of the disclosure and a heterologous moiety described above, such as albumin. Peptide linkers can provide flexibility to the chimeric polypeptide molecule. Linkers are not typically cleaved, however such cleavage can be desirable. In one embodiment, these linkers are not removed during processing.

A type of linker which can be present in a chimeric protein of the disclosure is a protease cleavable linker which comprises a cleavage site (i.e., a protease cleavage site substrate, e.g., a factor XIa, Xa, or thrombin cleavage site) and which can include additional linkers on either the N-terminal of C-terminal or both sides of the cleavage site. These cleavable linkers when incorporated into a construct of the disclosure result in a chimeric molecule having a heterologous cleavage site.

In one embodiment, a therapeutic protein encoded by a nucleic acid molecule of the instant disclosure comprises two or more Fc domains or moieties linked via a cscFc linker to form an Fc region comprised in a single polypeptide chain. The cscFc linker is flanked by at least one intracellular processing site, i.e., a site cleaved by an intracellular enzyme. Cleavage of the polypeptide at the at least one intracellular processing site results in a polypeptide which comprises at least two polypeptide chains.

Other peptide linkers can optionally be used in a construct of the disclosure, e.g., to connect a clotting factor protein to an Fc region. Some exemplary linkers that can be used in connection with the disclosure include, e.g., polypeptides comprising GlySer amino acids described in more detail below.

In one embodiment, the peptide linker is synthetic, i.e., non-naturally occurring. In one embodiment, a peptide linker includes peptides (or polypeptides) (which can or cannot be naturally occurring) which comprise an amino acid sequence that links or genetically fuses a first linear sequence of amino acids to a second linear sequence of amino acids to which it is not naturally linked or genetically fused in nature. For example, in one embodiment the peptide linker can comprise non-naturally occurring polypeptides which are modified forms of naturally occurring polypeptides (e.g., comprising a mutation such as an addition, substitution or deletion). In another embodiment, the peptide linker can comprise non-naturally occurring amino acids. In another embodiment, the peptide linker can comprise naturally occurring amino acids occurring in a linear sequence that does not occur in nature. In still another embodiment, the peptide linker can comprise a naturally occurring polypeptide sequence.

For example, in certain embodiments, a peptide linker can be used to fuse identical Fc moieties, thereby forming a homodimeric scFc region. In other embodiments, a peptide linker can be used to fuse different Fc moieties (e.g. a wild-type Fc moiety and an Fc moiety variant), thereby forming a heterodimeric scFc region.

In another embodiment, a peptide linker comprises or consists of a gly-ser linker. In one embodiment, a scFc or cscFc linker comprises at least a portion of an immunoglobulin hinge and a gly-ser linker. As used herein, the term "gly-ser linker" refers to a peptide that consists of glycine and serine residues. In certain embodiments, said gly-ser linker can be inserted between two other sequences of the peptide linker. In other embodiments, a gly-ser linker is attached at one or both ends of another sequence of the peptide linker. In yet other embodiments, two or more gly-ser linker are incorporated in series in a peptide linker. In one embodiment, a peptide linker of the disclosure comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule) and a series of gly/ser amino acid residues.

Peptide linkers of the disclosure are at least one amino acid in length and can be of varying lengths. In one embodiment, a peptide linker of the disclosure is from about 1 to about 50 amino acids in length. As used in this context, the term "about" indicates +/- two amino acid residues. Since linker length must be a positive integer, the length of from about 1 to about 50 amino acids in length, means a length of from 1-3 to 48-52 amino acids in length. In another embodiment, a peptide linker of the disclosure is from about 10 to about 20 amino acids in length. In another embodiment, a peptide linker of the disclosure is from about 15 to about 50 amino acids in length. In another embodiment, a peptide linker of the disclosure is from about 20 to about 45 amino acids in length. In another embodiment, a peptide linker of the disclosure is from about 15 to about 35 or about 20 to about 30 amino acids in length. In another embodiment, a peptide linker of the disclosure is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 500, 1000, or 2000 amino acids in length. In one embodiment, a peptide linker of the disclosure is 20 or 30 amino acids in length.

In some embodiments, the peptide linker can comprise at least two, at least three, at least four, at least five, at least 10, at least 20, at least 30, at least 40, at least 50, at least 60, at least 70, at least 80, at least 90, or at least 100 amino acids. In other embodiments, the peptide linker can comprise at least 200, at least 300, at least 400, at least 500, at least 600, at least 700, at least 800, at least 900, or at least 1,000 amino acids. In some embodiments, the peptide linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. The peptide linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids.

Peptide linkers can be introduced into polypeptide sequences using techniques known in the art. Modifications can be confirmed by DNA sequence analysis. Plasmid DNA can be used to transform host cells for stable production of the polypeptides produced.

13. Monomer-Dimer Hybrids

In some embodiments, the therapeutic protein of the disclosure comprises a monomer-dimer hybrid molecule comprising a clotting factor.

The term "monomer-dimer hybrid" used herein refers to a chimeric protein comprising a first polypeptide chain and a second polypeptide chain, which are associated with each other by a disulfide bond, wherein the first chain comprises a clotting factor, e.g., FVIII, and a first Fc region and the second chain comprises, consists essentially of, or consists of a second Fc region without the clotting factor. The monomer-dimer hybrid construct thus is a hybrid comprising a monomer aspect having only one clotting factor and a dimer aspect having two Fc regions.

14. Expression Control Sequences

In some embodiments, the nucleic acid molecule of the disclosure further comprises at least one expression control sequence. An expression control sequence, as used herein, is any regulatory nucleotide sequence, such as a promoter sequence or promoter-enhancer combination, which facilitates the efficient transcription and translation of the coding nucleic acid to which it is operably linked. For example, the nucleic acid molecule of the disclosure can be operably linked to at least one transcription control sequence. The gene expression control sequence can, for example, be a mammalian or viral promoter, such as a constitutive or inducible promoter.

Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the disclosure also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In one embodiment, the disclosure includes expression of a transgene under the control of a tissue specific promoter and/or enhancer. In another embodiment, the promoter or other expression control sequence selectively enhances expression of the transgene in liver cells. In certain embodiments, the promoter or other expression control sequence selective enhances expression of the transgene in hepatocytes, sinusoidal cells, and/or endothelial cells. In one particular embodiment, the promoter or other expression control sequence selective enhances expression of the transgene in endothelial cells. In certain embodiments, the promoter or other expression control sequence selective enhances expression of the transgene in muscle cells, the central nervous system, the eye, the liver, the heart, or any combination thereof. Examples of liver specific promoters include, but are not limited to, a mouse thyretin promoter (mTTR), an endogenous human factor VIII promoter (F8), human alpha-1-antitrypsin promoter (hAAT), human albumin minimal promoter, and mouse albumin promoter. In a particular embodiment, the promoter comprises a mTTR promoter. The mTTR promoter is described in R. H. Costa et al., 1986, Mol. Cell. Biol. 6:4697. The F8 promoter is described in Figueiredo and Brownlee, 1995, J. Biol. Chem. 270:11828-11838. In some embodiments, the promoter is selected from a liver specific promoter (e.g., α1-antitrypsin (AAT)), a muscle specific promoter (e.g., muscle creatine kinase (MCK), myosin heavy chain alpha (αMHC), myoglobin (MB), and desmin (DES)), a synthetic promoter (e.g., SPc5-12, 2R5Sc5-12, dMCK, and tMCK), and any combination thereof.

In one embodiment, the promoter is selected from the group consisting of a mouse thyretin promoter (mTTR), an endogenous human factor VIII promoter (F8), human alpha-1-antitrypsin promoter (hAAT), human albumin minimal promoter, mouse albumin promoter, TTPp, a CASI promoter, a CAG promoter, a cytomegalovirus (CMV) promoter, α1-antitrypsin (AAT), muscle creatine kinase (MCK), myosin heavy chain alpha (αMHC), myoglobin (MB), desmin (DES), SPc5-12, 2R5Sc5-12, dMCK, and tMCK, a phosphoglycerate kinase (PGK) promoter and any combination thereof.

Expression levels can be further enhanced to achieve therapeutic efficacy using one or more enhancers. One or more enhancers can be provided either alone or together with one or more promoter elements. Typically, the expression control sequence comprises a plurality of enhancer elements and a tissue specific promoter. In one embodiment, an enhancer comprises one or more copies of the α-1-microglobulin/bikunin enhancer (Rouet et al., 1992, J. Biol. Chem. 267:20765-20773; Rouet et al., 1995, Nucleic Acids Res. 23:395-404; Rouet et al., 1998, Biochem. J. 334:577-584; Ill et al., 1997, Blood Coagulation Fibrinolysis 8:S23-S30). In another embodiment, an enhancer is derived from liver specific transcription factor binding sites, such as EBP, DBP, HNF1, HNF3, HNF4, HNF6, with Enh1, comprising HNF1, (sense)-HNF3, (sense)-HNF4, (antisense)-HNF1, (antisense)-HNF6, (sense)-EBP, (antisense)-HNF4 (antisense).

In a particular example, a promoter useful for the disclosure comprises SEQ ID NO: 69 (i.e., ET promoter), which is also known as GenBank No. AY661265. See also Vigna et al., *Molecular Therapy* 11(5):763 (2005). Examples of other suitable vectors and gene regulatory elements are described in WO 02/092134, EP1395293, or U.S. Pat. Nos. 6,808,905, 7,745,179, or 7,179,903, which are incorporated by reference herein in their entireties.

In one embodiment, the nucleic acid molecules of the present disclosure further comprises an intronic sequence. In some embodiments, the intronic sequence is positioned 5' to the nucleic acid sequence encoding the FVIII polypeptide. In some embodiments, the intronic sequence is a naturally occurring intronic sequence. In some embodiments, the intronic sequence is a synthetic sequence. In some embodiments, the intronic sequence is derived from a naturally occurring intronic sequence. In certain embodiments, the intronic sequence comprises the SV40 small T intron. In one embodiment, the intronic sequence comprises SEQ ID NO: 115.

In some embodiments, the nucleic acid molecule further comprises a post-transcriptional regulatory element. In certain embodiments, the post-transcriptional regulatory element comprises a mutated woodchuck hepatitis virus post-transcriptional regulatory element (WPRE). In one particular embodiment, the post-transcriptional regulatory element comprises SEQ ID NO: 120.

In some embodiments, the nucleic acid molecule comprises a microRNA (miRNA) binding site. In one embodiment, the miRNA binding site is a miRNA binding site for miR-142-3p. In other embodiments, the miRNA binding site is selected from a miRNA binding site disclosed by Rennie et al., *RNA Biol.* 13(6):554-560 (2016), and STarMirDB, available at http://sfold.wadsworth.org/starmirDB.php, which are incorporated by reference herein in their entirety.

In some embodiments, the nucleic acid molecule comprises one or more DNA nuclear targeting sequences (DTSs). A DTS promotes translocation of DNA molecules containing such sequences into the nucleus. In certain embodiments, the DTS comprises an SV40 enhancer sequence. In certain embodiments, the DTS comprises a c-Myc enhancer sequence. In some embodiments, DTSs are between the first ITR and the second ITR. In some embodiments, the DTS is 3' to the first ITR and 5' to the therapeutic protein. In other embodiments, the DTS is 3' to the therapeutic protein and 5' to the second ITR.

In some embodiments, the nucleic acid molecule further comprises a 3'UTR poly(A) tail sequence. In one embodiment, the 3'UTR poly(A) tail sequence comprises bGH poly(A). In one embodiment, the 3'UTR poly(A) tail comprises an actin poly(A) site. In one embodiment, the 3'UTR poly(A) tail comprises a hemoglobin poly(A) site.

In one particular embodiment, the 3'UTR poly(A) tail sequence comprises SEQ ID NO: 122.

III. Tissue Specific Expression

In certain embodiments, it will be useful to include within the vector one or more miRNA target sequences which, for example, are operably linked to the clotting factor transgene. Thus, the disclosure also provides at least one miRNA sequence target operably linked to the clotting factor nucleotide sequence or otherwise inserted within a vector. More than one copy of a miRNA target sequence included in the vector can increase the effectiveness of the system. Also included are different miRNA target sequences. For example, vectors which express more than one transgene can have the transgene under control of more than one miRNA target sequence, which can be the same or different. The miRNA target sequences can be in tandem, but other arrangements are also included. The transgene expression cassette, containing miRNA target sequences, can also be inserted within the vector in antisense orientation. Antisense orientation can be useful in the production of viral particles to avoid expression of gene products which can otherwise be toxic to the producer cells. In other embodiments, the vector comprises 1, 2, 3, 4, 5, 6, 7 or 8 copies of the same or different miRNA target sequence. However, in certain other embodiments, the vector will not include any miRNA target sequence. Choice of whether or not to include a miRNA target sequence (and how many) will be guided by known parameters such as the intended tissue target, the level of expression required, etc.

In one embodiment, the target sequence is an miR-223 target which has been reported to block expression most effectively in myeloid committed progenitors and at least partially in the more primitive HSPC. miR-223 target can block expression in differentiated myeloid cells including granulocytes, monocytes, macrophages, myeloid dendritic cells. miR-223 target can also be suitable for gene therapy applications relying on robust transgene expression in the lymphoid or erythroid lineage. miR-223 target can also block expression very effectively in human HSC.

In another embodiment, the target sequence is an miR142 target (tccataaagt aggaaacact aca (SEQ ID NO: 43)). In one embodiment, the vector comprises 4 copies of miR-142 target sequences. In certain embodiments, the complementary sequence of hematopoietic-specific microRNAs, such as miR-142 (142T), is incorporated into the 3' untranslated region of a vector, e.g., lentiviral vectors (LV), making the transgene-encoding transcript susceptible to miRNA-mediated down-regulation. By this method, transgene expression can be prevented in hematopoietic-lineage antigen presenting cells (APC), while being maintained in non-hematopoietic cells (Brown et al., Nat Med 2006). This strategy can imposes a stringent post-transcriptional control on transgene expression and thus enables stable delivery and long-term expression of transgenes. In some embodiments, miR-142 regulation prevents immune-mediated clearance of transduced cells and/or induce antigen-specific Regulatory T cells (T regs) and mediate robust immunological tolerance to the transgene-encoded antigen.

In some embodiments, the target sequence is an miR181 target. Chen C-Z and Lodish H, Seminars in Immunology (2005) 17(2):155-165 discloses miR-181, a miRNA specifically expressed in B cells within mouse bone marrow (Chen and Lodish, 2005). It also discloses that some human miRNAs are linked to leukemias.

The target sequence can be fully or partially complementary to the miRNA. The term "fully complementary" means that the target sequence has a nucleic acid sequence which is 100% complementary to the sequence of the miRNA which recognizes it. The term "partially complementary" means that the target sequence is only in part complementary to the sequence of the miRNA which recognizes it, whereby the partially complementary sequence is still recognized by the miRNA. In other words, a partially complementary target sequence in the context of the present disclosure is effective in recognizing the corresponding miRNA and effecting prevention or reduction of transgene expression in cells expressing that miRNA. Examples of the miRNA target sequences are described at WO2007/000668, WO2004/094642, WO2010/055413, or WO2010/125471, which are incorporated herein by reference in their entireties.

In some embodiments, the transgene expression is targeted to the liver. In certain embodiments, the transgene expression is targeted to hepatocytes. In other embodiment, the transgene expression is targeted to endothelial cells. In one particular embodiment, the transgene expression is targeted to any tissue that naturally expressed endogenous FVIII.

In some embodiments, the transgene expression is targeted to the central nervous system. In certain embodiments, the transgene expression is targeted to neurons. In some embodiments, the transgene expression is targeted to afferent neurons. In some embodiments, the transgene expression is targeted to efferent neurons. In some embodiments, the transgene expression is targeted to interneurons. In some embodiments, the transgene expression is targeted to glial cells. In some embodiments, the transgene expression is targeted to astrocytes. In some embodiments, the transgene expression is targeted to oligodendrocytes. In some embodiments, the transgene expression is targeted to microglia. In some embodiments, the transgene expression is targeted to ependymal cells. In some embodiments, the transgene expression is targeted to Schwann cells. In some embodiments, the transgene expression is targeted to satellite cells.

In some embodiments, the transgene expression is targeted to muscle tissue. In some embodiments, the transgene expression is targeted to smooth muscle. In some embodiments, the transgene expression is targeted to cardiac muscle. In some embodiments, the transgene expression is targeted to skeletal muscle.

In some embodiments, the transgene expression is targeted to the eye. In some embodiments, the transgene expression is targeted to a photoreceptor cell. In some embodiments, the transgene expression is targeted to retinal ganglion cell.

IV. Host Cells

The disclosure also provides a host cell comprising a nucleic acid molecule or vector of the disclosure. As used herein, the term "transformation" shall be used in a broad sense to refer to the introduction of DNA into a recipient host cell that changes the genotype and consequently results in a change in the recipient cell.

"Host cells" refers to cells that have been transformed with vectors constructed using recombinant DNA techniques and encoding at least one heterologous gene. The host cells of the present disclosure are preferably of mammalian origin; most preferably of human or mouse origin. Those skilled in the art are credited with ability to preferentially determine particular host cell lines which are best suited for their purpose. Exemplary host cell lines include, but are not limited to, CHO, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte), PER.C6®, NS0, CAP, BHK21, and HEK 293 (human kidney). In one particular embodiment, the host cell is selected from the group consisting of: a CHO cell, a HEK293 cell, a BHK21 cell, a PER.C6® cell, a NS0 cell, a CAP cell and any combination thereof. In some embodiments, the host cells of the present disclosure are of insect origin. In one particular embodiment, the host cells are SF9 cells. Host cell lines are typically available from commercial services, the American Tissue Culture Collection, or from published literature.

Introduction of the nucleic acid molecules or vectors of the disclosure into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

Host cells comprising the isolated nucleic acid molecules or vectors of the disclosure are grown in an appropriate growth medium. As used herein, the term "appropriate growth medium" means a medium containing nutrients required for the growth of cells. Nutrients required for cell growth can include a carbon source, a nitrogen source, essential amino acids, vitamins, minerals, and growth factors. Optionally, the media can contain one or more selection factors. Optionally the media can contain bovine calf serum or fetal calf serum (FCS). In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g., MEM, DMEM, DMEM/F12). In one embodiment, the medium is CDoptiCHO (Invitrogen, Carlsbad, CA.). In another embodiment, the medium is CD17 (Invitrogen, Carlsbad, CA.). Selection of a medium appropriate for the particular cell line used is within the level of those ordinary skilled in the art.

V. Preparation of Polypeptides

The disclosure also provides a polypeptide encoded by a nucleic acid molecule of the disclosure. In other embodiments, the polypeptide of the disclosure is encoded by a vector comprising the nucleic molecules of the disclosure. In yet other embodiments, the polypeptide of the disclosure is produced by a host cell comprising the nucleic molecules of the disclosure.

In other embodiments, the disclosure also provides a method of producing a polypeptide with clotting factor, e.g., FVIII, activity, comprising culturing a host cell of the disclosure under conditions whereby a polypeptide with clotting factor, e.g., FVIII, activity is produced, and recovering the polypeptide with clotting factor, e.g., FVIII, activity. In some embodiments, the expression of the polypeptide with clotting factor, e.g., FVIII, activity is increased relative to a host cell cultured under the same conditions but comprising a reference nucleotide sequence (e.g., SEQ ID NO: 16, the parental FVIII gene sequence).

In other embodiments, the disclosure provides a method of increasing the expression of a polypeptide with clotting factor, e.g., FVIII, activity comprising culturing a host cell of the disclosure under conditions whereby a polypeptide with clotting factor, e.g., FVIII, activity is expressed by the nucleic acid molecule, wherein the expression of the polypeptide with clotting factor, e.g., FVIII, activity is increased relative to a host cell cultured under the same conditions comprising a reference nucleic acid molecule (e.g., SEQ ID NO: 16, the parental FVIII gene sequence).

In other embodiments, the disclosure provides a method of improving yield of a polypeptide with clotting factor, e.g., FVIII, activity comprising culturing a host cell under conditions whereby a polypeptide with clotting factor, e.g., FVIII, activity is produced by the nucleic acid molecule disclosed herein, wherein the yield of polypeptide with clotting factor, e.g., FVIII, activity is increased relative to a host cell cultured under the same conditions comprising a reference nucleic acid sequence (e.g., SEQ ID NO: 16, the parental FVIII gene sequence).

The therapeutic protein, e.g. the clotting factor, of the disclosure can be synthesized in a transgenic animal, such as a rodent, goat, sheep, pig, or cow. The term "transgenic animals" refers to non-human animals that have incorporated a foreign gene into their genome. Because this gene is present in germline tissues, it is passed from parent to offspring. Exogenous genes are introduced into single-celled embryos (Brinster et al. 1985, Proc. Natl. Acad. Sci. USA 82:4438). Methods of producing transgenic animals are known in the art including transgenics that produce immunoglobulin molecules (Wagner et al. 1981, Proc. Natl. Acad. Sci. USA 78: 6376; McKnight et al. 1983, Cell 34: 335; Brinster et al. 1983, Nature 306: 332; Ritchie et al. 1984, Nature 312: 517; Baldassarre et al. 2003, Theriogenology 59: 831; Robl et al. 2003, Theriogenology 59: 107; Malassagne et al. 2003, Xenotransplantation 10 (3): 267).

VII. Pharmaceutical Composition

Compositions containing a nucleic acid molecule, a polypeptide encoded by the nucleic acid molecule, a vector, or a host cell of the present disclosure can contain a suitable pharmaceutically acceptable carrier. For example, they can contain excipients and/or auxiliaries that facilitate processing of the active compounds into preparations designed for delivery to the site of action.

In one embodiment, the present disclosure is directed to a pharmaceutical composition comprising (a) a nucleic acid molecule, a vector, a polypeptide, or a host cell disclosed herein; and (b) a pharmaceutically acceptable excipient.

In some embodiments, the pharmaceutical composition further comprises a delivery agent. In certain embodiments, the delivery agent comprises a lipid nanoparticle (LNP). In other embodiments, the pharmaceutical composition further comprises liposomes, other polymeric molecules, and exosomes.

As used herein a "lipid nanoparticle" refers to a nanoparticle that comprises a plurality of lipid molecules physically associated with each other by intermolecular forces. The lipid nanoparticles may be, e.g., microspheres (including unilamellar and multilamellar vesicles, e.g. liposomes), a dispersed phase in an emulsion, micelles or an internal phase in a suspension.

In some embodiments, the present disclosure provides an encapsulated nucleic acid molecule composition which may include a lipid nanoparticle host encapsulating a nucleic acid molecule of the invention. The lipid nanoparticle may comprise one or more lipids (e.g., cationic lipids, non-cationic lipids, and PEG-modified lipids). In certain embodiments, lipid nanoparticles of the present disclosure are formulated to deliver one or more nucleic acid molcules of the invention to one or more target cells. Examples of suitable lipids include, without limitation, phosphatidyl compounds (e.g., phosphatidylethanolamine, sphingolipids, phosphatidylcholine, phosphatidylserine, phosphatidylglycerol, gangliosides, and cerebrosides). A "cationic lipid" refers to any lipid species that carry a net positive charge at a certain pH (e.g., physiological pH).

In certain embodiments, the lipid nanoparticles of the present disclosure have a certain N/P ratio. As used herein "N/P ratio" or "NP ratio" refers to the ratio of positively-chargeable polymer amine groups to negatively-charged nucleic acid phosphate groups. The N/P character of a lipid nanoparticle/nucleic acid molecule complex can influence properties such as net surface charge, stability, and size. The NP ratio of the lipid nanoparticles as described herein may be about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, and any ratio in between. For example, the NP ratio of the lipid nanoparticles as described herein may be about 18, about 36, or about 72.

Accordingly, in certain embodiments, a pharmaceutical composition comprises a nucleic acid molecule of the present disclosure encapsulated in a lipid nanoparticle, and a pharmaceutically acceptable excipient.

The pharmaceutical composition can be formulated for parenteral administration (i.e. intravenous, subcutaneous, or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

Suitable formulations for parenteral administration also include aqueous solutions of the active compounds in water-soluble form, for example, water-soluble salts. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides. Aqueous injection suspensions can contain substances, which increase the viscosity of the suspension, including, for example, sodium carboxymethyl cellulose, sorbitol and dextran. Optionally, the suspension can also contain stabilizers. Liposomes also can be used to encapsulate the molecules of the disclosure for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In other embodiments, the compositions comprise pharmaceutically acceptable substances such as wetting agents or minor amounts of auxiliary substances such as wetting or emulsifying agents, preservatives or buffers, which enhance the shelf life or effectiveness of the active ingredients.

Compositions of the disclosure can be in a variety of forms, including, for example, liquid (e.g., injectable and infusible solutions), dispersions, suspensions, semi-solid and solid dosage forms. The preferred form depends on the mode of administration and therapeutic application.

The composition can be formulated as a solution, micro emulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The active ingredient can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See, e.g., Sustained and Controlled Release Drug Delivery Systems, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the compositions. In one embodiment, the nucleic acid molecule of the disclosure is formulated with a clotting factor, or a variant, fragment, analogue, or derivative thereof. For example, the clotting factor includes, but is not limited to, factor V, factor VII, factor VIII, factor IX, factor X, factor XI, factor XII, factor XIII, prothrombin, fibrinogen, von Willebrand factor or recombinant soluble tissue factor (rsTF) or activated forms of any of the preceding. The clotting factor of hemostatic agent can also include anti-fibrinolytic drugs, e.g., epsilon-amino-caproic acid, tranexamic acid.

Dosage regimens can be adjusted to provide the optimum desired response. For example, a single bolus can be administered, several divided doses can be administered over time, or the dose can be proportionally reduced or increased as indicated by the exigencies of the therapeutic situation. It is advantageous to formulate parenteral compositions in dosage unit form for ease of administration and uniformity of dosage. See, e.g., Remington's Pharmaceutical Sciences (Mack Pub. Co., Easton, Pa. 1980).

In addition to the active compound, the liquid dosage form can contain inert ingredients such as water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols, and fatty acid esters of sorbitan.

Non-limiting examples of suitable pharmaceutical carriers are also described in Remington's Pharmaceutical Sciences by E. W. Martin. Some examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal administration, the composition can take the form of tablets or lozenges according to conventional protocols.

For administration by inhalation, the compounds for use according to the present disclosure are conveniently delivered in the form of a nebulized aerosol with or without excipients or in the form of an aerosol spray from a pressurized pack or nebulizer, with optionally a propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can also be formulated for rectal administration as a suppository or retention enema, e.g., containing conventional suppository bases such as cocoa butter or other glycerides.

In some embodiments, the composition is administered by a route selected from the group consisting of topical administration, intraocular administration, parenteral administration, intrathecal administration, subdural administration and oral administration. The parenteral administration can be intravenous or subcutaneous administration.

VIII. Methods of Treatment

In some aspects, the present disclosure is directed to methods of treating a disease or condition in a subject in need thereof, comprising administering a nucleic acid molecule, a vector, a polypeptide, or a pharmaceutical composition disclosed herein.

In some embodiments, the nucleic acid molecule comprises a first ITR, a second ITR, and a genetic cassette, wherein the genetic cassette encodes a target sequence, wherein the target sequence encodes a therapeutic protein, and wherein the nucleic acid molecule is used to treat a disease or condition in a subject in need thereof. In some embodiments, the disease or condition affects an organ selected from the muscle, central nervous system (CNS), ocular, liver, heart, kidney, pancreas, lungs, skin, bladder, urinary tract, and any combination thereof. In some embodiments, the subject has a disease or condition selected from the group consisting of DMD (Duchenne muscular dystrophy), XLMTM (X-linked myotubular myopathy), Parkinson, SMA (spinal muscular atrophy), Friedreich's Ataxia, GUCY2D-LCA (Leber Congenital Amaurosis), XLRS (X-Linked Retinoschisis), AMD (Age-related Macular Degeneration), ACHM (Achromatopsia), RPF65 mediated IRD, and any combination thereof.

In some embodiments, the nucleic acid molecule comprises a first ITR, a second ITR, and a genetic cassette, wherein the genetic cassette encodes a target sequence, wherein the target sequence encodes a miRNA, and wherein the nucleic acid molecule is used to treat a disease or condition in a subject in need thereof. In some embodiments, the disease or condition comprises Amyotrophic lateral sclerosis (ALS), Huntington's disease, and/or autosomal dominant retinitis pigmentosa.

In some embodiments, the nucleic acid molecule comprises a first ITR, a second ITR, and a genetic cassette, wherein the genetic cassette encodes a target sequence, wherein the target sequence encodes a clotting factor, and wherein the nucleic acid molecule is used to treat a bleeding disease or condition in a subject in need thereof. The bleeding disease or condition is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath and any combinations thereof. In still other embodiments, the subject is scheduled to undergo a surgery. In yet other embodiments, the treatment is prophylactic or on-demand.

The disclosure provides a method of treating a bleeding disorder comprising administering to a subject in need thereof a nucleic acid molecule, vector, or polypeptide of the disclosure. In some embodiments, the bleeding disorder is characterized by a deficiency in a clotting factor, e.g., FVIII. In some embodiments, the bleeding disorder is hemophilia. In some embodiments, the bleeding disorder is hemophilia A. In some embodiments of the method of treating a bleeding disorder, plasma activity of a clotting factor, e.g., FVIII, at 24 hours post administration is increased relative to a subject administered a reference nucleic acid molecule (e.g., SEQ ID NO: 16, the parental FVIII gene sequence), a vector comprising a reference nucleic acid molecule, or a polypeptide encoded by a reference nucleic acid molecule.

The disclosure also relates to a method of treating, ameliorating, or preventing a hemostatic disorder in a subject comprising administering a therapeutically effective amount of an isolated nucleic acid molecule of the disclosure or a polypeptide having clotting factor, e.g., FVIII, activity encoded by the nucleic acid molecule of the disclosure. The treatment, amelioration, and prevention by the isolated nucleic acid molecule or the encoded polypeptide can be a bypass therapy. The subject receiving bypass therapy can have already developed an inhibitor to a clotting factor, e.g., FVIII, or is subject to developing a clotting factor inhibitor.

The nucleic acid molecules, vectors, or polypeptides of the disclosure treat or prevent a hemostatic disorder by promoting the formation of a fibrin clot. The polypeptide having clotting factor, e.g., FVIII, activity encoded by the nucleic acid molecule of the disclosure can activate a member of a coagulation cascade. The clotting factor can be a participant in the extrinsic pathway, the intrinsic pathway or both.

The nucleic acid molecules, vectors, or polypeptides of the disclosure can be used to treat hemostatic disorders known to be treatable with a clotting factor. The hemostatic disorders that can be treated using methods of the disclosure include, but are not limited to, hemophilia A, hemophilia B, von Willebrand's disease, Factor XI deficiency (PTA deficiency), Factor XII deficiency, as well as deficiencies or structural abnormalities in fibrinogen, prothrombin, Factor V, Factor VII, Factor X, or Factor XIII, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath.

In some embodiments, the hemostatic disorder is an inherited disorder. In one embodiment, the subject has hemophilia A. In other embodiments, the hemostatic disorder is the result of a deficiency in a clotting factor. In other embodiments, the hemostatic disorder is the result of a deficiency in FVIII. In other embodiments, the hemostatic disorder can be the result of a defective FVIII clotting factor.

In another embodiment, the hemostatic disorder can be an acquired disorder. The acquired disorder can result from an underlying secondary disease or condition. The unrelated condition can be, as an example, but not as a limitation, cancer, an autoimmune disease, or pregnancy. The acquired disorder can result from old age or from medication to treat an underlying secondary disorder (e.g., cancer chemotherapy).

The disclosure also relates to methods of treating a subject that does not have a hemostatic disorder or a secondary disease or condition resulting in acquisition of a hemostatic disorder. The disclosure thus relates to a method of treating a subject in need of a general hemostatic agent comprising administering a therapeutically effective amount of the isolated nucleic acid molecule, vector, or polypeptide of the disclosure. For example, in one embodiment, the subject in need of a general hemostatic agent is undergoing, or is about to undergo, surgery. The isolated nucleic acid molecule, vector, or polypeptide of the disclosure can be administered prior to or after surgery as a prophylactic. The isolated nucleic acid molecule, vector, or polypeptide of the disclosure can be administered during or after surgery to control an acute bleeding episode. The surgery can include, but is not limited to, liver transplantation, liver resection, or stem cell transplantation.

In another embodiment, the isolated nucleic acid molecule, vector, or polypeptide of the disclosure can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding.

The isolated nucleic acid molecule, vector, or protein can be used to prophylactically treat a subject with a hemostatic disorder. The isolated nucleic acid molecule, vector, or protein can be used to treat an acute bleeding episode in a subject with a hemostatic disorder.

In another embodiment, expression of the clotting factor protein by administering the isolated nucleic acid molecule or vector of the disclosure does not induce an immune response in a subject. In some embodiments, the immune response comprises development of antibodies against a clotting factor. In one embodiment, the immune response comprises development of antibodies against FVIII. In some embodiments, the immune response comprises cytokine secretion. In some embodiments, the immune response comprises activation of B cells, T cells, or both B cells and T cells. In some embodiments, the immune response is an inhibitory immune response, wherein the immune response in the subject reduces the activity of a clotting factor protein relative to the activity of the clotting factor in a subject that has not developed an immune response. In certain embodiments, expression of a clotting factor protein by administering the isolated nucleic acid molecule or vector, of the disclosure prevents an inhibitory immune response against the clotting factor protein or the clotting factor protein expressed from the isolated nucleic acid molecule or the vector.

In some embodiments, an isolated nucleic acid molecule, vector, or protein composition of the disclosure is administered in combination with at least one other agent that promotes hemostasis. Said other agent that promotes hemostasis in a therapeutic with demonstrated clotting activity. As an example, but not as a limitation, the hemostatic agent can include FV, FVII, FIX, FX, FXI, FXII, FXIII, prothrombin, or fibrinogen or activated forms of any of the preceding. The clotting factor or hemostatic agent can also include anti-fibrinolytic drugs, e.g., epsilon-amino-caproic acid, tranexamic acid.

In one embodiment of the disclosure, the composition (e.g., the isolated nucleic acid molecule, vector, or polypeptide) is one in which the clotting factor is present in activatable form when administered to a subject. Such an activatable molecule can be activated in vivo at the site of clotting after administration to a subject.

Accordingly, in some embodiments, the present disclosure provides a method of treating a bleeding disorder in a subject in need thereof, comprising administering to the subject a nucleic acid molecule comprising a first inverted terminal repeat (ITR) and a second ITR flanking a genetic cassette comprising a heterologous polynucleotide sequence encoding a clotting factor, wherein the first ITR and/or second ITR are an ITR of a non-adeno-associated virus (non-AAV).

In some embodiments, the present disclosure provides a method of treating a bleeding disorder in a subject in need thereof, comprising administering to the subject a nucleic acid molecule comprising a first inverted terminal repeat (ITR) and a second ITR flanking a genetic cassette comprising a heterologous polynucleotide sequence encoding a clotting factor, wherein the first ITR and/or second ITR comprises a nucleotide sequence set forth in SEQ ID NO: 180, 181, 183, 184, 185, 186, 187 or 188. In some embodiments, the present disclosure provides a method of treating a bleeding disorder in a subject in need thereof, comprising administering to the subject a nucleic acid molecule comprising a first inverted terminal repeat (ITR) and a second ITR flanking a genetic cassette comprising a heterologous polynucleotide sequence encoding a clotting factor, wherein the first ITR and/or second ITR comprises a nucleotide sequence at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NO: 180, 181, 183, 184, 185, 186, 187 or 188, or a functional derivative thereof.

Accordingly, in some embodiments, the present disclosure provides a method of treating hemophilia A in a subject in need thereof, comprising administering to the subject a nucleic acid molecule comprising a first inverted terminal repeat (ITR) and a second ITR flanking a genetic cassette comprising a heterologous polynucleotide sequence encoding factor VIII, wherein the first ITR and/or second ITR are an ITR of a non-adeno-associated virus (non-AAV). In some embodiments, the present disclosure provides a method of treating hemophilia A in a subject in need thereof, comprising administering to the subject a nucleic acid molecule comprising a first inverted terminal repeat (ITR) and a second ITR flanking a genetic cassette comprising a heterologous polynucleotide sequence encoding factor VIII, wherein the first ITR and/or second ITR comprises a nucleotide sequence set forth in SEQ ID NO: 180, 181, 183, 184, 185, 186, 187 or 188. In some embodiments, the present disclosure provides a method of treating hemophilia A in a subject in need thereof, comprising administering to the subject a nucleic acid molecule comprising a first inverted terminal repeat (ITR) and a second ITR flanking a genetic cassette comprising a heterologous polynucleotide sequence encoding factor VIII, wherein the first ITR and/or second ITR comprises a nucleotide sequence at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NO: 180, 181, 183, 184, 185, 186, 187 or 188, or a functional derivative thereof.

Figure 7E:
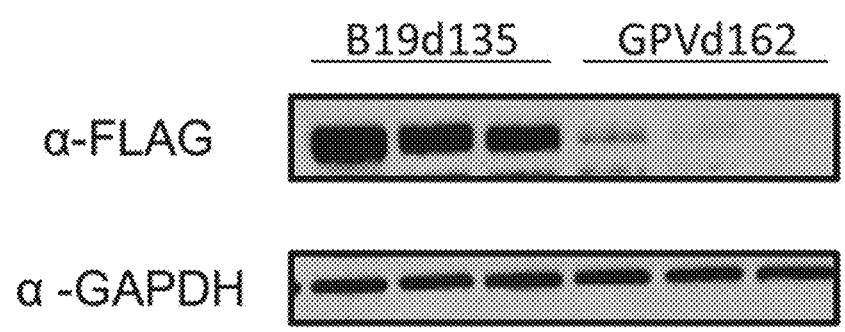
FIG. 7E shows a Western immunoblot of liver lysates from PKU mice treated with ssDNA containing the murine PAH transgene and either B19d135 or GPVd165 ITRs. Livers were collected at day 81 post treatment and protein lysates were extracted. Each well represents a single animal. The FLAG-tagged murine PAH protein was detected using the M2 anti-FLAG antibody and a GAPDH loading control was included for comparison.

The disclosure also provides a method of treating a metabolic disorder of the liver comprising administering to a subject in need thereof a nucleic acid molecule, vector, or polypeptide of the disclosure. In some embodiments, the metabolic disorder of the liver is selected from the group consisting of phenylketonuria ( FIG. 7E shows a Western immunoblot of liver lysates from PKU mice treated with ssDNA containing the murine PAH transgene and either B19d135 or GPCd165 ITRs. Livers were collected at day 81 post treatment and protein lysates were extracted. Each well represents a single animal. The FLAG-tagged murine PAH protein was detected using the M2 anti-FLAG antibody and a GAPDH loading control is included for comparison.)

a urea cycle disease (e.g., a deficiency in transcarbamylase (OTC), or argininosuccinate synthetase (ASS)), a lysosomal storage disorder (e.g., mucopolysaccharidoses), and a glycogen storage disease (e.g., Type I, II, III, IV glycogen storage disease). Other metabolic disorders of the liver include, without limitation, Wilson's disease, alpha-1 antitrypsin deficiency, gestational alloimmune liver disease (GALD), fatty acid oxidation defects, galactosemia, lipid storage diseases, tyrosinemia, and peroxisomal disorders.

In some embodiments, the present disclosure provides a method of treating a metabolic disorder of the liver in a subject in need thereof, comprising administering to the subject a nucleic acid molecule comprising a first inverted terminal repeat (ITR) and a second ITR flanking a genetic cassette comprising a heterologous polynucleotide sequence encoding a liver-associated metabolic enzyme that is deficient in the subject, wherein the first ITR and/or second ITR are an ITR of a non-adeno-associated virus (non-AAV). In some embodiments, the present disclosure provides a method of treating a metabolic disorder of the liver in a subject in need thereof, comprising administering to the subject a nucleic acid molecule comprising a first inverted terminal repeat (ITR) and a second ITR flanking a genetic cassette comprising a heterologous polynucleotide sequence encoding a therapeutic protein (e.g., a protein required for proper metabolic function of the liver), wherein the first ITR and/or second ITR comprises a nucleotide sequence set forth in SEQ ID NO: 180, 181, 183, 184, 185, 186, 187 or 188. In some embodiments, the present disclosure provides a method of treating a metabolic disorder of the liver in a subject in need thereof, comprising administering to the subject a nucleic acid molecule comprising a first inverted terminal repeat (ITR) and a second ITR flanking a genetic cassette comprising a heterologous polynucleotide sequence encoding a therapeutic protein (e.g., a protein required for proper metabolic function of the liver), wherein the first ITR and/or second ITR comprises a nucleotide sequence at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NO: 180, 181, 183, 184, 185, 186, 187 or 188, or a functional derivative thereof.

In some embodiments, the present disclosure provides a method of treating a phenylketonuria (PKU) in a subject in need thereof, comprising administering to the subject a nucleic acid molecule comprising a first inverted terminal repeat (ITR) and a second ITR flanking a genetic cassette comprising a heterologous polynucleotide sequence encoding phenylalanine hydroxylase (PAH), wherein the first ITR and/or second ITR are an ITR of a non-adeno-associated virus (non-AAV). In some embodiments, the present disclosure provides a method of treating phenylketonuria (PKU) in a subject in need thereof, comprising administering to the subject a nucleic acid molecule comprising a first inverted terminal repeat (ITR) and a second ITR flanking a genetic cassette comprising a heterologous polynucleotide sequence encoding phenylalanine hydroxylase (PAH), wherein the first ITR and/or second ITR comprises a nucleotide sequence set forth in SEQ ID NO: 180, 181, 183, 184, 185, 186, 187 or 188. In some embodiments, the present disclosure provides a method of treating phenylketonuria (PKU) in a subject in need thereof, comprising administering to the subject a nucleic acid molecule comprising a first inverted terminal repeat (ITR) and a second ITR flanking a genetic cassette comprising a heterologous polynucleotide sequence encoding phenylalanine hydroxylase, wherein the first ITR and/or second ITR comprises a nucleotide sequence at least about 75%, at least about 80%, at least about 85%, at least about 90%, at least about 95%, at least about 96%, at least about 97%, at least about 98%, at least about 99%, or 100% identical to a nucleotide sequence set forth in SEQ ID NO: 180, 181, 183, 184, 185, 186, 187 or 188, or a functional derivative thereof.

The isolated nucleic acid molecule, vector, or polypeptide can be administered intravenously, subcutaneously, intramuscularly, or via any mucosal surface, e.g., orally, sublingually, buccally, sublingually, nasally, rectally, vaginally or via pulmonary route. The clotting factor protein can be implanted within or linked to a biopolymer solid support that allows for the slow release of the chimeric protein to the desired site.

For oral administration, the pharmaceutical composition can take the form of tablets or capsules prepared by conventional means. The composition can also be prepared as a liquid for example a syrup or a suspension. The liquid can include suspending agents (e.g. sorbitol syrup, cellulose derivatives or hydrogenated edible fats), emulsifying agents (lecithin or acacia), non-aqueous vehicles (e.g. almond oil, oily esters, ethyl alcohol, or fractionated vegetable oils), and preservatives (e.g. methyl or propyl-p-hydroxybenzoates or sorbic acid). The preparations can also include flavoring, coloring and sweetening agents. Alternatively, the composition can be presented as a dry product for constitution with water or another suitable vehicle.

For buccal and sublingual administration, the composition can take the form of tablets, lozenges or fast dissolving films according to conventional protocols.

For administration by inhalation, the polypeptide having clotting factor activity for use according to the present disclosure are conveniently delivered in the form of an aerosol spray from a pressurized pack or nebulizer (e.g., in PBS), with a suitable propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

In one embodiment, the route of administration of the isolated nucleic acid molecule, vector, or polypeptide is parenteral. The term parenteral as used herein includes intravenous, intraarterial, intraperitoneal, intramuscular, subcutaneous, rectal or vaginal administration. The intravenous form of parenteral administration is preferred. While all these forms of administration are clearly contemplated as being within the scope of the disclosure, a form for administration would be a solution for injection, in particular for intravenous or intraarterial injection or drip. Usually, a suitable pharmaceutical composition for injection can comprise a buffer (e.g. acetate, phosphate or citrate buffer), a surfactant (e.g. polysorbate), optionally a stabilizer agent (e.g. human albumin), etc. However, in other methods compatible with the teachings herein, the isolated nucleic acid molecule, vector, or polypeptide can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject disclosure, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

The pharmaceutical composition can also be formulated for rectal administration as a suppository or retention enema, e.g., containing conventional suppository bases such as cocoa butter or other glycerides.

Effective doses of the compositions of the present disclosure, for the treatment of conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages can be titrated using routine methods known to those of skill in the art to optimize safety and efficacy.

The nucleic acid molecule, vector, or polypeptides of the disclosure can optionally be administered in combination with other agents that are effective in treating the disorder or condition in need of treatment (e.g., prophylactic or therapeutic).

As used herein, the administration of isolated nucleic acid molecules, vectors, or polypeptides of the disclosure in conjunction or combination with an adjunct therapy means the sequential, simultaneous, coextensive, concurrent, concomitant or contemporaneous administration or application of the therapy and the disclosed polypeptides. Those skilled in the art will appreciate that the administration or application of the various components of the combined therapeutic regimen can be timed to enhance the overall effectiveness of the treatment. A skilled artisan (e.g., a physician) would be readily be able to discern effective combined therapeutic regimens without undue experimentation based on the selected adjunct therapy and the teachings of the instant specification.

It will further be appreciated that the isolated nucleic acid molecule, vector, or polypeptide of the instant disclosure can be used in conjunction or combination with an agent or agents (e.g., to provide a combined therapeutic regimen). Exemplary agents with which a polypeptide or polynucleotide of the disclosure can be combined include agents that represent the current standard of care for a particular disorder being treated. Such agents can be chemical or biologic in nature. The term "biologic" or "biologic agent" refers to any pharmaceutically active agent made from living organisms and/or their products which is intended for use as a therapeutic.

The amount of agent to be used in combination with the polynucleotides or polypeptides of the instant disclosure can vary by subject or can be administered according to what is known in the art. See, e.g., Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., 9th ed. 1996). In another embodiment, an amount of such an agent consistent with the standard of care is administered.

In one embodiment, also disclosed herein is a kit, comprising the nucleic acid molecule disclosed herein and instructions for administering the nucleic acid molecule to a subject in need thereof. In another embodiment, disclosed herein is a baculovirus system for production of the nucleic acid molecule provided herein. The nucleic acid molecule is produced in insect cells. In another embodiment, a nanoparticle delivery system for expression constructs is provided. The expression construct comprises the nucleic acid molecule disclosed herein.

IX. Gene Therapy

Certain aspects of the present disclosure provide a method of expressing a genetic construct in a subject, comprising administering the isolated nucleic acid molecule of the disclosure to a subject in need thereof. In some aspects, the disclosure provides a method of increasing expression of a polypeptide in a subject comprising administering the isolated nucleic acid molecule of the disclosure to a subject in need thereof. In other aspects, the disclosure provides a method of modulating expression of a polypeptide in a subject in need thereof comprising administering an isolated nucleic acid molecule of the disclosure, e.g., a nucleic acid sequence comprising a miRNA, to the subject. In some aspects, the disclosure provides a method of down regulating the expression of a target gene in a subject in need thereof comprising administering an isolated nucleic acid molecule of the disclosure, e.g., a nucleic acid sequence comprising a miRNA, to the subject.

Somatic gene therapy has been explored as a possible treatment for a variety of conditions, including, but not limited to, hemophilia A. Gene therapy is a particularly appealing treatment for hemophilia because of its potential to cure the disease through continuous endogenous production of a clotting factor, e.g., FVIII, following a single administration of vector. Haemophilia A is well suited for a gene replacement approach because its clinical manifestations are entirely attributable to the lack of a single gene product (e.g., FVIII) that circulates in minute amounts (200 ng/ml) in the plasma.

The use of conventional viral based gene delivery has been shown to induce an immune response in humans. Viral capsid proteins can trigger various components of the human immune system. AAV based gene delivery has been attractive as AAV is a common virus in the human population, most people have been exposed to AAV, and AAV has been shown to be less immunogenic than, e.g., Adenovirus. Accordingly, most people have already developed an immune response against the particular variants to which they had previously been exposed. This pre-existing adaptive response can include NAbs and T cells that could diminish the clinical efficacy of subsequent re-infections with AAV and/or the elimination of cells that have been transduced, which disqualifies patients with pre-existing anti-AAV immunity to AVV based gene therapy treatment. The nucleic acid molecules of the present disclosure find use in non-viral based gene therapy. As viral capsids are not necessary for gene delivery using the nucleic acid molecules of the present disclosure, no immunity will be developed to viral components barring the subsequent re-administration (or re-dosing) of a subject. As such, the nucleic acid molecules of the present disclosure allow for re-dosing for long term gene delivery strategies.

In addition, as described herein, the nucleic acid molecules of the present disclosure comprise non-AAV parvoviral ITRs flanking a genetic cassette to drive stable transgene expression upon administration. The presence of the ITRs are necessary for stable transgene expression, as shown in FIG. 5, where nucleic acids without ITRs were unable to effect stable transgene expression (see, "dsDNA no ITR" and "minicircle").

A clotting factor protein of the disclosure can be produced in vivo in a mammal, e.g., a human patient, using a gene therapy approach to treatment of a bleeding disease or disorder selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath would be therapeutically beneficial. In one embodiment, the bleeding disease or disorder is hemophilia. In another embodiment, the bleeding disease or disorder is hemophilia A.

Other conditions are also suitable for treatment using the nucleic acid molecules disclosed herein. In certain embodiments, the methods described herein are used for treating a disease or condition that affects a target organ selected from the muscle, central nervous system (CNS), ocular, liver, heart, kidney, pancreas, lungs, skin, bladder, urinary tract, or any combination thereof. In certain embodiments, the methods described herein are used for treating a disease or condition selected from DMD (Duchenne muscular dystrophy), XLMTM (X-linked myotubular myopathy), Parkinson, SMA (spinal muscular atrophy), Friedreich's Ataxia, GUCY2D-LCA (Leber Congenital Amaurosis), XLRS (X-Linked Retinoschisis), AMD (Age-related Macular Degeneration), ACHM (Achromatopsia), RPF65 mediated IRD (Table 9).

TABLE 9

Diseases and disorders treatable by the methods disclosed herein.

| Disease | Target organ | Defective gene | Gene therapy |
|---|---|---|---|
| DMD (Duchenne muscular dystrophy) | Muscle | Dystrophin X-linked | Gene introduction |
| XLMTM (X-linked myotubular myopathy) | Muscle | MTM1 (myotubularin) | Gene introduction |
| Parkinson | CNS | Tyrosine hydroxylase, AADC, cyclohydrolase | Gene introduction |
| SMA (spinal muscular atrophy) | CNS | SMN1 | Gene introduction |
| Friedreich's Ataxia | CNS | FXN (Frataxin) | Gene introduction |
| GUCY2D-LCA Leber Congenital Amaurosis | Ocular | GUCY2D | Gene introduction |
| XLRS X-Linked Retinoschisis | Ocular | RS1 | Gene introduction |
| AMD Age-related Macular Degeneration | Ocular | CFH HTRA ARMS CFB/CC2 | Gene introduction |
| ACHM Achromatopsia | Ocular | CNGA/CNGB | Gene introduction |
| RPF65 mediated IRD | Ocular | Prf65 | Gene introduction |
| Lysosomal storage disorders | | | |
| MLD metachromatic leukodystrophy (Lysosomal storage disorder) | CNS | ARSA PSAP | Gene introduction |
| MPS Mucopolysaccharidoses (Lysosomal storage disorder) | Liver | IDUA (MPS I) IDS (MPS II) | Gene introduction |
| PKU Phenylketonuria (Lysosomal storage disorder) | Liver | PAH | Gene introduction |
| Pompe Glycogen storage disease type II | Heart, liver, muscle, CNS | GAA (acid alpha-glucosidase) | Gene introduction |
| Micro RNA therapies | | | |
| ALS Amyotrophic lateral sclerosis | CNS | SOD1[1] | miRNA |
| Huntington's disease | CNS | HTT[2] | miRNA |
| AdRP Autosomal Dominant Retinitis Pigmentosa | Ocular | RHO[3] (Rhodopsin) | miRNA |

[1]Mutation of SOD1 gene accounted to 20% of the inherited ALS case. Wildtype SOD1 has demonstrated antiapoptotic properties in neural cultures, while mutant SOD1 has been observed to promote apoptosis in spinal cord mitochondria, but not in liver mitochondria, though it is equally expressed in both. Down regulate mutated SOD1 expression might inhibit motor neuron degeneration in ALS.
[2]HD is one of several trinucleotide repeat disorders which are caused by the length of a repeated section of a gene exceeding a normal range. HTT contains a sequence of three DNA bases - cytosine-adenine-guanine (CAG) - repeated multiple times (i.e. . . . CAGCAGCAG . . . ), known as a trinucleotide repeat. CAG is the 3-letter genetic code (codon) for the amino acid glutamine, so a series of them results in the production of a chain of glutamine known as a polyglutamine tract (or polyQ tract), and the repeated part of the gene, the PolyQ region. Generally, people have fewer than 36 repeated glutamines in the polyQ region which results in production of the cytoplasmic protein Huntingtin. However, a sequence of 36 or more glutamines results in the production of a protein which has different characteristics. This altered form, called mutant huntingtin (mHTT), increases the decay rate of certain types of neurons. Generally, the number of CAG repeats is related to how much this process is affected, and accounts for about 60% of the variation of the age of the onset of symptoms. The remaining variation is attributed to environment and other genes that modify the mechanism of HD. 36-39 repeats result in a reduced-penetrance form of the disease, with a much later onset and slower progression of symptoms. In some cases the onset may be so late that symptoms are never noticed. With very large repeat counts, HD has full penetrance and can occur under the age of 20, when it is then referred to as juvenile HD, akinetic-rigid, or Westphal variant HD. This accounts for about 7% of HD carriers.
[3]Most of the RHO gene mutations responsible for retinitis pigmentosa alter the folding or transport of the rhodopsin protein. A few mutations cause rhodopsin to be constitutively activated instead of being activated in response to light. Studies suggest that altered versions of rhodopsin interfere with essential cell functions, causing rods to self-destruct (undergo apoptosis). Because rods are essential for vision under low-light conditions, the loss of these cells leads to progressive night blindness in people with retinitis pigmentosa.

In some embodiments, the methods described herein are used for treating a lysosomal storage disorder. In some embodiments, the lysosomal storage disorder is selected from MLD (metachromatic leukodystrophy), MPS (mucopolysaccharidoses), PKU (phenylketonuria), pompe glycogen storage disease type II, or any combination thereof.

In some embodiments, the methods described herein are used in a microRNA (miRNA) therapy. In some embodiments, the miRNA treats a condition caused by the overexpression of a gene or a protein. In some embodiments, the miRNA treats a condition caused by the accumulation of a protein. In some embodiments, the miRNA treats a condition caused by the misexpression of a gene or protein. In some embodiments, the miRNA treats a condition caused by the expression of a mutant gene. In some embodiments, the miRNA treats a condition caused by the expression of an heterologous gene. In certain embodiments, the miRNA therapy treats a condition selected from ALS (amytrophic lateral sclerosis), Huntington's disease, AdRP (autosomal dominant retinitis pigmentosa), and any combination thereof. In certain embodiments, the methods of the present disclosure comprise targeting treating ALS by administering a nucleic acid molecule disclosed herein, wherein the nucleic acid molecule comprises a genetic cassette encoding a miRNA, wherein the miRNA targets the expression of SOD1. In certain embodiments, the miRNA comprises the miR SOD1 artificial miRNA disclosed by Dirren et al., *Annals of Clinical and Translational Neurology* 2(2):167-84 (February 2015). Mutation of SOD1 gene accounts for 20% of inherited ALS cases. Wildtype SOD1 has demonstrated antiapoptotic properties in neural cultures, while mutant SOD1 has been observed to promote apoptosis in spinal cord mitochondria, but not in liver mitochondria, though it is equally expressed in both. Down regulation of mutated SOD1 expression might inhibit motor neuron degeneration in ALS.

In certain embodiments, the methods of the present disclosure comprise targeting treating Huntington's disease by administering a nucleic acid molecule disclosed herein, wherein the nucleic acid molecule comprises a genetic cassette encoding a miRNA, wherein the miRNA targets the expression of HTT. In certain embodiments, the miRNA comprises the miHTT engineered miRNA disclosed by Evers et al., *Molecular Therapy* 26(9):1-15 (epub ahead of print June 2018). Huntington's disease is one of several trinucleotide repeat disorders which are caused by the length of a repeated section of a gene exceeding a normal range. HTT contains a sequence of three DNA bases—cytosine-adenine-guanine (CAG)—repeated multiple times (i.e. . . . CAGCAGCAG . . . ), which is known as a trinucleotide repeat. CAG is the 3-letter genetic code (codon) for the amino acid glutamine, so a series of these repeats results in the production of a chain of glutamine known as a polyglutamine tract (or polyQ tract), and the repeated part of the gene, the PolyQ region. Generally, people have fewer than 36 repeated glutamines in the polyQ region which results in production of the cytoplasmic protein huntingtin. However, a sequence of 36 or more glutamines results in the production of a protein which has different characteristics. This altered form, called mutant huntingtin (mHTT), increases the decay rate of certain types of neurons. Generally, the number of CAG repeats is related to how much this process is affected, and accounts for about 60% of the variation of the age of the onset of symptoms. The remaining variation is attributed to environment and other genes that modify the mechanism of Huntington's disease. 36-39 repeats result in a reduced-penetrance form of the disease, with a much later onset and slower progression of symptoms. In some cases the onset may be so late that symptoms are never noticed. With very large repeat counts, Huntington's disease has full penetrance and can occur under the age of 20, when it is then referred to as juvenile Huntington's disease, akinetic-rigid, or Westphal variant Huntington's disease. This accounts for about 7% of Huntington's disease carriers.

In certain embodiments, the methods of the present disclosure comprise targeting treating Autosomal Dominant Retinitis Pigmentosa (AdRP) by administering a nucleic acid molecule disclosed herein, wherein the nucleic acid molecule comprises a genetic cassette encoding a miRNA, wherein the miRNA targets the expression of RHO (rhodopsin). In certain embodiments, the miRNA comprises miR-708 (see Behrman et al., *JCB* 192(6):919-27 (2011). Most of the RHO gene mutations responsible for retinitis pigmentosa alter the folding or transport of the rhodopsin protein. A few mutations cause rhodopsin to be constitutively activated instead of being activated in response to light. Studies suggest that altered versions of rhodopsin interfere with essential cell functions, causing rods to self-destruct (undergo apoptosis). Because rods are essential for vision under low-light conditions, the loss of these cells leads to progressive night blindness in people with retinitis pigmentosa.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

Having generally described this disclosure, a further understanding can be obtained by reference to the examples provided herein. These examples are for purposes of illustration only and are not intended to be limiting.

EXAMPLES

Example 1. Generation of FVIII Expression Constructs Bearing AAV and Non-AAV Parvoviral ITRs Example 1a. Cloning of Codon-Optimized FVIII Gene and Inverted Terminal Repeat (ITR) Regions from AAV into Genetic Cassettes FVIII genetic cassette was generated based on the genome of AAV serotype 2. However, ITR regions originated from any serotype (including synthetic) can be used in this approach (FIG. 1A).

Expression plasmid AAV2-FVIIIco6XTEN encoding a codon-optimized FVIII coding sequence under the regulation of a liver-specific promoter (TTPp) or a ubiquitous promoter (CAGp, FIGS. 1A and 1B) flanked by inverted terminal repeat (ITR) regions from AAV (AAV-FVIII) was designed for in vitro and in vivo expression, as shown in FIG. 1C. The genetic cassette also contains WPRE and bGHpA elements for optimal expression of the transgene (FIGS. 1A-1C). ITR-flanked codon-optimized FVIII sequence was cloned into a plasmid backbone comprising a ColE1 origin of replication and an expression cassette for beta-lactamase, which confers ampicillin resistance (FIG. 1C). Recognition sites for the restriction endonuclease PvuII flanking the expression cassette were engineered to allow for precise excision of the AAV-FVIII construct upon PvuII digestion (FIG. 1C).

Figure 2A:
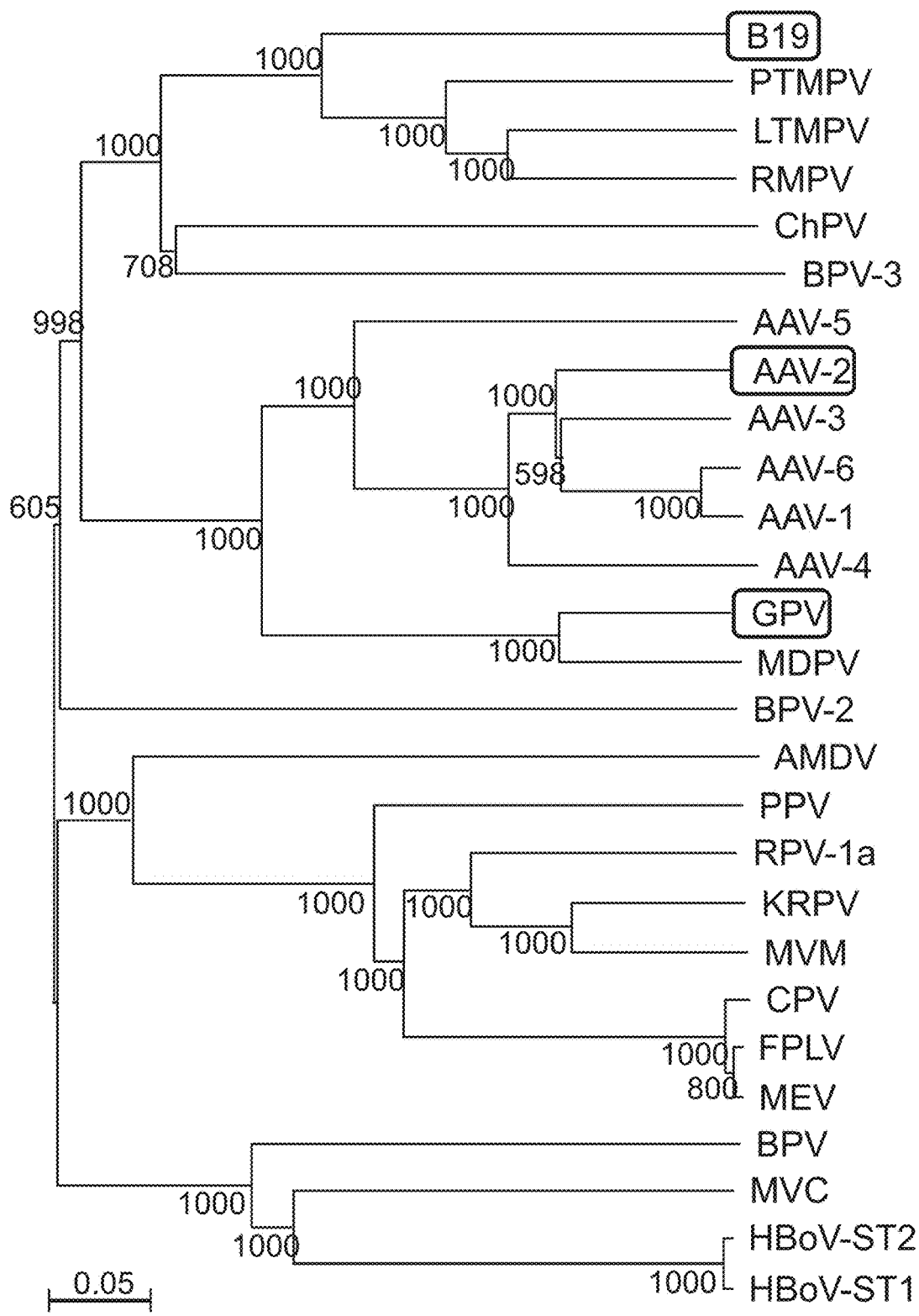
FIG. 2A is a phylogenetic tree illustrating that relationships between various parvovirus family members. B19, AAV-2, and GPV are marked by outlined boxes.

Example 1b. Cloning of Codon-Optimized FVIII Gene and Inverted Terminal Repeat (ITR) Regions from Non-AAV Parvoviruses into Genetic Cassettes Based on the phylogenic relationship between the members of the viral family Parvoviridae, which AAV belongs to (FIG. 2A), it was hypothesized that other non-AAV members of the genus *Dependovirus* and the members of the genus *Erythrovirus* utilize similar cellular mechanisms for the maintenance of the viral life cycle and establishment of persistent, latent infection. Therefore, the ITR regions originated from the genomes of these viruses could be utilized to develop AAV-like (but not AAV-based) genetic expression cassettes. The following parvoviruses were tested for the suitability of their ITR regions for the development of genetic constructs for gene therapy applications: *dependovirus* Goose parvovirus (GPV) strain B and *erythrovirus* B19 parvovirus (FIG. 2A).

Instability of parviral ITR regions during propagation of plasmid vectors in bacterial cells presents a challenge for the generation and manipulation of genetic constructs. Some genetic constructs containing the full-length AAV2 ITRs (145 nt) have been successfully generated but these constructs are highly unstable and most AAV2 ITR-based plasmids contain a truncated 130 nt version of the ITR region (exemplified in Table 1). Similarly, the plasmid constructs bearing full-length sequences of both B19 and GPV ITRs that were generated exhibited a high degree of instability in bacterial host (data not shown), which significantly limits the utility of these ITRs for the development of genetic vectors for gene therapy applications.

Figure 1D:
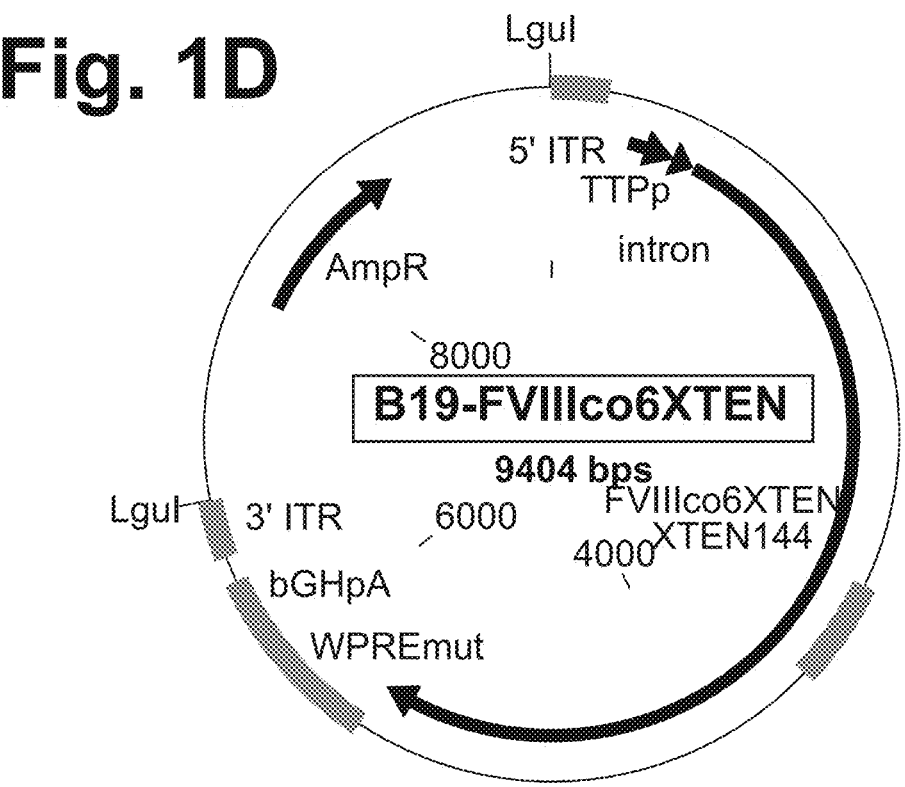
Figure 1E:
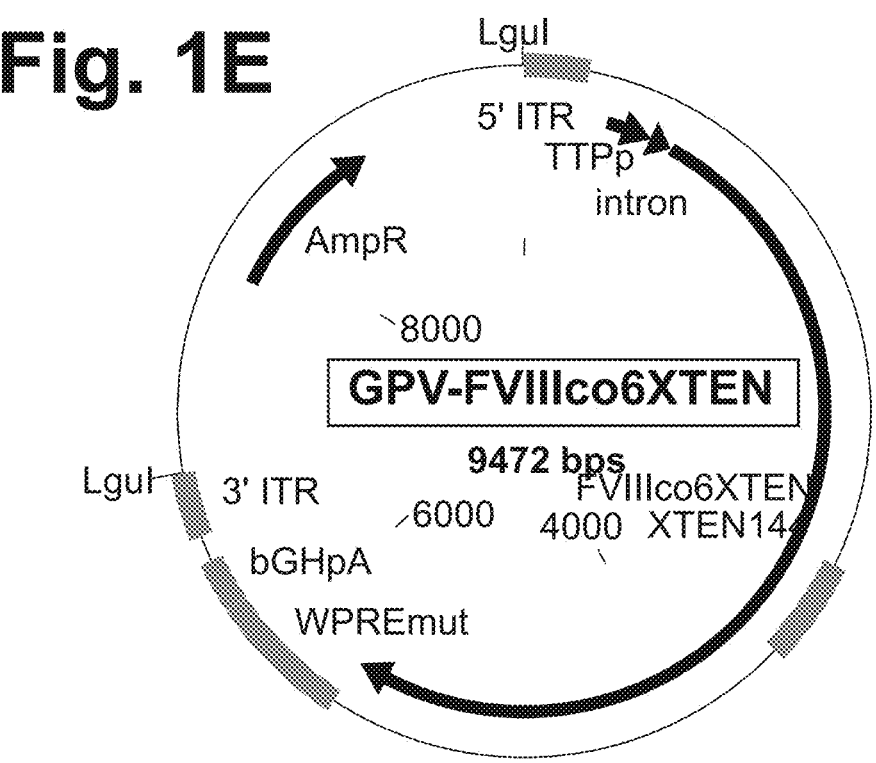
Figure 2B:
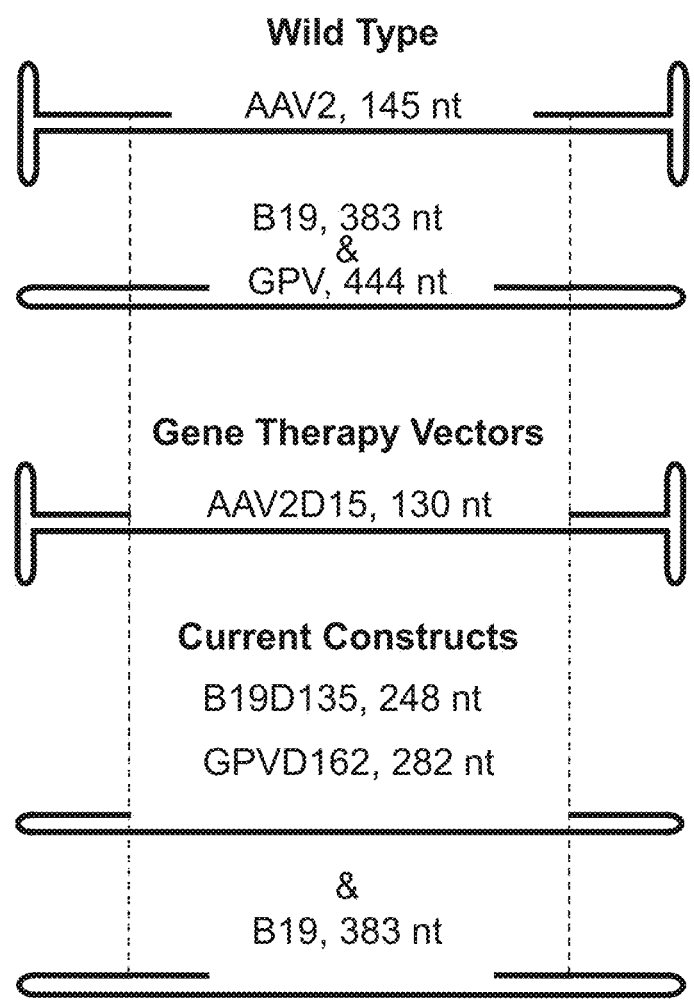
FIG. 2B is a schematic drawing of the various cassettes, including the hairpin structures.

Previously, a reverse genetics system for the rescue of recombinant B19 virus has been developed bearing a truncated version of the ITR (Manaresi, et al. Virology 508 (2017): 54-62) (Table 2B, ITR ID: B19d135). Thus, B19d135 ITR was utilized to generate a genetically stable FVIII expression plasmid B19-FVIIIco6XTEN (FIG. 1D). To further utilize this approach for the synthesis of the GPV ITR-based construct, full-length wild type sequences of B19, GPV, and AAV2 ITRs were compared (FIG. 3A). Based on the homology to the first 135 and 15 nucleotides of B19 and AVV2 ITR sequences, respectively, that are dispensable for ITR function, it was hypothesized that the first 162 nucleotides of the GPV ITR could be removed in order to synthesize stable genetic constructs with fully functional ITRs (FIG. 3A, boxed sequences). Therefore, similarly to the constructs AAV2-FVIIIco6XTEN and B19-FVIIIco6XTEN that bear truncated versions of their corresponding ITRs, GPVd162 was used (Table 2C) to generate a stable FVIII expression plasmid construct GPV-FVIIIco6XTEN (FIG. 1E). Notably, both full-length B19 and GPV ITRs are much longer than full-length AAV2 ITR (Table 1) and do not form the distinctive T-shaped hairpin structure of AAV ITRs (FIG. 2B).

Plasmids containing full length B19 ITR sequences exhibited a high degree of instability in bacterial host cells as a FVIIIco6XTEN expression construct containing only the 3'ITR could be generated. Using standard molecular cloning techniques, no positive clones could be obtained that contained both the 5' and 3' full length B19 ITRs. In order to generate a FVIIIco6XTEN expression construct, B19 wt-FVIIIco6XTEN, flanked by the full length B19 ITRs (FIG. 1F), the specific host E. coli strain PMC103 was used. PMC103 contains a deletion in the gene sbcC, which encodes an exonuclease that recognizes and eliminates cruciform DNA structures. Without being bound by theory, it was thought that use of the strain PMC103, lacking sbcC, may allow for the replication of long palindromes (i.e., sequences that contain complex secondary structure) and successful cloning of B19 wt-FVIIIco6XTEN as well as GPVwt-FVIIIco6XTEN. The resulting plasmid encodes the 383 base pair wildtype B19 5' and 3' ITR sequence (Table 2D) and another plasmid encodes the 444 base pair wildtype GPV 5' and 3' ITR sequence (Table 2F).

Figure 1F:
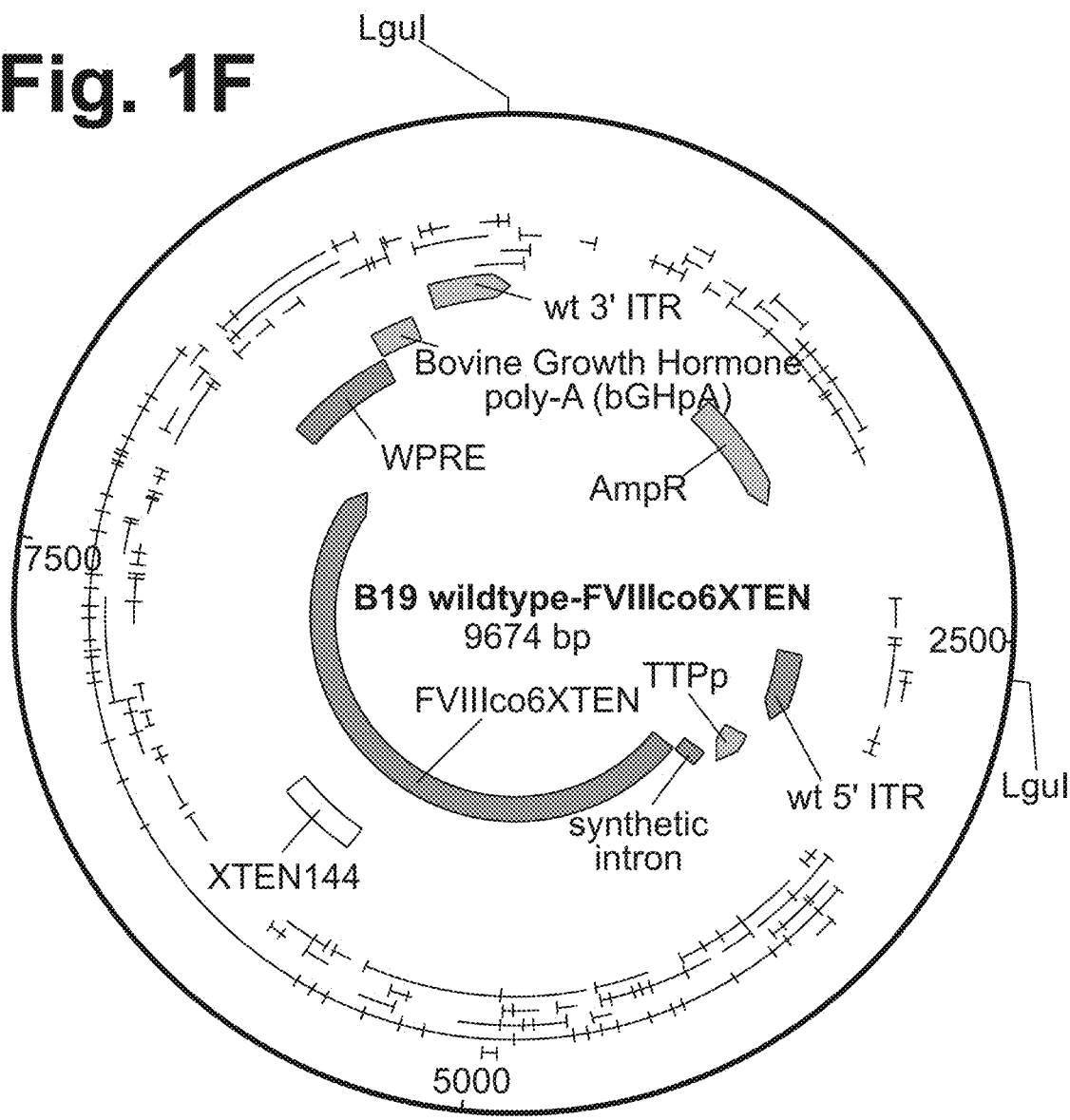

The plasmids B19-FVIIIco6XTEN (FIG. 1D; Table 2B), GPV-FVIIIco6XTEN (FIG. 1E; Table 2C) and B19 wt-FVIIIco6XTEN (FIG. 1F, Table 2D) containing FVIII-expression cassettes flanked by non-AAV parvoviral ITRs (B19d135, GPVd162, and B19 wt) were generated as described in Example 1a. Recognition sites for the restriction endonuclease LguI were used to flank all FVIII expression cassettes (FIGS. 1D-1F).

Example 1c. Preparation of Single-Stranded DNA Fragments Containing FVIII Expression Cassettes Flanked with AAV and Non-AAV Parvoviral ITRs It was hypothesized that formation of hairpin structures within the ITR regions flanking the FVIII expression cassette would drive persistent transduction of target cells. For proof-of-concept studies, AAV ITR-based plasmid AAV2-FVIIIco6XTEN and non-AAV ITR-based plasmids B19-FVIIIco6XTEN and GPV-FVIIIco6XTEN were digested with PvuII and LguI, respectively. Single-stranded (ss) AAV-FVIII, B19-FVIII, or GPV-FVIII fragment with formed hairpin ITR structures were generated by denaturing the double-stranded DNA fragment products (FVIII expression cassette and plasmid backbone) of PvuII or LguI digestion at 95° C. and then cooling down at 4° C. to allow the palindromic ITR sequences to fold (FIG. 1A-1B). The resulting ssAAV-FVIII, ssB19-FVIII, or ssGPV-FVIII was tested in the HemA (hemophilia A) mouse model for the ability to establish persistent transduction of hepatocytes.

Example 1d. Use of a Baculovirus Expression System to Generate FVIII Expression Constructs A baculovirus expression system described in Li et al., PLoS ONE 8(8): e69879 (2013) for production of AAV-FVIII, B19-FVIII, and GPV-FVIII constructs in a form of closed-end DNA (ceDNA) molecules in insect cells will be utilized. Systemic delivery of ceDNA expression cassettes has been demonstrated to establish persistent transduction of hepatocytes and drive stable long-term transgene expression in the liver.

Example 2. Systemic Injection of Genetic Constructs Comprising FVIII Expression Cassettes Flanked by AAV and Non-AAV Parvoviral ITRs Results in Long-Term FVIII Expression in HemA Mice Example 2a. In Vivo Evaluation of ssAAV-FVIII-Mediated FVIII Expression To validate the ability of ssAAV-FVIII bearing AAV ITR regions to mediate persistent transgene expression in vivo, the genetic expression cassette was delivered systemically via hydrodynamic injection (HDI) in 5-12-week old hemophilia A (HemA) mice (4 animals/group) at 5 µg, 10 µg, 20 µg of ssDNA genetic expression cassette (ssAAV-FVIII) (FIG. 4A). HDI results in primary delivery of the injected material into the liver of experimental animals. Plasma samples were collected from experimental animals at 18 hours, 3 days, 2 weeks, 3 weeks, 1 month, 2 months, 3 months and 4 months after a single hydrodynamic injection of ssAAV-FVIII. FVIII plasma activity in blood was analyzed by chromogenic FVIII activity assay. Control animals injected with 5 µg/mouse of the parental expression plasmid showed high levels of FVIII plasma activity shortly after administration. However, the level of circulating FVIII rapidly declined and became undetectable by 15 days post-injection (p.i.). In contrast, the experimental animals injected with 5, 10, and 20 µg/mouse of ssAAV-FVIII developed long-term expression of the transgene with stable levels of circulating FVIII about 8, 16, and 32% of normal FVIII level, respectively (FIG. 4A). A strong dose response was observed suggesting a high degree of correlation between injected dose and treatment outcome.

Example 2b. In Vivo Evaluation of ssB19-FVIII- and ssGPV-FVIII-Mediated FVIII Expression To evaluate in vivo expression of FVIII from ssB19-FVIII and ssGPV-FVIII that bear non-AAV parvoviral ITR regions B19d135 and GPVd162, respectively, 10 or 20 µg/mouse of ssB19-FVIII, and 10 or 50 µg/mouse of ssGPV-FVIII genetic expression cassette was delivered systemically via HDI in 5-12-week old hemophilia A (HemA) mice. Blood samples were collected at 1, 3, 7, 14, 21, 28, 42, 56, 84, 112, 140, and 168 days p.i. and FVIII activity in blood was analyzed by the chromogenic FVIII activity assay. As observed with the AAV-FVIII construct, control animals injected with 5 µg/mouse of parental FVIII expression plasmid showed high levels of FVIII plasma activity at 24 hours p.i. that rapidly declined and became undetectable by 14 days p.i. The experimental animals injected with ssB19-FVIII showed peak FVIII plasma activity at 3 days p.i. that then gradually declined over the period of 21 days and stabilized around 28 days p.i. (FIG. 4B) The HemA mice injected with ssGPV-FVIII, on the other hand, developed stable levels of FVIII plasma activity around day 112 that were maintained during the remaining observation period (FIG. 4C). Notably, the animals injected with 10 µg/mouse of either ssAAV-FVIII (FIG. 4A) or ssGPV-FVIII (FIG. 4C) developed highly similar stable levels of FVIII plasma activity suggesting that both AAV2 and GPV ITR regions comprise genetic factors required for efficient establishment of persistent transduction of target cells.

Example 2c. In Vivo Evaluation of ITR and Hairpin Requirement for Stable Long-Term Expression of FVIII in hemA Mice To compare the stability and long-term expression of single-stranded DNA cassettes to alternative nucleic acid therapeutics, the FVIIIco6XTEN plasmid construct (FIG. 1A) was digested with PvuII or AflII to create double-stranded linear DNA with or without the AAV ITR sequences. The linear double stranded DNA without ITRs was purified to generate the 'dsDNA No ITR' construct. Finally, ligation of the purified dsDNA without ITRs via overlapping AflII recognition sites resulted in the formation of minicircle DNA. This small, circular, plasmid-like DNA construct is devoid of any bacterial sequence and/or ITR sequence. HemA mice were injected with equimolar concentrations of DNA construct via hydrodynamic injection and FVIII activity levels were determined from plasma collections over 2-4 months. All DNA constructs generated initial therapeutic levels of FVIII in the 30-60% normal range, however, only single-stranded DNA demonstrated stable persistence of transgene expression at 32% for 4 months post injection (FIG. 5). All double stranded DNA and minicircle DNA reached stable levels of expression at 6-10% normal at days 14-42, however, these plateaus represent only 10% of the initial FVIII activity observed. Because transient and elevated levels of FVIII expression can result in the formation of neutralizing anti-drug antibodies, stable expression is required for immune tolerance in a hemophilia A setting.

Example 2d. In Vivo Comparison of Wildtype and Derivative B19 ITRs

To compare the effect of a B19 derivative ITR (B19d135, FIG. 1D, Table 2C) to the full length B19 ITR (Table 2C), FVIIIco6XTEN expression cassette flanked by the 248 base pair ITRs (FIG. 1F) was generated. Hemophilia A mice were hydrodynamically injected with 30 µg single stranded FVIII-DNA flanked by either B19d135 (FIG. 1D), GPVd165 (FIG. 1E), or wildtype B19 ITRs (FIG. 1F). Plasma was collected at 3, 7, 14, 21, 28, and 35 days post injection for all cohorts, with additional samples taken at days 42, 55, and 84 for B19d135 and GPVd165 constructs and analyzed for FVIII activity by chromogenic assay (FIG. 6). Compared to the derivative B19 ITR, the full length ITR resulted in a roughly 2.5-fold increase in FVIII expression. Furthermore, the expression of FVIII from the wildtype ITR was stable at the onset.

Example 2e. Evaluation of Re-Administration of Single-Stranded Naked DNA In Vivo A critical limitation in current gene therapy modalities is the inability to re-administer the therapeutic due to the formation of anti-drug antibodies against the viral capsid of the gene therapy vector. However, gene therapy systems absent in immunogenic proteins could be re-dosed to titrate the patient to a desired therapeutic level. To evaluate if our non-AAV ITR flanked single stranded cassettes could be re-administered, hemA mice were injected with 30 µg ssDNA containing the B19d135 and GPVd165 ITRs at days 0 and 35 (FIG. 6). Mice administered GPVd165-FVIII reached stable FVIII levels of approximately 5% normal during the first month of observation. Following a second dose of ssDNA, the levels of FVIII rose to 10% before decreasing slightly, demonstrating a 2-fold increase in FVIII levels. Mice administered B19d135-FVIII reached stable FVIII levels of 8% during the first week which rose roughly 3.5-fold to 30% before decreasing to 25%. These data demonstrate the re-administration of single-stranded DNA with non-AAV ITRs can increase the stable expression levels of FVIII in hemophilia A mice.

Example 3. Generation and In Vivo Evaluation of FVIII Expression Constructs Bearing Derivatives of B19d135 and GPVd162 Non-AAV Parvoviral ITRs Example 3a. Determination of Minimal Essential Sequences of B19 and GPV ITRs Based on the comparison between the ITR sequences of dependoviruses AAV2 and GPV, and erythrovirus B19 (Gene Bank accession numers NC_001401.2, U25749.1, and KY940273.1, respectively), minimal sequences of GPV and B19 parvovirus ITRs were designed that would be required with or without additional sequences (spacers, insertions, inversions, additions, and/or recombination with wild-type sequences of other parvoviral ITRs) for persistent transduction of eukaryotic cells with genetic constructs bearing such ITRs (FIGS. 3A and 3B). Sequence alignment of AAV2, GPV, and B19 ITRs revealed conserved regions B19v1 and GPVv1 between all three viral species (presented in Tables 2A-2C) as continuous sequences without spacer regions of variable sequence. Likewise, minimal essential sequence variants B19v3 and GPVv3 were designed based on sequence comparison between B19 and GPV ITRs. Since FVIII expression constructs bearing GPVd162 ITRs performed better in in vivo experiments than genetic constructs bearing B19d135 ITRs, it was hypothesized that B19v3 sequence comprises minimal B19 ITR sequence regions that are conserved between B19 and GPV ITR sequences, and GPVv3 sequence comprises minimal GPV ITR sequence regions that are present in the GPV ITR sequence and are lacking from the B19 ITR sequence (Tables 2B and 2C). The sequences B19v2 and GPVv2 were generated by excluding the first 135 and 162 nucleotides and corresponding complementary 135 and 162 nucleotides in the ITR palindrome regions of the B19 and GPV ITR sequences, respectively (Tables 2B and 2C).

Example 3b. Orientation of the Palindromic Regions of B19 and GPV ITRs and their Derivatives on Functional Genetic Constructs Part of parvoviral ITRs consists of a self-complimentary palindromic region. It has previously been demonstrated for recombinant infectious B19 parvoviruses that rescued viruses bearing palindromic regions in direct and reverse orientations exhibit similar growth properties (Manaresi, et al. Virology 508 (2017): 54-62). Therefore, genetic expression constructs bearing B19 and GPV ITRs and their derivatives are proposed to remain functional regardless of whether the palindromic regions of such ITRs are in direct, reverse, or any possible combination of 5' and 3' ITR combination with respect to the genetic expression cassette. To validate this hypothesis, B19d135 and GPVd162 ITRs, as well as wildtype B19 and GPV ITRs will be incorporated in the FVIIIco6XTEN expression cassette in forward, reverse, and inverted orientations using identical as well as reverse complimentary sequences for ITRs of the same species. Single-stranded DNA from these plasmids will be generated and tested in hemophilia A mice for liver directed FVIII expression driven by the TTPp promoter as described in Example 2a, 2b, and 2d. In addition to investigating all orientations of ITRs of the same species, combinations of GPV and B19 wildtype ITR and derivatives thereof will also be generated and tested for FVIII expression in hemophilia A mice. These expression cassettes will contain one ITR of B19 origin and one ITR of GPV origin to determine if non-homologous ITR sequences can enhance episomal concatemerization and long-term expression of the desired transgene. Hemophilia A mice will be injected via hydrodynamic injection with 10, 20, or 50 µg ssDNA containing the aforementioned expression cassettes and FVIII will be measured from murine plasma collected at weekly intervals post injection. The affect on FVIII expression and longevity in mice administered these expression cassettes will be directly compared with FVIII expression and longevity in mice administered B19d135, GPVd162, and corresponding wildtype ITR expression cassettes (Tables 2B, 2C, 2D, and 2F).

Example 3c. Systemic Injection of Genetic Constructs Bearing Derivatives of B19d135 and GPVd162 Non-AAV Parvoviral ITRs in HemA Mice To evaluate FVIII in vivo expression from ssDNA constructs that bear derivatives of B19d135 and GPVd162 non-AAV parvoviral ITRs, 5, 10, 20, or 50 µg/mouse of each ssDNA genetic expression cassette will be delivered systemically via HDI in 5-12-week old HemA mice. Blood samples will be collected at 1, 3, 7, 14, 21, and 28 days p.i., and then once monthly for a period of 4 months. FVIII activity in blood will be analyzed by the chromogenic FVIII activity assay.

Example 4. Production and In Vivo Evaluation of ceDNA Expression Constructs Bearing Derivatives of B19d135 and GPVd162 Non-AAV Parvoviral ITRs in Insect Cells

Example 4a. Use of a Baculovirus Expression System to Generate ceDNA Expression Constructs Bearing Derivatives of B19d135 and GPVd162 ITRs Similarly to AAV-FVIII, B19-FVIII, and GPV-FVIII constructs described in Example 1d, the baculovirus expression system will be used for production of FVIII expression for genetic constructs bearing derivatives of B19d135 and GPVd162 non-AAV parvoviral ITRs in a form of ceDNA in insect cells.

Example 4b. Systemic Injection of ceDNA Expression Constructs Bearing Derivatives of B19d135 and GPVd162 Non-AAV Parvoviral ITRs in HemA Mice To evaluate FVIII in vivo expression from ceDNA constructs that bear derivatives of B19d135 and GPVd162 non-AAV parvoviral ITRs, 5, 10, 20, or 50 µg/mouse of each ceDNA genetic expression cassette will be delivered systemically via HDI in 5-12-week old HemA mice. Blood samples will be collected at 1, 3, 7, 14, 21, and 28 days p.i., and then once monthly for a period of 4 months. FVIII activity in blood will be analyzed by the chromogenic FVIII activity assay.

Example 5. Generation of Lipid Nanoparticle Formulations of ssDNA and ceDNA FVIII Expression Constructs After each ssDNA or ceDNA is produced as described in Examples 1 and 4, each genetic construct will be formulated into lipid nanoparticles (LNPs) using appropriate lipid compositions by microfluidic mixing (LNP-ssDNA and LNP-ceDNA). The ratio of lipid to DNA (N/P) will be adjusted to optimize cellular transduction and FVIII expression. The parental plasmids encoding FVIII expression cassettes flanked by either AAV or non-AAV parvoviral ITRs formulated into LNPs will be used as controls for transduction efficiency.

Example 6. In Vitro and In Vivo Evaluation of LNP-ssDNA and LNP-ceDNA

Figure 8A:
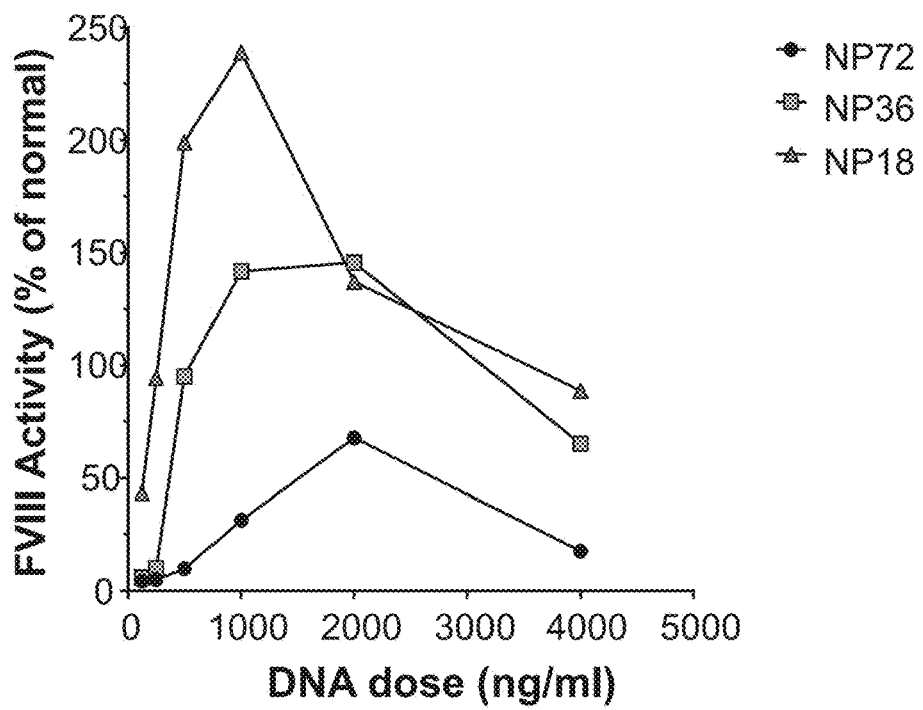
FIGS. 8A-B show FVIII activity levels in Huh7 cell supernatant following transduction with FVIII-AAV DNA (FIGS. 1A-1C) encapsulated lipid nanoparticles. Plasmid FVIII-AAV under the CAGp promoter (FIG. 1B) was encapsulated at three amine-to-phosphate (NP) ratios and applied to Huh7 cells at various concentrations determined by picogreen assay (FIG. 8A). Plasmid, double stranded linear (ds), and single-stranded (ss) AAV-FVIII under the TTPp promoter (FIG. 1A) was also encapsulated in lipid nanoparticles at two NP ratios and used to transduce Huh7 cells at various DNA concentrations (FIG. 8B). FVIII was measured by chromogenic activity assay compared to a human FACT plasma standard.
Figure 8B:
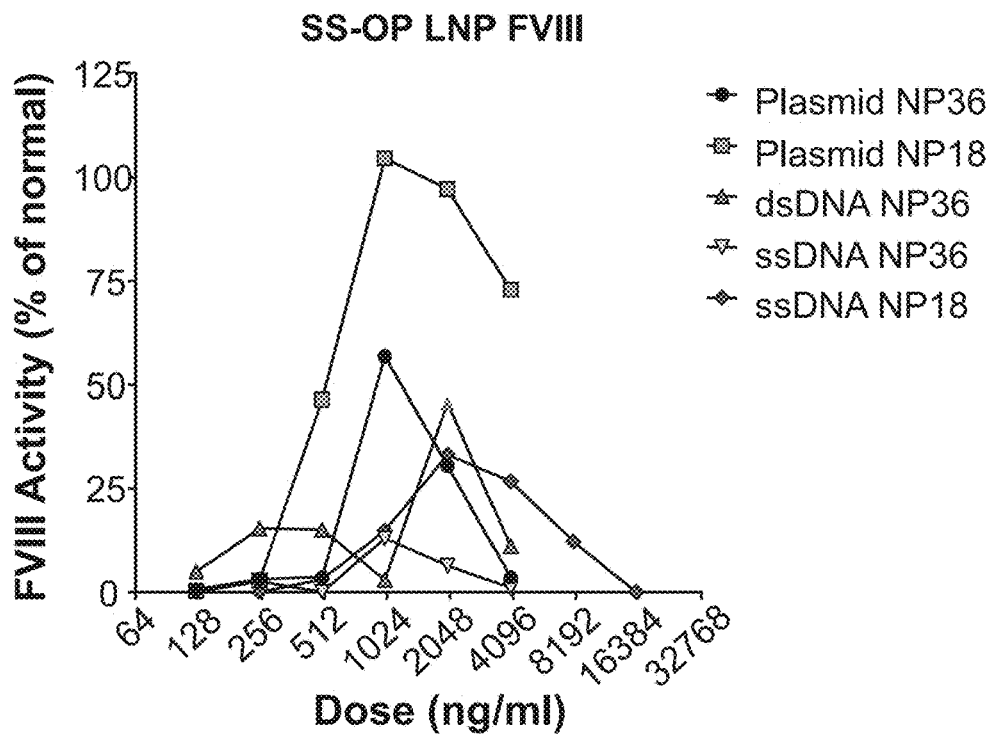

Example 6a. In Vitro Evaluation of ssDNA- and ceDNA-Mediated FVIII Expression in Cultured Hepatocytes ssDNA or ceDNA FVIII expression genetic constructs and corresponding parental control plasmids were formulated into LNPs, as described in Example 5, for targeted gene delivery. Huh7 cells were seeded into 24-well tissue culture plates at $1 \times 10^5$ cells/well and incubated overnight. On the next day, LNP-ssDNA or formulations were added onto the cells at 1000, 500, 250, 125 and 62.5 ng/well. Culture medium was harvested at 48 hours post-transduction following a media change at 24 hours post-transduction. FVIII activity in culture medium was measured by the chromogenic FVIII activity assay compared to a human plasma FACT standard. Plasmid bearing the FVIIIco6XTEN cassette under the CAGp promoter and flanked by AAV ITRs was encapsulated in lipid nanoparticles at N/P ratios of 72, 36, and 18 (FIG. 8A). Following transduction of Huh7 cells, FVIII was measured in the conditioned media. Transduction of cells with the N/P ratio of 18 generated increase FVIII levels of ratios of 36 and 72, with a peak dose of 1 µg/ml resulting in over 2 IU/ml. This data demonstrates the utility of LNP delivery in liver target cells. To investigate the transduction efficiency of ssDNA under a liver specific promoter via LNP delivery, the FVIIIco6XTEN cassette under the TTPp promoter was encapsulated at 2 N/p ratios and Huh7 cells were transduced (FIG. 8B). Consistent with our previous data (FIG. 8A), the N/P ratio of 18 resulted in increased FVIII activity levels compared to the ratio of 36. Additionally, this data demonstrated proof-of-concept LNP delivery of FVIII ssDNA in liver cells. After 24 hours, roughly $2\times10^5$ Huh7 cells transduced with 2 µg/ml single-stranded FVIIIco6XTEN-AAV produced 0.33 IU/ml FVIII.

In addition, it has been shown in the literature that cellular histones are regularly positioned along the rAAV episomes, creating a chromatin-like structure that is similar to the cellular chromosomal DNA nucleosome pattern. Therefore, the ability of these constructs to establish chromatin-like nucleosomal structures required for persistent transduction of target cells will also be assessed by Southern blot.

Example 6b. Evaluation of LNP-Formulated ssDNA- and ceDNA-Mediated Long-Term FVIII Expression in HemA Mice after Intravenous Administration 5-12-weeks old HemA mice will be administered either LNP-ssDNA, LNP-ceDNA, or LNP-pDNA (plasmid control) at 5, 10, 20, 40, 100 ug/mouse via IV injection, N=4/group. Blood samples will be collected at selected time points starting at 48 hours post-injection for up to 6 month and FVIII activity in blood will be analyzed by the chromogenic FVIII activity assay. FVIII expression profile in mice treated with LNP-ssDNA or LNP-ceDNA will be compared to that of mice treated with LNP-pDNA for each genetic construct described in Examples 1 and 4.

Example 6c. In Vivo Evaluation of ssDNA- or ceDNA-Mediated FVIII Expression after a Booster Injection A subset of mice treated with LNP-ssDNA or LNP-ceDNA in Example 6b will be given an additional IV injection boost of the corresponding LNPs at the same dose 2 months after the initial injection. Blood samples will be collected at selected time points starting at 48 hours after the booster injection for up to 6 months. FVIII activity in blood will be analyzed by the chromogenic FVIII activity assay. FVIII expression profile in mice treated with LNP-ssDNA or LNP-ceDNA will be compared to that of mice treated with corresponding LNP-pDNA.

Example 7. Utility of Genetic Expression Constructs Bearing ITRs of B19 or GPV Origin for General Use in Gene Therapy

Example 7a. Generation of Reporter Genetic Constructs Bearing ITRs of B19 or GPV Origin In order to demonstrate the utility of non-AAV ITR-based genetic expression systems as a platform for general use in gene therapy applications, reporter constructs comprising an expression cassette were generated with green fluorescent protein (GFP) or luciferase (luc) flanked with either B19d135 or GPVd162 ITRs based on the constructs described in Example 1b. Thus, the open reading frame (ORF) of FVIII in B19-FVIIIco6XTEN (FIG. 1C) and GPV-FVIIIco6XTEN (FIG. 1D) were replaced with either ORF of GFP or luc by conventional molecular cloning techniques.

Expression cassettes flanked by B19d135 or GPVd162 ITRs were also generated containing the murine phenylalanine hydroxylase (PAH) transgene (FIG. 7A), which were used to evaluate PAH expression and reduction of blood phenylalanine concentrations in a relevant mouse model of phenylketonuria. Using this model, PKU mice (n=3) were administered 200 µg of ssDNA flanked by non-AAV ITRs via hydrodynamic injection for liver expression. Blood samples were collected at days 3, 7, 14, 28, 42, 56, 70, and 81 and plasma was isolated for phenylalanine concentration determination (FIG. 7B-7C). Mice receiving the expression cassette containing the B19d135 ITR exhibited a reduction of phenylalanine levels from 370 µg/ml to 210 µg/ml at day 3 which was stably maintained through day 81 (FIG. 7B). Mice receiving the GPVd162 ITR cassette demonstrated reduction of blood phenylalanine levels from 350 µg/ml to 310 µg/ml at day 14 which continued to decline to a stable level of 250 µg/ml by day 42 (FIG. 7C). These decreases in blood phenylalanine concentrations represent a 45% and 30% reduction compared to concentrations prior to injection (FIG. 7D). To confirm the presence of murine PAH protein in the liver, a Western blot was performed on liver lysates taken from treated mice at day 81 post injection. Using the anti-FLAG tag antibody to detect murine PAH protein, FIG. 7E demonstrates detectable murine PAH protein in 5 of 6 animals treated, with significantly higher protein levels observed in mice treated with ssDNA containing the B19d135 ITRs. These data are consistent with the blood phenylalanine reductions observed in FIGS. 7B-7D. Together, these demonstrate that single stranded DNA delivery can result in long term expression of functional liver enzymes.

Sequences of the various PAH constructs used in the experiment are set forth in Tables 10A and 10B.

TABLE 10A

| B19-PAH construct bearing B19d135 ITRs (nucleotides 1-4146; SEQ ID NO: 197) | |
|---|---|
| Description | Sequence |
| 5' ITR (SEQ ID NO: 180) | CTCTGGGCCAGCTTGCTTGGGGTTGCCTTGACACTAAGACAAGCGGCGCGCCGCTTGATC TTAGTGGCACGTCAACCCCAAGCGCTGGCCCAGAGCCAACCCTAATTCCGGAAGTCCCGC CCACCGGAAGTGACGTCACAGGAAATGACGTCACAGGAAATGACGTAATTGTCCGCCATC TTGTACCGGAAGTCCCGCCTACCGGCGGCGACCGGCGGCATCTGATTTGGTGTCTTCTTT TAAATTTT |
| CAGp promoter (SEQ ID NO: 195) | CTAGTTATTAATAGTAATCAATTACGGGGTCATTAGTTCATAGCCCATATATGGAGTTCC GCGTTACATAACTTACGGTAAATGGCCCGCCTGGCTGACCGCCCAACGACCCCCGCCCAT TGACGTCAATAATGACGTATGTTCCCATAGTAACGCCAATAGGGACTTTCCATTGACGTC AATGGGTGGAGTATTTACGGTAAACTGCCCACTTGGCAGTACATCAAGTGTATCATATGC CAAGTACGCCCCCTATTGACGTCAATGACGGTAAATGGCCCGCCTGGCATTATGCCCAGT ACATGACCTTATGGGACTTTCCTACTTGGCAGTACATCTACGTATTAGTCATCGCTATTA CCATGCATGGTCGAGGTGAGCCCCACGTTCTGCTTCACTCTCCCCATCTCCCCCCCCTCC |

TABLE 10A-continued

| | |
|---|---|
| | CCACCCCCAATTTTGTATTTATTTATTTTTAATTATTTTGTGCAGCGATGGGGGCGGGG<br>GGGGGGGGGGGGCGCGCGCCAGGCGGGGCGGGGCGGGGCGAGGGGCGGGGCGGGGCGAGG<br>CGGAGAGGTGCGGCGGCAGCCAATCAGAGCGGCGCGCTCCGAAAGTTTCCTTTTATGGCG<br>AGGCGGCGGCGGCGGCGGCCCTATAAAAAGCGAAGCGCGCGGCGGGCG |
| Synthetic<br>Intron (SEQ ID<br>NO: 192) | GTGAGCGGGCGGGACGGCCCTTCTCCTTCGGGCTGTAATTAGCGCTTGGTTTAATGACGG<br>CTTGTTTCTTTTCTGTGGCTGCGTGAAAGCCTTGAGGGGCTCCGGGAGGGCCCTTTGTGC<br>GGGGGGAGCGGCTCGGGGCTGTCCGCGGGGGACGGCTGCCTTCGGGGGGGACGGGGCAG<br>GGCGGGGTTCGGCTTCTGGCGTGTGACCGGCGGCTCTAGAGCCTCTGCTAACCATGTTCA<br>TGCCTTCTTCTTTTTCCTACAG |
| Murine PAH<br>sequence<br>(SEQ ID<br>NO: 196) | ATGGACTACAAAGACCATGACGGTGATTATAAAGATCATGATATCGATTACAAGGATGAC<br>GATGACAAGGCTGCTGTGGTTCTGGAAAATGGCGTGCTGAGCCGGAAGCTGAGCGACTTC<br>GGACAAGAGACAAGCTACATCGAGGACAACAGCAACCAGAATGGCGCCGTGTCTCTGATC<br>TTCAGCCTGAAAGAAGAAGTGGGCGCCCTGGCCAAGGTGCTGAGACTGTTCGAGGAAAAC<br>GAGATCAATCTGACCCACATCGAGAGCAGACCCAGCAGACTGAACAAGGACGAGTACGAG<br>TTCTTCACCTACCTGGACAAGCGGAGCAAGCCTGTGCTGGGCAGCATCATCAAGAGCCTG<br>AGAAACGACATCGGCGCCACCGTGCACGAGCTGAGCAGAGACAAAGAAAAGAACACCGTG<br>CCATGGTTCCCCAGGACCATCCAAGAGCTGGACAGATTCGCCAACCAGATCCTGAGCTAT<br>GGCGCCGAGCTGGACGCTGATCACCCTGGCTTTAAGGACCCCGTGTACCGGGCCAGAAGA<br>AAGCAGTTTGCCGATATCGCCTACAACTACCGGCACGGCCAGCCTATTCCTCGGGTCGAG<br>TACACCGAGGAAGAGAGAAAGACCTGGGGCACCGTGTTCAGAACCCTGAAGGCCCTGTAC<br>AAGACCCACGCCTGCTACGAGCACAACCACATCTTCCCACTGCTGGAAAAGTACTGCGGC<br>TTCCGCGAGGACAATATCCCTCAGCTCGAAGACGTGTCCCAGTTCCTGCAGACCTGCACC<br>GGCTTTAGACTGAGGCCTGTTGCCGGACTGCTGAGCAGCAGAGATTTTCTCGGCGGCCTG<br>GCCTTCAGAGTGTTCCACTGTACCCAGTACATCAGACACGGCAGCAAGCCCATGTACACC<br>CCTGAGCCTGATATCTGCCACGAGCTGCTGGGACATGTGCCCCTGTTCAGCGATAGAAGC<br>TTCGCCCAGTTCAGCCAAGAGATCGGACTGGCTTCTCTGGGAGCCCCTGACGAGTACATT<br>GAGAAGCTGGCCACCATCTACTGGTTCACCGTGGAATTCGGCCTGCTGCAAAGAGGGCGAC<br>AGCATCAAGGCTTATGGCGCTGGACTGCTGTCTAGCTTCGGCGAGCTGCAGTACTGTCTG<br>AGCGACAAGCCTAAGCTGCTGCCCCTGGAACTGGAAAAGACCGCCTGCCAAGAGTACACA<br>GTGACCGAGTTCCAGCCTCTGTACTACGTGGCCGAGAGCTTCAACGACGCCAAAGAAAAA<br>GTGCGGACCTTCGCCGCCACCATTCCTCGGCCTTTTAGCGTCAGATACGACCCCTACACA<br>CAGCGCGTGGAAGTGCTGGACAACACACAGCAGCTGAAGATTCTGGCCGACTCCATCAAC<br>AGCGAAGTGGGCATTCTGTGTCACGCCCTGCAGAAGATCAAGAGCTGA |
| WPRE<br>(mutated<br>woodchuck<br>hepatitis virus<br>post-<br>transcriptional<br>regulatory<br>element)<br>(SEQ ID<br>NO: 120) | TCATAATCAACCTCTGGATTACAAAATTTGTGAAAGATTGACTGGTATTCTTAACTATGT<br>TGCTCCTTTTACGCTATGTGGATACGCTGCTTTAATGCCTTTGTATCATGCTATTGCTTC<br>CCGTATGGCTTTCATTTTCTCCTCCTTGTATAAATCCTGGTTGCTGTCTCTTTATGAGGA<br>GTTGTGGCCCGTTGTCAGGCAACGTGGCGTGGTGTGCACTGTGTTTGCTGACGCAACCCC<br>CACTGGTTGGGGCATTGCCACCACCTGTCAGCTCCTTTCCGGGACTTTCGCTTTCCCCCT<br>CCCTATTGCCACGGCGGAACTCATCGCCGCCTGCCTTGCCCGCTGCTGGACAGGGGCTCG<br>GCTGTTGGGCACTGACAATTCCGTGGTGTTGTCGGGGAAATCATCGTCCTTTCCTTGGCT<br>GCTCGCCTGTGTTGCCACCTGGATTCTGCGCGGGACGTCCTTCTGCTACGTCCCTTCGGC<br>CCTCAATCCAGCGGACCTTCCTTCCCGCGGCCTGCTGCCGGCTCTGCGGCCTCTTCCGCG<br>TCTTCGCCTTCGCCCTCAGACGAGTCGGATCTCCCTTTGGGCCGCCTCCCCGCTG |
| bGHpA<br>(bovine growth<br>hormone<br>polyadenylation<br>signal) (SEQ<br>ID NO: 122) | CGACTGTGCCTTCTAGTTGCCAGCCATCTGTTGTTTGCCCCTCCCCCGTGCCTTCCTTGA<br>CCCTGGAAGGTGCCACTCCCACTGTCCTTTCCTAATAAAATGAGGAAATTGCATCGCATT<br>GTCTGAGTAGGTGTCATTCTATTCTGGGGGGTGGGGTGGGGCAGGACAGCAAGGGGGAGG<br>ATTGGGAAGACAATAGCAGGCATGCTGGGGA |
| 3' ITR inverted<br>terminal<br>repeat (SEQ<br>ID NO: 181) | AAAATTTAAAAGAAGACACCCAAATCAGATGCCGCCGGTCGCCGCCGGTAGGCGGGACTTC<br>CGGTACAAGATGGCGGACAATTACGTCATTTCCTGTGACGTCATTTCCTGTGACGTCACT<br>TCCGGTGGGCGGGACTTCCGGAATTAGGGTTGGCTCTGGGCCAGCGCTTGGGGTTGACGT<br>GCCACTAAGATCAAGCGGCGCGCCGCTTGTCTTAGTGTCAAGGCAACCCCAAGCAAGCTG<br>GCCCAGAG |

| Full-length Sequence (SEQ ID NO: 197) |
|---|
| CTCTGGGCCAGCTTGCTTGGGGTTGCCTTGACACTAAGACAAGCGGCGCGCCGCTTGATCTTAGTGGCACGT<br>CAACCCCAAGCGCTGGCCCAGAGCCAACCCTAATTCCGGAAGTCCCGCCCACCGGAAGTGACGTCACAGGAA<br>ATGACGTCACAGGAAATGACGTAATTGTCCGCCATCTTGTACCGGAAGTCCCGCCTACCGGCGGCGACCGGC<br>GGCATCTGATTTGGTGTCTTCTTTTAAATTTTGCGGCAATTCAGTCGATAACTATAACGGTCCTAAGGTAGC<br>GATTTAAATACGCGCTCTCTTAAGGTAGCCCCGGAGCGCGTCAATTGGATCTGGATCCGGTACCGAATTCG<br>CGGCCGCCTCGACGACTAGCGTTTAGTAATGAGACGCACAAACTAATATCACAAACTGGAAATGTCTATCAA<br>TATATAGTTGCTCTAGTTATTAATAGTAATCAATTACGGGGTCATTAGTTCATAGCCCATATATGGAGTTCC<br>GCGTTACATAACTTACGGTAAATGGCCCGCCTGGCTGACCGCCCAACGACCCCCGCCCATTGACGTCAATAA<br>TGACGTATGTTCCCATAGTAACGCCAATAGGGACTTTCCATTGACGTCAATGGGTGGAGTATTTACGGTAAA<br>CTGCCCACTTGGCAGTACATCAAGTGTATCATATGCCAAGTACGCCCCCTATTGACGTCAATGACGGTAAAT<br>GGCCCGCCTGGCATTATGCCCAGTACATGACCTTATGGGACTTTCCTACTTGGCAGTACATCTACGTATTAG<br>TCATCGCTATTACCATGCATGGTCGAGGTGAGCCCCACGTTCTGCTTCACTCTCCCCATCTCCCCCCCCTCC<br>CCACCCCCAATTTTGTATTTATTTATTTTTAATTATTTTGTGCAGCGATGGGGGCGGGG<br>GGGGGGGGGGGGCGCGCGCCAGGCGGGGCGGGGCGGGGCGAGGGGCGGGGCGGGGCGAGG<br>CGGAGAGGTGCGGCGGCAGCCAATCAGAGCGGCGCGCTCCGAAAGTTTCCTTTTATGGCGAGGCGGCGGCGGCGGCGGCCCTATAAAAAGCGAAGC<br>GCGCGGCGGGCGGGAGTCGCTGCGCGCTGCCTTCGCCCCGTGCCCCGCTCCGCCGCCGCCTCGCGCCGCCCG<br>CCCCGGCTCTGACTGACCGCGTTACTCCCACAGGTGAGCGGGCGGGACGGCCCTTCTCCTTCGGGCTGTAAT<br>TAGCGCTTGGTTTAATGACGGCTTGTTTCTTTTCTGTGGCTGCGTGAAAGCCTTGAGGGGCTCCGGGAGGGC |

TABLE 10A-continued

```
CCTTTGTGCGGGGGGAGCGGCTCGGGGCTGTCCGCGGGGGGACGGCTGCCTTCGGGGGGGACGGGGCAGGGC
GGGGTTCGGCTTCTGGCGTGTGACCGGCGGCTCTAGAGCCTCTGCTAACCATGTTCATGCCTTCTTCTTTTT
CCTACAGCTCCTGGGCAACGTGCTGGTTATTGTGCTGTCTCATCATTTTGGCAAAGAATTGGATCGCGAAGC
CGCCACCATGGACTACAAAGACCATGACGGTGATTATAAAGATCATGATATCGATTACAAGGATGACGATGA
CAAGGCTGCTGTGGTTCTGGAAAATGGCGTGCTGAGCCGGAAGCTGAGCGACTTCGGACAAGAGACAAGCTA
CATCGAGGACAACAGCAACCAGAATGGCGCCGTGTCTCTGATCTTCAGCCTGAAAGAAGAAGTGGGCGCCCT
GGCCAAGGTGCTGAGACTGTTCGAGGAAAACGAGATCAATCTGACCCACATCGAGAGCAGACCCAGCAGACT
GAACAAGGACGAGTACGAGTTCTTCACCTACCTGGACAAGCGGACCAAGCCTGTGCTGGGCAGCATCATCAA
GAGCCTGAGAAACGACATCGGCGCCACCGTGCACGAGCTGAGCAGAGACAAAGAAAAGAACACCGTGCCATG
GTTCCCCAGGACCATCCAAGAGCTGGACAGATTCGCCAACCAGATCCTGAGCTATGGCGCCGAGCTGGACGC
TGATCACCCTGGCTTTAAGGACCCCGTGTACCGGGCCAGAAGAAAGCAGTTTGCCGATATCGCCTACAACTA
CCGGCACGGCCAGCCTATTCCTCGGGTCGAGTACACCGAGGAAGAGAGAAAGACCTGGGGCACCGTGTTCAG
AACCCTGAAGGCCCTGTACAAGACCCACGCCTGCTACGAGCAACCACATCTTCCCACTGCTGGAAAAGTA
CTGCGGCTTCCGCGAGGACAATATCCCTCAGCTCGAAGACGTGTCCCAGTTCCTGCAGACCTGCACCGGCTT
TAGACTGAGGCCTGTTGCCGGACTGCTGAGCAGCAGAGATTTTCTCGGCGGCCTGGCCTTCAGAGTGTTCCA
CTGTACCCAGTACATCAGACACGGCAGCAAGCCCATGTACACCCCTGAGCCTGATATCTGCCACGAGCTGCT
GGGACATGTGCCCCTGTTCAGCGATAGAAGCTTCGCCCAGTTCAGCCAAGAGATCGGACTGGCTTCTCTGGG
AGCCCCTGACGAGTACATTGAGAAGCTGGCCACCATCTACTGGTTCACCGTGGAATTCGGCCTGTGCAAAGA
GGGCGACAGCATCAAGGCTTATGGCGCTGGACTGCTGTCTAGCTTCGGCGAGCTGCAGTACTGTCTGAGCGA
CAAGCCTAAGCTGCTGCCCCTGGAACTGGAAAAGACCGCCTGCCAAGAGTACACAGTGACCGAGTTCCAGCC
TCTGTACTACGTGGCCGAGAGCTTCAACGACGCCAAAGAAAAAGTGCGGACCTTCGCCGCCACCATTCCTCG
GCCTTTTAGCGTCAGATACGACCCCTACACACAGCGCGTGGAAGTGCTGGACAACACACAGCAGCTGAAGAT
TCTGGCCGACTCCATCAACAGCGAAGTGGGCATTCTGTGTCACGCCCTGCAGAAGATCAAGAGCTGAGCAAG
TAATGAGCGCTGATCATAATCAACCTCTGGATTACAAAATTTGTGAAAGATTGACTGGTATTCTTAACTATG
TTGCTCCTTTTACGCTATGTGGATACGCTGCTTTAATGCCTTTGTATCATGCTATTGCTTCCCGTATGGCTT
TCATTTTCTCCTCCTTGTATAAATCCTGGTTGCTGTCTCTTTATGAGGAGTTGTGGCCCGTTGTCAGGCAAC
GTGGCGTGGTGTGCACTGTGTTTGCTGACGCAACCCCCACTGGTTGGGGCATTGCCACCACCTGTCAGCTCC
TTTCCGGGACTTTCGCTTTCCCCCTCCCTATTGCCACGGCGGAACTCATCGCCGCCTGCCTTGCCCGCTGCT
GGACAGGGGCTCGGCTGTTGGGCACTGACAATTCCGTGGTGTTGTCGGGGAAATCATCGTCCTTTCCTTGGC
TGCTCGCCTGTGTTGCCACCTGGATTCTGCGCGGGACGTCCTTCTGCTACGTCCCTTCGGCCCTCAATCCAG
CGGACCTTCCTTCCCGCGGCCTGCTGCCGGCTCTGCGGCCTCTTCCGCGTCTTCGCCTTCGCCCTCAGACGA
GTCGGATCTCCCTTTGGGCCGCCTCCCCGCTGATCAGCCTCGACTGTGCCTTCTAGTTGCCAGCCATCTGTT
GTTTGCCCCTCCCCCGTGCCTTCCTTGACCCTGGAAGGTGCCACTCCCACTGTCCTTTCCTAATAAAATGAG
GAAATTGCATCGCATTGTCTGAGTAGGTGTCATTCTATTCTGGGGGGTGGGGTGGGGCAGGACAGCAAGGGG
GAGGATTGGGAAGACAATAGCAGGCATGCTGGGGATGCGGTGGGCTCTATGGCTTCTGAGGCGGAAAGAACG
GGCTCGAGAAGCTTCTAGATATCCTCTCTTAAGGTAGCATCGAGATTTAAATTAGGGATAACAGGGTAATGG
CGCGGGCCGCAAAATTTAAAAGAAGACACCAAATCAGATGCCGCCGGTCGCCGCCGGTAGGCGGGACTTCCG
GTACAAGATGGCGGACAATTACGTCATTTCCTGTGACGTCATTTCCTGTGACGTCACTTCCGGTGGGCGGGA
CTTCCGGAATTAGGGTTGGCTCTGGGCAGCGCTTGGGGTTGACGTGCCACTAAGATCAAGCGGCGCGCCGC
TTGTCTTAGTGTCAAGGCAACCCCAAGCAAGCTGGCCCAGAG
```

TABLE 10B

| GPV-PAH construct bearing GPVd162 ITRs (nucleotides 1-4214; SEQ ID NO: 198) | |
|---|---|
| Description | Sequence |
| 5' ITR (SEQ ID NO: 183) | CGGTGACGTGTTTCCGGCTGTTAGGTTGACCACGCGCATGCCGCGCGGTCAGCCCAAT AGTT TABLE 10B-continued

|  | |
|---|---|
| | AGGAAAACGAGATCAATCTGACCCACATCGAGAGCAGACCCAGCAGACTGAACAAGGA<br>CGAGTACGAGTTCTTCACCTACCTGGACAAGCGGAGCAAGCCTGTGCTGGGCAGCATC<br>ATCAAGAGCCTGAGAAACGACATCGGCGCCACCGTGCACGAGCTGAGCAGAGACAAAG<br>AAAAGAACACCGTGCCATGGTTCCCCAGGACCATCCAAGAGCTGGACAGATTCGCCAA<br>CCAGATCCTGAGCTATGGCGCCGAGCTGGACGCTGATCACCCTGGCTTTAAGGACCCC<br>GTGTACCGGGCCAGAAGAAAGCAGTTTGCCGATATCGCCTACAACTACCGGCACGGCC<br>AGCCTATTCCTCGGGTCGAGTACACCGAGGAAGAGAGAAAGACCTGGGGCACCGTGTT<br>CAGAACCCTGAAGGCCCTGTACAAGACCCACGCCTGCTACGAGCACAACACATCTTC<br>CCACTGCTGGAAAAGTACTGCGGCTTCCGCGAGGACAATATCCCTCAGCTCGAAGACG<br>TGTCCCAGTTCCTGCAGACCTGCACCGGCTTTAGACTGAGGCCTGTTGCCGGACTGCT<br>GAGCAGCAGAGATTTTCTCGGCGGCCTGGCCTTCAGAGTGTTCCACTGTACCCAGTAC<br>ATCAGACACGGCAGCAAGCCCATGTACACCCCTGAGCCTGATATCTGCCACGAGCTGC<br>TGGGACATGTGCCCCTGTTCAGCGATAGAAGCTTCGCCCAGTTCAGCCAAGAGATCGG<br>ACTGGCTTCTCTGGGAGCCCCTGACGAGTACATTGAGAAGCTGGCCACCATCTACTGG<br>TTCACCGTGGAATTCGGCCTGTGCAAAGAGGGCGACAGCATCAAGGCTTATGGCGCTG<br>GACTGCTGTCTAGCTTCGGCGAGCTGCAGTACTGTCTGAGCGACAAGCCTAAGCTGCT<br>GCCCCTGGAACTGGAAAAGACCGCCTGCCAAGAGTACACAGTGACCGAGTTCCAGCCT<br>CTGTACTACGTGGCCGAGAGCTTCAACGACGCCAAAGAAAAAGTGCGGACCTTCGCCG<br>CCACCATTCCTCGGCCTTTTAGCGTCAGATACGACCCCTACACACAGCGCGTGGAAGT<br>GCTGGACAACACACAGCAGCTGAAGATTCTGGCCGACTCCATCAACAGCGAAGTGGGC<br>ATTCTGTGTCACGCCCTGCAGAAGATCAAGAGCTGA |
| WPRE (mutated woodchuck hepatitis virus post-transcriptional regulatory element) (SEQ ID NO: 120) | TCATAATCAACCTCTGGATTACAAAATTTGTGAAAGATTGACTGGTATTCTTAACTAT<br>GTTGCTCCTTTTACGCTATGTGGATACGCTGCTTTAATGCCTTTGTATCATGCTATTG<br>CTTCCCGTATGGCTTTCATTTTCTCCTCCTTGTATAAATCCTGGTTGCTGTCTCTTTA<br>TGAGGAGTTGTGGCCCGTTGTCAGGCAACGTGGCGTGGTGTGCACTGTGTTTGCTGAC<br>GCAACCCCCACTGGTTGGGGCATTGCCACCACCTGTCAGCTCCTTTCCGGGACTTTCG<br>CTTTCCCCCTCCCTATTGCCACGGCGGAACTCATCGCCGCCTGCCTTGCCCGCTGCTG<br>GACAGGGGCTCGGCTGTTGGGCACTGACAATTCCGTGGTGTTGTCGGGGAAATCATCG<br>TCCTTTCCTTGGCTGCTCGCCTGTGTTGCCACCTGGATTCTGCGCGGGACGTCCTTCT<br>GCTACGTCCCTTCGGCCCTCAATCCAGCGGACCTTCCTTCCCGCGGCCTGCTGCCGGC<br>TCTGCGGCCTCTTCCGCGTCTTCGCCTTCGCCCTCAGACGAGTCGGATCTCCCTTTGG<br>GCCGCCTCCCCGCTG |
| bGHpA (bovine growth hormone polyadenylation signal) (SEQ ID NO: 122) | CGACTGTGCCTTCTAGTTGCCAGCCATCTGTTGTTTGCCCCTCCCCCGTGCCTTCCTT<br>GACCCTGGAAGGTGCCACTCCCACTGTCCTTTCCTAATAAAATGAGGAAATTGCATCG<br>CATTGTCTGAGTAGGTGTCATTCTATTCTGGGGGGTGGGGTGGGGCAGGACAGCAAGG<br>GGGAGGATTGGGAAGACAATAGCAGGCATGCTGGGGA |
| 3' ITR inverted terminal repeat (SEQ ID NO: 184) | CACTTCCTGGCGCGCAAAATATCCTCTTGTCCTTGAGTCTCATTGGAGGGTTCGTTCG<br>TTCGAACCAGCCAATCAGGGAGGGGGAAGTGACGCAAGTTCGGTCACATGCTTCCG<br>GTGACGCACATCCGGTGACGTAGTTCCGGTCACGTGCTTCCTGTCACGTGTTTCCGGT<br>CACGTGACTTCCGGTCATGTGACTTCCGGTCACGTGTTTCCGGCTTAACTATTGGGCT<br>GACCGCGCGGCATGCGCGTGGTCAACCTAACAGCCGGAAACACGTCACCG |

| Full-length Sequence (SEQ ID NO: 198) |
|---|
| CGGTGACGTGTTTCCGGCTGTTAGGTTGACCACGCGCATGCCGCGCGGTCAGCCCAATAGTTAAGCCGGAAAC<br>ACGTCACCGGAAGTCACATGACCGGAAGTCACGTGACCGGAAACACGTGACAGGAAGCACGTGACCGGAACTA<br>CGTCACCGGATGTGCGTCACCGGAAGCATGTGACCGGAACTTGCGTCACTTCCCCCTCCCCTGATTGGCTGGT<br>TCGAACGAACGAACCCTCCAATGAGACTCAAGGACAAGAGGATATTTTGCGCGCCAGGAAGTGGCGGCAATTC<br>AGTCGATAACTATAACGGTCCTAAGGTAGCGATTTAAATACGCGCTCTCTTAAGGTAGCCCCGGGACGCGTCA<br>ATTGAGATCTGGATCCGGTACCGAATTCGCGGCCGCCTCGACGACTAGCATTTAGTAATGAGACGCACAAACT<br>AATATCACAAACTGGAAATGTCTATCAATATATAGTTGCTCTAGTTATTAATAGTAATCAATTACGGGGTCAT<br>TAGTTCATAGCCCATATATGGAGTTCCGCGTTACATAACTTACGGTAAATGGCCCGCCTGGCTGACCGCCCAA<br>CGACCCCCGCCCATTGACGTCAATAATGACGTATGTTCCCATAGTAACGCCAATAGGGACTTTCCATTGACGT<br>CAATGGGTGGAGTATTTACGGTAAACTGCCCACTTGGCAGTACATCAAGTGTATCATATGCCAAGTACGCCCC<br>CTATTGACGTCAATGACGGTAAATGGCCCGCCTGGCATTATGCCCAGTACATGACCTTATGGGACTTTCCTAC<br>TTGGCAGTACATCTACGTATTAGTCATCGCTATTACCATGCATGGTCGAGGTGAGCCCCACGTTCTGCTTCAC<br>TCTCCCCATCTCCCCCCCCTCCCCACCCCCAATTTTGTATTTATTTATTTTTTAATTATTTTGTGCAGCGATG<br>GGGGCGGGGGGGGGGGGGGCGCGCGCCAGGCGGGGCGGGGCGAGGGGCGGGGCGGGGCGAGGCGGA<br>GAGGTGCGGCGGCAGCCAATCAGAGCGGCGCGCTCCGAAAGTTTCCTTTTATGGCGAGGCGGCGGCGGCGGCG<br>GCCCTATAAAAAGCGAAGCGCGCGGCGGGCGGGAGTCGCTGCGCGCTGCCTTCGCCCCGTGCCCCGCTCCGCC<br>GCCGCCTCGCGCCGCCCGCCCCGGCTCTGACTGACCGCGTTACTCCCACAGGTGAGCGGGCGGGACGGCCCTT<br>CTCCTTCGGGCTGTAATTAGCGCTTGGTTTAATGACGGCTTGTTTCTTTTCTGTGGCTGCGTGAAAGCCTTGA<br>GGGGCTCCGGGAGGGCCCTTTGTGCGGGGGGAGCGGCTCGGGGCTGTCCGCGGGGGGACGGCTGCCTTCGGGG<br>GGGACGGGGCAGGGCGGGGTTCGGCTTCTGGCGTGTGACCGGCGGCTCTAGAGCCTCTGCTAACCATGTTCAT<br>GCCTTCTTCTTTTTCCTACAGCTCCTGGGCAACGTGCTGGTTATTGTGCTGTCTCATCATTTTGGCAAAGAAT<br>TGGATCGCGAAGCCGCCACCATGGACTACAAAGACCATGACGGTGATTATAAAGATCATGATATCGATTACAA<br>GGATGACGATGACAAGGCTGCTGTGGTTCTGGAAAATGGCGTGCTGAGCCGGAAGCTGAGCGACTTCGGACAA<br>GAGACAAGCTACATCGAGGACAACAGCAACCAGAATGGCGCCGTGTCTCTGATCTTCAGCCTGAAAGAAGAAG<br>TGGGCGCCCTGGCCAAGGTGCTGAGACTGTTCGAGGAAAACGAGATCAATCTGACCCACATCGAGAGCAGACC<br>CAGCAGACTGAACAAGGACGAGTACGAGTTCTTCACCTACCTGGACAAGCGGAGCAAGCCTGTGCTGGGCAGC<br>ATCATCAAGAGCCTGAGAAACGACATCGGCGCCACCGTGCACGAGCTGAGCAGAGACAAAGAAAAGAACACCG<br>TGCCATGGTTCCCCAGGACCATCCAAGAGCTGGACAGATTCGCCAACCAGATCCTGAGCTATGGCGCCGAGCT<br>GGACGCTGATCACCCTGGCTTTAAGGACCCCGTGTACCGGGCCAGAAGAAAGCAGTTTGCCGATATCGCCTAC<br>AACTACCGGCACGGCCAGCCTATTCCTCGGGTCGAGTACACCGAGGAAGAGAGAAAGACCTGGGGCACCGTGT<br>TCAGAACCCTGAAGGCCCTGTACAAGACCCACGCCTGCTACGAGCACAACACATCTTCCCACTGCTGGAAAA<br>GTACTGCGGCTTCCGCGAGGACAATATCCCTCAGCTCGAAGACGTGTCCCAGTTCCTGCAGACCTGCACCGGC |

TABLE 10B-continued

```
TTTAGACTGAGGCCTGTTGCCGGACTGCTGAGCAGCAGAGATTTTCTCGGCGGCCTGGCCTTCAGAGTGTTCC
ACTGTACCCAGTACATCAGACACGGCAGCAAGCCCATGTACACCCCTGAGCCTGATATCTGCCACGAGCTGCT
GGGACATGTGCCCCTGTTCAGCGATAGAAGCTTCGCCCAGTTCAGCCAAGAGATCGGACTGGCTTCTCTGGGA
GCCCCTGACGAGTACATTGAGAAGCTGGCCACCATCTACTGGTTCACCGTGGAATTCGGCCTGTGCAAAGAGG
GCGACAGCATCAAGGCTTATGGCGCTGGACTGCTGTCTAGCTTCGGCGAGCTGCAGTACTGTCTGAGCGACAA
GCCTAAGCTGCTGCCCCTGGAACTGGAAAAGACCGCCTGCCAAGAGTACACAGTGACCGAGTTCCAGCCTCTG
TACTACGTGGCCGAGAGCTTCAACGACGCCAAAGAAAAAGTGCGGACCTTCGCCGCCACCATTCCTCGGCCTT
TTAGCGTCAGATACGACCCCTACACACAGCGCGTGGAAGTGCTGGACAACACACAGCAGCTGAAGATTCTGGC
CGACTCCATCAACAGCGAAGTGGGCATTCTGTGTCACGCCCTGCAGAAGATCAAGAGCTGAGCAAGTAATGAG
CGCTGATCATAATCAACCTCTGGATTACAAAATTTGTGAAAGATTGACTGGTATTCTTAACTATGTTGCTCCT
TTTACGCTATGTGGATACGCTGCTTTAATGCCTTTGTATCATGCTATTGCTTCCCGTATGGCTTTCATTTTCT
CCTCCTTGTATAAATCCTGGTTGCTGTCTCTTTATGAGGAGTTGTGGCCCGTTGTCAGGCAACGTGGCGTGGT
GTGCACTGTGTTTGCTGACGCAACCCCCACTGGTTGGGGCATTGCCACCACCTGTCAGCTCCTTTCCGGGACT
TTCGCTTTCCCCCTCCCTATTGCCACGGCGGAACTCATCGCCGCCTGCCTTGCCCGCTGCTGGACAGGGGCTC
GGCTGTTGGGCACTGACAATTCCGTGGTGTTGTCGGGGAAATCATCGTCCTTTCCTTGGCTGCTCGCCTGTGT
TGCCACCTGGATTCTGCGCGGGACGTCCTTCTGCTACGTCCCTTCGGCCCTCAATCCAGCGGACCTTCCTTCC
CGCGGCCTGCTGCCGGCTCTGCGGCCTCTTCCGCGTCTTCGCCTTCGCCCTCAGACGAGTCGGATCTCCCTTT
GGGCCGCCTCCCCGCTGATCAGCCTCGACTGTGCCTTCTAGTTGCCAGCCATCTGTTGTTTGCCCCTCCCCCG
TGCCTTCCTTGACCCTGGAAGGTGCCACTCCCACTGTCCTTTCCTAATAAAATGAGGAAATTGCATCGCATTG
TCTGAGTAGGTGTCATTCTATTCTGGGGGGTGGGGTGGGGCAGGACAGCAAGGGGGAGGATTGGGAAGACAAT
AGCAGGCATGCTGGGGATGCGGTGGGCTCTATGGCTTCTGAGGCGGAAAGAACGGGCTCGAGAAGCTTCTAGA
TATCCTCTCTTAAGGTAGCATCGAGATTTAAATTAGGGATAACAGGGTAATGGCGCGGGCCGCCACTTCCTGG
CGCGCAAAATATCCTCTTGTCCTTGAGTCTCATTGGAGGGTTCGTTCGTTCGAACCAGCCAATCAGGGGAGGG
GGAAGTGACGCAAGTTCCGGTCACATGCTTCCGGTGACGCACATCCGGTGACGTAGTTCCGGTCACGTGCTTC
CTGTCACGTGTTTCCGGTCACGTGACTTCCGGTCATGTGACTTCCGGTGACGTGTTTCCGGCTTAACTATTGG
GCTGACCGCGCGGCATGCGCGTGGTCAACCTAACAGCCGGAAACACGTCACCG
```

Example 7b. Preparation of ssDNA Reporter Genetic Constructs Bearing ITRs of 819 or GPV Origin ssDNA reporter/PAH constructs will be prepared as described in Example 1c. Briefly, plasmids will be digested with LguI. ssDNA fragments with formed hairpin ITR structures will be generated by denaturing the double-stranded DNA fragment products (reporter expression cassette and plasmid backbone) of LguI digestion at 95° C. and then cooling down at 4° C. to allow the palindromic ITR sequences to fold (FIG. 1A). The resulting ssDNA constructs will be tested in mice for the ability to establish persistent transduction of liver, muscle tissue, photoreceptors in the eye, and central nervous system (CNS).

Example 7c. In Vivo Evaluation of ssDNA-Mediated Reporter Expression

To validate the ability of the ssDNA reporter constructs described in Example 7b to mediate persistent transgene expression in vivo, 5-12-week old mice (4 animals/group) will be injected with 5, 10, or 20 μg/mouse of reporter ssDNA systemically, locally to target muscle tissue and CNS cells, and/or subretinally to target photoreceptor cells.

To evaluate expression of PAH from B19 and GPV ITR-based expression constructs, a relevant disease mouse model will be used. These genetic constructs will be delivered systemically by HDI to target the liver.

SEQUENCE LISTING

```
<160> NUMBER OF SEQ ID NOS: 198

<210> SEQ ID NO 1
<211> LENGTH: 4374
<212> TYPE: DNA
<213> ORGANISM: Artificial Sequence
<220> FEATURE:
<223> OTHER INFORMATION: coFVIII-5

<400> SEQUENCE: 1
atgcaaatcg aactgagcac ctgtttcttc ctctgcctgc tgagattctg tttctccgcg    60
acccgccgat actacctggg agcagtggag ctctcctggg attacatgca gagcgacctt   120
ggggagctgc ccgtggatgc caggttccct ccccgggtgc caaagtcgtt tccgttcaac   180
acctccgtgg tgtacaagaa aactctgttc gtggagttca ccgaccacct gttcaatatc   240
gccaagccca gacctccctg gatggggctg ttgggaccta ccatccaagc ggaggtgtac   300
gacactgtgg tcatcactct gaagaacatg gcctcgcatc ccgtgtccct gcacgccgtg   360
ggagtgtctt actggaaagc gtccgagggg gccgaatacg acgaccagac ctcgcagaga   420
gaaaaggaag atgacaaggt gttcccagga ggatcgcaca cctacgtgtg gcaagtgttg   480
```

-continued

```
aaggagaacg gcccaatggc ctccgacccg ctgtgcctga cctactcgta cctgtcccac    540
gtggacctcg tgaaggacct caactcggga ctgattggag ccctgctggt ctgcagggaa    600
ggctcactgg cgaaagaaaa gactcagacc ttgcacaagt tcattctgct gttcgctgtg    660
ttcgacgagg gaagtcgtg gcacagcgag actaagaact ccctgatgca agatagagat    720
gccgcctccg cccgggcctg gcctaagatg cacaccgtga acggttacgt gaaccgctcc    780
ctccctggcc tgattggatg ccaccggaag tccgtgtact ggcacgtgat cgggatgggg    840
accaccccg aggtgcacag catcttcctg gaaggtcaca catttctcgt gcgcaaccac    900
cggcaggcct ccctggaaat cagccccatt accttcctca ctgcccagac tctgctgatg    960
gacctgggac agttcctgct gttctgccat atctcctccc accaacatga cggaatggag    1020
gcatacgtga aggtcgattc ctgccctgag gaacccagc tccgcatgaa gaacaatgag    1080
gaagccgagg actacgacga cgacctgacg gatagcgaga tggatgtggt ccggttcgat    1140
gacgataaca gccttccctt catccaaatt cgctcggtgg caaagaagca ccccaagacc    1200
tgggtgcatt acattgcggc ggaagaagag gactgggatt atgccccgct tgtcctcgct    1260
cctgacgacc ggagctacaa gagccagtac ctgaacaacg gtccacagag gatcggtaga    1320
aagtacaaga aggtccgctt catggcctat accgacgaaa ccttcaaaac tagagaggcc    1380
atccaacacg aatccggcat cctgggcccg ctcttgtacg gagaagtcgg cgacacccttt    1440
ctcattatct tcaagaacca ggcttccgg ccgtacaaca tctatccgca tgggatcact    1500
gacgtgcgcc cactgtactc gcggcgcctg cccaagggtg tcaaacacct gaaggatttt    1560
ccgatccttc cgggagaaat cttcaagtac aagtggaccg tgaccgtgga agatggccca    1620
actaagtctg accctagatg cctcacccgc tactactcat ccttcgtcaa catggagcgc    1680
gacctggcca gcggactgat cggcccgctg ctgatttgct acaaggaatc agtgaccaa    1740
cggggaaacc agatcatgtc ggataagagg aacgtcatcc tcttctccgt gtttgacgaa    1800
aaccggtcgt ggtacctgac tgaaaacatc cagcggttcc tccccaaccc cgcgggcgtg    1860
cagctggaag atcctgagtt tcaggcatca acatcatgc actccattaa cggctacgtg    1920
ttcgattcgc tgcagctgag cgtgtgtctg cacgaagtgg cctactggta catcctgtcc    1980
attggtgccc agactgactt cctgtccgtg tttttctccg gctacacgtt caagcacaag    2040
atggtgtacg aggacaccct gaccctcttc cctttttccg gcgaaactgt gtttatgagc    2100
atggagaatc ccggcctgtg gatcttgggc tgccacaaca gcgacttccg taacagagga    2160
atgactgcgc tgctcaaggt gtccagctgc gacaagaaca ccggagacta ttatgaggac    2220
tcatacgagg acatctccgc ctacctcctg tccaagaata cgccattga acctcggagc    2280
ttcagccaga accacccgt gcttaagaga catcaacggg agatcactag gaccaccctg    2340
cagtcagacc aggaggaaat cgactacgat gacaccatct cggtcgagat gaagaaggag    2400
gactttgaca tctacgacga agatgaaaac cagagcccga ggtcgttcca aaagaaaacc    2460
cgccactact ttattgctgc tgtcgagcgg ctgtgggact acggaatgtc gtcctcgccg    2520
cacgtgctcc gcaaccgagc ccagagcggc tcggtgccgc aattcaagaa ggtcgtgttc    2580
caggagttca ctgacgggag cttcactcag ccttttgtacc ggggagaact caatgaacat    2640
ctcggcctcc tcggacctta catcagagca gaagtggaag ataacatcat ggtcactttc    2700
cgtaaccaag ccagccgccc gtactcgttc tactcctccc tcatttctta cgaagaggac    2760
cagcggcagg gcgcagaacc gcgcaagaac ttcgtgaagc ccaacgaaac caagacctac    2820
ttctggaaag tgcagcatca tatggccccg actaaggacg agtttgactg caaagcctgg    2880
```

```
gcctacttct ccgatgtgga cttggagaag gacgtccact ccggcctcat cggtcccctg      2940
ctcgtgtgcc ataccaatac cctgaacccc gcacacggtc gccaggtcac cgtgcaggag      3000
ttcgctctgt tcttcactat cttcgacgaa actaagtcct ggtacttcac cgagaacatg      3060
gagaggaact gcagagcccc ctgtaacatc cagatggagg acccgacgtt caaggaaaac      3120
taccggttcc acgccattaa cggatacatc atggatacgc tgccgggtct tgtgatggcc      3180
caggatcaac ggatcagatg gtacttattg tcgatgggca gcaacgagaa catccactct      3240
attcacttct ccggtcatgt gttcactgtg cggaagaagg aagagtacaa gatggccctg      3300
tacaaccttt atcccggagt gttcgaaact gtggaaatgc tgccgtcgaa ggccggcatt      3360
tggcgcgtgg agtgtttgat tggagaacat ctccatgcgg ggatgtcaac cctgttcctg      3420
gtgtatagca acaagtgcca gactccgctt gggatggcgt caggacacat tagggatttc      3480
cagatcactg cgtccggcca gtacggccaa tgggccccta agctggcccg cctgcattac      3540
tccggatcca ttaacgcctg gtcaaccaag gagccattct cctggatcaa ggtgaccttt      3600
ctggccccca tgattatcca cggaattaag acccaggggg cccggcagaa gttctcctca      3660
ctgtacatca gccagttcat aatcatgtac tccctggacg gaaagaagtg gcaaacctac      3720 aggggggaaca gcaccggcac actgatggtc ttttcggaa atgtggactc ctccgggatt      3780
aagcataaca tcttcaaccc tccgattatc gctcggtaca ttagacttca ccctacccac      3840
tacagcattc gctccaccct gcggatggaa ctgatgggct gcgatctgaa ctcgtgcagc      3900
atgccgttgg gaatggagtc caaagcaatt tccgacgcgc agatcaccgc ctcgtcctac      3960
tttaccaaca tgttcgccac gtggtcaccg tccaaggccc ggctgcacct ccagggaaga      4020
tccaacgcat ggcggccaca ggtcaacaac cctaaggagt ggctccaggt ggacttccag      4080
aaaaccatga aggtcaccgg agtcacaacc cagggagtga agtcgctgct gacttctatg      4140
tacgtcaagg agttcctgat ctccagcagc caggacgggc accagtggac cctgttcttc      4200
caaaatggaa aggtcaaggt gtttcagggc aatcaggatt cattcacccc ggtggtgaac      4260
tcccttgatc cacccctcct gacccgctac cttcgcatcc acccacagtc ctgggtgcac      4320
cagatcgcgc tgaggatgga ggtcctggga tgcgaagccc aggacctgta ctga            4374
```

<210> SEQ ID NO 2
<211> LENGTH: 4374
<212> TYPE: DNA
<213> ORGANISM: Artificial Sequence
<220> FEATURE:
<223> OTHER INFORMATION: coFVIII-4

<400> SEQUENCE: 2

```
atgcagatcg agctgagcac gtgcttcttc ctgtgcctgc tgaggttctg cttcagcgcc       60
accaggaggt actacctggg cgccgtggag ctgagctggg actacatgca gagcgacctg      120
ggcgagctgc ccgtggacgc caggttcccc ccaggtgc ccaagagctt ccccttcaac        180
acgagcgtgg tgtacaagaa gaccctgttc gtggagttca ccgaccatct gttcaatatc      240
gccaagccca ggccccctg gatggggctg ctggggccca cgatccaggc cgaggtgtac       300
gacaccgtgg tcatcaccct gaagaacatg gccagcacc ccgtgagcct gcacgccgtg       360
ggcgtgagct actggaaggc cagcgagggc gccgagtacg acgaccagac cagccagagg      420
gagaaggagg acgacaaggt gttccccggc ggcagccaca cctacgtgtg gcaggtgctg      480
aaggagaatg ggcccatggc cagcgacccc ctgtgcctga cctactctta cctgagccac      540
```

```
gtggatctgg tgaaggacct gaacagcggc ctgatcggcg ccctgctggt gtgcagggag     600
ggcagcctgg ccaaggagaa gacccagacc ctgcacaagt tcatcctgct gttcgccgtg     660
ttcgacgagg gcaagagctg gcacagcgag accaagaaca gcctgatgca ggatagggac     720
gccgccagcg ccagggcctg gcccaagatg cacaccgtga acggctacgt gaacaggtct     780
ctgcccggcc tgatcggctg ccacaggaag agcgtgtact ggcacgtgat cggcatgggg     840 accaccccg aggtgcacag catcttcctg gagggccaca cgttcctggt gaggaatcac      900
aggcaggcca gcctggagat cagcccgatc accttcctga ccgcccagac cctgctgatg     960
gacctggggc agttcctgct gttctgccat atcagctctc accagcacga cggcatggag    1020
gcctacgtga aggtggatag ctgccccgag gagccccagc tgaggatgaa gaacaacgag    1080
gaggccgagg actacgacga cgacctgacc gacagcgaga tggacgtggt gaggttcgac    1140
gacgacaata gcccgagctt catccagatc aggagcgtgg ccaagaagca ccccaagacc    1200
tgggtgcatt acatcgccgc cgaggaggag gattgggact acgccccct ggtgctggcc     1260 cccgacgaca ggtcttacaa gagccagtac ctgaacaacg gccccagag gatcggcagg     1320 aagtacaaga aggtgaggtt catggcctac accgacgaga ccttcaagac cagggaggcg    1380
atccagcacg agagcgggat cctggggccc ctgctgtacg cgaggtggg cgacacgctg      1440 ctgatcatct tcaagaacca ggccagcagg ccgtacaata tctaccccca cgggatcacc    1500
gacgtgaggc ccctgtactc taggaggctg cccaagggcg tgaagcacct gaaggacttc    1560
cccatcctgc ccggcgagat cttcaagtac aagtggaccg tgaccgtgga ggacgggccc    1620
acgaagagcg accccaggtg cctgaccagg tactacagct ctttcgtgaa catggagagg    1680
gacctggcca gcggcctgat cgggcccctg ctgatctgct acaaggagag cgtggatcag    1740
aggggcaacc agatcatgag cgacaagagg aacgtgatcc tgttcagcgt gttcgacgag    1800
aataggtctt ggtacctgac cgagaatatc cagaggttcc tgcccaaccc cgccggcgtg    1860
cagctggagg atcccgagtt ccaggccagc aacatcatgc acagcatcaa cggctacgtg    1920
ttcgacagcc tgcagctgag cgtgtgcctg cacgaggtgg cctactggta catcctgagc    1980
atcggcgccc agaccgactt cctgagcgtg ttcttcagcg gctacacctt caagcacaag    2040
atggtgtacg aggatacct gaccctgttc cccttcagcg gcgagaccgt gttcatgagc     2100
atggagaacc ccggcctgtg gatcctgggc tgccataact ccgacttcag gaataggggc    2160
atgaccgccc tgctgaaggt gagctcttgc gacaagaaca ccggcgacta ctacgaggat    2220
agctacgagg atatcagcgc ctacctgctg agcaagaaca acgccatcga gcccaggtct    2280
ttcagccaga accccccgt gctgaagagg caccagaggg agatcaccag gacgaccctg      2340
cagagcgacc aggaggagat cgactacgac gacacgatca gcgtggagat gaagaaggag    2400
gatttcgaca tctacgacga ggacgagaat cagagcccca ggtctttcca agaagagacc    2460
aggcattact tcatcgccgc cgtggagagg ctgtgggact acggcatgag cagctctccc    2520
cacgtgctga ggaataggc ccagagcggc agcgtgcccc agttcaagaa ggtggtgttc      2580
caggagttca ccgacggcag cttcacccag cccctgtaca ggggcgagct gaacgagcac    2640
ctgggcctgc tggggcccta catcagggcc gaggtggaga taacatcat ggtgaccttc      2700 aggaatcagg ccagcaggcc ctatagcttc tatagctctc tgatcagcta cgaggaggat    2760
cagaggcagg cgccgagcc caggaagaac ttcgtgaagc ccaacgagac caagacctac     2820
ttctggaagg tgcagcacca catggccccc acgaaggacg agttcgactg caaggcctgg    2880
gcctacttca gcgacgtgga tctggagaag gacgtgcaca gcggcctgat cgggcccctg    2940
```

```
ctggtgtgcc acaccaacac cctgaacccc gcccacggca ggcaggtgac cgtgcaggag    3000
ttcgccctgt tcttcaccat cttcgacgag accaagagct ggtacttcac cgagaatatg    3060
gagaggaatt gcagggcccc ctgcaatatc cagatggagg acccgacctt caaggagaat    3120
tacaggttcc acgccatcaa cggctacatc atggacacgc tgcccggcct ggtcatggcc    3180
caggatcaga ggatcaggtg gtatctgctg agcatgggga gcaacgagaa tatccacagc    3240
atccacttca cgcgccacgt gttcaccgtg aggaagaagg aggagtacaa gatggccctg    3300
tacaatctgt accccggcgt gttcgagacc gtggagatgc tgcccagcaa ggccgggatc    3360 tggaggggtgg agtgcctgat cggcgagcac ctgcacgccg gcatgagcac gctgttcctg    3420
gtgtactcta acaagtgcca gaccccctg gggatggcca gcggccacat cagggacttc    3480
cagatcaccg ccagcggcca gtacggccag tgggccccca gctggccag gctgcactat    3540 tccggaagca tcaacgcctg gagcacgaag gagcccttca gctggatcaa ggtggatctg    3600
ctggccccca tgatcatcca cgggatcaag acccaggccg ccaggcagaa gttcagctct    3660
ctgtatatca gccagttcat catcatgtac tctctggacg gcaagaagtg gcagacctac    3720
aggggcaaca gcaccggcac gctgatggtg ttcttcggca acgtggactc tagcgggatc    3780
aagcacaata tcttcaaccc ccccatcatc gccaggtaca tcaggctgca ccccacccat    3840
tactctatca ggtctaccct gaggatggag ctgatgggct gcgacctgaa cagctgcagc    3900
atgcccctgg ggatggagag caaggccatc agcgacgccc agatcaccgc cagctcttac    3960
ttcaccaaca tgttcgccac ctggagcccg agcaaggcca ggctgcacct gcagggcagg    4020
tctaacgcct ggaggcccca ggtgaacaac cccaaggagt ggctgcaggt ggatttccag    4080
aagaccatga aggtgaccgg cgtgaccacg cagggcgtga agagcctgct gaccagcatg    4140
tacgtgaagg agttcctgat cagctctagc caggacggcc accagtggac cctgttcttc    4200
cagaacggca aggtgaaggt gttccagggc aaccaggata gcttcacccc cgtggtgaac    4260
agcctggacc ccccctgct gaccaggtat ctgaggatcc accccagag ctgggtgcac    4320 cagatcgccc tgaggatgga ggtgctgggc tgcgaggccc aggatctgta ttga        4374

<210> SEQ ID NO 3
<211> LENGTH: 4374
<212> TYPE: DNA
<213> ORGANISM: Artificial Sequence
<220> FEATURE:
<223> OTHER INFORMATION: coFVIII-52

<400> SEQUENCE: 3
atgcaaatcg aactgagcac ctgtttcttc ctctgcctgc tgagattctg tttctccgcg      60
acccgccgat actacctggg agcagtggag ctctcctggg attacatgca gagcgacctt     120
ggggagctgc ccgtggatgc caggttccct ccccgggtgc aaagtcgtt tccgttcaac      180 acctccgtgg tgtacaagaa aactctgttc gtggagttca ccgaccacct gttcaatatc     240
gccaagccca gacctccctg gatggggctg ttgggaccta ccatccaagc ggaggtgtac     300
gacactgtgg tcatcactct gaagaacatg gcctcgcatc ccgtgtccct gcacgccgtg     360
ggagtgtctt actggaaagc gtccgagggg gccgaatacg acgaccagac tcgcagagaa     420
gaaaaggaag atgacaaggt gttcccagga ggatcgcaca cctacgtgtg gcaagtgttg     480
aaggagaacg gccaatggc ctccgaccg ctgtgcctga cctactcgta cctgtcccac      540
gtggacctcg tgaaggacct caactcggga ctgattggag ccctgctggt ctgcagggaa     600
```

```
ggctcactgg cgaaagaaaa gactcagacc ttgcacaagt tcattctgct gttcgctgtg    660
ttcgacgagg ggaagtcgtg gcacagcgag actaagaact ccctgatgca agatagagat    720
gccgcctccg cccgggcctg gcctaagatg cacaccgtga acggttacgt gaaccgctcc    780
ctccctggcc tgattggatg ccaccggaag tccgtgtact ggcacgtgat cgggatgggg    840 accaccccog aggtgcacag catcttcctg gaaggtcaca catttctcgt gcgcaaccac    900
cggcaggcct ccctggaaat cagccccatt accttcctca ctgcccagac tctgctgatg    960
gacctgggac agttcctgct gttctgccat atctcctccc accaacatga cggaatggag   1020
gcatacgtga aggtcgattc ctgccctgag aaccccagc tccgcatgaa gaacaatgag    1080
gaagccgagg actacgacga cgacctgacg gatagcgaga tggatgtggt ccggttcgat   1140
gacgataaca gccttccctt catccaaatt cgctcggtgg caagaagca ccccaagacc    1200 tgggtgcatt acattgcggc ggaagaagag gactgggatt atgccccgct tgtcctcgct   1260
cctgacgacc ggagctacaa gagccagtac ctgaacaacg gtccacagag gatcggtaga   1320
aagtacaaga aggtccgctt catggcctat accgacgaaa ccttcaaaac tagagaggcc   1380
atccaacacg aatccggcat cctgggcccg ctcttgtacg gagaagtcgg cgacacccct   1440
ctcattatct tcaagaacca ggcttcccgg ccgtacaaca tctatccgca tgggatcact   1500
gacgtgcgcc cactgtactc gcggcgcctg cccaagggtg tcaaacacct gaaggatttt   1560
ccgatccttc cgggagaaat cttcaagtac aagtggaccg tgaccgtgga agatggccca   1620
actaagtctg accctagatg cctcacccgc tactactcat ccttcgtcaa catggagcgc   1680
gacctggcca gcggactgat cggccgctg ctgatttgct acaaggaatc agtgaccaa    1740 cggggaaacc agatcatgtc ggataagagg aacgtcatcc tcttctccgt gtttgacgaa   1800
aaccggtcgt ggtacctgac cgagaacatc cagaggttcc tgcccaaccc tgctggggtg   1860
cagctggagg accccgagtt ccaggccagc aacatcatgc acagcatcaa tggctacgtg   1920
ttcgacagcc tgcagctgag cgtgtgcctg cacgaggtgg cctactggta catcctgagc   1980
atcggcgccc agaccgactt cctgagcgtg ttcttctctg gctacacctt caagcacaag   2040
atggtgtatg aggacaccct gaccctgttc cccttcagcg ggagactgt cttcatgagc    2100 atggagaacc ctggcctgtg gatcctgggc tgccacaaca gcgacttcag gaacaggggc   2160
atgactgccc tgctgaaagt ctccagctgt gacaagaaca ccggggacta ctacgaggac   2220
agctacgagg acatcagcgc ctacctgctg agcaagaaca atgccatcga gcccaggagc   2280
ttctctcaga cccccccagt gctgaagagg caccagaggg agatcaccag gaccacccetg   2340 cagtctgacc aggaggagat cgactatgat gacaccatca gcgtggagat gaagaaggag   2400
gacttcgaca tctacgacga ggacgagaac cagagcccca ggagcttcca agaagagacc   2460
aggcactact tcattgctgc tgtggagagg ctgtgggact atggcatgtc cagcagcccc   2520
catgtgctga ggaacagggc ccagtctggc agcgtgcccc agttcaagaa agtcgtgttc   2580
caggagttca ccgacggcag cttcacccag ccctgtaca gagggagct gaacgagcac    2640 ctgggcctgc tgggccccta catcagggcc gaggtggagg acaacatcat ggtgaccttc   2700
aggaaccagg ccagcaggcc ctacagcttc tacagcagcc tgatcagcta cgaggaggac   2760
cagaggcagg gggctgagcc caggaagaac tttgtgaagc caatgaaac caagacctac    2820 ttctggaagg tgcagcacca catggccccc accaaggacg agttcgactg caaggcctgg   2880
gcctacttct ctgacgtgga cctggagaag gacgtgcact ctggcctgat ggccccctg    2940 ctggtgtgcc acaccaacac cctgaaccct gcccatggca ggcaggtgac tgtgcaggag   3000
```

| | | | |
|---|---|---|---|
| ttcgccctgt | tcttcaccat | cttcgatgaa | accaagagct ggtacttcac tgagaacatg | 3060 |
| gagaggaact | gcagggcccc | ctgcaacatc | cagatggagg accccaccct caaggagaac | 3120 |
| tacaggttcc | atgccatcaa | tggctacatc | atggacaccc tgcctggcct ggtcatggcc | 3180 |
| caggaccaga | ggatcaggtg | gtatctgctg | agcatgggca gcaacgagaa catccacagc | 3240 |
| atccacttct | ctggccacgt | gttcactgtg | aggaagaagg aggagtacaa gatggcccctg | 3300 |
| tacaacctgt | accctggggt | gttcgaaacc | gtggagatgc tgcccagcaa ggccggcatc | 3360 |
| tggagggtgg | agtgcctgat | tggggagcac | ctgcacgccg gcatgagcac cctgttcctg | 3420 |
| gtgtacagca | caagtgcca | gaccccctg | ggcatggcct ctggccacat cagggacttc | 3480 |
| cagatcactg | cctctggcca | gtacggccag | tgggcccca agctggccag gctgcactac | 3540 |
| tccgaagca | tcaatgcctg | gagcaccaag | gagccctca gctggatcaa agtggacctg | 3600 |
| ctggccccca | tgatcatcca | cggcatcaag | acccagggg ccaggcagaa gttctccagc | 3660 |
| ctgtacatca | gccagttcat | catcatgtac | agcctggacg gcaagaagtg gcagacctac | 3720 |
| aggggcaaca | gcaccggcac | cctgatggtg | ttcttcggca acgtggacag cagcggcatc | 3780 |
| aagcacaaca | tcttcaaccc | ccccatcatc | gccagataca tcaggctgca ccccacccac | 3840 |
| tacagcatca | ggagcaccct | gaggatggag | ctgatgggct gtgacctgaa cagctgcagc | 3900 |
| atgcccctgg | gcatggagag | caaggccatc | tctgacgccc agatcactgc ctccagctac | 3960 |
| ttcaccaaca | tgtttgccac | ctggagcccc | agcaaggcca ggctgcacct gcagggcagg | 4020 |
| agcaatgcct | ggaggcccca | ggtcaacaac | cccaaggagt ggctgcaggt ggacttccag | 4080 |
| aagaccatga | aggtgactgg | ggtgaccacc | cagggggtga gagcctgct gaccagcatg | 4140 |
| tacgtgaagg | agttcctgat | ctccagcagc | caggacggcc accagtggac cctgttcttc | 4200 |
| cagaatggca | aggtgaaggt | gttccagggc | aaccaggaca gcttcacccc tgtggtcaac | 4260 |
| agcctggacc | ccccctgct | gaccagatac | ctgaggatcc acccccagag ctgggtgcac | 4320 |
| cagatcgccc | tgaggatgga | ggtgctgggc | tgtgaggccc aggacctgta ctga | 4374 |

<210> SEQ ID NO 4
<211> LENGTH: 4374
<212> TYPE: DNA
<213> ORGANISM: Artificial Sequence
<220> FEATURE:
<223> OTHER INFORMATION: coFVIII-62

<400> SEQUENCE: 4

| | | | |
|---|---|---|---|
| atgcagattg | agctgtccac | ttgtttcttc | ctgtgcctcc tgcgcttctg tttctccgcc | 60 |
| actcgccggt | actaccttgg | agccgtggag | cttcatgggg actacatgca gagcgacctg | 120 |
| ggcgaactcc | ccgtggatgc | cagattcccc | cccgcgtgc caaagtcctt ccccttaac | 180 |
| acctccgtgg | tgtacaagaa | aaccctcttt | gtcgagttca ctgaccacct gttcaacatc | 240 |
| gccaagccgc | gccaccttg | gatgggcctc | ctggaccga ccattcaagc tgaagtgtac | 300 |
| gacaccgtgg | tgatcacccct | gaagaacatg | gcgtcccacc ccgtgtccct gcatgcggtc | 360 |
| ggagtgtcct | actggaaggc | ctccgaagga | gctgagtacg acgaccagac tagccagcgg | 420 |
| gaaaaggagg | acgataaagt | gttcccgggc | ggctcgcata cttacgtgtg gcaagtcctg | 480 |
| aaggaaaacg | gacctatggc | atccgatcct | ctgtgcctga cttactccta cctttcccat | 540 |
| gtggaccctcg | tgaaggacct | gaacagcggg | ctgattggtg cacttctcgt gtgccgcgaa | 600 |
| ggttcgctcg | ctaaggaaaa | gacccagacc | ctccataagt tcatccttt gttcgctgtg | 660 |

```
ttcgatgaag gaaagtcatg gcattccgaa actaagaact cgctgatgca ggaccgggat    720
gccgcctcag cccgcgcctg gcctaaaatg catacagtca acggatacgt gaatcggtca    780
ctgcccgggc tcatcggttg tcacagaaag tccgtgtact ggcacgtcat cggcatgggc    840
actacgcctg aagtgcactc catcttcctg gaagggcaca ccttcctcgt gcgcaaccac    900
cgccaggcct ctctggaaat ctccccgatt acctttctga ccgcccagac tctgctcatg    960
gacctggggc agttccttct cttctgccac atctccagcc atcagcacga cggaatggag   1020
gcctacgtga aggtggactc atgcccggaa gaacctcagt tgcggatgaa gaacaacgag   1080
gaggccgagg actatgacga cgatttgact gactccgaga tggacgtcgt gcggttcgat   1140
gacgacaaca gccccagctt catccagatt cgcagcgtgg ccaagaagca ccccaaaacc   1200
tgggtgcact acatcgcggc cgaggaagaa gattgggact acgcccgtt ggtgctggca   1260
cccgatgacc ggtcgtacaa gtcccagtat ctgaacaatg gtccgcagcg gattggcaga   1320
aagtacaaga aagtgcggtt catggcgtac actgacgaaa cgtttaagac ccgggaggcc   1380
attcaacatg agagcggcat tctgggacca ctgctgtacg agaggtcgg cgataccctg   1440
ctcatcatct tcaaaaacca ggcctcccgg ccttacaaca tctaccctca cggaatcacc   1500
gacgtgcggc cactctactc gcggcgcctg ccgaagggcg tcaagcacct gaaagacttc   1560
cctatcctgc cgggcgaaat cttcaagtat aagtggaccg tcaccgtgga ggacgggccc   1620
accaagagcc atcctaggtg tctgactcgg tactactcca gcttcgtgaa catggaacgg   1680
gacctggcat cgggactcat tggaccgctg ctgatctgct acaaagagtc ggtggatcaa   1740
cgcggcaacc agatcatgtc cgacaagcgc aacgtgatcc tgttctccgt gtttgatgaa   1800
aacagatcct ggtacctgac cgagaacatc cagaggttcc tgcccaaccc tgctggggtg   1860
cagctggagg accccgagtt ccaggccagc aacatcatgc acagcatcaa tggctacgtg   1920
ttcgacagcc tgcagctgag cgtgtgcctg cacgaggtgg cctactggta catcctgagc   1980
atcgcgccc agaccgactt cctgagcgtg ttcttctctg gctacacctt caagcacaag   2040
atggtgtatg aggacaccct gaccctgttc cccttcagcg gggagactgt cttcatgagc   2100
atggagaacc ctggcctgtg gatcctgggc tgccacaaca gcgacttcag gaacagggc   2160
atgactgccc tgctgaaagt ctccagctgt gacaagaaca ccggggacta ctacgaggac   2220
agctacgagg acatcagcgc ctacctgctg agcaagaaca atgccatcga gcccaggagc   2280
ttctctcaga accccccagt gctgaagagg caccagaggg agatcaccag gaccaccctg   2340
cagtctgacc aggaggagat cgactatgat gacaccatca gcgtggagat gaagaaggag   2400
gacttcgaca tctacgacga ggacgagaac cagagcccca ggagcttcca agaagaacc   2460
aggcactact tcattgctgc tgtggagagg ctgtgggact atggcatgtc cagcagcccc   2520
catgtgctga ggaacagggc ccagtctggc agcgtgcccc agttcaagaa agtcgtgttc   2580
caggagttca ccgacggcag cttcacccag ccctgtaca gagggagct gaacgagcac   2640
ctgggcctgc tgggccccta catcagggcc gaggtggagg acaacatcat ggtgaccttc   2700
aggaaccagg ccagcaggcc ctacagcttc tacagcagcc tgatcagcta cgaggaggac   2760
cagaggcagg ggctgagcc caggaagaac tttgtgaagc ccaatgaaac caagacctac   2820
ttctggaagg tgcagcacca catggccccc accaaggacg agttcgactg caaggcctgg   2880
gcctacttct ctgacgtgga cctggagaag gacgtgcact ctggcctgat tggcccctg    2940
ctggtgtgcc acaccaacac cctgaaccct gcccatggca gcaggtgac tgtgcaggag   3000
ttcgccctgt tcttcaccat cttcgatgaa accaagagct ggtacttcac tgagaacatg   3060
```

-continued

```
gagaggaact gcagggcccc ctgcaacatc cagatggagg acccacctt caaggagaac    3120 tacaggttcc atgccatcaa tggctacatc atggacaccc tgcctggcct ggtcatggcc    3180
caggaccaga ggatcaggtg gtatctgctg agcatgggca gcaacgagaa catccacagc    3240
atccacttct ctggccacgt gttcactgtg aggaagaagg aggagtacaa gatggccctg    3300
tacaacctgt accctggggt gttcgaaacc gtggagatgc tgcccagcaa ggccggcatc    3360
tggagggtgg agtgcctgat tggggagcac ctgcacgccg gcatgagcac cctgttcctg    3420
gtgtacagca acaagtgcca gacccccctg ggcatggcct ctggccacat cagggacttc    3480
cagatcactg cctctggcca gtacggccag tgggccccca gctggccag gctgcactac    3540 tccggaagca tcaatgcctg gagcaccaag gagcccttca gctggatcaa agtggacctg    3600 ctggcccca tgatcatcca cggcatcaag acccaggggg ccaggcagaa gttctccagc    3660
ctgtacatca gccagttcat catcatgtac agcctggacg gcaagaagtg gcagacctac    3720
aggggcaaca gcaccggcac cctgatggtg ttcttcggca acgtggacag cagcggcatc    3780
aagcacaaca tcttcaaccc cccatcatc gccagataca tcaggctgca ccccacccac    3840
tacagcatca ggagcaccct gaggatggag ctgatgggct gtgacctgaa cagctgcagc    3900
atgcccctgg gcatggagag caaggccatc tctgacgccc agatcactgc ctccagctac    3960
ttcaccaaca tgtttgccac ctggagcccc agcaaggcca ggctgcacct gcagggcagg    4020
agcaatgcct ggaggcccca ggtcaacaac cccaaggagt ggctgcaggt ggacttccag    4080
aagaccatga aggtgactgg ggtgaccacc caggggtga agagcctgct gaccagcatg    4140
tacgtgaagg agttcctgat ctccagcagc caggacggcc accagtggac cctgttcttc    4200
cagaatggca aggtgaaggt gttccagggc aaccaggaca gcttcacccc tgtggtcaac    4260
agcctggacc ccccctgct gaccagatac ctgaggatcc accccagag ctgggtgcac    4320 cagatcgccc tgaggatgga ggtgctgggc tgtgaggccc aggacctgta ctga         4374
```

<210> SEQ ID NO 5
<211> LENGTH: 4374
<212> TYPE: DNA
<213> ORGANISM: Artificial Sequence
<220> FEATURE:
<223> OTHER INFORMATION: coFVIII-25

<400> SEQUENCE: 5

```
atgcagattg agctgagcac ctgcttcttc ctgtgcctgc tgaggttctg cttctctgcc     60
accaggagat actacctggg cgccgtggag ctgagctggg actacatgca gtctgacctg    120
ggcgagctgc cagtggacgc caggttcccc ccagagtgc caagagctt cccttcaac     180 accagcgtgt gtacaagaa gacctgttc gtggagttca ctgaccacct gttcaacatc    240
gccaagccca ggccccctg gatgggcctg ctggccccca ccatccaggc cgaggtgtac    300
gacaccgtgt tcatcaccct gaagaacatg gccagccacc ccgtctccct gcacgccgtg    360
ggggtgagct actggaaggc ctctgagggc gccgagtacg acgaccagac cagccagagg    420
gagaaggagg acgacaaggt gttccctggg ggcagccaca cctacgtgtg gcaggtcctg    480
aaggagaacg gccccatggc ctctgacccc ctgtgcctga cctacagcta cctgagccac    540
gtggacctgg tgaaggacct gaactctggc ctgattgggg ccctgctggt gtgcagggag    600
ggcagcctgg ccaaggagaa gacccagacc ctgcacaagt tcatcctgct gttcgccgtg    660
ttcgacgagg gcaagagctg gcactctgaa accaagaaca gcctgatgca ggacagggac    720
```

```
gccgcctctg ccagggcctg gcccaagatg cacaccgtca acggctacgt caacaggagc    780
ctgcctggcc tgattggctg ccacaggaag agcgtgtact ggcatgtgat cggcatgggc    840
accacccctg aggtgcacag catcttcctg gagggccaca ccttcctggt caggaaccac    900
aggcaggcca gcctggagat cagccccatc accttcctga ccgcccagac cctgctgatg    960
gacctgggcc agttcctgct gttctgccac atctccagcc accagcacga cggcatggag   1020
gcctacgtga agtggacag ctgccctgag gagccccagc tgaggatgaa gaacaacgag   1080
gaggccgagg actatgatga cgacctgacc gacagcgaga tggacgtggt caggttcgac   1140
gacgacaaca gccccagctt catccagatc aggagcgtgg ccaagaagca ccccaagacc   1200
tgggtgcact acatcgctgc tgaggaggag gactgggact atgcccccct ggtgctggcc   1260
cctgatgaca ggagctacaa gagccagtac ctgaacaatg cccccagag gattggcagg   1320
aagtacaaga agtcaggtt catggcctac actgatgaaa ccttcaagac cagggaggcc   1380
atccagcatg agtctggcat cctgggcccc ctgctgtacg gggaggtggg ggacaccctg   1440
ctgatcatct tcaagaacca ggccagcagg ccctacaaca tctaccccca tggcatcacc   1500
gacgtgaggc ccctgtacag caggaggctg cctaagggg tgaagcacct gaaagacttc   1560
cccatcctgc ctggggagat cttcaagtac aagtggactg tgactgtgga ggacggcccc   1620
accaagagcg accccaggtg cctgaccaga tactacagca gcttcgtcaa catggagagg   1680
gacctggcct ctggcctgat tggccccctg ctgatctgct acaaggagtc tgtggaccag   1740
agggcaacc agatcatgag cgacaagagg aacgtgatcc tgttctctgt cttcgacgag   1800
aacaggagct ggtacctgac tgaaaacatc cagcggttcc tccccaaccc cgcgggcgtg   1860
cagctggaag atcctgagtt tcaggcatca acatcatgc actccattaa cggctacgtg   1920
ttcgattcgc tgcagctgag cgtgtgtctg cacgaagtgg cctactggta catcctgtcc   1980
attggtgccc agactgactt cctgtccgtg ttttctccg gctacacgtt caagcacaag   2040
atggtgtacg aggacaccct gaccctcttc ccttttcccg gcgaaactgt gtttatgagc   2100
atggagaatc ccggcctgtg gatcttgggc tgccacaaca gcgacttccg taacagagga   2160
atgactgcgt gctcaaggt gtccagctgc gacaagaaca ccggagacta ttatgaggac   2220
tcatacgagg acatctccgc ctacctcctg tccaagaata cgccattga acctcggagc   2280
ttcagccaga accacccgt gcttaagaga catcaacggg agatcactag gaccaccctg   2340
cagtcagacc aggaggaaat cgactacgat gacaccatct cggtcgagat gaagaaggag   2400
gactttgaca tctacgacga agatgaaaac cagagcccga ggtcgttcca aaagaaaacc   2460
cgccactact ttattgctgc tgtcgagcgg ctgtgggact acggaatgtc gtcctcgccg   2520
cacgtgctcc gcaaccgagc ccagagcggc tcggtgccgc aattcaagaa ggtcgtgttc   2580
caggagttca ctgacgggag cttcactcag cctttgtacc ggggagaact caatgaacat   2640
ctcggcctcc tcggaccctta catcagagca gaagtgaag ataacatcat ggtcactttc   2700
cgtaaccaag ccagccgccc gtactcgttc tactcctccc tcatttctta cgaagaggac   2760
cagcggcagg gcgcagaacc gcgcaagaac ttcgtgaagc ccaacgaaac caagacctac   2820
ttctggaaag tgcagcatca tatggccccg actaaggacg agtttgactg caaagcctgg   2880
gcctacttct ccgatgtgga cttggagaag gacgtccact ccggcctcat cggtcccctg   2940
ctcgtgtgcc ataccaatac cctgaacccc gcacacggtc gccaggtcac cgtgcaggag   3000
ttcgctctgt tcttcactat cttcgacgaa actaagtcct ggtacttcac cgagaacatg   3060
gagaggaact gcagagcccc ctgtaacatc cagatggagg acccgacgtt caaggaaaac   3120
```

| | | | |
|---|---|---|---|
| taccggttcc | acgccattaa | cggatacatc atggatacgc | tgccgggtct tgtgatggcc | 3180 |
| caggatcaac | ggatcagatg | gtacttattg tcgatgggca | gcaacgagaa catccactct | 3240 |
| attcacttct | ccggtcatgt | gttcactgtg cggaagaagg | aagagtacaa gatggccctg | 3300 |
| tacaaccttt | atcccggagt | gttcgaaact gtggaaatgc | tgccgtcgaa ggccggcatt | 3360 |
| tggcgcgtgg | agtgtttgat | tggagaacat ctccatgcgg | ggatgtcaac cctgttcctg | 3420 |
| gtgtatagca | acaagtgcca | gactccgctt gggatgcgt | caggacacat tagggatttc | 3480 |
| cagatcactg | cgtccggcca | gtacggccaa tgggccccta | agctggcccg cctgcattac | 3540 |
| tccggatcca | ttaacgcctg | gtcaaccaag gagccattct | cctggatcaa ggtggacctt | 3600 |
| ctggccccca | tgattatcca | cggaattaag acccagggg | cccggcagaa gttctcctca | 3660 |
| ctgtacatca | gccagttcat | aatcatgtac tccctggacg | gaaagaagtg gcaaacctac | 3720 |
| agggggaaca | gcaccggcac | actgatggtc tttttcggaa | atgtggactc ctccgggatt | 3780 |
| aagcataaca | tcttcaaccc | tccgattatc gctcggtaca | ttagacttca ccctacccac | 3840 |
| tacagcattc | gctccaccct | gcggatggaa ctgatgggct | gcgatctgaa ctcgtgcagc | 3900 |
| atgccgttgg | gaatggagtc | caaagcaatt tccgacgcgc | agatcaccgc ctcgtcctac | 3960 |
| tttaccaaca | tgttcgccac | gtggtcaccg tccaaggccc | ggctgcacct ccagggaaga | 4020 |
| tccaacgcat | ggcggccaca | ggtcaacaac cctaaggagt | ggctccaggt ggacttccag | 4080 |
| aaaaccatga | aggtcaccgg | agtcacaacc cagggagtga | agtcgctgct gacttctatg | 4140 |
| tacgtcaagg | agttcctgat | ctccagcagc caggacgggc | accagtggac cctgttcttc | 4200 |
| caaaatggaa | aggtcaaggt | gtttcagggc aatcaggatt | cattcacccc ggtggtgaac | 4260 |
| tcccttgatc | cacccctcct | gacccgctac cttcgcatcc | acccacagtc ctgggtgcac | 4320 |
| cagatcgcgc | tgaggatgga | ggtcctggga tgcgaagccc | aggacctgta ctga | 4374 |

<210> SEQ ID NO 6
<211> LENGTH: 4374
<212> TYPE: DNA
<213> ORGANISM: Artificial Sequence
<220> FEATURE:
<223> OTHER INFORMATION: coFVIII-26

<400> SEQUENCE: 6

| | | | |
|---|---|---|---|
| atgcagattg | agctgagcac | ctgcttcttc ctgtgcctgc | tgaggttctg cttctctgcc | 60 |
| accaggagat | actacctggg | cgccgtggag ctgagctggg | actacatgca gtctgacctg | 120 |
| ggcgagctgc | cagtggacgc | caggttcccc cccagagtgc | caagagcttt ccccttcaac | 180 |
| accagcgtgg | tgtacaagaa | gaccctgttc gtggagttca | ctgaccacct gttcaacatc | 240 |
| gccaagccca | ggccccctg | gatgggcctg ctgggcccca | ccatccaggc cgaggtgtac | 300 |
| gacaccgtgg | tcatcaccct | gaagaacatg gccagccacc | ccgtctccct gcacgccgtg | 360 |
| ggggtgagct | actggaaggc | ctctgagggc gccgagtacg | acgaccagac cagccagagg | 420 |
| gagaaggagg | acgacaaggt | gttccctggg ggcagccaca | cctacgtgtg caggtcctg | 480 |
| aaggagaacg | gccccatggc | ctctgacccc ctgtgcctga | cctacagcta cctgagccac | 540 |
| gtggacctgg | tgaaggacct | gaactctggc ctgattgggg | ccctgctggt gtgcagggag | 600 |
| ggcagcctgg | ccaaggagaa | gacccagacc ctgcacaagt | tcatcctgct gttcgccgtg | 660 |
| ttcgacgagg | gcaagagctg | gcactctgaa accaagaaca | gcctgatgca ggacagggac | 720 |
| gccgcctctg | ccagggcctg | gcccaagatg cacaccgtca | cggctacgt caacaggagc | 780 |

```
ctgcctggcc tgattggctg ccacaggaag agcgtgtact ggcatgtgat cggcatgggc    840
accacccctg aggtgcacag catcttcctg gagggccaca ccttcctggt caggaaccac    900
aggcaggcca gcctggagat cagccccatc accttcctga ccgcccagac cctgctgatg    960
gacctgggcc agttcctgct gttctgccac atctccagcc accagcacga cggcatggag   1020
gcctacgtga agtggacag ctgccctgag gagccccagc tgaggatgaa gaacaacgag    1080
gaggccgagg actatgatga cgacctgacc gacagcgaga tggacgtggt caggttcgac   1140
gacgacaaca gccccagctt catccagatc aggagcgtgg ccaagaagca ccccaagacc   1200
tgggtgcact acatcgctgc tgaggaggag gactgggact atgccccct ggtgctggcc    1260
cctgatgaca ggagctacaa gagccagtac ctgaacaatg gcccccagag gattggcagg   1320
aagtacaaga aagtcaggtt catggcctac actgatgaaa ccttcaagac cagggaggcc   1380
atccagcatg agtctggcat cctgggcccc ctgctgtacg gggaggtggg ggacaccctg   1440
ctgatcatct tcaagaacca ggccagcagg ccctacaaca tctacccca tggcatcacc    1500
gacgtgaggc ccctgtacag caggaggctg cctaagggg tgaagcacct gaaagacttc    1560
cccatcctgc ctggggagat cttcaagtac aagtggactg tgactgtgga ggacggcccc   1620
accaagagcg accccaggtg cctgaccaga tactacagca gcttcgtcaa catggagagg   1680
gacctggcct ctggcctgat tggccccctg ctgatctgct acaaggagtc tgtggaccag   1740
aggggcaacc agatcatgag cgacaagagg aacgtgatcc tgttctctgt cttcgacgag   1800
aacaggagct ggtacctcac tgaaaacatc cagaggttcc tcccaaaccc cgcaggagtg   1860
caactggagg accctgagtt tcaggcctcg aatatcatgc actcgattaa cggttacgtg   1920
ttcgactcgc tgcagctgag cgtgtgcctc catgaagtcg cttactggta cattctgtcc   1980
atcgcgccc agactgactt cctgagcgtg ttcttttccg gttacacctt taagcacaag   2040
atggtgtacg aagatacccct gaccctgttc cctttctccg gcgaaacggt gttcatgtcg   2100
atggagaacc cgggtctgtg gattctggga tgccacaaca gcgactttcg gaaccgcgga   2160
atgactgccc tgctgaaggt gtcctcatgc gacaagaaca ccggagacta ctacgaggac   2220
tcctacgagg atatctcagc ctacctcctg tccaagaaca cgcgatcga gccgcgcagc   2280
ttcagccaga cccgcctgt gctgaagagg caccagcgag aaattacccg gaccacctc    2340
caatcggatc aggaggaaat cgactacgac gacaccatct cggtggaaat gaagaaggaa   2400
gatttcgata tctacgacga ggacgaaaat cagtcccctc gctcattcca aaagaaaact   2460
agacactact ttatcgccgc ggtggaaaga ctgtgggact atggaatgtc atccagccct   2520
cacgtccttc ggaaccgggc ccagagcgga tcggtgcctc agttcaagaa agtggtgttc   2580
caggagttca ccgacggcag cttcacccag ccgctgtacc ggggagaact gaacgaacac   2640
ctgggcctgc tcggtcccta catccgcgcg gaagtggagg ataacatcat ggtgaccttc   2700
cgtaaccaag catccagacc ttactccttc tattcctccc tgatctcata cgaggaggac   2760
cagcgccaag gcgccgagcc ccgcaagaac ttcgtcaagc caacgagac taagacctac    2820
ttctggaagg tccaacacca tatggcccg accaaggatg agtttgactg caaggcctgg   2880
gcctacttct ccgacgtgga ccttgagaag atgtccatt ccggcctgat cgggccgctg    2940
ctcgtgtgtc acaccaacac cctgaaccca gcgcatggac gccaggtcac cgtccaggag   3000
tttgctctgt tcttcaccat ttttgacgaa actaagtcct ggtacttcac cgagaatatg   3060
gagcgaaact gtagagcgcc ctgcaatatc cagatggaag atccgacttt caaggagaac   3120
tatagattcc acgccatcaa cgggtacatc atggatactc tgccggggct ggtcatggcc   3180
```

```
caggatcaga ggattcggtg gtacttgctg tcaatgggat cgaacgaaaa cattcactcc    3240
attcacttct ccggtcacgt gttcactgtg cgcaagaagg aggagtacaa gatggcgctg    3300
tacaatctgt accccggggt gttcgaaact gtggagatgc tgccgtccaa ggccggcatc    3360
tggagagtgg agtgcctgat cggagagcac ctccacgcgg gatgtccac cctcttcctg     3420 gtgtactcga ataagtgcca accccgctg gcatggcct cgggccacat cagagacttc      3480
cagatcacag caagcggaca atacggccaa tgggcgccga agctggcccg cttgcactac    3540
tccggatcga tcaacgcatg gtccaccaag gaaccgttct cgtggattaa ggtggacctc    3600
ctggccccta tgattatcca cggaattaag acccagggcg ccaggcagaa gttctcctcc    3660
ctgtacatct cgcaattcat catcatgtac agcctggacg ggaagaagtg cagacttac     3720 aggggaaact ccaccggcac cctgatggtc tttttcggca acgtggattc ctccggcatt    3780
aagcacaaca tcttcaaccc accgatcata gccagatata ttaggctcca ccccactcac    3840
tactcaatcc gctcaactct tcggatgaa ctcatgggt gcgacctgaa ctcctgctcc      3900
atgccgttgg ggatggaatc aaaggctatt agcgacgccc agatcaccgc gagctcctac    3960
ttcactaaca tgttcgccac ctggagcccc tccaaggcca ggctgcactt gcagggacgg    4020
tcaaatgcct ggcggccgca agtgaacaat ccgaaggaat ggcttcaagt ggatttccaa    4080
aagaccatga agtgaccgg agtcaccacc caggggagtga agtcccttct gacctcgatg    4140
tatgtgaagg agttcctgat tagcagcagc caggacgggc accagtggac cctgttcttc    4200
caaaacggaa aggtcaaggt gttccagggg aaccaggact cgttcacacc cgtggtgaac    4260
tccctggacc ccccactgct gacgcggtac ttgaggattc atcctcagtc ctgggtccat    4320
cagattgcat tgcgaatgga agtcctgggc tgcgaggccc aggacctgta ctga          4374
```

<210> SEQ ID NO 7
<211> LENGTH: 1734
<212> TYPE: DNA
<213> ORGANISM: Artificial Sequence
<220> FEATURE:
<223> OTHER INFORMATION: coFVIII-52-NT58

<400> SEQUENCE: 7

```
gcgacccgcc gatactacct gggagcagtg gagctctcct gggattacat gcagagcgac     60
cttggggagc tgcccgtgga tgccaggttc cctccccggg tgccaaagtc gtttccgttc    120
aacacctccg tggtgtacaa gaaaactctg ttcgtggagt tcaccgacca cctgttcaat    180
atcgccaagc ccagacctcc ctggatgggg ctgttgggac ctaccatcca agcggaggtg    240
tacgacactg tggtcatcac tctgaagaac atggcctcgc atcccgtgtc cctgcacgcc    300
gtgggagtgt cttactggaa agcgtccgag ggggccgaat acgacgacca gacctcgcag    360
agagaaaagg aagatgacaa ggtgttccca ggaggatcgc acacctacgt gtggcaagtg    420
ttgaaggaga cgcccaat ggcctccgac ccgctgtgcc tgacctactc gtacctgtcc       480
cacgtggacc tcgtgaagga cctcaactcg ggactgattg agccctgct ggtctgcagg     540 gaaggctcac tggcgaaaga aaagactcag accttgcaca gttcattct gctgttcgct     600 gtgttcgacg aggggaagtc gtggcacagc gagactaaga actccctgat gcaagataga    660
gatgccgcct ccgccggc ctggcctaag atgcacaccg tgaacggtta cgtgaaccgc      720
tccctccctg gcctgattgg atgccaccgg aagtccgtgt actggcacgt gatcgggatg    780
gggaccaccc ccgaggtgca cagcatcttc ctggaaggtc acatttct cgtgcgcaac     840
```

| | |
|---|---|
| caccggcagg cctccctgga atcagcccc attaccttcc tcactgccca gactctgctg | 900 |
| atggacctgg gacagttcct gctgttctgc catatctcct cccaccaaca tgacggaatg | 960 |
| gaggcatacg tgaaggtcga ttcctgccct gaggaacccc agctccgcat gaagaacaat | 1020 |
| gaggaagccg aggactacga cgacgacctg acggatagcg agatggatgt ggtccggttc | 1080 |
| gatgacgata acagcccttc cttcatccaa attcgctcgg tggcaaagaa gcaccccaag | 1140 |
| acctgggtgc attacattgc ggcggaagaa gaggactggg attatgcccc gcttgtcctc | 1200 |
| gctcctgacg accggagcta caagagccag tacctgaaca cggtccaca gaggatcggt | 1260 |
| agaaagtaca gaaggtccg cttcatggcc tataccgacg aaaccttcaa aactagagag | 1320 |
| gccatccaac acgaatccgg catcctgggc ccgctcttgt acggagaagt cggcgacacc | 1380 |
| cttctcatta tcttcaagaa ccaggcttcc cggccgtaca acatctatcc gcatgggatc | 1440 |
| actgacgtgc gcccactgta ctcgcggcgc ctgcccaagg gtgtcaaaca cctgaaggat | 1500 |
| tttccgatcc ttccgggaga aatcttcaag tacaagtgga ccgtgaccgt ggaagatggc | 1560 |
| ccaactaagt ctgaccctag atgcctcacc cgctactact catccttcgt caacatggag | 1620 |
| cgcgacctgg ccagcggact gatcggcccg ctgctgattt gctacaagga atcagtggac | 1680 |
| caacggggaa accagatcat gtcggataag aggaacgtca tcctcttctc cgtg | 1734 |

<210> SEQ ID NO 8
<211> LENGTH: 2583
<212> TYPE: DNA
<213> ORGANISM: Artificial Sequence
<220> FEATURE:
<223> OTHER INFORMATION: coFVIII-52-CT

<400> SEQUENCE: 8

| | |
|---|---|
| tttgacgaaa accggtcgtg gtacctgacc gagaacatcc agaggttcct gcccaaccct | 60 |
| gctggggtgc agctggagga ccccgagttc caggccagca acatcatgca cagcatcaat | 120 |
| ggctacgtgt cgacagcct gcagctgagc gtgtgcctgc acgaggtggc ctactggtac | 180 |
| atcctgagca tcggcgccca gaccgacttc ctgagcgtgt tcttctctgg ctacaccttc | 240 |
| aagcacaaga tggtgtatga ggacaccctg accctgttcc ccttcagcgg ggagactgtc | 300 |
| ttcatgagca tggagaaccc tggcctgtgg atcctgggct gccacaacag cgacttcagg | 360 |
| aacaggggca tgactgccct gctgaaagtc tccagctgtg acaagaacac cggggactac | 420 |
| tacgaggaca gctacgagga catcagcgcc tacctgctga gcaagaacaa tgccatcgag | 480 |
| cccaggagct tctctcagaa cccccagtg ctgaagaggc accagaggga gatcaccagg | 540 |
| accaccctgc agtctgacca ggaggagatc gactatgatg acaccatcag cgtggagatg | 600 |
| aagaaggagg acttcgacat ctacgacgag gacgagaacc agagcccag gagcttccag | 660 |
| aagaagacca ggcactactt cattgctgct gtggagaggc tgtgggacta tggcatgtcc | 720 |
| agcagccccc atgtgctgag gaacagggcc cagtctggca gcgtgcccca gttcaagaaa | 780 |
| gtcgtgttcc aggagttcac cgacggcagc ttcacccagc cctgtacag aggggagctg | 840 |
| aacgagcacc tgggcctgct gggcccctac atcagggccg aggtggagga acatcatg | 900 |
| gtgaccttca ggaaccaggc cagcaggccc tacagcttct acagcagcct gatcagctac | 960 |
| gaggaggacc agaggcaggg ggctgagccc aggaagaact tgtgaagcc caatgaaacc | 1020 |
| aagacctact ctggaaggt gcagcaccac atggcccca ccaaggacga gttcgactgc | 1080 |
| aaggcctggg cctacttctc tgacgtggac ctggagaagg acgtgcactc tggcctgatt | 1140 |
| ggccccctgc tggtgtgcca caccaacacc ctgaaccctg cccatggcag gcaggtgact | 1200 |

| | |
|---|---|
| gtgcaggagt tcgccctgtt cttcaccatc ttcgatgaaa ccaagagctg gtacttcact | 1260 |
| gagaacatgg agaggaactg cagggccccc tgcaacatcc agatggagga ccccaccttc | 1320 |
| aaggagaact acaggttcca tgccatcaat ggctacatca tggacaccct gcctggcctg | 1380 |
| gtcatggccc aggaccagag gatcaggtgg tatctgctga gcatgggcag caacgagaac | 1440 |
| atccacagca tccacttctc tggccacgtg ttcactgtga ggaagaagga ggagtacaag | 1500 |
| atggccctgt acaacctgta ccctggggtg ttcgaaaccg tggagatgct gcccagcaag | 1560 |
| gccggcatct ggaggggtgga gtgcctgatt ggggagcacc tgcacgccgg catgagcacc | 1620 |
| ctgttcctgg tgtacagcaa caagtgccag accccctgg gcatggcctc tggccacatc | 1680 |
| agggacttcc agatcactgc ctctggccag tacggccagt gggcccccaa gctggccagg | 1740 |
| ctgcactact ccggaagcat caatgcctgg agcaccaagg agcccttcag ctggatcaaa | 1800 |
| gtggacctgc tggcccccat gatcatccac ggcatcaaga cccaggggggc caggcagaag | 1860 |
| ttctccagcc tgtacatcag ccagttcatc atcatgtaca gcctggacgg caagaagtgg | 1920 |
| cagacctaca ggggcaacag caccggcacc ctgatggtgt tcttcggcaa cgtggacagc | 1980 |
| agcggcatca agcacaacat cttcaacccc cccatcatcg ccagatacat caggctgcac | 2040 |
| cccacccact acagcatcag gagcaccctg aggatggagc tgatgggctg tgacctgaac | 2100 |
| agctgcagca tgcccctggg catggagagc aaggccatct tgacgcccca gatcactgcc | 2160 |
| tccagctact tcaccaacat gtttgccacc tggagcccca gcaaggccag gctgcacctg | 2220 |
| cagggcagga gcaatgcctg gaggccccag gtcaacaacc caaggagtg gctgcaggtg | 2280 |
| gacttccaga gaccatgaa ggtgactggg gtgaccaccc aggggggtgaa gagcctgctg | 2340 |
| accagcatgt acgtgaagga gttcctgatc tccagcagcc aggacggcca ccagtggacc | 2400 |
| ctgttcttcc agaatggcaa ggtgaaggtg ttccagggca ccaggacag cttcaccccct | 2460 |
| gtggtcaaca gcctggaccc cccccctgctg accagatacc tgaggatcca ccccagagc | 2520 |
| tgggtgcacc agatcgccct gaggatggag gtgctgggct gtgaggccca ggacctgtac | 2580 |
| tga | 2583 |

<210> SEQ ID NO 9
<211> LENGTH: 1734
<212> TYPE: DNA
<213> ORGANISM: Artificial Sequence
<220> FEATURE:
<223> OTHER INFORMATION: coFVIII-62-NT58

<400> SEQUENCE: 9

| | |
|---|---|
| gccactcgcc ggtactacct tggagccgtg gagctttcat gggactacat gcagagcgac | 60 |
| ctgggcgaac tccccgtgga tgccagattc cccccccgcg tgccaaagtc cttcccctt | 120 |
| aacacctccg tggtgtacaa gaaaacccctc tttgtcgagt tcactgacca cctgttcaac | 180 |
| atcgccaagc cgcgcccacc ttggatgggc tccctgggac cgaccattca agctgaagtg | 240 |
| tacgacaccg tggtgatcac cctgaagaac atggcgtccc accccgtgtc cctgcatgcg | 300 |
| gtcggagtgt cctactggaa ggcctccgaa ggagctgagt acgacgacca gactagccag | 360 |
| cgggaaaagg aggacgataa agtgttcccg ggcggctcgc atacttacgt gtggcaagtc | 420 |
| ctgaaggaaa acggacctat ggcatccgat cctctgtgcc tgacttactc ctaccttttcc | 480 |
| catgtggacc tcgtgaagga cctgaacagc gggctgattg gtgcacttct cgtgtgccgc | 540 |
| gaaggttcgc tcgctaagga aaagacccag accctccata agttcatcct tttgttcgct | 600 |

```
gtgttcgatg aaggaaagtc atggcattcc gaaactaaga actcgctgat gcaggaccgg    660
gatgccgcct cagcccgcgc ctggcctaaa atgcatacag tcaacggata cgtgaatcgg    720
tcactgcccg ggctcatcgg ttgtcacaga aagtccgtgt actggcacgt catcggcatg    780
ggcactacgc ctgaagtgca ctccatcttc ctggaagggc acaccttcct cgtgcgcaac    840
caccgccagg cctctctgga aatctccccg attacctttc tgaccgccca gactctgctc    900
atggacctgg ggcagttcct tctcttctgc acatctcca gccatcagca cgacggaatg    960
gaggcctacg tgaaggtgga ctcatgcccg gaagaacctc agttgcggat gaagaacaac   1020
gaggaggccg aggactatga cgacgatttg actgactccg agatggacgt cgtgcggttc   1080
gatgacgaca acagccccag cttcatccag attcgcagcg tggccaagaa gcaccccaaa   1140
acctgggtgc actacatcgc ggccgaggaa gaagattggg actacgcccc gttggtgctg   1200
gcacccgatg accggtcgta caagtcccag tatctgaaca atggtccgca gcggattggc   1260
agaaagtaca agaaagtgcg cttcatggcg tacactgacg aaacgtttaa gacccgggag   1320
gccattcaac atgagagcgg cattctggga ccactgctgt acgagaggt cggcgatacc   1380
ctgctcatca tcttcaaaaa ccaggcctcc cggccttaca acatctaccc tcacggaatc   1440
accgacgtgc ggccactcta ctcgcggcgc ctgccgaagg cgtcaagca cctgaaagac   1500
ttccctatcc tgccgggcga aatcttcaag tataagtgga ccgtcaccgt ggaggacggg   1560
cccaccaaga gcgatcctag tgtctgact cggtactact ccagcttcgt gaacatggaa   1620
cgggacctgg catcgggact cattggaccg ctgctgatct gctacaaaga gtcggtggat   1680
caacgcggca accagatcat gtccgacaag cgcaacgtga tcctgttctc cgtg          1734

<210> SEQ ID NO 10
<211> LENGTH: 2583
<212> TYPE: DNA
<213> ORGANISM: Artificial Sequence
<220> FEATURE:
<223> OTHER INFORMATION: coFVIII-62-CT

<400> SEQUENCE: 10
tttgatgaaa acagatcctg gtacctgacc gagaacatcc agaggttcct gcccaaccct     60
gctggggtgc agctggagga ccccgagttc caggccagca acatcatgca cagcatcaat    120
ggctacgtgt tcgacagcct gcagctgagc gtgtgcctgc acgaggtggc ctactgggtac    180
atcctgagca tcggcgccca gaccgacttc ctgagcgtgt tcttctctgg ctacaccttc    240
aagcacaaga tggtgtatga ggacaccctg accctgttcc ccttcagcgg ggagactgtc    300
ttcatgagca tggagaaccc tggcctgtgg atcctgggct gccacaacag cgacttcagg    360
aacaggggca tgactgccct gctgaaagtc tccagctgtg acaagaacac cggggactac    420
tacgaggaca gctacgagga catcagcgcc tacctgctga gcaagaacaa tgccatcgag    480
cccaggagct ctctcagaa ccccccagtg ctgaagaggc accagaggga gatcaccagg    540
accaccctgc agtctgacca ggaggagatc gactatgatg acaccatcag cgtggagatg    600
aagaaggagg acttcgacat ctacgacgag gacgagaacc agagcccccag gagcttccag    660
aagaagacca ggcactactt cattgctgct gtggagaggc tgtgggacta tggcatgtcc    720
agcagccccc atgtgctgag gaacagggcc cagtctggca gcgtgcccca gttcaagaaa    780
gtcgtgttcc aggagttcac cgacggcagc ttcacccagc ccctgtacag gggggagctg    840
aacgagcacc tgggcctgct gggccccta c atcagggccg aggtggagga caacatcatg    900
gtgaccttca ggaaccaggc cagcaggccc tacagcttct acagcagcct gatcagctac    960
```

```
gaggaggacc agaggcaggg ggctgagccc aggaagaact ttgtgaagcc caatgaaacc    1020
aagacctact tctggaaggt gcagcaccac atggccccca ccaaggacga gttcgactgc    1080
aaggcctggg cctacttctc tgacgtggac ctggagaagg acgtgcactc tggcctgatt    1140 ggcccctgc tggtgtgcca caccaacacc ctgaaccctg cccatggcag gcaggtgact     1200
gtgcaggagt tcgccctgtt cttcaccatc ttcgatgaaa ccaagagctg gtacttcact    1260
gagaacatgg agaggaactg cagggccccc tgcaacatcc agatggagga ccccaccttc    1320
aaggagaact acaggttcca tgccatcaat ggctacatca tggacaccct gcctggcctg    1380
gtcatggccc aggaccagag gatcaggtgg tatctgctga gcatgggcag caacgagaac    1440
atccacagca tccacttctc tggccacgtg ttcactgtga ggaagaagga ggagtacaag    1500
atggccctgt acaacctgta ccctggggtg ttcgaaaccg tggagatgct gcccagcaag    1560
gccggcatct ggaggtggga gtgcctgatt ggggagcacc tgcacgccgg catgagcacc    1620
ctgttcctgg tgtacagcaa caagtgccag accccctgg gcatggcctc tggccacatc     1680
agggacttcc agatcactgc ctctggccag tacggccagt gggcccccaa gctggccagg    1740
ctgcactact ccggaagcat caatgcctgg agcaccaagg agcccttcag ctggatcaaa    1800
gtggacctgc tggccccat gatcatccac ggcatcaaga cccaggggc caggcagaag      1860 ttctccagcc tgtacatcag ccagttcatc atcatgtaca gcctgacgg caagaagtgg    1920 cagacctaca ggggcaacag caccggcacc ctgatggtgt tcttcggcaa cgtggacagc    1980
agcggcatca gcacaacat cttcaacccc cccatcatcg ccagatacat caggctgcac      2040
cccacccact acagcatcag gagcaccctg aggatggagc tgatgggctg tgacctgaac    2100
agctgcagca tgcccctggg catggagagc aaggccatct tgacgcccca gatcactgcc    2160
tccagctact tcaccaacat gtttgccacc tggagcccca gcaaggccag gctgcacctg    2220
cagggcagga gcaatgcctg gagggcccag gtcaacaacc caaggagtg gctgcaggtg    2280 gacttccaga agaccatgaa ggtgactggg gtgaccaccc aggggggtgaa gagcctgctg    2340 accagcatgt acgtgaagga gttcctgatc tccagcagcc aggacggcca ccagtggacc    2400
ctgttcttcc agaatggcaa ggtgaaggtg ttccagggca ccaggacag cttcacccct    2460 gtggtcaaca gcctggaccc ccccctgctg accagatacc tgaggatcca cccccagagc    2520
tgggtgcacc agatcgccct gaggatggag gtgctgggct gtgaggccca ggacctgtac    2580
tga                                                                 2583
```

<210> SEQ ID NO 11
<211> LENGTH: 1734
<212> TYPE: DNA
<213> ORGANISM: Artificial Sequence
<220> FEATURE:
<223> OTHER INFORMATION: coFVIII-25-NT58

<400> SEQUENCE: 11

```
gccaccagga gatactacct gggcgccgtg gagctgagct gggactacat gcagtctgac     60
ctgggcgagc tgccagtgga cgccaggttc ccccccagag tgcccaagag cttccccttc    120
aacaccagcg tggtgtacaa gaagaccctg ttcgtggagt tcactgacca cctgttcaac    180
atcgccaagc ccaggccccc ctggatgggc ctgctgggcc ccaccatcca ggccgaggtg    240
tacgacaccg tggtcatcac cctgaagaac atggccagcc accccgtctc cctgcacgcc    300
gtgggggtga gctactggaa ggcctctgag ggcgccgagt acgacgacca gaccagccag    360
```

```
agggagaagg aggacgacaa ggtgttccct gggggcagcc acacctacgt gtggcaggtc    420
ctgaaggaga acggccccat ggcctctgac cccctgtgcc tgacctacag ctacctgagc    480
cacgtggacc tggtgaagga cctgaactct ggcctgattg gggccctgct ggtgtgcagg    540
gagggcagcc tggccaagga gaagacccag accctgcaca agttcatcct gctgttcgcc    600
gtgttcgacg agggcaagag ctggcactct gaaaccaaga acagcctgat gcaggacagg    660
gacgccgcct ctgccagggc ctggcccaag atgcacaccg tcaacggcta cgtcaacagg    720
agcctgcctg gcctgattgg ctgccacagg aagagcgtgt actggcatgt gatcggcatg    780
ggcaccaccc ctgaggtgca cagcatcttc ctggagggcc acaccttcct ggtcaggaac    840
cacaggcagg ccagcctgga gatcagcccc atcaccttcc tgaccgccca gaccctgctg    900
atggacctgg gccagttcct gctgttctgc cacatctcca gccaccagca cgacggcatg    960
gaggcctacg tgaaagtgga cagctgccct gaggagcccc agctgaggat gaagaacaac   1020
gaggaggccg aggactatga tgacgacctg accgacagcg agatggacgt ggtcaggttc   1080
gacgacgaca acagccccag cttcatccag atcaggagct ggccaagaa gcaccccaag   1140
```

*(note: line at 1140 reads: `gacgacgaca acagccccag cttcatccag atcaggagct ggccaagaa gcaccccaag`)*

```
acctgggtgc actacatcgc tgctgaggag gaggactggg actatgcccc cctggtgctg   1200
gcccctgatg acaggagcta caagagccag tacctgaaca atggccccca gaggattggc   1260
aggaagtaca aaaagtcag gttcatggcc tacactgatg aaaccttcaa gaccagggag   1320
gccatccagc atgagtctgg catcctgggc cccctgctgt acggggaggt ggggacacc   1380 ctgctgatca tcttcaagaa ccaggccagc aggccctaca acatctaccc ccatggcatc   1440
accgacgtga ggcccctgta cagcaggagg ctgcctaagg gggtgaagca cctgaaagac   1500
ttccccatcc tgcctgggga tcttcaag tacaagtgga ctgtgactgt ggaggacggc   1560
cccaccaaga gcgaccccag gtgcctgacc agatactaca gcagcttcgt caacatggag   1620
agggacctgg cctctggcct gattggcccc ctgctgatct gctacaagga gtctgtggac   1680
cagaggggca accagatcat gagcgacaag aggaacgtga cctgttctc tgtc          1734
```

<210> SEQ ID NO 12
<211> LENGTH: 2583
<212> TYPE: DNA
<213> ORGANISM: Artificial Sequence
<220> FEATURE:
<223> OTHER INFORMATION: coFVIII-25-CT

<400> SEQUENCE: 12

```
ttcgacgaga acaggagctg gtacctgact gaaaacatcc agcggttcct ccccaacccc     60
gcgggcgtgc agctggaaga tcctgagttt caggcatcaa acatcatgca ctccattaac    120
ggctacgtgt tcgattcgct gcagctgagc gtgtgtctgc acgaagtggc ctactggtac    180
atcctgtcca ttggtgccca gactgacttc ctgtccgtgt ttttctccgg ctacacgttc    240
aagcacaaga tggtgtacga ggacaccctg accctcttcc cttttccgg cgaaactgtg    300 tttatgagca tggagaatcc cggcctgtgg atcttgggct gccacaacag cgacttccgt    360
aacagaggaa tgactgcgct gctcaaggtg tccagctgcg acaagaacac cggagactat    420
tatgaggact catacgagga catctccgcc tacctcctgt ccaagaataa cgccattgaa    480
cctcggagct tcagccagaa cccacccgtg cttaagagac atcaacggga tcactagg     540 accacccctgc agtcagacca ggaggaaatc gactacgatg acaccatctc ggtcgagatg    600
aagaaggagg acttgacat ctacgacgaa gatgaaaacc agagcccgag gtcgttccaa    660
aagaaaaccc gccactactt tattgctgct gtcgagcggc tgtgggacta cggaatgtcg    720
```

```
tcctcgccgc acgtgctccg caaccgagcc cagagcggct cggtgccgca attcaagaag      780
gtcgtgttcc aggagttcac tgacgggagc ttcactcagc ctttgtaccg gggagaactc      840
aatgaacatc tcggcctcct cggaccttac atcagagcag aagtggaaga taacatcatg      900
gtcactttcc gtaaccaagc cagccgcccg tactcgttct actcctccct catttcttac      960
gaagaggacc agcggcaggg cgcagaaccg cgcaagaact tcgtgaagcc aacgaaacc      1020
aagacctact tctggaaagt gcagcatcat atggccccga ctaaggacga gtttgactgc     1080
aaagcctggg cctacttctc cgatgtggac ttggagaagg acgtccactc cggcctcatc     1140
ggtcccctgc tcgtgtgcca taccaatacc ctgaaccccg cacacggtcg ccaggtcacc     1200
gtgcaggagt tcgctctgtt cttcactatc ttcgacgaaa ctaagtcctg gtacttcacc     1260
gagaacatgg agaggaactg cagagccccc tgtaacatcc agatggagga cccgacgttc     1320
aaggaaaact accggttcca cgccattaac ggatacatca tggatacgct gccgggtctt     1380
gtgatggccc aggatcaacg gatcagatgg tacttattgt cgatgggcag caacgagaac     1440
atccactcta ttcacttctc cggtcatgtg ttcactgtgc ggaagaagga agagtacaag     1500
atggccctgt acaacctttta tcccggagtg ttcgaaactg tggaaatgct gccgtcgaag    1560
gccggcattt ggcgcgtgga gtgtttgatt ggagaacatc tccatgcggg gatgtcaacc     1620
ctgttcctgg tgtatagcaa caagtgccag actccgcttg gatggcgtc aggacacatt      1680
agggatttcc agatcactgc gtccggccag tacggccaat gggcccctaa gctggcccgc     1740
ctgcattact ccggatccat taacgcctgg tcaaccaagg agccattctc ctggatcaag     1800
gtggaccttc tggcccccat gattatccac ggaattaaga cccaggggc ccggcagaag      1860
ttctcctcac tgtacatcag ccagttcata atcatgtact ccctggacgg aaagaagtgg     1920
caaacctaca gggaacag caccggcaca ctgatggtct ttttcggaaa tgtggactcc        1980
tccgggatta agcataacat cttcaaccct ccgattatcg ctcggtacat tagacttcac     2040
cctacccact acagcattcg ctccaccctg cggatggaac tgatgggctg cgatctgaac     2100
tcgtgcagca tgccgttggg aatggagtcc aaagcaattt ccgacgcgca gatcaccgcc     2160
tcgtcctact ttaccaacat gttcgccacg tggtcaccgt ccaaggcccg gctgcacctc     2220
cagggaagat ccaacgcatg gcggccacag gtcaacaacc ctaaggagtg gctccaggtg     2280
gacttccaga aaaccatgaa ggtcaccgga gtcacaaccc agggagtgaa gtcgctgctg     2340
acttctatgt acgtcaagga gttcctgatc tccagcagcc aggacgggca ccagtggacc     2400
ctgttcttcc aaaatggaaa ggtcaaggtg tttcagggca atcaggattc attcaccccg     2460
gtggtgaact cccttgatcc accctcctg acccgctacc ttcgcatcca cccacagtcc      2520
tgggtgcacc agatcgcgct gaggatggag gtcctgggat gcgaagccca ggacctgtac     2580
tga                                                                   2583
```

<210> SEQ ID NO 13
<211> LENGTH: 1734
<212> TYPE: DNA
<213> ORGANISM: Artificial Sequence
<220> FEATURE:
<223> OTHER INFORMATION: coFVIII-26-NT58

<400> SEQUENCE: 13

```
gccaccagga gatactacct gggcgccgtg gagctgagct gggactacat gcagtctgac       60
ctgggcgagc tgccagtgga cgccaggttc ccccccagag tgcccaagag cttccccttc      120
```

| | |
|---|---:|
| aacaccagcg tggtgtacaa gaagaccctg ttcgtggagt tcactgacca cctgttcaac | 180 |
| atcgccaagc ccaggccccc ctggatgggc ctgctgggcc ccaccatcca ggccgaggtg | 240 |
| tacgacaccg tggtcatcac cctgaagaac atggccagcc accccgtctc cctgcacgcc | 300 |
| gtggggtga gctactggaa ggcctctgag ggcgccgagt acgacgacca gaccagccag | 360 |
| agggagaagg aggacgacaa ggtgttccct ggggcagcc acacctacgt gtggcaggtc | 420 |
| ctgaaggaga acgccccat ggcctctgac cccctgtgcc tgacctacag ctacctgagc | 480 |
| cacgtggacc tggtgaagga cctgaactct ggcctgattg ggccctgct ggtgtgcagg | 540 |
| gagggcagcc tggccaagga gaagacccag accctgcaca gttcatcct gctgttcgcc | 600 |
| gtgttcgacg agggcaagag ctggcactct gaaaccaaga acagcctgat gcaggacagg | 660 |
| gacgccgcct ctgccagggc ctggcccaag atgcacaccg tcaacggcta cgtcaacagg | 720 |
| agcctgcctg gcctgattgg ctgccacagg aagagcgtgt actggcatgt gatcggcatg | 780 |
| ggcaccaccc ctgaggtgca cagcatcttc ctggagggcc acaccttcct ggtcaggaac | 840 |
| cacaggcagg ccagcctgga gatcagcccc atcaccttcc tgaccgccca gacctgctg | 900 |
| atggacctgg gccagttcct gctgttctgc cacatctcca gccaccagca cgacggcatg | 960 |
| gaggcctacg tgaaagtgga cagctgccct gaggagcccc agctgaggat gaagaacaac | 1020 |
| gaggaggccg aggactatga tgacgacctg accgacagcg agatggacgt ggtcaggttc | 1080 |
| gacgacgaca acagccccag cttcatccag atcaggagct ggccaagaa gcaccccaag | 1140 |
| acctgggtgc actacatcgc tgctgaggag gaggactggg actatgcccc cctggtgctg | 1200 |
| gcccctgatg acaggagcta caagagccag tacctgaaca tggcccca gaggattggc | 1260 |
| aggaagtaca agaaagtcag gttcatggcc tacactgatg aaaccttcaa gaccagggag | 1320 |
| gccatccagc atgagtctgg catcctgggc cccctgctgt acggggaggt gggggacacc | 1380 |
| ctgctgatca tcttcaagaa ccaggccagc aggccctaca acatctaccc ccatggcatc | 1440 |
| accgacgtga ggcccctgta cagcaggagg ctgcctaagg gggtgaagca cctgaaagac | 1500 |
| ttccccatcc tgcctgggga gatcttcaag tacaagtgga ctgtgactgt ggaggacggc | 1560 |
| cccaccaaga gcgaccccag gtgcctgacc agatactaca gcagcttcgt caacatggag | 1620 |
| agggacctgg cctctggcct gattggcccc ctgctgatct gctacaagga gtctgtggac | 1680 |
| cagagggca accagatcat gagcgacaag aggaacgtga tcctgttctc tgtc | 1734 |

<210> SEQ ID NO 14
<211> LENGTH: 2583
<212> TYPE: DNA
<213> ORGANISM: Artificial Sequence
<220> FEATURE:
<223> OTHER INFORMATION: coFVIII-26-CT

<400> SEQUENCE: 14

| | |
|---|---:|
| ttcgacgaga acaggagctg gtacctcact gaaaacatcc agaggttcct cccaaacccc | 60 |
| gcaggagtgc aactggagga ccctgagttt caggcctcga atatcatgca ctcgattaac | 120 |
| ggttacgtgt tcgactcgct gcagctgagc gtgtgcctcc atgaagtcgc ttactggtac | 180 |
| attctgtcca tcggcgccca gactgacttc ctgagcgtgt tcttttccgg ttacaccttt | 240 |
| aagcacaaga tggtgtacga agatacctg accctgttcc ctttctccgg cgaaacggtg | 300 |
| ttcatgtcga tggagaaccc gggtctgtgg attctgggat gccacaacag cgactttcgg | 360 |
| aaccgcggaa tgactgccct gctgaaggtg tcctcatgcg acaagaacac cggagactac | 420 |
| tacgaggact cctacgagga tatctcagcc tacctcctgt ccaagaacaa cgcgatcgag | 480 |

```
ccgcgcagct tcagccagaa cccgcctgtg ctgaagaggc accagcgaga aattacccgg    540
accaccctcc aatcggatca ggaggaaatc gactacgacg acaccatctc ggtggaaatg    600
aagaaggaag atttcgatat ctacgacgag gacgaaaatc agtcccctcg ctcattccaa    660
aagaaaacta gacactactt tatcgccgcg gtggaaagac tgtgggacta tggaatgtca    720
tccagccctc acgtccttcg gaaccgggcc cagagcggat cggtgcctca gttcaagaaa    780
gtggtgttcc aggagttcac cgacggcagc ttcacccagc cgctgtaccg gggagaactg    840
aacgaacacc tgggcctgct cggtccctac atccgcgcgg aagtggagga taacatcatg    900
gtgaccttcc gtaaccaagc atccagacct tactccttct attcctccct gatctcatac    960
gaggaggacc agcgccaagg cgccgagccc cgcaagaact cgtcaagcc caacgagact    1020 aagacctact tctggaaggt ccaacaccat atggccccga ccaaggatga gtttgactgc    1080
aaggcctggg cctacttctc cgacgtggac cttgagaagg atgtccattc cggcctgatc    1140
gggccgctgc tcgtgtgtca caccaacacc ctgaacccag cgcatggacg ccaggtcacc    1200
gtccaggagt ttgctctgtt cttcaccatt tttgacgaaa ctaagtcctg gtacttcacc    1260
gagaatatgg agcgaaactg tagagcgccc tgcaatatcc agatgaaga tccgactttc    1320 aaggagaact atagattcca cgccatcaac gggtacatca tggatactct gccggggctg    1380
gtcatggccc aggatcagag gattcggtgg tacttgctgt caatgggatc gaacgaaaac    1440
attcactcca ttcacttctc cggtcacgtg ttcactgtgc gcaagaagga ggagtacaag    1500
atggcgctgt acaatctgta ccccggggtg ttcgaaactg tggagatgct gccgtccaag    1560
gccggcatct ggagagtgga gtgcctgatc ggagagcacc tccacgcggg gatgtccacc    1620
ctcttcctgg tgtactcgaa taagtgccag accccgctgg gcatggcctc gggccacatc    1680
agagacttcc agatcacagc aagcggacaa tacggccaat gggcgccgaa gctggcccgc    1740
ttgcactact cccggatcgat caacgcatgg tccaccaagg aaccgttctc gtggattaag    1800
gtggacctcc tggcccctat gattatccac ggaattaaga cccagggcgc caggcagaag    1860
ttctcctccc tgtacatctc gcaattcatc atcatgtaca gcctggacgg gaagaagtgg    1920
cagacttaca ggggaaactc caccggcacc ctgatggtct ttttcggcaa cgtggattcc    1980
tccggcatta agcacaacat cttcaaccca ccgatcatag ccagatatat taggctccac    2040
cccactcact actcaatccg ctcaactctt cggatggaac tcatggggtg cgacctgaac    2100
tcctgctcca tgccgttggg gatggaatca aaggctatta gcgacgccca gatcaccgcg    2160
agctcctact tcactaacat gttcgccacc tggagcccct ccaaggccag gctgcacttg    2220
cagggacggt caaatgcctg gcggccgcaa gtgaacaatc gaaggaatg gcttcaagtg    2280 gatttccaaa agaccatgaa agtgaccgga gtcaccaccc agggagtgaa gtcccttctg    2340
acctcgatgt atgtgaagga gttcctgatt agcagcagcc aggacgggca ccagtggacc    2400
ctgttcttcc aaaacggaaa ggtcaaggtg ttccagggga accaggactc gttcacaccc    2460
gtggtgaact ccctggaccc cccactgctg acgcggtact gaggattca tcctcagtcc    2520 tgggtccatc agattgcatt gcgaatggaa gtcctgggct gcgaggccca ggacctgtac    2580
tga                                                                 2583
```

<210> SEQ ID NO 15
<211> LENGTH: 2332
<212> TYPE: PRT
<213> ORGANISM: Homo sapiens -continued

```
<400> SEQUENCE: 15

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415
```

```
Gln Arg Ile Gly Arg Lys Tyr Lys Val Arg Phe Met Ala Tyr Thr
            420             425             430

Asp Glu Thr Phe Lys Thr Arg Glu Ala Ile Gln His Glu Ser Gly Ile
            435             440             445

Leu Gly Pro Leu Leu Tyr Gly Glu Val Gly Asp Thr Leu Leu Ile Ile
450             455             460

Phe Lys Asn Gln Ala Ser Arg Pro Tyr Asn Ile Tyr Pro His Gly Ile
465             470             475             480

Thr Asp Val Arg Pro Leu Tyr Ser Arg Arg Leu Pro Lys Gly Val Lys
            485             490             495

His Leu Lys Asp Phe Pro Ile Leu Pro Gly Ile Phe Lys Tyr Lys
            500             505             510

Trp Thr Val Thr Val Glu Asp Gly Pro Thr Lys Ser Asp Pro Arg Cys
            515             520             525

Leu Thr Arg Tyr Tyr Ser Ser Phe Val Asn Met Glu Arg Asp Leu Ala
530             535             540

Ser Gly Leu Ile Gly Pro Leu Leu Ile Cys Tyr Lys Glu Ser Val Asp
545             550             555             560

Gln Arg Gly Asn Gln Ile Met Ser Asp Lys Arg Asn Val Ile Leu Phe
            565             570             575

Ser Val Phe Asp Glu Asn Arg Ser Trp Tyr Leu Thr Glu Asn Ile Gln
            580             585             590

Arg Phe Leu Pro Asn Pro Ala Gly Val Gln Leu Glu Asp Pro Glu Phe
            595             600             605

Gln Ala Ser Asn Ile Met His Ser Ile Asn Gly Tyr Val Phe Asp Ser
            610             615             620

Leu Gln Leu Ser Val Cys Leu His Glu Val Ala Tyr Trp Tyr Ile Leu
625             630             635             640

Ser Ile Gly Ala Gln Thr Asp Phe Leu Ser Val Phe Phe Ser Gly Tyr
            645             650             655

Thr Phe Lys His Lys Met Val Tyr Glu Asp Thr Leu Thr Leu Phe Pro
            660             665             670

Phe Ser Gly Glu Thr Val Phe Met Ser Met Glu Asn Pro Gly Leu Trp
            675             680             685

Ile Leu Gly Cys His Asn Ser Asp Phe Arg Asn Arg Gly Met Thr Ala
            690             695             700

Leu Leu Lys Val Ser Ser Cys Asp Lys Asn Thr Gly Asp Tyr Tyr Glu
705             710             715             720

Asp Ser Tyr Glu Asp Ile Ser Ala Tyr Leu Leu Ser Lys Asn Asn Ala
            725             730             735

Ile Glu Pro Arg Ser Phe Ser Gln Asn Ser Arg His Pro Ser Thr Arg
            740             745             750

Gln Lys Gln Phe Asn Ala Thr Thr Ile Pro Glu Asn Asp Ile Glu Lys
            755             760             765

Thr Asp Pro Trp Phe Ala His Arg Thr Pro Met Pro Lys Ile Gln Asn
            770             775             780

Val Ser Ser Ser Asp Leu Leu Met Leu Leu Arg Gln Ser Pro Thr Pro
785             790             795             800

His Gly Leu Ser Leu Ser Asp Leu Gln Glu Ala Lys Tyr Glu Thr Phe
            805             810             815

Ser Asp Asp Pro Ser Pro Gly Ala Ile Asp Ser Asn Asn Ser Leu Ser
            820             825             830
```

-continued

Glu Met Thr His Phe Arg Pro Gln Leu His Ser Gly Asp Met Val
          835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
              885                 890                 895

Gly Thr Asp Asn Thr Ser Ser Leu Gly Pro Pro Ser Met Pro Val His
              900                 905                 910

Tyr Asp Ser Gln Leu Asp Thr Thr Leu Phe Gly Lys Lys Ser Ser Pro
              915                 920                 925

Leu Thr Glu Ser Gly Gly Pro Leu Ser Leu Ser Glu Glu Asn Asn Asp
930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
              965                 970                 975

Arg Ala His Gly Pro Ala Leu Leu Thr Lys Asp Asn Ala Leu Phe Lys
              980                 985                 990

Val Ser Ile Ser Leu Leu Lys Thr Asn Lys Thr Ser Asn Asn Ser Ala
              995                 1000                1005

Thr Asn Arg Lys Thr His Ile Asp Gly Pro Ser Leu Leu Ile Glu
     1010                1015                1020

Asn Ser Pro Ser Val Trp Gln Asn Ile Leu Glu Ser Asp Thr Glu
     1025                1030                1035

Phe Lys Lys Val Thr Pro Leu Ile His Asp Arg Met Leu Met Asp
     1040                1045                1050

Lys Asn Ala Thr Ala Leu Arg Leu Asn His Met Ser Asn Lys Thr
     1055                1060                1065

Thr Ser Ser Lys Asn Met Glu Met Val Gln Gln Lys Lys Glu Gly
     1070                1075                1080

Pro Ile Pro Pro Asp Ala Gln Asn Pro Asp Met Ser Phe Phe Lys
     1085                1090                1095

Met Leu Phe Leu Pro Glu Ser Ala Arg Trp Ile Gln Arg Thr His
     1100                1105                1110

Gly Lys Asn Ser Leu Asn Ser Gly Gln Gly Pro Ser Pro Lys Gln
     1115                1120                1125

Leu Val Ser Leu Gly Pro Glu Lys Ser Val Glu Gly Gln Asn Phe
     1130                1135                1140

Leu Ser Glu Lys Asn Lys Val Val Gly Lys Gly Glu Phe Thr
     1145                1150                1155

Lys Asp Val Gly Leu Lys Glu Met Val Phe Pro Ser Ser Arg Asn
     1160                1165                1170

Leu Phe Leu Thr Asn Leu Asp Asn Leu His Glu Asn Asn Thr His
     1175                1180                1185

Asn Gln Glu Lys Lys Ile Gln Glu Glu Ile Glu Lys Lys Glu Thr
     1190                1195                1200

Leu Ile Gln Glu Asn Val Val Leu Pro Gln Ile His Thr Val Thr
     1205                1210                1215

Gly Thr Lys Asn Phe Met Lys Asn Leu Phe Leu Leu Ser Thr Arg
     1220                1225                1230

Gln Asn Val Glu Gly Ser Tyr Asp Gly Ala Tyr Ala Pro Val Leu

```
                1235                1240                1245
Gln Asp Phe Arg Ser Leu Asn Asp Ser Thr Asn Arg Thr Lys Lys
    1250                1255                1260
His Thr Ala His Phe Ser Lys Lys Gly Glu Glu Glu Asn Leu Glu
    1265                1270                1275
Gly Leu Gly Asn Gln Thr Lys Gln Ile Val Glu Lys Tyr Ala Cys
    1280                1285                1290
Thr Thr Arg Ile Ser Pro Asn Thr Ser Gln Gln Asn Phe Val Thr
    1295                1300                1305
Gln Arg Ser Lys Arg Ala Leu Lys Gln Phe Arg Leu Pro Leu Glu
    1310                1315                1320
Glu Thr Glu Leu Glu Lys Arg Ile Ile Val Asp Asp Thr Ser Thr
    1325                1330                1335
Gln Trp Ser Lys Asn Met Lys His Leu Thr Pro Ser Thr Leu Thr
    1340                1345                1350
Gln Ile Asp Tyr Asn Glu Lys Glu Lys Gly Ala Ile Thr Gln Ser
    1355                1360                1365
Pro Leu Ser Asp Cys Leu Thr Arg Ser His Ser Ile Pro Gln Ala
    1370                1375                1380
Asn Arg Ser Pro Leu Pro Ile Ala Lys Val Ser Ser Phe Pro Ser
    1385                1390                1395
Ile Arg Pro Ile Tyr Leu Thr Arg Val Leu Phe Gln Asp Asn Ser
    1400                1405                1410
Ser His Leu Pro Ala Ala Ser Tyr Arg Lys Lys Asp Ser Gly Val
    1415                1420                1425
Gln Glu Ser Ser His Phe Leu Gln Gly Ala Lys Lys Asn Asn Leu
    1430                1435                1440
Ser Leu Ala Ile Leu Thr Leu Glu Met Thr Gly Asp Gln Arg Glu
    1445                1450                1455
Val Gly Ser Leu Gly Thr Ser Ala Thr Asn Ser Val Thr Tyr Lys
    1460                1465                1470
Lys Val Glu Asn Thr Val Leu Pro Lys Pro Asp Leu Pro Lys Thr
    1475                1480                1485
Ser Gly Lys Val Glu Leu Leu Pro Lys Val His Ile Tyr Gln Lys
    1490                1495                1500
Asp Leu Phe Pro Thr Glu Thr Ser Asn Gly Ser Pro Gly His Leu
    1505                1510                1515
Asp Leu Val Glu Gly Ser Leu Leu Gln Gly Thr Glu Gly Ala Ile
    1520                1525                1530
Lys Trp Asn Glu Ala Asn Arg Pro Gly Lys Val Pro Phe Leu Arg
    1535                1540                1545
Val Ala Thr Glu Ser Ser Ala Lys Thr Pro Ser Lys Leu Leu Asp
    1550                1555                1560
Pro Leu Ala Trp Asp Asn His Tyr Gly Thr Gln Ile Pro Lys Glu
    1565                1570                1575
Glu Trp Lys Ser Gln Glu Lys Ser Pro Glu Lys Thr Ala Phe Lys
    1580                1585                1590
Lys Lys Asp Thr Ile Leu Ser Leu Asn Ala Cys Glu Ser Asn His
    1595                1600                1605
Ala Ile Ala Ala Ile Asn Glu Gly Gln Asn Lys Pro Glu Ile Glu
    1610                1615                1620
Val Thr Trp Ala Lys Gln Gly Arg Thr Glu Arg Leu Cys Ser Gln
    1625                1630                1635
```

```
Asn Pro Pro Val Leu Lys Arg His Gln Arg Glu Ile Thr Arg Thr
    1640              1645              1650

Thr Leu Gln Ser Asp Gln Glu Glu Ile Asp Tyr Asp Asp Thr Ile
    1655              1660              1665

Ser Val Glu Met Lys Lys Glu Asp Phe Asp Ile Tyr Asp Glu Asp
    1670              1675              1680

Glu Asn Gln Ser Pro Arg Ser Phe Gln Lys Lys Thr Arg His Tyr
    1685              1690              1695

Phe Ile Ala Ala Val Glu Arg Leu Trp Asp Tyr Gly Met Ser Ser
    1700              1705              1710

Ser Pro His Val Leu Arg Asn Arg Ala Gln Ser Gly Ser Val Pro
    1715              1720              1725

Gln Phe Lys Lys Val Val Phe Gln Glu Phe Thr Asp Gly Ser Phe
    1730              1735              1740

Thr Gln Pro Leu Tyr Arg Gly Glu Leu Asn Glu His Leu Gly Leu
    1745              1750              1755

Leu Gly Pro Tyr Ile Arg Ala Glu Val Glu Asp Asn Ile Met Val
    1760              1765              1770

Thr Phe Arg Asn Gln Ala Ser Arg Pro Tyr Ser Phe Tyr Ser Ser
    1775              1780              1785

Leu Ile Ser Tyr Glu Glu Asp Gln Arg Gln Gly Ala Glu Pro Arg
    1790              1795              1800

Lys Asn Phe Val Lys Pro Asn Glu Thr Lys Thr Tyr Phe Trp Lys
    1805              1810              1815

Val Gln His His Met Ala Pro Thr Lys Asp Glu Phe Asp Cys Lys
    1820              1825              1830

Ala Trp Ala Tyr Phe Ser Asp Val Asp Leu Glu Lys Asp Val His
    1835              1840              1845

Ser Gly Leu Ile Gly Pro Leu Leu Val Cys His Thr Asn Thr Leu
    1850              1855              1860

Asn Pro Ala His Gly Arg Gln Val Thr Val Gln Glu Phe Ala Leu
    1865              1870              1875

Phe Phe Thr Ile Phe Asp Glu Thr Lys Ser Trp Tyr Phe Thr Glu
    1880              1885              1890

Asn Met Glu Arg Asn Cys Arg Ala Pro Cys Asn Ile Gln Met Glu
    1895              1900              1905

Asp Pro Thr Phe Lys Glu Asn Tyr Arg Phe His Ala Ile Asn Gly
    1910              1915              1920

Tyr Ile Met Asp Thr Leu Pro Gly Leu Val Met Ala Gln Asp Gln
    1925              1930              1935

Arg Ile Arg Trp Tyr Leu Leu Ser Met Gly Ser Asn Glu Asn Ile
    1940              1945              1950

His Ser Ile His Phe Ser Gly His Val Phe Thr Val Arg Lys Lys
    1955              1960              1965

Glu Glu Tyr Lys Met Ala Leu Tyr Asn Leu Tyr Pro Gly Val Phe
    1970              1975              1980

Glu Thr Val Glu Met Leu Pro Ser Lys Ala Gly Ile Trp Arg Val
    1985              1990              1995

Glu Cys Leu Ile Gly Glu His Leu His Ala Gly Met Ser Thr Leu
    2000              2005              2010

Phe Leu Val Tyr Ser Asn Lys Cys Gln Thr Pro Leu Gly Met Ala
    2015              2020              2025
```

| | | | | | | | | | | |
|---|---|---|---|---|---|---|---|---|---|---|
| Ser | Gly | His | Ile | Arg | Asp | Phe | Gln | Ile | Thr | Ala | Ser | Gly | Gln | Tyr |
| | 2030 | | | | 2035 | | | | 2040 | | | | | |
| Gly | Gln | Trp | Ala | Pro | Lys | Leu | Ala | Arg | Leu | His | Tyr | Ser | Gly | Ser |
| | 2045 | | | | 2050 | | | | 2055 | | | | | |
| Ile | Asn | Ala | Trp | Ser | Thr | Lys | Glu | Pro | Phe | Ser | Trp | Ile | Lys | Val |
| | 2060 | | | | 2065 | | | | 2070 | | | | | |
| Asp | Leu | Leu | Ala | Pro | Met | Ile | Ile | His | Gly | Ile | Lys | Thr | Gln | Gly |
| | 2075 | | | | 2080 | | | | 2085 | | | | | |
| Ala | Arg | Gln | Lys | Phe | Ser | Ser | Leu | Tyr | Ile | Ser | Gln | Phe | Ile | Ile |
| | 2090 | | | | 2095 | | | | 2100 | | | | | |
| Met | Tyr | Ser | Leu | Asp | Gly | Lys | Lys | Trp | Gln | Thr | Tyr | Arg | Gly | Asn |
| | 2105 | | | | 2110 | | | | 2115 | | | | | |
| Ser | Thr | Gly | Thr | Leu | Met | Val | Phe | Phe | Gly | Asn | Val | Asp | Ser | Ser |
| | 2120 | | | | 2125 | | | | 2130 | | | | | |
| Gly | Ile | Lys | His | Asn | Ile | Phe | Asn | Pro | Pro | Ile | Ile | Ala | Arg | Tyr |
| | 2135 | | | | 2140 | | | | 2145 | | | | | |
| Ile | Arg | Leu | His | Pro | Thr | His | Tyr | Ser | Ile | Arg | Ser | Thr | Leu | Arg |
| | 2150 | | | | 2155 | | | | 2160 | | | | | |
| Met | Glu | Leu | Met | Gly | Cys | Asp | Leu | Asn | Ser | Cys | Ser | Met | Pro | Leu |
| | 2165 | | | | 2170 | | | | 2175 | | | | | |
| Gly | Met | Glu | Ser | Lys | Ala | Ile | Ser | Asp | Ala | Gln | Ile | Thr | Ala | Ser |
| | 2180 | | | | 2185 | | | | 2190 | | | | | |
| Ser | Tyr | Phe | Thr | Asn | Met | Phe | Ala | Thr | Trp | Ser | Pro | Ser | Lys | Ala |
| | 2195 | | | | 2200 | | | | 2205 | | | | | |
| Arg | Leu | His | Leu | Gln | Gly | Arg | Ser | Asn | Ala | Trp | Arg | Pro | Gln | Val |
| | 2210 | | | | 2215 | | | | 2220 | | | | | |
| Asn | Asn | Pro | Lys | Glu | Trp | Leu | Gln | Val | Asp | Phe | Gln | Lys | Thr | Met |
| | 2225 | | | | 2230 | | | | 2235 | | | | | |
| Lys | Val | Thr | Gly | Val | Thr | Thr | Gln | Gly | Val | Lys | Ser | Leu | Leu | Thr |
| | 2240 | | | | 2245 | | | | 2250 | | | | | |
| Ser | Met | Tyr | Val | Lys | Glu | Phe | Leu | Ile | Ser | Ser | Ser | Gln | Asp | Gly |
| | 2255 | | | | 2260 | | | | 2265 | | | | | |
| His | Gln | Trp | Thr | Leu | Phe | Phe | Gln | Asn | Gly | Lys | Val | Lys | Val | Phe |
| | 2270 | | | | 2275 | | | | 2280 | | | | | |
| Gln | Gly | Asn | Gln | Asp | Ser | Phe | Thr | Pro | Val | Val | Asn | Ser | Leu | Asp |
| | 2285 | | | | 2290 | | | | 2295 | | | | | |
| Pro | Pro | Leu | Leu | Thr | Arg | Tyr | Leu | Arg | Ile | His | Pro | Gln | Ser | Trp |
| | 2300 | | | | 2305 | | | | 2310 | | | | | |
| Val | His | Gln | Ile | Ala | Leu | Arg | Met | Glu | Val | Leu | Gly | Cys | Glu | Ala |
| | 2315 | | | | 2320 | | | | 2325 | | | | | |
| Gln | Asp | Leu | Tyr | | | | | | | | | | | |
| | 2330 | | | | | | | | | | | | | |

<210> SEQ ID NO 16
<211> LENGTH: 4371
<212> TYPE: DNA
<213> ORGANISM: Artificial Sequence
<220> FEATURE:
<223> OTHER INFORMATION: BDD-FVIII (non-optimized; "parental"), Nucleotide Sequence

<400> SEQUENCE: 16

```
atgcaaatag agctctccac ctgcttcttt ctgtgccttt tgcgattctg ctttagtgcc     60
accagaagat actacctggg tgcagtggaa ctgtcatggg actatatgca aagtgatctc    120
ggtgagctgc ctgtggacgc aagatttcct cctagagtgc caaaatcttt tccattcaac    180
```

-continued

```
acctcagtcg tgtacaaaaa gactctgttt gtagaattca cggatcacct tttcaacatc      240
gctaagccaa ggccaccctg gatgggtctg ctaggtccta ccatccaggc tgaggtttat      300
gatacagtgg tcattacact taagaacatg gcttcccatc ctgtcagtct tcatgctgtt      360
ggtgtatcct actggaaagc ttctgaggga gctgaatatg atgatcagac cagtcaaagg      420
gagaaagaag atgataaagt cttccctggt ggaagccata catatgtctg gcaggtcctg      480
aaagagaatg gtccaatggc ctctgaccca ctgtgcctta cctactcata tctttctcat      540
gtggacctgg taaaagactt gaattcaggc ctcattggag ccctactagt atgtagagaa      600
gggagtctgg ccaaggaaaa gacacagacc ttgcacaaat ttatactact ttttgctgta      660
tttgatgaag ggaaaagttg gcactcagaa acaaagaact ccttgatgca ggatagggat      720
gctgcatctg ctcgggcctg gcctaaaatg cacacagtca atggttatgt aaacaggtct      780
ctgccaggtc tgattggatg ccacaggaaa tcagtctatt ggcatgtgat tggaatgggc      840
accactcctg aagtgcactc aatattcctc gaaggtcaca catttcttgt gaggaaccat      900
cgccaggcgt ccttggaaat ctcgccaata actttcctta ctgctcaaac actcttgatg      960
gaccttggac agtttctact gttttgtcat atctcttccc accaacatga tggcatggaa     1020
gcttatgtca agtagacag ctgtccagag gaaccccaac tacgaatgaa aaataatgaa      1080
gaagcggaag actatgatga tgatcttact gattctgaaa tggatgtggt caggtttgat     1140
gatgacaact ctccttcctt tatccaaatt cgctcagttg ccaagaagca tcctaaaact     1200
tgggtacatt acattgctgc tgaagaggag gactgggact atgctcccct tagtcctcgcc   1260 cccgatgaca gaagttataa aagtcaatat ttgaacaatg gccctcagcg gattggtagg     1320
aagtacaaaa aagtccgatt tatggcatac acagatgaaa cctttaagac tcgtgaagct     1380
attcagcatg aatcaggaat cttgggacct ttactttatg gggaagttgg agacacactg     1440
ttgattatat ttaagaatca agcaagcaga ccatataaca tctaccctca cggaatcact     1500
gatgtccgtc ctttgtattc aaggagatta ccaaaaggtg taaaacattt gaaggatttt     1560
ccaattctgc caggagaaat attcaaatat aaatggacag tgactgtaga agatgggcca     1620
actaaatcag atcctcggtg cctgacccgc tattactcta gtttcgttaa tatggagaga     1680
gatctagctt caggactcat tggccctctc ctcatctgct acaaagaatc tgtagatcaa     1740
agaggaaacc agataatgtc agacaagagg aatgtcatcc tgttttctgt atttgatgag     1800
aaccgaagct ggtacctcac agagaatata caacgctttc tccccaatcc agctggagtg     1860
cagcttgagg atccagagtt ccaagcctcc aacatcatgc acagcatcaa tggctatgtt     1920
tttgatagtt tgcagttgtc agtttgtttg catgaggtgg catactggta cattctaagc     1980
attggagcac agactgactt cctttctgtc ttcttctctg atatacctt caaacacaaa      2040 atggtctatg aagacacact caccctattc ccattctcag agaaactgt cttcatgtcg      2100 atggaaaacc caggtctatg gattctgggg tgccacaact cagactttcg aacagaggc     2160 atgaccgcct tactgaaggt ttctagttgt gacaagaaca ctggtgatta ttacgaggac     2220
agttatgaag atatttcagc atacttgctg agtaaaaaca atgccattga accaagaagc     2280
ttctctcaaa acccaccagt cttgaaacgc atcaacggg aataactcg tactactctt       2340 cagtcagatc aagaggaaat tgactatgat gataccatat cagttgaaat gaagaaggaa     2400
gattttgaca tttatgatga ggatgaaaat cagagccccc gcagctttca aaagaaaaca     2460
cgacactatt ttattgctgc agtggagagg ctctgggatt atgggatgag tagctcccca     2520
```

```
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata tataagagca gaagttgaag ataatatcat ggtaactttc    2700
agaaatcagg cctctcgtcc ctattccttc tattctagcc ttatttctta tgaggaagat    2760
cagaggcaag gagcagaacc tagaaaaaac tttgtcaagc taatgaaac caaaacttac    2820
tttttggaaag tgcaacatca tatggcaccc actaaagatg agtttgactg caaagcctgg    2880
gcttatttct ctgatgttga cctggaaaaa gatgtgcact caggcctgat ggacccctt    2940
ctggtctgcc acactaacac actgaaccct gctcatggga gacaagtgac agtacaggaa    3000
tttgctctgt ttttcaccat ctttgatgag accaaaagct ggtacttcac tgaaaatatg    3060
gaaagaaact gcagggctcc ctgcaatatc cagatggaag atcccacttt taaagagaat    3120
tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac actttttctg    3420
gtgtacagca ataagtgtca gactcccctg ggaatggctt ctggacacat tagagatttt    3480
cagattacag cttcaggaca atatggacag tgggccccaa agctggccag acttcattat    3540
tccggatcaa tcaatgcctg gagcaccaag gagcccttt cttggatcaa ggtggatctg    3600
ttggcaccaa tgattattca cggcatcaag acccagggtg cccgtcagaa gttctccagc    3660
ctctacatct ctcagtttat catcatgtat agtcttgatg gaagaagtg gcagacttat    3720
cgaggaaatt ccactggaac cttaatggtc ttctttggca atgtggattc atctgggata    3780
aaacacaata ttttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct ccaagggagg    4020
agtaatgcct ggagacctca ggtgaataat ccaaaagagt ggctgcaagt ggacttccag    4080
aagacaatga agtcacagg agtaactact cagggagtaa aatctctgct taccagcatg    4140
tatgtgaagg agttcctcat ctccagcagt caagatggcc atcagtggac tctcttttt    4200
cagaatggca agtaaaaggt ttttcaggga aatcaagact ccttcacacc tgtggtgaac    4260
tctctagacc caccgttact gactcgctac cttcgaattc accccagag ttgggtgcac    4320
cagattgccc tgaggatgga ggttctgggc tgcgaggcac aggacctcta c            4371
```

<210> SEQ ID NO 17
<211> LENGTH: 1438
<212> TYPE: PRT
<213> ORGANISM: Artificial Sequence
<220> FEATURE:
<223> OTHER INFORMATION: BDD-FVIII (non-optimized; "parental"), Amino
      Acid Sequence <400> SEQUENCE: 17

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

-continued

Arg Val Pro Lys Ser Phe Pro Phe Asn Thr Ser Val Tyr Lys Lys
            35                  40                  45

Thr Leu Phe Val Glu Phe Thr Asp His Leu Phe Asn Ile Ala Lys Pro
 50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
             100                 105                 110

Glu Tyr Asp Asp Gln Thr Ser Gln Arg Glu Lys Glu Asp Asp Lys Val
             115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile

```
              450             455             460
Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Pro Pro Val Leu Lys Arg His
            740                 745                 750

Gln Arg Glu Ile Thr Arg Thr Thr Leu Gln Ser Asp Gln Glu Glu Ile
        755                 760                 765

Asp Tyr Asp Asp Thr Ile Ser Val Glu Met Lys Lys Glu Asp Phe Asp
    770                 775                 780

Ile Tyr Asp Glu Asp Glu Asn Gln Ser Pro Arg Ser Phe Gln Lys Lys
785                 790                 795                 800

Thr Arg His Tyr Phe Ile Ala Ala Val Glu Arg Leu Trp Asp Tyr Gly
                805                 810                 815

Met Ser Ser Ser Pro His Val Leu Arg Asn Arg Ala Gln Ser Gly Ser
            820                 825                 830

Val Pro Gln Phe Lys Lys Val Val Phe Gln Glu Phe Thr Asp Gly Ser
        835                 840                 845

Phe Thr Gln Pro Leu Tyr Arg Gly Glu Leu Asn Glu His Leu Gly Leu
    850                 855                 860

Leu Gly Pro Tyr Ile Arg Ala Glu Val Glu Asp Asn Ile Met Val Thr
865                 870                 875                 880
```

-continued

```
Phe Arg Asn Gln Ala Ser Arg Pro Tyr Ser Phe Tyr Ser Ser Leu Ile
            885                 890                 895

Ser Tyr Glu Glu Asp Gln Arg Gln Gly Ala Glu Pro Arg Lys Asn Phe
            900                 905                 910

Val Lys Pro Asn Glu Thr Lys Thr Tyr Phe Trp Lys Val Gln His His
            915                 920                 925

Met Ala Pro Thr Lys Asp Glu Phe Asp Cys Lys Ala Trp Ala Tyr Phe
            930                 935                 940

Ser Asp Val Asp Leu Glu Lys Asp Val His Ser Gly Leu Ile Gly Pro
945                 950                 955                 960

Leu Leu Val Cys His Thr Asn Thr Leu Asn Pro Ala His Gly Arg Gln
            965                 970                 975

Val Thr Val Gln Glu Phe Ala Leu Phe Phe Thr Ile Phe Asp Glu Thr
            980                 985                 990

Lys Ser Trp Tyr Phe Thr Glu Asn Met Glu Arg Asn Cys Arg Ala Pro
            995                 1000                1005

Cys Asn Ile Gln Met Glu Asp Pro Thr Phe Lys Glu Asn Tyr Arg
            1010                1015                1020

Phe His Ala Ile Asn Gly Tyr Ile Met Asp Thr Leu Pro Gly Leu
            1025                1030                1035

Val Met Ala Gln Asp Gln Arg Ile Arg Trp Tyr Leu Leu Ser Met
            1040                1045                1050

Gly Ser Asn Glu Asn Ile His Ser Ile His Phe Ser Gly His Val
            1055                1060                1065

Phe Thr Val Arg Lys Lys Glu Glu Tyr Lys Met Ala Leu Tyr Asn
            1070                1075                1080

Leu Tyr Pro Gly Val Phe Glu Thr Val Glu Met Leu Pro Ser Lys
            1085                1090                1095

Ala Gly Ile Trp Arg Val Glu Cys Leu Ile Gly Glu His Leu His
            1100                1105                1110

Ala Gly Met Ser Thr Leu Phe Leu Val Tyr Ser Asn Lys Cys Gln
            1115                1120                1125

Thr Pro Leu Gly Met Ala Ser Gly His Ile Arg Asp Phe Gln Ile
            1130                1135                1140

Thr Ala Ser Gly Gln Tyr Gly Gln Trp Ala Pro Lys Leu Ala Arg
            1145                1150                1155

Leu His Tyr Ser Gly Ser Ile Asn Ala Trp Ser Thr Lys Glu Pro
            1160                1165                1170

Phe Ser Trp Ile Lys Val Asp Leu Leu Ala Pro Met Ile Ile His
            1175                1180                1185

Gly Ile Lys Thr Gln Gly Ala Arg Gln Lys Phe Ser Ser Leu Tyr
            1190                1195                1200

Ile Ser Gln Phe Ile Ile Met Tyr Ser Leu Asp Gly Lys Lys Trp
            1205                1210                1215

Gln Thr Tyr Arg Gly Asn Ser Thr Gly Thr Leu Met Val Phe Phe
            1220                1225                1230

Gly Asn Val Asp Ser Ser Gly Ile Lys His Asn Ile Phe Asn Pro
            1235                1240                1245

Pro Ile Ile Ala Arg Tyr Ile Arg Leu His Pro Thr His Tyr Ser
            1250                1255                1260

Ile Arg Ser Thr Leu Arg Met Glu Leu Met Gly Cys Asp Leu Asn
            1265                1270                1275
```

| Ser | Cys | Ser | Met | Pro | Leu | Gly | Met | Glu | Ser | Lys | Ala | Ile | Ser | Asp |
|-----|-----|-----|-----|-----|-----|-----|-----|-----|-----|-----|-----|-----|-----|-----|
|     | 1280 |     |     |     |     | 1285 |     |     |     | 1290 |     |     |     |     |

Ala Gln Ile Thr Ala Ser Ser Tyr Phe Thr Asn Met Phe Ala Thr
    1295            1300                1305

Trp Ser Pro Ser Lys Ala Arg Leu His Leu Gln Gly Arg Ser Asn
    1310            1315                1320

Ala Trp Arg Pro Gln Val Asn Asn Pro Lys Glu Trp Leu Gln Val
    1325            1330                1335

Asp Phe Gln Lys Thr Met Lys Val Thr Gly Val Thr Thr Gln Gly
    1340            1345                1350

Val Lys Ser Leu Leu Thr Ser Met Tyr Val Lys Glu Phe Leu Ile
    1355            1360                1365

Ser Ser Ser Gln Asp Gly His Gln Trp Thr Leu Phe Phe Gln Asn
    1370            1375                1380

Gly Lys Val Lys Val Phe Gln Gly Asn Gln Asp Ser Phe Thr Pro
    1385            1390                1395

Val Val Asn Ser Leu Asp Pro Pro Leu Leu Thr Arg Tyr Leu Arg
    1400            1405                1410

Ile His Pro Gln Ser Trp Val His Gln Ile Ala Leu Arg Met Glu
    1415            1420                1425

Val Leu Gly Cys Glu Ala Gln Asp Leu Tyr
    1430            1435

<210> SEQ ID NO 18
<211> LENGTH: 450
<212> TYPE: DNA
<213> ORGANISM: Artificial Sequence
<220> FEATURE:
<223> OTHER INFORMATION: XTEN nucleotide sequence

<400> SEQUENCE: 18

```
ggcgcgccaa catcagagag cgccacccct gaaagtggtc ccgggagcga gccagccaca      60
tctgggtcgg aaacgccagg cacaagtgag tctgcaactc ccgagtccgg acctggctcc     120
gagcctgcca ctagcggctc cgagactccg gaacttccg agagcgctac accagaaagc      180
ggacccggaa ccagtaccga acctagcgag ggctctgctc cgggcagccc agccggctct     240
cctacatcca cggaggaggg cacttccgaa tccgccaccc cggagtcagg gccaggatct     300
gaacccgcta cctcaggcag tgagacgcca ggaacgagcg agtccgctac accggagagt     360
gggccaggga gccctgctgg atctcctacg tccactgagg aagggtcacc agcgggctcg     420
cccaccagca ctgaagaagg tgcctcgagc                                      450
```

<210> SEQ ID NO 19
<211> LENGTH: 4824
<212> TYPE: DNA
<213> ORGANISM: Artificial Sequence
<220> FEATURE:
<223> OTHER INFORMATION: coFVIII-52-XTEN

<400> SEQUENCE: 19

```
atgcaaatcg aactgagcac ctgtttcttc ctctgcctgc tgagattctg tttctccgcg      60
acccgccgat actacctggg agcagtggag ctctcctggg attacatgca gagcgacctt     120
ggggagctgc ccgtggatgc caggttccct ccccgggtgc aaagtcgtt tccgttcaac      180 acctccgtgg tgtacaagaa aactctgttc gtggagttca ccgaccacct gttcaatatc     240
gccaagccca gacctccctg gatggggctg ttgggaccta ccatccaagc ggaggtgtac     300
```

```
gacactgtgg tcatcactct gaagaacatg gcctcgcatc ccgtgtccct gcacgccgtg      360
ggagtgtctt actggaaagc gtccgagggg gccgaatacg acgaccagac ctcgcagaga      420
gaaaaggaag atgacaaggt gttcccagga ggatcgcaca cctacgtgtg gcaagtgttg      480
aaggagaacg gcccaatggc ctccgacccg ctgtgcctga cctactcgta cctgtcccac      540
gtggacctcg tgaaggacct caactcggga ctgattggag ccctgctggt ctgcagggaa      600
ggctcactgg cgaaagaaaa gactcagacc ttgcacaagt tcattctgct gttcgctgtg      660
ttcgacgagg ggaagtcgtg gcacagcgag actaagaact ccctgatgca agatagagat      720
gccgcctccg cccgggcctg gcctaagatg cacaccgtga acggttacgt gaaccgctcc      780
ctccctggcc tgattggatg ccaccggaag tccgtgtact ggcacgtgat cgggatgggg      840
accaccccccg aggtgcacag catcttcctg gaaggtcaca catttctcgt gcgcaaccac      900
cggcaggcct ccctggaaat cagccccatt accttcctca ctgcccagac tctgctgatg      960
gacctgggac agttcctgct gttctgccat atctcctccc accaacatga cggaatggag     1020
gcatacgtga aggtcgattc ctgccctgag gaaccccagc tccgcatgaa gaacaatgag     1080
gaagccgagg actacgacga cgacctgacg gatagcgaga tggatgtggt ccggttcgat     1140
gacgataaca gcccttcctt catccaaatt cgctcggtgg caagaagcca ccccaagacc     1200
tgggtgcatt acattgcggc ggaagaagag gactgggatt atgccccgct tgtcctcgct     1260
cctgacgacc ggagctacaa gagccagtac ctgaacaacg gtccacagag gatcggtaga     1320
aagtacaaga aggtccgctt catggcctat accgacgaaa ccttcaaaac tagagaggcc     1380
atccaacacg aatccggcat cctgggcccg ctcttgtacg gagaagtcgg cgacacccctt    1440
ctcattatct tcaagaacca ggcttccgg ccgtacaaca tctatccgca tgggatcact      1500
gacgtgcgcc cactgtactc gcggcgcctg cccaagggtg tcaaacacct gaaggatttt     1560
ccgatccttc cgggagaaat cttcaagtac aagtggaccg tgaccgtgga agatggccca     1620
actaagtctg accctagatg cctcacccgc tactactcat ccttcgtcaa catggagcgc     1680
gacctggcca gcggactgat cggcccgctg ctgatttgct acaaggaatc agtggaccaa     1740
cggggaaacc agatcatgtc ggataagagg aacgtcatcc tcttctccgt gtttgacgaa     1800
aaccggtcgt ggtacctgac cgagaacatc cagaggttcc tgcccaaccc tgctggggtg     1860
cagctggagg accccgagtt ccaggccagc aacatcatgc acagcatcaa tggctacgtg     1920
ttcgacagcc tgcagctgag cgtgtgcctg cacgaggtgg cctactggta catcctgagc     1980
atcggcgccc agaccgactt cctgagcgtg ttcttctctg gctacacctt caagcacaag     2040
atggtgtatg aggacacccct gaccctgttc cccttcagcg gggagactgt cttcatgagc     2100
atggagaacc ctggcctgtg gatcctgggc tgccacaaca gcgacttcag gaacaggggc     2160
atgactgccc tgctgaaagt ctccagctgt gacaagaaca ccggggacta ctacgaggac     2220
agctacgagg acatcagcgc ctacctgctg agcaagaaca tgccatcga gcccaggagc     2280
ttctctctcaga acggcgcgcc aacatcagag agcgccaccc ctgaaagtgg tcccgggagc    2340
gagccagcca catctgggtc ggaaacgcca ggcacaagtg agtctgcaac tcccgagtcc     2400
ggacctggct ccgagcctgc cactagcggc tccgagactc cggaacttc cgagagcgct      2460
acaccagaaa gcggacccgg aaccagtacc gaacctagcg agggctctgc tccgggcagc     2520
ccagccggct ctcctacatc cacggaggag ggcacttccg aatccgccac cccggagtca     2580
gggccaggat ctgaacccgc tacctcaggc agtgagacgc aggaacgag cgagtccgct      2640
acaccggaga gtgggccagg gagccctgct ggatctccta cgtccactga ggaagggtca     2700
```

```
ccagcgggct cgcccaccag cactgaagaa ggtgcctcga gccccccagt gctgaagagg    2760
caccagaggg agatcaccag gaccaccctg cagtctgacc aggaggagat cgactatgat    2820
gacaccatca gcgtggagat gaagaaggag gacttcgaca tctacgacga ggacgagaac    2880
cagagcccca ggagcttcca gaagaagacc aggcactact tcattgctgc tgtggagagg    2940
ctgtgggact atggcatgtc cagcagcccc catgtgctga ggaacagggc ccagtctggc    3000
agcgtgcccc agttcaagaa agtcgtgttc caggagttca ccgacggcag cttcacccag    3060
cccctgtaca gagggagct gaacgagcac ctgggcctgc tgggccccta catcagggcc    3120
gaggtggagg acaacatcat ggtgaccttc aggaaccagg ccagcaggcc ctacagcttc    3180
tacagcagcc tgatcagcta cgaggaggac cagaggcagg gggctgagcc caggaagaac    3240
tttgtgaagc ccaatgaaac caagacctac ttctggaagg tgcagcacca catggccccc    3300
accaaggacg agttcgactg caaggcctgg gcctacttct ctgacgtgga cctggagaag    3360
gacgtgcact ctggcctgat tggcccctg ctggtgtgcc acaccaacac cctgaaccct    3420
gcccatggca ggcaggtgac tgtgcaggag ttcgccctgt tcttcaccat cttcgatgaa    3480
accaagagct ggtacttcac tgagaacatg gagaggaact gcagggcccc ctgcaacatc    3540
cagatggagg accccacctt caaggagaac tacaggttcc atgccatcaa tggctacatc    3600
atggacaccc tgcctggcct ggtcatggcc caggaccaga ggatcaggtg gtatctgctg    3660
agcatgggca gcaacgagaa catccacagc atccacttct ctggccacgt gttcactgtg    3720
aggaagaagg aggagtacaa gatggccctg tacaacctgt accctggggt gttcgaaacc    3780
gtggagatgc tgcccagcaa ggccggcatc tggagggtgg agtgcctgat tggggagcac    3840
ctgcacgccg gcatgagcac cctgttcctg gtgtacagca acaagtgcca gaccccctg    3900 ggcatggcct ctggccacat cagggacttc cagatcactg cctctggcca gtacggccag    3960 tgggcccca gctgccag gctgcactac tccggaagca tcaatgcctg gagcaccaag    4020
gagcccttca gctggatcaa agtggacctg ctggccccca tgatcatcca cggcatcaag    4080
acccaggggg ccaggcagaa gttctccagc ctgtacatca gccagttcat catcatgtac    4140
agcctggacg gcaagaagtg gcagacctac aggggcaaca gcaccggcac cctgatggtg    4200
ttcttcggca acgtggacag cagcggcatc aagcacaaca tcttcaaccc ccccatcatc    4260
gccagataca tcaggctgca ccccaccac tacagcatca ggagcaccct gaggatggag    4320
ctgatgggct gtgacctgaa cagctgcagc atgcccctgg gcatggagag caaggccatc    4380
tctgacgccc agatcactgc ctccagctac ttcaccaaca tgtttgccac ctggagcccc    4440
agcaaggcca ggctgcacct gcagggcagg agcaatgcct ggaggcccca ggtcaacaac    4500
cccaaggagt ggctgcaggt ggacttccag aagaccatga aggtgactgg ggtgaccacc    4560 caggggtga gagcctgct gaccagcatg tacgtgaagg agttcctgat ctccagcagc    4620
caggacggcc accagtggac cctgttcttc cagaatggca aggtgaaggt gttccagggc    4680
aaccaggaca gcttcacccc tgtggtcaac agcctggacc ccccctgct gaccagatac    4740 ctgaggatcc acccccagag ctgggtgcac cagatcgccc tgaggatgga ggtgctgggc    4800
tgtgaggccc aggacctgta ctga                                           4824
```

<210> SEQ ID NO 20
<211> LENGTH: 4824
<212> TYPE: DNA
<213> ORGANISM: Artificial Sequence
<220> FEATURE:

<223> OTHER INFORMATION: coFVIII-1-XTEN

<400> SEQUENCE: 20

```
atgcagattg agctgtctac ttgcttttc ctgtgcctgc tgaggttttg cttttccgct        60
acacgaaggt attatctggg ggctgtggaa ctgtcttggg attacatgca gagtgacctg       120
ggagagctgc cagtggacgc aaggtttccc cctagagtcc ctaagtcatt ccccttcaac       180
actagcgtgg tctacaagaa aacactgttc gtggagttta ctgatcacct gttcaacatc       240
gcaaagccta ggccaccctg gatgggactg ctggggccaa caatccaggc cgaggtgtac       300
gacaccgtgg tcattacact taagaacatg gcctcacacc ccgtgagcct gcatgctgtg       360
ggcgtcagct actggaaggc ttccgaagga gcagagtatg acgatcagac ttcccagaga       420
gaaaaagagg acgataaggt gtttcctggc ggatctcata cctacgtgtg gcaggtcctg       480
aaagagaatg cccctatggc ctccgaccct ctgtgcctga cctactctta tctgagtcac       540
gtggacctgg tcaaggatct gaacagcggc ctgatcggag ccctgctggt gtgcagggaa       600
ggaagcctgg ctaaggagaa acccagaca ctgcataagt tcattctgct gttcgccgtg        660
tttgacgaag ggaaatcatg gcacagcgag acaaagaata gtctgatgca ggacagggat       720
gccgcttcag ccagagcttg gcccaaaatg cacactgtga acggctacgt caatcgctca       780
ctgcctgggc tgatcggctg ccaccgaaag agcgtgtatt ggcatgtcat cgggatgggc       840
accacacctg aagtgcactc cattttcctg gagggacata ccttttctggt ccgcaaccac       900
cgacaggctt ccctggagat ctctccaatt accttcctga cagcacagac tctgctgatg       960
gacctggggc agttcctgct gttttgccac atcagctccc accagcatga tggcatggag      1020
gcttacgtga agtggactc ttgtcccgag gaacctcagc tgcggatgaa gaacaatgag       1080
gaagcagaag actatgacga tgacctgacc gactccgaga tggatgtggt ccgattcgat      1140
gacgataaca gcccctcctt tatccagatt agatctgtgg ccaagaaaca ccctaagaca      1200
tgggtccatt acatcgcagc cgaggaagag gactgggatt atgcaccact ggtgctggca      1260
ccagacgatc gctcctacaa atctcagtat ctgaacaatg gccacagag gattggcaga       1320
aagtacaaga aagtgcggtt catggcatat accgatgaga ccttcaagac tcgcgaagcc      1380
atccagcacg agagcggcat cctgggacca ctgctgtacg agaagtggg agacaccctg       1440
ctgatcattt tcaagaacca ggccagccgg ccttacaata tctatccaca tgggattaca      1500
gatgtgcgcc ctctgtacag caggagactg ccaaagggcg tcaaacacct gaaggacttc      1560
ccaatcctgc ccggagaaat cttcaagtac aagtggactg tcaccgtcga ggatggcccc      1620
actaagagcg accctcggtg cctgacccgc tactattcta gtttcgtgaa tatggaaaga      1680
gatctggcaa gcggactgat cggaccactg ctgatttgtt acaaagagag cgtggatcag      1740
agaggcaacc agatcatgtc cgacaagcgg aatgtgattc tgttcagtgt ctttgacgaa      1800
aacaggtcat ggtacctgac cgagaacatc cagagattcc tgcctaatcc agctggggtg      1860
cagctggaag atcctgagtt tcaggcatct aacatcatgc atagtattaa tggctacgtg      1920
ttcgacagtt tgcagctgag cgtgtgcctg cacgaggtcg cttactggta tatcctgagc      1980
attgggcac agacagattt cctgagcgtg ttcttttccg gctacacttt taagcataaa      2040
atggtctatg aggacacact gactctgttc cccttcagcg gcgaaaccgt gtttatgagc      2100
atggagaatc ccggactgtg gattctgggg tgccacaaca gcgatttcag aaatcgcgga      2160
atgactgccc tgctgaaagt gtcaagctgt gacaagaaca ccggggacta ctatgaagat      2220
tcatacgagg acatcagcgc atatctgctg tccaaaaaca atgccattga accccggtct      2280
```

```
tttagtcaga atggcgcgcc aacatcagag agcgccaccc ctgaaagtgg tcccgggagc   2340
gagccagcca catctgggtc ggaaacgcca ggcacaagtg agtctgcaac tcccgagtcc   2400
ggacctggct ccgagcctgc cactagcggc tccgagactc cgggaacttc cgagagcgct   2460
acaccagaaa gcggacccgg aaccagtacc gaacctagcg agggctctgc tccgggcagc   2520
ccagccggct ctcctacatc cacggaggag ggcacttccg aatccgccac cccggagtca   2580
gggccaggat ctgaacccgc tacctcaggc agtgagacgc caggaacgag cgagtccgct   2640
acaccggaga gtgggccagg gagccctgct ggatctccta cgtccactga ggaagggtca   2700
ccagcgggct cgcccaccag cactgaagaa ggtgcctcga gccctccagt gctgaagcgg   2760
caccagcgcg agatcacccg cactaccctg cagagtgatc aggaagagat cgactacgac   2820
gatacaattt ctgtggaaat gaagaaagag gacttcgata tctatgacga agatgagaac   2880
cagagtcctc gatcattcca gaagaaaacc aggcattact ttattgccgc agtggagcgg   2940
ctgtgggatt atggcatgtc ctctagtcct cacgtgctgc gaaatagggc ccagtcagga   3000
agcgtcccac agttcaagaa agtggtcttc caggagttta cagacgggtc ctttactcag   3060
ccactgtaca ggggcgaact gaacgagcac ctgggactgc tggggcccta tatcagagca   3120
gaagtggagg ataacattat ggtcaccttc agaaatcagg cctctcggcc ttacagtttt   3180
tattcaagcc tgatctctta cgaagaggac cagcgacagg gagctgaacc acgaaaaaac   3240
ttcgtgaagc ctaatgagac caaaacatac ttttggaagg tgcagcacca tatggcccca   3300
acaaaagacg agttcgattg caaggcatgg gcctattttt ctgacgtgga tctggagaag   3360
gacgtgcaca gtggcctgat tggcccactg ctggtgtgcc atactaacac cctgaatcca   3420
gcccacggcc ggcaggtcac tgtccaggag ttcgctctgt tctttaccat ctttgatgag   3480
acaaagagct ggtacttcac cgaaaacatg gagcgaaatt gcagggctcc atgtaacatt   3540
cagatggaag accccacatt caaggagaac taccgctttc atgctatcaa tggatacatc   3600
atggatactc tgcccgggct ggtcatggca caggaccaga gaatccggtg gtatctgctg   3660
agcatgggca gcaacgagaa tatccactca attcatttca gcgggcacgt gtttactgtc   3720
aggaagaaag aagagtacaa gatggccctg tacaacctgt atcccggcgt gttcgaaacc   3780
gtcgagatgc tgcctagcaa ggccggaatc tggagagtgg aatgcctgat tggagagcac   3840
ctgcatgctg gatgtctac cctgtttctg gtgtacagta taagtgtca gacaccctg   3900 ggaatggcat ccgggcatat cagggatttc cagattaccg catctggaca gtacggacag   3960
tgggcaccta agctggctag actgcactat tccggatctc tcaacgcttg gtccacaaaa   4020
gagcctttct cttggattaa ggtggacctg ctggccccaa tgatcattca tggcatcaaa   4080 actcaggag ctcggcagaa gttctcctct ctgtacatct cacagtttat catcatgtac   4140
agcctggatg ggaagaaatg gcagacatac cgcggcaata gcacaggaac tctgatggtg   4200
ttctttggca acgtggacag cagcggaatc aagcacaaca ttttcaatcc ccctatcatt   4260
gctagataca tccggctgca cccaacccat tattctattc gaagtacact gaggatggaa   4320
ctgatgggat gcgatctgaa cagttgttca atgcccctgg ggatggagtc caaggcaatc   4380
tctgacgccc agattaccgc cagctcctac ttcactaata tgtttgctac ctggagcccc   4440
tccaaagcaa gactgcacct gcaaggccgc agcaacgcat ggcgaccaca ggtgaacaat   4500
cccaaggagt ggttgcaggt cgatttcag aaaactatga aggtgaccgg ggtcacaact   4560
cagggcgtga aaagtctgct gacctcaatg tacgtcaagg agttcctgat ctctagttca   4620
```

-continued

```
caggacggac atcagtggac actgttcttt cagaacggga aggtgaaagt cttccagggc    4680
aatcaggatt cctttacacc tgtggtcaac agtctagacc ctccactgct gaccagatac    4740
ctgagaatcc accctcagtc ctgggtgcac cagattgccc tgagaatgga agtgctggga    4800
tgcgaggccc aggatctgta ctga                                            4824
```

```
<210> SEQ ID NO 21
<211> LENGTH: 6
<212> TYPE: DNA
<213> ORGANISM: Artificial Sequence
<220> FEATURE:
<223> OTHER INFORMATION: MAR/ARS

<400> SEQUENCE: 21 atattt                                                                  6

<210> SEQ ID NO 22
<211> LENGTH: 6
<212> TYPE: DNA
<213> ORGANISM: Artificial Sequence
<220> FEATURE:
<223> OTHER INFORMATION: MAR/ARS

<400> SEQUENCE: 22 aaatat                                                                  6

<210> SEQ ID NO 23
<211> LENGTH: 5
<212> TYPE: DNA
<213> ORGANISM: Artificial Sequence
<220> FEATURE:
<223> OTHER INFORMATION: destabilizing element

<400> SEQUENCE: 23 attta                                                                   5

<210> SEQ ID NO 24
<211> LENGTH: 5
<212> TYPE: DNA
<213> ORGANISM: Artificial Sequence
<220> FEATURE:
<223> OTHER INFORMATION: destabilizing element

<400> SEQUENCE: 24 taaat                                                                   5

<210> SEQ ID NO 25
<211> LENGTH: 6
<212> TYPE: DNA
<213> ORGANISM: Artificial Sequence
<220> FEATURE:
<223> OTHER INFORMATION: poly-T site

<400> SEQUENCE: 25 tttttt                                                                  6

<210> SEQ ID NO 26
<211> LENGTH: 7
<212> TYPE: DNA
<213> ORGANISM: Artificial Sequence
<220> FEATURE:
<223> OTHER INFORMATION: poly-A site

<400> SEQUENCE: 26 aaaaaaa                                                                 7
```

<210> SEQ ID NO 27
<211> LENGTH: 6
<212> TYPE: DNA
<213> ORGANISM: Artificial Sequence
<220> FEATURE:
<223> OTHER INFORMATION: splice site

<400> SEQUENCE: 27 ggtgat                                                                    6

<210> SEQ ID NO 28
<211> LENGTH: 5
<212> TYPE: DNA
<213> ORGANISM: Artificial Sequence
<220> FEATURE:
<223> OTHER INFORMATION: TATA box

<400> SEQUENCE: 28 tataa                                                                     5

<210> SEQ ID NO 29
<211> LENGTH: 5
<212> TYPE: DNA
<213> ORGANISM: Artificial Sequence
<220> FEATURE:
<223> OTHER INFORMATION: TATA box

<400> SEQUENCE: 29 ttata                                                                     5

<210> SEQ ID NO 30
<211> LENGTH: 8
<212> TYPE: DNA
<213> ORGANISM: Artificial Sequence
<220> FEATURE:
<223> OTHER INFORMATION: AU rich sequence element

<400> SEQUENCE: 30 attttatt                                                                  8

<210> SEQ ID NO 31
<211> LENGTH: 8
<212> TYPE: DNA
<213> ORGANISM: Artificial Sequence
<220> FEATURE:
<223> OTHER INFORMATION: AU rich sequence element

<400> SEQUENCE: 31 atttttaa                                                                  8

<210> SEQ ID NO 32
<211> LENGTH: 13
<212> TYPE: DNA
<213> ORGANISM: Artificial Sequence
<220> FEATURE:
<223> OTHER INFORMATION: kozak consensus sequence

<400> SEQUENCE: 32
gccgccacca tgc                                                           13

<210> SEQ ID NO 33
<211> LENGTH: 32
<212> TYPE: PRT
<213> ORGANISM: Artificial Sequence
<220> FEATURE:

<223> OTHER INFORMATION: CTP peptide

<400> SEQUENCE: 33

Asp Pro Arg Phe Gln Asp Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30

<210> SEQ ID NO 34
<211> LENGTH: 28
<212> TYPE: PRT
<213> ORGANISM: Artificial Sequence
<220> FEATURE:
<223> OTHER INFORMATION: CTP peptide

<400> SEQUENCE: 34

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 35
<211> LENGTH: 11
<212> TYPE: PRT
<213> ORGANISM: Artificial Sequence
<220> FEATURE:
<223> OTHER INFORMATION: albumin-binding peptide core sequence

<400> SEQUENCE: 35

Asp Ile Cys Leu Pro Arg Trp Gly Cys Leu Trp
1               5                   10

<210> SEQ ID NO 36
<211> LENGTH: 20
<212> TYPE: PRT
<213> ORGANISM: Artificial Sequence
<220> FEATURE:
<223> OTHER INFORMATION: PAS sequence

<400> SEQUENCE: 36

Ala Ser Pro Ala Ala Pro Ala Pro Ala Ser Pro Ala Ala Pro Ala Pro
1               5                   10                  15

Ser Ala Pro Ala
            20

<210> SEQ ID NO 37
<211> LENGTH: 20
<212> TYPE: PRT
<213> ORGANISM: Artificial Sequence
<220> FEATURE:
<223> OTHER INFORMATION: PAS sequence

<400> SEQUENCE: 37

Ala Ala Pro Ala Ser Pro Ala Pro Ala Ala Pro Ser Ala Pro Ala Pro
1               5                   10                  15

Ala Ala Pro Ser
            20

<210> SEQ ID NO 38
<211> LENGTH: 20
<212> TYPE: PRT
<213> ORGANISM: Artificial Sequence
<220> FEATURE:
<223> OTHER INFORMATION: PAS sequence

```
<400> SEQUENCE: 38

Ala Pro Ser Ser Pro Ser Pro Ser Ala Pro Ser Ser Pro Ser Pro Ala
1               5                   10                  15

Ser Pro Ser Ser
            20

<210> SEQ ID NO 39
<211> LENGTH: 19
<212> TYPE: PRT
<213> ORGANISM: Artificial Sequence
<220> FEATURE:
<223> OTHER INFORMATION: PAS sequence

<400> SEQUENCE: 39

Ala Pro Ser Ser Pro Ser Pro Ser Ala Pro Ser Ser Pro Ser Pro Ala
1               5                   10                  15

Ser Pro Ser

<210> SEQ ID NO 40
<211> LENGTH: 20
<212> TYPE: PRT
<213> ORGANISM: Artificial Sequence
<220> FEATURE:
<223> OTHER INFORMATION: PAS sequence

<400> SEQUENCE: 40

Ser Ser Pro Ser Ala Pro Ser Pro Ser Ser Pro Ala Ser Pro Ser Pro
1               5                   10                  15

Ser Ser Pro Ala
            20

<210> SEQ ID NO 41
<211> LENGTH: 24
<212> TYPE: PRT
<213> ORGANISM: Artificial Sequence
<220> FEATURE:
<223> OTHER INFORMATION: PAS sequence

<400> SEQUENCE: 41

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 42
<211> LENGTH: 20
<212> TYPE: PRT
<213> ORGANISM: Artificial Sequence
<220> FEATURE:
<223> OTHER INFORMATION: PAS sequence

<400> SEQUENCE: 42

Ala Ser Ala Ala Ala Pro Ala Ala Ala Ser Ala Ala Ala Ser Ala Pro
1               5                   10                  15

Ser Ala Ala Ala
            20

<210> SEQ ID NO 43
<211> LENGTH: 23
<212> TYPE: DNA
<213> ORGANISM: Artificial Sequence
<220> FEATURE:
<223> OTHER INFORMATION: miR142 target
```

-continued

```
<400> SEQUENCE: 43
tccataaagt aggaaacact aca                                         23

<210> SEQ ID NO 44
<211> LENGTH: 2332
<212> TYPE: PRT
<213> ORGANISM: Homo sapiens

<400> SEQUENCE: 44
```

| Ala | Thr | Arg | Arg | Tyr | Tyr | Leu | Gly | Ala | Val | Glu | Leu | Ser | Trp | Asp | Tyr |
|---|---|---|---|---|---|---|---|---|---|---|---|---|---|---|---|
| 1 | | | | 5 | | | | | 10 | | | | | 15 | |

| Met | Gln | Ser | Asp | Leu | Gly | Glu | Leu | Pro | Val | Asp | Ala | Arg | Phe | Pro | Pro |
| | | | 20 | | | | | 25 | | | | | 30 | | |

| Arg | Val | Pro | Lys | Ser | Phe | Pro | Phe | Asn | Thr | Ser | Val | Val | Tyr | Lys | Lys |
| | | 35 | | | | | 40 | | | | | 45 | | | |

| Thr | Leu | Phe | Val | Glu | Phe | Thr | Asp | His | Leu | Phe | Asn | Ile | Ala | Lys | Pro |
| | 50 | | | | | 55 | | | | | 60 | | | | |

| Arg | Pro | Pro | Trp | Met | Gly | Leu | Leu | Gly | Pro | Thr | Ile | Gln | Ala | Glu | Val |
| 65 | | | | | 70 | | | | | 75 | | | | | 80 |

| Tyr | Asp | Thr | Val | Val | Ile | Thr | Leu | Lys | Asn | Met | Ala | Ser | His | Pro | Val |
| | | | | 85 | | | | | 90 | | | | | 95 | |

| Ser | Leu | His | Ala | Val | Gly | Val | Ser | Tyr | Trp | Lys | Ala | Ser | Glu | Gly | Ala |
| | | | | 100 | | | | | 105 | | | | | 110 | |

| Glu | Tyr | Asp | Asp | Gln | Thr | Ser | Gln | Arg | Glu | Lys | Glu | Asp | Asp | Lys | Val |
| | | | 115 | | | | | 120 | | | | | 125 | | |

| Phe | Pro | Gly | Gly | Ser | His | Thr | Tyr | Val | Trp | Gln | Val | Leu | Lys | Glu | Asn |
| | 130 | | | | | 135 | | | | | 140 | | | | |

| Gly | Pro | Met | Ala | Ser | Asp | Pro | Leu | Cys | Leu | Thr | Tyr | Ser | Tyr | Leu | Ser |
| 145 | | | | | 150 | | | | | 155 | | | | | 160 |

| His | Val | Asp | Leu | Val | Lys | Asp | Leu | Asn | Ser | Gly | Leu | Ile | Gly | Ala | Leu |
| | | | | 165 | | | | | 170 | | | | | 175 | |

| Leu | Val | Cys | Arg | Glu | Gly | Ser | Leu | Ala | Lys | Glu | Lys | Thr | Gln | Thr | Leu |
| | | | 180 | | | | | 185 | | | | | 190 | | |

| His | Lys | Phe | Ile | Leu | Leu | Phe | Ala | Val | Phe | Asp | Glu | Gly | Lys | Ser | Trp |
| | | | 195 | | | | | 200 | | | | | 205 | | |

| His | Ser | Glu | Thr | Lys | Asn | Ser | Leu | Met | Gln | Asp | Arg | Asp | Ala | Ala | Ser |
| | 210 | | | | | 215 | | | | | 220 | | | | |

| Ala | Arg | Ala | Trp | Pro | Lys | Met | His | Thr | Val | Asn | Gly | Tyr | Val | Asn | Arg |
| 225 | | | | | 230 | | | | | 235 | | | | | 240 |

| Ser | Leu | Pro | Gly | Leu | Ile | Gly | Cys | His | Arg | Lys | Ser | Val | Tyr | Trp | His |
| | | | | 245 | | | | | 250 | | | | | 255 | |

| Val | Ile | Gly | Met | Gly | Thr | Thr | Pro | Glu | Val | His | Ser | Ile | Phe | Leu | Glu |
| | | | 260 | | | | | 265 | | | | | 270 | | |

| Gly | His | Thr | Phe | Leu | Val | Arg | Asn | His | Arg | Gln | Ala | Ser | Leu | Glu | Ile |
| | | 275 | | | | | 280 | | | | | 285 | | | |

| Ser | Pro | Ile | Thr | Phe | Leu | Thr | Ala | Gln | Thr | Leu | Leu | Met | Asp | Leu | Gly |
| | 290 | | | | | 295 | | | | | 300 | | | | |

| Gln | Phe | Leu | Leu | Phe | Cys | His | Ile | Ser | Ser | His | Gln | His | Asp | Gly | Met |
| 305 | | | | | 310 | | | | | 315 | | | | | 320 |

| Glu | Ala | Tyr | Val | Lys | Val | Asp | Ser | Cys | Pro | Glu | Glu | Pro | Gln | Leu | Arg |
| | | | | 325 | | | | | 330 | | | | | 335 | |

| Met | Lys | Asn | Asn | Glu | Glu | Ala | Glu | Asp | Tyr | Asp | Asp | Asp | Leu | Thr | Asp |
| | | | | 340 | | | | | 345 | | | | | 350 | |

| Ser | Glu | Met | Asp | Val | Val | Arg | Phe | Asp | Asp | Asp | Asn | Ser | Pro | Ser | Phe |

-continued

```
            355                 360                 365
Ile Gln Ile Arg Ser Val Ala Lys Lys His Pro Lys Thr Trp Val His
        370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Val Arg Phe Met Ala Tyr Thr
                420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
        450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
            515                 520                 525
Leu Thr Arg Tyr Tyr Ser Ser Phe Val Asn Met Glu Arg Asp Leu Ala
        530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
                580                 585                 590
Arg Phe Leu Pro Asn Pro Ala Gly Val Gln Leu Glu Asp Pro Glu Phe
            595                 600                 605
Gln Ala Ser Asn Ile Met His Ser Ile Asn Gly Tyr Val Phe Asp Ser
        610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
                660                 665                 670
Phe Ser Gly Glu Thr Val Phe Met Ser Met Glu Asn Pro Gly Leu Trp
            675                 680                 685
Ile Leu Gly Cys His Asn Ser Asp Phe Arg Asn Arg Gly Met Thr Ala
        690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Ser Arg His Pro Ser Thr Arg
                740                 745                 750
Gln Lys Gln Phe Asn Ala Thr Thr Ile Pro Glu Asn Asp Ile Glu Lys
            755                 760                 765
Thr Asp Pro Trp Phe Ala His Arg Thr Pro Met Pro Lys Ile Gln Asn
770                 775                 780
```

```
Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
        805                 810                 815

Ser Asp Asp Pro Ser Pro Gly Ala Ile Asp Ser Asn Asn Ser Leu Ser
    820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
        885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
    1115                1120                1125

Leu Val Ser Leu Gly Pro Glu Lys Ser Val Glu Gly Gln Asn Phe
    1130                1135                1140

Leu Ser Glu Lys Asn Lys Val Val Gly Lys Gly Glu Phe Thr
    1145                1150                1155

Lys Asp Val Gly Leu Lys Glu Met Val Phe Pro Ser Ser Arg Asn
    1160                1165                1170

Leu Phe Leu Thr Asn Leu Asp Asn Leu His Glu Asn Asn Thr His
    1175                1180                1185
```

```
Asn Gln Glu Lys Lys Ile Gln Glu Glu Ile Glu Lys Lys Glu Thr
1190                1195                1200

Leu Ile Gln Glu Asn Val Val Leu Pro Gln Ile His Thr Val Thr
1205                1210                1215

Gly Thr Lys Asn Phe Met Lys Asn Leu Phe Leu Leu Ser Thr Arg
1220                1225                1230

Gln Asn Val Glu Gly Ser Tyr Asp Gly Ala Tyr Ala Pro Val Leu
1235                1240                1245

Gln Asp Phe Arg Ser Leu Asn Asp Ser Thr Asn Arg Thr Lys Lys
1250                1255                1260

His Thr Ala His Phe Ser Lys Lys Gly Glu Glu Asn Leu Glu
1265                1270                1275

Gly Leu Gly Asn Gln Thr Lys Gln Ile Val Glu Lys Tyr Ala Cys
1280                1285                1290

Thr Thr Arg Ile Ser Pro Asn Thr Ser Gln Gln Asn Phe Val Thr
1295                1300                1305

Gln Arg Ser Lys Arg Ala Leu Lys Gln Phe Arg Leu Pro Leu Glu
1310                1315                1320

Glu Thr Glu Leu Glu Lys Arg Ile Ile Val Asp Asp Thr Ser Thr
1325                1330                1335

Gln Trp Ser Lys Asn Met Lys His Leu Thr Pro Ser Thr Leu Thr
1340                1345                1350

Gln Ile Asp Tyr Asn Glu Lys Glu Lys Gly Ala Ile Thr Gln Ser
1355                1360                1365

Pro Leu Ser Asp Cys Leu Thr Arg Ser His Ser Ile Pro Gln Ala
1370                1375                1380

Asn Arg Ser Pro Leu Pro Ile Ala Lys Val Ser Ser Phe Pro Ser
1385                1390                1395

Ile Arg Pro Ile Tyr Leu Thr Arg Val Leu Phe Gln Asp Asn Ser
1400                1405                1410

Ser His Leu Pro Ala Ala Ser Tyr Arg Lys Lys Asp Ser Gly Val
1415                1420                1425

Gln Glu Ser Ser His Phe Leu Gln Gly Ala Lys Lys Asn Asn Leu
1430                1435                1440

Ser Leu Ala Ile Leu Thr Leu Glu Met Thr Gly Asp Gln Arg Glu
1445                1450                1455

Val Gly Ser Leu Gly Thr Ser Ala Thr Asn Ser Val Thr Tyr Lys
1460                1465                1470

Lys Val Glu Asn Thr Val Leu Pro Lys Pro Asp Leu Pro Lys Thr
1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
1565                1570                1575

Glu Trp Lys Ser Gln Glu Lys Ser Pro Glu Lys Thr Ala Phe Lys
```

```
            1580                1585                1590

Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
    1640                1645                1650

Thr Leu Gln Ser Asp Gln Glu Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
    1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
    1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
    1895                1900                1905

Asp Pro Thr Phe Lys Glu Asn Tyr Arg Phe His Ala Ile Asn Gly
    1910                1915                1920

Tyr Ile Met Asp Thr Leu Pro Gly Leu Val Met Ala Gln Asp Gln
    1925                1930                1935

Arg Ile Arg Trp Tyr Leu Leu Ser Met Gly Ser Asn Glu Asn Ile
    1940                1945                1950

His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe
    1970                1975                1980
```

-continued

```
Glu Thr Val Glu Met Leu Pro Ser Lys Ala Gly Ile Trp Arg Val
    1985                1990                1995

Glu Cys Leu Ile Gly Glu His Leu His Ala Gly Met Ser Thr Leu
    2000                2005                2010

Phe Leu Val Tyr Ser Asn Lys Cys Gln Thr Pro Leu Gly Met Ala
    2015                2020                2025

Ser Gly His Ile Arg Asp Phe Gln Ile Thr Ala Ser Gly Gln Tyr
    2030                2035                2040

Gly Gln Trp Ala Pro Lys Leu Ala Arg Leu His Tyr Ser Gly Ser
    2045                2050                2055

Ile Asn Ala Trp Ser Thr Lys Glu Pro Phe Ser Trp Ile Lys Val
    2060                2065                2070

Asp Leu Leu Ala Pro Met Ile Ile His Gly Ile Lys Thr Gln Gly
    2075                2080                2085

Ala Arg Gln Lys Phe Ser Ser Leu Tyr Ile Ser Gln Phe Ile Ile
    2090                2095                2100

Met Tyr Ser Leu Asp Gly Lys Lys Trp Gln Thr Tyr Arg Gly Asn
    2105                2110                2115

Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Gln Asp Gly
    2255                2260                2265

His Gln Trp Thr Leu Phe Phe Gln Asn Gly Lys Val Lys Val Phe
    2270                2275                2280

Gln Gly Asn Gln Asp Ser Phe Thr Pro Val Val Asn Ser Leu Asp
    2285                2290                2295

Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
    2315                2320                2325

Gln Asp Leu Tyr
    2330
```

<210> SEQ ID NO 45
<211> LENGTH: 4
<212> TYPE: PRT
<213> ORGANISM: Artificial Sequence
<220> FEATURE:

<223> OTHER INFORMATION: amino acids 233-236 of human IgG1

<400> SEQUENCE: 45

Glu Leu Leu Gly
1

<210> SEQ ID NO 46
<211> LENGTH: 42
<212> TYPE: PRT
<213> ORGANISM: Artificial Sequence
<220> FEATURE:
<223> OTHER INFORMATION: XTEN AE42-4, protein sequence

<400> SEQUENCE: 46

Gly Ala Pro Gly Ser Pro Ala Gly Ser Pro Thr Ser Thr Glu Glu Gly
1               5                   10                  15

Thr Ser Glu Ser Ala Thr Pro Glu Ser Gly Pro Gly Ser Glu Pro Ala
            20                  25                  30

Thr Ser Gly Ser Glu Thr Pro Ala Ser Ser
        35                  40

<210> SEQ ID NO 47
<211> LENGTH: 126
<212> TYPE: DNA
<213> ORGANISM: Artificial Sequence
<220> FEATURE:
<223> OTHER INFORMATION: XTEN AE42-4, DNA sequence

<400> SEQUENCE: 47
ggcgcgccag gttctcctgc tggctccccc acctcaacag aagagggac  aagcgaaagc    60 gctacgcctg agagtggccc tggctctgag ccagccacct ccggctctga accccctgcc   120
tcgagc                                                              126

<210> SEQ ID NO 48
<211> LENGTH: 144
<212> TYPE: PRT
<213> ORGANISM: Artificial Sequence
<220> FEATURE:
<223> OTHER INFORMATION: XTEN AE144-2A, protein sequence

<400> SEQUENCE: 48

Thr Ser Thr Glu Pro Ser Glu Gly Ser Ala Pro Gly Ser Pro Ala Gly
1               5                   10                  15

Ser Pro Thr Ser Thr Glu Glu Gly Thr Ser Thr Glu Pro Ser Glu Gly
            20                  25                  30

Ser Ala Pro Gly Thr Ser Thr Glu Pro Ser Glu Gly Ser Ala Pro Gly
        35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly Thr Ser Glu Ser Ala Thr Pro Glu
65                  70                  75                  80

Ser Gly Pro Gly Ser Glu Pro Ala Thr Ser Gly Ser Glu Thr Pro Gly
                85                  90                  95

Thr Ser Thr Glu Pro Ser Glu Gly Ser Ala Pro Gly Thr Ser Thr Glu
                100                 105                 110

Pro Ser Glu Gly Ser Ala Pro Gly Thr Ser Glu Ser Ala Thr Pro Glu
            115                 120                 125

Ser Gly Pro Gly Thr Ser Glu Ser Ala Thr Pro Glu Ser Gly Pro Gly
        130                 135                 140

<210> SEQ ID NO 49
<211> LENGTH: 450
<212> TYPE: DNA
<213> ORGANISM: Artificial Sequence
<220> FEATURE:
<223> OTHER INFORMATION: XTEN AE144-2A, DNA sequence

<400> SEQUENCE: 49

```
ggcgcgccaa ccagtacgga gccgtccgag gggagcgcac caggaagccc ggctgggagc    60
ccgacttcta ccgaagaggg tacatctacc gaaccaagtg aaggttcagc accaggcacc   120
tcaacagaac cctctgaggg ctcggcgcct ggtacaagtg agtccgccac cccagaatcc   180
gggcctggga caagcacaga accttcggaa gggagtgccc ctggaacatc cgaatcggca   240
accccagaat cagggccagg atctgagccc gcgacttcgg gctccgagac gcctgggaca   300
tccaccgagc cctccgaagg atcagcccca ggcaccagca cggagccctc tgagggaagc   360
gcacctggta ccagcgaaag cgcaactccc gaatcaggtc ccggtacgag cgagtcggcg   420
accccggaga gcgggccagg tgcctcgagc                                    450
```

<210> SEQ ID NO 50
<211> LENGTH: 144
<212> TYPE: PRT
<213> ORGANISM: Artificial Sequence
<220> FEATURE:
<223> OTHER INFORMATION: XTEN AE144-3B, protein sequence

<400> SEQUENCE: 50

```
Ser Pro Ala Gly Ser Pro Thr Ser Thr Glu Glu Gly Thr Ser Glu Ser
1               5                   10                  15
Ala Thr Pro Glu Ser Gly Pro Gly Ser Glu Pro Ala Thr Ser Gly Ser
                20                  25                  30
Glu Thr Pro Gly Thr Ser Glu Ser Ala Thr Pro Glu Ser Gly Pro Gly
            35                  40                  45
Thr Ser Thr Glu Pro Ser Glu Gly Ser Ala Pro Gly Thr Ser Thr Glu
        50                  55                  60
Pro Ser Glu Gly Ser Ala Pro Gly Thr Ser Thr Glu Pro Ser Glu Gly
65                  70                  75                  80
Ser Ala Pro Gly Thr Ser Thr Glu Pro Ser Glu Gly Ser Ala Pro Gly
                85                  90                  95
Thr Ser Thr Glu Pro Ser Glu Gly Ser Ala Pro Gly Thr Ser Thr Glu
            100                 105                 110
Pro Ser Glu Gly Ser Ala Pro Gly Ser Pro Ala Gly Ser Pro Thr Ser
        115                 120                 125
Thr Glu Glu Gly Thr Ser Thr Glu Pro Ser Glu Gly Ser Ala Pro Gly
    130                 135                 140
```

<210> SEQ ID NO 51
<211> LENGTH: 450
<212> TYPE: DNA
<213> ORGANISM: Artificial Sequence
<220> FEATURE:
<223> OTHER INFORMATION: XTEN AE144-3B, DNA sequence

<400> SEQUENCE: 51

```
ggcgcgccaa gtcccgctgg aagcccaact agcaccgaag aggggacctc agagtccgcc    60
accccccgagt ccggccctgg ctctgagcct gccactagcg gctccgagac tcctggcaca   120
tccgaaagcg ctacacccga gagtggaccc ggcacctcta ccgagcccag tgagggctcc   180
```

-continued

```
gccoctggaa caagcaccga gcccagcgaa ggcagcgccc cagggacctc cacagagccc    240
agtgaaggca gtgctcctgg caccagcacc gaaccaagcg agggctctgc acccgggacc    300
tccaccgagc caagcgaagg ctctgcccct ggcacttcca ccgagcccag cgaaggcagc    360 gccoctggga gccccgctgg ctctcccacc agcactgagg agggcacatc taccgaacca    420
agtgaaggct ctgcaccagg tgcctcgagc                                    450
```

<210> SEQ ID NO 52
<211> LENGTH: 144
<212> TYPE: PRT
<213> ORGANISM: Artificial Sequence
<220> FEATURE:
<223> OTHER INFORMATION: XTEN AE144-4A, protein sequence

<400> SEQUENCE: 52

```
Thr Ser Glu Ser Ala Thr Pro Glu Ser Gly Pro Gly Ser Glu Pro Ala
  1               5                  10                  15

Thr Ser Gly Ser Glu Thr Pro Gly Thr Ser Glu Ser Ala Thr Pro Glu
              20                  25                  30

Ser Gly Pro Gly Ser Glu Pro Ala Thr Ser Gly Ser Glu Thr Pro Gly
          35                  40                  45

Thr Ser Glu Ser Ala Thr Pro Glu Ser Gly Pro Gly Thr Ser Thr Glu
      50                  55                  60

Pro Ser Glu Gly Ser Ala Pro Gly Thr Ser Glu Ser Ala Thr Pro Glu
 65                  70                  75                  80

Ser Gly Pro Gly Ser Pro Ala Gly Ser Pro Thr Ser Thr Glu Glu Gly
                  85                  90                  95

Ser Pro Ala Gly Ser Pro Thr Ser Thr Glu Glu Gly Ser Pro Ala Gly
             100                 105                 110

Ser Pro Thr Ser Thr Glu Glu Gly Thr Ser Glu Ser Ala Thr Pro Glu
             115                 120                 125

Ser Gly Pro Gly Thr Ser Thr Glu Pro Ser Glu Gly Ser Ala Pro Gly
         130                 135                 140
```

<210> SEQ ID NO 53
<211> LENGTH: 450
<212> TYPE: DNA
<213> ORGANISM: Artificial Sequence
<220> FEATURE:
<223> OTHER INFORMATION: XTEN AE144-4A, DNA sequence

<400> SEQUENCE: 53

```
ggcgcgccaa cgtccgaaag tgctaccoct gagtcaggcc tggtagtga gcctgccaca     60 agcggaagcg aaactccggg gacctcagag tctgccactc ccgaatcggg gccaggctct    120
gaaccggcca cttcagggag cgaaacacca ggaaacatcg gagagcgctac cccggagagc    180 gggccaggaa ctagtactga gcctagcgag ggaagtgcac ctggtacaag cgagtccgcc    240
acacccgagt ctggccctgg ctctccagcg ggctcaccca cgagcactga gagggctct     300 cccgctggca gcccaacgtc gacagaagaa ggatcaccag caggctcccc cacatcaaca    360
gaggagggta catcagaatc tgctactccc gagagtggac ccggtacctc cactgagccc    420
agcgagggga gtgcaccagg tgcctcgagc                                    450
```

<210> SEQ ID NO 54
<211> LENGTH: 144
<212> TYPE: PRT
<213> ORGANISM: Artificial Sequence
<220> FEATURE:

<223> OTHER INFORMATION: XTEN AE144-5A, protein sequence

<400> SEQUENCE: 54

Thr Ser Glu Ser Ala Thr Pro Glu Ser Gly Pro Gly Ser Glu Pro Ala
1               5                   10                  15

Thr Ser Gly Ser Glu Thr Pro Gly Thr Ser Glu Ser Ala Thr Pro Glu
            20                  25                  30

Ser Gly Pro Gly Ser Glu Pro Ala Thr Ser Gly Ser Glu Thr Pro Gly
        35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly Ser Pro Ala Gly Ser Pro Thr Ser
65                  70                  75                  80

Thr Glu Glu Gly Thr Ser Glu Ser Ala Thr Pro Glu Ser Gly Pro Gly
                85                  90                  95

Ser Glu Pro Ala Thr Ser Gly Ser Glu Thr Pro Gly Thr Ser Glu Ser
            100                 105                 110

Ala Thr Pro Glu Ser Gly Pro Gly Ser Pro Ala Gly Ser Pro Thr Ser
        115                 120                 125

Thr Glu Glu Gly Ser Pro Ala Gly Ser Pro Thr Ser Thr Glu Glu Gly
    130                 135                 140

<210> SEQ ID NO 55
<211> LENGTH: 450
<212> TYPE: DNA
<213> ORGANISM: Artificial Sequence
<220> FEATURE:
<223> OTHER INFORMATION: XTEN AE144-5A, DNA sequence

<400> SEQUENCE: 55
ggcgcgccaa catcagagag cgccacccct gaaagtggtc ccgggagcga gccagccaca      60
tctgggtcgg aaacgccagg cacaagtgag tctgcaactc ccgagtccgg acctggctcc     120
gagcctgcca ctagcggctc cgagactccg ggaacttccg agagcgctac accagaaagc     180
ggacccggaa ccagtaccga acctagcgag ggctctgctc gggcagccc agccggctct      240 cctacatcca cggaggaggg cacttccgaa tccgccaccc cggagtcagg gccaggatct     300
gaacccgcta cctcaggcag tgagacgcca ggaacgagcg agtccgctac accggagagt     360
gggccaggga gccctgctgg atctcctacg tccactgagg aagggtcacc agcgggctcg     420
cccaccagca ctgaagaagg tgcctcgagc                                      450

<210> SEQ ID NO 56
<211> LENGTH: 144
<212> TYPE: PRT
<213> ORGANISM: Artificial Sequence
<220> FEATURE:
<223> OTHER INFORMATION: XTEN AE144-6B, protein sequence

<400> SEQUENCE: 56

Thr Ser Thr Glu Pro Ser Glu Gly Ser Ala Pro Gly Thr Ser Glu Ser
1               5                   10                  15

Ala Thr Pro Glu Ser Gly Pro Gly Thr Ser Glu Ser Ala Thr Pro Glu
            20                  25                  30

Ser Gly Pro Gly Thr Ser Glu Ser Ala Thr Pro Glu Ser Gly Pro Gly
        35                  40                  45

Ser Glu Pro Ala Thr Ser Gly Ser Glu Thr Pro Gly Ser Glu Pro Ala
    50                  55                  60

Thr Ser Gly Ser Glu Thr Pro Gly Ser Pro Ala Gly Ser Pro Thr Ser
65                  70                  75                  80

Thr Glu Glu Gly Thr Ser Thr Glu Pro Ser Glu Gly Ser Ala Pro Gly
                85                  90                  95

Thr Ser Thr Glu Pro Ser Glu Gly Ser Ala Pro Gly Ser Glu Pro Ala
            100                 105                 110

Thr Ser Gly Ser Glu Thr Pro Gly Thr Ser Glu Ser Ala Thr Pro Glu
            115                 120                 125

Ser Gly Pro Gly Thr Ser Thr Glu Pro Ser Glu Gly Ser Ala Pro Gly
            130                 135                 140

<210> SEQ ID NO 57
<211> LENGTH: 450
<212> TYPE: DNA
<213> ORGANISM: Artificial Sequence
<220> FEATURE:
<223> OTHER INFORMATION: XTEN AE144-6B, DNA sequence

<400> SEQUENCE: 57
ggcgcgccaa catctaccga gccttccgaa ggctctgccc ctgggacctc agaatctgca      60 accectgaaa gcggccctgg aacctccgaa agtgccactc ccgagagcgg cccagggaca     120
agcgagtcag caaccectga gtctggaccc ggcagcgagc ctgcaacctc tggctcagag     180
actcccggct cagaaccogc tacctcaggc tccgagacac ccggctctcc tgctgggagt     240
cccacttcca ccgaggaagg aacatccact gagcctagtg agggctctgc ccctggaacc     300
agcacagagc caagtgaggg cagtgcacca ggatccgagc agcaaccag cgggtccgag      360 actcccggga cctctgagtc tgccaccca gagagcggac ccggcacttc aaccgagccc      420
tccgaaggat cagcaccagg tgcctcgagc                                      450

<210> SEQ ID NO 58
<211> LENGTH: 144
<212> TYPE: PRT
<213> ORGANISM: Artificial Sequence
<220> FEATURE:
<223> OTHER INFORMATION: XTEN AG144-1, protein sequence

<400> SEQUENCE: 58

Pro Gly Ser Ser Pro Ser Ala Ser Thr Gly Thr Gly Pro Gly Ser Ser
1               5                   10                  15

Pro Ser Ala Ser Thr Gly Thr Gly Pro Gly Thr Pro Gly Ser Gly Thr
                20                  25                  30

Ala Ser Ser Ser Pro Gly Ser Ser Thr Pro Ser Gly Ala Thr Gly Ser
            35                  40                  45

Pro Gly Ser Ser Pro Ser Ala Ser Thr Gly Thr Gly Pro Gly Ala Ser
            50                  55                  60

Pro Gly Thr Ser Ser Thr Gly Ser Pro Gly Thr Pro Gly Ser Gly Thr
65                  70                  75                  80

Ala Ser Ser Ser Pro Gly Ser Ser Thr Pro Ser Gly Ala Thr Gly Ser
                85                  90                  95

Pro Gly Thr Pro Gly Ser Gly Thr Ala Ser Ser Ser Pro Gly Ala Ser
            100                 105                 110

Pro Gly Thr Ser Ser Thr Gly Ser Pro Gly Ala Ser Pro Gly Thr Ser
            115                 120                 125

Ser Thr Gly Ser Pro Gly Thr Pro Gly Ser Gly Thr Ala Ser Ser Ser
            130                 135                 140

<210> SEQ ID NO 59
<211> LENGTH: 450
<212> TYPE: DNA
<213> ORGANISM: Artificial Sequence
<220> FEATURE:
<223> OTHER INFORMATION: XTEN AG144-1, DNA sequence

<400> SEQUENCE: 59

```
ggcgcgccac ccgggtcgtc cccgtcggcg tccaccggaa cagggccagg gtcatccccg      60
tcagcgtcga ctgggacggg acccgggaca cccggttcgg ggactgcatc ctcctcgcct     120
ggttcgtcca ccccgtcagg agccacgggt tcgccgggaa gcagcccaag cgcatccact     180
ggtacagggc ctggggcttc accgggtact tcatccacgg ggtcaccggg aacgcccgga     240
tcggggacgg cttcctcatc accaggatcg tcaacaccct cgggcgcaac gggcagcccc     300
ggaaccccctg gttcgggtac ggcgtcgtcg agccccggtg cgagcccggg aacaagctcg     360
acaggatcgc ctggggcgtc acccggcacg tcgagcacag gcagccccgg aaccccctgga     420
tcgggaaccg cgtcgtcaag cgcctcgagc                                      450
```

<210> SEQ ID NO 60
<211> LENGTH: 144
<212> TYPE: PRT
<213> ORGANISM: Artificial Sequence
<220> FEATURE:
<223> OTHER INFORMATION: XTEN AG144-A, protein sequence

<400> SEQUENCE: 60

```
Gly Ala Ser Pro Gly Thr Ser Ser Thr Gly Ser Pro Gly Ser Ser Pro
1               5                   10                  15
Ser Ala Ser Thr Gly Thr Gly Pro Gly Ser Ser Pro Ser Ala Ser Thr
            20                  25                  30
Gly Thr Gly Pro Gly Thr Pro Gly Ser Gly Thr Ala Ser Ser Ser Pro
        35                  40                  45
Gly Ser Ser Thr Pro Ser Gly Ala Thr Gly Ser Pro Gly Ser Ser Pro
    50                  55                  60
Ser Ala Ser Thr Gly Thr Gly Pro Gly Ala Ser Pro Gly Thr Ser Ser
65                  70                  75                  80
Thr Gly Ser Pro Gly Thr Pro Gly Ser Gly Thr Ala Ser Ser Ser Pro
                85                  90                  95
Gly Ser Ser Thr Pro Ser Gly Ala Thr Gly Ser Pro Gly Thr Pro Gly
            100                 105                 110
Ser Gly Thr Ala Ser Ser Ser Pro Gly Ala Ser Pro Gly Thr Ser Ser
        115                 120                 125
Thr Gly Ser Pro Gly Ala Ser Pro Gly Thr Ser Ser Thr Gly Ser Pro
    130                 135                 140
```

<210> SEQ ID NO 61
<211> LENGTH: 450
<212> TYPE: DNA
<213> ORGANISM: Artificial Sequence
<220> FEATURE:
<223> OTHER INFORMATION: XTEN AG144-A, DNA sequence

<400> SEQUENCE: 61

```
ggcgcgccag gtgcctcgcc gggaacatca tcaactggtt cacccgggtc atccccctcg      60
gcctcaaccg ggacgggtcc cggctcatcc cccagcgcca gcactggaac aggtcctggc     120
actcctggtt ccgtacggc atcgtcatcc ccggaaagct caacaccgtc cggagcgaca     180
ggatcaccctg gctcgtcacc ttcggcgtca actggaacgg ggccaggggc ctcacccgga     240
```

```
acgtcctcga ctgggtcgcc tggtacgccg ggatcaggaa cggcctcatc ctcgcctggg    300
tcctcaacgc cctcgggtgc gactggttcg ccgggaactc ctggctcggg gacggcctcg    360
tcgtcgcctg gggcatcacc ggggacgagc tccacggggt ccctggagc gtcaccgggg     420 acctcctcga caggtagccc ggcctcgagc                                     450
```

```
<210> SEQ ID NO 62
<211> LENGTH: 144
<212> TYPE: PRT
<213> ORGANISM: Artificial Sequence
<220> FEATURE:
<223> OTHER INFORMATION: XTEN AG144-B, protein sequence

<400> SEQUENCE: 62
```

Gly Thr Pro Gly Ser Gly Thr Ala Ser Ser Pro Gly Ser Ser Thr
1               5                   10                  15

Pro Ser Gly Ala Thr Gly Ser Pro Gly Ala Ser Pro Gly Thr Ser Ser
            20                  25                  30

Thr Gly Ser Pro Gly Thr Pro Gly Ser Gly Thr Ala Ser Ser Ser Pro
        35                  40                  45

Gly Ser Ser Thr Pro Ser Gly Ala Thr Gly Ser Pro Gly Ser Ser Pro
    50                  55                  60

Ser Ala Ser Thr Gly Thr Gly Pro Gly Ser Ser Pro Ser Ala Ser Thr
65                  70                  75                  80

Gly Thr Gly Pro Gly Ser Ser Thr Pro Ser Gly Ala Thr Gly Ser Pro
                85                  90                  95

Gly Ser Ser Thr Pro Ser Gly Ala Thr Gly Ser Pro Gly Ala Ser Pro
            100                 105                 110

Gly Thr Ser Ser Thr Gly Ser Pro Gly Ala Ser Pro Gly Thr Ser Ser
        115                 120                 125

Thr Gly Ser Pro Gly Ala Ser Pro Gly Thr Ser Ser Thr Gly Ser Pro
    130                 135                 140

```
<210> SEQ ID NO 63
<211> LENGTH: 450
<212> TYPE: DNA
<213> ORGANISM: Artificial Sequence
<220> FEATURE:
<223> OTHER INFORMATION: XTEN AG144-B, DNA sequence

<400> SEQUENCE: 63
ggcgcgccag gtacaccggg cagcggcacg gcttcgtcgt cacccggctc gtccacaccg    60
tcgggagcta cgggaagccc aggagcgtca ccggaacgt cgtcaacggg gtcaccgggt    120
acgccaggta gcgcacggc cagcagctcg ccaggttcat cgaccccgtc gggagcgact    180
gggtcgcccg gatcaagccc gtcagcttcc actggaacag gacccgggtc gtcgccgtca    240
gcctcaacgg ggacaggacc tggttcatcg acgccgtcag gggcgacagg ctcgcccgga    300
tcgtcaacac cctcgggggc aacggggagc cctggtgcgt cgcctggaac ctcatccacc    360
ggaagcccgg gggcctcgcc gggtacgagc tccacgggat cgcccggagc gtccccccgga   420 acttcaagca cagggagccc tgcctcgagc                                     450
```

```
<210> SEQ ID NO 64
<211> LENGTH: 144
<212> TYPE: PRT
<213> ORGANISM: Artificial Sequence
<220> FEATURE:
<223> OTHER INFORMATION: XTEN AG144-C, protein sequence
```

<400> SEQUENCE: 64

Gly Thr Pro Gly Ser Gly Thr Ala Ser Ser Pro Gly Ala Ser Pro
1               5                   10                  15

Gly Thr Ser Ser Thr Gly Ser Pro Gly Ala Ser Pro Gly Thr Ser Ser
                20                  25                  30

Thr Gly Ser Pro Gly Ala Ser Pro Gly Thr Ser Thr Gly Ser Pro
            35                  40                  45

Gly Ser Ser Pro Ser Ala Ser Thr Gly Thr Gly Pro Gly Thr Pro Gly
        50                  55                  60

Ser Gly Thr Ala Ser Ser Pro Gly Ala Ser Pro Gly Thr Ser Ser
65              70                  75                  80

Thr Gly Ser Pro Gly Ala Ser Pro Gly Thr Ser Thr Gly Ser Pro
            85                  90                  95

Gly Ala Ser Pro Gly Thr Ser Ser Thr Gly Ser Pro Gly Ser Ser Thr
                100                 105                 110

Pro Ser Gly Ala Thr Gly Ser Pro Gly Ser Ser Thr Pro Ser Gly Ala
            115                 120                 125

Thr Gly Ser Pro Gly Ala Ser Pro Gly Thr Ser Ser Thr Gly Ser Pro
            130                 135                 140

<210> SEQ ID NO 65
<211> LENGTH: 450
<212> TYPE: DNA
<213> ORGANISM: Artificial Sequence
<220> FEATURE:
<223> OTHER INFORMATION: XTEN AG144-C, DNA sequence

<400> SEQUENCE: 65

| | |
|---|---|
| ggcgcgccag gtacacccgg atcgggtaca gcgtcatcga gccccggtgc gtcacctggt | 60 |
| acgtcgagca cggggtcgcc aggggcgtcc cctgggacgt cctcaacagg ctcgcccggt | 120 |
| gcgtcacccg gcacgtcgtc cacgggttca cctggtagct ccccttccgc gtccactggc | 180 |
| accgggcctg gaactccggg gagcggcaca gcgagctcgt cgccgggagc atcgcctggg | 240 |
| acatcgagca ccgggtcgcc aggagcatcg cccggaacat ccagcacagg aagccccggc | 300 |
| gcgtcgcccg ggacatcaag cacaggttcc ccgggatcga gcacgccgtc cggagccact | 360 |
| ggatcaccag ggagctcgac accttccggc gcaacgggat cgcccggagc cagcccgggt | 420 |
| acgtcaagca ctggctcccc tgcctcgagc | 450 |

<210> SEQ ID NO 66
<211> LENGTH: 144
<212> TYPE: PRT
<213> ORGANISM: Artificial Sequence
<220> FEATURE:
<223> OTHER INFORMATION: XTEN AG144-F, protein sequence

<400> SEQUENCE: 66

Gly Ser Ser Pro Ser Ala Ser Thr Gly Thr Gly Pro Gly Ser Ser Pro
1               5                   10                  15

Ser Ala Ser Thr Gly Thr Gly Pro Gly Ala Ser Pro Gly Thr Ser Ser
                20                  25                  30

Thr Gly Ser Pro Gly Ala Ser Pro Gly Thr Ser Ser Thr Gly Ser Pro
            35                  40                  45

Gly Ser Ser Thr Pro Ser Gly Ala Thr Gly Ser Pro Gly Ser Ser Pro
        50                  55                  60

Ser Ala Ser Thr Gly Thr Gly Pro Gly Ala Ser Pro Gly Thr Ser Ser

|   |   |   |   | 65 |   |   |   | 70 |   |   |   | 75 |   |   |   | 80 |
|---|---|---|---|---|---|---|---|---|---|---|---|---|---|---|---|---|

Thr Gly Ser Pro Gly Ser Ser Pro Ser Ala Ser Thr Gly Thr Gly Pro
                    85                    90                    95

Gly Thr Pro Gly Ser Gly Thr Ala Ser Ser Pro Gly Ser Ser Thr
            100                 105                  110

Pro Ser Gly Ala Thr Gly Ser Pro Gly Ser Ser Thr Pro Ser Gly Ala
        115                  120                  125

Thr Gly Ser Pro Gly Ala Ser Pro Gly Thr Ser Ser Thr Gly Ser Pro
    130                  135                  140

<210> SEQ ID NO 67
<211> LENGTH: 450
<212> TYPE: DNA
<213> ORGANISM: Artificial Sequence
<220> FEATURE:
<223> OTHER INFORMATION: XTEN AG144-F, DNA sequence

<400> SEQUENCE: 67

| ggcgcgccag gctccagccc ctccgcgagc acgggaaccg gaccaggttc gtcaccctca | 60 |
|---|---|
| gcatcaacgg ggacgggacc ggggggcgtca ccaggaacgt cctccaccgg ctcgccgggt | 120 |
| gcatcacccg gaacgtcatc gaccggatcg ccagggagcc cgacgccatc aggcgcaaca | 180 |
| ggatcacctg gctcaagccc tagcgcgtca accggcacgg gtccgggtgc ctcccctggc | 240 |
| acgtccagca ccggatcacc cggatcgagc ccatccgcct caaccggaac cggacccggt | 300 |
| acaccagggt cgggaacagc ctcctcgtca ccaggctcct caaccccctc gggagccacg | 360 |
| ggttcgcccg gttcgtcaac gccttccgga gcaactggta gccccggagc atcgccagga | 420 |
| acttcgagca cggggtcgcc cgcctcgagc | 450 |

<210> SEQ ID NO 68
<211> LENGTH: 4374
<212> TYPE: DNA
<213> ORGANISM: Artificial Sequence
<220> FEATURE:
<223> OTHER INFORMATION: coFVIII-1 DNA Sequence

<400> SEQUENCE: 68

| atgcagattg agctgtctac ttgcttttc ctgtgcctgc tgaggttttg cttttccgct | 60 |
|---|---|
| acacgaaggt attatctggg ggctgtggaa ctgtcttggg attacatgca gagtgacctg | 120 |
| ggagagctgc cagtggacgc aaggtttccc cctagagtcc ctaagtcatt ccccttcaac | 180 |
| actagcgtgg tctacaagaa aacactgttc gtggagttta ctgatcacct gttcaacatc | 240 |
| gcaaagccta ggccaccctg gatgggactg ctggggccaa caatccaggc cgaggtgtac | 300 |
| gacaccgtgg tcattacact taagaacatg gcctcacacc ccgtgagcct gcatgctgtg | 360 |
| ggcgtcagct actggaaggc ttccgaagga gcagagtatg acgatcagac ttcccagaga | 420 |
| gaaaagagg acgataaggt gtttcctggc ggatctcata cctacgtgtg caggtcctg | 480 |
| aaagagaatg cccctatggc ctccgaccct ctgtgcctga cctactctta tctgagtcac | 540 |
| gtggacctgg tcaaggatct gaacagcggc ctgatcggag ccctgctggt gtgcagggaa | 600 |
| ggaagcctgg ctaaggagaa aacccagaca ctgcataagt tcattctgct gttcgccgtg | 660 |
| tttgacgaag ggaaatcatg gcacagcgag acaaagaata gtctgatgca ggacagggat | 720 |
| gccgcttcag ccagagcttg gcccaaaatg cacactgtga acggctacgt caatcgctca | 780 |
| ctgcctgggc tgatcggctg ccaccgaaag agcgtgtatt ggcatgtcat cgggatgggc | 840 |
| accacacctg aagtgcactc cattttcctg gagggacata cctttctggt ccgcaaccac | 900 |

```
cgacaggctt ccctggagat ctctccaatt accttcctga cagcacagac tctgctgatg    960
gacctggggc agttcctgct gttttgccac atcagctccc accagcatga tggcatggag   1020
gcttacgtga agtggactc ttgtcccgag aacctcagc tgcggatgaa gaacaatgag     1080
gaagcagaag actatgacga tgacctgacc gactccgaga tggatgtggt ccgattcgat    1140
gacgataaca gcccctcctt tatccagatt agatctgtgg ccaagaaaca ccctaagaca    1200
tgggtccatt acatcgcagc cgaggaagag gactgggatt atgcaccact ggtgctggca    1260
ccagacgatc gctcctacaa atctcagtat ctgaacaatg ggccacagag gattggcaga    1320
aagtacaaga aagtgcggtt catggcatat accgatgaga ccttcaagac tcgcgaagcc    1380
atccagcacg agagcggcat cctgggacca ctgctgtacg agaagtggg agacaccctg     1440 ctgatcattt tcaagaacca ggccagccgg cc ttacaata tctatccaca tgggattaca   1500
gatgtgcgcc ctctgtacag caggagactg ccaaggggcg tcaaacacct gaaggacttc    1560
ccaatcctgc ccggagaaat cttcaagtac aagtggactg tcaccgtcga ggatggcccc    1620
actaagagcg accctcggtg cctgacccgc tactattcta gtttcgtgaa tatggaaaga    1680
gatctggcaa gcggactgat cggaccactg ctgatttgtt acaaagagag cgtggatcag    1740
agaggcaacc agatcatgtc cgacaagcgg aatgtgattc tgttcagtgt ctttgacgaa    1800
aacaggtcat ggtacctgac cgagaacatc cagagattcc tgcctaatcc agctggggtg    1860
cagctggaag atcctgagtt tcaggcatct aacatcatgc atagtattaa tggctacgtg    1920
ttcgacagtt tgcagctgag cgtgtgcctg cacgaggtcg cttactggta tatcctgagc    1980 attgggcac agacagattt cctgagcgtg ttcttttccg gctacacttt taagcataaa    2040
atggtctatg aggacacact gactctgttc cccttcagcg gcgaaaccgt gtttatgagc    2100
atggagaatc ccggactgtg gattctgggg tgccacaaca gcgatttcag aaatcgcgga    2160
atgactgccc tgctgaaagt gtcaagctgt gacaagaaca ccggggacta ctatgaagat    2220
tcatacgagg acatcagcgc atatctgctg tccaaaaaca atgccattga accccggtct    2280
tttagtcaga atcctccagt gctgaagagg caccagaggg agatcacccg cactaccctg    2340
cagagtgatc aggaagagat cgactacgac gatacaattt ctgtggaaat gaagaaagag    2400
gacttcgata tctatgacga agatgagaac cagagtcctc gatcattcca gaagaaaacc    2460
aggcattact ttattgccgc agtggagcgg ctgtgggatt atggcatgtc ctctagtcct    2520
cacgtgctgc gaaatagggc ccagtcagga agcgtcccac agttcaagaa agtggtcttc    2580
caggagttta cagacgggtc ctttactcag ccactgtaca ggggcgaact gaacgagcac    2640
ctgggactgc tgggccccta tatcagagca gaagtggagg ataacattat ggtcaccttc    2700
agaaatcagg cctctcggcc ttacagtttt tattcaagcc tgatctctta cgaagaggac    2760
cagcgacagg gagctgaacc acgaaaaaac ttcgtgaagc ctaatgagac caaaacatac    2820
ttttggaagt gcagcaccca tatggcccca acaaaagacg agttcgattg caaggcatgg    2880
gcctattttt ctgacgtgga tctggagaag gacgtgcaca gtggcctgat ggcccactg     2940 ctggtgtgcc atactaacac cctgaatcca gcccacggcc ggcaggtcac tgtccaggag    3000
ttcgctctgt tctttaccat cttt gatgag acaaagagct ggtacttcac cgaaaacatg    3060
gagcgaaatt gcagggctcc atgtaacatt cagatggaag accccacatt caaggagaac    3120
taccgctttc atgctatcaa tggatacatc atggatactc tgcccgggct ggtcatggca    3180
caggaccaga gaatccggtg gtatctgctg agcatgggca gcaacgagaa tatccactca    3240
```

```
attcatttca gcgggcacgt gtttactgtc aggaagaaag aagagtacaa gatggccctg    3300
tacaacctgt atcccggcgt gttcgaaacc gtcgagatgc tgcctagcaa ggccggaatc    3360
tggagagtgg aatgcctgat tggagagcac ctgcatgctg ggatgtctac cctgtttctg    3420
gtgtacagta taagtgtca gacacccctg gaatggcat ccgggcatat cagggatttc     3480
cagattaccg catctggaca gtacggacag tgggcaccta agctggctag actgcactat    3540
tccggatcta tcaacgcttg gtccacaaaa gagcctttct cttggattaa ggtgacctg    3600
ctggccccaa tgatcattca tggcatcaaa actcaggag ctcggcagaa gttctcctct    3660
ctgtacatct cacagtttat catcatgtac agcctggatg ggaagaaatg cagacatac     3720
cgcggcaata gcacaggaac tctgatggtg ttctttggca acgtggacag cagcggaatc    3780
aagcacaaca tttttcaatcc ccctatcatt gctagataca tccggctgca cccaaccat    3840
tattctattc gaagtacact gaggatgaa ctgatgggat gcgatctgaa cagttgttca    3900
atgcccctgg ggatggagtc caaggcaatc tctgacgccc agattaccgc cagctcctac    3960
ttcactaata tgtttgctac ctggagccct tccaaagcaa gactgcacct gcaaggccgc    4020
agcaacgcat ggcgaccaca ggtgaacaat cccaaggagt ggttgcaggt cgattttcag    4080
aaaactatga aggtgaccgg ggtcacaact cagggcgtga aaagtctgct gacctcaatg    4140
tacgtcaagg agttcctgat ctctagttca caggacggac atcagtggac actgttcttt    4200
cagaacggga aggtgaaagt cttccagggc aatcaggatt cctttacacc tgtggtcaac    4260
agtctagacc ctccactgct gaccagatac ctgagaatcc accctcagtc ctgggtgcac    4320
cagattgccc tgagaatgga agtgctggga tgcgaggccc aggatctgta ctga         4374

<210> SEQ ID NO 69
<211> LENGTH: 577
<212> TYPE: DNA
<213> ORGANISM: Artificial Sequence
<220> FEATURE:
<223> OTHER INFORMATION: ET Promoter, DNA sequence

<400> SEQUENCE: 69
ctcgaggtca attcacgcga gttaataatt accagcgcgg gccaaataaa taatccgcga     60
ggggcaggtg acgtttgccc agcgcgcgct ggtaattatt aacctcgcga atattgattc    120
gaggccgcga ttgccgcaat cgcgaggggc aggtgacctt tgcccagcgc gcgttcgccc    180
cgccccggac ggtatcgata agcttaggag cttgggctgc aggtcgaggg cactgggagg    240
atgttgagta agatggaaaa ctactgatga cccttgcaga gacagagtat taggacatgt    300
ttgaacaggg gccgggcgat cagcaggtag ctctagagga tccccgtctg tctgcacatt    360
tcgtagagcg agtgttccga tactctaatc tccctaggca aggttcatat ttgtgtaggt    420
tacttattct cctttttgttg actaagtcaa taatcagaat cagcaggttt ggagtcagct    480
tggcagggat cagcagcctg ggttggaagg aggggtata aaagcccctt caccaggaga    540
agccgtcaca cagatccaca agctcctgcc accatgg                            577

<210> SEQ ID NO 70
<211> LENGTH: 4374
<212> TYPE: DNA
<213> ORGANISM: Artificial Sequence
<220> FEATURE:
<223> OTHER INFORMATION: coFVIII-5

<400> SEQUENCE: 70
atgcaaatcg aactgagcac ctgtttcttc ctctgcctgc tgagattctg tttctccgcg     60
```

-continued

```
acccgccgat actacctggg agcagtggag ctctcctggg attacatgca gagcgacctt     120
ggggagctgc ccgtggatgc caggttccct ccccgggtgc caaagtcgtt tccgttcaac     180
acctccgtgg tgtacaagaa aactctgttc gtggagttca ccgaccacct gttcaatatc     240
gccaagccca gacctccctg gatggggctg ttgggaccta ccatccaagc ggaggtgtac     300
gacactgtgg tcatcactct gaagaacatg gcctcgcatc ccgtgtccct gcacgccgtg     360
ggagtgtctt actggaaagc gtccgagggg gccgaatacg acgaccagac ctcgcagaga     420
gaaaaggaag atgacaaggt gttcccagga ggatcgcaca cctacgtgtg gcaagtgttg     480
aaggagaacg gcccaatggc ctccgacccg ctgtgcctga cctactcgta cctgtcccac     540
gtggacctcg tgaaggacct caactcggga ctgattggag ccctgctggt ctgcagggaa     600
ggctcactgg cgaaagaaaa gactcagacc ttgcacaagt tcattctgct gttcgctgtg     660
ttcgacgagg ggaagtcgtg gcacagcgag actaagaact ccctgatgca agatagagat     720
gccgcctccg cccgggcctg gcctaagatg cacaccgtga acggttacgt gaaccgctcc     780
ctccctggcc tgattggatg ccaccggaag tccgtgtact ggcacgtgat cgggatgggg     840
accaccccgg aggtgcacag catcttcctg gaaggtcaca catttctcgt gcgcaaccac     900
cggcaggcct ccctggaaat cagccccatt accttcctca ctgcccagac tctgctgatg     960
gacctgggac agttcctgct gttctgccat atctcctccc accaacatga cggaatggag    1020
gcatacgtga aggtcgattc ctgccctgag gaaccccagc tccgcatgaa gaacaatgag    1080
gaagccgagg actacgacga cgacctgacg gatagcgaga tggatgtggt ccggttcgat    1140
gacgataaca gcccttcctt catccaaatt cgctcggtgg caaagaagca ccccaagacc    1200
tgggtgcatt acattgcggc ggaagaagag gactgggatt atgccccgct tgtcctcgct    1260
cctgacgacc ggagctacaa gagccagtac ctgaacaacg gtccacagag gatcggtaga    1320
aagtacaaga aggtccgctt catggcctat accgacgaaa ccttcaaaac tagagaggcc    1380
atccaacacg aatccggcat cctgggcccg ctcttgtacg agaagtcgg cgacacccttt   1440
ctcattatct tcaagaacca ggcttcccgg ccgtacaaca tctatccgca tgggatcact    1500
gacgtgcgcc cactgtactc gcggcgcctg cccaagggtg tcaaacacct gaaggatttt    1560
ccgatccttc cgggagaaat cttcaagtac aagtggaccg tgaccgtgga agatggccca    1620
actaagtctg acccagatg cctcacccgc tactactcat ccttcgtcaa catggagcgc    1680
gacctggcca gcggactgat cggcccgctg ctgatttgct acaaggaatc agtggaccaa    1740
cggggaaacc agatcatgtc ggataagagg aacgtcatcc tcttctccgt gtttgacgaa    1800
aaccggtcgt ggtacctgac tgaaaacatc cagcggttcc tccccaaccc cgcgggcgtg    1860
cagctggaag atcctgagtt tcaggcatca aacatcatgc actccattaa cggctacgtg    1920
ttcgattcgc tgcagctgag cgtgtgtctg cacgaagtgg cctactggta catcctgtcc    1980
attggtgccc agactgactt cctgtccgtg tttttctccg gctacacgtt caagcacaag    2040
atggtgtacg aggacaccct gaccctcttc ccttttttcg gcgaaactgt gtttatgagc    2100
atggagaatc ccggcctgtg gatcttgggc tgccacaaca gcgacttccg taacagagga    2160
atgactgcgc tgctcaaggt gtccagctgc gacaagaaca ccgagactgc ttatgaggac    2220
tcatacgagg acatctccgc ctacctcctg tccaagaata cgccattgaa acctcggagc    2280
ttcagccaga acccacccgt gcttaagaga catcaacggg agatcactag gaccaccctg    2340
cagtcagacc aggaggaaat cgactacgat gacaccatct cggtcgagat gaagaaggag    2400
```

```
gactttgaca tctacgacga agatgaaaac cagagcccga ggtcgttcca aaagaaaacc    2460
cgccactact ttattgctgc tgtcgagcgg ctgtgggact acggaatgtc gtcctcgccg    2520
cacgtgctcc gcaaccgagc ccagagcggc tcggtgccgc aattcaagaa ggtcgtgttc    2580
caggagttca ctgacgggag cttcactcag cctttgtacc ggggagaact caatgaacat    2640
ctcggcctcc tcggacctta catcagagca gaagtggaag ataacatcat ggtcactttc    2700
cgtaaccaag ccagccgccc gtactcgttc tactcctccc tcatttctta cgaagaggac    2760
cagcggcagg gcgcagaacc gcgcaagaac ttcgtgaagc ccaacgaaac caagacctac    2820
ttctggaaag tgcagcatca tatggcccccg actaaggacg agtttgactg caaagcctgg    2880
gcctacttct ccgatgtgga cttggagaag gacgtccact ccggcctcat cggtcccctg    2940
ctcgtgtgcc ataccaatac cctgaacccc gcacacggtc gccaggtcac cgtgcaggag    3000
ttcgctctgt tcttcactat cttcgacgaa actaagtcct ggtacttcac cgagaacatg    3060
gagaggaact gcagagcccc ctgtaacatc cagatggagg acccgacgtt caaggaaaac    3120
taccggttcc acgccattaa cggatacatc atggatacgc tgccgggtct tgtgatggcc    3180
caggatcaac ggatcagatg gtacttattg tcgatgggca gcaacgagaa catccactct    3240
attcacttct ccggtcatgt gttcactgtg cggaagaagg aagagtacaa gatggccctg    3300
tacaaccttt atcccggagt gttcgaaact gtggaaatgc tgccgtcgaa ggccggcatt    3360
tggcgcgtgg agtgtttgat tggagaacat ctccatgcgg ggatgtcaac cctgttcctg    3420
gtgtatagca acaagtgcca gactccgctt gggatggcgt caggacacat tagggatttc    3480
cagatcactg cgtccggcca gtacggccaa tgggcccccta agctggcccg cctgcattac    3540
tccggatcca ttaacgcctg gtcaaccaag gagccattct cctggatcaa ggtggacctt    3600
ctggccccca tgattatcca cggaattaag acccagggggg cccggcagaa gttctcctca    3660
ctgtacatca gccagttcat aatcatgtac tccctggacg gaaagaagtg gcaaacctac    3720
aggggaacca gcaccggcac actgatggtc ttttttcggaa atgtggactc ctccgggatt    3780
aagcataaca tcttcaaccc tccgattatc gctcggtaca ttagacttca ccctacccac    3840
tacagcattc gctccaccct gcggatggaa ctgatgggct gcgatctgaa ctcgtgcagc    3900
atgccgttgg gaatggagtc caaagcaatt tccgacgcgc agatcaccgc ctcgtcctac    3960
tttaccaaca tgttcgccac gtggtcaccg tccaaggccc ggctgcacct ccagggaaga    4020
tccaacgcat ggcggccaca ggtcaacaac cctaaggagt ggctccaggt ggacttccag    4080
aaaaccatga aggtcaccgg agtcacaacc cagggagtga agtcgctgct gacttctatg    4140
tacgtcaagg agttcctgat ctccagcagc caggacgggc accagtggac cctgttcttc    4200
caaaatggaa aggtcaaggt gttcagggc aatcaggatt cattcacccc ggtggtgaac    4260
tcccttgatc caccccctcct gacccgctac cttcgcatcc acccacagtc ctgggtgcac    4320
cagatcgcgc tgaggatgga ggtcctggga tgcgaagccc aggacctgta ctga         4374
```

<210> SEQ ID NO 71
<211> LENGTH: 4374
<212> TYPE: DNA
<213> ORGANISM: Artificial Sequence
<220> FEATURE:
<223> OTHER INFORMATION: coFVIII-6

<400> SEQUENCE: 71

```
atgcagattg agctgtccac ttgtttcttc ctgtgcctcc tgcgcttctg tttctccgcc      60
actcgccggt actaccttgg agccgtggag cttttcatggg actacatgca gagcgacctg     120
```

-continued

```
ggcgaactcc ccgtggatgc cagattcccc ccccgcgtgc caaagtcctt cccctttaac      180
acctccgtgg tgtacaagaa aaccctcttt gtcgagttca ctgaccacct gttcaacatc      240
gccaagccgc gcccaccttg gatgggcctc ctgggaccga ccattcaagc tgaagtgtac      300
gacaccgtgg tgatcaccct gaagaacatg gcgtcccacc ccgtgtccct gcatgcggtc      360
ggagtgtcct actggaaggc ctccgaagga gctgagtacg acgaccagac tagccagcgg      420
gaaaaggagg acgataaagt gttcccgggc ggctcgcata cttacgtgtg gcaagtcctg      480
aaggaaaacg gacctatggc atccgatcct ctgtgcctga cttactccta cctttcccat      540
gtggacctcg tgaaggacct gaacagcggg ctgattggtg cacttctcgt gtgccgcgaa      600
ggttcgctcg ctaaggaaaa gacccagacc ctccataagt tcatccttt gttcgctgtg       660 ttcgatgaag gaaagtcatg gcattccgaa actaagaact cgctgatgca ggaccgggat      720
gccgcctcag cccgcgcctg gcctaaaatg catacagtca acggatacgt gaatcggtca      780
ctgcccgggc tcatcggttg tcacagaaag tccgtgtact ggcacgtcat cggcatgggc      840
actacgcctg aagtgcactc catcttcctg gaagggcaca ccttcctcgt gcgcaaccac      900
cgccaggcct ctctggaaat ctccccgatt acctttctga ccgcccagac tctgctcatg      960
gacctggggc agttccttct cttctgccac atctccagcc atcagcacga cggaatggag     1020
gcctacgtga aggtggactc atgcccggaa gaacctcagt gcggatgaa gaacaacgag      1080 gaggccgagg actatgacga cgatttgact gactccgaga tggacgtcgt gcggttcgat     1140
gacgacaaca gccccagctt catccagatt cgcagcgtgg ccaagaagca ccccaaaacc     1200
tgggtgcact acatcgcggc cgaggaagaa gattgggact acgccccgtt ggtgctggca     1260
cccgatgacc ggtcgtacaa gtcccagtat ctgaacaatg gtccgcagcg gattggcaga     1320
aagtacaaga aagtgcggtt catggcgtac actgacgaaa cgtttaagac ccgggaggcc     1380
attcaacatg agagcggcat tctgggacca ctgctgtacg gagaggtcgg cgatacctg      1440 ctcatcatct tcaaaaacca ggcctcccgg ccttacaaca tctaccctca cggaatcacc     1500
gacgtgcggc cactctactc gcggcgcctg ccgaagggcg tcaagcacct gaaagacttc     1560
cctatcctgc cgggcgaaat cttcaagtat aagtggaccg tcaccgtgga ggacgggccc     1620
accaagagcg atcctaggtg tctgactcgg tactactcca gcttcgtgaa catggaacgg     1680
gacctggcat cgggactcat tggaccgctg ctgatctgct acaaagagtc ggtggatcaa     1740
cgcggcaacc agatcatgtc cgacaagcgc aacgtgatcc tgttctccgt gtttgatgaa     1800
aacagatcct ggtacctcac tgaaaacatc cagaggttcc tcccaaaccc cgcaggagtg     1860
caactggagg accctgagtt tcaggcctcg aatatcatgc actcgattaa cggttacgtg     1920
ttcgactcgc tgcagctgag cgtgtgcctc catgaagtcg cttactggta cattctgtcc     1980
atcggcgccc agactgactt cctgagcgtg ttcttttccg gttacacctt taagcacaag     2040
atggtgtacg aagatacccc gaccctgttc cctttctccg cgcaaacggt gttcatgtcg     2100
atggagaacc cgggtctgtg gattctggga tgccacaaca gcgactttcg gaaccgcgga     2160
atgactgccc tgctgaaggt gtcctcatgc gacaagaaca ccggagacta ctacgaggac     2220
tcctacgagg atatctcagc ctacctcctg tccaagaaca acgcgatcga gccgcgcagc     2280
ttcagccaga acccgcctgt gctgaagagg caccagcgag aaattacccg gaccaccctc     2340
caatcggatc aggaggaaat cgactacgac gacaccatct cggtggaaat gaagaaggaa     2400
gatttcgata tctacgacga ggacgaaaat cagtcccctc gctcattcca aaagaaaact     2460
```

| | |
|---|---|
| agacactact ttatcgccgc ggtggaaaga ctgtgggact atggaatgtc atccagccct | 2520 |
| cacgtccttc ggaaccgggc ccagagcgga tcggtgcctc agttcaagaa agtggtgttc | 2580 |
| caggagttca ccgacggcag cttcacccag ccgctgtacc ggggagaact gaacgaacac | 2640 |
| ctgggcctgc tcggtcccta catccgcgcg gaagtggagg ataacatcat ggtgaccttc | 2700 |
| cgtaaccaag catccagacc ttactccttc tattcctccc tgatctcata cgaggaggac | 2760 |
| cagcgccaag gcgccgagcc ccgcaagaac ttcgtcaagc caacgagac taagacctac | 2820 |
| ttctggaagg tccaacacca tatggccccg accaaggatg agtttgactg caaggcctgg | 2880 |
| gcctacttct ccgacgtgga ccttgagaag gatgtccatt ccggcctgat cgggccgctg | 2940 |
| ctcgtgtgtc acaccaacac cctgaaccca gcgcatggac gccaggtcac cgtccaggag | 3000 |
| tttgctctgt tcttcaccat ttttgacgaa actaagtcct ggtacttcac cgagaatatg | 3060 |
| gagcgaaact gtagagcgcc ctgcaatatc cagatggaag atccgacttt caaggagaac | 3120 |
| tatagattcc acgccatcaa cgggtacatc atggatactc tgccggggct ggtcatggcc | 3180 |
| caggatcaga ggattcggtg gtacttgctg tcaatggat cgaacgaaaa cattcactcc | 3240 |
| attcacttct ccggtcacgt gttcactgtg cgcaagaagg aggagtacaa gatggcgctg | 3300 |
| tacaatctgt accccggggt gttcgaaact gtggagatgc tgccgtccaa ggccggcatc | 3360 |
| tggagagtgg agtgcctgat cggagagcac ctccacgcgg ggatgtccac cctcttcctg | 3420 |
| gtgtactcga ataagtgcca gacccgctg ggcatggcct cgggccacat cagagacttc | 3480 |
| cagatcacag caagcggaca atacggccaa tgggcgccga agctggcccg cttgcactac | 3540 |
| tccggatcga tcaacgcatg gtccaccaag gaaccgttct cgtggattaa ggtggacctc | 3600 |
| ctggccccta tgattatcca cggaattaag acccagggcg ccaggcagaa gttctcctcc | 3660 |
| ctgtacatct cgcaattcat catcatgtac agcctggacg ggaagaagtg gcagacttac | 3720 |
| aggggaaact ccaccggcac cctgatggtc ttttcggca acgtggattc ctccggcatt | 3780 |
| aagcacaaca tcttcaaccc accgatcata gccagatata ttaggctcca ccccactcac | 3840 |
| tactcaatcc gctcaactct tcggatggaa ctcatggggt gcgacctgaa ctcctgctcc | 3900 |
| atgccgttgg ggatggaatc aaaggctatt agcgacgccc agatcaccgc gagctcctac | 3960 |
| ttcactaaca tgttcgccac ctggagcccc tccaaggcca ggctgcactt gcagggacgg | 4020 |
| tcaaatgcct ggcggccgca agtgaacaat ccgaaggaat ggcttcaagt ggatttccaa | 4080 |
| aagaccatga aagtgaccgg agtcaccacc cagggagtga agtcccttct gacctcgatg | 4140 |
| tatgtgaagg agttcctgat tagcagcagc caggacgggc accagtggac cctgttcttc | 4200 |
| caaaacggaa aggtcaaggt gttccagggg aaccaggact cgttcacacc cgtggtgaac | 4260 |
| tccctggacc ccccactgct gacgcggtac ttgaggattc atcctcagtc ctgggtccat | 4320 |
| cagattgcat tgcgaatgga agtcctgggc tgcgaggccc aggacctgta ctga | 4374 |

```
<210> SEQ ID NO 72
<211> LENGTH: 4824
<212> TYPE: DNA
<213> ORGANISM: Artificial Sequence
<220> FEATURE:
<223> OTHER INFORMATION: coFVIII-6-XTEN

<400> SEQUENCE: 72
```

| | |
|---|---|
| atgcagattg agctgtccac ttgtttcttc ctgtgcctcc tgcgcttctg tttctccgcc | 60 |
| actcgccggt actaccttgg agccgtggag ctttcatggg actacatgca gagcgacctg | 120 |
| ggcgaactcc ccgtggatgc cagattcccc ccccgcgtgc caaagtcctt cccctttaac | 180 |

-continued

| | |
|---|---|
| acctccgtgg tgtacaagaa accctctttt gtcgagttca ctgaccacct gttcaacatc | 240 |
| gccaagccgc gcccaccttg gatgggcctc ctgggaccga ccattcaagc tgaagtgtac | 300 |
| gacaccgtgg tgatcaccct gaagaacatg gcgtcccacc ccgtgtccct gcatgcggtc | 360 |
| ggagtgtcct actggaaggc ctccgaagga gctgagtacg acgaccagac tagccagcgg | 420 |
| gaaaaggagg acgataaagt gttcccgggc ggctcgcata cttacgtgtg gcaagtcctg | 480 |
| aaggaaaacg gacctatggc atccgatcct ctgtgcctga cttactccta cctttcccat | 540 |
| gtggacctcg tgaaggacct gaacagcggg ctgattggtg cacttctcgt gtgccgcgaa | 600 |
| ggttcgctcg ctaaggaaaa gacccagacc ctccataagt tcatcctttt gttcgctgtg | 660 |
| ttcgatgaag gaaagtcatg gcattccgaa actaagaact cgctgatgca ggaccgggat | 720 |
| gccgcctcag cccgcgcctg gcctaaaatg catacagtca acggatacgt gaatcggtca | 780 |
| ctgcccgggc tcatcggttg tcacagaaag tccgtgtact ggcacgtcat cggcatgggc | 840 |
| actacgcctg aagtgcactc catcttcctg gaagggcaca ccttcctcgt gcgcaaccac | 900 |
| cgccaggcct ctctggaaat ctccccgatt acctttctga ccgcccagac tctgctcatg | 960 |
| gacctggggc agttccttct cttctgccac atctccagcc atcagcacga cggaatggag | 1020 |
| gcctacgtga aggtggactc atgcccggaa gaacctcagt tgcggatgaa gaacaacgag | 1080 |
| gaggccgagg actatgacga cgatttgact gactccgaga tggacgtcgt gcggttcgat | 1140 |
| gacgacaaca gccccagctt catccagatt cgcagcgtgg ccaagaagca ccccaaaacc | 1200 |
| tgggtgcact acatcgcggc cgaggaagaa gattgggact acgccccgtt ggtgctggca | 1260 |
| cccgatgacc ggtcgtacaa gtcccagtat ctgaacaatg gtccgcagcg gattggcaga | 1320 |
| aagtacaaga aagtgcggtt catggcgtac actgacgaaa cgtttaagac ccggaggcc | 1380 |
| attcaacatg agagcggcat tctgggacca ctgctgtacg agaggtcgg cgataccctg | 1440 |
| ctcatcatct tcaaaaacca ggcctcccgg ccttacaaca tctaccctca cggaatcacc | 1500 |
| gacgtgcggc cactctactc gcggcgcctg ccgaagggcg tcaagcacct gaaagacttc | 1560 |
| cctatcctgc cggcgaaat cttcaagtat aagtggaccg tcaccgtgga ggacgggccc | 1620 |
| accaagagcg atcctaggtg tctgactcgg tactactcca gcttcgtgaa catggaacgg | 1680 |
| gacctggcat cgggactcat tggaccgctg ctgatctgct acaaagagtc ggtggatcaa | 1740 |
| cgcggcaacc agatcatgtc cgacaagcgc aacgtgatcc tgttctccgt gtttgatgaa | 1800 |
| aacagatcct ggtacctcac tgaaaacatc cagaggttcc tcccaaaccc cgcaggagtg | 1860 |
| caactggagg accctgagtt tcaggcctcg aatatcatgc actcgattaa cggttacgtg | 1920 |
| ttcgactcgc tgcagctgag cgtgtgcctc catgaagtcg cttactggta cattctgtcc | 1980 |
| atcgcgccc agactgactt cctgagcgtg ttcttttccg gttacacctt taagcacaag | 2040 |
| atggtgtacg aagatacct gaccctgttc cctttctccg gcgaaacggt gttcatgtcg | 2100 |
| atggagaacc cggtctgtg gattctggga tgccacaaca gcgactttcg aaccgcgga | 2160 |
| atgactgccc tgctgaaggt gtcctcatgc gacaagaaca ccggagacta ctacgaggac | 2220 |
| tcctacgagg atatctcagc ctacctcctg tccaagaaca acgcgatcga gccgcgcagc | 2280 |
| ttcagccaga acggcgcgcc aacatcagag agcgccaccc ctgaaagtgg tcccgggagc | 2340 |
| gagccagcca catctgggtc ggaaacgcca ggcacaagtg agtctgcaac tcccgagtcc | 2400 |
| ggacctggct ccgagcctgc cactagcggc tccgagactc cgggaacttc cgagagcgct | 2460 |
| acaccagaaa gcggacccgg aaccagtacc gaacctagcg agggctctgc tccgggcagc | 2520 |

```
ccagccggct ctcctacatc cacggaggag ggcacttccg aatccgccac cccggagtca    2580
gggccaggat ctgaacccgc tacctcaggc agtgagacgc caggaacgag cgagtccgct    2640
acaccggaga gtgggccagg gagccctgct ggatctccta cgtccactga ggaagggtca    2700
ccagcgggct cgcccaccag cactgaagaa ggtgcctcga gcccgcctgt gctgaagagg    2760
caccagcgag aaattacccg gaccaccctc caatcggatc aggaggaaat cgactacgac    2820
gacaccatct cggtggaaat gaagaaggaa gatttcgata tctacgacga ggacgaaaat    2880
cagtcccctc gctcattcca aaagaaaact agacactact ttatcgccgc ggtggaaaga    2940
ctgtgggact atggaatgtc atccagccct cacgtccttc ggaaccgggc ccagagcgga    3000
tcggtgcctc agttcaagaa agtggtgttc caggagttca ccgacggcag cttcacccag    3060
ccgctgtacc ggggagaact gaacgaacac ctgggcctgc tcggtcccta catccgcgcg    3120
gaagtggagg ataacatcat ggtgaccttc cgtaaccaag catccagacc ttactccttc    3180
tattcctccc tgatctcata cgaggaggac cagcgccaag gcgccgagcc ccgcaagaac    3240
ttcgtcaagc ccaacgagac taagacctac ttctggaagg tccaacacca tatgcccccg    3300
accaaggatg agtttgactg caaggcctgg gcctacttct ccgacgtgga ccttgagaag    3360
gatgtccatt ccggcctgat cgggccgctg ctcgtgtgtc acaccaacac cctgaaccca    3420
gcgcatggac gccaggtcac cgtccaggag tttgctctgt tcttcaccat ttttgacgaa    3480
actaagtcct ggtacttcac cgagaatatg gagcgaaact gtagagcgcc ctgcaatatc    3540
cagatggaag atccgacttt caaggagaac tatagattcc acgccatcaa cgggtacatc    3600
atggatactc tgccggggct ggtcatggcc caggatcaga ggattcggtg gtacttgctg    3660
tcaatgggat cgaacgaaaa cattcactcc attcacttct ccggtcacgt gttcactgtg    3720
cgcaagaagg aggagtacaa gatggcgctg tacaatctgt accccggggt gttcgaaact    3780
gtggagatgc tgccgtccaa ggccggcatc tggagagtgg agtgcctgat cggagagcac    3840
ctccacgcgg ggatgtccac cctcttcctg gtgtactcga ataagtgcca gaccccgctg    3900
ggcatggcct cgggccacat cagagacttc cagatcacag caagcggaca atacggccaa    3960
tgggcgccga agctggcccg cttgcactac tccggatcga tcaacgcatg gtccaccaag    4020
gaaccgttct cgtggattaa ggtggacctc ctggccccta tgattatcca cggaattaag    4080
acccagggcg ccaggcagaa gttctcctcc ctgtacatct cgcaattcat catcatgtac    4140
agcctggacg ggaagaagtg gcagacttac aggggaaact ccaccggcac cctgatggtc    4200
tttttcggca acgtggattc ctccggcatt aagcacaaca tcttcaaccc accgatcata    4260
gccagatata ttaggctcca ccccactcac tactcaatcc gctcaactct tcggatggaa    4320
ctcatggggt gcgacctgaa ctcctgctcc atgccgttgg ggatggaatc aaaggctatt    4380
agcgacgccc agatcaccgc gagctcctac ttcactaaca tgttcgccac ctggagcccc    4440
tccaaggcca ggctgcactt gcagggacgg tcaaatgcct ggcggccgca agtgaacaat    4500
ccgaaggaat ggcttcaagt ggatttccaa aagaccatga agtgaccgg agtcaccacc    4560 cagggagtga agtcccttct gacctcgatg tatgtgaagg agttcctgat tagcagcagc    4620
caggacgggc accagtggac cctgttcttc caaaacggaa aggtcaaggt gttccagggg    4680
aaccaggact cgttcacacc cgtggtgaac tccctggacc cccactgct gacgcggtac    4740 ttgaggattc atcctcagtc ctgggtccat cagattgcat tgcgaatgga agtcctgggc    4800
tgcgaggccc aggacctgta ctga                                          4824
```

```
<210> SEQ ID NO 73
<211> LENGTH: 12
<212> TYPE: PRT
<213> ORGANISM: Artificial Sequence
<220> FEATURE:
<223> OTHER INFORMATION: AD motif

<400> SEQUENCE: 73

Gly Glu Ser Pro Gly Gly Ser Ser Gly Ser Glu Ser
1               5                   10

<210> SEQ ID NO 74
<211> LENGTH: 12
<212> TYPE: PRT
<213> ORGANISM: Artificial Sequence
<220> FEATURE:
<223> OTHER INFORMATION: AD motif

<400> SEQUENCE: 74

Gly Ser Glu Gly Ser Ser Gly Pro Gly Glu Ser Ser
1               5                   10

<210> SEQ ID NO 75
<211> LENGTH: 12
<212> TYPE: PRT
<213> ORGANISM: Artificial Sequence
<220> FEATURE:
<223> OTHER INFORMATION: AD motif

<400> SEQUENCE: 75

Gly Ser Ser Glu Ser Gly Ser Ser Glu Gly Gly Pro
1               5                   10

<210> SEQ ID NO 76
<211> LENGTH: 12
<212> TYPE: PRT
<213> ORGANISM: Artificial Sequence
<220> FEATURE:
<223> OTHER INFORMATION: AD motif

<400> SEQUENCE: 76

Gly Ser Gly Gly Glu Pro Ser Glu Ser Gly Ser Ser
1               5                   10

<210> SEQ ID NO 77
<211> LENGTH: 12
<212> TYPE: PRT
<213> ORGANISM: Artificial Sequence
<220> FEATURE:
<223> OTHER INFORMATION: AE, AM motif

<400> SEQUENCE: 77

Gly Ser Pro Ala Gly Ser Pro Thr Ser Thr Glu Glu
1               5                   10

<210> SEQ ID NO 78
<211> LENGTH: 12
<212> TYPE: PRT
<213> ORGANISM: Artificial Sequence
<220> FEATURE:
<223> OTHER INFORMATION: AE, AM, AQ motif

<400> SEQUENCE: 78

Gly Ser Glu Pro Ala Thr Ser Gly Ser Glu Thr Pro
1               5                   10

<210> SEQ ID NO 79
```

```
<211> LENGTH: 12
<212> TYPE: PRT
<213> ORGANISM: Artificial Sequence
<220> FEATURE:
<223> OTHER INFORMATION: AE, AM, AQ motif

<400> SEQUENCE: 79

Gly Thr Ser Glu Ser Ala Thr Pro Glu Ser Gly Pro
1               5                   10

<210> SEQ ID NO 80
<211> LENGTH: 12
<212> TYPE: PRT
<213> ORGANISM: Artificial Sequence
<220> FEATURE:
<223> OTHER INFORMATION: AE, AM, AQ motif

<400> SEQUENCE: 80

Gly Thr Ser Thr Glu Pro Ser Glu Gly Ser Ala Pro
1               5                   10

<210> SEQ ID NO 81
<211> LENGTH: 12
<212> TYPE: PRT
<213> ORGANISM: Artificial Sequence
<220> FEATURE:
<223> OTHER INFORMATION: AF, AM motif

<400> SEQUENCE: 81

Gly Ser Thr Ser Glu Ser Pro Ser Gly Thr Ala Pro
1               5                   10

<210> SEQ ID NO 82
<211> LENGTH: 12
<212> TYPE: PRT
<213> ORGANISM: Artificial Sequence
<220> FEATURE:
<223> OTHER INFORMATION: AF, AM motif

<400> SEQUENCE: 82

Gly Thr Ser Thr Pro Glu Ser Gly Ser Ala Ser Pro
1               5                   10

<210> SEQ ID NO 83
<211> LENGTH: 12
<212> TYPE: PRT
<213> ORGANISM: Artificial Sequence
<220> FEATURE:
<223> OTHER INFORMATION: AF, AM motif

<400> SEQUENCE: 83

Gly Thr Ser Pro Ser Gly Glu Ser Ser Thr Ala Pro
1               5                   10

<210> SEQ ID NO 84
<211> LENGTH: 12
<212> TYPE: PRT
<213> ORGANISM: Artificial Sequence
<220> FEATURE:
<223> OTHER INFORMATION: AF, AM motif

<400> SEQUENCE: 84

Gly Ser Thr Ser Ser Thr Ala Glu Ser Pro Gly Pro
1               5                   10

<210> SEQ ID NO 85
<211> LENGTH: 12
```

```
<212> TYPE: PRT
<213> ORGANISM: Artificial Sequence
<220> FEATURE:
<223> OTHER INFORMATION: AG, AM motif

<400> SEQUENCE: 85

Gly Thr Pro Gly Ser Gly Thr Ala Ser Ser Ser Pro
1               5                   10

<210> SEQ ID NO 86
<211> LENGTH: 12
<212> TYPE: PRT
<213> ORGANISM: Artificial Sequence
<220> FEATURE:
<223> OTHER INFORMATION: AG, AM motif

<400> SEQUENCE: 86

Gly Ser Ser Thr Pro Ser Gly Ala Thr Gly Ser Pro
1               5                   10

<210> SEQ ID NO 87
<211> LENGTH: 12
<212> TYPE: PRT
<213> ORGANISM: Artificial Sequence
<220> FEATURE:
<223> OTHER INFORMATION: AG, AM motif

<400> SEQUENCE: 87

Gly Ser Ser Pro Ser Ala Ser Thr Gly Thr Gly Pro
1               5                   10

<210> SEQ ID NO 88
<211> LENGTH: 12
<212> TYPE: PRT
<213> ORGANISM: Artificial Sequence
<220> FEATURE:
<223> OTHER INFORMATION: AG, AM motif

<400> SEQUENCE: 88

Gly Ala Ser Pro Gly Thr Ser Ser Thr Gly Ser Pro
1               5                   10

<210> SEQ ID NO 89
<211> LENGTH: 12
<212> TYPE: PRT
<213> ORGANISM: Artificial Sequence
<220> FEATURE:
<223> OTHER INFORMATION: AQ motif

<400> SEQUENCE: 89

Gly Glu Pro Ala Gly Ser Pro Thr Ser Thr Ser Glu
1               5                   10

<210> SEQ ID NO 90
<211> LENGTH: 12
<212> TYPE: PRT
<213> ORGANISM: Artificial Sequence
<220> FEATURE:
<223> OTHER INFORMATION: AQ motif

<400> SEQUENCE: 90

Gly Thr Gly Glu Pro Ser Ser Thr Pro Ala Ser Glu
1               5                   10

<210> SEQ ID NO 91
<211> LENGTH: 12
<212> TYPE: PRT
```

```
<213> ORGANISM: Artificial Sequence
<220> FEATURE:
<223> OTHER INFORMATION: AQ motif

<400> SEQUENCE: 91

Gly Ser Gly Pro Ser Thr Glu Ser Ala Pro Thr Glu
1               5                   10

<210> SEQ ID NO 92
<211> LENGTH: 12
<212> TYPE: PRT
<213> ORGANISM: Artificial Sequence
<220> FEATURE:
<223> OTHER INFORMATION: AQ motif

<400> SEQUENCE: 92

Gly Ser Glu Thr Pro Ser Gly Pro Ser Glu Thr Ala
1               5                   10

<210> SEQ ID NO 93
<211> LENGTH: 12
<212> TYPE: PRT
<213> ORGANISM: Artificial Sequence
<220> FEATURE:
<223> OTHER INFORMATION: AQ motif

<400> SEQUENCE: 93

Gly Pro Ser Glu Thr Ser Thr Ser Glu Pro Gly Ala
1               5                   10

<210> SEQ ID NO 94
<211> LENGTH: 12
<212> TYPE: PRT
<213> ORGANISM: Artificial Sequence
<220> FEATURE:
<223> OTHER INFORMATION: AQ motif

<400> SEQUENCE: 94

Gly Ser Pro Ser Glu Pro Thr Glu Gly Thr Ser Ala
1               5                   10

<210> SEQ ID NO 95
<211> LENGTH: 12
<212> TYPE: PRT
<213> ORGANISM: Artificial Sequence
<220> FEATURE:
<223> OTHER INFORMATION: BC motif

<400> SEQUENCE: 95

Gly Ser Gly Ala Ser Glu Pro Thr Ser Thr Glu Pro
1               5                   10

<210> SEQ ID NO 96
<211> LENGTH: 12
<212> TYPE: PRT
<213> ORGANISM: Artificial Sequence
<220> FEATURE:
<223> OTHER INFORMATION: BC motif

<400> SEQUENCE: 96

Gly Ser Glu Pro Ala Thr Ser Gly Thr Glu Pro Ser
1               5                   10

<210> SEQ ID NO 97
<211> LENGTH: 12
<212> TYPE: PRT
<213> ORGANISM: Artificial Sequence
```

```
<220> FEATURE:
<223> OTHER INFORMATION: BC motif

<400> SEQUENCE: 97

Gly Thr Ser Glu Pro Ser Thr Ser Glu Pro Gly Ala
1               5                   10

<210> SEQ ID NO 98
<211> LENGTH: 12
<212> TYPE: PRT
<213> ORGANISM: Artificial Sequence
<220> FEATURE:
<223> OTHER INFORMATION: BC motif

<400> SEQUENCE: 98

Gly Thr Ser Thr Glu Pro Ser Glu Pro Gly Ser Ala
1               5                   10

<210> SEQ ID NO 99
<211> LENGTH: 12
<212> TYPE: PRT
<213> ORGANISM: Artificial Sequence
<220> FEATURE:
<223> OTHER INFORMATION: BD motif

<400> SEQUENCE: 99

Gly Ser Thr Ala Gly Ser Glu Thr Ser Thr Glu Ala
1               5                   10

<210> SEQ ID NO 100
<211> LENGTH: 12
<212> TYPE: PRT
<213> ORGANISM: Artificial Sequence
<220> FEATURE:
<223> OTHER INFORMATION: BD motif

<400> SEQUENCE: 100

Gly Ser Glu Thr Ala Thr Ser Gly Ser Glu Thr Ala
1               5                   10

<210> SEQ ID NO 101
<211> LENGTH: 12
<212> TYPE: PRT
<213> ORGANISM: Artificial Sequence
<220> FEATURE:
<223> OTHER INFORMATION: BD motif

<400> SEQUENCE: 101

Gly Thr Ser Glu Ser Ala Thr Ser Glu Ser Gly Ala
1               5                   10

<210> SEQ ID NO 102
<211> LENGTH: 12
<212> TYPE: PRT
<213> ORGANISM: Artificial Sequence
<220> FEATURE:
<223> OTHER INFORMATION: BD motif

<400> SEQUENCE: 102

Gly Thr Ser Thr Glu Ala Ser Glu Gly Ser Ala Ser
1               5                   10

<210> SEQ ID NO 103
<211> LENGTH: 1607
<212> TYPE: PRT
<213> ORGANISM: Artificial Sequence
<220> FEATURE:
```

<223> OTHER INFORMATION: coFVIII-6-XTEN Protein Sequence

<400> SEQUENCE: 103

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400
```

```
Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
        420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
            485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Gly Ala Pro Thr
        755                 760                 765

Ser Glu Ser Ala Thr Pro Glu Ser Gly Pro Gly Ser Glu Pro Ala Thr
    770                 775                 780

Ser Gly Ser Glu Thr Pro Gly Thr Ser Glu Ala Thr Pro Glu Ser
785                 790                 795                 800

Gly Pro Gly Ser Glu Pro Ala Thr Ser Gly Ser Glu Thr Pro Gly Thr
                805                 810                 815

Ser Glu Ser Ala Thr Pro Glu Ser Gly Pro Gly Thr Ser Thr Glu Pro
```

```
                820             825             830
Ser Glu Gly Ser Ala Pro Gly Ser Pro Ala Gly Ser Pro Thr Ser Thr
            835             840             845
Glu Glu Gly Thr Ser Glu Ser Ala Thr Pro Glu Ser Gly Pro Gly Ser
850             855             860
Glu Pro Ala Thr Ser Gly Ser Glu Thr Pro Gly Thr Ser Glu Ser Ala
865             870             875             880
Thr Pro Glu Ser Gly Pro Gly Ser Pro Ala Gly Ser Pro Thr Ser Thr
            885             890             895
Glu Glu Gly Ser Pro Ala Gly Ser Pro Thr Ser Thr Glu Glu Gly Ala
            900             905             910
Ser Ser Pro Pro Val Leu Lys Arg His Gln Arg Glu Ile Thr Arg Thr
            915             920             925
Thr Leu Gln Ser Asp Gln Glu Glu Ile Asp Tyr Asp Asp Thr Ile Ser
            930             935             940
Val Glu Met Lys Lys Glu Asp Phe Asp Ile Tyr Asp Glu Asp Glu Asn
945             950             955             960
Gln Ser Pro Arg Ser Phe Gln Lys Lys Thr Arg His Tyr Phe Ile Ala
            965             970             975
Ala Val Glu Arg Leu Trp Asp Tyr Gly Met Ser Ser Pro His Val
            980             985             990
Leu Arg Asn Arg Ala Gln Ser Gly Ser Val Pro Gln Phe Lys Lys Val
            995             1000            1005
Val Phe Gln Glu Phe Thr Asp Gly Ser Phe Thr Gln Pro Leu Tyr
        1010            1015            1020
Arg Gly Glu Leu Asn Glu His Leu Gly Leu Leu Gly Pro Tyr Ile
        1025            1030            1035
Arg Ala Glu Val Glu Asp Asn Ile Met Val Thr Phe Arg Asn Gln
        1040            1045            1050
Ala Ser Arg Pro Tyr Ser Phe Tyr Ser Ser Leu Ile Ser Tyr Glu
        1055            1060            1065
Glu Asp Gln Arg Gln Gly Ala Glu Pro Arg Lys Asn Phe Val Lys
        1070            1075            1080
Pro Asn Glu Thr Lys Thr Tyr Phe Trp Lys Val Gln His His Met
        1085            1090            1095
Ala Pro Thr Lys Asp Glu Phe Asp Cys Lys Ala Trp Ala Tyr Phe
        1100            1105            1110
Ser Asp Val Asp Leu Glu Lys Asp Val His Ser Gly Leu Ile Gly
        1115            1120            1125
Pro Leu Leu Val Cys His Thr Asn Thr Leu Asn Pro Ala His Gly
        1130            1135            1140
Arg Gln Val Thr Val Gln Glu Phe Ala Leu Phe Phe Thr Ile Phe
        1145            1150            1155
Asp Glu Thr Lys Ser Trp Tyr Phe Thr Glu Asn Met Glu Arg Asn
        1160            1165            1170
Cys Arg Ala Pro Cys Asn Ile Gln Met Glu Asp Pro Thr Phe Lys
        1175            1180            1185
Glu Asn Tyr Arg Phe His Ala Ile Asn Gly Tyr Ile Met Asp Thr
        1190            1195            1200
Leu Pro Gly Leu Val Met Ala Gln Asp Gln Arg Ile Arg Trp Tyr
        1205            1210            1215
Leu Leu Ser Met Gly Ser Asn Glu Asn Ile His Ser Ile His Phe
        1220            1225            1230
```

-continued

Ser Gly His Val Phe Thr Val Arg Lys Lys Glu Glu Tyr Lys Met
1235                1240                1245

Ala Leu Tyr Asn Leu Tyr Pro Gly Val Phe Glu Thr Val Glu Met
1250                1255                1260

Leu Pro Ser Lys Ala Gly Ile Trp Arg Val Glu Cys Leu Ile Gly
1265                1270                1275

Glu His Leu His Ala Gly Met Ser Thr Leu Phe Leu Val Tyr Ser
1280                1285                1290

Asn Lys Cys Gln Thr Pro Leu Gly Met Ala Ser Gly His Ile Arg
1295                1300                1305

Asp Phe Gln Ile Thr Ala Ser Gly Gln Tyr Gly Gln Trp Ala Pro
1310                1315                1320

Lys Leu Ala Arg Leu His Tyr Ser Gly Ser Ile Asn Ala Trp Ser
1325                1330                1335

Thr Lys Glu Pro Phe Ser Trp Ile Lys Val Asp Leu Leu Ala Pro
1340                1345                1350

Met Ile Ile His Gly Ile Lys Thr Gln Gly Ala Arg Gln Lys Phe
1355                1360                1365

Ser Ser Leu Tyr Ile Ser Gln Phe Ile Ile Met Tyr Ser Leu Asp
1370                1375                1380

Gly Lys Lys Trp Gln Thr Tyr Arg Gly Asn Ser Thr Gly Thr Leu
1385                1390                1395

Met Val Phe Phe Gly Asn Val Asp Ser Ser Gly Ile Lys His Asn
1400                1405                1410

Ile Phe Asn Pro Pro Ile Ile Ala Arg Tyr Ile Arg Leu His Pro
1415                1420                1425

Thr His Tyr Ser Ile Arg Ser Thr Leu Arg Met Glu Leu Met Gly
1430                1435                1440

Cys Asp Leu Asn Ser Cys Ser Met Pro Leu Gly Met Glu Ser Lys
1445                1450                1455

Ala Ile Ser Asp Ala Gln Ile Thr Ala Ser Ser Tyr Phe Thr Asn
1460                1465                1470

Met Phe Ala Thr Trp Ser Pro Ser Lys Ala Arg Leu His Leu Gln
1475                1480                1485

Gly Arg Ser Asn Ala Trp Arg Pro Gln Val Asn Asn Pro Lys Glu
1490                1495                1500

Trp Leu Gln Val Asp Phe Gln Lys Thr Met Lys Val Thr Gly Val
1505                1510                1515

Thr Thr Gln Gly Val Lys Ser Leu Leu Thr Ser Met Tyr Val Lys
1520                1525                1530

Glu Phe Leu Ile Ser Ser Ser Gln Asp Gly His Gln Trp Thr Leu
1535                1540                1545

Phe Phe Gln Asn Gly Lys Val Lys Val Phe Gln Gly Asn Gln Asp
1550                1555                1560

Ser Phe Thr Pro Val Val Asn Ser Leu Asp Pro Pro Leu Leu Thr
1565                1570                1575

Arg Tyr Leu Arg Ile His Pro Gln Ser Trp Val His Gln Ile Ala
1580                1585                1590

Leu Arg Met Glu Val Leu Gly Cys Glu Ala Gln Asp Leu Tyr
1595                1600                1605

<210> SEQ ID NO 104
<211> LENGTH: 16

```
<212> TYPE: DNA
<213> ORGANISM: Artificial Sequence
<220> FEATURE:
<223> OTHER INFORMATION: Rep-binding site (RBS) for AAV2

<400> SEQUENCE: 104
gcgcgctcgc tcgctc                                                    16

<210> SEQ ID NO 105
<211> LENGTH: 6
<212> TYPE: DNA
<213> ORGANISM: Artificial Sequence
<220> FEATURE:
<223> OTHER INFORMATION: terminal resolution site (TRS) for AAV2

<400> SEQUENCE: 105 agttgg                                                                6

<210> SEQ ID NO 106
<211> LENGTH: 2328
<212> TYPE: PRT
<213> ORGANISM: Artificial Sequence
<220> FEATURE:
<223> OTHER INFORMATION: mature full length FVIII

<400> SEQUENCE: 106
```

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

```
Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
        290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
            355                 360                 365

Ile Gln Ile Arg Ser Val Ala Lys Lys His Pro Lys Thr Trp Val His
        370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Lys Arg Arg Leu Pro Lys Gly Val Lys His Leu
                485                 490                 495

Lys Asp Phe Pro Ile Leu Pro Gly Glu Ile Phe Lys Tyr Lys Trp Thr
            500                 505                 510

Val Thr Val Glu Asp Gly Pro Thr Lys Ser Asp Pro Arg Cys Leu Thr
        515                 520                 525

Arg Tyr Tyr Ser Ser Phe Val Asn Met Glu Arg Asp Leu Ala Ser Gly
    530                 535                 540

Leu Ile Gly Pro Leu Leu Ile Cys Tyr Lys Glu Ser Val Asp Gln Arg
545                 550                 555                 560

Gly Asn Gln Ile Met Ser Asp Lys Arg Asn Val Ile Leu Phe Ser Val
                565                 570                 575

Phe Asp Glu Asn Arg Ser Trp Tyr Leu Thr Glu Asn Ile Gln Arg Phe
            580                 585                 590

Leu Pro Asn Pro Ala Gly Val Gln Leu Glu Asp Pro Glu Phe Gln Ala
        595                 600                 605

Ser Asn Ile Met His Ser Ile Asn Gly Tyr Val Phe Asp Ser Leu Gln
    610                 615                 620

Leu Ser Val Cys Leu His Glu Val Ala Tyr Trp Tyr Ile Leu Ser Ile
625                 630                 635                 640

Gly Ala Gln Thr Asp Phe Leu Ser Val Phe Phe Ser Gly Tyr Thr Phe
                645                 650                 655

Lys His Lys Met Val Tyr Glu Asp Thr Leu Thr Leu Phe Pro Phe Ser
            660                 665                 670

Gly Glu Thr Val Phe Met Ser Met Glu Asn Pro Gly Leu Trp Ile Leu
```

-continued

```
            675                 680                 685
Gly Cys His Asn Ser Asp Phe Arg Asn Arg Gly Met Thr Ala Leu Leu
    690                 695                 700
Lys Val Ser Ser Cys Asp Lys Asn Thr Gly Asp Tyr Tyr Glu Asp Ser
705                 710                 715                 720
Tyr Glu Asp Ile Ser Ala Tyr Leu Leu Ser Lys Asn Asn Ala Ile Glu
                725                 730                 735
Pro Arg Ser Phe Ser Gln Asn Ser Arg His Pro Ser Thr Arg Gln Lys
            740                 745                 750
Gln Phe Asn Ala Thr Thr Ile Pro Glu Asn Asp Ile Glu Lys Thr Asp
                755                 760                 765
Pro Trp Phe Ala His Arg Thr Pro Met Pro Lys Ile Gln Asn Val Ser
            770                 775                 780
Ser Ser Asp Leu Leu Met Leu Leu Arg Gln Ser Pro Thr Pro His Gly
785                 790                 795                 800
Leu Ser Leu Ser Asp Leu Gln Glu Ala Lys Tyr Glu Thr Phe Ser Asp
                805                 810                 815
Asp Pro Ser Pro Gly Ala Ile Asp Ser Asn Asn Ser Leu Ser Glu Met
            820                 825                 830
Thr His Phe Arg Pro Gln Leu His His Ser Gly Asp Met Val Phe Thr
            835                 840                 845
Pro Glu Ser Gly Leu Gln Leu Arg Leu Asn Glu Lys Leu Gly Thr Thr
    850                 855                 860
Ala Ala Thr Glu Leu Lys Lys Leu Asp Phe Lys Val Ser Ser Thr Ser
865                 870                 875                 880
Asn Asn Leu Ile Ser Thr Ile Pro Ser Asp Asn Leu Ala Ala Gly Thr
                885                 890                 895
Asp Asn Thr Ser Ser Leu Gly Pro Pro Ser Met Pro Val His Tyr Asp
            900                 905                 910
Ser Gln Leu Asp Thr Thr Leu Phe Gly Lys Lys Ser Ser Pro Leu Thr
            915                 920                 925
Glu Ser Gly Gly Pro Leu Ser Leu Ser Glu Glu Asn Asn Asp Ser Lys
    930                 935                 940
Leu Leu Glu Ser Gly Leu Met Asn Ser Gln Glu Ser Ser Trp Gly Lys
945                 950                 955                 960
Asn Val Ser Ser Thr Glu Ser Gly Arg Leu Phe Lys Gly Lys Arg Ala
                965                 970                 975
His Gly Pro Ala Leu Leu Thr Lys Asp Asn Ala Leu Phe Lys Val Ser
            980                 985                 990
Ile Ser Leu Leu Lys Thr Asn Lys  Thr Ser Asn Asn Ser  Ala Thr Asn
            995                 1000                1005
Arg Lys  Thr His Ile Asp Gly  Pro Ser Leu Leu Ile  Glu Asn Ser
    1010                1015                1020
Pro Ser  Val Trp Gln Asn Ile  Ser Asp Thr Glu Phe  Lys Lys Val
    1025                1030                1035
Thr Pro  Leu Ile His Asp Arg  Met Leu Met Asp Lys  Asn Ala Thr
    1040                1045                1050
Ala Leu  Arg Leu Asn His Met  Ser Asn Lys Thr Thr  Ser Ser Lys
    1055                1060                1065
Asn Met  Glu Met Val Gln Gln  Lys Lys Glu Gly Pro  Ile Pro Pro
    1070                1075                1080
Asp Ala  Gln Asn Pro Asp Met  Ser Phe Phe Lys Met  Leu Phe Leu
    1085                1090                1095
```

-continued

```
Pro Glu Ser Ala Arg Trp Ile Gln Arg Thr His Gly Lys Asn Ser
    1100            1105                1110

Leu Asn Ser Gly Gln Gly Pro Ser Pro Lys Gln Leu Val Ser Leu
    1115            1120                1125

Gly Pro Glu Lys Ser Val Glu Gly Gln Asn Phe Leu Ser Glu Lys
    1130            1135                1140

Asn Lys Val Val Gly Lys Gly Glu Phe Thr Lys Asp Val Gly
    1145            1150                1155

Leu Lys Glu Met Val Phe Pro Ser Ser Arg Asn Leu Phe Leu Thr
    1160            1165                1170

Asn Leu Asp Asn Leu His Glu Asn Asn Thr His Asn Gln Glu Lys
    1175            1180                1185

Lys Ile Gln Glu Glu Ile Glu Lys Lys Glu Thr Leu Ile Gln Glu
    1190            1195                1200

Asn Val Val Leu Pro Gln Ile His Thr Val Thr Gly Thr Lys Asn
    1205            1210                1215

Phe Met Lys Asn Leu Phe Leu Leu Ser Thr Arg Gln Asn Val Glu
    1220            1225                1230

Gly Ser Tyr Asp Gly Ala Tyr Ala Pro Val Leu Gln Asp Phe Arg
    1235            1240                1245

Ser Leu Asn Asp Ser Thr Asn Arg Thr Lys Lys His Thr Ala His
    1250            1255                1260

Phe Ser Lys Lys Gly Glu Glu Asn Leu Glu Gly Leu Gly Asn
    1265            1270                1275

Gln Thr Lys Gln Ile Val Glu Lys Tyr Ala Cys Thr Thr Arg Ile
    1280            1285                1290

Ser Pro Asn Thr Ser Gln Gln Asn Phe Val Thr Gln Arg Ser Lys
    1295            1300                1305

Arg Ala Leu Lys Gln Phe Arg Leu Pro Leu Glu Glu Thr Glu Leu
    1310            1315                1320

Glu Lys Arg Ile Ile Val Asp Asp Thr Ser Thr Gln Trp Ser Lys
    1325            1330                1335

Asn Met Lys His Leu Thr Pro Ser Thr Leu Thr Gln Ile Asp Tyr
    1340            1345                1350

Asn Glu Lys Glu Lys Gly Ala Ile Thr Gln Ser Pro Leu Ser Asp
    1355            1360                1365

Cys Leu Thr Arg Ser His Ser Ile Pro Gln Ala Asn Arg Ser Pro
    1370            1375                1380

Leu Pro Ile Ala Lys Val Ser Ser Phe Pro Ser Ile Arg Pro Ile
    1385            1390                1395

Tyr Leu Thr Arg Val Leu Phe Gln Asp Asn Ser Ser His Leu Pro
    1400            1405                1410

Ala Ala Ser Tyr Arg Lys Lys Asp Ser Gly Val Gln Glu Ser Ser
    1415            1420                1425

His Phe Leu Gln Gly Ala Lys Lys Asn Asn Leu Ser Leu Ala Ile
    1430            1435                1440

Leu Thr Leu Glu Met Thr Gly Asp Gln Arg Glu Val Gly Ser Leu
    1445            1450                1455

Gly Thr Ser Ala Thr Asn Ser Val Thr Tyr Lys Lys Val Glu Asn
    1460            1465                1470

Thr Val Leu Pro Lys Pro Asp Leu Pro Lys Thr Ser Gly Lys Val
    1475            1480                1485
```

-continued

| | | | | | | | | | | | |
|---|---|---|---|---|---|---|---|---|---|---|---|
|Glu|Leu|Leu|Pro|Lys|Val|His|Ile|Tyr|Gln|Lys|Asp|Leu|Phe|Pro|
| |1490| | | |1495| | | | |1500| | | | |

Thr Glu Thr Ser Asn Gly Ser Pro Gly His Leu Asp Leu Val Glu
    1505            1510            1515

Gly Ser Leu Leu Gln Gly Thr Glu Gly Ala Ile Lys Trp Asn Glu
    1520            1525            1530

Ala Asn Arg Pro Gly Lys Val Pro Phe Leu Arg Val Ala Thr Glu
    1535            1540            1545

Ser Ser Ala Lys Thr Pro Ser Lys Leu Leu Asp Pro Leu Ala Trp
    1550            1555            1560

Asp Asn His Tyr Gly Thr Gln Ile Pro Lys Glu Glu Trp Lys Ser
    1565            1570            1575

Gln Glu Lys Ser Pro Glu Lys Thr Ala Phe Lys Lys Lys Asp Thr
    1580            1585            1590

Ile Leu Ser Leu Asn Ala Cys Glu Ser Asn His Ala Ile Ala Ala
    1595            1600            1605

Ile Asn Glu Gly Gln Asn Lys Pro Glu Ile Glu Val Thr Trp Ala
    1610            1615            1620

Lys Gln Gly Arg Thr Glu Arg Leu Cys Ser Gln Asn Pro Pro Val
    1625            1630            1635

Leu Lys Arg His Gln Arg Glu Ile Thr Arg Thr Thr Leu Gln Ser
    1640            1645            1650

Asp Gln Glu Glu Ile Asp Tyr Asp Asp Thr Ile Ser Val Glu Met
    1655            1660            1665

Lys Lys Glu Asp Phe Asp Ile Tyr Asp Glu Asp Glu Asn Gln Ser
    1670            1675            1680

Pro Arg Ser Phe Gln Lys Lys Thr Arg His Tyr Phe Ile Ala Ala
    1685            1690            1695

Val Glu Arg Leu Trp Asp Tyr Gly Met Ser Ser Ser Pro His Val
    1700            1705            1710

Leu Arg Asn Arg Ala Gln Ser Gly Ser Val Pro Gln Phe Lys Lys
    1715            1720            1725

Val Val Phe Gln Glu Phe Thr Asp Gly Ser Phe Thr Gln Pro Leu
    1730            1735            1740

Tyr Arg Gly Glu Leu Asn Glu His Leu Gly Leu Leu Gly Pro Tyr
    1745            1750            1755

Ile Arg Ala Glu Val Glu Asp Asn Ile Met Val Thr Phe Arg Asn
    1760            1765            1770

Gln Ala Ser Arg Pro Tyr Ser Phe Tyr Ser Ser Leu Ile Ser Tyr
    1775            1780            1785

Glu Glu Asp Gln Arg Gln Gly Ala Glu Pro Arg Lys Asn Phe Val
    1790            1795            1800

Lys Pro Asn Glu Thr Lys Thr Tyr Phe Trp Lys Val Gln His His
    1805            1810            1815

Met Ala Pro Thr Lys Asp Glu Phe Asp Cys Lys Ala Trp Ala Tyr
    1820            1825            1830

Phe Ser Asp Val Asp Leu Glu Lys Asp Val His Ser Gly Leu Ile
    1835            1840            1845

Gly Pro Leu Leu Val Cys His Thr Asn Thr Leu Asn Pro Ala His
    1850            1855            1860

Gly Arg Gln Val Thr Val Gln Glu Phe Ala Leu Phe Phe Thr Ile
    1865            1870            1875

Phe Asp Glu Thr Lys Ser Trp Tyr Phe Thr Glu Asn Met Glu Arg

```
                    1880            1885            1890
Asn Cys Arg Ala Pro Cys Asn Ile Gln Met Glu Asp Pro Thr Phe
            1895            1900            1905
Lys Glu Asn Tyr Arg Phe His Ala Ile Asn Gly Tyr Ile Met Asp
            1910            1915            1920
Thr Leu Pro Gly Leu Val Met Ala Gln Asp Gln Arg Ile Arg Trp
            1925            1930            1935
Tyr Leu Leu Ser Met Gly Ser Asn Glu Asn Ile His Ser Ile His
            1940            1945            1950
Phe Ser Gly His Val Phe Thr Val Arg Lys Glu Glu Tyr Lys
            1955            1960            1965
Met Ala Leu Tyr Asn Leu Tyr Pro Gly Val Phe Glu Thr Val Glu
            1970            1975            1980
Met Leu Pro Ser Lys Ala Gly Ile Trp Arg Val Glu Cys Leu Ile
            1985            1990            1995
Gly Glu His Leu His Ala Gly Met Ser Thr Leu Phe Leu Val Tyr
            2000            2005            2010
Ser Asn Lys Cys Gln Thr Pro Leu Gly Met Ala Ser Gly His Ile
            2015            2020            2025
Arg Asp Phe Gln Ile Thr Ala Ser Gly Gln Tyr Gly Gln Trp Ala
            2030            2035            2040
Pro Lys Leu Ala Arg Leu His Tyr Ser Gly Ser Ile Asn Ala Trp
            2045            2050            2055
Ser Thr Lys Glu Pro Phe Ser Trp Ile Lys Val Asp Leu Leu Ala
            2060            2065            2070
Pro Met Ile Ile His Gly Ile Lys Thr Gln Gly Ala Arg Gln Lys
            2075            2080            2085
Phe Ser Ser Leu Tyr Ile Ser Gln Phe Ile Ile Met Tyr Ser Leu
            2090            2095            2100
Asp Gly Lys Lys Trp Gln Thr Tyr Arg Gly Asn Ser Thr Gly Thr
            2105            2110            2115
Leu Met Val Phe Phe Gly Asn Val Asp Ser Ser Gly Ile Lys His
            2120            2125            2130
Asn Ile Phe Asn Pro Pro Ile Ile Ala Arg Tyr Ile Arg Leu His
            2135            2140            2145
Pro Thr His Tyr Ser Ile Arg Ser Thr Leu Arg Met Glu Leu Met
            2150            2155            2160
Gly Cys Asp Leu Asn Ser Cys Ser Met Pro Leu Gly Met Glu Ser
            2165            2170            2175
Lys Ala Ile Ser Asp Ala Gln Ile Thr Ala Ser Ser Tyr Phe Thr
            2180            2185            2190
Asn Met Phe Ala Thr Trp Ser Pro Ser Lys Ala Arg Leu His Leu
            2195            2200            2205
Gln Gly Arg Ser Asn Ala Trp Arg Pro Gln Val Asn Asn Pro Lys
            2210            2215            2220
Glu Trp Leu Gln Val Asp Phe Gln Lys Thr Met Lys Val Thr Gly
            2225            2230            2235
Val Thr Thr Gln Gly Val Lys Ser Leu Leu Thr Ser Met Tyr Val
            2240            2245            2250
Lys Glu Phe Leu Ile Ser Ser Ser Gln Asp Gly His Gln Trp Thr
            2255            2260            2265
Leu Phe Phe Gln Asn Gly Lys Val Lys Val Phe Gln Gly Asn Gln
            2270            2275            2280
```

Asp Ser Phe Thr Pro Val Val Asn Ser Leu Asp Pro Pro Leu Leu
2285             2290                2295

Thr Arg Tyr Leu Arg Ile His Pro Gln Ser Trp Val His Gln Ile
2300            2305                2310

Ala Leu Arg Met Glu Val Leu Gly Cys Glu Ala Gln Asp Leu Tyr
2315            2320                2325

<210> SEQ ID NO 107
<211> LENGTH: 7053
<212> TYPE: DNA
<213> ORGANISM: Artificial Sequence
<220> FEATURE:
<223> OTHER INFORMATION: mature full length FVIII

<400> SEQUENCE: 107

| | |
|---|---|
| atgcaaatag agctctccac ctgcttcttt ctgtgccttt gcgattctg ctttagtgcc | 60 |
| accagaagat actacctggg tgcagtggaa ctgtcatggg actatatgca aagtgatctc | 120 |
| ggtgagctgc ctgtggacgc aagatttcct cctagagtgc aaaatctttt ccattcaac | 180 |
| acctcagtcg tgtacaaaaa gactctgttt gtagaattca cggatcaccct tttcaacatc | 240 |
| gctaagccaa ggccacccctg gatgggtctg ctaggtccta ccatccaggc tgaggtttat | 300 |
| gatacagtgg tcattacact taagaacatg gcttcccatc ctgtcagtct tcatgctgtt | 360 |
| ggtgtatcct actggaaagc ttctgaggga gctgaatatg atgatcagac cagtcaaagg | 420 |
| gagaaagaag atgataaagt cttccctggt ggaagccata catatgtctg gcaggtcctg | 480 |
| aaagagaatg gtccaatggc ctctgaccca ctgtgcctta cctactcata tctttctcat | 540 |
| gtggacctgg taaaagactt gaattcaggc ctcattggag ccctactagt atgtagagaa | 600 |
| gggagtctgg ccaaggaaaa gacacagacc ttgcacaaat ttatactact ttttgctgta | 660 |
| tttgatgaag ggaaaagttg gcactcagaa acaaagaact ccttgatgca ggataggga t| 720 |
| gctgcatctg ctcgggcctg gcctaaaatg cacacagtca atggttatgt aaacaggtct | 780 |
| ctgccaggtc tgattggatg ccacaggaaa tcagtctatt ggcatgtgat tggaatgggc | 840 |
| accactcctg aagtgcactc aatattcctc gaaggtcaca catttcttgt gaggaaccat | 900 |
| cgccaggcgt ccttggaaat ctcgccaata actttcctta ctgctcaaac actcttgatg | 960 |
| gaccttggac agtttctact gttttgtcat atctcttccc accaacatga tggcatggaa | 1020 |
| gcttatgtca agtagacag ctgtccagag gaaccccaac tacgaatgaa aaataatgaa | 1080 |
| gaagcggaag actatgatga tgatcttact gattctgaaa tggatgtggt caggtttgat | 1140 |
| gatgacaact ctccttcctt tatccaaatt cgctcagttg ccaagaagca tcctaaaact | 1200 |
| tgggtacatt acattgctgc tgaagaggag gactgggact atgctccctt agtcctcgcc | 1260 |
| cccgatgaca aagttataa agtcaatat ttgaacaatg gccctcagcg gattggtagg | 1320 |
| aagtacaaaa agtccgatt tatggcatac acagatgaaa cctttaagac tcgtgaagct | 1380 |
| attcagcatg aatcaggaat cttgggacct ttactttatg ggaagttgg agacacactg | 1440 |
| ttgattatat ttaagaatca agcaagcaga ccatataaca tctaccctca cggaatcact | 1500 |
| gatgtccgtc ctttgtattc aaggagatta ccaaaaggtg taaacatttt gaaggatttt | 1560 |
| ccaattctgc caggagaaat attcaaatat aaatggacag tgactgtaga agatgggcca | 1620 |
| actaaatcag atcctcggtg cctgacccgc tattactcta gtttcgttaa tatggagaga | 1680 |
| gatctagctt caggactcat tggccctctc ctcatctgct acaaagaatc tgtagatcaa | 1740 |
| agaggaaacc agataatgtc agacaagagg aatgtcatcc tgttttctgt atttgatgag | 1800 |

```
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccct caaacacaaa    2040
atggtctatg aagacacact caccctattc ccattctcag agaaactgt cttcatgtcg    2100 atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga attcaagaca ccctagcact aggcaaaagc aatttaatgc caccacaatt    2340
ccagaaaatg acatagagaa gactgaccct tggtttgcac acagaacacc tatgcctaaa    2400
atacaaaatg tctcctctag tgatttgttg atgctcttgc gacagagtcc tactccacat    2460
gggctatcct tatctgatct ccaagaagcc aaatatgaga cttttctga tgatccatca    2520 cctggagcaa tagacagtaa taacagcctg tctgaaatga cacacttcag gccacagctc    2580
catcacagtg gggacatggt atttaccccct gagtcaggcc tccaattaag attaaatgag    2640
aaactgggga caactgcagc aacagagttg aagaaacttg atttcaaagt ttctagtaca    2700
tcaaataatc tgatttcaac aattccatca gacaatttgg cagcaggtac tgataataca    2760
agttccttag accccccaag tatgccagtt cattatgata gtcaattaga taccactcta    2820
tttggcaaaa agtcatctcc ccttactgag tctggtggac ctctgagctt gagtgaagaa    2880
aataatgatt caaagttgtt agaatcaggt ttaatgaata gccagaaaag ttcatgggga    2940
aaaaatgtat cgtcaacaga gagtggtagg ttatttaaag ggaaaagagc tcatggacct    3000
gctttgttga ctaaagataa tgccttattc aaagttagca tctctttgtt aaagacaaac    3060
aaaacttcca ataattcagc aactaataga aagactcaca ttgatggccc atcattatta    3120
attgagaata gtccatcagt ctggcaaaat atattagaaa gtgacactga gtttaaaaaa    3180
gtgacacctt tgattcatga cagaatgctt atggacaaaa atgctacagc tttgaggcta    3240
aatcatatgt caaataaaac tacttcatca aaaaacatgg aaatggtcca acagaaaaaa    3300
gagggcccca ttccaccaga tgcacaaaat ccagatatgt cgttcttta gatgctattc    3360 ttgccagaat cagcaaggtg gatacaaagg actcatggaa agaactctct gaactctggg    3420
caaggcccca gtccaaagca attagtatcc ttaggaccag aaaaatctgt ggaaggtcag    3480
aatttcttgt ctgagaaaaa caaagtggta gtaggaaagg gtgaatttac aaaggacgta    3540
ggactcaaag agatggtttt tccaagcagc agaaacctat ttcttactaa cttggataat    3600
ttacatgaaa ataatacaca caatcaagaa aaaaaaattc aggaagaaat agaaaagaag    3660
gaaacattaa tccaagagaa tgtagttttg cctcagatac atacagtgac tggcactaag    3720
aatttcatga agaacctttt cttactgagc actaggcaaa atgtagaagg ttcatatgac    3780
ggggcatatg ctccagtact tcaagatttt aggtcattaa atgattcaac aaatagaaca    3840
aagaaacaca cagctcattt ctcaaaaaaa gggaggaag aaaacttgga aggcttggga    3900
aatcaaacca agcaaattgt agagaaatat gcatgcacca caaggatatc tcctaataca    3960
agccagcaga attttgtcac gcaacgtagt aagagagctt tgaaacaatt cagactccca    4020
ctagaagaaa cagaacttga aaaaggata attgtggatg acacctcaac ccagtggtcc    4080
aaaaacatga acatttgac cccgagcacc ctcacacaga tagactacaa tgagaaggag    4140
```

```
aaagggggcca ttactcagtc tcccttatca gattgcctta cgaggagtca tagcatccct    4200
caagcaaata gatctccatt acccattgca aaggtatcat catttccatc tattagacct    4260
atatatctga ccagggtcct attccaagac aactcttctc atcttccagc agcatcttat    4320
agaaagaaag attctggggt ccaagaaagc agtcatttct tacaaggagc caaaaaaaat    4380
aacctttctt tagccattct aaccttggag atgactggtg atcaaagaga ggttggctcc    4440
ctggggacaa gtgccacaaa ttcagtcaca tacaagaaag ttgagaacac tgttctcccg    4500
aaaccagact tgcccaaaac atctggcaaa gttgaattgc ttccaaaagt tcacatttat    4560
cagaaggacc tattccctac ggaaactagc aatgggtctc ctggccatct ggatctcgtg    4620
gaagggagcc ttcttcaggg aacagaggga gcgattaagt ggaatgaagc aaacagacct    4680
ggaaaagttc cctttctgag agtagcaaca gaaagctctg caaagactcc ctccaagcta    4740
ttggatcctc ttgcttggga taaccactat ggtactcaga taccaaaaga agagtggaaa    4800
tcccaagaga agtcaccaga aaaaacagct tttaagaaaa aggataccat tttgtccctg    4860
aacgcttgtg aaagcaatca tgcaatagca gcaataaatg agggacaaaa taagcccgaa    4920
atagaagtca cctgggcaaa gcaaggtagg actgaaaggc tgtgctctca aaacccacca    4980
gtcttgaaac gccatcaacg ggaataaact cgtactactc ttcagtcaga tcaagaggaa    5040
attgactatg atgataccat atcagttgaa atgaagaagg aagattttga catttatgat    5100
gaggatgaaa atcagagccc ccgcagcttt caaaagaaaa cacgcactat ttttattgct    5160
gcagtggaga ggctctggga ttatgggatg agtagctccc cacatgttct aagaaacagg    5220
gctcagagtg gcagtgtccc tcagttcaag aaagttgttt ccaggaatt tactgatggc    5280 tcctttactc agcccttata ccgtggagaa ctaaatgaac atttgggact cctggggcca    5340
tatataagag cagaagttga agataatatc atggtaactt tcagaaatca ggcctctcgt    5400
ccctattcct tctattctag ccttatttct tatgaggaag atcagaggca aggagcagaa    5460
cctagaaaaa actttgtcaa gcctaatgaa accaaaactt acttttggaa agtgcaacat    5520
catatggcac ccactaaaga tgagtttgac tgcaaagcct gggcttattt ctctgatgtt    5580
gacctggaaa agatgtgcca ctcaggcctg attggacccc ttctggtctg ccacactaac    5640
acactgaacc ctgctcatgg gagacaagtg acagtacagg aatttgctct gtttttcacc    5700
atctttgatg agaccaaaag ctggtacttc actgaaaata tggaaagaaa ctgcagggct    5760
ccctgcaata tccagatgga agatcccact tttaaagaga attatcgctt ccatgcaatc    5820
aatggctaca taatggatac actacctggc ttagtaatgg ctcaggatca aaggattcga    5880
tggtatctgc tcagcatggg cagcaatgaa acatccatt ctattcattt cagtggacat    5940
gtgttcactg tacgaaaaaa agaggagtat aaaatggcac tgtacaatct ctatccaggt    6000 gttttttgaga cagtggaaat gttaccatcc aaagctggaa tttgcgggt ggaatgcctt    6060 attggcgagc atctacatgc tgggatgagc acacttttc tggtgtacag caataagtgt    6120
cagactcccc tgggaatggc ttctggacac attagagatt tcagattac agcttcagga    6180 caatatggac agtgggcccc aaagctggcc agacttcatt attccggatc aatcaatgcc    6240
tggagcacca aggagccctt tcttggatc aaggtggatc tgttggcacc aatgattatt    6300
cacggcatca agacccaggg tgcccgtcag aagttctcca gcctctacat ctctcagttt    6360
atcatcatgt atagtcttga tgggaagaag tggcagactt atcgaggaaa ttccactgga    6420
accttaatgg tcttctttgg caatgtggat tcatctggga taaacacaa tatttttaac    6480 cctccaatta ttgctcgata catccgtttg cacccaactc attatagcat tcgcagcact    6540
```

```
cttcgcatgg agttgatggg ctgtgattta aatagttgca gcatgccatt gggaatggag    6600
agtaaagcaa tatcagatgc acagattact gcttcatcct actttaccaa tatgtttgcc    6660
acctggtctc cttcaaaagc tcgacttcac ctccaaggga ggagtaatgc ctggagacct    6720
caggtgaata atccaaaaga gtggctgcaa gtggacttcc agaagacaat gaaagtcaca    6780
ggagtaacta ctcagggagt aaaatctctg cttaccagca tgtatgtgaa ggagttcctc    6840
atctccagca gtcaagatgg ccatcagtgg actctctttt ttcagaatgg caaagtaaag    6900 gttttttcagg gaaatcaaga ctccttcaca cctgtggtga actctctaga cccaccgtta    6960
ctgactcgct accttcgaat tcaccccag agttgggtgc accagattgc cctgaggatg    7020
gaggttctgg gctgcgaggc acaggacctc tac                                 7053
```

<210> SEQ ID NO 108

<400> SEQUENCE: 108

000

<210> SEQ ID NO 109
<211> LENGTH: 1718
<212> TYPE: PRT
<213> ORGANISM: Artificial Sequence
<220> FEATURE:
<223> OTHER INFORMATION: BIVV001 BDD-FVIII(XTEN) Sequence (no Fc)

<400> SEQUENCE: 109

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
```

```
                225                 230                 235                 240
        Ser Leu Pro Gly Leu Ile Gly Cys His Arg Lys Ser Val Tyr Trp His
                        245                 250                 255

Val Ile Gly Met Gly Thr Thr Pro Glu Val His Ser Ile Phe Leu Glu
                        260                 265                 270

Gly His Thr Phe Leu Val Arg Asn His Arg Gln Ala Ser Leu Glu Ile
                        275                 280                 285

Ser Pro Ile Thr Phe Leu Thr Ala Gln Thr Leu Leu Met Asp Leu Gly
                        290                 295                 300

Gln Phe Leu Leu Phe Cys His Ile Ser Ser His Gln His Asp Gly Met
        305                 310                 315                 320

Glu Ala Tyr Val Lys Val Asp Ser Cys Pro Glu Pro Gln Leu Arg
                        325                 330                 335

Met Lys Asn Asn Glu Glu Ala Glu Asp Tyr Asp Asp Asp Leu Thr Asp
                        340                 345                 350

Ser Glu Met Asp Val Val Arg Phe Asp Asp Asn Ser Pro Ser Phe
                        355                 360                 365

Ile Gln Ile Arg Ser Val Ala Lys Lys His Pro Lys Thr Trp Val His
                        370                 375                 380

Tyr Ile Ala Ala Glu Glu Asp Trp Asp Tyr Ala Pro Leu Val Leu
        385                 390                 395                 400

Ala Pro Asp Asp Arg Ser Tyr Lys Ser Gln Tyr Leu Asn Asn Gly Pro
                        405                 410                 415

Gln Arg Ile Gly Arg Lys Tyr Lys Lys Val Arg Phe Met Ala Tyr Thr
                        420                 425                 430

Asp Glu Thr Phe Lys Thr Arg Glu Ala Ile Gln His Glu Ser Gly Ile
                        435                 440                 445

Leu Gly Pro Leu Leu Tyr Gly Glu Val Gly Asp Thr Leu Leu Ile Ile
                        450                 455                 460

Phe Lys Asn Gln Ala Ser Arg Pro Tyr Asn Ile Tyr Pro His Gly Ile
        465                 470                 475                 480

Thr Asp Val Arg Pro Lys Arg Arg Leu Pro Lys Gly Val Lys His Leu
                        485                 490                 495

Lys Asp Phe Pro Ile Leu Pro Gly Glu Ile Phe Lys Tyr Lys Trp Thr
                        500                 505                 510

Val Thr Val Glu Asp Gly Pro Thr Lys Ser Asp Pro Arg Cys Leu Thr
                        515                 520                 525

Arg Tyr Tyr Ser Ser Phe Val Asn Met Glu Arg Asp Leu Ala Ser Gly
        530                 535                 540

Leu Ile Gly Pro Leu Leu Ile Cys Tyr Lys Glu Ser Val Asp Gln Arg
        545                 550                 555                 560

Gly Asn Gln Ile Met Ser Asp Lys Arg Asn Val Ile Leu Phe Ser Val
                        565                 570                 575

Phe Asp Glu Asn Arg Ser Trp Tyr Leu Thr Glu Asn Ile Gln Arg Phe
                        580                 585                 590

Leu Pro Asn Pro Ala Gly Val Gln Leu Glu Asp Pro Glu Phe Gln Ala
                        595                 600                 605

Ser Asn Ile Met His Ser Ile Asn Gly Tyr Val Phe Asp Ser Leu Gln
                        610                 615                 620

Leu Ser Val Cys Leu His Glu Val Ala Tyr Trp Tyr Ile Leu Ser Ile
        625                 630                 635                 640

Gly Ala Gln Thr Asp Phe Leu Ser Val Phe Phe Ser Gly Tyr Thr Phe
                        645                 650                 655
```

```
Lys His Lys Met Val Tyr Glu Asp Thr Leu Thr Leu Phe Pro Phe Ser
            660                 665                 670

Gly Glu Thr Val Phe Met Ser Met Glu Asn Pro Gly Leu Trp Ile Leu
            675                 680                 685

Gly Cys His Asn Ser Asp Phe Arg Asn Arg Gly Met Thr Ala Leu Leu
            690                 695                 700

Lys Val Ser Ser Cys Asp Lys Asn Thr Gly Asp Tyr Tyr Glu Asp Ser
705                 710                 715                 720

Tyr Glu Asp Ile Ser Ala Tyr Leu Leu Ser Lys Asn Asn Ala Ile Glu
                725                 730                 735

Pro Arg Ser Phe Ser Gln Asn Gly Thr Ser Glu Ser Ala Thr Pro Glu
            740                 745                 750

Ser Gly Pro Gly Ser Glu Pro Ala Thr Ser Gly Ser Glu Thr Pro Gly
            755                 760                 765

Thr Ser Glu Ser Ala Thr Pro Glu Ser Gly Pro Gly Ser Glu Pro Ala
            770                 775                 780

Thr Ser Gly Ser Glu Thr Pro Gly Thr Ser Glu Ser Ala Thr Pro Glu
785                 790                 795                 800

Ser Gly Pro Gly Thr Ser Thr Glu Pro Ser Glu Gly Ser Ala Pro Gly
            805                 810                 815

Ser Pro Ala Gly Ser Pro Thr Ser Thr Glu Glu Gly Thr Ser Glu Ser
            820                 825                 830

Ala Thr Pro Glu Ser Gly Pro Gly Ser Glu Pro Ala Thr Ser Gly Ser
            835                 840                 845

Glu Thr Pro Gly Thr Ser Glu Ser Ala Thr Pro Glu Ser Gly Pro Gly
            850                 855                 860

Ser Pro Ala Gly Ser Pro Thr Ser Thr Glu Glu Gly Ser Pro Ala Gly
865                 870                 875                 880

Ser Pro Thr Ser Thr Glu Glu Gly Thr Ser Thr Glu Pro Ser Glu Gly
                885                 890                 895

Ser Ala Pro Gly Thr Ser Glu Ser Ala Thr Pro Glu Ser Gly Pro Gly
            900                 905                 910

Thr Ser Glu Ser Ala Thr Pro Glu Ser Gly Pro Gly Thr Ser Glu Ser
            915                 920                 925

Ala Thr Pro Glu Ser Gly Pro Gly Ser Glu Pro Ala Thr Ser Gly Ser
            930                 935                 940

Glu Thr Pro Gly Ser Glu Pro Ala Thr Ser Gly Ser Glu Thr Pro Gly
945                 950                 955                 960

Ser Pro Ala Gly Ser Pro Thr Ser Thr Glu Glu Gly Thr Ser Thr Glu
                965                 970                 975

Pro Ser Glu Gly Ser Ala Pro Gly Thr Ser Thr Glu Pro Ser Glu Gly
            980                 985                 990

Ser Ala Pro Gly Ser Glu Pro Ala Thr Ser Gly Ser Glu Thr Pro Gly
            995                 1000                1005

Thr Ser Glu Ser Ala Thr Pro Glu Ser Gly Pro Gly Thr Ser Thr
            1010                1015                1020

Glu Pro Ser Glu Gly Ser Ala Pro Ala Ser Ser Glu Ile Thr Arg
            1025                1030                1035

Thr Thr Leu Gln Ser Asp Gln Glu Glu Ile Asp Tyr Asp Asp Thr
            1040                1045                1050

Ile Ser Val Glu Met Lys Lys Glu Asp Phe Asp Ile Tyr Asp Glu
            1055                1060                1065
```

```
Asp Glu Asn Gln Ser Pro Arg Ser Phe Gln Lys Lys Thr Arg His
    1070                1075                1080

Tyr Phe Ile Ala Ala Val Glu Arg Leu Trp Asp Tyr Gly Met Ser
    1085                1090                1095

Ser Ser Pro His Val Leu Arg Asn Arg Ala Gln Ser Gly Ser Val
    1100                1105                1110

Pro Gln Phe Lys Lys Val Val Phe Gln Glu Phe Thr Asp Gly Ser
    1115                1120                1125

Phe Thr Gln Pro Leu Tyr Arg Gly Glu Leu Asn Glu His Leu Gly
    1130                1135                1140

Leu Leu Gly Pro Tyr Ile Arg Ala Glu Val Glu Asp Asn Ile Met
    1145                1150                1155

Val Thr Phe Arg Asn Gln Ala Ser Arg Pro Tyr Ser Phe Tyr Ser
    1160                1165                1170

Ser Leu Ile Ser Tyr Glu Glu Asp Gln Arg Gln Gly Ala Glu Pro
    1175                1180                1185

Arg Lys Asn Phe Val Lys Pro Asn Glu Thr Lys Thr Tyr Phe Trp
    1190                1195                1200

Lys Val Gln His His Met Ala Pro Thr Lys Asp Glu Phe Asp Cys
    1205                1210                1215

Lys Ala Trp Ala Tyr Phe Ser Asp Val Asp Leu Glu Lys Asp Val
    1220                1225                1230

His Ser Gly Leu Ile Gly Pro Leu Leu Val Cys His Thr Asn Thr
    1235                1240                1245

Leu Asn Pro Ala His Gly Arg Gln Val Thr Val Gln Glu Phe Ala
    1250                1255                1260

Leu Phe Phe Thr Ile Phe Asp Glu Thr Lys Ser Trp Tyr Phe Thr
    1265                1270                1275

Glu Asn Met Glu Arg Asn Cys Arg Ala Pro Cys Asn Ile Gln Met
    1280                1285                1290

Glu Asp Pro Thr Phe Lys Glu Asn Tyr Arg Phe His Ala Ile Asn
    1295                1300                1305

Gly Tyr Ile Met Asp Thr Leu Pro Gly Leu Val Met Ala Gln Asp
    1310                1315                1320

Gln Arg Ile Arg Trp Tyr Leu Leu Ser Met Gly Ser Asn Glu Asn
    1325                1330                1335

Ile His Ser Ile His Phe Ser Gly His Val Phe Thr Val Arg Lys
    1340                1345                1350

Lys Glu Glu Tyr Lys Met Ala Leu Tyr Asn Leu Tyr Pro Gly Val
    1355                1360                1365

Phe Glu Thr Val Glu Met Leu Pro Ser Lys Ala Gly Ile Trp Arg
    1370                1375                1380

Val Glu Cys Leu Ile Gly Glu His Leu His Ala Gly Met Ser Thr
    1385                1390                1395

Leu Phe Leu Val Tyr Ser Asn Lys Cys Gln Thr Pro Leu Gly Met
    1400                1405                1410

Ala Ser Gly His Ile Arg Asp Phe Gln Ile Thr Ala Ser Gly Gln
    1415                1420                1425

Tyr Gly Gln Trp Ala Pro Lys Leu Ala Arg Leu His Tyr Ser Gly
    1430                1435                1440

Ser Ile Asn Ala Trp Ser Thr Lys Glu Pro Phe Ser Trp Ile Lys
    1445                1450                1455

Val Asp Leu Leu Ala Pro Met Ile Ile His Gly Ile Lys Thr Gln
```

Gly Ala Arg Gln Lys Phe Ser Ser Leu Tyr Ile Ser Gln Phe Ile
1475                1480                1485

Ile Met Tyr Ser Leu Asp Gly Lys Lys Trp Gln Thr Tyr Arg Gly
1490                1495                1500

Asn Ser Thr Gly Thr Leu Met Val Phe Phe Gly Asn Val Asp Ser
1505                1510                1515

Ser Gly Ile Lys His Asn Ile Phe Asn Pro Pro Ile Ile Ala Arg
1520                1525                1530

Tyr Ile Arg Leu His Pro Thr His Tyr Ser Ile Arg Ser Thr Leu
1535                1540                1545

Arg Met Glu Leu Met Gly Cys Asp Leu Asn Ser Cys Ser Met Pro
1550                1555                1560

Leu Gly Met Glu Ser Lys Ala Ile Ser Asp Ala Gln Ile Thr Ala
1565                1570                1575

Ser Ser Tyr Phe Thr Asn Met Phe Ala Thr Trp Ser Pro Ser Lys
1580                1585                1590

Ala Arg Leu His Leu Gln Gly Arg Ser Asn Ala Trp Arg Pro Gln
1595                1600                1605

Val Asn Asn Pro Lys Glu Trp Leu Gln Val Asp Phe Gln Lys Thr
1610                1615                1620

Met Lys Val Thr Gly Val Thr Thr Gln Gly Val Lys Ser Leu Leu
1625                1630                1635

Thr Ser Met Tyr Val Lys Glu Phe Leu Ile Ser Ser Ser Gln Asp
1640                1645                1650

Gly His Gln Trp Thr Leu Phe Phe Gln Asn Gly Lys Val Lys Val
1655                1660                1665

Phe Gln Gly Asn Gln Asp Ser Phe Thr Pro Val Val Asn Ser Leu
1670                1675                1680

Asp Pro Pro Leu Leu Thr Arg Tyr Leu Arg Ile His Pro Gln Ser
1685                1690                1695

Trp Val His Gln Ile Ala Leu Arg Met Glu Val Leu Gly Cys Glu
1700                1705                1710

Ala Gln Asp Leu Tyr
1715

<210> SEQ ID NO 110
<211> LENGTH: 6526
<212> TYPE: DNA
<213> ORGANISM: Artificial Sequence
<220> FEATURE:
<223> OTHER INFORMATION: NB15.1v32 construct (AAV-FVIIIco6XTEN-ssDNA)

<400> SEQUENCE: 110
ctgcgcgctc gctcgctcac tgaggccgcc cgggcaaagc ccgggcgtcg ggcgaccttt       60
ggtcgcccgg cctcagtgag cgagcgagcg cgcagagagg gagtggccaa ctccatcact      120
aggggttcct gcggcaattc agtcgataac tataacggtc ctaaggtagc gatttaaata      180
cgcgctctct taaggtagcc ccgggacgcg tcaattgaga tctggatccg gtaccgaatt      240
cgcggccgcc tcgacgacta gcgtttaatt aaacgcgtgt ctgtctgcac atttcgtaga      300
gcgagtgttc cgatactcta atctccctag gcaaggttca tatttgtgta ggttacttat      360
tctccttttg ttgactaagt caataatcag aatcagcagg tttggagtca gcttggcagg      420
gatcagcagc ctgggttgga aggagggggt ataaagccc cttcaccagg agaagccgtc      480

| | |
|---|---|
| acacagatcc acaagctcct gaggtaagtg ccgtgtgtgg ttcccgcggg cctggcctct | 540 |
| ttacgggtta tggcccttgc gtgccttgaa ttactgacac tgacatccac ttttttcttt | 600 |
| tctccacagc tagcgccacc atgcagattg agctgtccac ttgtttcttc ctgtgcctcc | 660 |
| tgcgcttctg tttctccgcc actcgccggt actaccttgg agccgtggag ctttcatggg | 720 |
| actacatgca gagcgacctg ggcgaactcc ccgtggatgc cagattcccc cccgcgtgc | 780 |
| caaagtcctt ccccttttaac acctccgtgg tgtacaagaa aaccctcttt gtcgagttca | 840 |
| ctgaccacct gttcaacatc gccaagccgc gcccaccttg gatgggcctc ctgggaccga | 900 |
| ccattcaagc tgaagtgtac gacaccgtgg tgatcaccct gaagaacatg gcgtcccacc | 960 |
| ccgtgtccct gcatgcggtc ggagtgtcct actggaaggc ctccgaagga gctgagtacg | 1020 |
| acgaccagac tagccagcgg gaaaaggagg acgataaagt gttcccgggc ggctcgcata | 1080 |
| cttacgtgtg gcaagtcctg aaggaaaacg gacctatggc atccgatcct ctgtgcctga | 1140 |
| cttactccta cctttcccat gtggacctcg tgaaggacct gaacagcggg ctgattggtg | 1200 |
| cacttctcgt gtgccgcgaa ggttcgctcg ctaaggaaaa gacccagacc ctccataagt | 1260 |
| tcatccttttt gttcgctgtg ttcgatgaag gaaagtcatg gcattccgaa actaagaact | 1320 |
| cgctgatgca ggaccgggat gccgcctcag cccgcgcctg gcctaaaatg catacagtca | 1380 |
| acggatacgt gaatcggtca ctgcccgggc tcatcggttg tcacagaaag tccgtgtact | 1440 |
| ggcacgtcat cggcatgggc actacgcctg aagtgcactc catcttcctg gaagggcaca | 1500 |
| ccttcctcgt gcgcaaccac cgccaggcct ctctggaaat ctccccgatt acctttctga | 1560 |
| ccgcccagac tctgctcatg gacctggggc agttccttct cttctgccac atctccagcc | 1620 |
| atcagcacga cggaatggag gcctacgtga aggtggactc atgcccggaa gaacctcagt | 1680 |
| tgcggatgaa gaacaacgag gaggccgagg actatgacga cgatttgact gactccgaga | 1740 |
| tggacgtcgt gcggttcgat gacgacaaca gccccagctt catccagatt cgcagcgtgg | 1800 |
| ccaagaagca ccccaaaacc tgggtgcact acatcgcggc cgaggaagaa gattgggact | 1860 |
| acgccccgtt ggtgctggca cccgatgacc ggtcgtacaa gtcccagtat ctgaacaatg | 1920 |
| gtccgcagcg gattggcaga aagtacaaga agtgcggtt catggcgtac actgacgaaa | 1980 |
| cgtttaagac ccgggaggcc attcaacatg agagcggcat tctgggacca ctgctgtacg | 2040 |
| gagaggtcgg cgatacccctg ctcatcatct tcaaaaacca ggcctcccgg ccttacaaca | 2100 |
| tctaccctca cggaatcacc gacgtgcggc cactctactc gcggcgcctg ccgaagggcg | 2160 |
| tcaagcacct gaaagacttc cctatcctgc cgggcgaaat cttcaagtat aagtggaccg | 2220 |
| tcaccgtgga ggacgggccc accaagagcg atcctaggtg tctgactcgg tactactcca | 2280 |
| gcttcgtgaa catggaacgg gacctggcat cgggactcat tggaccgctg ctgatctgct | 2340 |
| acaaagagtc ggtggatcaa cgcggcaacc agatcatgtc cgacaagcgc aacgtgatcc | 2400 |
| tgttctccgt gtttgatgaa aacagatcct ggtacctcac tgaaaacatc cagaggttcc | 2460 |
| tcccaaaccc cgcaggagtg caactggagg accctgagtt tcaggcctcg aatatcatgc | 2520 |
| actcgattaa cggttacgtg ttcgactcgc tgcaactgag cgtgtgcctc catgaagtcg | 2580 |
| cttactggta cattctgtcc atcggcgccc agactgactt cctgagcgtg ttcttttccg | 2640 |
| gttacacctt taagcacaag atggtgtacg aagataccct gaccctgttc cctttctccg | 2700 |
| gcgaaacggt gttcatgtcg atggagaacc cgggtctgtg gattctggga tgccacaaca | 2760 |
| gcgactttcg gaaccgcgga atgactgccc tgctgaaggt gtcctcatgc gacaagaaca | 2820 |
| ccggagacta ctacgaggac tcctacgagg atatctcagc ctacctcctg tccaagaaca | 2880 |

```
acgcgatcga gccgcgcagc ttcagccaga acggcgcgcc aacatcagag agcgccaccc   2940
ctgaaagtgg tcccgggagc gagccagcca catctgggtc ggaaacgcca ggcacaagtg   3000
agtctgcaac tcccgagtcc ggacctggct ccgagcctgc cactagcggc tccgagactc   3060
cgggaacttc cgagagcgct acaccagaaa gcggacccgg aaccagtacc gaacctagcg   3120
agggctctgc tccgggcagc ccagccggct ctcctacatc cacggaggag ggcacttccg   3180
aatccgccac cccggagtca gggccaggat ctgaacccgc tacctcaggc agtgagacgc   3240
caggaacgag cgagtccgct acaccggaga gtgggccagg agccctgctg gatctcccta   3300
cgtccactga ggaagggtca ccagcgggct cgcccaccag cactgaagaa ggtgcctcga   3360
gcccgcctgt gctgaagagg caccagcgag aaattacccg gaccaccctc caatcggatc   3420
aggaggaaat cgactacgac gacaccatct cggtggaaat gaagaaggaa gatttcgata   3480
tctacgacga ggacgaaaat cagtcccctc gctcattcca aaagaaaact agacactact   3540
ttatcgccgc ggtggaaaga ctgtgggact atggaatgtc atccagccct cacgtccttc   3600
ggaaccgggc ccagagcgga tcggtgcctc agttcaagaa agtggtgttc caggagttca   3660 ccgacgcag cttcacccag ccgctgtacc ggggagaact gaacgaacac ctgggcctgc   3720
tcggtcccta catccgcgcg gaagtggagg ataacatcat ggtgaccttc cgtaaccaag   3780
catccagacc ttactccttc tattcctccc tgatctcata cgaggaggac cagcgccaag   3840
gcgccgagcc ccgcaagaac ttcgtcaagc ccaacgagac taagacctac ttctggaagg   3900
tccaacacca tatggccccg accaaggatg agtttgactg caaggcctgg gcctacttct   3960
ccgacgtgga ccttgagaag gatgtccatt ccggcctgat cgggccgctg ctcgtgtgtc   4020
acaccaacac cctgaaccca gcgcatggac gccaggtcac cgtccaggag tttgctctgt   4080
tcttcaccat ttttgacgaa actaagtcct ggtacttcac cgagaatatg gagcgaaact   4140
gtagagcgcc ctgcaatatc cagatggaag atccgacttt caaggagaac tatagattcc   4200
acgccatcaa cgggtacatc atggatactc tgccggggct ggtcatggcc caggatcaga   4260
ggattcggtg gtacttgctg tcaatggat cgaacgaaaa cattcactcc attcacttct   4320
ccggtcacgt gttcactgtg cgcaagaagg aggagtacaa gatggcgctg tacaatctgt   4380
accccggggt gttcgaaact gtggagatgc tgccgtccaa ggccggcatc tggagagtgg   4440
agtgcctgat cggagagcac ctccacgcgg ggatgtccac cctcttcctg gtgtactcga   4500
ataagtgcca gaccccgctg gcatggcct cgggccacat cagagacttc cagatcacag   4560
caagcggaca atacgccaa tgggcgccga agctggcccg cttgcactac tccggatcga   4620
tcaacgcatg gtccaccaag gaaccgttct cgtggattaa ggtggacctc ctggccccta   4680
tgattatcca cggaattaag acccaggcg ccaggcagaa gttctcctcc ctgtacatct   4740
cgcaattcat catcatgtac agcctggacg ggaagaagtg gcagacttac aggggaaact   4800
ccaccggcac cctgatggtc tttttcggca acgtggattc ctccggcatt aagcacaaca   4860
tcttcaaccc accgatcata gccagatata ttaggctcca ccccactcac tactcaatcc   4920
gctcaactct tcggatggaa ctcatggggt gcgacctgaa ctcctgctcc atgccgttgg   4980
ggatggaatc aaaggctatt agcgacgccc agatcaccgc gagctcctac ttcactaaca   5040
tgttcgccac ctggagcccc tccaaggcca ggctgcactt gcaggacgg tcaaatgcct   5100 ggcggccgca agtgaacaat ccgaaggaat ggcttcaagt ggatttccaa aagaccatga   5160
aagtgaccgg agtcaccacc cagggagtga agtcccttct gacctcgatg tatgtgaagg   5220
```

```
agttcctgat tagcagcagc caggacgggc accagtggac cctgttcttc caaaacggaa    5280
aggtcaaggt gttccagggg aaccaggact cgttcacacc cgtggtgaac tccctggacc    5340
ccccactgct gacgcggtac ttgaggattc atcctcagtc ctgggtccat cagattgcat    5400
tgcgaatgga agtcctgggc tgcgaggccc aggacctgta ctgaatcagc ctgagctcgc    5460
tgatcataat caacctctgg attacaaaat ttgtgaaaga ttgactggta ttcttaacta    5520
tgttgctcct tttacgctat gtggatacgc tgctttaatg cctttgtatc atgctattgc    5580
ttcccgtatg gctttcattt tctcctcctt gtataaatcc tggttgctgt ctctttatga    5640
ggagttgtgg cccgttgtca ggcaacgtgg cgtggtgtgc actgtgtttg ctgacgcaac    5700
ccccactggt tggggcattg ccaccacctg tcagctcctt ccgggacttt cgctttccc     5760 cctccctatt gccacggcgg aactcatcgc cgcctgcctt gcccgctgct ggacaggggc    5820
tcggctgttg ggcactgaca attccgtggt gttgtcgggg aaatcatcgt cctttccttg    5880
gctgctcgcc tgtgttgcca cctggattct gcgcgggacg tccttctgct acgtcccttc    5940
ggccctcaat ccagcggacc ttccttcccg cggcctgctg ccggctctgc ggcctcttcc    6000
gcgtcttcgc cttcgccctc agacgagtcg atctccctt gggccgcct cccgctgat      6060 cagcctcgac tgtgccttct agttgccagc catctgttgt ttgcccctcc ccgtgcctt    6120 ccttgaccct ggaaggtgcc actcccactg tcctttccta ataaaatgag gaaattgcat    6180
cgcattgtct gagtaggtgt cattctattc tggggggtgg ggtggggcag gacagcaagg    6240
gggaggattg ggaagacaat agcaggcatg ctggggatgc ggtgggctct atggcttctg    6300
aggcggaaag aacgggctcg agaagcttct agatatcctc tcttaaggta gcatcgagat    6360
ttaaattagg gataacaggg taatggcgcg ggccgcagga accctagtg atggagttgg    6420 ccactccctc tctgcgcgct cgctcgctca ctgaggccgg gcgaccaaag gtcgcccgac    6480
gcccgggctt tgcccgggcg gcctcagtga gcgagcgagc gcgcag                 6526

<210> SEQ ID NO 111
<211> LENGTH: 130
<212> TYPE: DNA
<213> ORGANISM: Artificial Sequence
<220> FEATURE:
<223> OTHER INFORMATION: 5'ITR (5'-end AAV2 inverted terminal repeat)

<400> SEQUENCE: 111
ctgcgcgctc gctcgctcac tgaggccgcc cgggcaaagc ccgggcgtcg gcgaccttt    60 ggtcgcccgg cctcagtgag cgagcgagcg cgcagagagg gagtggccaa ctccatcact   120
aggggttcct                                                          130

<210> SEQ ID NO 112
<211> LENGTH: 142
<212> TYPE: DNA
<213> ORGANISM: Artificial Sequence
<220> FEATURE:
<223> OTHER INFORMATION: Plasmid Backbone Sequence (PBS)-1

<400> SEQUENCE: 112
gcggcaattc agtcgataac tataacggtc ctaaggtagc gatttaaata cgcgctctct   60
taaggtagcc ccgggacgcg tcaattgaga tctggatccg gtaccgaatt cgcggccgcc   120
tcgacgacta gcgtttaatt aa                                            142

<210> SEQ ID NO 113
<211> LENGTH: 229
```

```
<212> TYPE: DNA
<213> ORGANISM: Artificial Sequence
<220> FEATURE:
<223> OTHER INFORMATION: TTPp (liver-specific promoter)

<400> SEQUENCE: 113
acgcgtgtct gtctgcacat ttcgtagagc gagtgttccg atactctaat ctccctaggc    60
aaggttcata tttgtgtagg ttacttattc tccttttgtt gactaagtca ataatcagaa   120
tcagcaggtt tggagtcagc ttggcaggga tcagcagcct gggttggaag gagggggtat   180
aaaagcccct tcaccaggag aagccgtcac acagatccac aagctcctg               229

<210> SEQ ID NO 114

<400> SEQUENCE: 114

000

<210> SEQ ID NO 115
<211> LENGTH: 106
<212> TYPE: DNA
<213> ORGANISM: Artificial Sequence
<220> FEATURE:
<223> OTHER INFORMATION: Synthetic Intron

<400> SEQUENCE: 115
gtaagtgccg tgtgtggttc ccgcgggcct ggcctcttta cgggttatgg cccttgcgtg    60
ccttgaatta ctgacactga catccacttt ttctttttct ccacag                  106

<210> SEQ ID NO 116
<211> LENGTH: 11
<212> TYPE: DNA
<213> ORGANISM: Artificial Sequence
<220> FEATURE:
<223> OTHER INFORMATION: Plasmid Backbone Sequence (PBS)-3

<400> SEQUENCE: 116
ctagcgccac c                                                         11

<210> SEQ ID NO 117
<211> LENGTH: 4824
<212> TYPE: DNA
<213> ORGANISM: Artificial Sequence
<220> FEATURE:
<223> OTHER INFORMATION: FVIIIco6XTEN (open reading frame for codon-
      optimized FVIII version 6 containing XTEN144)

<400> SEQUENCE: 117
atgcagattg agctgtccac ttgtttcttc ctgtgcctcc tgcgcttctg tttctccgcc    60
actcgccggt actaccttgg agccgtggag ctttcatggg actacatgca gagcgacctg   120
ggcgaactcc ccgtggatgc cagattcccc cccgcgtgc caaagtcctt ccccttttaac   180 acctccgtgg tgtacaagaa aaccctcttt gtcgagttca ctgaccacct gttcaacatc   240
gccaagccgc gcccaccttg gatgggcctc ctgggaccga ccattcaagc tgaagtgtac   300
gacaccgtgg tgatcaccct gaagaacatg gcgtcccacc ccgtgtccct gcatgcggtc   360
ggagtgtcct actggaaggc ctccgaagga gctgagtacg acgaccagac tagccagcgg   420
gaaaaggagg acgataaagt gttcccgggc ggctcgcata cttacgtgtg gcaagtcctg   480
aaggaaaacg gacctatggc atccgatcct ctgtgcctga cttactccta cctttcccat   540
gtggacctcg tgaaggacct gaacagcggg ctgattggtg cacttctcgt gtgccgcgaa   600
```

```
ggttcgctcg ctaaggaaaa gacccagacc ctccataagt tcatcctttt gttcgctgtg    660
ttcgatgaag gaaagtcatg gcattccgaa actaagaact cgctgatgca ggaccgggat    720
gccgcctcag cccgcgcctg gcctaaaatg catacagtca acggatacgt gaatcggtca    780
ctgcccgggc tcatcggttg tcacagaaag tccgtgtact ggcacgtcat cggcatgggc    840
actacgcctg aagtgcactc catcttcctg aagggcaca ccttcctcgt gcgcaaccac    900
cgccaggcct ctctggaaat ctccccgatt accttctga ccgcccagac tctgctcatg    960
gacctggggc agttccttct cttctgccac atctccagcc atcagcacga cggaatggag   1020
gcctacgtga aggtggactc atgcccggaa gaacctcagt tgcggatgaa gaacaacgag   1080
gaggccgagg actatgacga cgatttgact gactccgaga tggacgtcgt gcggttcgat   1140
gacgacaaca gccccagctt catccagatt cgcagcgtgg ccaagaagca ccccaaaacc   1200
tgggtgcact acatcgcggc cgaggaagaa gattgggact acgcccgtt ggtgctggca    1260
cccgatgacc ggtcgtacaa gtcccagtat ctgaacaatg gtccgcagcg gattggcaga   1320
aagtacaaga aagtgcggtt catggcgtac actgacgaaa cgtttaagac ccggggaggcc   1380
attcaacatg agagcggcat tctgggacca ctgctgtacg gagaggtcgg cgataccctg   1440
ctcatcatct tcaaaaacca ggcctcccgg ccttacaaca tctaccctca cggaatcacc   1500
gacgtgcggc cactctactc gcggcgcctg ccgaagggcg tcaagcacct gaaagacttc   1560
cctatcctgc cgggcgaaat cttcaagtat aagtggaccg tcaccgtgga ggacgggccc   1620
accaagagcg atcctaggtg tctgactcgg tactactcca gcttcgtgaa catggaacgg   1680
gacctggcat cgggactcat tggaccgctg ctgatctgct acaaagagtc ggtggatcaa   1740
cgcggcaacc agatcatgtc cgacaagcgc aacgtgatcc tgttctccgt gtttgatgaa   1800
aacagatcct ggtacctcac tgaaaacatc cagaggttcc tcccaaaccc cgcaggagtg   1860
caactggagg accctgagtt tcaggcctcg aatatcatgc actcgattaa cggttacgtg   1920
ttcgactcgc tgcaactgag cgtgtgcctc catgaagtcg cttactggta cattctgtcc   1980
atcggcgccc agactgactt cctgagcgtg ttcttttccg gttacacctt taagcacaag   2040
atggtgtacg aagataccct gaccctgttc ccttttctccg gcgaaacggt gttcatgtcg   2100
atggagaacc cgggtctgtg gattctggga tgccacaaca gcgactttcg gaaccgcgga   2160
atgactgccc tgctgaaggt gtcctcatgc gacaagaaca ccggagacta ctacgaggac   2220
tcctacgagg atatctcagc ctacctcctg tccaagaaca acgcgatcga gccgcgcagc   2280
ttcagccaga acggcgcgcc aacatcgag agcgccaccc ctgaaagtgg tcccgggagc   2340
gagccagcca catctgggtc ggaaacgcca ggcacaagtg agtctgcaac tcccgagtcc   2400
ggacctggct ccgagcctgc cactagcggc tccgagactc cgggaacttc cgagagcgct   2460
acaccagaaa gcggacccgg aaccagtacc gaacctagcg agggctctgc tccgggcagc   2520
ccagccggct ctcctacatc cacggaggag ggcacttccg aatccgccac cccggagtca   2580
gggccaggat ctgaacccgc tacctcaggc agtgagacgc caggaacgag cgagtccgct   2640
acaccggaga gtgggccagg gagccctgct ggatctccta cgtccactga ggaagggtca   2700
ccagcgggct cgcccaccag cactgaagaa ggtgcctcga gccgcctgt gctgaagagg   2760
caccagcgag aaattacccg gaccaccctc caatcggatc aggaggaaat cgactacgac   2820
gacaccatct cggtggaaat gaagaaggaa gatttcgata tctacgacga ggacgaaaat   2880
cagtccccctc gctcattcca aaagaaaact agacactact ttatcgccgc ggtggaaaga   2940
ctgtgggact atggaatgtc atccagccct cacgtccttc ggaaccgggc ccagagcgga   3000
```

```
tcggtgcctc agttcaagaa agtggtgttc caggagttca ccgacggcag cttcacccag    3060
ccgctgtacc ggggagaact gaacgaacac ctgggcctgc tcggtcccta catccgcgcg    3120
gaagtggagg ataacatcat ggtgaccttc cgtaaccaag catccagacc ttactccttc    3180
tattcctccc tgatctcata cgaggaggac cagcgccaag gcgccgagcc ccgcaagaac    3240
ttcgtcaagc ccaacgagac taagacctac ttctggaagg tccaacacca tatggccccg    3300
accaaggatg agtttgactg caaggcctgg gcctacttct ccgacgtgga ccttgagaag    3360
gatgtccatt ccggcctgat cgggccgctg ctcgtgtgtc acaccaacac cctgaaccca    3420
gcgcatggac gccaggtcac cgtccaggag tttgctctgt tcttcaccat ttttgacgaa    3480
actaagtcct ggtacttcac cgagaatatg gagcgaaact gtagagcgcc ctgcaatatc    3540
cagatggaag atccgacttt caaggagaac tatagattcc acgccatcaa cgggtacatc    3600
atggatactc tgccggggct ggtcatggcc caggatcaga ggattcggtg gtacttgctg    3660
tcaatgggat cgaacgaaaa cattcactcc attcacttct ccggtcacgt gttcactgtg    3720
cgcaagaagg aggagtacaa gatggcgctg tacaatctgt accccggggt gttcgaaact    3780
gtggagatgc tgccgtccaa ggccggcatc tggagagtgg agtgcctgat cggagagcac    3840
ctccacgcgg ggatgtccac cctcttcctg gtgtactcga ataagtgcca gaccccgctg    3900
ggcatggcct cgggccacat cagagacttc cagatcacag caagcggaca atacggccaa    3960
tgggcgccga agctggcccg cttgcactac tccggatcga tcaacgcatg gtccaccaag    4020
gaaccgttct cgtggattaa ggtggacctc ctggccccta tgattatcca cggaattaag    4080
acccagggcg ccaggcagaa gttctcctcc ctgtacatct cgcaattcat catcatgtac    4140
agcctggacg ggaagaagtg gcagacttac aggggaaact ccaccggcac cctgatggtc    4200 ttttcggca acgtggattc ctccggcatt aagcacaaca tcttcaaccc accgatcata    4260
gccagatata ttaggctcca ccccactcac tactcaatcc gctcaactct tcggatggaa    4320
ctcatggggt gcgacctgaa ctcctgctcc atgccgttgg ggatggaatc aaaggctatt    4380
agcgacgccc agatcaccgc gagctcctac ttcactaaca tgttcgccac ctggagcccc    4440
tccaaggcca ggctgcactt gcagggacgg tcaaatgcct ggcggccgca agtgaacaat    4500
ccgaaggaat ggcttcaagt ggatttccaa aagaccatga agtgaccgg agtcaccacc    4560 cagggagtga agtcccttct gacctcgatg tatgtgaagg agttcctgat tagcagcagc    4620
caggacgggc accagtggac cctgttcttc caaaacggaa aggtcaaggt gttccagggg    4680
aaccaggact cgttcacacc cgtggtgaac tccctggacc ccccactgct gacgcggtac    4740
ttgaggattc atcctcagtc ctgggtccat cagattgcat tgcgaatgga agtcctgggc    4800
tgcgaggccc aggacctgta ctga    4824
```

<210> SEQ ID NO 118
<211> LENGTH: 450
<212> TYPE: DNA
<213> ORGANISM: Artificial Sequence
<220> FEATURE:
<223> OTHER INFORMATION: XTEN144

<400> SEQUENCE: 118

```
ggcgcgccaa catcagagag cgccaccccct gaaagtggtc ccgggagcga gccagccaca      60
tctgggtcgg aaacgccagg cacaagtgag tctgcaactc ccgagtccgg acctggctcc     120
gagcctgcca ctagcggctc cgagactccg ggaacttccg agagcgctac accagaaagc     180
```

```
ggacccggaa ccagtaccga acctagcgag ggctctgctc cgggcagccc agccggctct      240
cctacatcca cggaggaggg cacttccgaa tccgccaccc cggagtcagg gccaggatct      300
gaacccgcta cctcaggcag tgagacgcca ggaacgagcg agtccgctac accggagagt      360
gggccaggga gccctgctgg atctcctacg tccactgagg aagggtcacc agcgggctcg      420
cccaccagca ctgaagaagg tgcctcgagc                                      450
```

```
<210> SEQ ID NO 119
<211> LENGTH: 19
<212> TYPE: DNA
<213> ORGANISM: Artificial Sequence
<220> FEATURE:
<223> OTHER INFORMATION: Plasmid Backbone Sequence (PBS)-4

<400> SEQUENCE: 119
atcagcctga gctcgctga                                                   19
```

```
<210> SEQ ID NO 120
<211> LENGTH: 595
<212> TYPE: DNA
<213> ORGANISM: Artificial Sequence
<220> FEATURE:
<223> OTHER INFORMATION: WPRE (mutated woodchuck hepatitis virus post-
      transcriptional regulatory element)

<400> SEQUENCE: 120
tcataatcaa cctctggatt acaaaatttg tgaaagattg actggtattc ttaactatgt       60
tgctcctttt acgctatgtg gatacgctgc tttaatgcct ttgtatcatg ctattgcttc      120
ccgtatggct ttcattttct cctccttgta taaatcctgg ttgctgtctc tttatgagga      180
gttgtggccc gttgtcaggc aacgtggcgt ggtgtgcact gtgtttgctg acgcaacccc      240
cactggttgg ggcattgcca ccacctgtca gctccttttcc gggactttcg ctttccccct      300
ccctattgcc acggcggaac tcatcgccgc ctgccttgcc cgctgctgga caggggctcg      360
gctgttgggc actgacaatt ccgtggtgtt gtcggggaaa tcatcgtcct ttccttggct      420
gctcgcctgt gttgccacct ggattctgcg cgggacgtcc ttctgctacg tcccttcggc      480
cctcaatcca gcggaccttc cttcccgcgg cctgctgccg gctctgcggc ctcttccgcg      540
tcttcgcctt cgccctcaga cgagtcggat ctccctttgg gccgcctccc cgctg          595
```

```
<210> SEQ ID NO 121
<211> LENGTH: 8
<212> TYPE: DNA
<213> ORGANISM: Artificial Sequence
<220> FEATURE:
<223> OTHER INFORMATION: Plasmid Backbone Sequence (PBS)-5

<400> SEQUENCE: 121 atcagcct                                                                8
```

```
<210> SEQ ID NO 122
<211> LENGTH: 211
<212> TYPE: DNA
<213> ORGANISM: Artificial Sequence
<220> FEATURE:
<223> OTHER INFORMATION: bGHpA (bovine growth hormone polyadenylation
      signal)

<400> SEQUENCE: 122
cgactgtgcc ttctagttgc cagccatctg ttgtttgccc ctcccccgtg ccttccttga       60
ccctggaagg tgccactccc actgtccttt cctaataaaa tgaggaaatt gcatcgcatt      120
```

```
gtctgagtag gtgtcattct attctggggg gtggggtggg gcaggacagc aaggggggagg        180 attgggaaga caatagcagg catgctgggg a                                        211

<210> SEQ ID NO 123
<211> LENGTH: 119
<212> TYPE: DNA
<213> ORGANISM: Artificial Sequence
<220> FEATURE:
<223> OTHER INFORMATION: Plasmid Backbone Sequence (PBS)-6

<400> SEQUENCE: 123
tgcggtgggc tctatggctt ctgaggcgga aagaacgggc tcgagaagct tctagatatc         60
ctctcttaag gtagcatcga gatttaaatt agggataaca gggtaatggc gcgggccgc         119

<210> SEQ ID NO 124
<211> LENGTH: 130
<212> TYPE: DNA
<213> ORGANISM: Artificial Sequence
<220> FEATURE:
<223> OTHER INFORMATION: 3'ITR (3'-end AAV2 inverted terminal repeat)

<400> SEQUENCE: 124
aggaacccct agtgatggag ttggccactc cctctctgcg cgctcgctcg ctcactgagg         60
ccgggcgacc aaaggtcgcc cgacgcccgg gctttgcccg gcggcctca gtgagcgagc        120 gagcgcgcag                                                               130

<210> SEQ ID NO 125
<211> LENGTH: 415
<212> TYPE: PRT
<213> ORGANISM: Artificial Sequence
<220> FEATURE:
<223> OTHER INFORMATION: Mature FIX polypeptide

<400> SEQUENCE: 125

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
```

```
                180             185             190
Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
        210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
        290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
        370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 126
<211> LENGTH: 415
<212> TYPE: PRT
<213> ORGANISM: Artificial Sequence
<220> FEATURE:
<223> OTHER INFORMATION: Mature Padua(R338L)FIX Polypeptide

<400> SEQUENCE: 126

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
                20                  25                  30

Glu Asn Thr Glu Arg Thr Thr Glu Phe Trp Lys Gln Tyr Val Asp Gly
            35                  40                  45

Asp Gln Cys Glu Ser Asn Pro Cys Leu Asn Gly Gly Ser Cys Lys Asp
        50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
```

```
            130                 135                 140
Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                    165                 170                 175

Asp Phe Thr Arg Val Val Gly Gly Glu Asp Ala Lys Pro Gly Gln Phe
                180                 185                 190

Pro Trp Gln Val Val Leu Asn Gly Lys Val Asp Ala Phe Cys Gly Gly
            195                 200                 205

Ser Ile Val Asn Glu Lys Trp Ile Val Thr Ala Ala His Cys Val Glu
        210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
                260                 265                 270

Leu Glu Leu Asp Glu Pro Leu Val Leu Asn Ser Tyr Val Thr Pro Ile
            275                 280                 285

Cys Ile Ala Asp Lys Glu Tyr Thr Asn Ile Phe Leu Lys Phe Gly Ser
        290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Leu Ser Thr Lys Phe Thr Ile Tyr Asn Asn Met Phe Cys Ala Gly
                340                 345                 350

Phe His Glu Gly Gly Arg Asp Ser Cys Gln Gly Asp Ser Gly Gly Pro
            355                 360                 365

His Val Thr Glu Val Glu Gly Thr Ser Phe Leu Thr Gly Ile Ile Ser
        370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 127
<211> LENGTH: 46
<212> TYPE: PRT
<213> ORGANISM: Artificial Sequence
<220> FEATURE:
<223> OTHER INFORMATION: FIX Signal Polypeptide and Propeptide

<400> SEQUENCE: 127

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg
            35                  40                  45

<210> SEQ ID NO 128
<211> LENGTH: 8442
<212> TYPE: DNA
<213> ORGANISM: Artificial Sequence
<220> FEATURE:
<223> OTHER INFORMATION: human VWF
```

<400> SEQUENCE: 128

```
atgattcctg ccagatttgc cggggtgctg cttgctctgg ccctcatttt gccagggacc    60
ctttgtgcag aaggaactcg cggcaggtca tccacggccc gatgcagcct tttcggaagt   120
gacttcgtca acacctttga tgggagcatg tacagctttg cgggatactg cagttacctc   180
ctggcagggg gctgccagaa acgctccttc tcgattattg ggacttccca gaatggcaag   240
agagtgagcc tctccgtgta tcttggggaa ttttttgaca tccatttgtt tgtcaatggt   300
accgtgacac aggggggacca aagagtctcc atgccctatg cctccaaagg gctgtatcta   360
gaaactgagc tgggtacta caagctgtcc ggtgaggcct atggctttgt ggccaggatc   420
gatggcagcg gcaactttca gtcctgctg tcagacagat acttcaacaa gacctgcggg   480
ctgtgtggca actttaacat ctttgctgaa gatgacttta tgacccaaga agggaccttg   540
acctcggacc ttatgactt tgccaactca tgggctctga gcagtggaga cagtggtgt   600
gaacgggcat ctcctcccag cagctcatgc aacatctcct ctggggaaat gcagaagggc   660
ctgtgggagc agtgccagct tctgaagagc acctcggtgt ttgcccgctg ccaccctctg   720
gtggaccccg agccttttgt ggccctgtgt gagaagactt tgtgtgagtg tgctgggggg   780
ctggagtgcg cctgccctgc cctcctggag tacgcccgga cctgtgccca ggagggaatg   840
gtgctgtacg gctggaccga ccacagcgcg tgcagcccag tgtgccctgc tggtatggag   900
tataggcagt gtgtgtcccc ttgcgccagg acctgccaga gcctgcacat caatgaaatg   960
tgtcaggagc gatgcgtgga tggctgcagc tgccctgagg acagctcct ggatgaaggc  1020
ctctgcgtgg agagcaccga gtgtcctgc gtgcattccg gaaagcgcta ccctcccggc  1080
acctccctct ctcgagactg caacacctgc atttgccgaa acagccagtg gatctgcagc  1140
aatgaagaat gtccagggga gtgccttgtc actggtcaat cccacttcaa gagctttgac  1200
aacagatact tcaccttcag tgggatctgc cagtacctgc tggcccggga ttgccaggac  1260
cactccttct ccattgtcat tgagactgtc cagtgtgctg atgaccgcga cgctgtgtgc  1320
acccgctccg tcaccgtccg gctgcctggc ctgcacaaca gccttgtgaa actgaagcat  1380
ggggcaggag ttgccatgga tggccaggac atccagctcc ccctcctgaa aggtgacctc  1440
cgcatccagc atacagtgac ggcctccgtg cgcctcagct acgggaagga cctgcagatg  1500
gactgggatg gccgcgggag gctgctggtg aagctgtccc ccgtctatgc cgggaagacc  1560
tgcggcctgt gtgggaatta caatggcaac cagggcgacg acttccttac ccctctgggg  1620
ctggcrgagc cccgggtgga ggacttcggg aacgcctgga agctgcacgg ggactgccag  1680
gacctgcaga agcagcacag cgatccctgc gccctcaacc cgcgcatgac caggttctcc  1740
gaggaggcgt gcgcggtcct gacgtccccc acattcgagg cctgccatcg tgccgtcagc  1800
ccgctgccct acctgcggaa ctgccgctac gacgtgtgct cctgctcgga cggccgcgag  1860
tgcctgtgcg cgcgccctggc cagctatgcc gcggcctgcg cggggagagg cgtgcgcgtc  1920
gcgtggcgcg agccaggccg ctgtgagctg aactgcccga aaggccaggt gtacctgcag  1980
tgcgggaccc cctgcaacct gacctgccgc tctctctctt acccggatga ggaatgcaat  2040
gaggcctgcc tggagggctg cttctgcccc cagggctct acatgatga gggggggac  2100
tgcgtgccca ggcccagtg cccctgttac tatgacggtg agatcttcca gccagaagac  2160
atcttctcag accatcacac catgtgctac tgtgaggatg gcttcatgca ctgtaccatg  2220
agtggagtcc ccggaagctt gctgcctgac gctgtcctca gcagtcccct gtctcatcgc  2280
```

```
agcaaaagga gcctatcctg tcggccccca atggtcaagc tggtgtgtcc cgctgacaac    2340
ctgcgggctg aagggctcga gtgtaccaaa acgtgccaga actatgacct ggagtgcatg    2400
agcatgggct gtgtctctgg ctgcctctgc ccccgggca tggtccggca tgagaacaga     2460
tgtgtggccc tggaaaggtg tccctgcttc catcagggca aggagtatgc ccctggagaa    2520
acagtgaaga ttggctgcaa cacttgtgtc tgtcgggacc ggaagtggaa ctgcacagac    2580
catgtgtgtg atgccacgtg ctccacgatc ggcatggccc actacctcac cttcgacggg    2640
ctcaaatacc tgttccccgg ggagtgccag tacgttctgg tgcaggatta ctgcggcagt    2700
aaccctggga cctttcggat cctagtgggg aataagggat gcagccaccc ctcagtgaaa    2760
tgcaagaaac gggtcaccat cctggtggag ggaggagaga ttgagctgtt tgacggggag    2820
gtgaatgtga agaggcccat gaaggatgag actcactttg aggtggtgga gtctggccgg    2880
tacatcattc tgctgctggg caaagccctc tccgtggtct gggaccgcca cctgagcatc    2940
tccgtggtcc tgaagcagac ataccaggag aaagtgtgtg gcctgtgtgg aattttgat    3000
ggcatccaga acaatgacct caccagcagc aacctccaag tggaggaaga ccctgtggac    3060
tttgggaact cctggaaagt gagctcgcag tgtgctgaca ccagaaaagt gcctctggac    3120
tcatcccctg ccacctgcca taacaacatc atgaagcaga cgatggtgga ttcctcctgt    3180
agaatcctta ccagtgacgt cttccaggac tgcaacaagc tggtggaccc cgagccatat    3240
ctggatgtct gcatttacga cacctgctcc tgtgagtcca ttggggactg cgcctgcttc    3300
tgcgacacca ttgctgccta tgcccacgtg tgtgcccagc atggcaaggt ggtgacctgg    3360
aggacggcca cattgtgccc ccagagctgc gaggagagga tctccgggga gaacgggtat    3420
gagtgtgagt ggcgctataa cagctgtgca cctgcctgtc aagtcacgtg tcagcaccct    3480
gagccactgg cctgccctgt gcagtgtgtg gagggctgcc atgcccactg ccctccaggg    3540
aaaatcctgg atgagctttt gcagacctgc gttgaccctg aagactgtcc agtgtgtgag    3600
gtggctggcc ggcgttttgc ctcaggaaag aaagtcacct gaatcccag tgaccctgag    3660
cactgccaga tttgccactg tgatgttgtc aacctcacct gtgaagcctg ccaggagccg    3720
ggaggcctgg tggtgcctcc cacagatgcc ccggtgagcc ccaccactct gtatgtggag    3780
gacatctcgg aaccgccgtt gcacgatttc tactgcagca ggctactgga cctggtcttc    3840
ctgctggatg ctcctccag gctgtccgag gctgagtttg aagtgctgaa ggcctttgtg    3900
gtggacatga tggagcggct gcgcatctcc cagaagtggg tccgcgtggc cgtggtggag    3960
taccacgacg gctcccacgc ctacatcggg ctcaaggacc ggaagcgacc gtcagagctg    4020
cggcgcattg ccagccaggt gaagtatgcg ggcagccagg tggcctccac cagcgaggtc    4080
ttgaaataca cactgttcca aatcttcagc aagatcgacc gccctgaagc ctcccgcatc    4140
gccctgctcc tgatggccag ccaggagccc caacggatgt cccggaactt tgtccgctac    4200
gtccagggcc tgaagaagaa gaaggtcatt gtgatcccgg tgggcattgg gccccatgcc    4260
aacctcaagc agatccgcct catcgagaag caggcccctg agaacaaggc cttcgtgctg    4320
agcagtgtgg atgagctgga gcagcaaagg gacgagatcg ttagctacct ctgtgacctt    4380
gcccctgaag cccctcctcc tactctgccc ccgacatgg cacaagtcac tgtgggcccg    4440
gggctcttgg gggtttcgac cctggggccc aagaggaact ccatggttct ggatgtggcg    4500
ttcgtcctgg aaggatcgga caaaattggt gaagccgact tcaacaggag caaggagttc    4560
atggaggagg tgattcagcg gatggatgtg ggccaggaca gcatccacgt cacggtgctg    4620
cagtactcct acatggtgac cgtggagtac cccttcagcg aggcacagtc caaaggggac    4680
```

-continued

```
atcctgcagc gggtgcgaga gatccgctac cagggcggca acaggaccaa cactgggctg   4740
gccctgcggt acctctctga ccacagcttc ttggtcagcc agggtgaccg ggagcaggcg   4800
cccaacctgg tctacatggt caccggaaat cctgcctctg atgagatcaa gaggctgcct   4860
ggagacatcc aggtggtgcc cattggagtg ggccctaatg ccaacgtgca ggagctggag   4920
aggattggct ggcccaatgc ccctatcctc atccaggact ttgagacgct ccccgagag    4980 gctcctgacc tggtgctgca gaggtgctgc tccggagagg ggctgcagat ccccaccctc   5040
tcccctgcac ctgactgcag ccagcccctg acgtgatcc ttctcctgga tggctcctcc    5100
agtttcccag cttcttattt tgatgaaatg aagagtttcg ccaaggcttt catttcaaaa   5160
gccaatatag ggcctcgtct cactcaggtg tcagtgctgc agtatggaag catcaccacc   5220
attgacgtgc catggaacgt ggtcccggag aaagcccatt tgctgagcct tgtggacgtc   5280
atgcagcggg agggaggccc cagccaaatc ggggatgcct gggctttgc tgtgcgatac    5340 ttgacttcag aaatgcatgg tgccaggccg ggagcctcaa aggcggtggt catcctggtc   5400
acggacgtct ctgtggattc agtggatgca gcagctgatg ccgccaggtc aacagagtg    5460 acagtgttcc ctattggaat tggagatcgc tacgatgcag cccagctacg gatcttggca   5520
ggcccagcag gcgactccaa cgtggtgaag ctccagcgaa tcgaagacct ccctaccatg   5580
gtcaccttgg gcaattcctt cctccacaaa ctgtgctctg gatttgttag gatttgcatg   5640
gatgaggatg ggaatgagaa gaggcccggg gacgtctgga ccttgccaga ccagtgccac   5700
accgtgactt gccagccaga tggccagacc ttgctgaaga gtcatcgggt caactgtgac   5760 cggggggctga ggccttcgtg ccctaacagc cagtcccctg ttaaagtgga agagacctgt   5820
ggctgccgct ggacctgccc ctgygtgtgc acaggcagct ccactcggca catcgtgacc   5880
tttgatgggc agaatttcaa gctgactggc agctgttctt atgtcctatt tcaaaacaag   5940
gagcaggacc tggaggtgat tctccataat ggtgcctgca gccctggagc aaggcagggc   6000
tgcatgaaat ccatcgaggt gaagcacagt gccctctccg tcgagstgca cagtgacatg   6060
gaggtgacgg tgaatgggag actggtctct gttccttacg tgggtgggaa catggaagtc   6120
aacgtttatg gtgccatcat gcatgaggtc agattcaatc accttggtca catcttcaca   6180
ttcactccac aaaacaatga gttccaactg cagctcagcc ccaagacttt tgcttcaaag   6240
acgtatggtc tgtgtgggat ctgtgatgag aacggagcca atgacttcat gctgagggat   6300
ggcacagtca ccacagactg gaaaacactt gttcaggaat ggactgtgca gcggccaggg   6360
cagacgtgcc agcccatcct ggaggagcag tgtcttgtcc ccgacagctc ccactgccag   6420
gtcctcctct taccactgtt tgctgaatgc cacaaggtcc tggctccagc cacattctat   6480
gccatctgcc agcaggacag ttgccaccag gagcaagtgt gtgaggtgat cgcctcttat   6540
gcccacctct gtcggaccaa cggggtctgc gttgactgga ggacacctga tttctgtgct   6600
atgtcatgcc caccatctct ggtctacaac cactgtgagc atggctgtcc ccggcactgt   6660
gatggcaacg tgagctcctg tggggaccat ccctccgaag gctgtttctg ccctccagat   6720
aaagtcatgt tggaaggcag ctgtgtccct gaagaggcct gcactcagtg cattggtgag   6780
gatggagtcc agcaccagtt cctggaagcc tgggtcccgg accaccagcc tgtcagatc    6840 tgcacatgcc tcagcgggcg gaaggtcaac tgcacaacgc agccctgccc cacggccaaa   6900
gctcccacgt gtgccctgtg tgaagtagcc cgcctccgcc agaatgcaga ccagtgctgc   6960
cccgagtatg agtgtgtgtg tgacccagtg agctgtgacc tgcccccagt gcctcactgt   7020
```

-continued

| | |
|---|---|
| gaacgtggcc tccagcccac actgaccaac cctggcgagt gcagacccaa cttcacctgc | 7080 |
| gcctgcagga aggaggagtg caaaagagtg tccccaccct cctgcccccc gcaccgtttg | 7140 |
| cccacccttc ggaagaccca gtgctgtgat gagtatgagt gtgcctgcaa ctgtgtcaac | 7200 |
| tccacagtga gctgtcccct tgggtacttg gcctcaaccg ccaccaatga ctgtggctgt | 7260 |
| accacaacca cctgccttcc cgacaaggtg tgtgtccacc gaagcaccat ctaccctgtg | 7320 |
| ggccagttct gggaggaggg ctgcgatgtg tgcacctgca ccgacatgga ggatgccgtg | 7380 |
| atgggcctcc gcgtggccca gtgctcccag aagccctgtg aggacagctg tcggtcgggc | 7440 |
| ttcacttacg ttctgcatga aggcgagtgc tgtggaaggt gcctgccatc tgcctgtgag | 7500 |
| gtggtgactg gctaccgcg gggggactcc cagtcttcct ggaagagtgt cggctcccag | 7560 |
| tgggcctccc cggagaaccc ctgcctcatc aatgagtgtg tccgagtgaa ggaggaggtc | 7620 |
| tttatacaac aaaggaacgt ctcctgcccc cagctggagg tccctgtctg cccctcgggc | 7680 |
| tttcagctga gctgtaagac ctcagcgtgc tgcccaagct gtcgctgtga gcgcatggag | 7740 |
| gcctgcatgc tcaatggcac tgtcattggg cccgggaaga ctgtgatgat cgatgtgtgc | 7800 |
| acgacctgcc gctgcatggt gcaggtgggg gtcatctctg gattcaagct ggagtgcagg | 7860 |
| aagaccacct gcaaccctg ccccctgggt tacaaggaag aaaataacac aggtgaatgt | 7920 |
| tgtgggagat gtttgcctac ggcttgcacc attcagctaa gaggaggaca gatcatgaca | 7980 |
| ctgaagcgtg atgagacgct ccaggatggc tgtgatactc acttctgcaa ggtcaatgag | 8040 |
| agaggagagt acttctggga gaagagggtc acaggctgcc cacccttga tgaacacaag | 8100 |
| tgtcttgctg agggaggtaa aattatgaaa attccaggca cctgctgtga cacatgtgag | 8160 |
| gagcctgagt gcaacgacat cactgccagg ctgcagtatg tcaaggtggg aagctgtaag | 8220 |
| tctgaagtag aggtggatat ccactactgc cagggcaaat gtgccagcaa agccatgtac | 8280 |
| tccattgaca tcaacgatgt gcaggaccag tgctcctgct gctctccgac acggacggag | 8340 |
| cccatgcagg tggcccctgca ctgcaccaat ggctctgttg tgtaccatga ggttctcaat | 8400 |
| gccatggagt gcaaatgctc ccccaggaag tgcagcaagt ga | 8442 |

<210> SEQ ID NO 129
<211> LENGTH: 2809
<212> TYPE: PRT
<213> ORGANISM: Artificial Sequence
<220> FEATURE:
<223> OTHER INFORMATION: human VWF
<220> FEATURE:
<221> NAME/KEY: misc_feature
<222> LOCATION: (540)..(540)
<223> OTHER INFORMATION: Xaa can be any naturally occurring amino acid
<220> FEATURE:
<221> NAME/KEY: misc_feature
<222> LOCATION: (1944)..(1944)
<223> OTHER INFORMATION: Xaa can be any naturally occurring amino acid
<220> FEATURE:
<221> NAME/KEY: misc_feature
<222> LOCATION: (2012)..(2012)
<223> OTHER INFORMATION: Xaa can be any naturally occurring amino acid

<400> SEQUENCE: 129

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

```
Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
                100                 105                 110

Tyr Ala Ser Lys Gly Leu Tyr Leu Glu Thr Glu Ala Gly Tyr Tyr Lys
                115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
                180                 185                 190

Leu Ser Ser Gly Glu Gln Trp Cys Glu Arg Ala Ser Pro Pro Ser Ser
    195                 200                 205

Ser Cys Asn Ile Ser Ser Gly Glu Met Gln Lys Gly Leu Trp Glu Gln
210                 215                 220

Cys Gln Leu Leu Lys Ser Thr Ser Val Phe Ala Arg Cys His Pro Leu
225                 230                 235                 240

Val Asp Pro Glu Pro Phe Val Cys Glu Lys Thr Leu Cys Glu Cys Ala
                245                 250                 255

Gly Gly Leu Glu Cys Ala Cys Pro Ala Leu Leu Glu Tyr Ala Arg Thr
                260                 265                 270

Cys Ala Gln Glu Gly Met Val Leu Tyr Gly Trp Thr Asp His Ser Ala
    275                 280                 285

Cys Ser Pro Val Cys Pro Ala Gly Met Glu Tyr Arg Gln Cys Val Ser
    290                 295                 300

Pro Cys Ala Arg Thr Cys Gln Ser Leu His Ile Asn Glu Met Cys Gln
305                 310                 315                 320

Glu Arg Cys Val Asp Gly Cys Ser Cys Pro Glu Gly Gln Leu Leu Asp
                325                 330                 335

Glu Gly Leu Cys Val Glu Ser Thr Glu Cys Pro Cys Val His Ser Gly
                340                 345                 350

Lys Arg Tyr Pro Pro Gly Thr Ser Leu Ser Arg Asp Cys Asn Thr Cys
                355                 360                 365

Ile Cys Arg Asn Ser Gln Trp Ile Cys Ser Asn Glu Glu Cys Pro Gly
    370                 375                 380

Glu Cys Leu Val Thr Gly Gln Ser His Phe Lys Ser Phe Asp Asn Arg
385                 390                 395                 400

Tyr Phe Thr Phe Ser Gly Ile Cys Gln Tyr Leu Leu Ala Arg Asp Cys
                405                 410                 415

Gln Asp His Ser Phe Ser Ile Val Ile Glu Thr Val Gln Cys Ala Asp
                420                 425                 430

Asp Arg Asp Ala Val Cys Thr Arg Ser Val Thr Val Arg Leu Pro Gly
                435                 440                 445

Leu His Asn Ser Leu Val Lys Leu Lys His Gly Ala Gly Val Ala Met
    450                 455                 460

Asp Gly Gln Asp Ile Gln Leu Pro Leu Leu Lys Gly Asp Leu Arg Ile
```

```
            465                 470                 475                 480
        Gln His Thr Val Thr Ala Ser Val Arg Leu Ser Tyr Gly Glu Asp Leu
                            485                 490                 495
        Gln Met Asp Trp Asp Gly Arg Gly Arg Leu Leu Val Lys Leu Ser Pro
                            500                 505                 510
        Val Tyr Ala Gly Lys Thr Cys Gly Leu Cys Gly Asn Tyr Asn Gly Asn
                            515                 520                 525
        Gln Gly Asp Asp Phe Leu Thr Pro Ser Gly Leu Xaa Glu Pro Arg Val
                            530                 535                 540
        Glu Asp Phe Gly Asn Ala Trp Lys Leu His Gly Asp Cys Gln Asp Leu
        545                 550                 555                 560
        Gln Lys Gln His Ser Asp Pro Cys Ala Leu Asn Pro Arg Met Thr Arg
                            565                 570                 575
        Phe Ser Glu Glu Ala Cys Ala Val Leu Thr Ser Pro Thr Phe Glu Ala
                            580                 585                 590
        Cys His Arg Ala Val Ser Pro Leu Pro Tyr Leu Arg Asn Cys Arg Tyr
                            595                 600                 605
        Asp Val Cys Ser Cys Ser Asp Gly Arg Glu Cys Leu Cys Gly Ala Ser
                            610                 615                 620
        Tyr Ala Ala Ala Cys Ala Gly Arg Gly Val Arg Val Ala Trp Arg Glu
        625                 630                 635                 640
        Pro Gly Arg Cys Glu Leu Asn Cys Pro Lys Gly Gln Val Tyr Leu Gln
                            645                 650                 655
        Cys Gly Thr Pro Cys Asn Leu Thr Cys Arg Ser Leu Ser Tyr Pro Asp
                            660                 665                 670
        Glu Glu Cys Asn Glu Ala Cys Leu Glu Gly Cys Phe Cys Pro Pro Gly
                            675                 680                 685
        Leu Tyr Met Asp Glu Arg Gly Asp Cys Val Pro Lys Ala Gln Cys Pro
                            690                 695                 700
        Cys Tyr Tyr Asp Gly Glu Ile Phe Gln Pro Glu Asp Ile Phe Ser Asp
        705                 710                 715                 720
        His His Thr Met Cys Tyr Cys Glu Asp Gly Phe Met His Cys Thr Met
                            725                 730                 735
        Ser Gly Val Pro Gly Ser Leu Leu Pro Asp Ala Val Leu Ser Ser Pro
                            740                 745                 750
        Leu Ser His Arg Ser Lys Arg Ser Leu Ser Cys Arg Pro Pro Met Val
                            755                 760                 765
        Lys Leu Val Cys Pro Ala Asp Asn Leu Arg Ala Glu Gly Leu Glu Cys
                            770                 775                 780
        Thr Lys Thr Cys Gln Asn Tyr Asp Leu Glu Cys Met Ser Met Gly Cys
        785                 790                 795                 800
        Val Ser Gly Cys Leu Cys Pro Pro Gly Met Val Arg His Glu Asn Arg
                            805                 810                 815
        Cys Val Ala Leu Glu Arg Cys Pro Cys Phe His Gln Gly Lys Glu Tyr
                            820                 825                 830
        Ala Pro Gly Glu Thr Val Lys Ile Gly Cys Asn Thr Cys Val Cys Arg
                            835                 840                 845
        Asp Arg Lys Trp Asn Cys Thr Asp His Val Cys Asp Ala Thr Cys Ser
                            850                 855                 860
        Thr Ile Gly Met Ala His Tyr Leu Thr Phe Asp Gly Leu Lys Tyr Leu
        865                 870                 875                 880
        Phe Pro Gly Glu Cys Gln Tyr Val Leu Val Gln Asp Tyr Cys Gly Ser
                            885                 890                 895
```

```
Asn Pro Gly Thr Phe Arg Ile Leu Val Gly Asn Lys Gly Cys Ser His
            900                 905                 910

Pro Ser Val Lys Cys Lys Lys Arg Val Thr Ile Leu Val Glu Gly Gly
        915                 920                 925

Glu Ile Glu Leu Phe Asp Gly Glu Val Asn Val Lys Arg Pro Met Lys
    930                 935                 940

Asp Glu Thr His Phe Glu Val Val Ser Gly Arg Tyr Ile Ile Leu
945                 950                 955                 960

Leu Leu Gly Lys Ala Leu Ser Val Val Trp Asp Arg His Leu Ser Ile
                965                 970                 975

Ser Val Val Leu Lys Gln Thr Tyr Gln Glu Lys Val Cys Gly Leu Cys
            980                 985                 990

Gly Asn Phe Asp Gly Ile Gln Asn Asn Asp Leu Thr Ser Ser Asn Leu
        995                 1000                1005

Gln Val Glu Glu Asp Pro Val Asp Phe Gly Asn Ser Trp Lys Val
    1010                1015                1020

Ser Ser Gln Cys Ala Asp Thr Arg Lys Val Pro Leu Asp Ser Ser
    1025                1030                1035

Pro Ala Thr Cys His Asn Asn Ile Met Lys Gln Thr Met Val Asp
    1040                1045                1050

Ser Ser Cys Arg Ile Leu Thr Ser Asp Val Phe Gln Asp Cys Asn
    1055                1060                1065

Lys Leu Val Asp Pro Glu Pro Tyr Leu Asp Val Cys Ile Tyr Asp
    1070                1075                1080

Thr Cys Ser Cys Glu Ser Ile Gly Asp Cys Ala Cys Phe Cys Asp
    1085                1090                1095

Thr Ile Ala Ala Tyr Ala His Val Cys Ala Gln His Gly Lys Val
    1100                1105                1110

Val Thr Trp Arg Thr Ala Thr Leu Cys Pro Gln Ser Cys Glu Glu
    1115                1120                1125

Arg Asn Leu Arg Glu Asn Gly Tyr Glu Cys Glu Trp Arg Tyr Asn
    1130                1135                1140

Ser Cys Ala Pro Ala Cys Gln Val Thr Cys Gln His Pro Glu Pro
    1145                1150                1155

Leu Ala Cys Pro Val Gln Cys Val Glu Gly Cys His Ala His Cys
    1160                1165                1170

Pro Pro Gly Lys Ile Leu Asp Glu Leu Leu Gln Thr Cys Val Asp
    1175                1180                1185

Pro Glu Asp Cys Pro Val Cys Glu Val Ala Gly Arg Arg Phe Ala
    1190                1195                1200

Ser Gly Lys Lys Val Thr Leu Asn Pro Ser Asp Pro Glu His Cys
    1205                1210                1215

Gln Ile Cys His Cys Asp Val Val Asn Leu Thr Cys Glu Ala Cys
    1220                1225                1230

Gln Glu Pro Gly Gly Leu Val Val Pro Pro Thr Asp Ala Pro Val
    1235                1240                1245

Ser Pro Thr Thr Leu Tyr Val Glu Asp Ile Ser Glu Pro Pro Leu
    1250                1255                1260

His Asp Phe Tyr Cys Ser Arg Leu Leu Asp Leu Val Phe Leu Leu
    1265                1270                1275

Asp Gly Ser Ser Arg Leu Ser Glu Ala Glu Phe Glu Val Leu Lys
    1280                1285                1290
```

-continued

Ala Phe Val Val Asp Met Met Glu Arg Leu Arg Ile Ser Gln Lys
1295                1300                1305

Trp Val Arg Val Ala Val Val Glu Tyr His Asp Gly Ser His Ala
1310                1315                1320

Tyr Ile Gly Leu Lys Asp Arg Lys Arg Pro Ser Glu Leu Arg Arg
1325                1330                1335

Ile Ala Ser Gln Val Lys Tyr Ala Gly Ser Gln Val Ala Ser Thr
1340                1345                1350

Ser Glu Val Leu Lys Tyr Thr Leu Phe Gln Ile Phe Ser Lys Ile
1355                1360                1365

Asp Arg Pro Glu Ala Ser Arg Ile Ala Leu Leu Leu Met Ala Ser
1370                1375                1380

Gln Glu Pro Gln Arg Met Ser Arg Asn Phe Val Arg Tyr Val Gln
1385                1390                1395

Gly Leu Lys Lys Lys Lys Val Ile Val Ile Pro Val Gly Ile Gly
1400                1405                1410

Pro His Ala Asn Leu Lys Gln Ile Arg Leu Ile Glu Lys Gln Ala
1415                1420                1425

Pro Glu Asn Lys Ala Phe Val Leu Ser Ser Val Asp Glu Leu Glu
1430                1435                1440

Gln Gln Arg Asp Glu Ile Val Ser Tyr Leu Cys Asp Leu Ala Pro
1445                1450                1455

Glu Ala Pro Pro Pro Thr Leu Pro Pro Asp Met Ala Gln Val Thr
1460                1465                1470

Val Gly Pro Gly Leu Leu Gly Val Ser Thr Leu Gly Pro Lys Arg
1475                1480                1485

Asn Ser Met Val Leu Asp Val Ala Phe Val Leu Glu Gly Ser Asp
1490                1495                1500

Lys Ile Gly Glu Ala Asp Phe Asn Arg Ser Lys Glu Phe Met Glu
1505                1510                1515

Glu Val Ile Gln Arg Met Asp Val Gly Gln Asp Ser Ile His Val
1520                1525                1530

Thr Val Leu Gln Tyr Ser Tyr Met Val Thr Val Glu Tyr Pro Phe
1535                1540                1545

Ser Glu Ala Gln Ser Lys Gly Asp Ile Leu Gln Arg Val Arg Glu
1550                1555                1560

Ile Arg Tyr Gln Gly Gly Asn Arg Thr Asn Thr Gly Leu Ala Leu
1565                1570                1575

Arg Tyr Leu Ser Asp His Ser Phe Leu Val Ser Gln Gly Asp Arg
1580                1585                1590

Glu Gln Ala Pro Asn Leu Val Tyr Met Val Thr Gly Asn Pro Ala
1595                1600                1605

Ser Asp Glu Ile Lys Arg Leu Pro Gly Asp Ile Gln Val Val Pro
1610                1615                1620

Ile Gly Val Gly Pro Asn Ala Asn Val Gln Glu Leu Glu Arg Ile
1625                1630                1635

Gly Trp Pro Asn Ala Pro Ile Leu Ile Gln Asp Phe Glu Thr Leu
1640                1645                1650

Pro Arg Glu Ala Pro Asp Leu Val Leu Gln Arg Cys Cys Ser Gly
1655                1660                1665

Glu Gly Leu Gln Ile Pro Thr Leu Ser Pro Ala Pro Asp Cys Ser
1670                1675                1680

Gln Pro Leu Asp Val Ile Leu Leu Leu Asp Gly Ser Ser Ser Phe

-continued

```
            1685                1690                1695
Pro Ala Ser Tyr Phe Asp Glu Met Lys Ser Phe Ala Lys Ala Phe
            1700                1705                1710
Ile Ser Lys Ala Asn Ile Gly Pro Arg Leu Thr Gln Val Ser Val
            1715                1720                1725
Leu Gln Tyr Gly Ser Ile Thr Thr Ile Asp Val Pro Trp Asn Val
            1730                1735                1740
Val Pro Glu Lys Ala His Leu Leu Ser Leu Val Asp Val Met Gln
            1745                1750                1755
Arg Glu Gly Gly Pro Ser Gln Ile Gly Asp Ala Leu Gly Phe Ala
            1760                1765                1770
Val Arg Tyr Leu Thr Ser Glu Met His Gly Ala Arg Pro Gly Ala
            1775                1780                1785
Ser Lys Ala Val Val Ile Leu Val Thr Asp Val Ser Val Asp Ser
            1790                1795                1800
Val Asp Ala Ala Ala Asp Ala Ala Arg Ser Asn Arg Val Thr Val
            1805                1810                1815
Phe Pro Ile Gly Ile Gly Asp Arg Tyr Asp Ala Ala Gln Leu Arg
            1820                1825                1830
Ile Leu Ala Gly Pro Ala Gly Asp Ser Asn Val Val Lys Leu Gln
            1835                1840                1845
Arg Ile Glu Asp Leu Pro Thr Met Val Thr Leu Gly Asn Ser Phe
            1850                1855                1860
Leu His Lys Leu Cys Ser Gly Phe Val Arg Ile Cys Met Asp Glu
            1865                1870                1875
Asp Gly Asn Glu Lys Arg Pro Gly Asp Val Trp Thr Leu Pro Asp
            1880                1885                1890
Gln Cys His Thr Val Thr Cys Gln Pro Asp Gly Gln Thr Leu Leu
            1895                1900                1905
Lys Ser His Arg Val Asn Cys Asp Arg Gly Leu Arg Pro Ser Cys
            1910                1915                1920
Pro Asn Ser Gln Ser Pro Val Lys Val Glu Glu Thr Cys Gly Cys
            1925                1930                1935
Arg Trp Thr Cys Pro Xaa Val Cys Thr Gly Ser Ser Thr Arg His
            1940                1945                1950
Ile Val Thr Phe Asp Gly Gln Asn Phe Lys Leu Thr Gly Ser Cys
            1955                1960                1965
Ser Tyr Val Leu Phe Gln Asn Lys Glu Gln Asp Leu Glu Val Ile
            1970                1975                1980
Leu His Asn Gly Ala Cys Ser Pro Gly Ala Arg Gln Gly Cys Met
            1985                1990                1995
Lys Ser Ile Glu Val Lys His Ser Ala Leu Ser Val Glu Xaa His
            2000                2005                2010
Ser Asp Met Glu Val Thr Val Asn Gly Arg Leu Val Ser Val Pro
            2015                2020                2025
Tyr Val Gly Gly Asn Met Glu Val Asn Val Tyr Gly Ala Ile Met
            2030                2035                2040
His Glu Val Arg Phe Asn His Leu Gly His Ile Phe Thr Phe Thr
            2045                2050                2055
Pro Gln Asn Asn Glu Phe Gln Leu Gln Leu Ser Pro Lys Thr Phe
            2060                2065                2070
Ala Ser Lys Thr Tyr Gly Leu Cys Gly Ile Cys Asp Glu Asn Gly
            2075                2080                2085
```

-continued

```
Ala Asn Asp Phe Met Leu Arg Asp Gly Thr Val Thr Thr Asp Trp
    2090                2095                2100

Lys Thr Leu Val Gln Glu Trp Thr Val Gln Arg Pro Gly Gln Thr
    2105                2110                2115

Cys Gln Pro Ile Leu Glu Glu Gln Cys Leu Val Pro Asp Ser Ser
    2120                2125                2130

His Cys Gln Val Leu Leu Leu Pro Leu Phe Ala Glu Cys His Lys
    2135                2140                2145

Val Leu Ala Pro Ala Thr Phe Tyr Ala Ile Cys Gln Gln Asp Ser
    2150                2155                2160

Cys His Gln Glu Gln Val Cys Glu Val Ile Ala Ser Tyr Ala His
    2165                2170                2175

Leu Cys Arg Thr Asn Gly Val Cys Val Asp Trp Arg Thr Pro Asp
    2180                2185                2190

Phe Cys Ala Met Ser Cys Pro Pro Ser Leu Val Tyr Asn His Cys
    2195                2200                2205

Glu His Gly Cys Pro Arg His Cys Asp Gly Asn Val Ser Ser Cys
    2210                2215                2220

Gly Asp His Pro Ser Glu Gly Cys Phe Cys Pro Pro Asp Lys Val
    2225                2230                2235

Met Leu Glu Gly Ser Cys Val Pro Glu Glu Ala Cys Thr Gln Cys
    2240                2245                2250

Ile Gly Glu Asp Gly Val Gln His Gln Phe Leu Glu Ala Trp Val
    2255                2260                2265

Pro Asp His Gln Pro Cys Gln Ile Cys Thr Cys Leu Ser Gly Arg
    2270                2275                2280

Lys Val Asn Cys Thr Thr Gln Pro Cys Pro Thr Ala Lys Ala Pro
    2285                2290                2295

Thr Cys Gly Leu Cys Glu Val Ala Arg Leu Arg Gln Asn Ala Asp
    2300                2305                2310

Gln Cys Cys Pro Glu Tyr Glu Cys Val Cys Asp Pro Val Ser Cys
    2315                2320                2325

Asp Leu Pro Pro Val Pro His Cys Glu Arg Gly Leu Gln Pro Thr
    2330                2335                2340

Leu Thr Asn Pro Gly Glu Cys Arg Pro Asn Phe Thr Cys Ala Cys
    2345                2350                2355

Arg Lys Glu Glu Cys Lys Arg Val Ser Pro Pro Ser Cys Pro Pro
    2360                2365                2370

His Arg Leu Pro Thr Leu Arg Lys Thr Gln Cys Cys Asp Glu Tyr
    2375                2380                2385

Glu Cys Ala Cys Asn Cys Val Asn Ser Thr Val Ser Cys Pro Leu
    2390                2395                2400

Gly Tyr Leu Ala Ser Thr Ala Thr Asn Asp Cys Gly Cys Thr Thr
    2405                2410                2415

Thr Thr Cys Leu Pro Asp Lys Val Cys Val His Arg Ser Thr Ile
    2420                2425                2430

Tyr Pro Val Gly Gln Phe Trp Glu Glu Gly Cys Asp Val Cys Thr
    2435                2440                2445

Cys Thr Asp Met Glu Asp Ala Val Met Gly Leu Arg Val Ala Gln
    2450                2455                2460

Cys Ser Gln Lys Pro Cys Glu Asp Ser Cys Arg Ser Gly Phe Thr
    2465                2470                2475
```

Tyr Val Leu His Glu Gly Glu Cys Cys Gly Arg Cys Leu Pro Ser
    2480                2485                2490

Ala Cys Glu Val Val Thr Gly Ser Pro Arg Gly Asp Ser Gln Ser
    2495                2500                2505

Ser Trp Lys Ser Val Gly Ser Gln Trp Ala Ser Pro Glu Asn Pro
    2510                2515                2520

Cys Leu Ile Asn Glu Cys Val Arg Val Lys Glu Glu Val Phe Ile
    2525                2530                2535

Gln Gln Arg Asn Val Ser Cys Pro Gln Leu Glu Val Pro Val Cys
    2540                2545                2550

Pro Ser Gly Phe Gln Leu Ser Cys Lys Thr Ser Ala Cys Cys Pro
    2555                2560                2565

Ser Cys Arg Cys Glu Arg Met Glu Ala Cys Met Leu Asn Gly Thr
    2570                2575                2580

Val Ile Gly Pro Gly Lys Thr Val Met Ile Asp Val Cys Thr Thr
    2585                2590                2595

Cys Arg Cys Met Val Gln Val Gly Val Ile Ser Gly Phe Lys Leu
    2600                2605                2610

Glu Cys Arg Lys Thr Thr Cys Asn Pro Cys Pro Leu Gly Tyr Lys
    2615                2620                2625

Glu Glu Asn Asn Thr Gly Glu Cys Cys Gly Arg Cys Leu Pro Thr
    2630                2635                2640

Ala Cys Thr Ile Gln Leu Arg Gly Gly Gln Ile Met Thr Leu Lys
    2645                2650                2655

Arg Asp Glu Thr Leu Gln Asp Gly Cys Asp Thr His Phe Cys Lys
    2660                2665                2670

Val Asn Glu Arg Gly Glu Tyr Phe Trp Glu Lys Arg Val Thr Gly
    2675                2680                2685

Cys Pro Pro Phe Asp Glu His Lys Cys Leu Ala Glu Gly Gly Lys
    2690                2695                2700

Ile Met Lys Ile Pro Gly Thr Cys Cys Asp Thr Cys Glu Glu Pro
    2705                2710                2715

Glu Cys Asn Asp Ile Thr Ala Arg Leu Gln Tyr Val Lys Val Gly
    2720                2725                2730

Ser Cys Lys Ser Glu Val Glu Val Asp Ile His Tyr Cys Gln Gly
    2735                2740                2745

Lys Cys Ala Ser Lys Ala Met Tyr Ser Ile Asp Ile Asn Asp Val
    2750                2755                2760

Gln Asp Gln Cys Ser Cys Cys Ser Pro Thr Arg Thr Glu Pro Met
    2765                2770                2775

Gln Val Ala Leu His Cys Thr Asn Gly Ser Val Val Tyr His Glu
    2780                2785                2790

Val Leu Asn Ala Met Glu Cys Lys Cys Ser Pro Arg Lys Cys Ser
    2795                2800                2805

Lys

<210> SEQ ID NO 130
<211> LENGTH: 36
<212> TYPE: PRT
<213> ORGANISM: Artificial Sequence
<220> FEATURE:
<223> OTHER INFORMATION: AE36

<400> SEQUENCE: 130

Gly Ser Pro Ala Gly Ser Pro Thr Ser Thr Glu Glu Gly Thr Ser Glu

-continued

```
                1               5                  10                  15
Ser Ala Thr Pro Glu Ser Gly Pro Gly Ser Glu Pro Ala Thr Ser Gly
                20                  25                  30

Ser Glu Thr Pro
        35

<210> SEQ ID NO 131
<211> LENGTH: 42
<212> TYPE: PRT
<213> ORGANISM: Artificial Sequence
<220> FEATURE:
<223> OTHER INFORMATION: AE42

<400> SEQUENCE: 131

Gly Ala Pro Gly Ser Pro Ala Gly Ser Pro Thr Ser Thr Glu Glu Gly
1               5                   10                  15

Thr Ser Glu Ser Ala Thr Pro Glu Ser Gly Pro Gly Ser Glu Pro Ala
                20                  25                  30

Thr Ser Gly Ser Glu Thr Pro Ala Ser Ser
            35                  40

<210> SEQ ID NO 132
<211> LENGTH: 78
<212> TYPE: PRT
<213> ORGANISM: Artificial Sequence
<220> FEATURE:
<223> OTHER INFORMATION: AE72

<400> SEQUENCE: 132

Gly Ala Pro Thr Ser Glu Ser Ala Thr Pro Glu Ser Gly Pro Gly Ser
1               5                   10                  15

Glu Pro Ala Thr Ser Gly Ser Glu Thr Pro Gly Thr Ser Glu Ser Ala
                20                  25                  30

Thr Pro Glu Ser Gly Pro Gly Ser Glu Pro Ala Thr Ser Gly Ser Glu
            35                  40                  45

Thr Pro Gly Thr Ser Glu Ser Ala Thr Pro Glu Ser Gly Pro Gly Thr
        50                  55                  60

Ser Thr Glu Pro Ser Glu Gly Ser Ala Pro Gly Ala Ser Ser
65                  70                  75

<210> SEQ ID NO 133
<211> LENGTH: 78
<212> TYPE: PRT
<213> ORGANISM: Artificial Sequence
<220> FEATURE:
<223> OTHER INFORMATION: AE78

<400> SEQUENCE: 133

Gly Ala Pro Thr Ser Glu Ser Ala Thr Pro Glu Ser Gly Pro Gly Ser
1               5                   10                  15

Glu Pro Ala Thr Ser Gly Ser Glu Thr Pro Gly Thr Ser Glu Ser Ala
                20                  25                  30

Thr Pro Glu Ser Gly Pro Gly Ser Glu Pro Ala Thr Ser Gly Ser Glu
            35                  40                  45

Thr Pro Gly Thr Ser Glu Ser Ala Thr Pro Glu Ser Gly Pro Gly Thr
        50                  55                  60

Ser Thr Glu Pro Ser Glu Gly Ser Ala Pro Gly Ala Ser Ser
65                  70                  75

<210> SEQ ID NO 134
```

-continued

```
<211> LENGTH: 143
<212> TYPE: PRT
<213> ORGANISM: Artificial Sequence
<220> FEATURE:
<223> OTHER INFORMATION: AE144

<400> SEQUENCE: 134

Gly Ser Glu Pro Ala Thr Ser Gly Ser Glu Thr Pro Gly Thr Ser Glu
1               5                   10                  15

Ser Ala Thr Pro Glu Ser Gly Pro Gly Ser Glu Pro Ala Thr Ser Gly
            20                  25                  30

Ser Glu Thr Pro Gly Ser Pro Ala Gly Ser Pro Thr Ser Thr Glu Glu
        35                  40                  45

Gly Thr Ser Thr Glu Pro Ser Glu Gly Ser Ala Pro Gly Ser Glu Pro
    50                  55                  60

Ala Thr Ser Gly Ser Glu Thr Pro Gly Ser Glu Pro Ala Thr Ser Gly
65                  70                  75                  80

Ser Glu Thr Pro Gly Ser Glu Pro Ala Thr Ser Gly Ser Glu Thr Pro
                85                  90                  95

Gly Thr Ser Thr Glu Pro Ser Glu Gly Ser Ala Pro Gly Thr Ser Glu
            100                 105                 110

Ser Ala Pro Glu Ser Gly Pro Gly Ser Glu Pro Ala Thr Ser Gly Ser
        115                 120                 125

Glu Thr Pro Gly Thr Ser Thr Glu Pro Ser Glu Gly Ser Ala Pro
    130                 135                 140

<210> SEQ ID NO 135
<211> LENGTH: 144
<212> TYPE: PRT
<213> ORGANISM: Artificial Sequence
<220> FEATURE:
<223> OTHER INFORMATION: AE144_6B

<400> SEQUENCE: 135

Thr Ser Thr Glu Pro Ser Glu Gly Ser Ala Pro Gly Thr Ser Glu Ser
1               5                   10                  15

Ala Thr Pro Glu Ser Gly Pro Gly Thr Ser Glu Ser Ala Thr Pro Glu
            20                  25                  30

Ser Gly Pro Gly Thr Ser Glu Ser Ala Thr Pro Glu Ser Gly Pro Gly
        35                  40                  45

Ser Glu Pro Ala Thr Ser Gly Ser Glu Thr Pro Gly Ser Glu Pro Ala
    50                  55                  60

Thr Ser Gly Ser Glu Thr Pro Gly Ser Pro Ala Gly Ser Pro Thr Ser
65                  70                  75                  80

Thr Glu Glu Gly Thr Ser Thr Glu Pro Ser Glu Gly Ser Ala Pro Gly
                85                  90                  95

Thr Ser Thr Glu Pro Ser Glu Gly Ser Ala Pro Gly Ser Glu Pro Ala
            100                 105                 110

Thr Ser Gly Ser Glu Thr Pro Gly Thr Ser Glu Ser Ala Thr Pro Glu
        115                 120                 125

Ser Gly Pro Gly Thr Ser Thr Glu Pro Ser Glu Gly Ser Ala Pro Gly
    130                 135                 140

<210> SEQ ID NO 136
<211> LENGTH: 144
<212> TYPE: PRT
<213> ORGANISM: Artificial Sequence
<220> FEATURE:
<223> OTHER INFORMATION: AG144
```

<400> SEQUENCE: 136

Gly Thr Pro Gly Ser Gly Thr Ala Ser Ser Pro Gly Ser Ser Thr
1               5                   10                  15

Pro Ser Gly Ala Thr Gly Ser Pro Gly Ser Pro Ser Ala Ser Thr
            20                  25                  30

Gly Thr Gly Pro Gly Ser Ser Pro Ser Ala Ser Thr Gly Thr Gly Pro
        35                  40                  45

Gly Ala Ser Pro Gly Thr Ser Thr Gly Ser Pro Gly Ala Ser Pro
    50                  55                  60

Gly Thr Ser Ser Thr Gly Ser Pro Gly Ser Ser Thr Pro Ser Gly Ala
65                  70                  75                  80

Thr Gly Ser Pro Gly Ser Ser Pro Ser Ala Ser Thr Gly Thr Gly Pro
                85                  90                  95

Gly Ala Ser Pro Gly Thr Ser Ser Thr Gly Ser Pro Gly Ser Ser Pro
                100                 105                 110

Ser Ala Ser Thr Gly Thr Gly Pro Gly Thr Pro Gly Ser Gly Thr Ala
            115                 120                 125

Ser Ser Ser Pro Gly Ser Ser Thr Pro Ser Gly Ala Thr Gly Ser Pro
        130                 135                 140

<210> SEQ ID NO 137
<211> LENGTH: 144
<212> TYPE: PRT
<213> ORGANISM: Artificial Sequence
<220> FEATURE:
<223> OTHER INFORMATION: AG144_A

<400> SEQUENCE: 137

Gly Ala Ser Pro Gly Thr Ser Ser Thr Gly Ser Pro Gly Ser Ser Pro
1               5                   10                  15

Ser Ala Ser Thr Gly Thr Gly Pro Gly Ser Ser Pro Ser Ala Ser Thr
            20                  25                  30

Gly Thr Gly Pro Gly Thr Pro Gly Ser Gly Thr Ala Ser Ser Ser Pro
        35                  40                  45

Gly Ser Ser Thr Pro Ser Gly Ala Thr Gly Ser Pro Gly Ser Ser Pro
    50                  55                  60

Ser Ala Ser Thr Gly Thr Gly Pro Gly Ala Ser Pro Gly Thr Ser Ser
65                  70                  75                  80

Thr Gly Ser Pro Gly Thr Pro Gly Ser Gly Thr Ala Ser Ser Ser Pro
                85                  90                  95

Gly Ser Ser Thr Pro Ser Gly Ala Thr Gly Ser Pro Gly Thr Pro Gly
                100                 105                 110

Ser Gly Thr Ala Ser Ser Ser Pro Gly Ala Ser Pro Gly Thr Ser Ser
            115                 120                 125

Thr Gly Ser Pro Gly Ala Ser Pro Gly Thr Ser Ser Thr Gly Ser Pro
        130                 135                 140

<210> SEQ ID NO 138
<211> LENGTH: 288
<212> TYPE: PRT
<213> ORGANISM: Artificial Sequence
<220> FEATURE:
<223> OTHER INFORMATION: AE288

<400> SEQUENCE: 138

Gly Thr Ser Glu Ser Ala Thr Pro Glu Ser Gly Pro Gly Ser Glu Pro
1               5                   10                  15

-continued

Ala Thr Ser Gly Ser Glu Thr Pro Gly Thr Ser Glu Ser Ala Thr Pro
            20                  25                  30

Glu Ser Gly Pro Gly Ser Glu Pro Ala Thr Ser Gly Ser Glu Thr Pro
        35                  40                  45

Gly Thr Ser Glu Ser Ala Thr Pro Glu Ser Gly Pro Gly Thr Ser Thr
    50                  55                  60

Glu Pro Ser Glu Gly Ser Ala Pro Gly Ser Pro Ala Gly Ser Pro Thr
65                  70                  75                  80

Ser Thr Glu Glu Gly Thr Ser Glu Ser Ala Thr Pro Glu Ser Gly Pro
                85                  90                  95

Gly Ser Glu Pro Ala Thr Ser Gly Ser Glu Thr Pro Gly Thr Ser Glu
            100                 105                 110

Ser Ala Thr Pro Glu Ser Gly Pro Gly Ser Pro Ala Gly Ser Pro Thr
        115                 120                 125

Ser Thr Glu Glu Gly Ser Pro Ala Gly Ser Pro Thr Ser Thr Glu Glu
    130                 135                 140

Gly Thr Ser Thr Glu Pro Ser Glu Gly Ser Ala Pro Gly Thr Ser Glu
145                 150                 155                 160

Ser Ala Thr Pro Glu Ser Gly Pro Gly Thr Ser Glu Ser Ala Thr Pro
                165                 170                 175

Glu Ser Gly Pro Gly Thr Ser Glu Ser Ala Thr Pro Glu Ser Gly Pro
            180                 185                 190

Gly Ser Glu Pro Ala Thr Ser Gly Ser Glu Thr Pro Gly Ser Glu Pro
        195                 200                 205

Ala Thr Ser Gly Ser Glu Thr Pro Gly Ser Pro Ala Gly Ser Pro Thr
    210                 215                 220

Ser Thr Glu Glu Gly Thr Ser Thr Glu Pro Ser Glu Gly Ser Ala Pro
225                 230                 235                 240

Gly Thr Ser Thr Glu Pro Ser Glu Gly Ser Ala Pro Gly Ser Glu Pro
                245                 250                 255

Ala Thr Ser Gly Ser Glu Thr Pro Gly Thr Ser Glu Ser Ala Thr Pro
            260                 265                 270

Glu Ser Gly Pro Gly Thr Ser Thr Glu Pro Ser Glu Gly Ser Ala Pro
        275                 280                 285

<210> SEQ ID NO 139
<211> LENGTH: 288
<212> TYPE: PRT
<213> ORGANISM: Artificial Sequence
<220> FEATURE:
<223> OTHER INFORMATION: AE288_2

<400> SEQUENCE: 139

Gly Ser Pro Ala Gly Ser Pro Thr Ser Thr Glu Glu Gly Thr Ser Glu
1               5                   10                  15

Ser Ala Thr Pro Glu Ser Gly Pro Gly Ser Glu Pro Ala Thr Ser Gly
            20                  25                  30

Ser Glu Thr Pro Gly Thr Ser Glu Ser Ala Thr Pro Glu Ser Gly Pro
        35                  40                  45

Gly Thr Ser Thr Glu Pro Ser Glu Gly Ser Ala Pro Gly Thr Ser Thr
    50                  55                  60

Glu Pro Ser Glu Gly Ser Ala Pro Gly Thr Ser Thr Glu Pro Ser Glu
65                  70                  75                  80

Gly Ser Ala Pro Gly Thr Ser Thr Glu Pro Ser Glu Gly Ser Ala Pro
                85                  90                  95

```
Gly Thr Ser Thr Glu Pro Ser Glu Gly Ser Ala Pro Gly Thr Ser Thr
                100                 105                 110

Glu Pro Ser Glu Gly Ser Ala Pro Gly Ser Pro Ala Gly Ser Pro Thr
            115                 120                 125

Ser Thr Glu Glu Gly Thr Ser Thr Glu Pro Ser Glu Gly Ser Ala Pro
        130                 135                 140

Gly Thr Ser Glu Ser Ala Thr Pro Glu Ser Gly Pro Gly Ser Glu Pro
145                 150                 155                 160

Ala Thr Ser Gly Ser Glu Thr Pro Gly Thr Ser Glu Ser Ala Thr Pro
                165                 170                 175

Glu Ser Gly Pro Gly Ser Glu Pro Ala Thr Ser Gly Ser Glu Thr Pro
            180                 185                 190

Gly Thr Ser Glu Ser Ala Thr Pro Glu Ser Gly Pro Gly Thr Ser Thr
        195                 200                 205

Glu Pro Ser Glu Gly Ser Ala Pro Gly Thr Ser Glu Ser Ala Thr Pro
    210                 215                 220

Glu Ser Gly Pro Gly Ser Pro Ala Gly Ser Pro Thr Ser Thr Glu Glu
225                 230                 235                 240

Gly Ser Pro Ala Gly Ser Pro Thr Ser Thr Glu Glu Gly Ser Pro Ala
                245                 250                 255

Gly Ser Pro Thr Ser Thr Glu Glu Gly Thr Ser Glu Ser Ala Thr Pro
            260                 265                 270

Glu Ser Gly Pro Gly Thr Ser Thr Glu Pro Ser Glu Gly Ser Ala Pro
        275                 280                 285
```

<210> SEQ ID NO 140
<211> LENGTH: 288
<212> TYPE: PRT
<213> ORGANISM: Artificial Sequence
<220> FEATURE:
<223> OTHER INFORMATION: AG288

<400> SEQUENCE: 140

```
Pro Gly Ala Ser Pro Gly Thr Ser Ser Thr Gly Ser Pro Gly Ala Ser
1               5                   10                  15

Pro Gly Thr Ser Ser Thr Gly Ser Pro Gly Thr Pro Gly Ser Gly Thr
            20                  25                  30

Ala Ser Ser Ser Pro Gly Ser Ser Thr Pro Ser Gly Ala Thr Gly Ser
        35                  40                  45

Pro Gly Thr Pro Gly Ser Gly Thr Ala Ser Ser Ser Pro Gly Ser Ser
    50                  55                  60

Thr Pro Ser Gly Ala Thr Gly Ser Pro Gly Pro Gly Ser Ser Gly Thr
65                  70                  75                  80

Ala Ser Ser Ser Pro Gly Ser Ser Thr Pro Ser Gly Ala Thr Gly Ser
                85                  90                  95

Pro Gly Ser Ser Thr Pro Ser Gly Ala Thr Gly Ser Pro Gly Ser Ser
            100                 105                 110

Pro Ser Ala Ser Thr Gly Thr Gly Pro Gly Ser Ser Pro Ser Ala Ser
        115                 120                 125

Thr Gly Thr Gly Pro Gly Ala Ser Pro Gly Thr Ser Ser Thr Gly Ser
    130                 135                 140

Pro Gly Thr Pro Gly Ser Gly Thr Ala Ser Ser Ser Pro Gly Ser Ser
145                 150                 155                 160

Thr Pro Ser Gly Ala Thr Gly Ser Pro Gly Ser Ser Pro Ser Ala Ser
                165                 170                 175
```

-continued

```
Thr Gly Thr Gly Pro Gly Ser Ser Pro Ser Ala Ser Thr Gly Thr Gly
            180                 185                 190

Pro Gly Ala Ser Pro Gly Thr Ser Ser Thr Gly Ser Pro Gly Ala Ser
            195                 200                 205

Pro Gly Thr Ser Ser Thr Gly Ser Pro Gly Ser Ser Thr Pro Ser Gly
            210                 215                 220

Ala Thr Gly Ser Pro Gly Ser Ser Pro Ser Ala Ser Thr Gly Thr Gly
225                 230                 235                 240

Pro Gly Ala Ser Pro Gly Thr Ser Ser Thr Gly Ser Pro Gly Ser Ser
                245                 250                 255

Pro Ser Ala Ser Thr Gly Thr Gly Pro Gly Thr Pro Gly Ser Gly Thr
            260                 265                 270

Ala Ser Ser Ser Pro Gly Ser Ser Thr Pro Ser Gly Ala Thr Gly Ser
            275                 280                 285

<210> SEQ ID NO 141
<211> LENGTH: 576
<212> TYPE: PRT
<213> ORGANISM: Artificial Sequence
<220> FEATURE:
<223> OTHER INFORMATION: AE576

<400> SEQUENCE: 141

Gly Ser Pro Ala Gly Ser Pro Thr Ser Thr Glu Glu Gly Thr Ser Glu
1               5                   10                  15

Ser Ala Thr Pro Glu Ser Gly Pro Gly Thr Ser Thr Glu Pro Ser Glu
            20                  25                  30

Gly Ser Ala Pro Gly Ser Pro Ala Gly Ser Pro Thr Ser Thr Glu Glu
            35                  40                  45

Gly Thr Ser Thr Glu Pro Ser Glu Gly Ser Ala Pro Gly Thr Ser Thr
        50                  55                  60

Glu Pro Ser Glu Gly Ser Ala Pro Gly Thr Ser Glu Ser Ala Thr Pro
65                  70                  75                  80

Glu Ser Gly Pro Gly Ser Glu Pro Ala Thr Ser Gly Ser Glu Thr Pro
                85                  90                  95

Gly Ser Glu Pro Ala Thr Ser Gly Ser Glu Thr Pro Gly Ser Pro Ala
            100                 105                 110

Gly Ser Pro Thr Ser Thr Glu Glu Gly Thr Ser Glu Ser Ala Thr Pro
            115                 120                 125

Glu Ser Gly Pro Gly Thr Ser Thr Glu Pro Ser Glu Gly Ser Ala Pro
        130                 135                 140

Gly Thr Ser Thr Glu Pro Ser Glu Gly Ser Ala Pro Gly Ser Pro Ala
145                 150                 155                 160

Gly Ser Pro Thr Ser Thr Glu Glu Gly Thr Ser Thr Glu Pro Ser Glu
                165                 170                 175

Gly Ser Ala Pro Gly Thr Ser Thr Glu Pro Ser Glu Gly Ser Ala Pro
            180                 185                 190

Gly Thr Ser Glu Ser Ala Thr Pro Glu Ser Gly Pro Gly Thr Ser Thr
            195                 200                 205

Glu Pro Ser Glu Gly Ser Ala Pro Gly Thr Ser Glu Ser Ala Thr Pro
        210                 215                 220

Glu Ser Gly Pro Gly Ser Glu Pro Ala Thr Ser Gly Ser Glu Thr Pro
225                 230                 235                 240

Gly Thr Ser Thr Glu Pro Ser Glu Gly Ser Ala Pro Gly Thr Ser Thr
                245                 250                 255
```

Glu Pro Ser Glu Gly Ser Ala Pro Gly Thr Ser Glu Ser Ala Thr Pro
            260                 265                 270

Glu Ser Gly Pro Gly Thr Ser Glu Ser Ala Thr Pro Glu Ser Gly Pro
        275                 280                 285

Gly Ser Pro Ala Gly Ser Pro Thr Ser Thr Glu Glu Gly Thr Ser Glu
    290                 295                 300

Ser Ala Thr Pro Glu Ser Gly Pro Gly Ser Glu Pro Ala Thr Ser Gly
305                 310                 315                 320

Ser Glu Thr Pro Gly Thr Ser Glu Ser Ala Thr Pro Glu Ser Gly Pro
                325                 330                 335

Gly Thr Ser Thr Glu Pro Ser Glu Gly Ser Ala Pro Gly Thr Ser Thr
            340                 345                 350

Glu Pro Ser Glu Gly Ser Ala Pro Gly Thr Ser Thr Glu Pro Ser Glu
        355                 360                 365

Gly Ser Ala Pro Gly Thr Ser Thr Glu Pro Ser Glu Gly Ser Ala Pro
    370                 375                 380

Gly Thr Ser Thr Glu Pro Ser Glu Gly Ser Ala Pro Gly Thr Ser Thr
385                 390                 395                 400

Glu Pro Ser Glu Gly Ser Ala Pro Gly Ser Pro Ala Gly Ser Pro Thr
                405                 410                 415

Ser Thr Glu Glu Gly Thr Ser Thr Glu Pro Ser Glu Gly Ser Ala Pro
            420                 425                 430

Gly Thr Ser Glu Ser Ala Thr Pro Glu Ser Gly Pro Gly Ser Glu Pro
        435                 440                 445

Ala Thr Ser Gly Ser Glu Thr Pro Gly Thr Ser Glu Ser Ala Thr Pro
    450                 455                 460

Glu Ser Gly Pro Gly Ser Glu Pro Ala Thr Ser Gly Ser Glu Thr Pro
465                 470                 475                 480

Gly Thr Ser Glu Ser Ala Thr Pro Glu Ser Gly Pro Gly Thr Ser Thr
                485                 490                 495

Glu Pro Ser Glu Gly Ser Ala Pro Gly Thr Ser Glu Ser Ala Thr Pro
            500                 505                 510

Glu Ser Gly Pro Gly Ser Pro Ala Gly Ser Pro Thr Ser Thr Glu Glu
        515                 520                 525

Gly Ser Pro Ala Gly Ser Pro Thr Ser Thr Glu Glu Gly Ser Pro Ala
    530                 535                 540

Gly Ser Pro Thr Ser Thr Glu Glu Gly Thr Ser Glu Ser Ala Thr Pro
545                 550                 555                 560

Glu Ser Gly Pro Gly Thr Ser Thr Glu Pro Ser Glu Gly Ser Ala Pro
                565                 570                 575

<210> SEQ ID NO 142
<211> LENGTH: 576
<212> TYPE: PRT
<213> ORGANISM: Artificial Sequence
<220> FEATURE:
<223> OTHER INFORMATION: AG576

<400> SEQUENCE: 142

Pro Gly Thr Pro Gly Ser Gly Thr Ala Ser Ser Ser Pro Gly Ser Ser
1               5                   10                  15

Thr Pro Ser Gly Ala Thr Gly Ser Pro Gly Ser Ser Pro Ser Ala Ser
            20                  25                  30

Thr Gly Thr Gly Pro Gly Ser Ser Pro Ser Ala Ser Thr Gly Thr Gly
        35                  40                  45

Pro Gly Ser Ser Thr Pro Ser Gly Ala Thr Gly Ser Pro Gly Ser Ser
                50                  55                  60

Thr Pro Ser Gly Ala Thr Gly Ser Pro Gly Ala Ser Pro Gly Thr Ser
 65                  70                  75                  80

Ser Thr Gly Ser Pro Gly Ala Ser Pro Gly Thr Ser Ser Thr Gly Ser
                 85                  90                  95

Pro Gly Ala Ser Pro Gly Thr Ser Ser Thr Gly Ser Pro Gly Thr Pro
                100                 105                 110

Gly Ser Gly Thr Ala Ser Ser Pro Gly Ala Ser Pro Gly Thr Ser
                115                 120                 125

Ser Thr Gly Ser Pro Gly Ala Ser Pro Gly Thr Ser Ser Thr Gly Ser
                130                 135                 140

Pro Gly Ala Ser Pro Gly Thr Ser Ser Thr Gly Ser Pro Gly Ser Ser
145                 150                 155                 160

Pro Ser Ala Ser Thr Gly Thr Gly Pro Gly Thr Pro Gly Ser Gly Thr
                165                 170                 175

Ala Ser Ser Ser Pro Gly Ala Ser Pro Gly Thr Ser Ser Thr Gly Ser
                180                 185                 190

Pro Gly Ala Ser Pro Gly Thr Ser Ser Thr Gly Ser Pro Gly Ala Ser
                195                 200                 205

Pro Gly Thr Ser Ser Thr Gly Ser Pro Gly Ser Ser Thr Pro Ser Gly
                210                 215                 220

Ala Thr Gly Ser Pro Gly Ser Ser Thr Pro Ser Gly Ala Thr Gly Ser
225                 230                 235                 240

Pro Gly Ala Ser Pro Gly Thr Ser Ser Thr Gly Ser Pro Gly Thr Pro
                245                 250                 255

Gly Ser Gly Thr Ala Ser Ser Pro Gly Ser Ser Thr Pro Ser Gly
                260                 265                 270

Ala Thr Gly Ser Pro Gly Ser Ser Thr Pro Ser Gly Ala Thr Gly Ser
                275                 280                 285

Pro Gly Ser Ser Thr Pro Ser Gly Ala Thr Gly Ser Pro Gly Ser Ser
                290                 295                 300

Pro Ser Ala Ser Thr Gly Thr Gly Pro Gly Ala Ser Pro Gly Thr Ser
305                 310                 315                 320

Ser Thr Gly Ser Pro Gly Ala Ser Pro Gly Thr Ser Ser Thr Gly Ser
                325                 330                 335

Pro Gly Thr Pro Gly Ser Gly Thr Ala Ser Ser Pro Gly Ala Ser
                340                 345                 350

Pro Gly Thr Ser Ser Thr Gly Ser Pro Gly Ala Ser Pro Gly Thr Ser
                355                 360                 365

Ser Thr Gly Ser Pro Gly Ala Ser Pro Gly Thr Ser Ser Thr Gly Ser
                370                 375                 380

Pro Gly Ala Ser Pro Gly Thr Ser Ser Thr Gly Ser Pro Gly Thr Pro
385                 390                 395                 400

Gly Ser Gly Thr Ala Ser Ser Pro Gly Ser Ser Thr Pro Ser Gly
                405                 410                 415

Ala Thr Gly Ser Pro Gly Thr Pro Gly Ser Gly Thr Ala Ser Ser
                420                 425                 430

Pro Gly Ser Ser Thr Pro Ser Gly Ala Thr Gly Ser Pro Gly Thr Pro
                435                 440                 445

Gly Ser Gly Thr Ala Ser Ser Pro Gly Ser Ser Thr Pro Ser Gly
                450                 455                 460

Ala Thr Gly Ser Pro Gly Ser Ser Thr Pro Ser Gly Ala Thr Gly Ser
465                 470                 475                 480

Pro Gly Ser Ser Pro Ser Ala Ser Thr Gly Thr Gly Pro Gly Ser Ser
                485                 490                 495

Pro Ser Ala Ser Thr Gly Thr Gly Pro Gly Ala Ser Pro Gly Thr Ser
            500                 505                 510

Ser Thr Gly Ser Pro Gly Thr Pro Gly Ser Gly Thr Ala Ser Ser Ser
        515                 520                 525

Pro Gly Ser Ser Thr Pro Ser Gly Ala Thr Gly Ser Pro Gly Ser Ser
    530                 535                 540

Pro Ser Ala Ser Thr Gly Thr Gly Pro Gly Ser Ser Pro Ser Ala Ser
545                 550                 555                 560

Thr Gly Thr Gly Pro Gly Ala Ser Pro Gly Thr Ser Ser Thr Gly Ser
                565                 570                 575

<210> SEQ ID NO 143
<211> LENGTH: 864
<212> TYPE: PRT
<213> ORGANISM: Artificial Sequence
<220> FEATURE:
<223> OTHER INFORMATION: AE864

<400> SEQUENCE: 143

Gly Ser Pro Ala Gly Ser Pro Thr Ser Thr Glu Glu Gly Thr Ser Glu
1               5                   10                  15

Ser Ala Thr Pro Glu Ser Gly Pro Gly Thr Ser Thr Glu Pro Ser Glu
            20                  25                  30

Gly Ser Ala Pro Gly Ser Pro Ala Gly Ser Pro Thr Ser Thr Glu Glu
        35                  40                  45

Gly Thr Ser Thr Glu Pro Ser Glu Gly Ser Ala Pro Gly Thr Ser Thr
    50                  55                  60

Glu Pro Ser Glu Gly Ser Ala Pro Gly Thr Ser Glu Ser Ala Thr Pro
65                  70                  75                  80

Glu Ser Gly Pro Gly Ser Glu Pro Ala Thr Ser Gly Ser Glu Thr Pro
                85                  90                  95

Gly Ser Glu Pro Ala Thr Ser Gly Ser Glu Thr Pro Gly Ser Pro Ala
                100                 105                 110

Gly Ser Pro Thr Ser Thr Glu Glu Gly Thr Ser Glu Ser Ala Thr Pro
            115                 120                 125

Glu Ser Gly Pro Gly Thr Ser Thr Glu Pro Ser Glu Gly Ser Ala Pro
        130                 135                 140

Gly Thr Ser Thr Glu Pro Ser Glu Gly Ser Ala Pro Gly Ser Pro Ala
145                 150                 155                 160

Gly Ser Pro Thr Ser Thr Glu Glu Gly Thr Ser Thr Glu Pro Ser Glu
                165                 170                 175

Gly Ser Ala Pro Gly Thr Ser Thr Glu Pro Ser Glu Gly Ser Ala Pro
                180                 185                 190

Gly Thr Ser Glu Ser Ala Thr Pro Glu Ser Gly Pro Gly Thr Ser Thr
            195                 200                 205

Glu Pro Ser Glu Gly Ser Ala Pro Gly Thr Ser Glu Ser Ala Thr Pro
        210                 215                 220

Glu Ser Gly Pro Gly Ser Glu Pro Ala Thr Ser Gly Ser Glu Thr Pro
225                 230                 235                 240

Gly Thr Ser Thr Glu Pro Ser Glu Gly Ser Ala Pro Gly Thr Ser Thr
                245                 250                 255

```
Glu Pro Ser Glu Gly Ser Ala Pro Gly Thr Ser Glu Ser Ala Thr Pro
                260                 265                 270

Glu Ser Gly Pro Gly Thr Ser Glu Ser Ala Thr Pro Glu Ser Gly Pro
            275                 280                 285

Gly Ser Pro Ala Gly Ser Pro Thr Ser Thr Glu Glu Gly Thr Ser Glu
        290                 295                 300

Ser Ala Thr Pro Glu Ser Gly Pro Gly Ser Glu Pro Ala Thr Ser Gly
305                 310                 315                 320

Ser Glu Thr Pro Gly Thr Ser Glu Ser Ala Thr Pro Glu Ser Gly Pro
                325                 330                 335

Gly Thr Ser Thr Glu Pro Ser Glu Gly Ser Ala Pro Gly Thr Ser Thr
                340                 345                 350

Glu Pro Ser Glu Gly Ser Ala Pro Gly Thr Ser Thr Glu Pro Ser Glu
                355                 360                 365

Gly Ser Ala Pro Gly Thr Ser Thr Glu Pro Ser Glu Gly Ser Ala Pro
            370                 375                 380

Gly Thr Ser Thr Glu Pro Ser Glu Gly Ser Ala Pro Gly Thr Ser Thr
385                 390                 395                 400

Glu Pro Ser Glu Gly Ser Ala Pro Gly Ser Pro Ala Gly Ser Pro Thr
                405                 410                 415

Ser Thr Glu Glu Gly Thr Ser Thr Glu Pro Ser Glu Gly Ser Ala Pro
            420                 425                 430

Gly Thr Ser Glu Ser Ala Thr Pro Glu Ser Gly Pro Gly Ser Glu Pro
            435                 440                 445

Ala Thr Ser Gly Ser Glu Thr Pro Gly Thr Ser Glu Ser Ala Thr Pro
450                 455                 460

Glu Ser Gly Pro Gly Ser Glu Pro Ala Thr Ser Gly Ser Glu Thr Pro
465                 470                 475                 480

Gly Thr Ser Glu Ser Ala Thr Pro Glu Ser Gly Pro Gly Thr Ser Thr
                485                 490                 495

Glu Pro Ser Glu Gly Ser Ala Pro Gly Thr Ser Glu Ser Ala Thr Pro
            500                 505                 510

Glu Ser Gly Pro Gly Ser Pro Ala Gly Ser Pro Thr Ser Thr Glu Glu
            515                 520                 525

Gly Ser Pro Ala Gly Ser Pro Thr Ser Thr Glu Glu Gly Ser Pro Ala
530                 535                 540

Gly Ser Pro Thr Ser Thr Glu Glu Gly Thr Ser Glu Ser Ala Thr Pro
545                 550                 555                 560

Glu Ser Gly Pro Gly Thr Ser Thr Glu Pro Ser Glu Gly Ser Ala Pro
                565                 570                 575

Gly Thr Ser Glu Ser Ala Thr Pro Glu Ser Gly Pro Gly Ser Glu Pro
            580                 585                 590

Ala Thr Ser Gly Ser Glu Thr Pro Gly Thr Ser Glu Ser Ala Thr Pro
            595                 600                 605

Glu Ser Gly Pro Gly Ser Glu Pro Ala Thr Ser Gly Ser Glu Thr Pro
            610                 615                 620

Gly Thr Ser Glu Ser Ala Thr Pro Glu Ser Gly Pro Gly Thr Ser Thr
625                 630                 635                 640

Glu Pro Ser Glu Gly Ser Ala Pro Gly Ser Pro Ala Gly Ser Pro Thr
                645                 650                 655

Ser Thr Glu Glu Gly Thr Ser Glu Ser Ala Thr Pro Glu Ser Gly Pro
            660                 665                 670

Gly Ser Glu Pro Ala Thr Ser Gly Ser Glu Thr Pro Gly Thr Ser Glu
```

```
              675                 680                 685
Ser Ala Thr Pro Glu Ser Gly Pro Gly Ser Pro Ala Gly Ser Pro Thr
            690                 695                 700

Ser Thr Glu Glu Gly Ser Pro Ala Gly Ser Pro Thr Ser Thr Glu Glu
705                 710                 715                 720

Gly Thr Ser Thr Glu Pro Ser Glu Gly Ser Ala Pro Gly Thr Ser Glu
                725                 730                 735

Ser Ala Thr Pro Glu Ser Gly Pro Gly Thr Ser Glu Ser Ala Thr Pro
            740                 745                 750

Glu Ser Gly Pro Gly Thr Ser Glu Ser Ala Thr Pro Glu Ser Gly Pro
            755                 760                 765

Gly Ser Glu Pro Ala Thr Ser Gly Ser Glu Thr Pro Gly Ser Glu Pro
            770                 775                 780

Ala Thr Ser Gly Ser Glu Thr Pro Gly Ser Pro Ala Gly Ser Pro Thr
785                 790                 795                 800

Ser Thr Glu Glu Gly Thr Ser Thr Glu Pro Ser Glu Gly Ser Ala Pro
                805                 810                 815

Gly Thr Ser Thr Glu Pro Ser Glu Gly Ser Ala Pro Gly Ser Glu Pro
                820                 825                 830

Ala Thr Ser Gly Ser Glu Thr Pro Gly Thr Ser Glu Ser Ala Thr Pro
            835                 840                 845

Glu Ser Gly Pro Gly Thr Ser Thr Glu Pro Ser Glu Gly Ser Ala Pro
            850                 855                 860

<210> SEQ ID NO 144
<211> LENGTH: 864
<212> TYPE: PRT
<213> ORGANISM: Artificial Sequence
<220> FEATURE:
<223> OTHER INFORMATION: AG864

<400> SEQUENCE: 144

Gly Ala Ser Pro Gly Thr Ser Ser Thr Gly Ser Pro Gly Ser Ser Pro
1               5                   10                  15

Ser Ala Ser Thr Gly Thr Gly Pro Gly Ser Ser Pro Ser Ala Ser Thr
            20                  25                  30

Gly Thr Gly Pro Gly Thr Pro Gly Ser Gly Thr Ala Ser Ser Ser Pro
        35                  40                  45

Gly Ser Ser Thr Pro Ser Gly Ala Thr Gly Ser Pro Gly Ser Ser Pro
50                  55                  60

Ser Ala Ser Thr Gly Thr Gly Pro Gly Ala Ser Pro Gly Thr Ser Ser
65                  70                  75                  80

Thr Gly Ser Pro Gly Thr Pro Gly Ser Gly Thr Ala Ser Ser Ser Pro
                85                  90                  95

Gly Ser Ser Thr Pro Ser Gly Ala Thr Gly Ser Pro Gly Thr Pro Gly
                100                 105                 110

Ser Gly Thr Ala Ser Ser Ser Pro Gly Ala Ser Pro Gly Thr Ser Ser
        115                 120                 125

Thr Gly Ser Pro Gly Ala Ser Pro Gly Thr Ser Ser Thr Gly Ser Pro
    130                 135                 140

Gly Thr Pro Gly Ser Gly Thr Ala Ser Ser Ser Pro Gly Ser Ser Thr
145                 150                 155                 160

Pro Ser Gly Ala Thr Gly Ser Pro Gly Ala Ser Pro Gly Thr Ser Ser
                165                 170                 175

Thr Gly Ser Pro Gly Thr Pro Gly Ser Gly Thr Ala Ser Ser Ser Pro
```

```
            180                 185                 190
Gly Ser Ser Thr Pro Ser Gly Ala Thr Gly Ser Pro Gly Ser Ser Pro
            195                 200                 205
Ser Ala Ser Thr Gly Thr Gly Pro Gly Ser Ser Pro Ser Ala Ser Thr
            210                 215                 220
Gly Thr Gly Pro Gly Ser Ser Thr Pro Ser Gly Ala Thr Gly Ser Pro
225                 230                 235                 240
Gly Ser Ser Thr Pro Ser Gly Ala Thr Gly Ser Pro Gly Ala Ser Pro
            245                 250                 255
Gly Thr Ser Ser Thr Gly Ser Pro Gly Ala Ser Pro Gly Thr Ser Ser
            260                 265                 270
Thr Gly Ser Pro Gly Ala Ser Pro Gly Thr Ser Ser Thr Gly Ser Pro
            275                 280                 285
Gly Thr Pro Gly Ser Gly Thr Ala Ser Ser Ser Pro Gly Ala Ser Pro
            290                 295                 300
Gly Thr Ser Ser Thr Gly Ser Pro Gly Ala Ser Pro Gly Thr Ser Ser
305                 310                 315                 320
Thr Gly Ser Pro Gly Ala Ser Pro Gly Thr Ser Ser Thr Gly Ser Pro
            325                 330                 335
Gly Ser Ser Pro Ser Ala Ser Thr Gly Thr Gly Pro Gly Thr Pro Gly
            340                 345                 350
Ser Gly Thr Ala Ser Ser Ser Pro Gly Ala Ser Pro Gly Thr Ser Ser
            355                 360                 365
Thr Gly Ser Pro Gly Ala Ser Pro Gly Thr Ser Ser Thr Gly Ser Pro
            370                 375                 380
Gly Ala Ser Pro Gly Thr Ser Ser Thr Gly Ser Pro Gly Ser Ser Thr
385                 390                 395                 400
Pro Ser Gly Ala Thr Gly Ser Pro Gly Ser Ser Thr Pro Ser Gly Ala
            405                 410                 415
Thr Gly Ser Pro Gly Ala Ser Pro Gly Thr Ser Ser Thr Gly Ser Pro
            420                 425                 430
Gly Thr Pro Gly Ser Gly Thr Ala Ser Ser Ser Pro Gly Ser Ser Thr
            435                 440                 445
Pro Ser Gly Ala Thr Gly Ser Pro Gly Ser Ser Thr Pro Ser Gly Ala
            450                 455                 460
Thr Gly Ser Pro Gly Ser Ser Thr Pro Ser Gly Ala Thr Gly Ser Pro
465                 470                 475                 480
Gly Ser Ser Pro Ser Ala Ser Thr Gly Thr Gly Pro Gly Ala Ser Pro
            485                 490                 495
Gly Thr Ser Ser Thr Gly Ser Pro Gly Ala Ser Pro Gly Thr Ser Ser
            500                 505                 510
Thr Gly Ser Pro Gly Thr Pro Gly Ser Gly Thr Ala Ser Ser Ser Pro
            515                 520                 525
Gly Ala Ser Pro Gly Thr Ser Ser Thr Gly Ser Pro Gly Ala Ser Pro
            530                 535                 540
Gly Thr Ser Ser Thr Gly Ser Pro Gly Ala Ser Pro Gly Thr Ser Ser
545                 550                 555                 560
Thr Gly Ser Pro Gly Ala Ser Pro Gly Thr Ser Ser Thr Gly Ser Pro
            565                 570                 575
Gly Thr Pro Gly Ser Gly Thr Ala Ser Ser Ser Pro Gly Ser Ser Thr
            580                 585                 590
Pro Ser Gly Ala Thr Gly Ser Pro Gly Thr Pro Gly Ser Gly Thr Ala
            595                 600                 605
```

```
Ser Ser Ser Pro Gly Ser Ser Thr Pro Ser Gly Ala Thr Gly Ser Pro
            610                 615                 620

Gly Thr Pro Gly Ser Gly Thr Ala Ser Ser Ser Pro Gly Ser Ser Thr
625                 630                 635                 640

Pro Ser Gly Ala Thr Gly Ser Pro Gly Ser Ser Thr Pro Ser Gly Ala
                645                 650                 655

Thr Gly Ser Pro Gly Ser Ser Pro Ser Ala Ser Thr Gly Thr Gly Pro
                660                 665                 670

Gly Ser Ser Pro Ser Ala Ser Thr Gly Thr Gly Pro Gly Ala Ser Pro
                675                 680                 685

Gly Thr Ser Ser Thr Gly Ser Pro Gly Thr Pro Gly Ser Gly Thr Ala
            690                 695                 700

Ser Ser Ser Pro Gly Ser Ser Thr Pro Ser Gly Ala Thr Gly Ser Pro
705                 710                 715                 720

Gly Ser Ser Pro Ser Ala Ser Thr Gly Thr Gly Pro Gly Ser Ser Pro
                725                 730                 735

Ser Ala Ser Thr Gly Thr Gly Pro Gly Ala Ser Pro Gly Thr Ser Ser
                740                 745                 750

Thr Gly Ser Pro Gly Ala Ser Pro Gly Thr Ser Ser Thr Gly Ser Pro
            755                 760                 765

Gly Ser Ser Thr Pro Ser Gly Ala Thr Gly Ser Pro Gly Ser Ser Pro
            770                 775                 780

Ser Ala Ser Thr Gly Thr Gly Pro Gly Ala Ser Pro Gly Thr Ser Ser
785                 790                 795                 800

Thr Gly Ser Pro Gly Ser Ser Pro Ser Ala Ser Thr Gly Thr Gly Pro
                805                 810                 815

Gly Thr Pro Gly Ser Gly Thr Ala Ser Ser Ser Pro Gly Ser Ser Thr
                820                 825                 830

Pro Ser Gly Ala Thr Gly Ser Pro Gly Ser Ser Thr Pro Ser Gly Ala
                835                 840                 845

Thr Gly Ser Pro Gly Ala Ser Pro Gly Thr Ser Ser Thr Gly Ser Pro
            850                 855                 860

<210> SEQ ID NO 145
<211> LENGTH: 72
<212> TYPE: PRT
<213> ORGANISM: Artificial Sequence
<220> FEATURE:
<223> OTHER INFORMATION: XTEN_AE72_2A_1

<400> SEQUENCE: 145

Thr Ser Thr Glu Pro Ser Glu Gly Ser Ala Pro Gly Ser Pro Ala Gly
1               5                   10                  15

Ser Pro Thr Ser Thr Glu Glu Gly Thr Ser Thr Glu Pro Ser Glu Gly
            20                  25                  30

Ser Ala Pro Gly Thr Ser Thr Glu Pro Ser Glu Gly Ser Ala Pro Gly
                35                  40                  45

Thr Ser Glu Ser Ala Thr Pro Glu Ser Gly Pro Gly Thr Ser Thr Glu
    50                  55                  60

Pro Ser Glu Gly Ser Ala Pro Gly
65                  70

<210> SEQ ID NO 146
<211> LENGTH: 72
<212> TYPE: PRT
<213> ORGANISM: Artificial Sequence
```

<220> FEATURE:
<223> OTHER INFORMATION: XTEN_AE72_2A_2

<400> SEQUENCE: 146

Thr Ser Glu Ser Ala Thr Pro Glu Ser Gly Pro Gly Ser Glu Pro Ala
1               5                   10                  15

Thr Ser Gly Ser Glu Thr Pro Gly Thr Ser Thr Glu Pro Ser Glu Gly
                20                  25                  30

Ser Ala Pro Gly Thr Ser Thr Glu Pro Ser Glu Gly Ser Ala Pro Gly
            35                  40                  45

Thr Ser Glu Ser Ala Thr Pro Glu Ser Gly Pro Gly Thr Ser Glu Ser
        50                  55                  60

Ala Thr Pro Glu Ser Gly Pro Gly
65                  70

<210> SEQ ID NO 147
<211> LENGTH: 72
<212> TYPE: PRT
<213> ORGANISM: Artificial Sequence
<220> FEATURE:
<223> OTHER INFORMATION: XTEN_AE72_3B_1

<400> SEQUENCE: 147

Ser Pro Ala Gly Ser Pro Thr Ser Thr Glu Glu Gly Thr Ser Glu Ser
1               5                   10                  15

Ala Thr Pro Glu Ser Gly Pro Gly Ser Glu Pro Ala Thr Ser Gly Ser
                20                  25                  30

Glu Thr Pro Gly Thr Ser Glu Ser Ala Thr Pro Glu Ser Gly Pro Gly
            35                  40                  45

Thr Ser Thr Glu Pro Ser Glu Gly Ser Ala Pro Gly Thr Ser Thr Glu
        50                  55                  60

Pro Ser Glu Gly Ser Ala Pro Gly
65                  70

<210> SEQ ID NO 148
<211> LENGTH: 72
<212> TYPE: PRT
<213> ORGANISM: Artificial Sequence
<220> FEATURE:
<223> OTHER INFORMATION: XTEN_AE72_3B_2

<400> SEQUENCE: 148

Thr Ser Thr Glu Pro Ser Glu Gly Ser Ala Pro Gly Thr Ser Thr Glu
1               5                   10                  15

Pro Ser Glu Gly Ser Ala Pro Gly Thr Ser Thr Glu Pro Ser Glu Gly
                20                  25                  30

Ser Ala Pro Gly Thr Ser Thr Glu Pro Ser Glu Gly Ser Ala Pro Gly
            35                  40                  45

Ser Pro Ala Gly Ser Pro Thr Ser Thr Glu Glu Gly Thr Ser Thr Glu
        50                  55                  60

Pro Ser Glu Gly Ser Ala Pro Gly
65                  70

<210> SEQ ID NO 149
<211> LENGTH: 72
<212> TYPE: PRT
<213> ORGANISM: Artificial Sequence
<220> FEATURE:
<223> OTHER INFORMATION: XTEN_AE72_4A_2

<400> SEQUENCE: 149

```
Thr Ser Glu Ser Ala Thr Pro Glu Ser Gly Pro Gly Ser Pro Ala Gly
1               5                   10                  15

Ser Pro Thr Ser Thr Glu Gly Ser Pro Ala Gly Ser Pro Thr Ser
            20                  25                  30

Thr Glu Glu Gly Ser Pro Ala Gly Ser Pro Thr Ser Thr Glu Glu Gly
        35                  40                  45

Thr Ser Glu Ser Ala Thr Pro Glu Ser Gly Pro Gly Thr Ser Thr Glu
        50                  55                  60

Pro Ser Glu Gly Ser Ala Pro Gly
65                  70
```

<210> SEQ ID NO 150
<211> LENGTH: 72
<212> TYPE: PRT
<213> ORGANISM: Artificial Sequence
<220> FEATURE:
<223> OTHER INFORMATION: XTEN_AE72_5A_2

<400> SEQUENCE: 150

```
Ser Pro Ala Gly Ser Pro Thr Ser Thr Glu Glu Gly Thr Ser Glu Ser
1               5                   10                  15

Ala Thr Pro Glu Ser Gly Pro Gly Ser Glu Pro Ala Thr Ser Gly Ser
            20                  25                  30

Glu Thr Pro Gly Thr Ser Glu Ser Ala Thr Pro Glu Ser Gly Pro Gly
        35                  40                  45

Ser Pro Ala Gly Ser Pro Thr Ser Thr Glu Glu Gly Ser Pro Ala Gly
        50                  55                  60

Ser Pro Thr Ser Thr Glu Glu Gly
65                  70
```

<210> SEQ ID NO 151
<211> LENGTH: 72
<212> TYPE: PRT
<213> ORGANISM: Artificial Sequence
<220> FEATURE:
<223> OTHER INFORMATION: XTEN_AE72_6B_1

<400> SEQUENCE: 151

```
Thr Ser Thr Glu Pro Ser Glu Gly Ser Ala Pro Gly Thr Ser Glu Ser
1               5                   10                  15

Ala Thr Pro Glu Ser Gly Pro Gly Thr Ser Glu Ser Ala Thr Pro Glu
            20                  25                  30

Ser Gly Pro Gly Thr Ser Glu Ser Ala Thr Pro Glu Ser Gly Pro Gly
        35                  40                  45

Ser Glu Pro Ala Thr Ser Gly Ser Glu Thr Pro Gly Ser Glu Pro Ala
        50                  55                  60

Thr Ser Gly Ser Glu Thr Pro Gly
65                  70
```

<210> SEQ ID NO 152
<211> LENGTH: 72
<212> TYPE: PRT
<213> ORGANISM: Artificial Sequence
<220> FEATURE:
<223> OTHER INFORMATION: XTEN_AE72_6B_2

<400> SEQUENCE: 152

```
Ser Pro Ala Gly Ser Pro Thr Ser Thr Glu Glu Gly Thr Ser Thr Glu
1               5                   10                  15
```

```
Pro Ser Glu Gly Ser Ala Pro Gly Thr Ser Thr Glu Pro Ser Glu Gly
            20                  25                  30

Ser Ala Pro Gly Ser Glu Pro Ala Thr Ser Gly Ser Glu Thr Pro Gly
            35                  40                  45

Thr Ser Glu Ser Ala Thr Pro Glu Ser Gly Pro Gly Thr Ser Thr Glu
            50                  55                  60

Pro Ser Glu Gly Ser Ala Pro Gly
65                  70

<210> SEQ ID NO 153
<211> LENGTH: 72
<212> TYPE: PRT
<213> ORGANISM: Artificial Sequence
<220> FEATURE:
<223> OTHER INFORMATION: XTEN_AE72_1A_1

<400> SEQUENCE: 153

Ser Pro Ala Gly Ser Pro Thr Ser Thr Glu Glu Gly Thr Ser Glu Ser
1               5                   10                  15

Ala Thr Pro Glu Ser Gly Pro Gly Thr Ser Thr Glu Pro Ser Glu Gly
            20                  25                  30

Ser Ala Pro Gly Ser Pro Ala Gly Ser Pro Thr Ser Thr Glu Glu Gly
            35                  40                  45

Thr Ser Thr Glu Pro Ser Glu Gly Ser Ala Pro Gly Thr Ser Thr Glu
            50                  55                  60

Pro Ser Glu Gly Ser Ala Pro Gly
65                  70

<210> SEQ ID NO 154
<211> LENGTH: 72
<212> TYPE: PRT
<213> ORGANISM: Artificial Sequence
<220> FEATURE:
<223> OTHER INFORMATION: XTEN_AE72_1A_2

<400> SEQUENCE: 154

Thr Ser Glu Ser Ala Thr Pro Glu Ser Gly Pro Gly Ser Glu Pro Ala
1               5                   10                  15

Thr Ser Gly Ser Glu Thr Pro Gly Ser Glu Pro Ala Thr Ser Gly Ser
            20                  25                  30

Glu Thr Pro Gly Ser Pro Ala Gly Ser Pro Thr Ser Thr Glu Glu Gly
            35                  40                  45

Thr Ser Glu Ser Ala Thr Pro Glu Ser Gly Pro Gly Thr Ser Thr Glu
            50                  55                  60

Pro Ser Glu Gly Ser Ala Pro Gly
65                  70

<210> SEQ ID NO 155
<211> LENGTH: 144
<212> TYPE: PRT
<213> ORGANISM: Artificial Sequence
<220> FEATURE:
<223> OTHER INFORMATION: XTEN_AE144_1A

<400> SEQUENCE: 155

Ser Pro Ala Gly Ser Pro Thr Ser Thr Glu Glu Gly Thr Ser Glu Ser
1               5                   10                  15

Ala Thr Pro Glu Ser Gly Pro Gly Thr Ser Thr Glu Pro Ser Glu Gly
            20                  25                  30

Ser Ala Pro Gly Ser Pro Ala Gly Ser Pro Thr Ser Thr Glu Glu Gly
```

```
                    35                  40                  45

Thr Ser Thr Glu Pro Ser Glu Gly Ala Pro Gly Thr Ser Thr Glu
 50                  55                  60

Pro Ser Glu Gly Ser Ala Pro Gly Thr Ser Glu Ser Ala Thr Pro Glu
 65                  70                  75                  80

Ser Gly Pro Gly Ser Glu Pro Ala Thr Ser Gly Ser Glu Thr Pro Gly
                     85                  90                  95

Ser Glu Pro Ala Thr Ser Gly Ser Glu Thr Pro Gly Ser Pro Ala Gly
                    100                 105                 110

Ser Pro Thr Ser Thr Glu Glu Gly Thr Ser Glu Ser Ala Thr Pro Glu
                    115                 120                 125

Ser Gly Pro Gly Thr Ser Thr Glu Pro Ser Glu Gly Ser Ala Pro Gly
                    130                 135                 140
```

<210> SEQ ID NO 156
<211> LENGTH: 150
<212> TYPE: PRT
<213> ORGANISM: Artificial Sequence
<220> FEATURE:
<223> OTHER INFORMATION: AE150

<400> SEQUENCE: 156

```
Gly Ala Pro Gly Ser Glu Pro Ala Thr Ser Gly Ser Glu Thr Pro Gly
  1               5                  10                  15

Thr Ser Glu Ser Ala Thr Pro Glu Ser Gly Pro Gly Ser Glu Pro Ala
                 20                  25                  30

Thr Ser Gly Ser Glu Thr Pro Gly Ser Pro Ala Gly Ser Pro Thr Ser
                 35                  40                  45

Thr Glu Glu Gly Thr Ser Thr Glu Pro Ser Glu Gly Ser Ala Pro Gly
 50                  55                  60

Ser Glu Pro Ala Thr Ser Gly Ser Glu Thr Pro Gly Ser Glu Pro Ala
 65                  70                  75                  80

Thr Ser Gly Ser Glu Thr Pro Gly Ser Glu Pro Ala Thr Ser Gly Ser
                     85                  90                  95

Glu Thr Pro Gly Thr Ser Thr Glu Pro Ser Glu Gly Ser Ala Pro Gly
                    100                 105                 110

Thr Ser Glu Ser Ala Thr Pro Glu Ser Gly Pro Gly Ser Glu Pro Ala
                    115                 120                 125

Thr Ser Gly Ser Glu Thr Pro Gly Thr Ser Thr Glu Pro Ser Glu Gly
                    130                 135                 140

Ser Ala Pro Ala Ser Ser
145                 150
```

<210> SEQ ID NO 157
<211> LENGTH: 150
<212> TYPE: PRT
<213> ORGANISM: Artificial Sequence
<220> FEATURE:
<223> OTHER INFORMATION: G150

<400> SEQUENCE: 157

```
Gly Ala Pro Gly Thr Pro Gly Ser Gly Thr Ala Ser Ser Ser Pro Gly
  1               5                  10                  15

Ser Ser Thr Pro Ser Gly Ala Thr Gly Ser Pro Gly Ser Ser Pro Ser
                 20                  25                  30

Ala Ser Thr Gly Thr Gly Pro Gly Ser Ser Pro Ser Ala Ser Thr Gly
                 35                  40                  45
```

```
Thr Gly Pro Gly Ala Ser Pro Gly Thr Ser Ser Thr Gly Ser Pro Gly
        50                  55                  60

Ala Ser Pro Gly Thr Ser Ser Thr Gly Ser Pro Gly Ser Ser Thr Pro
 65                 70                  75                  80

Ser Gly Ala Thr Gly Ser Pro Gly Ser Ser Pro Ser Ala Ser Thr Gly
                85                  90                  95

Thr Gly Pro Gly Ala Ser Pro Gly Thr Ser Ser Thr Gly Ser Pro Gly
            100                 105                 110

Ser Ser Pro Ser Ala Ser Thr Gly Thr Gly Pro Gly Thr Pro Gly Ser
            115                 120                 125

Gly Thr Ala Ser Ser Pro Gly Ser Ser Thr Pro Ser Gly Ala Thr
            130                 135                 140

Gly Ser Pro Ala Ser Ser
145             150
```

<210> SEQ ID NO 158
<211> LENGTH: 294
<212> TYPE: PRT
<213> ORGANISM: Artificial Sequence
<220> FEATURE:
<223> OTHER INFORMATION: AE294

<400> SEQUENCE: 158

```
Gly Ala Pro Gly Thr Ser Glu Ser Ala Thr Pro Glu Ser Gly Pro Gly
 1               5                  10                  15

Ser Glu Pro Ala Thr Ser Gly Ser Glu Thr Pro Gly Thr Ser Glu Ser
             20                  25                  30

Ala Thr Pro Glu Ser Gly Pro Gly Ser Glu Pro Ala Thr Ser Gly Ser
         35                  40                  45

Glu Thr Pro Gly Thr Ser Glu Ser Ala Thr Pro Glu Ser Gly Pro Gly
     50                  55                  60

Thr Ser Thr Glu Pro Ser Glu Gly Ser Ala Pro Gly Ser Pro Ala Gly
 65                  70                  75                  80

Ser Pro Thr Ser Thr Glu Glu Gly Thr Ser Glu Ser Ala Thr Pro Glu
                 85                  90                  95

Ser Gly Pro Gly Ser Glu Pro Ala Thr Ser Gly Ser Glu Thr Pro Gly
            100                 105                 110

Thr Ser Glu Ser Ala Thr Pro Glu Ser Gly Pro Gly Ser Pro Ala Gly
            115                 120                 125

Ser Pro Thr Ser Thr Glu Glu Gly Ser Pro Ala Gly Ser Pro Thr Ser
            130                 135                 140

Thr Glu Glu Gly Thr Ser Thr Glu Pro Ser Glu Gly Ser Ala Pro Gly
145                 150                 155                 160

Thr Ser Glu Ser Ala Thr Pro Glu Ser Gly Pro Gly Thr Ser Glu Ser
                165                 170                 175

Ala Thr Pro Glu Ser Gly Pro Gly Thr Ser Glu Ser Ala Thr Pro Glu
            180                 185                 190

Ser Gly Pro Gly Ser Glu Pro Ala Thr Ser Gly Ser Glu Thr Pro Gly
        195                 200                 205

Ser Glu Pro Ala Thr Ser Gly Ser Glu Thr Pro Gly Ser Pro Ala Gly
    210                 215                 220

Ser Pro Thr Ser Thr Glu Glu Gly Thr Ser Thr Glu Pro Ser Glu Gly
225                 230                 235                 240

Ser Ala Pro Gly Thr Ser Thr Glu Pro Ser Glu Gly Ser Ala Pro Gly
                245                 250                 255
```

```
Ser Glu Pro Ala Thr Ser Gly Ser Glu Thr Pro Gly Thr Ser Glu Ser
            260                 265                 270

Ala Thr Pro Glu Ser Gly Pro Gly Thr Ser Thr Glu Pro Ser Glu Gly
        275                 280                 285

Ser Ala Pro Ala Ser Ser
    290

<210> SEQ ID NO 159
<211> LENGTH: 294
<212> TYPE: PRT
<213> ORGANISM: Artificial Sequence
<220> FEATURE:
<223> OTHER INFORMATION: AG294

<400> SEQUENCE: 159

Gly Ala Pro Pro Gly Ala Ser Pro Gly Thr Ser Ser Thr Gly Ser Pro
1               5                   10                  15

Gly Ala Ser Pro Gly Thr Ser Ser Thr Gly Ser Pro Gly Thr Pro Gly
            20                  25                  30

Ser Gly Thr Ala Ser Ser Ser Pro Gly Ser Ser Thr Pro Ser Gly Ala
        35                  40                  45

Thr Gly Ser Pro Gly Thr Pro Gly Ser Gly Thr Ala Ser Ser Ser Pro
    50                  55                  60

Gly Ser Ser Thr Pro Ser Gly Ala Thr Gly Ser Pro Gly Thr Pro Gly
65                  70                  75                  80

Ser Gly Thr Ala Ser Ser Ser Pro Gly Ser Ser Thr Pro Ser Gly Ala
                85                  90                  95

Thr Gly Ser Pro Gly Ser Ser Thr Pro Ser Gly Ala Thr Gly Ser Pro
                100                 105                 110

Gly Ser Ser Pro Ser Ala Ser Thr Gly Thr Gly Pro Gly Ser Ser Pro
            115                 120                 125

Ser Ala Ser Thr Gly Thr Gly Pro Gly Ala Ser Pro Gly Thr Ser Ser
        130                 135                 140

Thr Gly Ser Pro Gly Thr Pro Gly Ser Gly Thr Ala Ser Ser Ser Pro
145                 150                 155                 160

Gly Ser Ser Thr Pro Ser Gly Ala Thr Gly Ser Pro Gly Ser Ser Pro
                165                 170                 175

Ser Ala Ser Thr Gly Thr Gly Pro Gly Ser Ser Pro Ser Ala Ser Thr
                180                 185                 190

Gly Thr Gly Pro Gly Ala Ser Pro Gly Thr Ser Ser Thr Gly Ser Pro
            195                 200                 205

Gly Ala Ser Pro Gly Thr Ser Ser Thr Gly Ser Pro Gly Ser Ser Thr
        210                 215                 220

Pro Ser Gly Ala Thr Gly Ser Pro Gly Ser Ser Pro Ser Ala Ser Thr
225                 230                 235                 240

Gly Thr Gly Pro Gly Ala Ser Pro Gly Thr Ser Ser Thr Gly Ser Pro
                245                 250                 255

Gly Ser Ser Pro Ser Ala Ser Thr Gly Thr Gly Pro Gly Thr Pro Gly
                260                 265                 270

Ser Gly Thr Ala Ser Ser Ser Pro Gly Ser Ser Thr Pro Ser Gly Ala
            275                 280                 285

Thr Gly Ser Ala Ser Ser
    290

<210> SEQ ID NO 160
<211> LENGTH: 1016
```

```
<212> TYPE: PRT
<213> ORGANISM: Artificial Sequence
<220> FEATURE:
<223> OTHER INFORMATION: FIX-Linker-Albumin

<400> SEQUENCE: 160
```

| | | | | | | | | | | | | | | |
|---|---|---|---|---|---|---|---|---|---|---|---|---|---|---|
| Tyr | Asn | Ser | Gly | Lys | Leu | Glu | Glu | Phe | Val | Gln | Gly | Asn | Leu | Glu | Arg |
| 1 | | | | 5 | | | | | 10 | | | | | 15 | |
| Glu | Cys | Met | Glu | Glu | Lys | Cys | Ser | Phe | Glu | Glu | Ala | Arg | Glu | Val | Phe |
| | | | 20 | | | | | 25 | | | | | 30 | | |
| Glu | Asn | Thr | Glu | Arg | Thr | Thr | Glu | Phe | Trp | Lys | Gln | Tyr | Val | Asp | Gly |
| | | | 35 | | | | | 40 | | | | | 45 | | |
| Asp | Gln | Cys | Glu | Ser | Asn | Pro | Cys | Leu | Asn | Gly | Gly | Ser | Cys | Lys | Asp |
| | 50 | | | | | 55 | | | | | 60 | | | | |
| Asp | Ile | Asn | Ser | Tyr | Glu | Cys | Trp | Cys | Pro | Phe | Gly | Phe | Glu | Gly | Lys |
| 65 | | | | | 70 | | | | | 75 | | | | | 80 |
| Asn | Cys | Glu | Leu | Asp | Val | Thr | Cys | Asn | Ile | Lys | Asn | Gly | Arg | Cys | Glu |
| | | | | 85 | | | | | 90 | | | | | 95 | |
| Gln | Phe | Cys | Lys | Asn | Ser | Ala | Asp | Asn | Lys | Val | Val | Cys | Ser | Cys | Thr |
| | | | 100 | | | | | 105 | | | | | 110 | | |
| Glu | Gly | Tyr | Arg | Leu | Ala | Glu | Asn | Gln | Lys | Ser | Cys | Glu | Pro | Ala | Val |
| | | | 115 | | | | | 120 | | | | | 125 | | |
| Pro | Phe | Pro | Cys | Gly | Arg | Val | Ser | Val | Ser | Gln | Thr | Ser | Lys | Leu | Thr |
| | 130 | | | | | 135 | | | | | 140 | | | | |
| Arg | Ala | Glu | Thr | Val | Phe | Pro | Asp | Val | Asp | Tyr | Val | Asn | Ser | Thr | Glu |
| 145 | | | | | 150 | | | | | 155 | | | | | 160 |
| Ala | Glu | Thr | Ile | Leu | Asp | Asn | Ile | Thr | Gln | Ser | Thr | Gln | Ser | Phe | Asn |
| | | | | 165 | | | | | 170 | | | | | 175 | |
| Asp | Phe | Thr | Arg | Val | Val | Gly | Gly | Glu | Asp | Ala | Lys | Pro | Gly | Gln | Phe |
| | | | 180 | | | | | 185 | | | | | 190 | | |
| Pro | Trp | Gln | Val | Val | Leu | Asn | Gly | Lys | Val | Asp | Ala | Phe | Cys | Gly | Gly |
| | | | 195 | | | | | 200 | | | | | 205 | | |
| Ser | Ile | Val | Asn | Glu | Lys | Trp | Ile | Val | Thr | Ala | Ala | His | Cys | Val | Glu |
| | 210 | | | | | 215 | | | | | 220 | | | | |
| Thr | Gly | Val | Lys | Ile | Thr | Val | Val | Ala | Gly | Glu | His | Asn | Ile | Glu | Glu |
| 225 | | | | | 230 | | | | | 235 | | | | | 240 |
| Thr | Glu | His | Thr | Glu | Gln | Lys | Arg | Asn | Val | Ile | Arg | Ile | Ile | Pro | His |
| | | | | 245 | | | | | 250 | | | | | 255 | |
| His | Asn | Tyr | Asn | Ala | Ala | Ile | Asn | Lys | Tyr | Asn | His | Asp | Ile | Ala | Leu |
| | | | 260 | | | | | 265 | | | | | 270 | | |
| Leu | Glu | Leu | Asp | Glu | Pro | Leu | Val | Leu | Asn | Ser | Tyr | Val | Thr | Pro | Ile |
| | | | 275 | | | | | 280 | | | | | 285 | | |
| Cys | Ile | Ala | Asp | Lys | Glu | Tyr | Thr | Asn | Ile | Phe | Leu | Lys | Phe | Gly | Ser |
| | 290 | | | | | 295 | | | | | 300 | | | | |
| Gly | Tyr | Val | Ser | Gly | Trp | Gly | Arg | Val | Phe | His | Lys | Gly | Arg | Ser | Ala |
| 305 | | | | | 310 | | | | | 315 | | | | | 320 |
| Leu | Val | Leu | Gln | Tyr | Leu | Arg | Val | Pro | Leu | Val | Asp | Arg | Ala | Thr | Cys |
| | | | | 325 | | | | | 330 | | | | | 335 | |
| Leu | Arg | Ser | Thr | Lys | Phe | Thr | Ile | Tyr | Asn | Asn | Met | Phe | Cys | Ala | Gly |
| | | | 340 | | | | | 345 | | | | | 350 | | |
| Phe | His | Glu | Gly | Gly | Arg | Asp | Ser | Cys | Gln | Gly | Asp | Ser | Gly | Gly | Pro |
| | | | 355 | | | | | 360 | | | | | 365 | | |
| His | Val | Thr | Glu | Val | Glu | Gly | Thr | Ser | Phe | Leu | Thr | Gly | Ile | Ile | Ser |
| | 370 | | | | | 375 | | | | | 380 | | | | |

```
Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr Pro
            405                 410                 415

Val Ser Gln Thr Ser Lys Leu Thr Arg Ala Glu Thr Val Phe Pro Asp
            420                 425                 430

Val Asp Ala His Lys Ser Glu Val Ala His Arg Phe Lys Asp Leu Gly
            435                 440                 445

Glu Glu Asn Phe Lys Ala Leu Val Leu Ile Ala Phe Ala Gln Tyr Leu
        450                 455                 460

Gln Gln Cys Pro Phe Glu Asp His Val Lys Leu Val Asn Glu Val Thr
465             470                 475                 480

Glu Phe Ala Lys Thr Cys Val Ala Asp Glu Ser Ala Glu Asn Cys Asp
                485                 490                 495

Lys Ser Leu His Thr Leu Phe Gly Asp Lys Leu Cys Thr Val Ala Thr
                500                 505                 510

Leu Arg Glu Thr Tyr Gly Glu Met Ala Asp Cys Cys Ala Lys Gln Glu
            515                 520                 525

Pro Glu Arg Asn Glu Cys Phe Leu Gln His Lys Asp Asp Asn Pro Asn
530                 535                 540

Leu Pro Arg Leu Val Arg Pro Glu Val Asp Val Met Cys Thr Ala Phe
545                 550                 555                 560

His Asp Asn Glu Glu Thr Phe Leu Lys Lys Tyr Leu Tyr Glu Ile Ala
                565                 570                 575

Arg Arg His Pro Tyr Phe Tyr Ala Pro Glu Leu Leu Phe Phe Ala Lys
            580                 585                 590

Arg Tyr Lys Ala Ala Phe Thr Glu Cys Cys Gln Ala Ala Asp Lys Ala
        595                 600                 605

Ala Cys Leu Leu Pro Lys Leu Asp Glu Leu Arg Asp Glu Gly Lys Ala
            610                 615                 620

Ser Ser Ala Lys Gln Arg Leu Lys Cys Ala Ser Leu Gln Lys Phe Gly
625                 630                 635                 640

Glu Arg Ala Phe Lys Ala Trp Ala Val Ala Arg Leu Ser Gln Arg Phe
                645                 650                 655

Pro Lys Ala Glu Phe Ala Glu Val Ser Lys Leu Val Thr Asp Leu Thr
            660                 665                 670

Lys Val His Thr Glu Cys Cys His Gly Asp Leu Leu Glu Cys Ala Asp
        675                 680                 685

Asp Arg Ala Asp Leu Ala Lys Tyr Ile Cys Glu Asn Gln Asp Ser Ile
690                 695                 700

Ser Ser Lys Leu Lys Glu Cys Cys Glu Lys Pro Leu Leu Glu Lys Ser
705                 710                 715                 720

His Cys Ile Ala Glu Val Glu Asn Asp Glu Met Pro Ala Asp Leu Pro
                725                 730                 735

Ser Leu Ala Ala Asp Phe Val Glu Ser Lys Asp Val Cys Lys Asn Tyr
            740                 745                 750

Ala Glu Ala Lys Asp Val Phe Leu Gly Met Phe Leu Tyr Glu Tyr Ala
        755                 760                 765

Arg Arg His Pro Asp Tyr Ser Val Val Leu Leu Leu Arg Leu Ala Lys
            770                 775                 780

Thr Tyr Glu Thr Thr Leu Glu Lys Cys Cys Ala Ala Ala Asp Phe Cys
785                 790                 795                 800

Tyr Ala Lys Val Phe Asp Glu Phe Lys Pro Leu Val Glu Glu Pro Gln
```

```
                        805                 810                 815
Asn Leu Ile Lys Gln Asn Cys Glu Leu Phe Glu Gln Leu Gly Glu Tyr
                    820                 825                 830

Lys Phe Gln Asn Ala Leu Leu Val Arg Tyr Thr Lys Lys Val Pro Gln
                835                 840                 845

Val Ser Thr Pro Thr Leu Val Glu Val Ser Arg Asn Leu Gly Lys Val
            850                 855                 860

Gly Ser Lys Cys Cys Lys His Pro Glu Ala Lys Arg Met Pro Cys Ala
865                 870                 875                 880

Glu Asp Tyr Leu Ser Val Val Leu Asn Gln Leu Cys Val Leu His Glu
                885                 890                 895

Lys Thr Pro Val Ser Asp Arg Val Thr Lys Cys Cys Thr Glu Ser Leu
            900                 905                 910

Val Asn Arg Arg Pro Cys Phe Ser Ala Leu Glu Val Asp Glu Thr Tyr
        915                 920                 925

Val Pro Lys Glu Phe Asn Ala Glu Thr Phe Thr Phe His Ala Asp Ile
    930                 935                 940

Cys Thr Leu Ser Glu Lys Glu Arg Gln Ile Lys Lys Gln Thr Ala Leu
945                 950                 955                 960

Val Glu Leu Val Lys His Lys Pro Lys Ala Thr Lys Glu Gln Leu Lys
                965                 970                 975

Ala Val Met Asp Asp Phe Ala Ala Phe Val Glu Lys Cys Cys Lys Ala
            980                 985                 990

Asp Asp Lys Glu Thr Cys Phe Ala  Glu Glu Gly Lys Lys  Leu Val Ala
        995                 1000                1005

Ala Ser  Gln Ala Ala Leu Gly  Leu
    1010                1015

<210> SEQ ID NO 161
<211> LENGTH: 424
<212> TYPE: PRT
<213> ORGANISM: Artificial Sequence
<220> FEATURE:
<223> OTHER INFORMATION: FIX

<400> SEQUENCE: 161

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
                20                  25                  30

Glu Asn Thr Glu Arg Thr Thr Glu Phe Trp Lys Gln Tyr Val Asp Gly
            35                  40                  45

Asp Gln Cys Glu Ser Asn Pro Cys Leu Asn Gly Gly Ser Cys Lys Asp
        50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
```

145                 150                 155                 160
Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr Pro
                405                 410                 415

Val Ser Gln Thr Ser Lys Leu Thr
            420

<210> SEQ ID NO 162
<211> LENGTH: 9
<212> TYPE: PRT
<213> ORGANISM: Artificial Sequence
<220> FEATURE:
<223> OTHER INFORMATION: Linker

<400> SEQUENCE: 162

Arg Ala Glu Thr Val Phe Pro Asp Val
1               5

<210> SEQ ID NO 163
<211> LENGTH: 585
<212> TYPE: PRT
<213> ORGANISM: Artificial Sequence
<220> FEATURE:
<223> OTHER INFORMATION: Albumin

<400> SEQUENCE: 163

Asp Ala His Lys Ser Glu Val Ala His Arg Phe Lys Asp Leu Gly Glu
1               5                   10                  15

```
Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                      70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
```

```
                435                 440                 445
Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 164
<211> LENGTH: 763
<212> TYPE: PRT
<213> ORGANISM: Artificial Sequence
<220> FEATURE:
<223> OTHER INFORMATION: FIX(XTEN)-Fc

<400> SEQUENCE: 164

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Gly Pro Ser Pro Gly Ser Pro Thr Ser Thr Glu Glu
```

```
              210                 215                 220
Gly Thr Ser Glu Ser Ala Thr Pro Glu Ser Gly Pro Gly Ser Glu Pro
225                 230                 235                 240

Ala Thr Ser Gly Ser Glu Thr Pro Gly Thr Ser Glu Ser Ala Thr Pro
                    245                 250                 255

Glu Ser Gly Pro Gly Thr Ser Thr Glu Pro Ser Glu Gly Ser Ala Pro
                260                 265                 270

Gly Thr Ser Thr Glu Pro Ser Glu Gly Ser Ala Pro Gly Ala Ser Ser
                275                 280                 285

Asn Ile Thr Gln Ser Thr Gln Ser Phe Asn Asp Phe Thr Arg Val Val
            290                 295                 300

Gly Gly Glu Asp Ala Lys Pro Gly Gln Phe Pro Trp Gln Val Val Leu
305                 310                 315                 320

Asn Gly Lys Val Asp Ala Phe Cys Gly Gly Ser Ile Val Asn Glu Lys
                325                 330                 335

Trp Ile Val Thr Ala Ala His Cys Val Glu Thr Gly Val Lys Ile Thr
                340                 345                 350

Val Val Ala Gly Glu His Asn Ile Glu Glu Thr Glu His Thr Glu Gln
                355                 360                 365

Lys Arg Asn Val Ile Arg Ile Pro His His Asn Tyr Asn Ala Ala
                370                 375                 380

Ile Asn Lys Tyr Asn His Asp Ile Ala Leu Leu Glu Leu Asp Glu Pro
385                 390                 395                 400

Leu Val Leu Asn Ser Tyr Val Thr Pro Ile Cys Ile Ala Asp Lys Glu
                405                 410                 415

Tyr Thr Asn Ile Phe Leu Lys Phe Gly Ser Gly Tyr Val Ser Gly Trp
                420                 425                 430

Gly Arg Val Phe His Lys Gly Arg Ser Ala Leu Val Leu Gln Tyr Leu
                435                 440                 445

Arg Val Pro Leu Val Asp Arg Ala Thr Cys Leu Leu Ser Thr Lys Phe
450                 455                 460

Thr Ile Tyr Asn Asn Met Phe Cys Ala Gly Phe His Glu Gly Gly Arg
465                 470                 475                 480

Asp Ser Cys Gln Gly Asp Ser Gly Gly Pro His Val Thr Glu Val Glu
                485                 490                 495

Gly Thr Ser Phe Leu Thr Gly Ile Ile Ser Trp Gly Glu Glu Cys Ala
                500                 505                 510

Met Lys Gly Lys Tyr Gly Ile Tyr Thr Lys Val Ser Arg Tyr Val Asn
                515                 520                 525

Trp Ile Lys Glu Lys Thr Lys Leu Thr Asp Lys Thr His Thr Cys Pro
530                 535                 540

Pro Cys Pro Ala Pro Glu Leu Leu Gly Gly Pro Ser Val Phe Leu Phe
545                 550                 555                 560

Pro Pro Lys Pro Lys Asp Thr Leu Met Ile Ser Arg Thr Pro Glu Val
                565                 570                 575

Thr Cys Val Val Val Asp Val Ser His Glu Asp Pro Glu Val Lys Phe
                580                 585                 590

Asn Trp Tyr Val Asp Gly Val Glu Val His Asn Ala Lys Thr Lys Pro
                595                 600                 605

Arg Glu Glu Gln Tyr Asn Ser Thr Tyr Arg Val Val Ser Val Leu Thr
                610                 615                 620

Val Leu His Gln Asp Trp Leu Asn Gly Lys Glu Tyr Lys Cys Lys Val
625                 630                 635                 640
```

-continued

```
Ser Asn Lys Ala Leu Pro Ala Pro Ile Glu Lys Thr Ile Ser Lys Ala
            645                 650                 655

Lys Gly Gln Pro Arg Glu Pro Gln Val Tyr Thr Leu Pro Pro Ser Arg
        660                 665                 670

Asp Glu Leu Thr Lys Asn Gln Val Ser Leu Thr Cys Leu Val Lys Gly
        675                 680                 685

Phe Tyr Pro Ser Asp Ile Ala Val Glu Trp Glu Ser Asn Gly Gln Pro
    690                 695                 700

Glu Asn Asn Tyr Lys Thr Thr Pro Pro Val Leu Asp Ser Asp Gly Ser
705                 710                 715                 720

Phe Phe Leu Tyr Ser Lys Leu Thr Val Asp Lys Ser Arg Trp Gln Gln
                725                 730                 735

Gly Asn Val Phe Ser Cys Ser Val Met His Glu Ala Leu His Asn His
            740                 745                 750

Tyr Thr Gln Lys Ser Leu Ser Leu Ser Pro Gly
            755                 760

<210> SEQ ID NO 165
<211> LENGTH: 712
<212> TYPE: PRT
<213> ORGANISM: Artificial Sequence
<220> FEATURE:
<223> OTHER INFORMATION: FIX-FXIa-AE288

<400> SEQUENCE: 165

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240
```

```
Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
                260                 265                 270

Leu Glu Leu Asp Glu Pro Leu Val Leu Asn Ser Tyr Val Thr Pro Ile
                275                 280                 285

Cys Ile Ala Asp Lys Glu Tyr Thr Asn Ile Phe Leu Lys Phe Gly Ser
290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
                340                 345                 350

Phe His Glu Gly Gly Arg Asp Ser Cys Gln Gly Asp Ser Gly Gly Pro
                355                 360                 365

His Val Thr Glu Val Glu Gly Thr Ser Phe Leu Thr Gly Ile Ile Ser
                370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr Gly
                405                 410                 415

Lys Leu Thr Arg Ala Glu Thr Gly Gly Thr Ser Glu Ser Ala Thr Pro
                420                 425                 430

Glu Ser Gly Pro Gly Ser Glu Pro Ala Thr Ser Gly Ser Glu Thr Pro
                435                 440                 445

Gly Thr Ser Glu Ser Ala Thr Pro Glu Ser Gly Pro Gly Ser Glu Pro
                450                 455                 460

Ala Thr Ser Gly Ser Glu Thr Pro Gly Thr Ser Glu Ser Ala Thr Pro
465                 470                 475                 480

Glu Ser Gly Pro Gly Thr Ser Thr Glu Pro Ser Glu Gly Ser Ala Pro
                485                 490                 495

Gly Ser Pro Ala Gly Ser Pro Thr Ser Thr Glu Glu Gly Thr Ser Glu
                500                 505                 510

Ser Ala Thr Pro Glu Ser Gly Pro Gly Ser Glu Pro Ala Thr Ser Gly
                515                 520                 525

Ser Glu Thr Pro Gly Thr Ser Glu Ser Ala Thr Pro Glu Ser Gly Pro
                530                 535                 540

Gly Ser Pro Ala Gly Ser Pro Thr Ser Thr Glu Glu Gly Ser Pro Ala
545                 550                 555                 560

Gly Ser Pro Thr Ser Thr Glu Glu Gly Thr Ser Thr Glu Pro Ser Glu
                565                 570                 575

Gly Ser Ala Pro Gly Thr Ser Glu Ser Ala Thr Pro Glu Ser Gly Pro
                580                 585                 590

Gly Thr Ser Glu Ser Ala Thr Pro Glu Ser Gly Pro Gly Thr Ser Glu
                595                 600                 605

Ser Ala Thr Pro Glu Ser Gly Pro Gly Ser Glu Pro Ala Thr Ser Gly
                610                 615                 620

Ser Glu Thr Pro Gly Ser Glu Pro Ala Thr Ser Gly Ser Glu Thr Pro
625                 630                 635                 640

Gly Ser Pro Ala Gly Ser Pro Thr Ser Thr Glu Glu Gly Thr Ser Thr
                645                 650                 655
```

-continued

```
Glu Pro Ser Glu Gly Ser Ala Pro Gly Thr Ser Thr Glu Pro Ser Glu
            660                 665                 670

Gly Ser Ala Pro Gly Ser Glu Pro Ala Thr Ser Gly Ser Glu Thr Pro
        675                 680                 685

Gly Thr Ser Glu Ser Ala Thr Pro Glu Ser Gly Pro Gly Thr Ser Thr
    690                 695                 700

Glu Pro Ser Glu Gly Ser Ala Pro
705             710

<210> SEQ ID NO 166
<211> LENGTH: 944
<212> TYPE: PRT
<213> ORGANISM: Artificial Sequence
<220> FEATURE:
<223> OTHER INFORMATION: FIX-Fc-Fc

<400> SEQUENCE: 166

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Pro His His Asn
    290                 295                 300
```

-continued

```
Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
            325                 330                 335

Ala Asp Lys Glu Tyr Thr Asn Ile Phe Leu Lys Phe Gly Ser Gly Tyr
        340                 345                 350

Val Ser Gly Trp Gly Arg Val Phe His Lys Gly Arg Ser Ala Leu Val
    355                 360                 365

Leu Gln Tyr Leu Arg Val Pro Leu Val Asp Arg Ala Thr Cys Leu Arg
370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
            405                 410                 415

Thr Glu Val Glu Gly Thr Ser Phe Leu Thr Gly Ile Ile Ser Trp Gly
        420                 425                 430

Glu Glu Cys Ala Met Lys Gly Lys Tyr Gly Ile Tyr Thr Lys Val Ser
    435                 440                 445

Arg Tyr Val Asn Trp Ile Lys Glu Lys Thr Lys Leu Thr Asp Lys Thr
450                 455                 460

His Thr Cys Pro Pro Cys Pro Ala Pro Glu Leu Leu Gly Gly Pro Ser
465                 470                 475                 480

Val Phe Leu Phe Pro Pro Lys Pro Lys Asp Thr Leu Met Ile Ser Arg
            485                 490                 495

Thr Pro Glu Val Thr Cys Val Val Val Asp Val Ser His Glu Asp Pro
        500                 505                 510

Glu Val Lys Phe Asn Trp Tyr Val Asp Gly Val Glu Val His Asn Ala
    515                 520                 525

Lys Thr Lys Pro Arg Glu Glu Gln Tyr Asn Ser Thr Tyr Arg Val Val
530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Pro Ala Pro Ile Glu Lys Thr
            565                 570                 575

Ile Ser Lys Ala Lys Gly Gln Pro Arg Glu Pro Gln Val Tyr Thr Leu
        580                 585                 590

Pro Pro Ser Arg Asp Glu Leu Thr Lys Asn Gln Val Ser Leu Thr Cys
    595                 600                 605

Leu Val Lys Gly Phe Tyr Pro Ser Asp Ile Ala Val Glu Trp Glu Ser
610                 615                 620

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
            645                 650                 655

Arg Trp Gln Gln Gly Asn Val Phe Ser Cys Ser Val Met His Glu Ala
        660                 665                 670

Leu His Asn His Tyr Thr Gln Lys Ser Leu Ser Leu Ser Pro Gly Lys
    675                 680                 685

Arg Arg Arg Arg Ser Gly Gly Gly Ser Gly Gly Gly Gly Ser Gly
690                 695                 700

Gly Gly Ser Gly Gly Gly Gly Ser Arg Arg Arg Arg Asp Lys Thr
705                 710                 715                 720

His Thr Cys Pro Pro Cys Pro Ala Pro Glu Leu Leu Gly Gly Pro Ser
```

```
                725                 730                 735
Val Phe Leu Phe Pro Pro Lys Pro Lys Asp Thr Leu Met Ile Ser Arg
            740                 745                 750

Thr Pro Glu Val Thr Cys Val Val Asp Val Ser His Glu Asp Pro
        755                 760                 765

Glu Val Lys Phe Asn Trp Tyr Val Asp Gly Val Glu Val His Asn Ala
        770                 775                 780

Lys Thr Lys Pro Arg Glu Glu Gln Tyr Asn Ser Thr Tyr Arg Val Val
785                 790                 795                 800

Ser Val Leu Thr Val Leu His Gln Asp Trp Leu Asn Gly Lys Glu Tyr
                805                 810                 815

Lys Cys Lys Val Ser Asn Lys Ala Leu Pro Ala Pro Ile Glu Lys Thr
            820                 825                 830

Ile Ser Lys Ala Lys Gly Gln Pro Arg Glu Pro Gln Val Tyr Thr Leu
        835                 840                 845

Pro Pro Ser Arg Asp Glu Leu Thr Lys Asn Gln Val Ser Leu Thr Cys
850                 855                 860

Leu Val Lys Gly Phe Tyr Pro Ser Asp Ile Ala Val Glu Trp Glu Ser
865                 870                 875                 880

Asn Gly Gln Pro Glu Asn Asn Tyr Lys Thr Thr Pro Pro Val Leu Asp
                885                 890                 895

Ser Asp Gly Ser Phe Phe Leu Tyr Ser Lys Leu Thr Val Asp Lys Ser
            900                 905                 910

Arg Trp Gln Gln Gly Asn Val Phe Ser Cys Ser Val Met His Glu Ala
        915                 920                 925

Leu His Asn His Tyr Thr Gln Lys Ser Leu Ser Leu Ser Pro Gly Lys
        930                 935                 940

<210> SEQ ID NO 167
<211> LENGTH: 383
<212> TYPE: DNA
<213> ORGANISM: Artificial Sequence
<220> FEATURE:
<223> OTHER INFORMATION: Parvovirus B19 KY940273.1

<400> SEQUENCE: 167
ccaaatcaga tgccgccggt cgccgccggt aggcgggact tccggtacaa gatggcggac      60
aattacgtca tttcctgtga cgtcatttcc tgtgacgtca cttccggtgg gcgggacttc    120
cggaattagg gttggctctg gccagcttgc ttggggttgc ccttgacact aagacaagcg    180
gcgcgccgct tgatcttagt ggcacgtcaa ccccaagcgc tggcccagag ccaaccctaa    240
ttccggaagt cccgccacc ggaagtgacg tcacaggaaa tgacgtcaca ggaaatgacg    300
taattgtccg ccatcttgta ccggaagtcc cgcctaccgg cggcgaccgg cggcatctga    360
tttggtgtct tcttttaaat ttt                                             383

<210> SEQ ID NO 168
<211> LENGTH: 248
<212> TYPE: DNA
<213> ORGANISM: Artificial Sequence
<220> FEATURE:
<223> OTHER INFORMATION: Parvorius B19 d135

<400> SEQUENCE: 168
ctctgggcca gcttgcttgg ggttgccttg acactaagac aagcggcgcg ccgcttgatc      60
ttagtggcac gtcaaccca agcgctggcc cagagccaac cctaattccg gaagtcccgc    120
```

```
ccaccggaag tgacgtcaca ggaaatgacg tcacaggaaa tgacgtaatt gtccgccatc    180
ttgtaccgga agtcccgcct accggcggcg accggcggca tctgatttgg tgtcttcttt    240
taaatttt                                                             248

<210> SEQ ID NO 169
<211> LENGTH: 129
<212> TYPE: DNA
<213> ORGANISM: Artificial Sequence
<220> FEATURE:
<223> OTHER INFORMATION: Parvovirus v1  AAV2

<400> SEQUENCE: 169
cggcgcgccg cttgatctta gtggcacgtc aaccagcgct ggcccagagc caaccctaat     60
tccggaagtc ctcagtccgc catcttgccc gcctaccggc ggcgaccggc ggcatcattt    120
ggtgttctt                                                            129

<210> SEQ ID NO 170
<211> LENGTH: 113
<212> TYPE: DNA
<213> ORGANISM: Artificial Sequence
<220> FEATURE:
<223> OTHER INFORMATION: Parvovirus V2

<400> SEQUENCE: 170
ctctgggcca gcttgcttgg ggttgccttg acactaagac aagcggcgcg ccgcttgatc     60
ttagtggcac gtcaaccca agcgctggcc cagagtgtct tcttttaaat ttt            113

<210> SEQ ID NO 171
<211> LENGTH: 340
<212> TYPE: DNA
<213> ORGANISM: Artificial Sequence
<220> FEATURE:
<223> OTHER INFORMATION: Parvovirus V3

<400> SEQUENCE: 171
caaatcagat gccgccggtc gccgccggta ggcgggactt ccggtacaag atggcggaca     60
attacgtcat ttcctgtgac gtatttcctg tgacgtactt ccgtggcgg gacttccgga    120 attttggctc tgggccagct tgcttggggt tgccttgacc aagcgcgcgc cgcttgatca    180
ccccaagcgc tggcccagag ccacctaacc ggaagtcccc ccaccggaag tgacgtcaca    240
ggaaagacgt cacaggaagt aattgtccgc catcttgtac cggaagtccc gcaccggcgg    300
cgaccggcgg catctgattt ggtgtcttct tttaaatttt                          340

<210> SEQ ID NO 172
<211> LENGTH: 444
<212> TYPE: DNA
<213> ORGANISM: Artificial Sequence
<220> FEATURE:
<223> OTHER INFORMATION: Parvovirus U25749.1

<400> SEQUENCE: 172
ctcattggag ggttcgttcg ttcgaaccag ccaatcaggg gaggggaag tgacgcaagt      60 tccggtcaca tgcttccggt gacgcacatc cggtgacgta gttccggtca cgtgcttcct    120
gtcacgtgtt tccggtcacg tgacttccgg tcatgtgact tccggtgacg tgtttccggc    180
tgttaggttg accacgcgca tgccgcgcgg tcagcccaat agttaagccg gaaacacgtc    240
accggaagtc acatgaccgg aagtcacgtg accggaaaca cgtgacagga agcacgtgac    300
cggaactacg tcaccggatg tgcgtcaccg gaagcatgtg accggaactt gcgtcacttc    360
```

-continued cccctcccct gattggctgg ttcgaacgaa cgaaccctcc aatgagactc aaggacaaga     420
ggatattttg cgcgccagga agtg     444

<210> SEQ ID NO 173
<211> LENGTH: 282
<212> TYPE: DNA
<213> ORGANISM: Artificial Sequence
<220> FEATURE:
<223> OTHER INFORMATION: Parvovirus GPV AAV2 V1

<400> SEQUENCE: 173
cggtgacgtg tttccggctg ttaggttgac cacgcgcatg ccgcgcggtc agcccaatag     60
ttaagccgga aacacgtcac cggaagtcac atgaccggaa gtcacgtgac cggaaacacg     120
tgacaggaag cacgtgaccg gaactacgtc accggatgtg cgtcaccgga agcatgtgac     180
cggaacttgc gtcacttccc cctcccctga ttggctggtt cgaacgaacg aaccctccaa     240
tgagactcaa ggacaagagg atattttgcg cgccaggaag tg     282

<210> SEQ ID NO 174
<211> LENGTH: 145
<212> TYPE: DNA
<213> ORGANISM: Artificial Sequence
<220> FEATURE:
<223> OTHER INFORMATION: Parvovirus GPV AAV2 V1

<400> SEQUENCE: 174
ttgaccacgc gcatgccgcg cggtcagccc aatagttaag ccgggtgacc acacgtgaca     60
ggaagcacgg gatgtgcgtc accggaagca gtgaccgggc tggttcgaac gaacgaaccc     120
tccaactcaa ggacaagagg atatt     145

<210> SEQ ID NO 175
<211> LENGTH: 120
<212> TYPE: DNA
<213> ORGANISM: Artificial Sequence
<220> FEATURE:
<223> OTHER INFORMATION: Parvovirus GPV V2

<400> SEQUENCE: 175
cggtgacgtg tttccggctg ttaggttgac cacgcgcatg ccgcgcggtc agcccaatag     60
ttaagccgga aacacgtcac cgactcaagg acaagaggat attttgcgcg ccaggaagtg     120

<210> SEQ ID NO 176
<211> LENGTH: 102
<212> TYPE: DNA
<213> ORGANISM: Artificial Sequence
<220> FEATURE:
<223> OTHER INFORMATION: Parvovirus GPV V3

<400> SEQUENCE: 176
gggaacaatc aggggaagtg accggtgacg tcatgtaact tgcgtcactt cccgttcgaa     60
cgaacgaacg agactcaagg acaagaggcg cgccaggaag tg     102

<210> SEQ ID NO 177
<211> LENGTH: 145
<212> TYPE: DNA
<213> ORGANISM: Artificial Sequence
<220> FEATURE:
<223> OTHER INFORMATION: Parvovirus AAV2 NC_001401.2

<400> SEQUENCE: 177

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcct                                           145

<210> SEQ ID NO 178
<211> LENGTH: 130
<212> TYPE: DNA
<213> ORGANISM: Artificial Sequence
<220> FEATURE:
<223> OTHER INFORMATION: Parvovirus Gtx

<400> SEQUENCE: 178
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct                                                            130

<210> SEQ ID NO 179
<211> LENGTH: 6762
<212> TYPE: DNA
<213> ORGANISM: Artificial Sequence
<220> FEATURE:
<223> OTHER INFORMATION: B19-FVIII construct

<400> SEQUENCE: 179
ctctgggcca gcttgcttgg ggttgccttg acactaagac aagcggcgcg ccgcttgatc      60
ttagtggcac gtcaacccca agcgctggcc cagagccaac cctaattccg gaagtcccgc     120
ccaccggaag tgacgtcaca ggaaatgacg tcacaggaaa tgacgtaatt gtccgccatc     180
ttgtaccgga agtcccgcct accggcggcg accggcggca tctgatttgg tgtcttcttt     240
taaattttgc ggcaattcag tcgataacta taacggtcct aaggtagcga tttaaatacg     300
cgctctctta aggtagcccc gggacgcgtc aattgagatc tggatccggt accgaattcg     360
cggccgcctc gacgactagc gtttaattaa acgcgtgtct gtctgcacat ttcgtagagc     420
gagtgttccg atactctaat ctccctaggc aaggttcata tttgtgtagg ttacttattc     480
tccttttgtt gactaagtca ataatcagaa tcagcaggtt tggagtcagc ttggcaggga     540
tcagcagcct gggttggaag gagggggtat aaaagcccct tcaccaggag aagccgtcac     600
acagatccac aagctcctga ggtaagtgcc gtgtgtggtt cccgcgggcc tggcctcttt     660
acgggttatg gcccttgcgt gccttgaatt actgacactg acatccactt tttctttttc     720
tccacagcta gcgccaccat gcagattgag ctgtccactt gtttcttcct gtgcctcctg     780
cgcttctgtt tctccgccac tcgccggtac taccttggag ccgtggagct ttcatgggac     840
tacatgcaga gcgacctggg cgaactcccc gtggatgcca gattcccccc ccgcgtgcca     900
aagtccttcc cctttaacac ctccgtggtg tacaagaaaa ccctctttgt cgagttcact     960
gaccacctgt tcaacatcgc caagccgcgc ccaccttgga tgggcctcct gggaccgacc    1020
attcaagctg aagtgtacga caccgtggtg atcaccctga agaacatggc gtcccacccc    1080
gtgtccctgc atgcggtcgg agtgtcctac tggaaggcct ccgaaggagc tgagtacgac    1140
gaccagacta gccagcggga aaaggaggac gataaagtgt tcccgggcgg ctcgcatact    1200
tacgtgtggc aagtcctgaa ggaaaacgga cctatggcat ccgatcctct gtgcctgact    1260
tactcctacc tttcccatgt ggacctcgtg aaggacctga acagcgggct gattggtgca    1320
cttctcgtgt gccgcgaagg ttcgctcgct aaggaaaaga cccagaccct ccataagttc    1380
atccttttgt tcgctgtgtt cgatgaagga aagtcatggc attccgaaac taagaactcg    1440

```
ctgatgcagg accgggatgc cgcctcagcc cgcgcctggc ctaaaatgca tacagtcaac    1500
ggatacgtga atcggtcact gcccgggctc atcggttgtc acagaaagtc cgtgtactgg    1560
cacgtcatcg gcatgggcac tacgcctgaa gtgcactcca tcttcctgga agggcacacc    1620
ttcctcgtgc gcaaccaccg ccaggcctct ctggaaatct ccccgattac ctttctgacc    1680
gcccagactc tgctcatgga cctggggcag ttccttctct tctgccacat ctccagccat    1740
cagcacgacg gaatggaggc ctacgtgaag gtggactcat gcccggaaga acctcagttg    1800
cggatgaaga acaacgagga ggccgaggac tatgacgacg atttgactga ctccgagatg    1860
gacgtcgtgc ggttcgatga cgacaacagc cccagcttca tccagattcg cagcgtggcc    1920
aagaagcacc ccaaaaccctg ggtgcactac atcgcggccg aggaagaaga ttgggactac    1980
gccccgttgg tgctggcacc cgatgaccgg tcgtacaagt cccagtatct gaacaatggt    2040
ccgcagcgga ttggcagaaa gtacaagaaa gtgcggttca tggcgtacac tgacgaaacg    2100
tttaagaccc gggaggccat tcaacatgag agcggcattc tgggaccact gctgtacgga    2160
gaggtcggcg ataccctgct catcatcttc aaaaaccagg cctcccggcc ttacaacatc    2220
taccctcacg gaatcaccga cgtgcggcca ctctactcgc ggcgcctgcc gaagggcgtc    2280
aagcacctga aagacttccc tatcctgccg gcgaaatct tcaagtataa gtggaccgtc    2340
accgtggagg acgggcccac caagagcgat cctaggtgtc tgactcggta ctactccagc    2400
ttcgtgaaca tggaacggga cctggcatcg ggactcattg gaccgctgct gatctgctac    2460
aaagagtcgg tggatcaacg cggcaaccag atcatgtccg acaagcgcaa cgtgatcctg    2520
ttctccgtgt ttgatgaaaa cagatcctgg tacctcactg aaaacatcca gaggttcctc    2580
ccaaaccccg caggagtgca actggaggac cctgagtttc aggcctcgaa tatcatgcac    2640
tcgattaacg gttacgtgtt cgactcgctg caactgagcg tgtgcctcca tgaagtcgct    2700
tactggtaca ttctgtccat cggcgcccag actgacttcc tgagcgtgtt cttttccggt    2760 tacacctttta agcacaagat ggtgtacgaa gatacccctga ccctgttccc tttctccggc    2820
gaaacggtgt tcatgtcgat ggagaacccg ggtctgtgga ttctgggatg ccacaacagc    2880
gactttcgga accgcggaat gactgccctg ctgaaggtgt cctcatgcga caagaacacc    2940
ggagactact acgaggactc ctacgaggat atctcagcct acctcctgtc caagaacaac    3000
gcgatcgagc cgcgcagctt cagccagaac ggcgcgccaa catcagagag cgccacccct    3060
gaaagtggtc ccgggagcga gccagccaca tctgggtcgg aaacgccagg cacaagtgag    3120
tctgcaactc ccgagtccgg acctggctcc gagcctgcca ctagcggctc cgagactccg    3180
ggaacttccg agagcgctac accagaaagc ggacccggaa ccagtaccga acctagcgag    3240
ggctctgctc cgggcagccc agccggctct cctacatcca cggaggaggg cacttccgaa    3300
tccgccaccc cggagtcagg gccaggatct gaacccgcta cctcaggcag tgagacgcca    3360
ggaacgagcg agtccgctac accggagagt gggccaggga gccctgctgg atctcctacg    3420
tccactgagg aagggtcacc agcgggctcg cccaccagca ctgaagaagg tgcctcgagc    3480
ccgcctgtgc tgaagaggca ccagcagaaa attacccgga ccaccctcca atcggatcag    3540
gaggaaatcg actacgacga caccatctcg gtggaaatga agaggaaga tttcgatatc    3600 tacgacgagg acgaaaatca gtcccctcgc tcattccaaa agaaaactag acactacttt    3660
atcgccgcgc tggaaagact gtgggactat ggaatgtcat ccagccctca cgtccttcgg    3720
aaccgggccc agagcggatc ggtgcctcag ttcaagaaag tggtgttcca ggagttcacc    3780
```

```
gacggcagct tcacccagcc gctgtaccgg ggagaactga acgaacacct gggcctgctc    3840
ggtccctaca tccgcgcgga agtggaggat aacatcatgg tgaccttccg taaccaagca    3900
tccagacctt actccttcta ttcctccctg atctcatacg aggaggacca gcgccaaggc    3960
gccgagcccc gcaagaactt cgtcaagccc aacgagacta agacctactt ctggaaggtc    4020
caacaccata tggccccgac caaggatgag tttgactgca aggcctgggc ctacttctcc    4080
gacgtggacc ttgagaagga tgtccattcc ggcctgatcg gccgctgct cgtgtgtcac     4140 accaacaccc tgaacccagc gcatggacgc caggtcaccg tccaggagtt tgctctgttc    4200
ttcaccattt ttgacgaaac taagtcctgg tacttcaccg agaatatgga gcgaaactgt    4260
agagcgccct gcaatatcca gatggaagat ccgactttca aggagaacta tagattccac    4320
gccatcaacg ggtacatcat ggatactctg ccggggctgg tcatggccca ggatcagagg    4380
attcggtggt acttgctgtc aatgggatcg aacgaaaaca ttcactccat tcacttctcc    4440
ggtcacgtgt tcactgtgcg caagaaggag gagtacaaga tggcgctgta caatctgtac    4500
cccggggtgt tcgaaactgt ggagatgctg ccgtccaagg ccggcatctg gagagtggag    4560
tgcctgatcg gagagcacct ccacgcgggg atgtccaccc tcttcctggt gtactcgaat    4620
aagtgccaga ccccgctggg catggcctcg gccacatca gagacttcca gatcacagca     4680
agcggacaat acggccaatg ggcgccgaag ctggcccgct gcactactc cggatcgatc     4740 aacgcatggt ccaccaagga accgttctcg tggattaagg tggacctcct ggcccctatg    4800
attatccacg gaattaagac ccagggcgcc aggcagaagt tctcctccct gtacatctcg    4860
caattcatca tcatgtacag cctggacggg aagaagtggc agacttacag gggaaactcc    4920
accggcaccc tgatggtctt tttcggcaac gtggattcct ccggcattaa gcacaacatc    4980
ttcaacccac cgatcatagc cagatatatt aggctccacc ccactcacta ctcaatccgc    5040
tcaactcttc ggatggaact catggggtgc gacctgaact cctgctccat gccgttgggg    5100
atggaatcaa aggctattag cgacgcccag atcaccgcga gctcctactt cactaacatg    5160
ttcgccacct ggagcccctc caaggccagg ctgcacttgc agggacggtc aaatgcctgg    5220
cggccgcaag tgaacaatcc gaaggaatgg cttcaagtgg atttccaaaa gaccatgaaa    5280
gtgaccggag tcaccaccca gggagtgaag tcccttctga cctcgatgta tgtgaaggag    5340
ttcctgatta gcagcagcca ggacgggcac cagtggaccc tgttcttcca aaacggaaag    5400
gtcaaggtgt tccaggggaa ccaggactcg ttcacacccg tggtgaactc cctggacccc    5460
ccactgctga cgcggtactt gaggattcat cctcagtcct gggtccatca gattgcattg    5520
cgaatggaag tcctgggctg cgaggcccag gacctgtact gaatcagcct gagctcgctg    5580
atcataatca acctctggat tacaaaattt gtgaaagatt gactggtatt cttaactatg    5640
ttgctccttt tacgctatgt ggatacgctg ctttaatgcc tttgtatcat gctattgctt    5700
cccgtatggc tttcattttc tcctccttgt ataaatcctg gttgctgtct ctttatgagg    5760
agttgtggcc cgttgtcagg caacgtggcg tggtgtgcac tgtgtttgct gacgcaaccc    5820
ccactggttg gggcattgcc accacctgtc agctcctttc cgggactttc gctttccccc    5880
tccctattgc cacggcggaa ctcatcgccg cctgccttgc ccgctgctgg acagggctc     5940 ggctgttggg cactgacaat tccgtggtgt tgtcgggaa atcatcgtcc tttccttggc     6000
tgctcgcctg tgttgccacc tggattctgc gcgggacgtc cttctgctac gtcccttcgg    6060
ccctcaatcc agcggacctt ccttcccgcg gcctgctgcc ggctctgcgg cctcttccgc    6120
gtcttcgcct tcgccctcag acgagtcgga tctccctttg ggccgcctcc ccgctgatca    6180
```

```
gcctcgactg tgccttctag ttgccagcca tctgttgttt gcccctcccc cgtgccttcc    6240
ttgaccctgg aaggtgccac tcccactgtc ctttcctaat aaaatgagga aattgcatcg    6300
cattgtctga gtaggtgtca ttctattctg ggggtgggg tggggcagga cagcaagggg     6360
gaggattggg aagacaatag caggcatgct ggggatgcgg tgggctctat ggcttctgag    6420
gcggaaagaa cgggctcgag aagcttctag atatcctctc ttaaggtagc atcgagattt    6480
aaattaggga taacaggta atggcgcggg ccgcaaaatt taaaagaaga caccaaatca     6540
gatgccgccg gtcgccgccg gtaggcggga cttccggtac aagatggcgg acaattacgt    6600
catttcctgt gacgtcattt cctgtgacgt cacttccggt gggcgggact tccggaatta    6660 ggggttggctc tgggccagcg cttggggttg acgtgccact aagatcaagc ggcgcgccgc   6720
ttgtcttagt gtcaaggcaa ccccaagcaa gctggcccag ag                      6762
```

<210> SEQ ID NO 180
<211> LENGTH: 248
<212> TYPE: DNA
<213> ORGANISM: Artificial Sequence
<220> FEATURE:
<223> OTHER INFORMATION: 5' ITR

<400> SEQUENCE: 180

```
ctctgggcca gcttgcttgg ggttgccttg acactaagac aagcggcgcg ccgcttgatc     60
ttagtggcac gtcaacccca agcgctggcc cagagccaac cctaattccg gaagtcccgc    120
ccaccggaag tgacgtcaca ggaaatgacg tcacaggaaa tgacgtaatt gtccgccatc    180
ttgtaccgga agtcccgcct accggcggcg accggcggca tctgatttgg tgtcttcttt    240
taaattttt                                                           248
```

<210> SEQ ID NO 181
<211> LENGTH: 248
<212> TYPE: DNA
<213> ORGANISM: Artificial Sequence
<220> FEATURE:
<223> OTHER INFORMATION: 3' ITR

<400> SEQUENCE: 181

```
aaaatttaaa agaagacacc aaatcagatg ccgccggtcg ccgccggtag gcgggacttc     60
cggtacaaga tggcggacaa ttacgtcatt tcctgtgacg tcatttcctg tgacgtcact    120
tccggtgggc gggacttccg gaattagggt tggctctggg ccagcgcttg ggttgacgt     180 gccactaaga tcaagcggcg cgccgcttgt cttagtgtca aggcaacccc aagcaagctg    240
gcccagag                                                            248
```

<210> SEQ ID NO 182
<211> LENGTH: 6830
<212> TYPE: DNA
<213> ORGANISM: Artificial Sequence
<220> FEATURE:
<223> OTHER INFORMATION: Synthetic polynucleotide sequence

<400> SEQUENCE: 182

```
cggtgacgtg tttccggctg ttaggttgac cacgcgcatg ccgcgcggtc agcccaatag     60
ttaagccgga aacacgtcac cggaagtcac atgaccggaa gtcacgtgac cggaaacacg    120
tgacaggaag cacgtgaccg gaactacgtc accggatgtg cgtcaccgga agcatgtgac    180
cggaacttgc gtcacttccc cctcccctga ttggctggtt cgaacgaacg aaccctccaa    240
```

```
tgagactcaa ggacaagagg atattttgcg cgccaggaag tggcggcaat tcagtcgata    300
actataacgg tcctaaggta gcgatttaaa tacgcgctct cttaaggtag ccccgggacg    360
cgtcaattga gatctggatc cggtaccgaa ttcgcggccg cctcgacgac tagcgtttaa    420
ttaaacgcgt gtctgtctgc acatttcgta gagcgagtgt tccgatactc taatctccct    480
aggcaaggtt catatttgtg taggttactt attctccttt tgttgactaa gtcaataatc    540
agaatcagca ggtttggagt cagcttggca gggatcagca gcctgggttg aaggagggg    600 gtataaaagc cccttcacca ggagaagccg tcacacagat ccacaagctc ctgaggtaag    660
tgccgtgtgt ggtccccgcg ggcctggcct ctttacgggt tatggccctt gcgtgccttg    720
aattactgac actgacatcc acttttttct tttctccaca gctagcgcca ccatgcagat    780
tgagctgtcc acttgtttct tcctgtgcct cctgcgcttc tgtttctccg ccactcgccg    840
gtactacctt ggagccgtgg agctttcatg ggactacatg cagagcgacc tgggcgaact    900
ccccgtggat gccagattcc ccccccgcgt gccaaagtcc ttccccttta acacctccgt    960
ggtgtacaag aaaaccctct tgtcgagtt cactgaccac ctgttcaaca tcgccaagcc   1020
gcgcccacct tggatgggcc tcctgggacc gaccattcaa gctgaagtgt acgacaccgt   1080
ggtgatcacc ctgaagaaca tggcgtccca ccccgtgtcc ctgcatgcgg tcggagtgtc   1140
ctactggaag gcctccgaag gagctgagta cgacgaccag actagccagc gggaaaagga   1200
ggacgataaa gtgttcccgg gcggctcgca tacttacgtg tggcaagtcc tgaaggaaaa   1260
cggacctatg gcatccgatc ctctgtgcct gacttactcc tacctttccc atgtggacct   1320
cgtgaaggac ctgaacagcg ggctgattgg tgcacttctc gtgtgccgcg aaggttcgct   1380
cgctaaggaa aagacccaga ccctccataa gttcatcctt ttgttcgctg tgttcgatga   1440
aggaaagtca tggcattccg aaactaagaa ctcgctgatg caggacccgg atgccgcctc   1500
agcccgcgcc tggcctaaaa tgcatacagt caacggatac gtgaatcggt cactgcccgg   1560
gctcatcggt tgtcacagaa agtccgtgta ctggcacgtc atcggcatgg gcactacgcc   1620
tgaagtgcac tccatcttcc tggaagggca caccttcctc gtgcgcaacc accgccaggc   1680
ctctctggaa atctcccccga ttaccttct gaccgcccag actctgctca tggacctggg   1740
gcagttcctt ctcttctgcc acatctccag ccatcagcac gacggaatgg aggcctacgt   1800
gaaggtggac tcatgcccgg aagaacctca gttgcggatg aagaacaacg aggaggccga   1860
ggactatgac gacgatttga ctgactccga gatggacgtc gtgcggttcg atgacgacaa   1920
cagccccagc ttcatccaga ttcgcagcgt ggccaagaag cacccaaaa cctgggtgca   1980 ctacatcgcg gccgaggaag aagattggga ctacgccccg ttggtgctgg cacccgatga   2040
ccggtcgtac aagtcccagt atctgaacaa tggtccgcag cggattggca gaaagtacaa   2100
gaaagtgcgg ttcatggcgt acactgacga aacgtttaag acccgggagg ccattcaaca   2160
tgagagcggc attctgggac cactgctgta cggagaggtc ggcgataccc tgctcatcat   2220
cttcaaaaac caggcctccc ggccttacaa catctaccct cacggaatca ccgacgtgcg   2280
gccactctac tcgcggcgcc tgccgaaggg cgtcaagcac ctgaaagact ccctatcct   2340 gccgggcgaa atcttcaagt ataagtggac cgtcaccgtg gaggacgggc caccaagag   2400 cgatcctagg tgtctgactc ggtactactc cagcttcgtg aacatggaac gggacctggc   2460
atcgggactc attggaccgc tgctgatctg ctacaaagag tcggtggatc aacgcggcaa   2520
ccagatcatg tccgacaagc gcaacgtgat cctgttctcc gtgtttgatg aaaacagatc   2580
ctggtacctc actgaaaaca tccagaggtt cctcccaaac cccgcaggag tgcaactgga   2640
```

```
ggaccctgag tttcaggcct cgaatatcat gcactcgatt aacgttacg tgttcgactc      2700
gctgcaactg agcgtgtgcc tccatgaagt cgcttactgg tacattctgt ccatcggcgc      2760
ccagactgac ttcctgagcg tgttcttttc cggttacacc tttaagcaca agatggtgta      2820
cgaagatacc ctgaccctgt tcccttttctc cggcgaaacg tgttcatgt cgatggagaa      2880
cccgggtctg tggattctgg gatgccacaa cagcgacttt cggaaccgcg aatgactgc       2940
cctgctgaag gtgtcctcat gcgacaagaa caccggagac tactacgagg actcctacga      3000
ggatatctca gcctacctcc tgtccaagaa caacgcgatc gagccgcgca gcttcagcca      3060
gaacggcgcg ccaacatcag agagcgccac ccctgaaagt ggtcccggga gcgagccagc      3120
cacatctggg tcggaaacgc caggcacaag tgagtctgca actcccgagt ccggacctgg      3180
ctccgagcct gccactagcg gctccgagac tccgggaact tccgagagcg ctacaccaga      3240
aagcggaccc ggaaccagta ccgaacctag cgagggctct gctccgggca gcccagccgg      3300
ctctcctaca tccacggagg agggcacttc cgaatccgcc accccggagt cagggccagg      3360
atctgaaccc gctacctcag gcagtgagac gccaggaacg agcgagtccg ctacaccgga      3420
gagtgggcca gggagccctg ctggatctcc tacgtccact gaggaagggt caccagcggg      3480
ctcgcccacc agcactgaag aaggtgcctc gagcccgcct gtgctgaaga ggcaccagcg      3540
agaaattacc cggaccaccc tccaatcgga tcaggaggaa atcgactacg acgacaccat      3600
ctcggtggaa atgaagaagg aagatttcga tatctacgac gaggacgaaa atcagtcccc      3660
tcgctcattc caaaagaaaa ctagacacta ctttatcgcc gcggtggaaa gactgtggga      3720
ctatggaatg tcatccagcc ctcacgtcct tcggaaccgg gcccagagcg gatcggtgcc      3780
tcagttcaag aaagtggtgt tccaggagtt caccgacggc agcttcaccc agccgctgta      3840
ccggggagaa ctgaacgaac acctgggcct gctcggtccc tacatccgcg cggaagtgga      3900
ggataacatc atggtgacct tccgtaacca agcatccaga ccttactcct tctattcctc      3960
cctgatctca tacgaggagg accagcgcca aggcgccgag ccccgcaaga acttcgtcaa      4020
gcccaacgag actaagacct acttctggaa ggtccaacac catatggccc cgaccaagga      4080
tgagtttgac tgcaaggcct gggcctactt ctccgacgtg gaccttgaga aggatgtcca      4140
ttccggcctg atcgggccgc tgctcgtgtg tcacaccaac accctgaacc cagcgcatgg      4200
acgccaggtc accgtccagg agtttgctct gttcttcacc atttttgacg aaactaagtc      4260
ctggtacttc accgagaata tggagcgaaa ctgtagagcg ccctgcaata tccagatgga      4320
agatccgact ttcaaggaga actatagatt ccacgccatc aacgggtaca tcatggatac      4380
tctgccgggg ctggtcatgg cccaggatca gaggattcgg tggtacttgc tgtcaatggg      4440
atcgaacgaa acattcact ccattccactt tccggtcac gtgttcactg tgcgcaagaa      4500
ggaggagtac aagatggcgc tgtacaatct gtaccccggg gtgttcgaaa ctgtggagat      4560
gctgccgtcc aaggccggca tctggagagt ggagtgcctg atcggagagc acctccacgc      4620
ggggatgtcc accctcttcc tggtgtactc gaataagtgc cagaccccgc tgggcatggc      4680
ctcgggccac atcagagact tccagatcac agcaagcgga caatacgcc aatgggcgcc       4740
gaagctggcc cgcttgcact actccggatc gatcaacgca tggtccacca aggaaccgtt      4800
ctcgtggatt aaggtggacc tcctggcccc tatgattatc cacggaatta agacccaggg      4860
cgccaggcag aagttctcct ccctgtacat ctcgcaattc atcatcatgt acagcctgga      4920
cgggaagaag tggcagactt acaggggaaa ctccaccggc accctgatgg tcttttttcgg      4980
```

```
caacgtggat tcctccggca ttaagcacaa catcttcaac ccaccgatca tagccagata    5040
tattaggctc cacccactc actactcaat ccgctcaact cttcggatgg aactcatggg     5100
gtgcgacctg aactcctgct ccatgccgtt ggggatggaa tcaaaggcta ttagcgacgc    5160
ccagatcacc gcgagctcct acttcactaa catgttcgcc acctggagcc cctccaaggc    5220
caggctgcac ttgcagggac ggtcaaatgc ctggcggccg caagtgaaca atccgaagga    5280
atggcttcaa gtggatttcc aaaagaccat gaaagtgacc ggagtcacca cccagggagt    5340
gaagtcccct ctgacctcga tgtatgtgaa ggagttcctg attagcagca gccaggacgg    5400
gcaccagtgg accctgttct tccaaaacgg aaaggtcaag gtgttccagg gaaccagga    5460 ctcgttcaca cccgtggtga actccctgga ccccccactg ctgacgcggt acttgaggat    5520
tcatcctcag tcctgggtcc atcagattgc attgcgaatg gaagtcctgg gctgcgaggc    5580
ccaggacctg tactgaatca gcctgagctc gctgatcata atcaacctct ggattacaaa    5640
atttgtgaaa gattgactgg tattcttaac tatgttgctc cttttacgct atgtggatac    5700
gctgctttaa tgcctttgta tcatgctatt gcttcccgta tggctttcat tttctcctcc    5760
ttgtataaat cctggttgct gtctctttat gaggagttgt ggcccgttgt caggcaacgt    5820
ggcgtggtgt gcactgtgtt tgctgacgca accccactg gttggggcat tgccaccacc    5880
tgtcagctcc tttccgggac tttcgctttc ccctcccta ttgccacggc ggaactcatc    5940
gccgcctgcc ttgcccgctg ctggacaggg gctcggctgt tgggcactga caattccgtg    6000
gtgttgtcgg ggaaatcatc gtcctttcct ggctgctcg cctgtgttgc cacctggatt    6060
ctgcgcggga cgtccttctg ctacgtccct tcggccctca atccagcgga ccttccttcc    6120
cgcggcctgc tgccggctct gcggcctctt ccgcgtcttc gccttcgccc tcagacgagt    6180
cggatctccc tttgggccgc ctccccgctg atcagcctcg actgtgcctt ctagttgcca    6240
gccatctgtt gtttgcccct ccccgtgcc ttccttgacc ctggaaggtg ccactcccac    6300 tgtccttttcc taataaaatg aggaaattgc atcgcattgt ctgagtaggt gtcattctat    6360 tctgggggt ggggtggggc aggacagcaa ggggggaggat tgggaagaca atagcaggca    6420
tgctggggat gcggtgggct ctatggcttc tgaggcggaa agaacgggct cgagaagctt    6480
ctagatatcc tctcttaagg tagcatcgag atttaaatta gggataacag ggtaatggcg    6540
cgggccgcca cttcctggcg cgcaaaatat cctcttgtcc ttgagtctca ttggagggtt    6600
cgttcgttcg aaccagccaa tcaggggagg gggaagtgac gcaagttccg gtcacatgct    6660
tccggtgacg cacatccggt gacgtagttc cggtcacgtg cttcctgtca cgtgtttccg    6720
gtcacgtgac ttccggtcat gtgacttccg gtgacgtgtt tccggcttaa ctattgggct    6780
gaccgcgcgg catgcgcgtg gtcaacctaa cagccggaaa cacgtcaccg                6830
```

<210> SEQ ID NO 183
<211> LENGTH: 282
<212> TYPE: DNA
<213> ORGANISM: Artificial Sequence
<220> FEATURE:
<223> OTHER INFORMATION: 5' ITR

<400> SEQUENCE: 183

```
cggtgacgtg tttccggctg ttaggttgac cacgcgcatg ccgcgcggtc agcccaatag     60
ttaagccgga aacacgtcac cggaagtcac atgaccggaa gtcacgtgac cggaaacacg    120
tgacaggaag cacgtgaccg gaactacgtc accggatgtg cgtcaccgga agcatgtgac    180
cggaacttgc gtcacttccc cctcccctga ttggctggtt cgaacgaacg aaccctccaa    240
```
tgagactcaa ggacaagagg atattttgcg cgccaggaag tg                          282

<210> SEQ ID NO 184
<211> LENGTH: 282
<212> TYPE: DNA
<213> ORGANISM: Artificial Sequence
<220> FEATURE:
<223> OTHER INFORMATION: 3' ITR

<400> SEQUENCE: 184
cacttcctgg cgcgcaaaat atcctcttgt ccttgagtct cattggaggg ttcgttcgtt      60
cgaaccagcc aatcagggga gggggaagtg acgcaagttc cggtcacatg cttccggtga     120
cgcacatccg gtgacgtagt tccggtcacg tgcttcctgt cacgtgtttc cggtcacgtg     180
acttccggtc atgtgacttc cggtgacgtg tttccggctt aactattggg ctgaccgcgc     240
ggcatgcgcg tggtcaacct aacagccgga aacacgtcac cg                        282

<210> SEQ ID NO 185
<211> LENGTH: 383
<212> TYPE: DNA
<213> ORGANISM: Artificial Sequence
<220> FEATURE:
<223> OTHER INFORMATION: 5' ITR

<400> SEQUENCE: 185
ccaaatcaga tgccgccggt cgccgccggt aggcgggact tccggtacaa gatggcggac      60
aattacgtca tttcctgtga cgtcatttcc tgtgacgtca cttccggtgg gcgggacttc     120
cggaattagg gttggctctg gccagcttg cttggggttg ccttgacact aagacaagcg      180
gcgcgccgct tgatcttagt ggcacgtcaa ccccaagcgc tggcccagag ccaaccctaa     240
ttccggaagt cccgcccacc ggaagtgacg tcacaggaaa tgacgtcaca ggaaatgacg     300
taattgtccg ccatcttgta ccggaagtcc cgcctaccgg cggcgaccgg cggcatctga     360
tttggtgtct tcttttaaat ttt                                             383

<210> SEQ ID NO 186
<211> LENGTH: 383
<212> TYPE: DNA
<213> ORGANISM: Artificial Sequence
<220> FEATURE:
<223> OTHER INFORMATION: 3' ITR

<400> SEQUENCE: 186
aaaatttaaa agaagacacc aaatcagatg ccgccggtcg ccgccggtag gcgggacttc      60
cggtacaaga tggcggacaa ttacgtcatt tcctgtgacg tcatttcctg tgacgtcact     120
tccggtgggc gggacttccg gaattagggt tggctctggg ccagcgcttg ggttgacgt     180 gccactaaga tcaagcggcg cgccgcttgt cttagtgtca aggcaacccc aagcaagctg     240
gcccagagcc aaccctaatt ccggaagtcc cgcccaccgg aagtgacgtc acaggaaatg     300
acgtcacagg aaatgacgta attgtccgcc atcttgtacc ggaagtcccg cctaccggcg     360
gcgaccggcg gcatctgatt tgg                                             383

<210> SEQ ID NO 187
<211> LENGTH: 444
<212> TYPE: DNA
<213> ORGANISM: Artificial Sequence
<220> FEATURE:
<223> OTHER INFORMATION: 5' ITR

<400> SEQUENCE: 187

```
ctcattggag ggttcgttcg ttcgaaccag ccaatcaggg gaggggaag tgacgcaagt         60
tccggtcaca tgcttccggt gacgcacatc cggtgacgta gttccggtca cgtgcttcct        120
gtcacgtgtt tccggtcacg tgacttccgg tcatgtgact tccggtgacg tgtttccggc        180
tgttaggttg accacgcgca tgccgcgcgg tcagcccaat agttaagccg gaaacacgtc        240
accggaagtc acatgaccgg aagtcacgtg accggaaaca cgtgacagga agcacgtgac        300
cggaactacg tcaccggatg tgcgtcaccg gaagcatgtg accggaactt gcgtcacttc        360
cccctcccct gattggctgg ttcgaacgaa cgaaccctcc aatgagactc aaggacaaga        420
ggatattttg cgcgccagga agtg                                               444
```

<210> SEQ ID NO 188
<211> LENGTH: 444
<212> TYPE: DNA
<213> ORGANISM: Artificial Sequence
<220> FEATURE:
<223> OTHER INFORMATION: 3' ITR

<400> SEQUENCE: 188

```
cacttcctgg cgcgcaaaat atcctcttgt ccttgagtct cattggaggg ttcgttcgtt         60
cgaaccagcc aatcagggga gggggaagtg acgcaagttc cggtcacatg cttccggtga        120
cgcacatccg gtgacgtagt tccggtcacg tgcttcctgt cacgtgtttc cggtcacgtg        180
acttccggtc atgtgacttc cggtgacgtg tttccggctt aactattggg ctgaccgcgc        240
ggcatgcgcg tggtcaacct aacagccgga aacacgtcac cggaagtcac atgaccggaa        300
gtcacgtgac cggaaacacg tgacaggaag cacgtgaccg gaactacgtc accggatgtg        360
cgtcaccgga agcatgtgac cggaacttgc gtcacttccc cctcccctga ttggctggtt        420
cgaacgaacg aaccctccaa tgag                                               444
```

<210> SEQ ID NO 189
<211> LENGTH: 7032
<212> TYPE: DNA
<213> ORGANISM: Artificial Sequence
<220> FEATURE:
<223> OTHER INFORMATION: Synthetic polynucleotide sequence

<400> SEQUENCE: 189

```
ccaaatcaga tgccgccggt cgccgccggt aggcgggact tccggtacaa gatggcggac         60
aattacgtca tttcctgtga cgtcatttcc tgtgacgtca cttccggtgg gcgggacttc        120
cggaattagg gttggctctg ggccagcttg cttggggttg ccttgacact aagacaagcg        180
gcgcgccgct tgatcttagt ggcacgtcaa ccccaagcgc tggcccagag ccaaccctaa        240
ttccggaagt cccgcccacc ggaagtgacg tcacaggaaa tgacgtcaca ggaaatgacg        300
taattgtccg ccatcttgta ccggaagtcc cgcctaccgg cggcgaccgg cggcatctga        360
tttggtgtct tcttttaaat tttgcggcaa ttcagtcgat aactataacg gtcctaaggt        420
agcgatttaa atacgcgctc tcttaaggta gccccgggac gcgtcaattg agatctggat        480
ccggtaccga attcgcggcc gcctcgacga ctagcgttta attaaacgcg tgtctgtctg        540
cacatttcgt agagcgagtg ttccgatact ctaatctccc taggcaaggt tcatatttgt        600
gtaggttact tattctcctt ttgttgacta agtcaataat cagaatcagc aggtttggag        660
tcagcttggc agggatcagc agcctgggtt ggaaggaggg ggtataaaag ccccttcacc        720
aggagaagcc gtcacacaga tccacaagct cctgaggtaa gtgccgtgtg tggttcccgc        780
```

```
gggcctggcc tctttacggg ttatggccct tgcgtgcctt gaattactga cactgacatc      840 cacttttct ttttctccac agctagcgcc accatgcaga ttgagctgtc cacttgtttc       900
ttcctgtgcc tcctgcgctt ctgtttctcc gccactcgcc ggtactacct tggagccgtg      960
gagctttcat gggactacat gcagagcgac ctgggcgaac tccccgtgga tgccagattc     1020 ccccccgcg tgccaaagtc cttcccttt aacacctccg tggtgtacaa gaaaaccctc       1080
tttgtcgagt tcactgacca cctgttcaac atcgccaagc cgcgcccacc ttggatgggc     1140
ctcctgggac cgaccattca agctgaagtg tacgacaccg tggtgatcac cctgaagaac     1200
atggcgtccc accccgtgtc cctgcatgcg gtcggagtgt cctactggaa ggcctccgaa     1260
ggagctgagt acgacgacca gactagccag cgggaaaagg aggacgataa agtgttcccg     1320 gcggctcgc atacttacgt gtggcaagtc ctgaaggaaa acggacctat ggcatccgat      1380
cctctgtgcc tgacttactc ctacctttcc catgtggacc tcgtgaagga cctgaacagc     1440
gggctgattg gtgcacttct cgtgtgccgc gaaggttcgc tcgctaagga aaagacccag     1500
accctccata agttcatcct tttgttcgct gtgttcgatg aaggaaagtc atggcattcc     1560
gaaactaaga actcgctgat gcaggaccgg gatgccgcct cagcccgcgc ctggcctaaa     1620
atgcatacag tcaacggata cgtgaatcgg tcactgcccg ggctcatcgg ttgtcacaga    1680
aagtccgtgt actggcacgt catcggcatg ggcactacgc ctgaagtgca ctccatcttc     1740
ctggaagggc acaccttcct cgtgcgcaac caccgccagg cctctctgga aatctccccg     1800
attacctttc tgaccgccca gactctgctc atggacctgg ggcagttcct tctcttctgc     1860
cacatctcca gccatcagca cgacggaatg gaggcctacg tgaaggtgga ctcatgcccg     1920
gaagaacctc agttgcggat gaagaacaac gaggaggccg aggactatga cgacgatttg     1980
actgactccg agatggacgt cgtgcggttc gatgacgaca acagccccag cttcatccag     2040
attcgcagcg tggccaagaa gcaccccaaa acctgggtgc actacatcgc ggccgaggaa     2100
gaagattggg actacgcccc gttggtgctg gcacccgatg accggtcgta caagtcccag     2160
tatctgaaca atggtccgca gcggattggc agaaagtaca agaaagtgcg gttcatggcg     2220
tacactgacg aaacgtttaa gacccgggag gccattcaac atgagagcgg cattctggga     2280
ccactgctgt acggagaggt cggcgatacc ctgctcatca tcttcaaaaa ccaggcctcc     2340
cggccttaca acatctaccc tcacggaatc accgacgtgc ggccactcta ctcgcggcgc     2400
ctgccgaagg gcgtcaagca cctgaaagac ttccctatcc tgccgggcga aatcttcaag     2460
tataagtgga ccgtcaccgt ggaggacggg cccaccaaga gcgatcctag gtgtctgact     2520
cggtactact ccagcttcgt gaacatggaa cgggacctgg catcgggact cattggaccg     2580
ctgctgatct gctacaaaga gtcggtggat caacgcggca accagatcat gtccgacaag     2640
cgcaacgtga tcctgttctc cgtgtttgat gaaaacagat cctggtacct cactgaaaac     2700
atccagaggt tcctcccaaa ccccgcagga gtgcaactgg aggaccctga gtttcaggcc     2760
tcgaatatca tgcactcgat taacggttac gtgttcgact cgctgcaact gagcgtgtgc     2820
ctccatgaag tcgcttactg gtacattctg tccatcggcg cccagactga cttcctgagc     2880
gtgttctttt ccggttacac ctttaagcac aagatggtgt acgaagatac cctgaccctg     2940
ttcccttcct ccggcgaaac ggtgttcatg tcgatggaga acccgggtct gtggattctg     3000
ggatgccaca acagcgactt tcggaaccgc ggaatgactg ccctgctgaa ggtgtcctca     3060
tgcgacaaga acaccggaga ctactacgag gactcctacg aggatatctc agcctacctc     3120
```

```
ctgtccaaga caacgcgat cgagccgcgc agcttcagcc agaacggcgc gccaacatca    3180
gagagcgcca ccoctgaaag tggtcccggg agcgagccag ccacatctgg gtcggaaacg    3240
ccaggcacaa gtgagtctgc aactcccgag tccggacctg gctccgagcc tgccactagc    3300
ggctccgaga ctccgggaac ttccgagagc gctacaccag aaagcggacc cggaaccagt    3360
accgaaccta gcgagggctc tgctccgggc agcccagccg gctctcctac atccacggag    3420
gagggcactt ccgaatccgc caccccgag tcagggccag gatctgaacc cgctacctca    3480
ggcagtgaga cgccaggaac gagcgagtcc gctacaccgg agagtgggcc agggagccct    3540
gctggatctc ctacgtccac tgaggaaggg tcaccagcgg gctcgcccac cagcactgaa    3600
gaaggtgcct cgagcccgcc tgtgctgaag aggcaccagc gagaaattac ccggaccacc    3660
ctccaatcgg atcaggagga aatcgactac gacgacacca tctcggtgga aatgaagaag    3720
gaagatttcg atatctacga cgaggacgaa aatcagtccc ctcgctcatt ccaaaagaaa    3780
actagacact actttatcgc cgcggtggaa agactgtggg actatggaat gtcatccagc    3840
cctcacgtcc ttcggaaccg ggcccagagc ggatcggtgc ctcagttcaa gaaagtggtg    3900
ttccaggagt tcaccgacgg cagcttcacc cagccgctgt accggggaga actgaacgaa    3960
cacctgggcc tgctcggtcc ctacatccgc gcggaagtgg aggataacat catggtgacc    4020
ttccgtaacc aagcatccag accttactcc ttctattcct ccctgatctc atacgaggag    4080
gaccagcgcc aaggcgccga gccccgcaag aacttcgtca gcccaacga gactaagacc    4140
tacttctgga aggtccaaca ccatatggcc ccgaccaagg atgagtttga ctgcaaggcc    4200
tgggcctact tctccgacgt ggaccttgag aaggatgtcc attccggcct gatcgggccg    4260
ctgctcgtgt gtcacaccaa cacctgaac ccagcgcatg gacgccaggt caccgtccag    4320
gagtttgctc tgttcttcac cattttgac gaaactaagt cctggtactt caccgagaat    4380
atggagcgaa actgtagagc gccctgcaat atccagatgg aagatccgac tttcaaggag    4440
aactatagat tccacgccat caacgggtac atcatggata tctgccgggg ctggtcatg     4500
gcccaggatc agaggattcg gtggtacttg ctgtcaatgg gatcgaacga aaacattcac    4560
tccattcact tctccggtca cgtgttcact gtgcgcaaga aggaggagta caagatggcg    4620
ctgtacaatc tgtaccccgg ggtgttcgaa actgtggaga tgctgccgtc caaggccggc    4680
atctggagag tggagtgcct gatcggagag cacctccacg cgggggatgtc caccctcttc    4740
ctggtgtact cgaataagtg ccagaccccg ctgggcatgg cctcgggcca catcagagac    4800
ttccagatca cagcaagcgg acaatacggc caatgggcgc cgaagctggc ccgcttgcac    4860
tactccggat cgatcaacgc atggtccacc aaggaaccgt tctcgtggat taaggtggac    4920
ctcctggccc ctatgattat ccacggaatt aagacccagg gcgccaggca gaagttctcc    4980
tccctgtaca tctcgcaatt catcatcatg tacagcctgg acgggaagaa gtggcagact    5040
tacaggggaa actccaccgg caccctgatg gtcttttcg gcaacgtgga ttcctccggc    5100
attaagcaca acatcttcaa cccaccgatc atagccagat atattaggct ccaccccact    5160
cactactcaa tccgctcaac tcttcggatg gaactcatgg ggtgcgacct gaactcctgc    5220
tccatgccgt tggggatgga atcaaaggct attagcgacg cccagatcac cgcgagctcc    5280
tacttcacta acatgttcgc cacctggagc ccctccaagg ccaggctgca cttgcaggga    5340
cggtcaaatg cctggcggcc gcaagtgaac aatccgaagg aatggcttca agtggatttc    5400
caaaagacca tgaaagtgac cggagtcacc acccaggga tgaagtccct tctgacctcg    5460
atgtatgtga aggagttcct gattagcagc agccaggacg ggcaccagtg gacccctgttc    5520
```

| | |
|---|---|
| ttccaaaacg gaaaggtcaa ggtgttccag gggaaccagg actcgttcac acccgtggtg | 5580 |
| aactccctgg acccccact gctgacgcgg tacttgagga ttcatcctca gtcctgggtc | 5640 |
| catcagattg cattgcgaat ggaagtcctg ggctgcgagg cccaggacct gtactgaatc | 5700 |
| agcctgagct cgctgatcat aatcaacctc tggattacaa atttgtgaa agattgactg | 5760 |
| gtattcttaa ctatgttgct cctttacgc tatgtggata cgctgcttta atgcctttgt | 5820 |
| atcatgctat tgcttcccgt atggctttca ttttctcctc cttgtataaa tcctggttgc | 5880 |
| tgtctcttta tgaggagttg tggcccgttg tcaggcaacg tggcgtggtg tgcactgtgt | 5940 |
| ttgctgacgc aacccccact ggttggggca ttgccaccac ctgtcagctc ctttccggga | 6000 |
| cttttcgcttt ccccctccct attgccacgg cggaactcat cgccgcctgc cttgcccgct | 6060 |
| gctggacagg ggctcggctg ttgggcactg acaattccgt ggtgttgtcg gggaaatcat | 6120 |
| cgtcctttcc ttggctgctc gcctgtgttg ccacctggat tctgcgcggg acgtccttct | 6180 |
| gctacgtccc ttcggccctc aatccagcgg accttccttc ccgcgccctg ctgccggctc | 6240 |
| tgcggcctct tccgcgtctt cgccttcgcc ctcagacgag tcggatctcc ctttgggccg | 6300 |
| cctccccgct gatcagcctc gactgtgcct tctagttgcc agccatctgt tgtttgcccc | 6360 |
| tcccccgtgc cttccttgac cctggaaggt gccactccca ctgtcctttc ctaataaaat | 6420 |
| gaggaaattg catcgcattg tctgagtagg tgtcattcta ttctgggggg tggggtgggg | 6480 |
| caggacagca aggggggagga ttgggaagac aatagcaggc atgctgggga tgcggtgggc | 6540 |
| tctatggctt ctgaggcgga agaacgggc tcgagaagct tctagatatc ctctcttaag | 6600 |
| gtagcatcga gatttaaatt agggataaca gggtaatggc gcggccgca aatttaaaa | 6660 |
| gaagacacca atcagatgc cgccggtcgc cgccggtagg cgggacttcc ggtacaagat | 6720 |
| ggcggacaat tacgtcattt cctgtgacgt catttcctgt gacgtcactt ccggtgggcg | 6780 |
| ggacttccgg aattagggtt ggctctgggc cagcgcttgg ggttgacgtg ccactaagat | 6840 |
| caagcggcgc gccgcttgtc ttagtgtcaa ggcaacccca agcaagctgg cccagagcca | 6900 |
| accctaattc cggaagtccc gcccaccgga agtgacgtca caggaaatga cgtcacagga | 6960 |
| aatgacgtaa ttgtccgcca tcttgtaccg gaagtcccgc ctaccggcgg cgaccggcgg | 7020 |
| catctgattt gg | 7032 |

<210> SEQ ID NO 190
<211> LENGTH: 6824
<212> TYPE: DNA
<213> ORGANISM: Artificial Sequence
<220> FEATURE:
<223> OTHER INFORMATION: Synthetic polynucleotide sequence

<400> SEQUENCE: 190

| | |
|---|---|
| ctgcgcgctc gctcgctcac tgaggccgcc cgggcaaagc ccgggcgtcg ggcgaccttt | 60 |
| ggtcgcccgg cctcagtgag cgagcagcg cgcagagagg gagtggccaa ctccatcact | 120 |
| aggggttcct gcggcaattc agtcgataac tataacggtc taaggtagc gatttaaata | 180 |
| cgcgctctct taaggtagcc ccgggacgcg tcaattgaga tctggatccg gtaccgaatt | 240 |
| cgcggccgcc tcgacgacta gcgtttaatt aaatcgaggt gagccccacg ttctgcttca | 300 |
| ctctccccat ctcccccccc tcccaccccc caattttgta tttatttatt ttttaattat | 360 |
| tttgtgcagc gatggggggcg gggggggggg ggggcgcgc gccaggcggg gcggggcggg | 420 |
| gcgaggggcg gggcggggcg aggcggagag gtgcggcggc agccaatcag agcggcgcgc | 480 |

```
tccgaaagtt tccttttatg gcgaggcggc ggcggcggcg gccctataaa aagcgaagcg    540
cgcggcgggc gggagtcgct gcgcgctgcc ttcgccccgt gccccgctcc gccgccgcct    600
cgcgccgccc gccccggctc tgactgaccg cgttactccc acaggtgagc gggcgggacg    660
gcccttctcc ttcgggctgt aattagcgct tggtttaatg acggcttgtt tcttttctgt    720
ggctgcgtga aagccttgag gggctccggg agggcccttt gtgcggggg agcggctcgg     780 ggctgtccgc ggggggacgg ctgccttcgg ggggacggg gcagggcggg gttcggcttc     840
tggcgtgtga ccggcggctc tagagcctct gctaaccatg ttcatgcctt cttcttttc    900 ctacaggcta cgccaccat gcagattgag ctgtccactt gtttcttcct gtgcctcctg     960
cgcttctgtt tctccgccac tcgccggtac taccttggag ccgtggagct ttcatgggac   1020
tacatgcaga gcgacctggg cgaactcccc gtggatgcca gattcccccc cgcgtgcca    1080 aagtccttcc cctttaacac ctccgtggtg tacaagaaaa ccctctttgt cgagttcact   1140
gaccacctgt tcaacatcgc caagccgcgc ccaccttgga tgggcctcct gggaccgacc   1200
attcaagctg aagtgtacga caccgtgtg atcaccctga gaacatggc gtcccacccc     1260 gtgtccctgc atgcggtcgg agtgtcctac tggaaggcct ccgaaggagc tgagtacgac   1320
gaccagacta gccagcggga aaaggaggac gataaagtgt tcccgggcgg ctcgcatact   1380
tacgtgtggc aagtcctgaa ggaaaacgga cctatggcat ccgatcctct gtgcctgact   1440
tactcctacc tttcccatgt ggacctcgtg aaggacctga cagcgggct gattggtgca    1500 cttctcgtgt gccgcgaagg ttcgctcgct aaggaaaaga cccagaccct ccataagttc   1560
atccttttgt tcgctgtgtt cgatgaagga agtcatggc attccgaaac taagaactcg    1620
ctgatgcagg accgggatgc cgcctcagcc cgcgcctggc ctaaaatgca tacagtcaac   1680
ggatacgtga atcggtcact gcccgggctc atcggttgtc acagaaagtc cgtgtactgg   1740
cacgtcatcg gcatgggcac tacgcctgaa gtgcactcca tcttcctgga agggcacacc   1800
ttcctcgtgc gcaaccaccg ccaggcctct ctggaaatct ccccgattac ctttctgacc   1860
gcccagactc tgctcatgga cctggggcag ttccttctct tctgccacat ctccagccat   1920
cagcacgacg gaatggaggc ctacgtgaag gtggactcat gcccggaaga acctcagttg   1980
cggatgaaga caacgagga ggccgaggac tatgacgacg atttgactga ctccgagatg   2040
gacgtcgtgc ggttcgatga cgacaacagc cccagcttca tccagattcg cagcgtggcc   2100
aagaagcacc ccaaaacctg ggtgcactac atcgcggccg aggaagaaga ttgggactac   2160
gccccgttgg tgctggcacc cgatgaccgg tcgtacaagt cccagtatct gaacaatggt   2220
ccgcagcgga ttggcagaaa gtacaagaaa gtgcggttca tggcgtacac tgacgaaacg   2280
tttaagaccc gggaggccat tcaacatgag agcggcattc tgggaccact gctgtacgga   2340
gaggtcggcg ataccctgct catcatcttc aaaaaccagg cctcccggcc ttacaacatc   2400
taccctcacg gaatcaccga cgtgcggcca ctctactcgc ggcgcctgcc gaagggcgtc   2460
aagcacctga aagacttccc tatcctgccg ggcgaaatct tcaagtataa gtggaccgtc   2520
accgtggagg acgggcccac caagagcgat cctaggtgtc tgactcggta ctactccagc   2580
ttcgtgaaca tggaacggga cctggcatcg ggactcattg accgctgct gatctgctac    2640 aaagagtcgg tggatcaacg cggcaaccag atcatgtccg acaagcgcaa cgtgatcctg   2700
ttctccgtgt ttgatgaaaa cagatcctgg tacctcactg aaaacatcca gaggttcctc   2760
ccaaaccccg caggagtgca actggaggac cctgagtttc aggcctcgaa tatcatgcac   2820
tcgattaacg gttacgtgtt cgactcgctg caactgagcg tgtgcctcca tgaagtcgct   2880
```

```
tactggtaca ttctgtccat cggcgcccag actgacttcc tgagcgtgtt cttttccggt    2940
tacaccttta agcacaagat ggtgtacgaa gatacccctga ccctgttccc tttctccggc    3000
gaaacggtgt tcatgtcgat ggagaacccg ggtctgtgga ttctgggatg ccacaacagc    3060
gactttcgga accgcggaat gactgccctg ctgaaggtgt cctcatgcga caagaacacc    3120
ggagactact acgaggactc ctacgaggat atctcagcct acctcctgtc caagaacaac    3180
gcgatcgagc cgcgcagctt cagccagaac ggcgcgccaa catcagagag cgccacccct    3240
gaaagtggtc ccgggagcga gccagccaca tctgggtcgg aaacgccagg cacaagtgag    3300
tctgcaactc ccgagtccgg acctggctcc gagcctgcca ctagcggctc cgagactccg    3360
ggaacttccg agagcgctac accagaaagc ggacccggaa ccagtaccga acctagcgag    3420
ggctctgctc cgggcagccc agccggctct cctacatcca cggaggaggg cacttccgaa    3480
tccgccaccc cggagtcagg gccaggatct gaacccgcta cctcaggcag tgagacgcca    3540
ggaacgagcg agtccgctac accggagagt gggccaggga gccctgctgg atctcctacg    3600
tccactgagg aagggtcacc agcgggctcg cccaccagca ctgaagaagg tgcctcgagc    3660
ccgcctgtgc tgaagaggca ccagcgagaa attacccgga ccaccctcca atcggatcag    3720
gaggaaatcg actacgacga caccatctcg gtggaaatga agaaggaaga tttcgatatc    3780
tacgacgagg acgaaaatca gtcccctcgc tcattccaaa agaaaactag acactacttt    3840
atcgccgcgg tggaaagact gtgggactat ggaatgtcat ccagccctca cgtccttcgg    3900
aaccgggccc agagcggatc ggtgcctcag ttcaagaaag tggtgttcca ggagttcacc    3960
gacggcagct tcacccagcc gctgtaccgg ggagaactga acgaacacct gggcctgctc    4020
ggtccctaca tccgcgcgga agtggaggat aacatcatgg tgaccttccg taaccaagca    4080
tccagacctt actccttcta ttcctccctg atctcatacg aggaggacca cgccaaggc     4140
gccgagcccc gcaagaactt cgtcaagccc aacgagacta agacctactt ctggaaggtc    4200
caacaccata tggcccccgac caaggatgag tttgactgca aggcctgggc ctacttctcc    4260
gacgtggacc ttgagaagga tgtccattcc ggcctgatcg ggccgctgct cgtgtgtcac    4320
accaacaccc tgaacccagc gcatggacgc caggtcaccg tccaggagtt tgctctgttc    4380
ttcaccattt ttgacgaaac taagtcctgg tacttcaccg agaatatgga gcgaaactgt    4440
agagcgccct gcaatatcca gatggaagat ccgactttca aggagaacta tagattccac    4500
gccatcaacg ggtacatcat ggatactctg ccggggctgg tcatggccca ggatcagagg    4560
attcggtggt acttgctgtc aatgggatcg aacgaaaaca ttcactccat tcacttctcc    4620
ggtcacgtgt tcactgtgcg caagaaggag gagtacaaga tggcgctgta caatctgtac    4680
cccgggtgt tcgaaactgt ggagatgctg ccgtccaagg ccggcatctg gagagtggag    4740
tgcctgatcg gagagcacct ccacgcgggg atgtccaccc tcttcctggt gtactcgaat    4800
aagtgccaga ccccgctggg catggcctcg ggccacatca gagacttcca gatcacagca    4860
agcggacaat acggccaatg ggcgccgaag ctggcccgct gcactactc cggatcgatc    4920
aacgcatggt ccaccaagga accgttctcg tggattaagg tggacctcct ggcccctatg    4980
attatccacg gaattaagac ccagggcgcc aggcagaagt tctcctccct gtacatctcg    5040
caattcatca tcatgtacag cctggacggg aagaagtggc agacttacag gggaaactcc    5100
accggcaccc tgatggtctt tttcggcaac gtggattcct ccggcattaa gcacaacatc    5160
ttcaacccac cgatcatagc cagatatatt aggctccacc ccactcacta ctcaatccgc    5220
```

| | | |
|---|---|---|
| tcaactcttc ggatggaact catggggtgc gacctgaact cctgctccat gccgttgggg | 5280 | |
| atggaatcaa aggctattag cgacgcccag atcaccgcga gctcctactt cactaacatg | 5340 | |
| ttcgccacct ggagcccctc caaggccagg ctgcacttgc agggacggtc aaatgcctgg | 5400 | |
| cggccgcaag tgaacaatcc gaaggaatgg cttcaagtgg atttccaaaa gaccatgaaa | 5460 | |
| gtgaccggag tcaccaccca gggagtgaag tcccttctga cctcgatgta tgtgaaggag | 5520 | |
| ttcctgatta gcagcagcca ggacgggcac cagtggaccc tgttcttcca aaacggaaag | 5580 | |
| gtcaaggtgt tccaggggaa ccaggactcg ttcacacccg tggtgaactc cctggacccc | 5640 | |
| ccactgctga cgcggtactt gaggattcat cctcagtcct gggtccatca gattgcattg | 5700 | |
| cgaatggaag tcctgggctg cgaggcccag gacctgtact gaatcagcct gagctcgctg | 5760 | |
| atcataatca acctctggat tacaaaattt gtgaaagatt gactggtatt cttaactatg | 5820 | |
| ttgctccttt tacgctatgt ggatacgctg ctttaatgcc tttgtatcat gctattgctt | 5880 | |
| cccgtatggc tttcattttc tcctccttgt ataaatcctg gttgctgtct ctttatgagg | 5940 | |
| agttgtggcc cgttgtcagg caacgtggcg tggtgtgcac tgtgtttgct gacgcaaccc | 6000 | |
| ccactggttg gggcattgcc accacctgtc agctccttc cgggactttc gctttccccc | 6060 | |
| tccctattgc cacggcggaa ctcatcgccg cctgccttgc ccgctgctgg acaggggctc | 6120 | |
| ggctgttggg cactgacaat tccgtggtgt tgtcggggaa atcatcgtcc tttccttggc | 6180 | |
| tgctcgcctg tgttgccacc tggattctgc gcgggacgtc cttctgctac gtcccttcgg | 6240 | |
| ccctcaatcc agcggacctt ccttcccgcg gcctgctgcc ggctctgcgg cctcttccgc | 6300 | |
| gtcttcgcct tcgccctcag acgagtcgga tctcccttg gccgcctcc ccgctgatca | 6360 | |
| gcctcgactg tgccttctag ttgccagcca tctgttgttt gcccctcccc cgtgccttcc | 6420 | |
| ttgaccctgg aaggtgccac tcccactgtc ctttcctaat aaaatgagga aattgcatcg | 6480 | |
| cattgtctga gtaggtgtca ttctattctg gggggtgggg tggggcagga cagcaagggg | 6540 | |
| gaggattggg aagacaatag caggcatgct ggggatgcgg tgggctctat ggcttctgag | 6600 | |
| gcggaaagaa cgggctcgag aagcttctag atatcctctc ttaaggtagc atcgagattt | 6660 | |
| aaattaggga taacagggta atggcgcggg ccgcaggaac ccctagtgat ggagttggcc | 6720 | |
| actccctctc tgcgcgctcg ctcgctcact gaggccgggc gaccaaaggt cgcccgacgc | 6780 | |
| ccgggctttg cccgggcggc ctcagtgagc gagcgagcgc gcag | 6824 | |

<210> SEQ ID NO 191
<211> LENGTH: 278
<212> TYPE: DNA
<213> ORGANISM: Artificial Sequence
<220> FEATURE:
<223> OTHER INFORMATION: Synthetic polynucleotide sequence

<400> SEQUENCE: 191

| | | |
|---|---|---|
| tcgaggtgag ccccacgttc tgcttcactc tccccatctc cccccctcc ccacccccaa | 60 | |
| ttttgtattt atttattttt taattatttt gtgcagcgat ggggcggg ggggggggg | 120 | |
| ggcgcgcgcc aggcggggcg gggcggggcg aggggcgggg cggggcgagg cggagaggtg | 180 | |
| cggcggcagc caatcagagc ggcgcgctcc gaaagtttcc ttttatggcg aggcggcggc | 240 | |
| ggcggcggcc ctataaaaag cgaagcgcgc ggcgggcg | 278 | |

<210> SEQ ID NO 192
<211> LENGTH: 262
<212> TYPE: DNA
<213> ORGANISM: Artificial Sequence

```
<220> FEATURE:
<223> OTHER INFORMATION: Synthetic polynucleotide sequence

<400> SEQUENCE: 192
gtgagcgggc gggacggccc ttctccttcg ggctgtaatt agcgcttggt ttaatgacgg      60
cttgtttctt ttctgtggct gcgtgaaagc cttgaggggc tccgggaggg ccctttgtgc     120 gggggagcg gctcggggct gtccgcgggg ggacggctgc cttcgggggg gacggggcag     180 ggcgggttc ggcttctggc gtgtgaccgg cggctctaga gcctctgcta accatgttca     240
tgccttcttc tttttcctac ag                                              262

<210> SEQ ID NO 193
<211> LENGTH: 130
<212> TYPE: DNA
<213> ORGANISM: Artificial Sequence
<220> FEATURE:
<223> OTHER INFORMATION: 3' ITR

<400> SEQUENCE: 193
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gagcgcgcag                                                            130

<210> SEQ ID NO 194
<211> LENGTH: 7154
<212> TYPE: DNA
<213> ORGANISM: Artificial Sequence
<220> FEATURE:
<223> OTHER INFORMATION: Synthetic polynucleotide sequence

<400> SEQUENCE: 194
ctcattggag ggttcgttcg ttcgaaccag ccaatcaggg gaggggggaag tgacgcaagt      60 tccggtcaca tgcttccggt gacgcacatc cggtgacgta gttccggtca cgtgcttcct     120
gtcacgtgtt tccggtcacg tgacttccgg tcatgtgact ccggtgacg tgtttccggc     180 tgttaggttg accacgcgca tgccgcgcgg tcagcccaat agttaagccg gaaacacgtc     240
accggaagtc acatgaccgg aagtcacgtg accggaaaca cgtgacagga agcacgtgac     300
cggaactacg tcaccggatg tgcgtcaccg gaagcatgtg accggaactt gcgtcacttc     360
ccctccccct gattggctgg ttcgaacgaa cgaaccctcc aatgagactc aaggacaaga     420
ggatattttg cgcgccagga agtggcggca attcagtcga taactataac ggtcctaagg     480
tagcgattta aatacgcgct ctcttaaggt agccccggga cgcgtcaatt gagatctgga     540
tccggtaccg aattcgcggc cgcctcgacg actagcgttt aattaaacgc gtgtctgtct     600
gcacatttcg tagagcgagt gttccgatac tctaatctcc ctaggcaagg ttcatatttg     660
tgtaggttac ttattctcct tttgttgact aagtcaataa tcagaatcag caggtttgga     720
gtcagcttgg cagggatcag cagcctgggt tggaaggagg gggtataaaa gccccttcac     780
caggagaagc cgtcacacag atccacaagc tcctgaggta agtgccgtgt gtggttcccg     840
cgggcctggc ctctttacgg gttatggccc ttgcgtgcct tgaattactg acactgacat     900
ccactttttc tttttctcca cagctagcgc accatgcag attgagctgt ccacttgttt     960
cttcctgtgc ctcctgcgct tctgtttctc cgccactcgc cggtactacc ttggagccgt    1020
ggagctttca tgggactaca tgcagagcga cctgggcgaa ctcccgtgg atgccagatt    1080 ccccccccgc gtgccaaagt ccttcccctt taacacctcc gtggtgtaca gaaaaaccct    1140
```

```
ctttgtcgag ttcactgacc acctgttcaa catcgccaag ccgcgcccac cttggatggg    1200
cctcctggga ccgaccattc aagctgaagt gtacgacacc gtggtgatca ccctgaagaa    1260
catggcgtcc cacccgtgt ccctgcatgc ggtcggagtg tcctactgga aggcctccga    1320
aggagctgag tacgacgacc agactagcca gcgggaaaag gaggacgata aagtgttccc    1380
gggcggctcg catacttacg tgtggcaagt cctgaaggaa aacggaccta tggcatccga    1440
tcctctgtgc ctgacttact cctaccttc ccatgtggac ctcgtgaagg acctgaacag    1500
cgggctgatt ggtgcacttc tcgtgtgccg cgaaggttcg ctcgctaagg aaaagaccca    1560
gaccctccat aagttcatcc ttttgttcgc tgtgttcgat gaaggaaagt catggcattc    1620
cgaaactaag aactcgctga tgcaggaccg ggatgccgcc tcagcccgcg cctggcctaa    1680
aatgcataca gtcaacggat acgtgaatcg gtcactgccc gggctcatcg gttgtcacag    1740
aaagtccgtg tactggcacg tcatcggcat gggcactacg cctgaagtgc actccatctt    1800
cctggaaggg cacaccttcc tcgtgcgcaa ccaccgccag gcctctctgg aaatctcccc    1860
gattaccttt ctgaccgccc agactctgct catggacctg gggcagttcc ttctcttctg    1920
ccacatctcc agccatcagc acgacggaat ggaggcctac gtgaaggtgg actcatgccc    1980
ggaagaacct cagttgcgga tgaagaacaa cgaggaggcc gaggactatg acgacgattt    2040
gactgactcc gagatggacg tcgtgcggtt cgatgacgac aacagcccca gcttcatcca    2100
gattcgcagc gtggccaaga agcaccccaa aacctgggtg cactacatcg cggccgagga    2160
agaagattgg gactacgccc cgttggtgct ggcacccgat gaccggtcgt acaagtccca    2220
gtatctgaac aatggtccgc agcggattgg cagaaagtac aagaaagtgc ggttcatggc    2280
gtacactgac gaaacgtttta agacccggga ggccattcaa catgagagcg gcattctggg    2340
accactgctg tacggagagg tcggcgatac cctgctcatc atcttcaaaa accaggcctc    2400
ccggccttac aacatctacc ctcacggaat caccgacgtg cggccactct actcgcggcg    2460
cctgccgaag ggcgtcaagc acctgaagga cttccctatc ctgccgggcg aaatcttcaa    2520
gtataagtgg accgtcaccg tggaggacgg gcccaccaag agcgatccta ggtgtctgac    2580
tcggtactac tccagcttcg tgaacatgga acgggacctg gcatcgggac tcattggacc    2640
gctgctgatc tgctacaaag agtcggtgga tcaacgcggc aaccagatca tgtccgacaa    2700
gcgcaacgtg atcctgttct ccgtgtttga tgaaaacaga tcctggtacc tcactgaaaa    2760
catccagagg ttcctcccaa accccgcagg agtgcaactg gaggaccctg agtttcaggc    2820
ctcgaatatc atgcactcga ttaacggtta cgtgttcgac tcgctgcaac tgagcgtgtg    2880
cctccatgaa gtcgcttact ggtacattct gtccatcggc gcccagactg acttcctgag    2940
cgtgttcttt tccggttaca cctttaagca caagatggtg tacgaagata ccctgaccct    3000
gttccctttc tccggcgaaa cggtgttcat gtcgatggag aacccgggtc tgtggattct    3060
gggatgccac aacagcgact tcggaaccgg cggaatgact gccctgctga aggtgtcctc    3120
atgcgacaag aacaccggag actactacga ggactcctac gaggatatct cagcctacct    3180
cctgtccaag aacaacgcga tcgagccgcg cagcttcagc cagaacggcg cgccaacatc    3240
agagagcgcc acccctgaaa gtggtccggg agcgagcca gccacatctg ggtcggaaac    3300
gccaggcaca agtgagtctg caactcccga gtccggacct ggctccgagc ctgccactag    3360
cggctccgag actccgggaa cttccgagag cgctacacca gaaagcggac ccggaaccag    3420
taccgaacct agcgagggct ctgctccggg cagcccagcc ggctctccta catccaccgga    3480 ggagggcact tccgaatccg ccaccccgga gtcagggcca ggatctgaac ccgctacctc    3540
```

-continued

| | |
|---|---|
| aggcagtgag acgccaggaa cgagcgagtc cgctacaccg gagagtgggc cagggagccc | 3600 |
| tgctggatct cctacgtcca ctgaggaagg gtcaccagcg ggctcgccca ccagcactga | 3660 |
| agaaggtgcc tcgagcccgc ctgtgctgaa gaggcaccag cgagaaatta cccggaccac | 3720 |
| cctccaatcg gatcaggagg aaatcgacta cgacgcacc atctcggtgg aaatgaagaa | 3780 |
| ggaagatttc gatatctacg acgaggacga aaatcagtcc cctcgctcat tccaaaagaa | 3840 |
| aactagacac tactttatcg ccgcggtgga aagactgtgg gactatggaa tgtcatccag | 3900 |
| ccctcacgtc cttcggaacc gggcccagag cggatcggtg cctcagttca agaaagtggt | 3960 |
| gttccaggag ttcaccgacg gcagcttcac ccagccgctg taccggggag aactgaacga | 4020 |
| acacctgggc ctgctcggtc cctacatccg cgcggaagtg gaggataaca tcatggtgac | 4080 |
| cttccgtaac caagcatcca gaccttactc cttctattcc tccctgatct catacgagga | 4140 |
| ggaccagcgc caaggcgccg agccccgcaa gaacttcgtc aagcccaacg agactaagac | 4200 |
| ctacttctgg aaggtccaac accatatggc cccgaccaag gatgagtttg actgcaaggc | 4260 |
| ctgggcctac ttctccgacg tggaccttga aaggatgtc cattccggcc tgatcgggcc | 4320 |
| gctgctcgtg tgtcacacca acaccctgaa cccagcgcat ggacgccagg tcaccgtcca | 4380 |
| ggagtttgct ctgttcttca ccattttga cgaaactaag tcctggtact tcaccgagaa | 4440 |
| tatggagcga aactgtagag cgccctgcaa tatccagatg gaagatccga ctttcaagga | 4500 |
| gaactataga ttccacgcca tcaacgggta catcatggat actctgccgg ggctggtcat | 4560 |
| ggcccaggat cagaggattc ggtggtactt gctgtcaatg ggatcgaacg aaaacattca | 4620 |
| ctccattcac ttctccggtc acgtgttcac tgtgcgcaag aaggaggagt acaagatggc | 4680 |
| gctgtacaat ctgtaccccg gggtgttcga aactgtggag atgctgccgt ccaaggccgg | 4740 |
| catctggaga gtggagtgcc tgatcggaga gcacctccac gcggggatgt ccaccctctt | 4800 |
| cctggtgtac tcgaataagt gccagacccc gctgggcatg gcctcgggcc acatcagaga | 4860 |
| cttccagatc acagcaagcg gacaatacgg ccaatgggcg ccgaagctgg cccgcttgca | 4920 |
| ctactccgga tcgatcaacg catggtccac caaggaaccg ttctcgtgga ttaaggtgga | 4980 |
| cctcctggcc cctatgatta ccacggaat taagacccag ggcgccaggc agaagttctc | 5040 |
| ctccctgtac atctcgcaat tcatcatcat gtacagcctg gacgggaaga agtggcagac | 5100 |
| ttacaggga aactccaccg gcaccctgat ggtcttttc ggcaacgtgg attcctccgg | 5160 |
| cattaagcac aacatcttca acccaccgat catagccaga tatattaggc tccaccccac | 5220 |
| tcactactca atccgctcaa ctcttcggat ggaactcatg gggtgcgacc tgaactcctg | 5280 |
| ctccatgccg ttggggatgg aatcaaaggc tattagcgac gcccagatca ccgcgagctc | 5340 |
| ctacttcact aacatgttcg ccacctggag cccctccaag gccaggctgc acttgcaggg | 5400 |
| acggtcaaat gcctggcggc cgcaagtgaa caatccgaag gaatggcttc aagtggattt | 5460 |
| ccaaaagacc atgaaagtga ccggagtcac caccccaggga gtgaagtccc ttctgacctc | 5520 |
| gatgtatgtg aaggagttcc tgattagcag cagccaggac gggcaccagt ggaccctgtt | 5580 |
| cttccaaaac ggaaaggtca aggtgttcca ggggaaccag gactcgttca cacccgtggt | 5640 |
| gaactccctg dacccccac tgctgacgcg gtacttgagg attcatcctc agtcctgggt | 5700 |
| ccatcagatt gcattgcgaa tggaagtcct gggctgcgag gcccaggacc tgtactgaat | 5760 |
| cagcctgagc tcgctgatca taatcaacct ctggattaca aaatttgtga aagattgact | 5820 |
| ggtattctta actatgttgc tccttttacg ctatgtggat acgctgcttt aatgcctttg | 5880 |

| | |
|---|---|
| tatcatgcta ttgcttcccg tatggctttc attttctcct ccttgtataa atcctggttg | 5940 |
| ctgtctcttt atgaggagtt gtggcccgtt gtcaggcaac gtggcgtggt gtgcactgtg | 6000 |
| tttgctgacg caaccccac tggttggggc attgccacca cctgtcagct cctttccggg | 6060 |
| actttcgctt tccccctccc tattgccacg gcggaactca tcgccgcctg ccttgcccgc | 6120 |
| tgctggacag gggctcggct gttgggcact gacaattccg tggtgttgtc ggggaaatca | 6180 |
| tcgtcctttc cttggctgct cgcctgtgtt gccacctgga ttctgcgcgg gacgtccttc | 6240 |
| tgctacgtcc cttcggccct caatccagcg gaccttcctt cccgcggcct gctgccggct | 6300 |
| ctgcggcctc ttccgcgtct tcgccttcgc cctcagacga tcggatctc cctttgggcc | 6360 |
| gcctccccgc tgatcagcct cgactgtgcc ttctagttgc cagccatctg ttgtttgccc | 6420 |
| ctcccccgtg ccttccttga ccctggaagg tgccactccc actgtccttt cctaataaaa | 6480 |
| tgaggaaatt gcatcgcatt gtctgagtag gtgtcattct attctggggg gtggggtggg | 6540 |
| gcaggacagc aagggggagg attgggaaga caatagcagg catgctgggg atgcggtggg | 6600 |
| ctctatggct tctgaggcgg aaagaacggg ctcgagaagc ttctagatat cctctcttaa | 6660 |
| ggtagcatcg agatttaaat tagggataac agggtaatgg cgcgggccgc cacttcctgg | 6720 |
| cgcgcaaaat atcctcttgt ccttgagtct cattggaggg ttcgttcgtt cgaaccagcc | 6780 |
| aatcagggga gggggaagtg acgcaagttc cggtcacatg cttccggtga cgcacatccg | 6840 |
| gtgacgtagt tccggtcacg tgcttcctgt cacgtgtttc cggtcacgtg acttccggtc | 6900 |
| atgtgacttc cggtgacgtg tttccggctt aactattggg ctgaccgcgc ggcatgcgcg | 6960 |
| tggtcaacct aacagccgga aacacgtcac cggaagtcac atgaccggaa gtcacgtgac | 7020 |
| cggaaacacg tgacaggaag cacgtgaccg gaactacgtc accggatgtg cgtcaccgga | 7080 |
| agcatgtgac cggaacttgc gtcacttccc cctcccctga ttggctggtt cgaacgaacg | 7140 |
| aaccctccaa tgag | 7154 |

<210> SEQ ID NO 195
<211> LENGTH: 648
<212> TYPE: DNA
<213> ORGANISM: Artificial Sequence
<220> FEATURE:
<223> OTHER INFORMATION: Synthetic polynucleotide sequence

<400> SEQUENCE: 195

| | |
|---|---|
| ctagttatta atagtaatca attacggggt cattagttca tagcccatat atggagttcc | 60 |
| gcgttacata acttacggta aatggcccgc ctggctgacc gcccaacgac ccccgcccat | 120 |
| tgacgtcaat aatgacgtat gttcccatag taacgccaat agggactttc cattgacgtc | 180 |
| aatgggtgga gtatttacgg taaactgccc acttggcagt acatcaagtg tatcatatgc | 240 |
| caagtacgcc ccctattgac gtcaatgacg gtaaatggcc cgcctggcat tatgcccagt | 300 |
| acatgacctt atgggacttt cctacttggc agtacatcta cgtattagtc atcgctatta | 360 |
| ccatgcatgg tcgaggtgag ccccacgttc tgcttcactc tccccatctc ccccccctcc | 420 |
| ccacccccaa ttttgtattt atttattttt taattatttt gtgcagcgat ggggggcggg | 480 |
| ggggggggg ggcgcgcgcc aggcggggcg ggcggggcg aggggcgggg cggggcgagg | 540 |
| cggagaggtg cggcggcagc caatcagagc ggcgcgctcc gaaagtttcc ttttatggcg | 600 |
| aggcggcggc ggcggcggcc ctataaaaag cgaagcgcgc ggcgggcg | 648 |

<210> SEQ ID NO 196
<211> LENGTH: 1428

<212> TYPE: DNA
<213> ORGANISM: Artificial Sequence
<220> FEATURE:
<223> OTHER INFORMATION: Synthetic polynucleotide sequence

<400> SEQUENCE: 196

| | | | | | |
|---|---|---|---|---|---|
| atggactaca | aagaccatga | cggtgattat | aaagatcatg | atatcgatta | caaggatgac | 60 |
| gatgacaagg | ctgctgtggt | tctggaaaat | ggcgtgctga | gccggaagct | gagcgacttc | 120 |
| ggacaagaga | caagctacat | cgaggacaac | agcaaccaga | tggcgccgt | gtctctgatc | 180 |
| ttcagcctga | agaagaagt | gggcgccctg | gccaaggtgc | tgagactgtt | cgaggaaaac | 240 |
| gagatcaatc | tgacccacat | cgagagcaga | cccagcagac | tgaacaagga | cgagtacgag | 300 |
| ttcttcacct | acctggacaa | gcggagcaag | cctgtgctgg | gcagcatcat | caagagcctg | 360 |
| agaaacgaca | tcggcgccac | cgtgcacgag | ctgagcagag | acaaagaaaa | gaacaccgtg | 420 |
| ccatggttcc | ccaggaccat | ccaagagctg | gacagattcg | ccaaccagat | cctgagctat | 480 |
| ggcgccgagc | tggacgctga | tcaccctggc | tttaaggacc | ccgtgtaccg | ggccagaaga | 540 |
| aagcagtttg | ccgatatcgc | ctacaactac | cggcacggcc | agcctattcc | tcgggtcgag | 600 |
| tacaccgagg | aagagagaaa | gacctggggc | accgtgttca | gaaccctgaa | ggccctgtac | 660 |
| aagacccacg | cctgctacga | gcacaaccac | atcttcccac | tgctggaaaa | gtactgcggc | 720 |
| ttccgcgagg | acaatatccc | tcagctcgaa | gacgtgtccc | agttcctgca | gacctgcacc | 780 |
| ggctttagac | tgaggcctgt | tgccggactg | ctgagcagca | gagattttct | cggcggcctg | 840 |
| gccttcagag | tgttccactg | tacccagtac | atcagacacg | gcagcaagcc | catgtacacc | 900 |
| cctgagcctg | atatctgcca | cgagctgctg | ggacatgtgc | cctgttcag | cgatagaagc | 960 |
| ttcgcccagt | tcagccaaga | gatcggactg | gcttctctgg | agcccctga | cgagtacatt | 1020 |
| gagaagctgg | ccaccatcta | ctggttcacc | gtggaattcg | gcctgtgcaa | agagggcgac | 1080 |
| agcatcaagg | cttatggcgc | tggactgctg | tctagcttcg | gcgagctgca | gtactgtctg | 1140 |
| agcgacaagc | ctaagctgct | gcccctggaa | ctggaaaaga | ccgcctgcca | agagtacaca | 1200 |
| gtgaccgagt | tccagcctct | gtactacgtg | gccgagagct | tcaacgacgc | caaagaaaaa | 1260 |
| gtgcggacct | tcgccgccac | cattcctcgg | ccttttagcg | tcagatacga | ccctacaca | 1320 |
| cagcgcgtgg | aagtgctgga | caacacacag | cagctgaaga | ttctggccga | ctccatcaac | 1380 |
| agcgaagtgg | gcattctgtg | tcacgccctg | cagaagatca | gagctga | | 1428 |

<210> SEQ ID NO 197
<211> LENGTH: 4146
<212> TYPE: DNA
<213> ORGANISM: Artificial Sequence
<220> FEATURE:
<223> OTHER INFORMATION: Synthetic polynucleotide sequence

<400> SEQUENCE: 197

| | | | | | |
|---|---|---|---|---|---|
| ctctgggcca | gcttgcttgg | ggttgccttg | acactaagac | aagcggcgcg | ccgcttgatc | 60 |
| ttagtggcac | gtcaaccca | agcgctggcc | cagagccaac | cctaattccg | gaagtcccgc | 120 |
| ccaccggaag | tgacgtcaca | ggaaatgacg | tcacaggaaa | tgacgtaatt | gtccgccatc | 180 |
| ttgtaccgga | agtcccgcct | accggcgcg | accggcggca | tctgatttgg | tgtcttcttt | 240 |
| taaattttgc | ggcaattcag | tcgataacta | taacggtcct | aaggtagcga | tttaaatacg | 300 |
| cgctctctta | aggtagcccc | gggacgcgt | aattgagatc | tggatccggt | accgaattcg | 360 |
| cggccgcctc | gacgactagc | gtttagtaat | gagacgcaca | aactaatatc | acaaactgga | 420 |

```
aatgtctatc aatatatagt tgctctagtt attaatagta atcaattacg gggtcattag    480
ttcatagccc atatatggag ttccgcgtta cataacttac ggtaaatggc ccgcctggct    540
gaccgcccaa cgaccccgc ccattgacgt caataatgac gtatgttccc atagtaacgc    600
caatagggac tttccattga cgtcaatggg tggagtattt acggtaaact gcccacttgg    660
cagtacatca agtgtatcat atgccaagta cgccccctat tgacgtcaat gacggtaaat    720
ggcccgcctg gcattatgcc cagtacatga ccttatggga cttcctact tggcagtaca    780 tctacgtatt agtcatcgct attaccatgc atggtcgagg tgagccccac gttctgcttc    840
actctcccca tctccccccc ctccccaccc ccaattttgt atttatttat tttttaatta    900
ttttgtgcag cgatggggc ggggggggg ggggggcgcg cgccaggcgg ggcggggcgg    960 ggcgagggc ggggcgggc gaggcggaga ggtgcggcgg cagccaatca gagcggcgcg    1020
ctccgaaagt ttccttttat ggcgaggcgg cggcggcggc ggcccataa aaagcgaagc    1080 gcgcggcggg cggagtcgc tgcgcgctgc cttcgccccg tgccccgctc cgccgccgcc    1140
tcgcgccgcc cgcccccggct ctgactgacc gcgttactcc cacaggtgag cgggcgggac    1200
ggcccttctc cttcgggctg taattagcgc ttggtttaat gacggcttgt ttcttttctg    1260
tggctgcgtg aaagccttga ggggctccgg gaggccctt tgtgcggggg gagcggctcg    1320
gggctgtccg cgggggacg gctgccttcg ggggggacgg ggcagggcgg ggttcggctt    1380
ctggcgtgtg accggcggct ctagagcctc tgctaaccat gttcatgcct tcttctttt    1440 cctacagctc ctgggcaacg tgctggttat tgtgctgtct catcattttg gcaaagaatt    1500
ggatcgcgaa gccgccacca tggactacaa agaccatgac ggtgattata aagatcatga    1560
tatcgattac aaggatgacg atgacaaggc tgctgtggtt ctggaaaatg gcgtgctgag    1620
ccggaagctg agcgacttcg acaagagac aagctacatc gaggacaaca gcaaccagaa    1680
tggcgccgtg tctctgatct tcagcctgaa agaagaagtg ggcgccctgg ccaaggtgct    1740
gagactgttc gaggaaaacg agatcaatct gacccacatc gagagcagac ccagcagact    1800
gaacaaggac gagtacgagt cttcaccta cctggacaag cggagcaagc ctgtgctggg    1860
cagcatcatc aagagcctga aaacgacat cggcgccacc gtgcacgagc tgagcagaga    1920
caaagaaaag aacaccgtgc catggttccc caggaccatc caagagctgg acagattcgc    1980
caaccagatc ctgagctatg cgccgagct ggacgctgat cacctggct ttaaggaccc    2040 cgtgtaccgg gccagaagaa agcagtttgc cgatatcgcc tacaactacc ggcacggcca    2100
gcctattcct cgggtcgagt acaccgagga agagaaag acctggggca ccgtgttcag    2160
aaccctgaag gccctgtaca gacccacgc ctgctacgag cacaaccaca tcttcccact    2220
gctggaaaag tactgcggct tccgcgagga caatatccct cagctcgaag acgtgtccca    2280
gttcctgcag acctgcaccg ctttagact gaggcctgtt gccggactgc tgagcagcag    2340
agattttctc ggcggcctgg ccttcagagt gttccactgt acccagtaca tcagacacgg    2400
cagcaagccc atgtacaccc ctgagcctga tatctgccac gagctgctgg acatgtgcc    2460 cctgttcagc gatagaagct cgcccagtt cagccaagag atcggactgg cttctctggg    2520 agccctgac gagtacattg agaagctggc caccatctac tggttcaccg tggaattcgg    2580
cctgtgcaaa gagggcgaca gcatcaaggc ttatggcgct ggactgctgt ctagcttcgg    2640
cgagctgcag tactgtctga gcgacaagcc taagctgctg ccctggaac tggaaaagac    2700 cgcctgccaa gagtacacag tgaccgagtt ccagcctctg tactacgtgg ccgagagctt    2760
caacgacgcc aaagaaaag tgcggacctt cgccgccacc attcctcggc cttttagcgt    2820
```

```
cagatacgac ccctacacac agcgcgtgga agtgctggac aacacacagc agctgaagat    2880
tctggccgac tccatcaaca gcgaagtggg cattctgtgt cacgccctgc agaagatcaa    2940
gagctgagca agtaatgagc gctgatcata atcaacctct ggattacaaa atttgtgaaa    3000
gattgactgg tattcttaac tatgttgctc cttttacgct atgtggatac gctgctttaa    3060
tgcctttgta tcatgctatt gcttcccgta tggctttcat tttctcctcc ttgtataaat    3120
cctggttgct gtctctttat gaggagttgt ggcccgttgt caggcaacgt ggcgtggtgt    3180
gcactgtgtt tgctgacgca accccactg gttgggcat tgccaccacc tgtcagctcc     3240
tttccgggac tttcgctttc cccctccta ttgccacggc ggaactcatc gccgcctgcc     3300
ttgcccgctg ctggacaggg gctcggctgt tgggcactga caattccgtg tgttgtcgg    3360 ggaaatcatc gtcctttcct tggctgctcg cctgtgttgc cacctggatt ctgcgcggga    3420
cgtccttctg ctacgtccct tcggccctca atccagcgga ccttccttcc gcggcctgc    3480 tgccggctct gcggcctctt ccgcgtcttc gccttcgccc tcagacgagt cggatctccc    3540
tttgggccgc ctccccgctg atcagcctcg actgtgcctt ctagttgcca gccatctgtt    3600
gtttgcccct ccccgtgcc ttccttgacc ctggaaggtg ccactcccac tgtcctttcc     3660
taataaaatg aggaaattgc atcgcattgt ctgagtaggt gtcattctat tctgggggt     3720 ggggtggggc aggacagcaa gggggaggat tgggaagaca atagcaggca tgctggggat    3780
gcggtgggct ctatggcttc tgaggcggaa agaacgggct cgagaagctt ctagatatcc    3840
tctcttaagg tagcatcgag atttaaatta gggataacag ggtaatgcg cgggccgcaa     3900 aatttaaaag aagacaccaa atcagatgcc gccggtcgcc gccggtaggc gggacttccg    3960
gtacaagatg gcggacaatt acgtcatttc ctgtgacgtc atttcctgtg acgtcacttc    4020
cggtgggcgg gacttccgga attagggttg gctctgggcc agcgcttggg gttgacgtgc    4080
cactaagatc aagcggcgcg ccgcttgtct tagtgtcaag gcaaccccaa gcaagctggc    4140
ccagag                                                                4146
```

<210> SEQ ID NO 198
<211> LENGTH: 4214
<212> TYPE: DNA
<213> ORGANISM: Artificial Sequence
<220> FEATURE:
<223> OTHER INFORMATION: Synthetic polynucleotide sequence

<400> SEQUENCE: 198

```
cggtgacgtg tttccggctg ttaggttgac cacgcgcatg ccgcgcggtc agcccaatag      60
ttaagccgga aacacgtcac cggaagtcac atgaccggaa gtcacgtgac cggaaacacg     120
tgacaggaag cacgtgaccg gaactacgtc accggatgtg cgtcaccgga agcatgtgac    180
cggaacttgc gtcacttccc cctccctga ttggctggtt cgaacgaacg aaccctccaa     240
tgagactcaa ggacaagagg atattttgcg cgccaggaag tggcggcaat tcagtcgata    300
actataacgg tcctaaggta gcgatttaaa tacgcgctct cttaaggtag ccccgggacg    360
cgtcaattga gatctggatc cggtaccgaa ttcgcggccg cctcgacgac tagcgtttag    420
taatgagacg cacaaactaa tatcacaaac tggaaatgtc tatcaatata tagttgctct    480
agttattaat agtaatcaat tacggggtca ttagttcata gcccatatat ggagttccgc    540
gttacataac ttacggtaaa tggcccgcct ggctgaccgc ccaacgaccc ccgcccattg    600
acgtcaataa tgacgtatgt tcccatagta acgccaatag ggactttcca ttgacgtcaa    660
```

```
tgggtggagt atttacggta aactgcccac ttggcagtac atcaagtgta tcatatgcca    720
agtacgcccc ctattgacgt caatgacggt aaatggcccg cctggcatta tgcccagtac    780
atgaccttat gggactttcc tacttggcag tacatctacg tattagtcat cgctattacc    840
atgcatggtc gaggtgagcc ccacgttctg cttcactctc cccatctccc ccccctcccc    900 accccccaatt ttgtatttat ttatttttta attattttgt gcagcgatgg gggcgggggg    960 ggggggggggg cgcgcgccag gcggggcggg gcggggcgag gggcggggcg gggcgaggcg   1020
gagaggtgcg gcggcagcca atcagagcgg cgcgctccga aagtttcctt ttatggcgag   1080
gcggcggcgg cggcggccct ataaaaagcg aagcgcgcgg cgggcgggag tcgctgcgcg   1140
ctgccttcgc cccgtgcccc gctccgccgc cgcctcgcgc cgcccgcccc ggctctgact   1200
gaccgcgtta ctcccacagg tgagcgggcg ggacggccct tctccttcgg gctgtaatta   1260
gcgcttggtt taatgacggc ttgtttcttt tctgtggctg cgtgaaagcc ttgaggggct   1320 ccggagggc cctttgtgcg ggggagcgg ctcggggctg tccgcggggg gacggctgcc   1380 ttcgggggg acgggcagg gcggggttcg gcttctggcg tgtgaccggc ggctctagag   1440
cctctgctaa ccatgttcat gccttcttct ttttcctaca gctcctgggc aacgtgctgg   1500
ttattgtgct gtctcatcat tttggcaaag aattggatcg cgaagccgcc accatggact   1560
acaaagacca tgacggtgat tataaagatc atgatatcga ttacaaggat gacgatgaca   1620
aggctgctgt ggttctggaa aatggcgtgc tgagccggaa gctgagcgac ttcggacaag   1680
agacaagcta catcgaggac aacagcaacc agaatggcgc cgtgtctctg atcttcagcc   1740
tgaaagaaga agtgggcgcc ctggccaagg tgctgagact gttcgaggaa aacgagatca   1800
atctgaccca catcgagagc agacccagca gactgaacaa ggacgagtac gagttcttca   1860
cctacctgga caagcggagc aagcctgtgc tgggcagcat catcaagagc ctgagaaacg   1920
acatcggcgc caccgtgcac gagctgagca gagacaaaga aaagaacacc gtgccatggt   1980
tccccaggac catccaagag ctggacagat tcgccaacca gatcctgagc tatggcgccg   2040
agctggacgc tgatcaccct ggctttaagg accccgtgta ccgggccaga gaaagcagt   2100 ttgccgatat cgcctacaac taccggcacg gccagcctat tcctcgggtc gagtacaccg   2160
aggaagagag aaagacctgg ggcaccgtgt tcagaaccct gaaggccctg tacaagaccc   2220
acgcctgcta cgagcacaac cacatcttcc cactgctgga aaagtactgc ggcttccgcg   2280
aggacaatat ccctcagctc gaagacgtgt cccagttcct gcagacctgc accggcttta   2340
gactgaggcc tgttgccgga ctgctgagca gcagagattt tctcggcggc ctggccttca   2400
gagtgttcca ctgtacccag tacatcagac acggcagcaa gcccatgtac acccctgagc   2460
ctgatatctg ccacgagctg ctgggacatg tgccctgtt cagcgataga gcttcgccc   2520 agttcagcca agagatcgga ctggcttctc tgggagcccc tgacgagtac attgagaagc   2580
tggccaccat ctactggttc accgtggaat tcggcctgtg caaagagggc gacagcatca   2640
aggcttatgg cgctggactg ctgtctagct tcggcgagct gcagtactgt ctgagcgaca   2700
agcctaagct gctgcccctg gaactggaaa agaccgcctg ccaagagtac acagtgaccg   2760
agttccagcc tctgtactac gtggccgaga gcttcaacga cgccaaagaa aaagtgcgga   2820
ccttcgccgc caccattcct cggccttta gcgtcagata cgacccctac acacagcgcg   2880
tggaagtgct ggacaacaca cagcagctga gattctggc cgactccatc aacagcgaag   2940
tgggcattct gtgtcacgcc ctgcagaaga tcaagagctc agcaagtaat gagcgctgat   3000
cataatcaac ctctggatta caaaatttgt gaaagattga ctggtattct taactatgtt   3060
```

```
gctccttta    cgctatgtgg   atacgctgct   ttaatgcctt   tgtatcatgc   tattgcttcc   3120
cgtatggctt   tcattttctc   ctccttgtat   aaatcctggt   tgctgtctct   ttatgaggag   3180
ttgtggcccg   ttgtcaggca   acgtggcgtg   gtgtgcactg   tgtttgctga   cgcaaccccc   3240
actggttggg   gcattgccac   cacctgtcag   ctcctttccg   ggactttcgc   tttcccctc    3300 cctattgcca   cggcggaact   catcgccgcc   tgccttgccc   gctgctggac   aggggctcgg   3360
ctgttgggca   ctgacaattc   cgtggtgttg   tcggggaaat   catcgtcctt   tccttggctg   3420
ctcgcctgtg   ttgccacctg   gattctgcgc   gggacgtcct   tctgctacgt   cccttcggcc   3480
ctcaatccag   cggaccttcc   ttcccgcggc   ctgctgccgg   ctctgcggcc   tcttccgcgt   3540
cttcgccttc   gccctcagac   gagtcggatc   tcccttgggg   ccgcctcccc   gctgatcagc   3600
ctcgactgtg   ccttctagtt   gccagccatc   tgttgtttgc   ccctccccg    tgccttcctt   3660 gaccctggaa   ggtgccactc   ccactgtcct   ttcctaataa   aatgaggaaa   ttgcatcgca   3720
ttgtctgagt   aggtgtcatt   ctattctggg   gggtggggtg   gggcaggaca   gcaaggggga   3780
ggattgggaa   gacaatagca   ggcatgctgg   ggatgcggtg   ggctctatgg   cttctgaggc   3840
ggaaagaacg   ggctcgagaa   gcttctagat   atcctctctt   aaggtagcat   cgagatttaa   3900
attagggata   acagggtaat   ggcgcgggcc   gccacttcct   ggcgcgcaaa   atatcctctt   3960
gtccttgagt   ctcattggag   ggttcgttcg   ttcgaaccag   ccaatcaggg   gaggggaag    4020 tgacgcaagt   tccggtcaca   tgcttccggt   gacgcacatc   cggtgacgta   gttccggtca   4080
cgtgcttcct   gtcacgtgtt   tccggtcacg   tgacttccgg   tcatgtgact   tccggtgacg   4140
tgtttccggc   ttaactattg   ggctgaccgc   gcggcatgcg   cgtggtcaac   ctaacagccg   4200
gaaacacgtc   accg                                                           4214
```

What is claimed is:

1. A nucleic acid molecule comprising a first inverted terminal repeat (ITR) and a second ITR flanking a genetic cassette comprising a heterologous polynucleotide sequence, wherein the first ITR is a B19d135 5' ITR consisting of the nucleotide sequence set forth in SEQ ID NO: 180 or the second ITR is a B19d135 3' ITR consisting of the nucleotide sequence set forth in SEQ ID NO: 181.

2. The nucleic acid molecule of claim 1, wherein the first ITR consists of the nucleotide sequence set forth in SEQ ID NO: 180 and the second ITR consists of the nucleotide sequence set forth in SEQ ID NO: 181.

3. The nucleic acid molecule of claim 1, further comprising a tissue-specific promoter.

4. The nucleic acid molecule of claim 3, wherein the promoter is a tristetraprolin (TTP) promoter.

5. The nucleic acid molecule of claim 1, wherein the heterologous polynucleotide sequence further comprises a synthetic intronic sequence.

6. The nucleic acid molecule of claim 5, wherein the intronic sequence comprises the nucleotide sequence of SEQ ID NO: 115 or 192.

7. The nucleic acid molecule of claim 1, wherein the genetic cassette further comprises a post-transcriptional regulatory element.

8. The nucleic acid molecule of claim 7, wherein the post-transcriptional regulatory element comprises a mutated woodchuck hepatitis virus post-transcriptional regulatory element (WPRE), a microRNA binding site, a DNA nuclear targeting sequence, or any combination thereof.

9. The nucleic acid molecule of claim 8, wherein the microRNA binding site comprises a binding site to miR142-3p.

10. The nucleic acid molecule of claim 1, wherein the nucleic acid molecule comprises from 5' to 3': the first ITR, the genetic cassette, and the second ITR; wherein the genetic cassette comprises a tissue-specific promoter sequence, an intronic sequence, the heterologous polynucleotide sequence, a post-transcriptional regulatory element, and a 3'UTR poly (A) tail sequence.

11. The nucleic acid molecule of claim 10, wherein:
(a) the tissue specific promoter sequence comprises a TTP promoter;
(b) the intron is a synthetic intron;
(c) the post-transcriptional regulatory element comprises WPRE; and
(d) the 3'UTR poly (A) tail sequence comprises bGHpA.

12. The nucleic acid molecule of claim 1, wherein the heterologous polynucleotide sequence encodes a factor VIII (FVIII) protein.

13. The nucleic acid molecule of claim 12, wherein the FVIII protein comprises an amino acid sequence at least about 70% identical to the amino acid sequence of SEQ ID NO:109.

14. The nucleic acid molecule of claim 12, wherein the heterologous polynucleotide sequence further encodes a protein heterologous moiety, wherein the heterologous moiety is an Fc region of an immunoglobulin constant domain.

15. The nucleic acid molecule of claim 14, wherein the heterologous moiety is inserted into the FVIII protein immediately downstream of amino acid 745 corresponding to mature FVIII (SEQ ID NO:106).

16. The nucleic acid molecule of claim 12, wherein the heterologous polynucleotide sequence encoding the FVIII protein comprises the nucleotide sequence of SEQ ID NO: 107 or the nucleotide sequence of SEQ ID NO: 71.

17. The nucleic acid molecule of claim 1, wherein the heterologous polynucleotide sequence encodes a clotting factor.

18. The nucleic acid molecule of claim 1, wherein the genetic cassette further comprises a 3'UTR poly (A) tail sequence.

19. The nucleic acid molecule of claim 18, wherein the 3'UTR poly (A) tail sequence is selected from the group consisting of bGH poly (A), actin poly (A), and hemoglobin poly (A).

20. The nucleic acid molecule of claim 1, wherein the nucleic acid molecule is formulated with a delivery agent.

21. The nucleic acid molecule of claim 20, wherein the delivery agent comprises a lipid nanoparticle.

22. A host cell comprising the nucleic acid molecule of claim 1.

23. A pharmaceutical composition comprising the nucleic acid molecule of claim 1, and a pharmaceutically acceptable excipient.

24. A nucleic acid molecule comprising a first ITR and a second ITR flanking a genetic cassette comprising a heterologous polynucleotide sequence, wherein the first ITR is a GPVd162 5' ITR consisting of the nucleotide sequence set forth in SEQ ID NO: 183 or the second ITR is a GPVd162 3' ITR consisting of the nucleotide sequence set forth in SEQ ID NO: 184.

25. The nucleic acid molecule of claim 24, wherein the first ITR consists of the nucleotide sequence set forth in SEQ ID NO: 183 and the second ITR consists of the nucleotide sequence set forth in SEQ ID NO: 184.

26. The nucleic acid molecule of claim 24, further comprising a tissue-specific promoter.

27. The nucleic acid molecule of claim 26, wherein the promoter is a TTP promoter.

28. The nucleic acid molecule of claim 24, wherein the heterologous polynucleotide sequence further comprises a synthetic intronic sequence.

29. The nucleic acid molecule of claim 28, wherein the intronic sequence comprises the nucleotide sequence of SEQ ID NO: 115 or 192.

30. The nucleic acid molecule of claim 24, wherein the heterologous polynucleotide sequence encodes a clotting factor.

31. The nucleic acid molecule of claim 24, wherein the genetic cassette further comprises a post-transcriptional regulatory element.

32. The nucleic acid molecule of claim 31, wherein the post-transcriptional regulatory element comprises a mutated woodchuck hepatitis virus post-transcriptional regulatory element (WPRE), a microRNA binding site, a DNA nuclear targeting sequence, or any combination thereof.

33. The nucleic acid molecule of claim 32, wherein the microRNA binding site comprises a binding site to miR142-3p.

34. The nucleic acid molecule of claim 24, wherein the nucleic acid molecule comprises from 5' to 3': the first ITR, the genetic cassette, and the second ITR; wherein the genetic cassette comprises a tissue-specific promoter sequence, an intronic sequence, the heterologous polynucleotide sequence, a post-transcriptional regulatory element, and a 3'UTR poly (A) tail sequence.

35. The nucleic acid molecule of claim 34, wherein:
(a) the tissue specific promoter sequence comprises a TTP promoter;
(b) the intron is a synthetic intron;
(c) the post-transcriptional regulatory element comprises WPRE; and
(d) the 3'UTR poly (A) tail sequence comprises bGHpA.

36. The nucleic acid molecule of claim 24, wherein the genetic cassette further comprises a 3'UTR poly (A) tail sequence.

37. The nucleic acid molecule of claim 36, wherein the 3'UTR poly (A) tail sequence is selected from the group consisting of bGH poly (A), actin poly (A), and hemoglobin poly (A).

38. The nucleic acid molecule of claim 24, wherein the heterologous polynucleotide sequence encodes a FVIII protein.

39. The nucleic acid molecule of claim 38, wherein the FVIII protein comprises an amino acid sequence at least about 70% identical to the amino acid sequence of SEQ ID NO:109.

40. The nucleic acid molecule of claim 38, wherein the heterologous polynucleotide sequence further encodes a protein heterologous moiety, wherein the heterologous moiety is an Fc region of an immunoglobulin constant domain.

41. The nucleic acid molecule of claim 40, wherein the heterologous moiety is inserted into the FVIII protein immediately downstream of amino acid 745 corresponding to mature FVIII (SEQ ID NO:106).

42. The nucleic acid molecule of claim 38, wherein the heterologous polynucleotide sequence encoding the FVIII protein comprises the nucleotide sequence of SEQ ID NO: 107 or the nucleotide sequence of SEQ ID NO: 71.

43. The nucleic acid molecule of claim 24, wherein the nucleic acid molecule is formulated with a delivery agent.

44. The nucleic acid molecule of claim 43, wherein the delivery agent comprises a lipid nanoparticle.

45. A host cell comprising the nucleic acid molecule of claim 24.

46. A pharmaceutical composition comprising the nucleic acid molecule of claim 24, and a pharmaceutically acceptable excipient.

\* \* \* \* \*